United States Patent
Gillard et al.

(10) Patent No.: US 7,326,791 B2
(45) Date of Patent: Feb. 5, 2008

(54) CARBOXYLIC ACID AMIDES, THE PREPARATION THEREOF, AND THEIR USE AS PHARMACEUTICAL COMPOSITIONS

(75) Inventors: James Gillard, Rosemere (CA); Sandra Ruth Handschuh, Warthausen (DE); Herbert Nar, Ochsenhausen (DE); Roland Pfau, Biberach (DE); Henning Priepke, Warthausen (DE); Wolfgang Wienen, Biberach/Rissegg (DE); Annette Mario Schuler-Metz, Ulm (DE); Eckhart Bauer, Biberach (DE); Georg Dahmann, Attenweiler (DE); Kai Gerlach, Ulm (DE)

(73) Assignee: Boehringer Ingelheim Pharma GmbH & Co., KG, Ingelheim (DE)

( * ) Notice: Subject to any disclaimer, the term of this patent is extended or adjusted under 35 U.S.C. 154(b) by 398 days.

(21) Appl. No.: 10/741,727

(22) Filed: Dec. 19, 2003

(65) Prior Publication Data

US 2004/0220169 A1 Nov. 4, 2004

Related U.S. Application Data

(60) Provisional application No. 60/498,788, filed on Aug. 29, 2003, provisional application No. 60/437,442, filed on Dec. 30, 2002.

(30) Foreign Application Priority Data

Dec. 19, 2002 (DE) .............................. 102 59 407
Aug. 2, 2003 (DE) .............................. 103 35 545

(51) Int. Cl.
*A61K 31/4184* (2006.01)
*C07D 401/12* (2006.01)
*C07D 403/12* (2006.01)
*C07D 417/12* (2006.01)

(52) U.S. Cl. ................................... 548/309.7; 514/394
(58) Field of Classification Search ............. 548/309.7
See application file for complete search history.

(56) References Cited

U.S. PATENT DOCUMENTS

| | | | |
|---|---|---|---|
| 6,087,380 A | 7/2000 | Hauel et al. | |
| 6,114,532 A | 9/2000 | Ries et al. | |
| 6,248,770 B1 | 6/2001 | Ries et al. | |
| 6,414,008 B1 | 7/2002 | Hauel et al. | |
| 6,451,832 B2 | 9/2002 | Ries et al. | |
| 6,469,039 B1 | 10/2002 | Hauel et al. | |
| 6,593,355 B2 | 7/2003 | Ries et al. | |
| 6,710,055 B2 | 3/2004 | Hauel et al. | |
| 6,747,023 B1 | 6/2004 | Kobayashi et al. | |
| 7,192,968 B2 | 3/2007 | Yoshino et al. | |
| 2002/0183519 A1 | 12/2002 | Nar et al. | |
| 2004/0176603 A1 | 9/2004 | Priepke et al. | |
| 2005/0203078 A1 | 9/2005 | Priepke et al. | |
| 2005/0272792 A1 * | 12/2005 | Gerlach et al. | 514/394 |

FOREIGN PATENT DOCUMENTS

| CA | 2 277 949 A1 | 8/1998 |
|---|---|---|
| CA | 2 319 494 A1 | 8/1999 |
| CA | 2 337 804 A1 | 1/2000 |
| CA | 2 393 916 A1 | 7/2001 |
| CA | 2 439 231 A1 | 9/2002 |
| WO | WO98/37075 | 8/1999 |
| WO | WO99/40072 | 8/1999 |
| WO | WO 00/01704 | 1/2000 |
| WO | 0009480 A1 | 2/2000 |
| WO | 0026197 A1 | 5/2000 |
| WO | 0071512 A1 | 11/2000 |
| WO | 0076970 A2 | 12/2000 |
| WO | 0076971 A1 | 12/2000 |
| WO | WO 01/47896 | 7/2001 |
| WO | 0174774 A1 | 10/2001 |
| WO | 0196303 A1 | 12/2001 |
| WO | 0196304 A1 | 12/2001 |
| WO | 0196323 A1 | 12/2001 |
| WO | 0226720 A2 | 4/2002 |
| WO | WO 02/072558 A1 | 9/2002 |

OTHER PUBLICATIONS

International Search Report for PCT/EP03/14195 mailed Mar. 25, 2004.
Wei He et al; Benzimidazoles and Isosteric Compounds as Potent and Selective Factor Xa Inhibitors; Bioorganic & Medicinal Chemistry Letters (2002) vol. 12 pp. 919-922; Elsevier Science Ltd.
John J. Masters et al; Bicyclic S1-Binding Constructs in Series of Phenyl Glycine-Based Inhibitors of Human Factor XA; Abstract Medi (2002) 284.

* cited by examiner

*Primary Examiner*—Laura L. Stockton
(74) *Attorney, Agent, or Firm*—Michael P. Morris; Edouard G. Lebel; Timothy X. Witkowski

(57) ABSTRACT

Substituted carboxylic acid amides of general formula

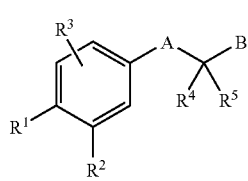

(I)

wherein A, B, and $R^1$ to $R^5$ are as defined herein, and the tautomers and the salts thereof, particularly the physiologically acceptable salts thereof with inorganic or organic acids or bases, which have valuable properties, such as antithrombotic activity and factor Xa-inhibiting activity.

4 Claims, No Drawings

CARBOXYLIC ACID AMIDES, THE PREPARATION THEREOF, AND THEIR USE AS PHARMACEUTICAL COMPOSITIONS

RELATED APPLICATIONS

This application claims benefit of U.S. Ser. No. 60/437,442, filed Dec. 30, 2002, and U.S. Ser. No. 60/498,788, filed Aug. 29, 2003, and claims priority to German Application. No. 102 59 407.4, filed Dec. 19, 2002, and German Application No. 103 35 545.6, filed Aug. 2, 2003, each of which is hereby incorporated by reference in its entirety.

FIELD OF THE INVENTION

The present invention relates to new substituted carboxylic acid amides of general formula

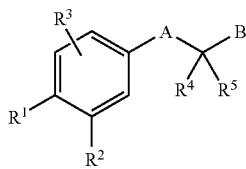

the tautomers, the enantiomers, the diastereomers, the mixtures thereof and the salts thereof, particularly the physiologically acceptable salts thereof with inorganic or organic acids or bases, which have valuable properties.

The compounds of the above general formula I as well as the tautomers, the enantiomers, the diastereomers, the mixtures thereof and the salts thereof, particularly the physiologically acceptable salts thereof with inorganic or organic acids or bases, and their stereoisomers have valuable pharmacological properties, particularly an antithrombotic activity and a factor Xa-inhibiting activity.

The present application thus relates to the new compounds of the above general formula I, the preparation thereof, the pharmaceutical compositions containing the pharmacologically effective compounds, the preparation thereof and their use.

In the above general formula I in a 1st embodiment $R_1$ denotes an amino, $C_{1-5}$-alkylamino, $C_{3-7}$-cycloalkylamino or (phenyl-$C_{1-3}$-alkyl)-amino group which may additionally be substituted in each case at the amino nitrogen atom by a phenylcarbonyl or phenylsulfonyl group or by $C_{1-5}$-alkyl or $C_{1-5}$-alkylcarbonyl group optionally substituted in the alkyl moiety by a hydroxy, $C_{1-3}$-alkyloxy or carboxy group, a group which may be converted in vivo into a carboxy group, an amino, $C_{1-3}$-alkylamino, di-($C_{1-3}$-alkyl)-amino or a 4- to 7-membered cycloalkyleneimino group, while in the above-mentioned substituted $C_{1-5}$-alkyl group two heteroatoms are separated from one another by at least two carbon atoms, a 4- to 7-membered cycloalkyleneiminocarbonyl or cycloalkyleneiminosulfonyl group, while the cycloalkyleneimino moiety may be substituted in the carbon skeleton by a fluorine, chlorine or bromine atom, one or two $C_{1-3}$-alkyl, $C_{2-3}$-alkenyl, $C_{2-3}$-alkynyl, hydroxy-$C_{1-3}$-alkyl, $C_{1-3}$-alkyloxy-$C_{1-3}$-alkyl, phenyl-$C_{1-3}$-alkyl, 1,1-diphenyl-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-3}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, N—($C_{1-3}$-alkylcarbonyl)-$C_{1-3}$-alkylamino-$C_{1-3}$-alkyl, carboxy-$C_{1-3}$-alkyl, $C_{1-3}$-alkyloxy-carbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-3}$-alkylsulfonylamino-$C_{1-3}$-alkyl, aminocarbonylamino-$C_{1-3}$-alkyl, $C_{1-3}$-alkylaminocarbonylamino-$C_{1-3}$-alkyl, di-($C_{1-3}$-alkyl)-aminocarbonylamino-$C_{1-3}$-alkyl, carboxy, $C_{1-3}$-alkyloxycarbonyl, benzyloxycarbonyl, $C_{1-3}$-alkylcarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, aminocarbonyl-$C_{1-3}$-alkylaminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, trifluoromethylcarbonylamino, a mono-, di- or trifluoromethylamino, a phenyl or a 5- to 6-membered heteroaryl group, with the proviso that in the substitution of a methylene group adjacent to the imino group two heteroatoms are separated from one another by at least two carbon atoms, and/or a methylene group in the 3 position of a 5-membered cycloalkyleneimino group may be replaced by a sulfur atom, a sulfinyl or sulfonyl group or a methylene group in the 4 position of a 6- or 7-membered cycloalkyleneimino group may be replaced by an oxygen or sulfur atom, a carbonyl, sulfinyl or sulfonyl group or by an —NH— group optionally substituted by a $C_{1-3}$-alkyl, hydroxy, formyl or $C_{1-3}$-alkylcarbonyl group, while additionally a methylene group adjacent to the abovementioned optionally substituted —NH— group may be replaced by a carbonyl, sulfinyl or sulfonyl group, with the proviso that in the substitution of the abovementioned 6- to 7-membered cycloalkyleneimino groups wherein a methylene group is replaced by an oxygen or sulfur atom, a sulfinyl or sulfonyl group, two heteroatoms are separated from one another by at least two carbon atoms, a 5- to 7-membered cycloalkenyleneiminocarbonyl or cycloalkenyleneiminosulfonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{3-6}$-cycloalkylamino-$C_{1-3}$-alkyl, phenyl, phenyl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, an aminocarbonyl or aminosulfonyl group optionally substituted by one or two $C_{1-5}$-alkyl, $C_{2-3}$-alkenyl, $C_{2-3}$-alkynyl, $C_{3-6}$-cycloalkyl or 5- to 7-membered cycloalkyleneimino groups, while the substituents may be identical or different and in each case one of the $C_{1-5}$-alkyl groups may be substituted by one or two hydroxy-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-5}$-alkyloxycarbonylamino-$C_{1-3}$-alkyl, $C_{3-6}$cycloalkylamino-$C_{1-3}$-alkyl, aminocarbonyl, $C_{1-3}$-alkylaminocarbonyl, N—($C_{3-7}$-cycloalkyl)-$C_{1-3}$-alkylaminocarbonyl, N-(phenyl-$C_{1-3}$-alkyl)-$C_{1-5}$-alkylaminocarbonyl, di-($C_{1-3}$-alkyl)-aminocarbonyl or a 4- to 7-membered cycloalkyleneiminocarbonyl group, a $C_{1-7}$-alkylcarbonyl or $C_{3-7}$-cycloalkylcarbonyl group, where
the methylene group in the 2, 3 or 4 position in a $C_{3-7}$-cycloalkylcarbonyl group may be replaced by an oxygen or sulfur atom, a carbonyl, sulfinyl, sulfonyl or a —NH— group, wherein:
the hydrogen atom of the —NH— group may be replaced by a $C_{1-3}$-alkyl or $C_{1-3}$-alkylcarbonyl group, a phenylcarbonyl or heteroarylcarbonyl group which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl or $C_{1-3}$-alkoxy group, a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while
the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl or $C_{1-3}$-alkoxy group and/or
a —$CH_2$—$CH_2$— group in a 5- to 7-membered cycloalkyleneimino group may be replaced by a —NH—CO—, —CO—NH—, —CO—N($CH_3$)— or a —N($CH_3$)—CO— group or
a methylene group, which is adjacent to the nitrogen atom, in a 5- to 7-membered cycloalkyleneimino group may be replaced by a carbonyl group, or a group of formula

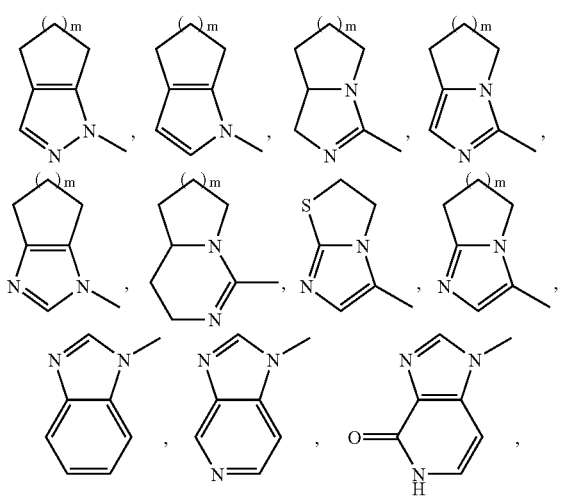

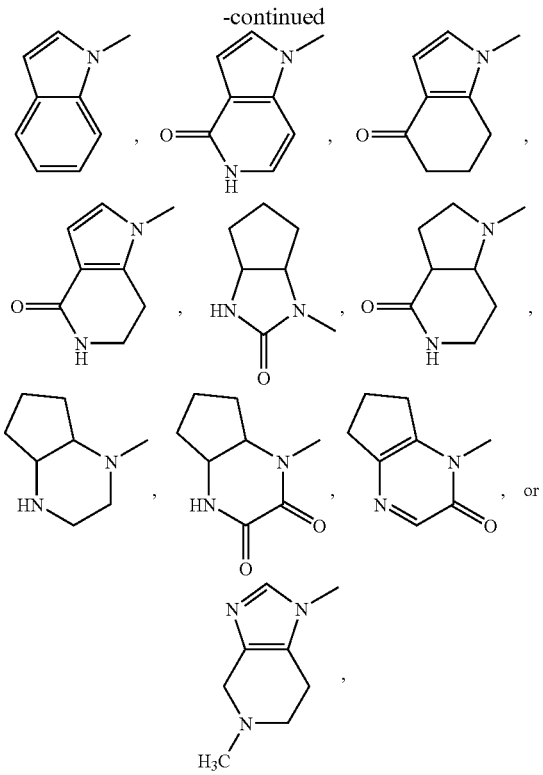

wherein in the heterocyclic moiety in each case a hydrogen atom may be replaced by a $C_{1-3}$-alkyl, $C_{1-3}$-alkyloxy, $C_{1-3}$-alkyloxycarbonyl, $C_{1-5}$-alkyloxycarbonylamino-$C_{1-3}$-alkyl, methylsulfonylmethyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, morpholin-4-yl-$C_{1-3}$-alkyl, piperazinyl-$C_{1-3}$-alkyl, N—($C_{1-3}$-alkyl)piperazin-4-yl-$C_{1-3}$-alkyl, aminocarbonyl, $C_{1-3}$-alkylaminocarbonyl or di-($C_{1-3}$-alkyl)-aminocarbonyl group and
m denotes the number 1 or 2, $R^2$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, $C_{1-3}$-alkoxy, a mono-, di- or trifluoromethoxy group, $R^3$ denotes a hydrogen atom or a $C_{1-3}$-alkyl group, $R^4$ denotes a hydrogen atom, a $C_{2-3}$-alkenyl or $C_{2-3}$-alkynyl group or a straight-chain or branched $C_{1-5}$-alkyl group which is optionally substituted by a fluorine atom, a mono-, di- or trifluoromethyl, a nitrile, hydroxy, a $C_{1-5}$-alkyloxy group wherein the hydrogen atoms may be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-3}$-alkyloxy, $C_{1-5}$-alkyloxycarbonyl-$C_{1-3}$-alkyloxy, $C_{1-8}$-alkyloxycarbonylamino, chloro-$C_{2-3}$-alkylaminocarbonylamino, mercapto, $C_{1-3}$-alkylsulfanyl, $C_{1-3}$-alkylsulfinyl, $C_{1-3}$-alkylsulfonyl, $C_{1-3}$-alkylcarbonylamino-$C_{1-3}$-alkylsulfanyl, $C_{1-3}$-alkylcarbonylamino-$C_{1-3}$-alkylsulfinyl, $C_{1-3}$-alkylcarbonylamino-$C_{1-3}$-alkylsulfonyl, carboxy, $C_{1-3}$-alkyloxycarbonyl, allyloxycarbonyl, propargyloxycarbonyl, benzyloxycarbonyl, aminocarbonyl, $C_{1-3}$-alkylaminocarbonyl, di-($C_{1-3}$-alkyl)-aminocarbonyl, aminosulfonyl, amino, $C_{1-3}$-alkylamino, di-($C_{1-3}$-alkyl)-amino, $C_{1-5}$-alkylcarbonylamino, $C_{1-3}$-alkylsulfonylamino, N—($C_{1-3}$-alkylsulfonyl)-$C_{1-3}$-alkylamino, $C_{3-6}$-cycloalkylcarbonylamino, aminocarbonylamino, $C_{1-3}$-alkylaminocarbonylamino, di-($C_{1-3}$-alkyl)-aminocarbonylamino, a 4- to 7-membered cycloalkyleneiminocarbonylamino, benzyloxycarbonylamino, phenylcarbonylamino, heteroaryl or guanidino group, a group of general formula

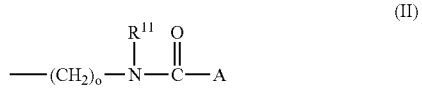
(II)

wherein:
  o denotes one of the numbers 2, 3, 4 or 5,
  $R^{11}$ denotes a hydrogen atom or a $C_{1-3}$-alkyl group and
  A denotes a heteroaryl group or a $C_{5-7}$-cycloalkyl group wherein:
    the methyne group may be replaced in the 1 position by a nitrogen atom and/or
    a methylene group may be replaced by an oxygen or sulfur atom, an —NH—, —N(OH)—, —N($C_{1-3}$-alkyl)-, —N($C_{1-3}$-alkylcarbonyl)-, or —N(heteroaryl)-group and/or
    a methylene group adjacent to an —NH—, —N(OH)—, —N($C_{1-3}$-alkyl)-, —N($C_{1-3}$-alkylcarbonyl)-, or —N(heteroaryl)-group may additionally be replaced by a carbonyl, sulfinyl or sulfonyl group, a 4- to 7-membered cycloalkyleneiminocarbonyl-$C_{1-3}$-alkyl group, where
  a methylene group of the cycloalkyleneimino moiety may be substituted by a $C_{1-3}$-alkyl group optionally substituted by a hydroxy, amino, $C_{1-3}$-alkylamino, di-($C_{1-3}$-alkyl)-amino, a 4- to 7-membered cycloalkyleneimino or $C_{1-5}$-alkyloxycarbonylamino group, an aminocarbonyl, $C_{1-3}$-alkylaminocarbonyl or di-($C_{1-3}$-alkyl)-aminocarbonyl group and a methylene group of the cycloalkyleneimino moiety not adjacent to the imino group may be substituted by a hydroxy, amino, $C_{1-3}$-alkylamino or di-($C_{1-3}$-alkyl)-amino-group and/or
  a methylene group in the 4 position of a 6- or 7-membered cycloalkyleneimino group may be replaced by an oxygen or sulfur atom, by a carbonyl, sulfinyl, sulfonyl or by an —NH— group optionally substituted by a $C_{1-3}$-alkyl group and additionally a methylene group adjacent to an abovementioned —NH— or —N($C_{1-3}$-alkyl)-group may be replaced by a carbonyl group, or
  a methylene group in the 2 position of a 5-membered cycloalkyleneimino group may be replaced by a carbonyl, sulfinyl or sulfonyl group, a $C_{1-3}$-alkyl group which is terminally substituted by a group of formula

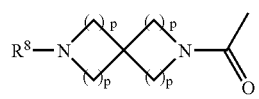
(III)

wherein:
  p in each case denotes one of the numbers 1 or 2 and
  $R^8$ denotes a hydrogen atom, a $C_{1-3}$-alkyl or $C_{1-3}$-alkylcarbonyl group, a phenyl or heteroaryl, phenylcarbonyl-$C_{1-3}$-alkyl, phenyl-$C_{1-3}$-alkyl or heteroaryl-$C_{1-3}$-alkyl group which is optionally mono- or polysubstituted by fluorine, chlorine or bromine atoms, $C_{1-3}$-alkyl, amino, $C_{1-3}$-alkylamino, di-($C_{1-3}$-alkyl)-amino, hydroxy, $C_{1-4}$-alkyloxy, mono-, di- or trifluoromethoxy, benzyloxy, carboxy-$C_{1-3}$-alkyloxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, a 4- to 7-membered cycloalkyleneiminocarbonyl-$C_{1-3}$-alkoxy, carboxy or $C_{1-3}$-alkyloxycarbonyl group, a $C_{3-6}$-cycloalkyl or a 4- to 7-membered cycloalkyleneimino group optionally substituted by a $C_{1-3}$-alkylcarbonyl or $C_{1-4}$-alkyloxycarbonyl group which is bound via a carbon atom, or a 3- to 7-membered cycloalkyl-$C_{1-3}$-alkyl or cycloalkyleneimino-$C_{1-3}$-alkyl group wherein in the cyclic moiety a methylene group may be replaced by an —NH— group optionally substituted by a $C_{1-3}$-alkyl or $C_{1-3}$-alkylcarbonyl group and wherein additionally a methylene group adjacent to an —NH—, —N($C_{1-3}$-alkylcarbonyl)- or —N($C_{1-3}$-alkyl)-group may be replaced in each case by a carbonyl or sulfonyl group, with the proviso that a cycloalkyleneimino group as hereinbefore defined wherein two nitrogen atoms are separated from one another by precisely one —CH$_2$— group is excluded, $R^5$ denotes a hydrogen atom or a $C_{1-3}$-alkyl group or $R^4$ and $R^5$ together with the carbon atom to which they are bound denote a $C_{3-7}$-cycloalkyl group, while
  one of the methylene groups of the $C_{3-7}$-cycloalkyl group may be replaced by an imino, $C_{1-3}$-alkylimino, acylimino or sulfonylimino group, A denotes a carbonylamino or aminocarbonyl group, while the hydrogen atom of the amino function may optionally be substituted by a $C_{1-3}$-alkyl group, and B denotes a group of formula

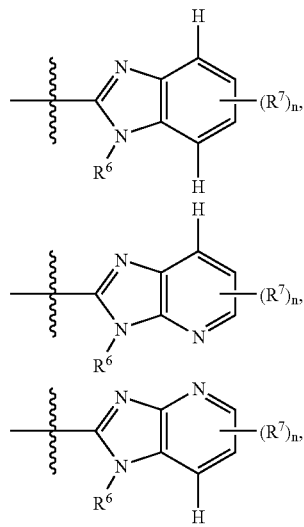

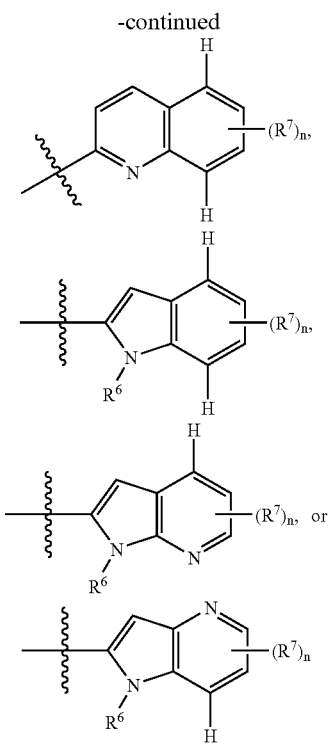

wherein:
n denotes the number 1 or 2,
R⁶ denotes a hydrogen atom or a $C_{1-3}$-alkyl, hydroxy, $C_{1-5}$-alkyloxycarbonyl, carboxy-$C_{1-3}$-alkyl, $C_{1-3}$-alkyloxycarbonyl-$C_{1-3}$-alkyl, amino or $C_{1-3}$-alkylamino group and
R⁷ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy, amino, nitro or cyano group, while, unless otherwise stated, by the phrase "heteroaryl group" is meant a monocyclic 5- or 6-membered heteroaryl group optionally substituted in the carbon skeleton by a fluorine, chlorine, bromine or iodine atom, a $C_{1-3}$-alkyl, amino, $C_{1-3}$-alkylamino, di-($C_{1-3}$-alkyl)-amino, $C_{1-3}$-alkyloxy, carboxy, $C_{1-3}$-alkoxy-carbonyl or $C_{1-3}$-alkoxycarbonylamino group, while
the 6-membered heteroaryl group contains one, two or three nitrogen atoms and
the 5-membered heteroaryl group contains an imino group optionally substituted by a $C_{1-3}$-alkyl or phenyl-$C_{1-3}$-alkyl group, or an oxygen or sulfur atom or
an imino group optionally substituted by a $C_{1-3}$-alkyl, amino-$C_{2-3}$-alkyl, $C_{1-3}$-alkylamino-$C_{2-3}$-alkyl, di-($C_{1-3}$alkyl)-amino-$C_{2-3}$-alkyl, a 4- to 7-membered cycloalkyleneimino-$C_{1-3}$-alkyl or phenyl-$C_{1-3}$-alkyl group, or an oxygen or sulfur atom and additionally a nitrogen atom or
an imino group optionally substituted by a $C_{1-3}$-alkyl or phenyl-$C_{1-3}$-alkyl group and two or three nitrogen atoms,
and also a phenyl ring optionally substituted by a fluorine, chlorine or bromine atom, a $C_{1-3}$-alkyl, hydroxy or $C_{1-3}$-alkyloxy group may be fused to the above-mentioned monocyclic heteroaryl groups via two adjacent carbon atoms
and the bond is effected via a nitrogen atom or via a carbon atom of the heterocyclic moiety or a fused-on phenyl ring, while unless otherwise stated the alkyl and alkoxy groups contained in the above definitions which have more than two carbon atoms may be straight-chain or branched and the alkyl groups in the abovementioned dialkylated groups, for example, the dialkylamino groups, may be identical or different, and the hydrogen atoms of the methyl or ethyl groups contained in the above-mentioned definitions may be wholly or partly replaced by fluorine atoms.

Examples of monocyclic heteroaryl groups are the pyridyl, N-oxypyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thiophenyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]isothiazolyl, benzo[d]isothiazolyl, benzoxazolyl, benzo[c]isoxazolyl, benzo[d]isoxazolyl, benzo[1,2,5]oxadiazolyl, benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxyquinolinyl, isoquinolinyl, quinazolinyl, N-oxyquinazolinyl, quinoxalinyl, phthalazinyl, indolyl, isoindolyl or 1-oxa-2,3-diazaindenyl group.

Examples of the $C_{1-8}$-alkyl groups mentioned in the preceding definitions are the methyl, ethyl, 1-propyl, 2-propyl, n-butyl, sec-butyl, tert-butyl, 1-pentyl, 2-pentyl, 3-pentyl, 1-hexyl, 2-hexyl, 3-hexyl, 1-heptyl, 2-heptyl, 3-heptyl, 4-heptyl, 1-octyl, 2-octyl, 3-octyl or 4-octyl group.

Examples of the $C_{1-8}$-alkyloxy groups mentioned in the preceding definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy, 1-hexyloxy, 2-hexyloxy, 3-hexyloxy, 1-heptyloxy, 2-heptyloxy, 3-heptyloxy, 4-heptyloxy, 1-octyloxy, 2-octyloxy, 3-octyloxy or 4-octyloxy group.

By a group which may be converted in vivo into a carboxy group is meant, for example, a carboxy group esterified with an alcohol wherein the alcohol moiety is preferably a $C_{1-6}$-alkanol, a phenyl-$C_{1-3}$-alkanol, a $C_{3-9}$-cycloalkanol, a $C_{5-7}$-cycloalkenol, a $C_{3-5}$-alkenol, a phenyl-$C_{3-5}$-alkenol, a $C_{3-5}$-alkynol or phenyl-$C_{3-5}$-alkynol, with the proviso that no bond to the oxygen atom starts from a carbon atom which carries a double or triple bond, a $C_{3-8}$-cycloalkyl-$C_{1-3}$-alkanol or an alcohol of formula

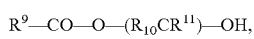

wherein:
R⁹ denotes a $C_{1-8}$-alkyl, $C_{5-7}$-cycloalkyl, phenyl or phenyl-$C_{1-3}$-alkyl group,
R¹⁰ denotes a hydrogen atom, a $C_{1-3}$-alkyl, $C_{5-7}$-cycloalkyl or phenyl group and
R¹¹ denotes a hydrogen atom or a $C_{1-3}$-alkyl group.

Preferred groups which may be cleaved from a carboxy group in vivo include a $C_{1-6}$-alkoxy group such as the methoxy, ethoxy, n-propyloxy, isopropyloxy, n-butyloxy, n-pentyloxy, n-hexyloxy or cyclohexyloxy group or a phenyl-$C_{1-3}$-alkoxy group such as the benzyloxy group.

Those compounds of general formula I wherein $R^1$ contains a group which may be converted in vivo into a carboxy group are prodrugs for those compounds of general formula I wherein $R^1$ contains a carboxy group.

A 2nd embodiment of the present invention comprises those compounds of general formula I wherein:

$R^1$, $R^2$, $R^4$, $R^5$, A and B are defined as described in the 1st embodiment and $R^3$ denotes the hydrogen atom, the tautomers, the diastereomers, the enantiomers, the mixtures thereof and the salts thereof.

A 3rd embodiment of the present invention comprises the compounds of general formula

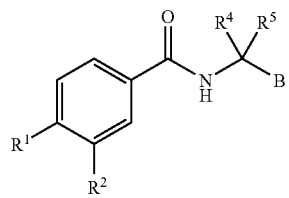

(Ia)

wherein:

$R^1$, $R^2$, $R^4$, $R^5$ and B are defined as described in the 1st embodiment, while $R^4$ does not denote the hydrogen atom, and $R^6$ denotes the hydrogen atom, the tautomers, the diastereomers, the enantiomers, the mixtures thereof and the salts thereof.

A 4th embodiment of the present invention comprises the compounds of general formula I, wherein:

$R^1$ to $R^5$ and A are defined as described in the 1st embodiment, while $R^2$ does not denote the hydrogen atom, and B denotes a group of formula

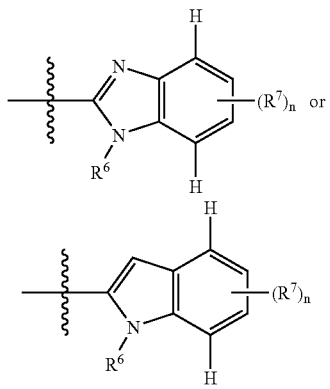

while n, $R^6$ and $R^7$ are defined as described in the 1st embodiment, the tautomers, the enantiomers, the diastereomers, the mixtures thereof and the salts thereof.

A 5th embodiment comprises those compounds of general formula I, wherein:

$R^1$, $R^2$, $R^4$, $R^5$, A and B are defined as described in the 4th embodiment and $R^3$ denotes the hydrogen atom, the tautomers, the diastereomers, the enantiomers, the mixtures thereof and the salts thereof.

A 6th embodiment of the present invention comprises the compounds of general formula

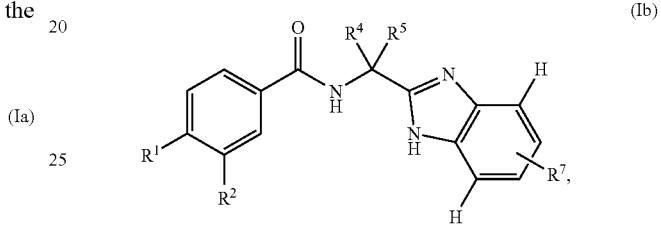

(Ib)

wherein:

$R^1$, $R^2$, $R^4$ and $R^5$ are defined as in the 4th embodiment, while $R^4$ does not denote the hydrogen atom, and $R^7$ denotes a fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a $C_{1-3}$-alkyloxy, trifluoromethoxy or cyano group, the tautomers, the diastereomers, the enantiomers, the mixtures thereof and the salts thereof.

A 7th embodiment of the present invention comprises the compounds of general formula I, wherein:

$R^1$ denotes an amino, $C_{1-5}$-alkylamino, $C_{3-7}$-cycloalkylamino or (phenyl-$C_{1-3}$-alkyl)-amino group which may additionally be substituted in each case at the amino nitrogen atom by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or a 4- to 7-membered cycloalkyleneimino group, while in the above-mentioned substituted $C_{1-5}$-alkyl group two heteroatoms are separated from one another by at least two carbon atoms, a 4- to 7-membered cycloalkyleneiminocarbonyl or cycloalkyleneiminosulfonyl group, while the cycloalkyleneimino moiety in the carbon skeleton may be substituted by one or two $C_{1-3}$-alkyl, hydroxy-$C_{1-3}$-alkyl, $C_{1-3}$-alkyloxy-$C_{1-3}$-alkyl, phenyl-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, $C_{1-5}$-alkylamino-$C_{1-3}$-alkyl, di-($C_{1-5}$-alkyl)-amino-$C_{1-3}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$- alkyl, $C_{1-5}$-alkyloxycarbonylamino-$C_{1-3}$-alkyl, $C_{1-3}$-alkylcarbonylamino-$C_{1-3}$-alkyl, $C_{1-3}$-alkylsulfonylamino-$C_{1-3}$-alkyl, aminocarbonylamino-$C_{1-3}$-alkyl, $C_{1-3}$-alkylaminocarbonylamino-$C_{1-3}$-alkyl, di-($C_{1-3}$-alkyl)-aminocarbonylamino-$C_{1-3}$-alkyl, $C_{1-3}$-alkyloxycarbonyl, aminocarbonyl, $C_{1-3}$-alkylaminocarbonyl, di-($C_{1-3}$-alkyl)-aminocarbonyl, amino, $C_{1-3}$-alkylamino, di-($C_{1-3}$-alkyl)-amino, a phenyl or a 5- to 6-membered heteroaryl group, with the proviso that in the substitution of a methylene group adjacent to the imino group two heteroatoms are separated from one another by at least two carbon atoms, and/or a methylene group in the 3 position of a 5-membered cycloalkyleneimino group may be replaced by a sulfur atom, a sulfinyl or sulfonyl group or a methylene group in the 4 position of a 6- or 7-membered cycloalkyleneimino group may be replaced by an oxygen or sulfur atom, a carbonyl or by an —NH— group optionally substituted by a methyl or hydroxy group, while additionally a methylene group adjacent to the abovementioned —NH— group may be replaced by a carbonyl group, a 5- to 7-membered cycloalkenyleneiminocarbonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl or $C_{3-6}$-cycloalkylamino-$C_{1-3}$-alkyl groups, while the double bond is not bound to a nitrogen atom and may be fused to a 5- or 6-membered heteroaryl group, an aminocarbonyl group optionally substituted by one or two $C_{1-5}$-alkyl, allyl, propargyl, $C_{3-6}$-cycloalkyl or 5- to 7-membered cycloalkyleneimino groups, while the substituents may be identical or different and in each case one of the $C_{1-5}$-alkyl groups may be substituted by one or two hydroxy-$C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl or $C_{3-6}$-cycloalkylamino-$C_{1-3}$-alkyl group, a $C_{1-3}$-alkyl group optionally monosubstituted by a di-($C_{1-3}$-alkyl)-amino, heteroaryl or a 4- to 7-membered cycloalkyleneimino group, while a —CH$_2$—CH$_2$— group in a 5- to 7-membered cycloalkyleneimino group may be replaced by a —NH—CO—, —CO—NH—, —CO—N(CH$_3$)—, or a —N(CH$_3$)—CO— group or a methylene group, which is adjacent to the nitrogen atom, in a 5- to 7-membered cycloalkyleneimino group may be replaced by a carbonyl group, or a group of formula

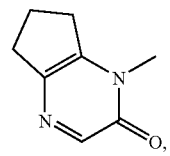

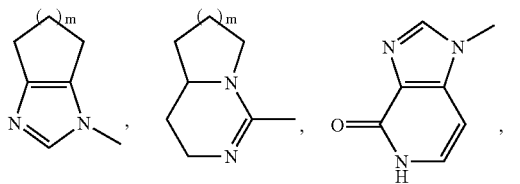

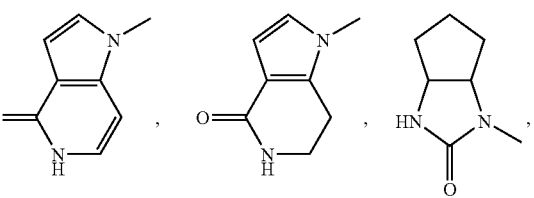

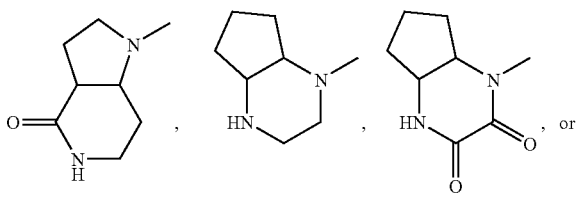

wherein in the heterocyclic moiety a hydrogen atom may be replaced in each case by a $C_{1-3}$-alkyloxycarbonyl, $C_{1-5}$-alkyloxycarbonylamino-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl or aminocarbonyl group and m denotes the number 1 or 2, $R^2$ denotes a fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl or $C_{1-3}$-alkyloxy group wherein the hydrogen atoms may be wholly or partly replaced by fluorine atoms, $R^3$ denotes a hydrogen atom, $R^4$ denotes a hydrogen atom, a $C_{2-3}$-alkenyl or $C_{2-3}$-alkynyl group or a straight-chain or branched $C_{1-5}$-alkyl group which is optionally substituted by a hydroxy, a $C_{1-3}$-alkyloxy group wherein the hydrogen atoms may be wholly or partly replaced by fluorine atoms, an allyloxy, propargyloxy, benzyloxy, carboxy-$C_{1-3}$-alkyloxy, $C_{1-5}$-alkyloxycarbonyl-$C_{1-3}$-alkyloxy, $C_{1-5}$-alkyloxycarbonylamino, chloro-$C_{1-3}$-alkylaminocarbonylamino, mercapto, $C_{1-3}$-alkylsulfanyl, $C_{1-3}$-alkylsulfinyl, $C_{1-3}$-alkylsulfonyl, carboxy, $C_{1-3}$-alkyloxycarbonyl, aminocarbonyl, $C_{1-3}$-alkylaminocarbonyl, di-($C_{1-3}$-alkyl)-aminocarbonyl, amino, $C_{1-3}$-alkylamino, di-($C_{1-3}$-alkyl)-amino, a 4- to 7-membered cycloalkyleneimino, $C_{1-5}$-alkylcarbonylamino, $C_{3-6}$-cycloalkylcarbonylamino, $C_{1-3}$-alkylsulfonylamino, benzyloxycarbonylamino or phenylcarbonylamino group, a 4- to 7-membered cycloalkyleneiminocarbonyl-$C_{1-3}$-alkyl group, while
- a methylene group of the cycloalkyleneimino moiety may be substituted by a $C_{1-3}$-alkyl group optionally substituted by a hydroxy, amino, $C_{1-3}$-alkylamino, di-($C_{1-3}$-alkyl)-amino, a 4- to 7-membered cycloalkyleneimino or $C_{1-5}$-alkyloxycarbonylamino group and a methylene group of the cycloalkyleneimino moiety not adjacent to the imino group may be substituted by a hydroxy, amino, $C_{1-3}$-alkylamino, di-($C_{1-3}$-alkyl)-amino, aminocarbonyl, $C_{1-3}$-alkylaminocarbonyl or di-($C_{1-3}$-alkyl)-aminocarbonyl group and/or
- a methylene group in the 4 position of a 6- or 7-membered cycloalkyleneimino group may be replaced by an oxygen or sulfur atom, by a carbonyl, sulfinyl, sulfonyl or by an —NH— group optionally substituted by a $C_{1-3}$-alkyl group and additionally a methylene group adjacent to an abovementioned —NH— or —N($C_{1-3}$-alkyl)-group may be replaced by a carbonyl group, a $C_{1-3}$-alkyl group which is terminally substituted by a group of formula

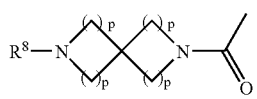

wherein:
p denotes one of the numbers 1 or 2 and
$R^8$ denotes a hydrogen atom, a $C_{1-3}$-alkyl or $C_{1-3}$-alkylcarbonyl group, a phenyl, thiophenyl or pyridinyl, phenyl-$C_{1-3}$-alkyl, tetrazolyl-$C_{1-3}$-alkyl, imidazolyl-$C_{1-3}$-alkyl, thiazolyl-$C_{1-3}$-alkyl or thiophenyl-$C_{1-3}$-alkyl group which is optionally substituted by a chlorine atom, a hydroxy, $C_{1-4}$-alkyloxy, trifluoromethoxy, carboxy or $C_{1-3}$-alkyloxycarbonyl group, $R^5$ denotes a hydrogen atom, A denotes a carbonylamino or aminocarbonyl group and B denotes a group of formula

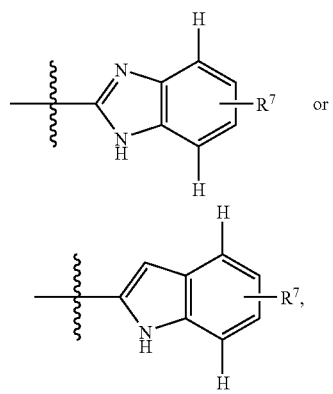

wherein:
$R^7$ denotes a fluorine, chlorine or bromine atom, while, unless otherwise stated, by the phrase "heteroaryl group" used in the above definitions is meant a monocyclic 5- or 6-membered heteroaryl group optionally substituted in the carbon skeleton by a $C_{1-3}$-alkyl, $C_{1-3}$-alkylamino, di-($C_{1-3}$-alkyl)-amino, carboxy, $C_{1-3}$-alkoxy-carbonyl or $C_{1-3}$-alkoxycarbonylamino group, while
- the 6-membered heteroaryl group contains one, two or three nitrogen atoms and
- the 5-membered heteroaryl group contains an imino group optionally substituted by a $C_{1-3}$-alkyl or phenyl-$C_{1-3}$-alkyl group, or an oxygen or sulfur atom or
- an imino group optionally substituted by a $C_{1-3}$-alkyl, amino-$C_{2-3}$-alkyl, $C_{1-3}$-alkylamino-$C_{2-3}$-alkyl, di-($C_{1-3}$-alkyl)-amino-$C_{2-3}$-alkyl, a 4- to 7-membered cycloalkyleneimino-$C_{1-3}$-alkyl or phenyl-$C_{1-3}$-alkyl group, or an oxygen or sulfur atom and additionally a nitrogen atom or
- an imino group optionally substituted by a $C_{1-3}$-alkyl or phenyl-$C_{1-3}$-alkyl group and two or three nitrogen atoms,
- and also a phenyl ring optionally substituted by a chlorine or bromine atom may be fused to the abovementioned monocyclic heteroaryl groups via two adjacent carbon atoms
- and the bond is effected via a nitrogen atom or via a carbon atom of the heterocyclic moiety or a fused-on phenyl ring, while unless otherwise stated the alkyl and alkoxy groups contained in the above definitions which have more than two carbon atoms may be straight-chain or branched and the alkyl groups in the abovementioned dialkylated groups, for example, the dialkylamino groups, may be identical or different, and the hydrogen atoms of the methyl or ethyl groups contained in the above-mentioned definitions may be wholly or partly replaced by fluorine atoms, the tautomers, the enantiomers, the diastereomers, the mixtures thereof and the salts thereof.

An 8th embodiment of the present invention comprises the compounds of general formula

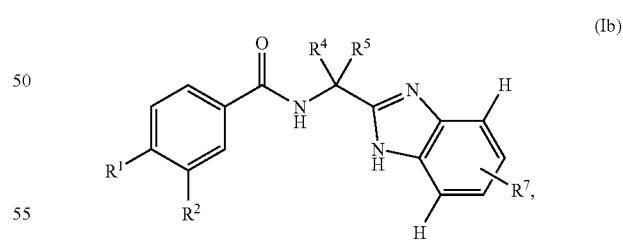

wherein:
$R^1$, $R^2$, $R^4$ and $R^5$ are defined as described in the 7th embodiment, while $R^4$ does not denote the hydrogen atom, and $R^7$ denotes a chlorine or bromine atom, the tautomers, the diastereomers, the enantiomers, the mixtures thereof and the salts thereof.

A 9th embodiment of the present invention comprises the compounds of general formula

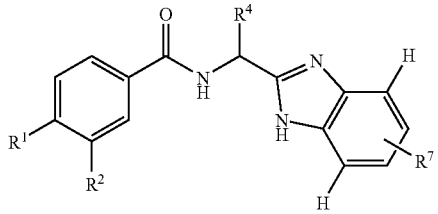

(Ic)

wherein:

$R^1$ denotes a group of formula

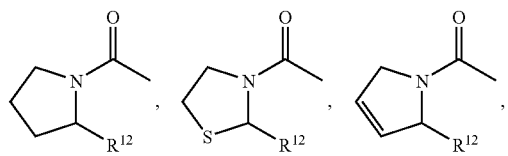

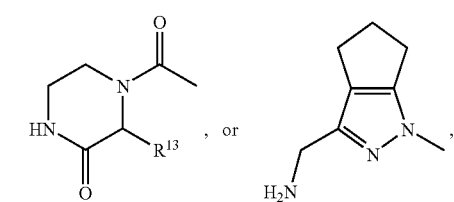

, or while $R^{12}$ denotes the hydrogen atom, a methyl, aminomethyl, $C_{1-3}$-alkylamino-$C_{1-2}$-alkyl, di-($C_{1-3}$-alkyl)-amino-$C_{1-2}$-alkyl, pyrrolidin-1-ylmethyl or 2-(pyrrolidin-1-yl) ethyl group and $R^{13}$ denotes a hydrogen atom, a methyl or aminomethyl group, $R^2$ denotes a fluorine, chlorine or bromine atom, a methyl, ethyl, trifluoromethyl or methoxy group, $R^4$ denotes a $C_{1-4}$-alkyl group which may be substituted by a fluorine atom, a hydroxy, $C_{1-3}$-alkyloxy, trifluoromethoxy, 2,2,2-trifluoroethyloxy, allyloxy, propargyloxy, mercapto, $C_{1-4}$-alkylsulfanyl, $C_{1-4}$-alkylsulfinyl, $C_{1-4}$-alkylsulfonyl, amino, $C_{1-3}$-alkylcarbonylamino, $C_{1-3}$-alkylsulfonylamino, carboxy, aminocarbonyl, $C_{1-3}$-alkylaminocarbonyl, di-($C_{1-3}$-alkyl)-aminocarbonyl or a 4- to 7-membered cycloalkyleneiminocarbonyl group, a phenyl, thiophenyl, phenyl-$C_{1-3}$-alkyl, tetrazolyl-$C_{1-3}$-alkyl, imidazolyl-$C_{1-3}$-alkyl, thiazolyl-$C_{1-3}$-alkyl or thiophenyl-$C_{1-3}$-alkyl group and $R^7$ denotes a chlorine or bromine atom, the tautomers, the enantiomers, the diastereomers, the mixtures thereof and the salts thereof.

A 10th embodiment of the present invention comprises the compounds of general formula

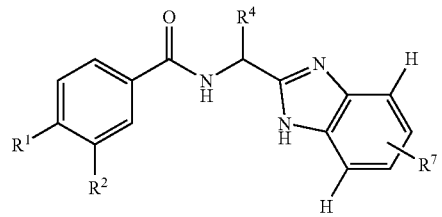

(Ic)

wherein:

$R^1$ denotes a group of formula

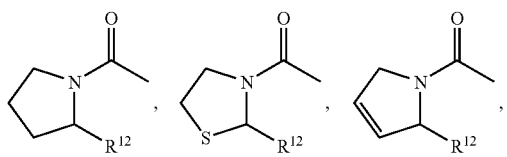

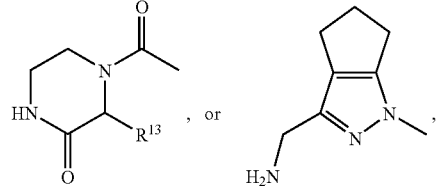

, or wherein:

$R^{12}$ denotes the hydrogen atom, a methyl, aminomethyl, $C_{1-3}$-alkylamino-$C_{1-2}$-alkyl, di-($C_{1-3}$-alkyl)-amino-$C_{1-2}$-alkyl, pyrrolidin-1-ylmethyl or 2-(pyrrolidin-1-yl) ethyl group and $R^{13}$ denotes a hydrogen atom, a methyl or aminomethyl group, $R^2$ denotes a fluorine, chlorine or bromine atom, a methyl, ethyl, trifluoromethyl or methoxy group, $R^4$ denotes a $C_{1-4}$-alkyl group which is substituted by a fluorine atom, a hydroxy, $C_{1-3}$-alkyloxy, trifluoromethoxy, 2,2,2-trifluoroethyloxy, allyloxy, propargyloxy, mercapto, $C_{1-4}$-alkyl-sulfanyl, $C_{1-4}$-alkylsulfinyl, $C_{1-4}$-alkylsulfonyl, amino, $C_{1-3}$-alkylcarbonylamino, $C_{1-3}$-alkylsulfonylamino, carboxy, aminocarbonyl, $C_{1-3}$-alkylaminocarbonyl, di-($C_{1-3}$-alkyl)-aminocarbonyl or a 4- to 7-membered cycloalkyleneiminocarbonyl group, a phenyl, thiophenyl, phenyl-$C_{1-3}$-alkyl, tetrazolyl-$C_{1-3}$-alkyl, imidazolyl-$C_{1-3}$-alkyl, thiazolyl-$C_{1-3}$-alkyl or thiophenyl-$C_{1-3}$-alkyl group and $R^7$ denotes a chlorine or bromine atom, the tautomers, the diastereomers, the enantiomers, the mixtures thereof and the salts thereof.

An 11th embodiment of the present invention comprises the compounds of the above general formula I, wherein:

$R^1$ denotes a 2,5-dihydro-1H-pyrrol-1-ylcarbonyl, pyrrolidin-1-ylcarbonyl, N-acetyl-N-cyclobutylamino, 2-(N-tert-butoxycarbonylaminomethyl)pyrrolidin-1-ylcarbonyl, 2-(aminomethyl)pyrrolidin-1-ylcarbonyl, 3-oxopiperazin-1-ylcarbonyl, 4-methyl-3-oxopiperazin-1-ylcarbonyl, 2,3-dihydroimidazo[2,1-b]thiazol-5-yl, thiazolidin-3-ylcarbonyl, 1,2,3,6-tetrahydropyridin-1-ylcarbonyl, 2-methylthiomorpholin-4-ylcarbonyl, thiomorpholin-4-ylcarbonyl, N-isopropyl-N-methylaminocarbonyl, 2-methoxymethylpyrrolidin-1-ylcarbonyl, 3-(pyrrolidin-1-ylmethyl)piperidin-1-ylcarbonyl, azetidin-1-ylcarbonyl, 2-methylpyrrolidin-1-ylcarbonyl, N-isobutyl-N-methylaminocarbonyl, [1,4]oxazepan-1-ylcarbonyl, 2,5-dimethylpyrrolidin-1-ylcarbonyl, piperidin-1-ylcarbonyl, 4-hydroxypiperidin-1-ylcarbonyl, 4-acetylpiperazin-1-ylcarbonyl, N,N-diethylaminocarbonyl, 3-methylpiperidin-1-ylcarbonyl, 4-methylpiperidin-1-ylcarbonyl, 2-aminomethylpiperidin-1-ylcarbonyl, 3-aminomethylpiperidin-1-ylcarbonyl, 3-(2-aminoethyl)piperidin-1-ylcarbonyl, 3-aminopiperidin-1-ylcarbonyl, N-(2-dimethylamino)ethyl-N-ethylaminocarbonyl, 2-(N-tert-butoxycarbonylamino-ethyl]pyrrolidin-1-ylcarbonyl, 2-(aminoethyl)pyrrolidin-1-ylcarbonyl, 2-(aminocarbonyl)pyrrolidin-1-ylcarbonyl, 1-oxothiazolidin-3-ylcarbonyl, 1,1-dioxothiazolidin-3-ylcarbonyl, 2-ethoxycarbonylmethyl-3-oxopiperazin-1-ylcarbonyl, 2-dimethylaminocarbonylmethyl-3-oxopiperazin-1-ylcarbonyl, 2-aminomethyl-3-oxopiperazin-1-ylcarbonyl, (2-acetylaminoethyl)pyrrolidin-1-ylcarbonyl, dimethylaminocarbonyl, 2-hydroxymethylpyrrolidin-1-ylcarbonyl, 2-(methylsulfonylaminomethyl)pyrrolidin-1-ylcarbonyl, 2-(acetylaminomethyl)pyrrolidin-1-ylcarbonyl, pyrrolidin-1-ylsulfonyl, 2-(2-ethoxycarbonylethyl)pyrrolidin-1-ylcarbonyl, 2-[(3-ethylureido)methyl]pyrrolidin-1-ylcarbonyl, 4,5,6,7-tetrahydrobenzimidazol-1-yl, 3-(ethoxycarbonyl)-5,6-dihydro-4H-cyclopentapyrazol-1-yl, 3-(tert-butoxycarbonylamino)methyl-5,6-dihydro-4H-cyclopentapyrazol-1-yl, 3-(aminocarbonyl)-5,6-dihydro-4H-cyclopentapyrazol-1-yl, 3-aminomethyl-5,6-dihydro-4H-cyclopentapyrazol-1-yl, 4-formylpiperazin-1-ylcarbonyl, N-ethyl-N-(piperidin-4-yl)aminocarbonyl, 2-(2-dimethylaminoethyl)piperidin-1-ylcarbonyl, 2-(piperidin-1-ylmethyl)piperidin-1-ylcarbonyl, 2-(3-diethylaminopropyl)piperidin-1-ylcarbonyl, 2-(N-butyl-N-ethylaminomethyl)piperidin-1-ylcarbonyl, 2-(N-cyclohexyl-N-methylaminomethyl)piperidin-1-ylcarbonyl, 1,4,6,7-tetrahydroimidazo[4,5-c]pyridin-5-ylcarbonyl, 6,7-dihydro-4H-thieno[3,2-c]pyridin-5-ylcarbonyl, 2-(pyrrolidin-1-ylmethyl)pyrrolidin-1-ylcarbonyl, 2-(ethoxycarbonyl)pyrrolidin-1-ylcarbonyl, 4-hydroxypiperazin-1-ylcarbonyl, 2-(methyloxycarbonyl)pyrrolidin-1-ylcarbonyl, 2-(benzyloxycarbonyl)pyrrolidin-1-ylcarbonyl, 3,4,5,6-tetrahydro-2H-[2,3]-bipyridinyl-1-ylcarbonyl, N-(2-aminoethyl)-N-ethylaminocarbonyl, N-(3-aminopropyl)-N-ethylaminocarbonyl, N-cyclopropyl-N-methylaminocarbonyl, 1,4,6,7-tetrahydropyrazol-[4,3-c]pyridin-5-ylcarbonyl, 2-(pyridin-2-yl)pyrrolidin-1-ylcarbonyl, 2-(pyridin-4-yl)pyrrolidin-1-ylcarbonyl, 2,5-dimethyl-2,5-dihydropyrrol-1-ylcarbonyl, 2,5-dimethyl-2,5-dihydropyrrol-1-ylcarbonyl, 2-phenylaminomethylpyrrolidin-1-ylcarbonyl, 2-benzylpyrrolidin-1-ylcarbonyl, 2-phenethylpyrrolidin-1-ylcarbonyl, 2-isopropylpyrrolidin-1-ylcarbonyl, 2-methylpiperidin-1-ylcarbonyl, 4-oxopiperidin-1-ylcarbonyl, [1,4]-diazepan-1-ylcarbonyl, 2-(dimethylaminocarbonyl)pyrrolidin-1-ylcarbonyl, 2-(methylaminocarbonyl)pyrrolidin-1-ylcarbonyl, 2-(aminocarbonylmethylaminocarbonyl)pyrrolidin-1-ylcarbonyl, 2-benzhydrylpyrrolidin-1-ylcarbonyl, 3-(2,2,2-trifluoroacetylamino)pyrrolidin-1-ylcarbonyl, 3-dimethylaminopyrrolidin-1-ylcarbonyl, imidazol-1-ylmethyl, 2-oxopyrrolidin-1-ylmethyl, 3-oxopiperazin-1-ylmethyl, 2-(ethoxycarbonylmethyl)pyrrolidin-1-ylcarbonyl, 2-dimethylaminomethylpyrrolidin-1-ylcarbonyl, 2-(carboxymethyl)pyrrolidin-1-ylcarbonyl, 2-(carboxyethyl)pyrrolidin-1-ylcarbonyl, pyrrol-1-ylcarbonyl, 2-methylpyrrolidin-1-ylcarbonyl, 2-(tert-butoxycarbonylaminomethyl)thiazolidin-3-ylcarbonyl, 2-aminomethylthiazolidin-3-ylcarbonyl, N-ethyl-N-(6-methoxyhexanoyl)amino, 3-fluoropyrrolidin-1-ylcarbonyl, 2-methylaminocarbonylethylpyrrolidin-1-yl, N-acetyl-N-cyclopentylamino, 2-methyl-aminocarbonylmethylpyrrolidin-1-yl, 2-(imidazol-1-ylmethyl)pyrrolidin-1-ylcarbonyl, 2-[(N-acetyl-N-methylamino)methyl]pyrrolidin-1-ylcarbonyl, benzoyl, 3-methyl-5,6-dihydro-4H-cyclopentapyrazol-1-yl, 4-oxo-4,5,6,7-tetrahydroindol-1-yl, 4,5,6,7-tetrahydroindol-1-yl, 4,5,6,7-tetrahydroindazol-1-yl, 4-oxo-2-propyl-4,5-dihydroimidazo[4,5-c]pyridin-1-yl, 2-methyl-5,6-dihydro-4H-cyclopentaimidazol-1-yl, 2-methyl-4,5,6,7-tetrahydrobenzimidazol-1-yl, 2-hydroxycarbonylmethyl-3-oxopiperazin-1-ylcarbonyl, 4-methoxyimidazo[4,5-c]pyridin-1-yl, 2-carboxypyrrolidin-1-ylcarbonyl, 2-dimethylaminomethylbenzimidazol-1-yl, 4-oxo-4,5-dihydroimidazo[4,5-c]pyridin-1-yl, 2-dimethylaminomethylindol-1-yl, 4-oxo-4,5-dihydropyrrol-[3,2-c]pyridin-1-yl, 3-oxo-[1,4]diazepan-1-ylcarbonyl, 2-(pyrrolidin-1-yl)methyl-5,6-dihydro-4H-cyclopentaimidazol-1-yl, 2-(2-(pyrrolidin-1-yl)ethyl)-5,6-dihydro-4H-cyclopentaimidazol-1-yl, 2-(pyrrolidin-1-yl)methyl-4,5,6,7-tetrahydrobenzimidazol-1-yl, 2-(2-pyrrolidin-1-ylethyl)-4,5,6,7-tetrahydrobenzimidazol-1-yl, 2-(morpholin-4-yl)methyl-5,6-dihydro-4H-cyclopentaimidazol-1-yl, 2-(2-(morpholin-4-yl)ethyl)-5,6-dihydro-4H-cyclopentaimidazol-1-yl, 2-(morpholin-4-yl)methyl-4,5,6,7-tetrahydrobenzimidazol-1-yl, 2-(2-(morpholin-4-yl)ethyl)-4,5,6,7-tetrahydrobenzimidazol-1-yl, 2-oxohexahydrocyclopentaimidazol-1-yl, 4-oxo-4,5,6,7-tetrahydropyrrol[3,2-c]pyridin-1-yl, 4-oxooctahydropyrrol[3,2-c]pyridin-1-yl, octahydrocyclopentapyrazin-1-yl, 2,3-dioxooctahydrocyclopentapyrazin-1-yl, 2-oxo-2,5,6,7-tetrahydrocyclopentapyrazin-1-yl, 5,6,7,7a-tetrahydro-1H-pyrrol-[1,2-c]-imidazol-3-yl or 3,4,4a,5,6,7-hexahydropyrrol-[1,2-c]pyrimidin-1-yl group, $R^2$ denotes a fluorine, chlorine or bromine atom, a $C_{1-3}$-alkyl group wherein the hydrogen atoms may be wholly or partly replaced by fluorine atoms, a $C_{1-3}$-alkyloxy or a $C_{2-3}$-alkynyl group, $R^3$ denotes a hydrogen atom, $R^4$ denotes a hydrogen atom or a methyl, ethyl, propyl, isopropyl, isobutyl, tert-butyl, hydroxymethyl, 1-hydroxyethyl, methoxymethyl, 2-methoxyethyl, phenyl, 2-chlorophenyl, 3-chlorophenyl, 4-chlorophenyl, benzyl, 4-hydroxybenzyl, 4-methoxy-carbonylmethoxyphenylmethyl, pyridin-4-ylmethyl, pyridin-2-ylmethyl, piperidin-1-ylmethyl, piperidin-3-ylmethyl, 1H-imidazol-4-ylmethyl, aminocarbonylmethyl, 4-benzyloxycarbonylaminobutyl, 2-methylsulfanylethyl, 2-methylsulfinylethyl, 2-methylsulfonylethyl, ethylsulfanylmethyl, ethylsulfinylmethyl, ethylsulfonylmethyl, aminomethyl, 2-aminoethyl, 3-aminopropyl, 4-aminobutyl, 2-phenylethyl, acetylaminomethyl, methylsulfonylaminomethyl, phenylcarbonylaminomethyl, 3-acetylaminopropyl, 4-acetylaminobutyl, 2,2,2-trifluoroethyl, hydroxymethyl, tert-butoxycarbonylaminomethyl, 3-(tert-butoxycarbonylamino)propyl, 4-hydroxybenzyl, 2-carboxyethyl, 2-(benzyloxycarbonyl)ethyl, 2-(ethylaminocarbonyl)ethyl, 2-(pyrrolidin-1-ylcarbonyl)ethyl, 2-(diethylaminocarbonyl)ethyl, tetrazol-2-ylmethyl, carboxymethyloxymethyl, tert-butoxycarbonylmethyloxymethyl, 2-(benzyloxycarbonylamino)ethyl, 2-(aminosulfonyl)ethyl, 2-(2-oxoimidazolidin-1-yl)ethyl, 2-(2-chloroethyl)ureido]ethyl, 1-methoxy-1-methylethyl, 1-(3-tert-butoxycarbonyl)piperidin-3-yl, 1-acetylpiperidin-3-yl, 2-(pyridin-4-yl)ethyl, 2-[3-(dimethylamino)pyrrolidin-1-yl-carbonyl]ethyl, 2-(3-hydroxypyrrolidin-1-yl)carbonylethyl, 2-[2-(hydroxymethyl)pyrrolidin-1-ylcarbonyl]ethyl, 2-(2-methyl-2,6-diazaspiro[3.4]oct-6-ylcarbonyl)ethyl, 2-[2-(aminocarbonyl)pyrrolidin-1-ylcarbonyl]ethyl, 2-[2-(tert-butoxycarbonylaminomethyl)pyrrolidin-1-ylcarbonyl]ethyl, 2-[3-(hydroxymethylpyrrolidin-1-yl)carbonyl]ethyl, 2-(1,1-dioxo-1-thiomorpholin-4-ylcarbonyl)ethyl, 2-(4-methyl-3-oxopiperazin-1-ylcarbonyl)ethyl, 2-(2-aminomethylpyrrolidin-1-ylcarbonyl)ethyl, isopropoxycarbonyloxymethyl, 2-(2-isopropylaminothiazol-4-yl)ethyl, 2-(5-chloro-1H-benzimidazol-2-yl)ethyl, 5-chloro-1H-benzimidazol-2-yl, thiophen-3-yl, 2-methylsulfonylaminoethyl, benzyloxymethyl, methylsulfanylmethyl, 2-(1,1-dioxoisothiazolidin-2-yl)ethyl, ethoxymethyl, 1-methoxyethyl, allyloxymethyl, 1-tert-butyloxyethyl, 1-hydroxyethyl, prop-2-ynyloxymethyl, 2-(1H-tetrazol-5-yl)ethyl, 1-prop-2-ynyl, 4-[(5-oxopyrrolidin-3-yl)carbonylamino]butyl, 4-[(pyridin-3-yl-)carbonylamino]butyl, 4-[(5-oxopyrrolidin-2-yl)carbonylamino]butyl, 4-[(pyridin-4-yl)carbonylamino]butyl, 4-(1-methylpyrrolidin-2-ylcarbonylamino)butyl, prop-2-enyl, acetylaminomethylsulfanylmethyl, 2-aminocarbonylethyl, 1H-indol-3-yl)methyl, 4-hydroxy-3,5-dimethylphenylmethyl, methoxycarbonylmethyl, 4-hydroxy-2,6-dimethylphenylmethyl, 4-difluoromethoxyphenylmethyl, 3-bromophenylmethyl, 4-trifluoromethylphenylmethyl, 4-ureidobutyl, 3-ureidopropyl, 4-amino-3,5-dibromophenylcarbonylmethyl, allyloxycarbonylmethyl, 3,4-dimethoxyphenylmethyl, thiazol-4-ylmethyl, 3,5-difluorophenylmethyl, 4-fluorophenylmethyl, mercaptomethyl, 1-methyl-1H-imidazol-5-ylmethyl, 1H-benzimidazol-5-ylmethyl, cyclopropylmethyl, 2,2,2-trifluoroethyloxymethyl, trifluoromethoxymethyl, difluoromethoxymethyl or monofluoromethoxymethyl group, $R^5$ denotes a hydrogen atom, A denotes an aminocarbonyl or carbonylamino group and B denotes a group of formula

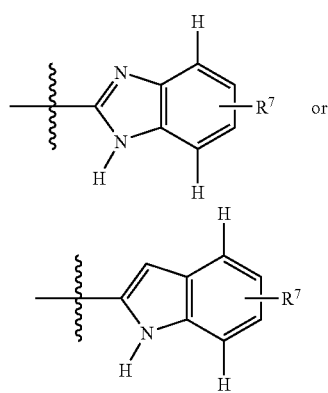

wherein:
$R^7$ denotes a fluorine, chlorine or bromine atom or a methyl group, the tautomers, the enantiomers, the diastereomers, the mixtures thereof and the salts thereof.

For example, the following preferred compounds of general formula I may be mentioned:
(1) N-[1-(5-chloro-1H-benzimidazol-2-yl)ethyl]-3-methyl-4-(2,5-dihydropyrrol-1-ylcarbonyl)benzamide,
(2) N-[1-(5-chloro-1H-benzimidazol-2-yl)ethyl]-3-methyl-4-(pyrrolidin-1-ylcarbonyl)benzamide,
(3) N-(5-chloro-1H-benzimidazol-2-yl)methyl-3-methyl-4-(pyrrolidin-1-ylcarbonyl)benzamide,
(4) N-[1-(5-chloro-1H-benzimidazol-2-yl)-2-phenylethyl]-3-methyl-4-(pyrrolidin-1-ylcarbonyl)benzamide,
(5) N-[1-(5-chloro-1H-benzimidazol-2-yl)-2-phenylethyl]-3-methyl-4-(2,5-dihydropyrrol-1-ylcarbonyl)benzamide,
(6) N-[1-(5-chloro-1H-benzimidazol-2-yl)ethyl]-3-ethynyl-4-(pyrrolidin-1-ylcarbonyl)benzamide,
(7) N-[1-(5-chloro-1H-benzimidazol-2-yl)ethyl]-3-ethyl-4-(pyrrolidin-1-ylcarbonyl)benzamide,
(8) N-[1-(5-chloro-1H-benzimidazol-2-yl)ethyl]-3-methyl-4-(N-cyclobutyl-N-acetylamino)benzamide,
(9) N-[1-(5-chloro-1H-benzimidazol-2-yl)ethyl]-3-chloro-4-[2-(N-tert-butoxycarbonylaminomethyl)pyrrolidin-1-ylcarbonyl]benzamide,
(10) (S)—N-[1-(5-chloro-1H-benzimidazol-2-yl)-2-(pyridin-4-yl)ethyl]-3-methyl-4-(pyrrolidin-1-ylcarbonyl)benzamide,
(11) (S)—N-[1-(5-chloro-1H-benzimidazol-2-yl)-2-(pyridin-2-yl)ethyl]-3-methyl-4-(pyrrolidin-1-ylcarbonyl)benzamide,
(12) N-[1-(5-fluoro-1H-benzimidazol-2-yl)ethyl]-3-methyl-4-(pyrrolidin-1-ylcarbonyl)benzamide,
(13) N-[1-(5-cyano-1H-benzimidazol-2-yl)ethyl]-3-methyl-4-(pyrrolidin-1-ylcarbonyl)benzamide,
(14) N-[1-(5-methoxy-1H-benzimidazol-2-yl)ethyl]-3-methyl-4-(pyrrolidin-1ylcarbonyl)benzamide,
(15) (S)—N-[1-(5-chloro-1H-benzimidazol-2-yl)-2-(1H-imidazol-4-yl)ethyl]-3-methyl-4-(pyrrolidin-1-ylcarbonyl)benzamide,
(16) (R)- and (S)-4-(2-aminomethylpyrrolidin-1-ylcarbonyl)-3-chloro-N-[(1S)-1-(5-chloro-1H-benzimidazol-2-yl)-2-(pyridin-4-yl)ethyl]benzamide,
(17) N-[1-(5-chloro-1H-benzimidazol-2-yl)ethyl]-3-chloro-4-(2-aminomethylpyrrolidin-1-ylcarbonyl)benzamide,
(18) 1-[N-(5-methyl-1H-benzimidazol-2-yl)]ethyl-3-methyl-4-(pyrrolidin-1-ylcarbonyl)benzamide,
(19) 3-chloro-N-(5-chloro-1H-benzimidazol-2-ylmethyl)-4-(3-oxopiperazin-1-ylcarbonyl)benzamide,
(20) 3-chloro-N-(5-chloro-1H-benzimidazol-2-ylmethyl)-4-(4-methyl-3-oxopiperazin-1-ylcarbonyl)benzamide,
(21) 3-chloro-N-(5-chloro-1H-benzimidazol-2-ylmethyl)-4-(2-aminomethylpyrrolidin-1-ylcarbonyl)benzamide,
(22) N-(5-chloro-1H-benzimidazol-2-ylmethyl)-4-(2,3-dihydroimidazo[2,1-b]thiazol-5-yl)benzamide,
(23) 2-(5-chloro-1H-benzimidazol-2-yl)-N-[3-methyl-4-(pyrrolidin-1-ylcarbonyl)phenyl]acetamide,
(24) 3-methyl-4-(pyrrolidine-1-carbonyl)-N-[1-(5-trifluoromethyl-1H-benzimidazol-2-yl)ethyl]benzamide,
(25) (S)—N-[2-aminocarbonyl-1-(5-chloro-1H-benzimidazol-2-yl)ethyl]-3-methyl-4-(pyrrolidin-1-ylcarbonyl)benzamide,
(26) 3-chloro-N-(5-chloro-1H-benzimidazol-2-ylmethyl)-4-(2,5-dihydropyrrol-1-ylcarbonyl)benzamide,
(27) 3-chloro-N-(5-chloro-1H-benzimidazol-2-ylmethyl)-4-(thiazolidin-3-ylcarbonyl)benzamide
(28) 3-chloro-N-(5-chloro-1H-benzimidazol-2-ylmethyl)-4-(1,2,3,6-tetrahydropyridin-1-ylcarbonyl)benzamide,
(29) 3-chloro-N-(5-chloro-1H-benzimidazol-2-ylmethyl)-4-(2-methylthiomorpholin-4-ylcarbonyl)benzamide,
(30) 3-chloro-N-(5-chloro-1H-benzimidazol-2-ylmethyl)-4-(thiomorpholin-4-ylcarbonyl)benzamide,
(31) 3-chloro-N-(5-chloro-1H-benzimidazol-2-ylmethyl)-4-(N-isopropyl-N-methylaminocarbonyl)benzamide,

(32) (R)-3-chloro-N-(5-chloro-1H-benzimidazol-2-ylmethyl)-4-(2-methoxymethylpyrrolidin-1-ylcarbonyl)benzamide,
(33) 3-chloro-N-(5-chloro-1H-benzimidazol-2-ylmethyl)-4-[3-(pyrrolidin-1-ylmethyl)piperidin-1-ylcarbonyl]benzamide,
(34) (S)-3-chloro-N-(5-chloro-1H-benzimidazol-2-ylmethyl)-4-(2-methoxymethylpyrrolidin-1-ylcarbonyl)benzamide,
(35) 3-chloro-N-(5-chloro-1H-benzimidazol-2-ylmethyl)-4-(azetidin-1-ylcarbonyl)benzamide,
(36) 3-chloro-N-(5-chloro-1H-benzimidazol-2-ylmethyl)-4-(2-methylpyrrolidin-1-ylcarbonyl)benzamide,
(37) 3-chloro-N-(5-chloro-1H-benzimidazol-2-ylmethyl)-4-(N-isobutyl-N-methylaminocarbonyl)benzamide,
(38) 3-chloro-N-(5-chloro-1H-benzimidazol-2-ylmethyl)-4-([1,4]oxazepan-1-ylcarbonyl)benzamide,
(39) 3-chloro-N-(5-chloro-1H-benzimidazol-2-ylmethyl)-4-(2,5-dimethylpyrrolidin-1-ylcarbonyl)benzamide,
(40) 3-chloro-N-(5-chloro-1H-benzimidazol-2-ylmethyl)-4-(piperidin-1-ylcarbonyl)benzamide,
(41) 3-chloro-N-(5-chloro-1H-benzimidazol-2-ylmethyl)-4-(4-hydroxypiperidin-1-ylcarbonyl)benzamide,
(42) 4-(4-acetylpiperazin-1-ylcarbonyl)-3-chloro-N-(5-chloro-1H-benzimidazol-2-ylmethyl)benzamide,
(43) 3-chloro-N-(5-chloro-1H-benzimidazol-2-ylmethyl)-4-(pyrrolidin-1-ylcarbonyl)benzamide,
(44) 3-chloro-N-(5-chloro-1H-benzimidazol-2-ylmethyl)-4-(N,N-diethylaminocarbonyl)benzamide,
(45) 3-chloro-N-(5-chloro-1H-benzimidazol-2-ylmethyl)-4-(3-methylpiperidin-1-ylcarbonyl)benzamide,
(46) 3-chloro-N-(5-chloro-1H-benzimidazol-2-ylmethyl)-4-(4-methylpiperidin-1ylcarbonyl)benzamide,
(47) 4-(2-aminomethylpiperidin-1-ylcarbonyl)-3-chloro-N-(5-chloro-1H-benzimidazol-2-ylmethyl)benzamide,
(48) 4-(3-aminomethylpiperidin-1-ylcarbonyl)-3-chloro-N-(5-chloro-1H-benzimidazol-2-ylmethyl)benzamide,
(49) 4-[3-(2-aminoethyl)piperidin-1-ylcarbonyl]-3-chloro-N-(5-chloro-1H-benzimidazol-2-ylmethyl)benzamide,
(50) 4-(2-aminomethylpyrrolidin-1-ylcarbonyl)-3-chloro-N-(5-chloro-1H-benzimidazol-2-ylmethyl)benzamide,
(51) 4-(3-aminopiperidin-1-ylcarbonyl)-3-chloro-N-(5-chloro-1H-benzimidazol-2-ylmethyl)benzamide,
(52) N-(6-chloroquinolin-2-ylmethyl)-3-methyl-4-(pyrrolidin-1-ylcarbonyl)benzamide,
(53) N-[1-(5-chloro-1H-benzimidazol-2-yl)ethyl]-N-ethyl-3-methyl-4-(pyrrolidin-1-ylcarbonyl)benzamide,
(54) N-(6-bromo-3H-imidazo[4,5-b]pyridin-2-yl)methyl-3-methyl-4-(pyrrolidin-1-ylcarbonyl)benzamide,
(55) N-(6-bromo-3H-imidazo[4,5-b]pyridin-2-yl)methyl-3-methyl-4-(2,5-dihydropyrrol-1-ylcarbonyl)benzamide,
(56) N-[1-(5-bromo-1H-benzimidazol-2-yl)ethyl]-3-methyl-4-(pyrrolidin-1-ylcarbonyl)benzamide,
(57) N-[(5-chloro-1H-benzimidazol-2-yl)phenylmethyl]-3-methyl-4-(pyrrolidin-1ylcarbonyl)benzamide,
(58) N-[1-(1H-benzimidazol-2-yl)ethyl]-3-methyl-4-(pyrrolidin-1-ylcarbonylbenzamide,
(59) N-[1-(5-chloro-1H-benzimidazol-2-yl)-5-benzyloxycarbonylaminopentyl]-3-methyl-4-(pyrrolidin-1-ylcarbonyl)benzamide,
(60) N-[1-(5-chloro-1H-benzimidazol-2-yl)ethyl]-3-chloro-4-(3-oxopiperazin-1-ylcarbonyl)benzamide,
(61) N-[1-(5-chloro-1H-benzimidazol-2-yl)-3-methylbutyl]-3-methyl-4-(pyrrolidin-1-ylcarbonyl)benzamide,
(62) N-[1-(5-chloro-1H-benzimidazol-2-yl)]ethyl-4-(pyrrolidin-1-ylcarbonyl)benzamide,
(63) (S)—N-[1-(5-chloro-1H-benzimidazol-2-yl)]ethyl-3-methyl-4-(pyrrolidin-1-ylcarbonyl)benzamide,
(64) N-[1-(5-chloro-1H-benzimidazol-2-yl)]ethyl-3-chloro-4-[N-(2-dimethylamino)ethyl-N-ethylaminocarbonyl]benzamide,
(65) N-[1-(5-chloro-1H-benzimidazol-2-yl)]ethyl-3-bromo-4-(pyrrolidin-1-ylcarbonyl)benzamide,
(66) N-[1-(5-chloro-1H-benzimidazol-2-yl)]ethyl-3-trifluoromethyl-4-(pyrrolidin-1-ylcarbonyl)benzamide,
(67) 4-(2-aminomethylpyrrolidin-1-ylcarbonyl)-N-[2-aminocarbonyl-1-(5-chloro-1H-benzimidazol-2-yl)ethyl]-3-chlorobenzamide,
(68) 4-(2-aminomethylpyrrolidin-1-ylcarbonyl)-3-chloro-N-[1-(5-chloro-1H-benzimidazol-2-yl)-2-(1H-imidazol-4-yl)ethyl]benzamide,
(69) 4-(2-aminomethylpyrrolidin-1-ylcarbonyl)-3-chloro-N-[1-(5-chloro-1H-benzimidazol-2-yl)-2-(pyridin-2-yl)ethyl]benzamide,
(70) N-[(1S)-1-(5-chloro-1H-benzimidazol-2-yl)ethyl]-3-methyl-4-[(2R/S)-2-(N-tert-butoxycarbonylaminomethyl)pyrrolidin-1-ylcarbonyl]benzamide,
(71) N-[(1S)-1-(5-chloro-1H-benzimidazol-2-yl)ethyl]-3-methyl-4-[(2R/S)-2-aminomethylpyrrolidin-1-ylcarbonyl]benzamide,
(72) N-[(1S)-1-(5-chloro-1H-benzimidazol-2-yl)ethyl]-3-chloro-4-[(2R/S)-2-(N-tert-butoxycarbonylaminomethyl)pyrrolidin-1-ylcarbonyl]benzamide,
(73) N-[(1S)-1-(5-chloro-1H-benzimidazol-2-yl)ethyl]-3-chloro-4-[(2R/S)-2-aminomethylpyrrolidin-1-ylcarbonyl)benzamide,
(74) N-[(1S)-1-(5-chloro-1H-benzimidazol-2-yl)ethyl]-3-chloro-4-[(2S)-2-(N-tert-butoxycarbonylaminomethyl)pyrrolidin-1-ylcarbonyl]benzamide,
(75) N-[(1S)-1-(5-chloro-1H-benzimidazol-2-yl)ethyl]-3-chloro-4-[(2R)-2-(N-tert-butoxycarbonylaminomethyl)pyrrolidin-1-ylcarbonyl]benzamide,
(76) N-[(1S)-1-(5-chloro-1H-benzimidazol-2-yl)ethyl]-3-chloro-4-{(2S)-2-[2-(N-tert-butoxycarbonylamino)ethyl]pyrrolidin-1-ylcarbonyl}benzamide,
(77) N-[(1S)-1-(5-chloro-1H-benzimidazol-2-yl)ethyl]-3-chloro-4-[(2S)-2-aminomethylpyrrolidin-1-ylcarbonyl]benzamide,
(78) N-[(1S)-1-(5-chloro-1H-benzimidazol-2-yl)ethyl]-3-chloro-4-[(2R)-2-aminomethylpyrrolidin-1-ylcarbonyl]benzamide,
(79) N-[(1S)-1-(5-chloro-1H-benzimidazol-2-yl)ethyl]-3-chloro-4-[(2S)-2-(2aminoethyl)pyrrolidin-1-ylcarbonyl]benzamide,
(80) N-[(1R/S)-1-(5-chloro-1H-benzimidazol-2-yl)ethyl]-3-chloro-4-[(2S)-2-aminocarbonylpyrrolidin-1-ylcarbonyl]benzamide,
(81) N-[(1R/S)-1-(5-chloro-1H-benzimidazol-2-yl)ethyl]-3-chloro-4-[(2R)-2-aminocarbonylpyrrolidin-1-ylcarbonyl]benzamide,
(82) N-[(1S)-1-(5-chloro-1H-benzimidazol-2-yl)butyl]-3-chloro-4-[(2S)-2-(N-tert-butoxycarbonylaminomethyl)pyrrolidin-1-ylcarbonyl]benzamide,
(83) N-[(1S)-1-(5-chloro-1H-benzimidazol-2-yl)-3-methylsulfanylpropyl]-3-chloro-4-[(2S)-2-(N-tert-butoxycarbonylaminomethyl)pyrrolidin-1-ylcarbonyl]benzamide,
(84) N-[(1S)-1-(5-chloro-1H-benzimidazol-2-yl)butyl]-3-chloro-4-[(2S)-2-aminomethylpyrrolidin-1-ylcarbonyl]benzamide,
(85) N-[(1S)-1-(5-chloro-1H-benzimidazol-2-yl)-3-methylsulfinylpropyl]-3-chloro-4-[(2S)-2-(N-tert-butoxycarbonylaminomethyl)pyrrolidin-1-ylcarbonyl]benzamide,

(86) N-[(1S)-1-(5-chloro-1H-benzimidazol-2-yl)-3-methylsulfonylpropyl]-3-chloro-4-[(2S)-2-(N-tert-butoxycarbonylaminomethyl)pyrrolidin-1-ylcarbonyl]benzamide,

(87) N-[(1S)-1-(5-chloro-1H-benzimidazol-2-yl)-3-methylsulfanylpropyl]-3-chloro-4-[(2S)-2-aminomethylpyrrolidin-1-ylcarbonyl]benzamide,

(88) N-[(1S)-1-(5-chloro-1H-benzimidazol-2-yl)-3-methylsulfinylpropyl]-3-chloro-4-[(2S)-2-aminomethylpyrrolidin-1-ylcarbonyl]benzamide,

(89) N-[(1S)-1-(5-chloro-1H-benzimidazol-2-yl)-3-methylsulfonylpropyl]-3-chloro-4-[(2S)-2-aminomethylpyrrolidin-1-ylcarbonyl]benzamide,

(90) rac.-3-chloro-N-[1-(5-chloro-1H-benzimidazol-2-yl)ethyl]-4-(thiazolidin-3-ylcarbonyl)benzamide,

(91) rac.-3-chloro-N-[1-(5-chloro-1H-benzimidazol-2-yl)ethyl]4-(1-oxothiazolidin-3-ylcarbonyl)benzamide,

(92) rac.-3-chloro-N-[1-(5-chloro-1H-benzimidazol-2-yl)ethyl]4-(1,1-dioxothiazolidin-3-ylcarbonyl)benzamide,

(93) N-[(1S)-5-(benzyloxycarbonylamino)-1-(5-chloro-1H-benzimidazol-2-yl)pentyl]-3-methyl-4-(pyrrolidin-1-ylcarbonyl)benzamide,

(94) N-[(1S)-5-amino-1-(5-chloro-1H-benzimidazol-2-yl)pentyl]-3-methyl-4-(pyrrolidin-1-ylcarbonyl)benzamide,

(95) N-[(1S)-1-(5-chloro-1H-benzimidazol-2-yl)-3-phenylpropyl]-3-methyl-4-(pyrrolidin-1-ylcarbonyl)benzaminde,

(96) N-[(1S)-5-acetylamino-1-(5-chloro-1H-benzimidazol-2-yl)pentyl]-3-methyl-4-(pyrrolidin-1-ylcarbonyl)benzamide,

(97) N-[(1S)-1-(5-chloro-1H-benzimidazol-2-yl)-3-methylsulfanylpropyl]-3-methyl-4-(pyrrolidin-1-ylcarbonyl)benzamide,

(98) rac.-N-[1-(5-chloro-1H-benzimidazol-2-yl)ethyl]-3-chloro-4-(pyrrolidin-1-ylcarbonyl)benzamide,

(99) rac.-N-[1-(5-chloro-1H-benzimidazol-2-yl)-3,3,3-trifluoropropyl]-3-methyl-4-(pyrrolidin-1-ylcarbonyl)benzamide, (100) rac.-N-[1-(5-chloro-1H-benzimidazol-2-yl)-2-hydroxyethyl]-3-methyl-4-(pyrrolidin-1-ylcarbonyl)benzamide, (101) rac.-N-[2-tert-butoxycarbonylamino-1-(5-chloro-1H-benzimidazol-2-yl)ethyl]-3-methyl-4-(pyrrolidin-1-ylcarbonyl)benzamide, (102) rac.-N-[2-amino-1-(5-chloro-1H-benzimidazol-2-yl)ethyl]-3-methyl-4-(pyrrolidin-1-ylcarbonyl)benzamide, (103) rac.-N-[1-(5-chloro-1H-benzimidazol-2-yl)-2-(4-hydroxyphenyl)ethyl]-3-methyl-4-(pyrrolidin-1-ylcarbonyl)benzamide, (104) rac.-N-[2-acetylamino-1-(5-chloro-1H-benzimidazol-2-yl)ethyl]-3-methyl-4-(pyrrolidin-1-ylcarbonyl)benzamide, (105) rac.-N-[2-benzoylamino-1-(5-chloro-1H-benzimidazol-2-yl)ethyl]-3-methyl-4-(pyrrolidin-1-ylcarbonyl)benzamide, (106) N-[1-(5-chloro-1H-benzimidazol-2-yl)-1-methylethyl]-3-methyl-4-(pyrrolidin-1-ylcarbonyl)benzamide, (107) N-[1-(5-chloro-1H-benzimidazol-2-yl)cyclopropyl]-3-methyl-4-(pyrrolidin-1-ylcarbonyl)benzamide, (108) N-[1-(5-chloro-1H-benzimidazol-2-yl)cyclohexyl]-3-methyl-4-(pyrrolidin-1-ylcarbonyl)benzamide, (109) rac.-N-[1-(5-chloro-1H-benzimidazol-2-yl)-3-hydroxycarbonylpropyl]-3-methyl-4-(pyrrolidin-1-ylcarbonyl)benzamide, (110) N-[(1S)-1-(5-chloro-1H-benzimidazol-2-yl)-3-hydroxycarbonylpropyl]-3-methyl-4-(pyrrolidin-1-ylcarbonyl)benzamide, (111) rac.-N-[3-benzyloxycarbonyl-1-(5-chloro-1H-benzimidazol-2-yl)propyl]-3-methyl-4(pyrrolidin-1-ylcarbonyl)benzamide, (112) N-[(1S)-3-benzyloxycarbonyl-1-(5-chloro-1H-benzimidazol-2-yl)propyl]-3-methyl-4-(pyrrolidin-1-ylcarbonyl)benzamide, (113) rac.-N-[1-(5-chloro-1H-benzimidazol-2-yl)-3-ethylaminocarbonylpropyl]-3-methyl-4-(pyrrolidin-1-ylcarbonyl)benzamide, (114) rac.-N-[1-(5-chloro-1H-benzimidazol-2-yl)-3-(pyrrolidin-1-ylcarbonyl)propyl]-3-methyl-4-(pyrrolidin-1-ylcarbonyl)benzamide, (115) N-[(1S)-1-(5-chloro-1H-benzimidazol-2-yl)-3-(pyrrolidin-1-ylcarbonyl)propyl]-3-methyl-4-(pyrrolidin-1-ylcarbonyl)benzamide, (116) rac.-N-[1-(5-chloro-1H-benzimidazol-2-yl)-3-diethylaminocarbonylpropyl]-3-methyl-4-(pyrrolidin-1-ylcarbonyl)benzamide, (117) N-[(1S)-1-(5-chloro-1H-benzimidazol-2-yl)-2-tetrazol-2-ylethyl]-3-methyl-4-(pyrrolidin-1-ylcarbonyl)benzamide, (118) N-[(1R)-1-(5-chloro-1H-benzimidazol-2-yl)-2-hydroxyethyl]-3-methyl-4-(pyrrolidin-1-ylcarbonyl)benzamide, (119) N-[(1S)-4-(tert-butoxycarbonylamino)-1-(5-chloro-1H-benzimidazol-2-yl)butyl]-3-methyl-4-(pyrrolidine-1-carbonyl)benzamide, (120) rac.-N-[1-(5-chloro-1H-benzimidazol-2-yl)-2-(piperdin-1-yl)ethyl]-3-methyl-4-(pyrrolidin-1-ylcarbonyl)benzamide, (121) N-[(1R,2R)-1-(5-chloro-1H-benzimidazol-2-yl)-2-hydroxypropyl]-3-methyl-4-(pyrrolidin-1-ylcarbonyl)benzamide, (122) N-[(5-chloro-1H-benzimidazol-2-yl)cyclobutyl]-3-methyl-4-(pyrrolidin-1-ylcarbonyl)benzamide, (123) N-[(1S)-4-amino-1-(5-chloro-1H-benzimidazol-2-yl)butyl]-3-methyl-4-(pyrrolidin-1-ylcarbonyl)benzamide, (124) N-[(1S)-2-acetylamino-1-(5-chloro-1H-benzimidazol-2-yl)ethyl]-3-methyl-4-(pyrrolidin-1-ylcarbonyl)benzamide, (125) N-[(1S)-1-(5-chloro-1H-benzimidazol-2-yl)-2-methylsulfonylaminoethyl]-3-methyl-4-(pyrrolidin-1-ylcarbonyl)benzamide, (126) rac.-N-[1-(5-chloro-1H-benzimidazol-2-yl)-2-methoxyethyl]-3-methyl-4-(pyrrolidin-1-ylcarbonyl)benzamide, (127) 3-bromo-N-[(1S)-1-(5-chloro-1H-benzimidazol-2-yl)-2-ethyl]4-(2,5-dihydropyrrol-1-ylcarbonyl)benzamide, (128) N-[(1S)-1-(5-chloro-1H-benzimidazol-2-yl)-3-methoxypropyl]-3-methyl-4-(pyrrolidin-1-ylcarbonyl)benzamide, (129) N-[(1S)-4-acetylamino-1-(5-chloro-1H-benzimidazol-2-yl)butyl]-3-methyl-4-(pyrrolidin-1-ylcarbonyl)benzamide, (130) rac.-N-[(5-chloro-1H-benzimidazol-2-yl)-(3-chlorophenyl)methyl]-3-methyl-4-(pyrrolidin-1-ylcarbonyl)benzamide, (131) N-[(1R)-2-(C-tert-butoxycarbonylmethyloxy)-1-(5-chloro-1H-benzimidazol-2-yl)ethyl]-3-methyl-4-(pyrrolidin-1-ylcarbonyl)benzamide, (132) N-[(1R)-2-(hydroxycarbonylmethyloxy)-1-(5-chloro-1H-benzimidazol-2-yl)ethyl]-3-methyl-4-(pyrrolidin-1-ylcarbonyl)benzamide, (133) 3-chloro-N-(5-chloro-1H-benzimidazol-2-ylmethyl)-4-(3-oxopiperazin-1-ylcarbonyl)benzamide, (134) rac.-4-(2-aminomethylpyrrolidin-1-ylcarbonyl)-3-chloro-N-(5-chloro-1H-benzimidazol-2-ylmethyl)benzamide,
(135) 3-chloro-N-(5-chloro-1H-benzimidazol-2-ylmethyl)-4-(4-methyl-3-oxopiperazin-1-ylcarbonyl)benzamide,
(136) 3-chloro-N-[1-(5-chloro-1H-benzimidazol-2-yl)ethyl]4-(2-ethoxycarbonylmethyl-3-oxopiperazin-1-ylcarbonyl)benzamide,
(137) 3-chloro-N-[1-(5-chloro-1H-benzimidazol-2-yl)ethyl]4-(2-dimethylaminocarbonylmethyl-3-oxopiperazin-1-ylcarbonyl)benzamide,
(138) 4-(2-aminomethyl-3-oxopiperazin-1-ylcarbonyl)-3-chloro-N-[1-(5-chloro-1H-benzimidazol-2-yl)ethyl]benzamide,
(139) 3-chloro-N-[(1S)-1-(5-chloro-1H-benzimidazol-2-yl)ethyl]-4-(3-oxopiperazin-1-ylcarbonyl)benzamide,
(140) N-[(1S)-1-(5-chloro-1H-benzimidazol-2-yl)-3-methylsulfinylpropyl]-3-methyl-4-(pyrrolidin-1-ylcarbonyl)benzamide,
(141) N-[(1S)-1-(5-chloro-1H-benzimidazol-2-yl)-3-methylsulfonylpropyl]-3-methyl-4-(pyrrolidin-1-ylcarbonyl)benzamide,
(142) rac.-N-[(5-chloro-1H-benzimidazol-2-yl)phenylmethyl]-3-methyl-4-(pyrrolidin-1-ylcarbonyl)benzamide,
(143) rac.-N-[1-(5-chloro-1H-benzimidazol-2-yl)phenylmethyl]-4-(2,5-dihydropyrrol-1ylcarbonyl)-3-methylbenzamide,
(144) N-[(1S)-1-(5-chloro-1H-benzimidazol-2-yl)propyl]-3-methyl-4-(pyrrolidin-1-ylcarbonyl)benzamide,
(145) N-[(1S)-1-(5-chloro-1H-benzimidazol-2-yl)-2-methylpropyl]4-(2,5-dihydropyrrol-1-ylcarbonyl)-3-methylbenzamide,
(146) N-[(1S)-1-(5-chloro-1H-benzimidazol-2-yl)-2-methylpropyl]-3-methyl-4-(pyrrolidin-1-ylcarbonyl)benzamide,
(147) 4-[(2S)-2-(2-acetylaminoethyl)pyrrolidin-1-ylcarbonyl]-3-chloro-N-[(1S)-1-(5-chloro-1H-benzimidazol-2-yl)ethyl]benzamide,
(148) N-[(1S)-3-(benzyloxycarbonylamino)-1-(5-chloro-1H-benzimidazol-2-yl)propyl]-3-methyl-4-(pyrrolidin-1-ylcarbonyl)benzamide,
(149) N-[(1S)-1-(5-chloro-1H-benzimidazol-2-yl)-2,2-dimethylpropyl]-3-methyl-4-(pyrrolidin-1-ylcarbonyl)benzamide,
(150) 3-chloro-N-[(1S)-1-(5-chloro-1H-benzimidazol-2-yl)ethyl]4-(dimethylaminocarbonyl)benzamide,
(151) N-[(1S)-3-amino-1-(5-chloro-1H-benzimidazol-2-yl)propyl]-3-methyl-4-(pyrrolidin-1-ylcarbonyl)benzamide,
(152) N-[(1S)-1-(5-chloro-1H-benzimidazol-2-yl)ethyl]-3-fluoro-4-(pyrrolidin-1-ylcarbonyl)benzamide,
(153) N-[(1S)-1-(5-chloro-1H-benzimidazol-2-yl)-3-methylsulfonylaminopropyl]-3-methyl-4-(pyrrolidin-1-ylcarbonyl)benzamide,
(154) N-[(1S)-1-(5-chloro-1H-benzimidazol-2-yl)-3-(2-oxoimidazolidin-1-yl)propyl]-3-methyl-4-(pyrrolidin-1-ylcarbonyl)benzamide,
(155) N-{(1S)-1-(5-chloro-1H-benzimidazol-2-yl)-3-[3-(2-chloroethyl)ureido]propyl}-3-methyl-4-(pyrrolidin-1-ylcarbonyl)benzamide,
(156) rac.-N-[1-(5-chloro-1H-benzimidazol-2-yl)-2-methoxy-2-methylpropyl]-3-methyl-4-(pyrrolidin-1-ylcarbonyl)benzamide,
(157) 3-chloro-N-[(1R)-1-(5-chloro-1H-benzimidazol-2-yl)-2-ethylsulfanylethyl]4-(pyrrolidin-1-ylcarbonyl)benzamide,
(158) N-[(1S)-1-(5-chloro-1H-benzimidazol-2-yl)butyl]-3-methyl-4-(pyrrolidin-1-ylcarbonyl)benzamide,
(159) N-[(1S)-1-(5-chloro-1H-benzimidazol-2-yl)ethyl]-3-methoxy-4-(pyrrolidin-1-ylcarbonyl)benzamide,
(160) N-[(1S)-1-(5-chloro-1H-benzimidazol-2-yl)-3-hydroxypropyl]-3-methyl-4-(pyrrolidin-1-ylcarbonyl)benzamide,
(161) 3-bromo-N-[(1S)-1-(5-chloro-1H-benzimidazol-2-yl)-3-methylsulfanylpropyl]-4-(pyrrolidin-1-ylcarbonyl)benzamide,
(162) 3-chloro-N-[(1R)-1-(5-chloro-1H-benzimidazol-2-yl)-2-(ethylsulfinyl)ethyl]-4-(pyrrolidin-1-ylcarbonyl)benzamide,
(163) 3-chloro-N-[(1S)-1-(5-chloro-1H-benzimidazol-2-yl)-3-(methylsulfanyl)propyl]-4-(pyrrolidin-1-ylcarbonyl)benzamide,
(164) 3-chloro-N-[(1R)-1-(5-chloro-1H-benzimidazol-2-yl)-2-(ethylsulfonyl)ethyl]-4-(pyrrolidin-1-ylcarbonyl)benzamide,
(165) 3-bromo-N-[(1S)-1-(5-chloro-1H-benzimidazol-2-yl)-3-(methylsulfonyl)propyl]-4-(pyrrolidin-1-ylcarbonyl)benzamide,
(166) 3-chloro-N-[(1S)-1-(5-chloro-1H-benzimidazol-2-yl)ethyl]-4-[(2R)-2-hydroxymethylpyrrolidin-1-ylcarbonyl]benzamide,
(167) 3-chloro-N-[(1S)-1-(5-chloro-1H-benzimidazol-2-yl)ethyl]-4-[(2S)-2-hydroxymethylpyrrolidin-1-ylcarbonyl]benzamide,
(168) N-{(1H-benzimidazol-2-yl)-[1-(3-tert-butoxycarbonyl)piperidin-3-yl]methyl}-3-methyl-4-(pyrrolidin-1-ylcarbonyl)benzamide,
(169) N-{[1-(3-tert-butoxycarbonyl)piperidin-3-yl]-(5-chloro-1H-benzimidazol-2-yl)methyl}-3-methyl-4-(pyrrolidin-1-ylcarbonyl)benzamide,
(170) 3-bromo-N-[(1S)-1-(5-chloro-1H-benzimidazol-2-yl)-3-methylsulfinylpropyl]-4-(pyrrolidin-1-ylcarbonyl)benzamide,
(171) N-[(5-chloro-1H-benzimidazol-2-yl)-(piperidin-3-yl)methyl]-3-methyl-4-(pyrrolidin-1-ylcarbonyl)benzamide,
(172) 3-chloro-N-[(1S)-1-(5-chloro-1H-benzimidazol-2-yl)ethyl]4-[(2R,S)-(2-methylpyrrolidin-1-ylcarbonyl)]benzamide,
(173) 3-chloro-N-[(1S)-1-(5-chloro-1H-benzimidazol-2-yl)ethyl]4-[(2R)-2-(methylsulfonylaminomethyl)pyrrolidin-1-ylcarbonyl]benzamide,
(174) 4-[(2R)-2-(acetylaminomethyl)pyrrolidin-1-ylcarbonyl]-3-chloro-N-[(1S)-1-(5-chloro-1H-benzimidazol-2-yl)ethyl]benzamide,
(175) N-[(1R)-1-(5-chloro-1H-benzimidazol-2-yl)ethyl]-3-methyl-4-(pyrrolidin-1ylcarbonyl)benzamide,
(176) (1R)-3-bromo-N-[1-(5-chloro-1H-benzimidazol-2-yl)-2-hydroxyethyl]4-(2,5-dihydropyrrol-1-ylcarbonyl)benzamide,
(177) (1R)-3-methyl-N-[1-(5-chloro-1H-benzimidazol-2-yl)-2-methoxyethyl]4-(2,5-dihydropyrrol-1-ylcarbonyl)benzamide,
(178) (1R)-3-chloro-N-[1-(5-chloro-1H-benzimidazol-2-yl)-2-hydroxyethyl]4-(2,5-dihydropyrrol-1-ylcarbonyl)benzamide,
(179) rac.-N-[1-(5-chloro-1H-imidazo[4,5-b]pyridin-2-yl)ethyl]-3-methyl-4-(pyrrolidin-1-ylcarbonyl)benzamide,
(180) rac.-N-[1-(5-chloro-1-methyl-1H-benzimidazol-2-yl)ethyl]-3-methyl-4-(pyrrolidin-1-ylcarbonyl)benzamide,
(181) rac.-N-[1-(6-chloro-1-methyl-1H-benzimidazol-2-yl)ethyl]-3-methyl-4-(pyrrolidin-1-ylcarbonyl)benzamide,
(182) rac.-N-{1-[6-chloro-1-(methoxycarbonylmethyl)-1H-benzimidazol-2-yl]-2-(4-hydroxyphenyl)ethyl}-3-methyl-4-(pyrrolidin-1-ylcarbonyl)benzamide, (183) rac.-N-{1-[6-chloro-1-(methoxycarbonylmethyl)-1H-benzimidazol-2-yl]-2-(4-methoxycarbonylmethoxyphenyl)ethyl}-3-methyl-4-(pyrrolidin-1-ylcarbonyl)benzamide,
(184) rac.-N-{1-[6-chloro-1-(hydroxycarbonylmethyl)-1H-benzimidazol-2-yl]-2-(4-hydroxyphenyl)ethyl}-3-methyl-4-(pyrrolidin-1-ylcarbonyl)benzamide,
(185) N-[(1S)-1-(7-amino-5-chloro-1H-benzimidazol-2-yl)ethyl]-3-methyl-4-(pyrrolidin-1-ylcarbonyl)benzamide,
(186) 3-methyl-N-[(1S)-1-(5-nitro-1H-benzimidazol-2-yl)ethyl]-4-(pyrrolidin 1-ylcarbonyl)benzamide,
(187) 3-methyl-N-[(1S)-1-(5-amino-1H-benzimidazol-2-yl)ethyl]4-(pyrrolidin-1-ylcarbonyl)benzamide,
(188) 3-chloro-N-[(1S)-1-(6-chloro-1H-benzimidazol-2-yl)ethyl]4-(pyrrolidin 1-ylsulfonyl)benzamide,
(189) N-[(1-acetylpiperidin-3-yl)-(5-chloro-1H-benzimidazol-2-yl)methyl]-3-methyl-4-(pyrrolidin-1-ylcarbonyl)benzamide,
(190) N-[(1-acetylpiperidin-3-yl)-(5-chloro-1H-benzimidazol-2-yl)methyl]-3-methyl-4-(pyrrolidin-1-ylcarbonyl)benzamide,
(191) N-[(1S)-1-(5-chloro-1H-benzimidazol-2-yl)-3-(pyridin-4-yl)propyl]-3-methyl-4-(pyrrolidin-1-ylcarbonyl)benzamide,
(192) N-[(1S)-3-(benzyloxycarbonylamino)-1-(5-chloro-1H-benzimidazol-2-yl)propyl]-3-methyl-4-(2,5-dihydropyrrol-1-ylcarbonyl)benzamide,
(193) N-{(1S)-1-(5-chloro-1H-benzimidazol-2-yl)-3-[(3R,S)-3-dimethylaminopyrrolidin-1-yl]carbonylpropyl}-3-methyl-4-(pyrrolidin-1-ylcarbonyl)benzamide,
(194) N-{(1S)-1-(5-chloro-1H-benzimidazol-2-yl)-3-[(3R)-3-hydroxypyrrolidin-1-yl]carbonylpropyl}-3-methyl-4-(pyrrolidin-1-ylcarbonyl)benzamide,
(195) N-{(1S)-1-(5-chloro-1H-benzimidazol-2-yl)-3-[(3S)-3-hydroxypyrrolidin-1-ylcarbonyl]propyl}-3-methyl-4-(pyrrolidin-1-ylcarbonyl)benzamide,
(196) N-{(1S)-1-(5-chloro-1H-benzimidazol-2-yl)-3-[(2R)-2-hydroxymethylpyrrolidin-1ylcarbonyl]propyl}-3-methyl-4-(pyrrolidin-1-ylcarbonyl)benzamide,
(197) N-{(1S)-1-(5-chloro-1H-benzimidazol-2-yl)-3-[(2S)-2-hydroxymethylpyrrolidin-1-ylcarbonyl]propyl}-3-methyl-4-(pyrrolidin-1-ylcarbonyl)benzamide,
(198) N-[(1S)-1-(5-chloro-1H-benzimidazol-2-yl)-3-(2-methyl-2,6-diazaspiro[3.4]oct-6-ylcarbonyl)propyl]-3-methyl-4-(pyrrolidin-1-ylcarbonyl)benzamide,
(199) N-{(1S)-3-[(1S)-2-(aminocarbonyl)pyrrolidin-1-ylcarbonyl]-1-(5-chloro-1H-benzimidazol-2-yl)propyl}-3-methyl-4-(pyrrolidin-1-ylcarbonyl)benzamide,
(200) N-{(1S)-3-[(1R)-2-(aminocarbonyl)pyrrolidin-1-ylcarbonyl]-1-(5-chloro-1H-benzimidazol-2-yl)propyl}-3-methyl-4-(pyrrolidin-1-ylcarbonyl)benzamide,
(201) N-{(1S)-1-(5-chloro-1H-benzimidazol-2-yl)-3-[(2S)-2-tert-butoxycarbonylaminomethylpyrrolidin-1-ylcarbonyl]propyl}-3-methyl-4-4-(pyrrolidin 1-ylcarbonyl)benzamide,
(202) N-{(1S)-1-(5-chloro-1H-benzimidazol-2-yl)-3-[(2R)-2-tert-butoxycarbonylaminomethylpyrrolidin-1-ylcarbonyl]propyl}-3-methyl-4-(pyrrolidin-1-ylcarbonyl)benzamide,
(203) N-{(1S)-1-(5-chloro-1H-benzimidazol-2-yl)-3-[(3R,S)-hydroxymethylpyrrolidin-1-yl)carbonyl]propyl}-3-methyl-4-(pyrrolidin-1-ylcarbonyl)benzamide,
(204) N-[(1S)-1-(5-chloro-1H-benzimidazol-2-yl)-3-(1,1-dioxo-1-thiomorpholin-4-ylcarbonyl)propyl]-3-methyl-4-(pyrrolidin-1-ylcarbonyl)benzamide,
(205) N-[(1S)-1-(5-chloro-1H-benzimidazol-2-yl)-3-[(4-methyl-3-oxopiperazin-1-ylcarbonyl)propyl]-3-methyl-4-(pyrrolidin-1-ylcarbonyl)benzamide,
(206) rac.-N-[(5-chloro-1H-benzimidazol-2-yl)-(4-chlorophenyl)methyl]-3-methyl-4(pyrrolidin-1-ylcarbonyl)benzamide,
(207) rac.-N-[(5-chloro-1H-benzimidazol-2-yl)-(2-chlorophenyl)methyl]-3-methyl-4-(pyrrolidin-1-ylcarbonyl)benzamide,
(208) N-[(1R)-1-(5-chloro-1H-benzimidazol-2-yl)-2-methoxyethyl]-3-methyl-4-(pyrrolidin-1-ylcarbonyl)benzamide,
(209) 3-chloro-N-[(1R)-1-(5-chloro-1H-benzimidazol-2-yl)-2-methoxyethyl]-4-(2,5-dihydropyrrol-1-ylcarbonyl)benzamide,
(210) 3-bromo-N-[(1R)-1-(5-chloro-1H-benzimidazol-2-yl)-2-methoxyethyl]-4-(pyrrolidin-1-ylcarbonyl)benzamide,
(211) 4-{(2R)-2-[2-(tert-butoxycarbonylamino)ethyl]pyrrolidin-1-ylcarbonyl}-3-chloro-N-[(1S)-1-(5-chloro-1H-benzimidazol-2-yl)ethyl]benzamide,
(212) 3-chloro-N-[(1S)-1-(5-chloro-1H-benzimidazol-2-yl)ethyl]-4-[2-(2-ethoxycarbonylethyl)pyrrolidin-1-ylcarbonyl]benzamide,
(213) 3-chloro-N-[(1S)-1-(5-chloro-1H-benzimidazol-2-yl)ethyl]-4-{(2R)-2-[(3-ethylureido)methyl]pyrrolidin-1-ylcarbonyl}benzamide,
(214) 4-[(2R)-2-(2-aminoethyl)pyrrolidin-1-ylcarbonyl]-3-chloro-N-[(1S)-1-(5-chloro-1H-benzimidazol-2-yl)ethyl]benzamide,
(215) 3-bromo-N-[(1R)-1-(5-chloro-1H-benzimidazol-2-yl)-2-methoxyethyl]-4-(2,5-dihydropyrrol-1-ylcarbonyl)benzamide,
(216) rac.-N-[1-(5-chloro-1H-benzimidazol-2-yl)ethyl]-4-(4,5,6,7-tetrahydrobenzimidazol-1-yl)-3-trifluoromethylbenzamide,
(217) rac.-N-[1-(5-chloro-1H-benzimidazol-2-yl)ethyl]4-[3-(ethoxycarbonyl)-5,6-dihydro-4H-cyclopentapyrazol-1-yl]-3-trifluoromethylbenzamide,
(218) 4-[3-(tert-butoxycarbonylamino)methyl-5,6-dihydro-4H-cyclopentapyrazol-1-yl]-N-(5-chloro-1H-benzimidazol-2-ylmethyl)-3-trifluoromethylbenzamide,
(219) rac.-4-[3-(aminocarbonyl)-5,6-dihydro-4H-cyclopentapyrazol-1-yl]-N-[1-(5-chloro-1H-benzimidazol-2-yl)ethyl]-3-trifluoromethylbenzamide,
(220) 4-(3-aminomethyl-5,6-dihydro-4H-cyclopentapyrazol-1-yl)-N-[(1S)-1-(5-chloro-1H-benzimidazol-2-yl)ethyl]-3-trifluoromethylbenzamide,
(221) 4-[3-(tert-butoxycarbonylamino)methyl-5,6-dihydro-4H-cyclopentapyrazol-1-yl]-N-[(1S)-1-(5-chloro-1H-benzimidazol-2-yl)ethyl]-3-trifluoromethylbenzamide,
(222) 4-(3-aminomethyl-5,6-dihydro-4H-cyclopentapyrazol-1-yl)-N-(5-chloro-1H-benzimidazol-2-ylmethyl)-3-trifluoromethylbenzamide,
(223) 3-methyl-N-[(1R)-1-(5-chloro-1H-benzimidazol-2-yl)-2-hydroxyethyl]4-(2,5-dihydropyrrol-1-ylcarbonyl)benzamide,
(224) N-{(1S)-1-(5-chloro-1H-benzimidazol-2-yl)-3-[(2S)-2-aminomethylpyrrolidin-1-ylcarbonyl]propyl}-3-methyl-4-(pyrrolidin-1-ylcarbonyl)benzamide,
(225) N-{(1S)-1-(5-chloro-1H-benzimidazol-2-yl)-3-[(2R)-2-aminomethylpyrrolidin-1-ylcarbonyl]propyl}-3-methyl-4-(pyrrolidin-1-ylcarbonyl)benzamide,
(226) N-(5-chloro-1H-indol-2-ylmethyl)-3-methyl-4-(pyrrolidin-1-ylcarbonyl)benzamide,
(227) rac.-3-chloro-N-[1-(5-chloro-1H-benzimidazol-2-yl)ethyl]4-(4-formylpiperazin-1-ylcarbonyl)benzamide, (228) rac.-3-chloro-N-[1-(5-chloro-1H-benzimidazol-2-yl)ethyl]-4-[N-ethyl-N-(piperidin-4-yl)aminocarbonyl]benzamide,
(229) 3-chloro-N-[1-(5-chloro-1H-benzimidazol-2-yl)ethyl]-4-[2-(2-dimethylaminoethyl)piperidin-1-ylcarbonyl]benzamide,
(230) 3-chloro-N-[1-(5-chloro-1H-benzimidazol-2-yl)ethyl]-4-[2-(piperidin-1-ylmethyl)piperidin-1-ylcarbonyl]benzamide,
(231) 3-chloro-N-[1-(5-chloro-1H-benzimidazol-2-yl)ethyl]-4-[2-(3-diethylaminopropyl)piperidin-1-ylcarbonyl]benzamide,
(232) 4-[2-(N-butyl-N-ethylaminomethyl)piperidin-1-ylcarbonyl]-3-chloro-N-[1-(5-chloro-1H-benzimidazol-2-yl)ethyl]benzamide,
(233) 3-chloro-N-[1-(5-chloro-1H-benzimidazol-2-yl)ethyl] 4-[2-(N-cyclohexyl-N-methylaminomethyl)piperidin-1-ylcarbonyl]benzamide,
(234) 3-chloro-N-[1-(5-chloro-1H-benzimidazol-2-yl)ethyl]-4-(thiomorpholin-4-ylcarbonyl)benzamide,
(235) 3-chloro-N-[(1R,S)-1-(5-chloro-1H-benzimidazol-2-yl)ethyl]-4-[(2R)-2-methoxymethylpyrrolidin-1-ylcarbonyl]benzamide,
(236) rac.-3-chloro-N-[1-(5-chloro-1H-benzimidazol-2-yl)ethyl]-4-(1,4,6,7-tetrahydroimidazo[4,5-c]pyridin-5-ylcarbonyl)benzamide,
(237) 3-chloro-N-[(1R,S)-1-(5-chloro-1H-benzimidazol-2-yl)ethyl]-4-[(2S)-2-methoxymethylpyrrolidin-1-ylcarbonyl]benzamide,
(238) 4-(2-aminomethylpiperidin-1-ylcarbonyl)-3-chloro-N-[1-(5-chloro-1H-benzimidazol-2-yl)ethyl]benzamide,
(239) 4-(3-aminomethylpiperidin-1-ylcarbonyl)-3-chloro-N-[1-(5-chloro-1H-benzimidazol-2-yl)ethyl]benzamide,
(240) rac.-3-chloro-N-[1-(5-chloro-1H-benzimidazol-2-yl)ethyl] 4-(6,7-dihydro-4H-thieno[3,2-c]pyridin-5-ylcarbonyl)benzamide,
(241) 3-chloro-N-[(1R,S)-1-(5-chloro-1H-benzimidazol-2-yl)ethyl]-4-[(2S)-2-(pyrrolidin 1-ylmethyl)pyrrolidin-1-ylcarbonyl]benzamide,
(242) 3-chloro-N-[(1R,S)-1-(5-chloro-1H-benzimidazol-2-yl)ethyl]4-[(2S)-2-(ethoxy-carbonyl)pyrrolidin-1-ylcarbonyl]benzamide,
(243) 4-[3-(2-aminoethyl)piperidin-1-ylcarbonyl]-3-chloro-N-[1-(5-chloro-1H-benzimidazol-2-yl)ethyl]benzamide,
(244) rac.-3-chloro-N-[1-(5-chloro-1H-benzimidazol-2-yl)ethyl]-4-(4-hydroxypiperazin-1-ylcarbonyl)benzamide,
(245) 3-chloro-N-[1-(5-chloro-1H-benzimidazol-2-yl)ethyl]-4-[2-(methyloxycarbonyl)pyrrolidin-1-ylcarbonyl]benzamide,
(246) 4-[2-(benzyloxycarbonyl)pyrrolidin-1-ylcarbonyl]-3-chloro-N-[1-(5-chloro-1H-benzimidazol-2-yl)ethyl]benzamide,
(247) 3-chloro-N-[1-(5-chloro-1H-benzimidazol-2-yl)ethyl] 4-(3,4,5,6-tetrahydro-2H-[2,3]-bipyridinyl-1-ylcarbonyl)benzamide,
(248) rac.-4-[N-(2-aminoethyl)-N-ethylaminocarbonyl]-3-chloro-N-[1-(5-chloro-1H-benzimidazol-2-yl)ethyl]benzamide,
(249) rac.-4-[N-(3-aminopropyl)-N-ethylaminocarbonyl]-3-chloro-N-[1-(5-chloro-1H-benzimidazol-2-yl)ethyl]benzamide,
(250) rac.-3-chloro-N-[1-(5-chloro-1H-benzimidazol-2-yl)ethyl]4-(N-cyclopropyl-N-methylaminocarbonyl]benzamide,
(251) rac.-3-chloro-N-[1-(5-chloro-1H-benzimidazol-2-yl)ethyl]4-(2,5-dimethylpyrrolidin-1-ylcarbonyl)benzamide,
(252) rac.-3-chloro-N-[1-(5-chloro-1H-benzimidazol-2-yl)ethyl]4-(1,4,6,7-tetrahydropyrazol-[4,3-c]pyridin-5-ylcarbonyl)benzamide,
(253) 3-chloro-N-[1-(5-chloro-1H-benzimidazol-2-yl)ethyl] 4-[2-(pyridin-2-yl)pyrrolidin-1-ylcarbonyl]benzamide,
(254) rac.-3-chloro-N-[1-(5-chloro-1H-benzimidazol-2-yl)ethyl]4-[2-(pyridin-4-yl)pyrrolidin-1-ylcarbonyl]benzamide,
(255) rac.-3-chloro-N-[1-(5-chloro-1H-benzimidazol-2-yl)ethyl]4-(2,5-dimethyl-2,5-dihydropyrrol-1-ylcarbonyl)benzamide,
(256) 3-chloro-N-[(1R,S)-1-(5-chloro-1H-benzimidazol-2-yl)ethyl]4-[(2S)-2-phenylaminomethylpyrrolidin-1-ylcarbonyl]benzamide,
(257) 4-(2-benzylpyrrolidin-1-ylcarbonyl)-3-chloro-N-[1-(5-chloro-1H-benzimidazol-2-yl)ethyl]benzamide,
(258) 3-chloro-N-[1-(5-chloro-1H-benzimidazol-2-yl)ethyl] 4-(2-phenethylpyrrolidin-1-ylcarbonyl)benzamide,
(259) 3-chloro-N-[1-(5-chloro-1H-benzimidazol-2-yl)ethyl] 4-(2-isopropylpyrrolidin-1-ylcarbonyl)benzamide,
(260) 3-chloro-N-[(1R,S)-1-(5-chloro-1H-benzimidazol-2-yl)ethyl]4-[(2R)-2-phenylaminomethylpyrrolidin-1-ylcarbonyl]benzamide,
(261) rac.-3-chloro-N-[1-(5-chloro-1H-benzimidazol-2-yl)ethyl]-4-(piperidin 1-ylcarbonyl)benzamide,
(262) 3-chloro-N-[1-(5-chloro-1H-benzimidazol-2-yl)ethyl]-4-(2-methylpiperidin-1-ylcarbonyl)benzamide,
(263) rac.-3-chloro-N-[1-(5-chloro-1H-benzimidazol-2-yl)ethyl]-4-(4-hydroxypiperidin-1-ylcarbonyl)benzamide,
(264) rac.-4-(4-acetylpiperazin-1-ylcarbonyl)-3-chloro-N-[1-(5-chloro-1H-benzimidazol-2-yl)ethyl]benzamide,
(265) 3-chloro-N-[(1R,S)-1-(5-chloro-1H-benzimidazol-2-yl)ethyl]-4-[(2R)-2-(ethoxycarbonyl)pyrrolidin-1-ylcarbonyl]benzamide,
(266) rac.-3-chloro-N-[1-(5-chloro-1H-benzimidazol-2-yl)ethyl]-4-(4-oxopiperidin-1-ylcarbonyl)benzamide,
(267) rac.-3-chloro-N-[1-(5-chloro-1H-benzimidazol-2-yl)ethyl]-4-([1,4]-diazepan-1-ylcarbonyl)benzamide,
(268) 3-chloro-N-[(1R,S)-1-(5-chloro-1H-benzimidazol-2-yl)ethyl]-4-[(2S)-2-(dimethylaminocarbonyl)pyrrolidin-1-ylcarbonyl]benzamide,
(269) 3-chloro-N-[(1R,S)-1-(5-chloro-1H-benzimidazol-2-yl)ethyl]-4-[(2S)-2-(methylaminocarbonyl)pyrrolidin-1-ylcarbonyl]benzamide,
(270) 4-[(2S)-2-(aminocarbonylmethylaminocarbonyl)pyrrolidin-1-ylcarbonyl]-3-chloro-N-[(1R,S)-1-(5-chloro-1H-benzimidazol-2-yl)ethyl]benzamide,
(271) 4-((2S)-2-benzhydrylpyrrolidin-1-ylcarbonyl)-3-chloro-N-[1-(5-chloro-1H-benzimidazol-2-yl)ethyl]benzamide,
(272) rac.-3-chloro-N-[1-(5-chloro-1H-benzimidazol-2-yl)ethyl]-4-[3-(2,2,2-trifluoroacetylamino)pyrrolidin-1-ylcarbonyl]benzamide,
(273) 3-chloro-N-[1-(5-chloro-1H-benzimidazol-2-yl)ethyl]-4-(3-dimethylaminopyrrolidin-1-ylcarbonyl)benzamide,
(274) N-[(1S)-1-(5-chloro-1H-benzimidazol-2-yl)ethyl]4-(imidazol-1-ylmethyl)-3-methoxybenzamide,
(275) N-[(1S)-1-(5-chloro-1H-benzimidazol-2-yl)ethyl]-3-methoxy-4-(2-oxopyrrolidin-1-ylmethyl)benzamide,
(276) N-[(1S)-1-(5-chloro-1H-benzimidazol-2-yl)ethyl]-3-methoxy-4-(3-oxopiperazin-1-ylmethyl)benzamide
(277) 3-bromo-N-[(1R)-1-(5-chloro-1H-benzimidazol-2-yl)-2-hydroxyethyl]-4-(pyrrolidin-1-ylcarbonyl)benzamide, (278) N-[(1R)-1-(5-chloro-1H-benzimidazol-2-yl)-2-methoxyethyl]4-(2,5-dihydropyrrol-1-ylcarbonyl)-3-trifluoromethylbenzamide,
(279) N-[(1R)-1-(5-chloro-1H-benzimidazol-2-yl)-2-methoxyethyl]4-(pyrrolidin-1-ylcarbonyl)-3-trifluoromethylbenzamide,
(280) 3-chloro-N-[(1R)-1-(5-chloro-1H-benzimidazol-2-yl)-2-isopropoxycarbonyloxyethyl]-4-(2,5-dihydropyrrol-1-ylcarbonyl)benzamide,
(281) N-[(1S)-1-(5-chloro-1H-benzimidazol-2-yl)-3-(2-isopropylaminothiazol-4-yl)propyl]3-methyl-4-(pyrrolidin-1-ylcarbonyl)benzamide,
(282) N-[(1S)-1,3-bis-(5-chloro-1H-benzimidazol-2-yl)propyl]-3-methyl-4-(pyrrolidin-1-ylcarbonyl)benzamide,
(283) 3-chloro-N-[(1S)-1-(5-chloro-1H-benzimidazol-2-yl)ethyl]4-[(2S)-2-(ethoxycarbonylmethyl)pyrrolidin-1-ylcarbonyl]benzamide,
(284) 3-chloro-N-[(1S)-1-(5-chloro-1H-benzimidazol-2-yl)ethyl]4-[(2R/S)-2-dimethylaminomethylpyrrolidin-1-ylcarbonyl]benzamide,
(285) 3-chloro-N-[(1S)-1-(5-chloro-1H-benzimidazol-2-yl)ethyl]4-[(2S)-2-(hydroxycarbonylmethyl)pyrrolidin-1-ylcarbonyl]benzamide,
(286) 3-chloro-N-[(1S)-1-(5-chloro-1H-benzimidazol-2-yl)ethyl]4-[(2R/S)-2-(hydroxycarbonylethyl)pyrrolidin-1-ylcarbonyl]benzamide,
(287) N-[(1S)-3-[1-(benzyloxycarbonyl)piperidin-4-yl]-1-(5-chloro-1H-benzimidazol-2-yl)propyl]-3-methyl-4-(pyrrolidin-1-ylcarbonyl)benzamide,
(288) rac.-N-[(5-chloro-1H-benzimidazol-2-yl)thiophen-3-ylmethyl]4-(2,5-dihydropyrrol-1-ylcarbonyl)-3-methylbenzamide,
(289) N-[(1S)-1-(5-chloro-1H-benzimidazol-2-yl)-3-methanesulfonylaminopropyl]-4-(2,5-dihydropyrrol-1-ylcarbonyl)-3-methylbenzamide,
(290) N-[(1S)-1-(5-chloro-1H-benzimidazol-2-yl)-3-piperidin-4-ylpropyl]-3-methyl-4-(pyrrolidin-1-ylcarbonyl)benzamide,
(291) rac.-N-[1-(5-chloro-1H-benzimidazol-2-yl)ethyl]-3-methyl-4-(pyrrol-1-ylcarbonyl)benzamide,
(292) 3-bromo-N-[(1S)-1-(5-chloro-1H-benzimidazol-2-yl)ethyl]-4-(thiazolidin-3-ylcarbonyl)benzamide,
(293) 3-bromo-N-[(1S)-1-(5-chloro-1H-benzimidazol-2-yl)ethyl]-4-[(2R/S)-2-methylpyrrolidin-1-ylcarbonyl]benzamide,
(294) 3-bromo-4-[(2R/S)-2-(tert-butoxycarbonylaminomethyl)thiazolidin-3-ylcarbonyl]-N-[(1S)-1-(5-chloro-1H-benzimidazol-2-yl)ethyl]benzamide,
(295) N-[(1S)-1-(6-amino-5-chloro-1H-benzimidazol-2-yl)ethyl]-3-methyl-4-(pyrrolidin-1-ylcarbonyl)benzamide,
(296) 4-[(2R/S)-2-aminomethylthiazolidin-3-ylcarbonyl]-3-bromo-N-[(1S)-1-(5-chloro-1H-benzimidazol-2-yl)ethyl]benzamide,
(297) N-[(1S)-1-(5-chloro-1H-benzimidazol-2-yl)ethyl]-4-[N-ethyl-N-(6-methoxyhexanoyl)amino]-3-methylbenzamide,
(298) N-[(1S)-1-(5-chloro-1H-benzimidazol-2-yl)ethyl]-4-[(3R/S)-3-fluoropyrrolidin-1-ylcarbonyl]-3-methylbenzamide,
(299) N-[(1R)-2-benzyloxy-1-(5-chloro-1H-benzimidazol-2-yl)ethyl]-3-bromo-4-(2,5-dihydropyrrol-1-ylcarbonyl)benzamide,
(300) N-[(1S)-1-(5-chloro-1H-benzimidazol-2-yl)butyl]-4-(2,5-dihydropyrrol-1-ylcarbonyl)-3-methylbenzamide,
(301) 3-chloro-N-[(1S)-1-(5-chloro-1H-benzimidazol-2-yl)butyl]-4-(2,5-dihydropyrrol-1-ylcarbonyl)benzamide,
(302) 3-bromo-N-[(1S)-1-(5-chloro-1H-benzimidazol-2-yl)butyl]-4-(2,5-dihydropyrrol-1-ylcarbonyl)benzamide,
(303) 3-chloro-N-[(1S)-1-(5-chloro-1H-benzimidazol-2-yl)ethyl]4-[(2S)-2-(pyrrolidin-1-ylmethyl)pyrrolidin-1-ylcarbonyl]benzamide,
(304) 3-chloro-N-[(1S)-1-(5-chloro-1H-benzimidazol-2-yl)ethyl]4-[(2R/S)-2-(2-pyrrolidin-1-ylcarbonylethyl)pyrrolidin-1-ylcarbonyl]benzamide,
(305) 3-chloro-N-[(1S)-1-(5-chloro-1H-benzimidazol-2-yl)ethyl]4-[(2R)-2-(ethoxycarbonylmethyl)pyrrolidin-1-ylcarbonyl]benzamide,
(306) N-[(1S)-1-(5-chloro-1H-benzimidazol-2-yl)ethyl]-4-(2,5-dihydropyrrol-1-ylcarbonyl)-3-methylbenzamide,
(307) 3-chloro-N-[(1S)-1-(5-chloro-1H-benzimidazol-2-yl)ethyl]4-(2,5-dihydropyrrol-1-ylcarbonyl)benzamide,
(308) 3-chloro-N-[(1S)-1-(5-chloro-1H-benzimidazol-2-yl)ethyl]4-[(2R/S)-2-(2-methyl-aminocarbonylethyl)pyrrolidin-1-ylcarbonyl]benzamide,
(309) 3-chloro-N-[(1S)-1-(5-chloro-1H-benzimidazol-2-yl)ethyl]4-[(2R)-2-(hydroxycarbonylmethyl)pyrrolidin-1-ylcarbonyl]benzamide,
(310) 3-bromo-N-[(1S)-1-(5-bromo-1H-benzimidazol-2-yl)ethyl]4-(2,5-dihydropyrrol-1-ylcarbonyl)benzamide,
(311) N-[(1R)-1-(5-chloro-1H-benzimidazol-2-yl)-2-methylsulfanylethyl]-4-(2,5-dihydropyrrol-1-ylcarbonyl)-3-methylbenzamide,
(312) 4-(N-acetyl-N-cyclopentylamino)-N-[(1S)-1-(5-chloro-1H-benzimidazol-2-yl)-2-methylsulfanylethyl]-3-methylbenzamide,
(313) 4-(N-acetyl-N-cyclopentylamino)-N-[(1S)-1-(5-chloro-1H-benzimidazol-2-yl)ethyl]-3methylbenzamide,
(314) 3-chloro-N-[(1S)-1-(5-chloro-1H-benzimidazol-2-yl)ethyl]4-[(2R)-2-methylamino-carbonylmethylpyrrolidin-1-yl]benzamide,
(315) N-[(1S)-1-(5-chloro-1H-benzimidazol-2-yl)ethyl]4-(2,5-dihydropyrrol-1-ylcarbonyl)-3-trifluoromethylbenzamide,
(316) 3-chloro-N-[(1S)-1-(5-chloro-1H-benzimidazol-2-yl)ethyl]4-[(2R)-2-(imidazol 1-ylmethyl)pyrrolidin-1-ylcarbonyl]benzamide,
(317) 3-chloro-N-[(1S)-1-(5-chloro-1H-benzimidazol-2-yl)ethyl]4-[(2R)-2-(pyrrolidin-1-ylmethyl)pyrrolidin-1-ylcarbonyl]benzamide,
(318) 3-bromo-N-[(1R)-1-(5-bromo-1H-benzimidazol-2-yl)-2-methoxyethyl]4-(2,5-di-hydropyrrol-1-ylcarbonyl)benzamide,
(319) N-[(1S)-1-(5-chloro-1H-benzimidazol-2-yl)butyl]4-(2,5-dihydropyrrol-1-ylcarbonyl)-2-trifluoromethylbenzamide,
(320) N-[(1S)-1-(5-chloro-1H-benzimidazol-2-yl)-3-(1,1-dioxoisothiazolidin-2-yl)propyl]-3-methyl-4-(pyrrolidin-1-ylcarbonyl)benzamide,
(321) 3-bromo-N-[(1R)-1-(5-chloro-1H-benzimidazol-2-yl)-2-ethoxyethyl]-4-(2,5-dihydropyrrol-1-ylcarbonyl)benzamide,
(322) 3-chloro-N-[(1R,2R)-1-(5-chloro-1H-benzimidazol-2-yl)-2-methoxypropyl]4-(2,5-dihydropyrrol-1-ylcarbonyl)benzamide,
(323) N-[(1R)-2-allyloxy-1-(5-chloro-1H-benzimidazol-2-yl)ethyl]4-(2,5-dihydropyrrol-1-ylcarbonyl)-3-methylbenzamide,
(324) N-[(1R,2S)-2-tert-butoxy-1-(5-chloro-1H-benzimidazol-2-yl)propyl]-4-(2,5-dihydropyrrol-1-ylcarbonyl)-3-methylbenzamide,
(325) N-[(1R,2S)-1-(5-chloro-1H-benzimidazol-2-yl)-2-hydroxypropyl]4-(2,5-dihydropyrrol-1-ylcarbonyl)-3-methylbenzamide, (326) 4-{(2R)-2-[(N-acetyl-N-methylamino)methyl]pyrrolidin-1-ylcarbonyl}-N-[(1S)-1-(5-chloro-1H-benzimidazol-2-yl)ethyl]-3-chlorobenzamide,
(327) 4-benzoyl-N-[(1S)-1-(5-chloro-1H-benzimidazol-2-yl)ethyl]-3-methylbenzamide,
(328) 3-bromo-N-[(1R)-1-(5-chloro-1H-benzimidazol-2-yl)-2-prop-2-ynyloxyethyl]-4-(2,5-dihydropyrrol-1-ylcarbonyl)benzamide,
(329) N-[(1S)-1-(5-chloro-1H-benzimidazol-2-yl)-3-(1H-tetrazol-5-yl)propyl]-3-methyl-4-(pyrrolidin-1-ylcarbonyl)benzamide,
(330) N-[(1S)-1-(5-chloro-1H-benzimidazol-2-yl)ethyl]4-(3-methyl-5,6-dihydro-4H-cyclopentapyrazol-1-yl)-3-trifluoromethylbenzamide,
(331) 3-chloro-N-[(1S)-1-(5-chloro-1H-benzimidazol-2-yl)ethyl]4-(4-oxo-4,5,6,7-tetrahydroindol-1-yl)benzamide,
(332) N-[(1R)-1-(5-chloro-1H-benzimidazol-2-yl)-2-hydroxyethyl]4-(2,5-dihydropyrrol-1-ylcarbonyl)-3-trifluoromethylbenzamide,
(333) N-[(1S)-1-(5-chloro-1H-benzimidazol-2-yl)but-3-ynyl]-3-methyl-4-(pyrrolidin-1-ylcarbonyl)benzamide,
(334) N-[(1S)-1-(5-hydroxy-1H-benzimidazol-2-yl)ethyl]-3-methyl-4-(pyrrolidin-1-ylcarbonyl)benzamide,
(335) 3-chloro-N-[(1S)-1-(5-chloro-1H-benzimidazol-2-yl)ethyl]4-(4,5,6,7-tetrahydroindol-1-yl)benzamide,
(336) 3-chloro-N-[(1S)-1-(5-chloro-1H-benzimidazol-2-yl)ethyl]4-(4,5,6,7-tetrahydroindazol-1-yl)benzamide,
(337) rac.-N-[1-(5-chloro-1H-indol-2-yl)ethyl]-3-methyl-4-(pyrrolidin-1-ylcarbonyl)benzamide,
(338) rac.-N-[(5-chloro-1H-indol-2-yl)phenylmethyl]-3-methyl-4-(pyrrolidin-1-ylcarbonyl)benzamide,
(339) rac.-3-chloro-N-[(5-chloro-1H-indol-2-yl)phenylmethyl]-4-(2,5-dihydropyrrol-1-ylcarbonyl)benzamide,
(340) rac.-N-[3-chloro-4-(2,5-dihydropyrrol-1-ylcarbonyl)phenyl]-2-(5-chloro-1H-indol-2-yl)acetamide,
(341) N-[(1S)-1-(5-chloro-1H-benzimidazol-2-yl)-3-methylsulfanylpropyl]-4-(4-oxo-2-propyl-4,5-dihydroimidazo[4,5-c]pyridin-1-yl)-3-trifluoromethylbenzamide,
(342) N-[(1S)-1-(5-chloro-1H-benzimidazol-2-yl)ethyl]4-(2-methyl-5,6-dihydro-4H-cyclopentaimidazol-1-yl)-3-trifluoromethylbenzamide,
(343) N-[(1S)-1-(5-chloro-1H-benzimidazol-2-yl)ethyl]-4-(2-methyl-4,5,6,7-tetrahydrobenzimidazol-1-yl)-3-trifluoromethylbenzamide,
(344) rac.-3-chloro-N-[1-(5-chloro-1H-benzimidazol-2-yl)ethyl]4-[2-hydroxycarbonylmethyl-3-oxopiperazin-1-ylcarbonyl]benzamide,
(345) N-[(1S)-1-(5-chloro-1H-benzimidazol-2-yl)ethyl]-4-(4-methoxyimidazo[4,5-c]pyridin-1-yl)-3-trifluoromethylbenzamide,
(346) rac.-3-chloro-N-[1-(5-chloro-1H-benzimidazol-2-yl)ethyl]-4-(2-hydroxycarbonylpyrrolidin-1-ylcarbonyl)benzamide,
(347) N-[(1S)-1-(5-chloro-1H-benzimidazol-2-yl)ethyl]4-(2-dimethylaminomethylbenzimidazol-1-yl)-3-trifluoromethylbenzamide,
(348) N-[(1S)-1-(5-chloro-1H-benzimidazol-2-yl)ethyl]-4-(4-oxo-4,5-dihydroimidazo-[4,5-c]pyridin-1-yl)-3-trifluoromethylbenzamide,
(349) N-[(1S)-1-(5-chloro-1H-benzimidazol-2-yl)ethyl]-4-(2-dimethylaminomethyl-indol-1-yl)-3-trifluoromethylbenzamide,
(350) N-[(1S)-1-(5-chloro-1H-benzimidazol-2-yl)ethyl]-4-(4-oxo-4,5-dihydropyrrol-[3,2-c]pyridin-1-yl)-3-trifluoromethylbenzamide,
(351) 3-chloro-N-[(1S)-1-(5-chloro-1H-benzimidazol-2-yl)ethyl]-4-(2-methyl-4,5,6,7-tetra-hydrobenzimidazol-1-yl)benzamide,
(352) 3-chloro-N-[(1S)-1-(5-chloro-1H-benzimidazol-2-yl)ethyl]-4-(3-oxo-[1,4]diazepan-1-ylcarbonyl)benzamide,
(353) N-{(1S)-1-(5-chloro-1H-benzimidazol-2-yl)-5-[(5-oxopyrrolidin-3-yl)carbonylamino]pentyl}-3-methyl-4-(pyrrolidin-1-ylcarbonyl)benzamide,
(354) N-{(1S)-1-(5-chloro-1H-benzimidazol-2-yl)-5-[(pyridin-3-yl-)carbonylamino]pentyl}-3-methyl-4-(pyrrolidin-1-ylcarbonyl)benzamide,
(355) N-{(1S)-1-(5-chloro-1H-benzimidazol-2-yl)-5-[(5-oxopyrrolidin-2-yl)carbonylamino]pentyl}-3-methyl-4-(pyrrolidin-1-ylcarbonyl)benzamide,
(356) N-{(1S)-1-(5-chloro-1H-benzimidazol-2-yl)-5-[(pyridin-4-yl)carbonylamino]pentyl}-3methyl-4-(pyrrolidin-1-ylcarbonyl)benzamide,
(357) N-{(1S)-1-(5-chloro-1H-benzimidazol-2-yl)-5-[(2S)-(1-methylpyrrolidin-2-yl)carbonylamino]pentyl}-3-methyl-4-(pyrrolidin-1-ylcarbonyl)benzamide,
(358) 2-(5-chloro-1H-indol-2-yl)-N-[3-methyl-4-(pyrrolidin-1-ylcarbonyl)phenyl]pentenoic acid amide,
(359) N-[(1R)-2-benzyloxy-1-(5-chloro-1H-benzimidazol-2-yl)ethyl]-3-methyl-4-(pyrrolidin-1-ylcarbonyl)benzamide,
(360) N-[(1R)-2-(acetylaminomethylsulfanyl)-1-(5-chloro-1H-benzimidazol-2-yl)ethyl]-3-methyl-4-(pyrrolidin-1-ylcarbonyl)benzamide,
(361) N-[(1S)-3-aminocarbonyl-1-(5-chloro-1H-benzimidazol-2-yl)propyl]-3-methyl-4-(pyrrolidin-1-ylcarbonyl)benzamide,
(362) N-[(1S)-1-(5-chloro-1H-benzimidazol-2-yl)-2-(1H-indol-3-yl)ethyl]-3-methyl-4-(pyrrolidin-1-ylcarbonyl)benzamide,
(363) rac.-N-[1-(5-chloro-1H-benzimidazol-2-yl)-2-(4-hydroxy-3,5-dimethylphenyl)ethyl]-3-methyl-4-(pyrrolidin-1-ylcarbonyl)benzamide,
(364) N-[(1S)-1-(5-chloro-1H-benzimidazol-2-yl)-2-methoxycarbonylethyl]-3-methyl-4-(pyrrolidin-1-ylcarbonyl)benzamide,
(365) rac.-N-[1-(5-chloro-1H-benzimidazol-2-yl)-2-(4-hydroxy-2,6-dimethylphenyl)ethyl]-3-methyl-4-(pyrrolidin-1-ylcarbonyl)benzamide,
(366) rac.-N-[1-(5-chloro-1H-benzimidazol-2-yl)-2-(4-difluoromethoxyphenyl)ethyl]-3-methyl-4-(pyrrolidin-1-ylcarbonyl)benzamide,
(367) rac.-N-[2-(3-bromophenyl)-1-(5-chloro-1H-benzimidazol-2-yl)ethyl]-3-methyl-4-(pyrrolidin-1-ylcarbonyl)benzamide,
(368) N-[(1S)-1-(5-chloro-1H-benzimidazol-2-yl)-2-(4-trifluoromethylphenyl)ethyl]-3-methyl-4-(pyrrolidin-1-ylcarbonyl)benzamide,
(369) N-[(1S)-1-(5-chloro-1H-benzimidazol-2-yl)-5-ureidopentyl]-3-methyl-4-(pyrrolidin-1-ylcarbonyl)benzamide,
(370) N-[(1S)-1-(5-chloro-1H-benzimidazol-2-yl)-5-ureidobutyl]-3-methyl-4-(pyrrolidin-1-ylcarbonyl)benzamide,
(371) rac.-N-[2-(4-amino-3,5-dibromophenylcarbonyl)-1-(5-chloro-1H-benzimidazol-2-yl)ethyl]-3-methyl-4-(pyrrolidin-1-ylcarbonyl)benzamide,
(372) N-[(1S)-2-allyloxycarbonyl-1-(5-chloro-1H-benzimidazol-2-yl)ethyl]-3-methyl-4-(pyrrolidin-1-ylcarbonyl)benzamide,
(373) N-[(1S)-1-(5-chloro-1H-benzimidazol-2-yl)-2-(3,4-dimethoxyphenyl)ethyl]-3-methyl-4-(pyrrolidin-1-ylcarbonyl)benzamide, (374) N-[(1S)-1-(5-chloro-1H-benzimidazol-2-yl)-2-(thiazol-4-yl)ethyl]-3-methyl-4-(pyrrolidin-1-ylcarbonyl)benzamide,
(375) N-[(1S)-1-(5-chloro-1H-benzimidazol-2-yl)-2-(3,5-difluorophenyl)ethyl]-3-methyl-4-(pyrrolidin-1-ylcarbonyl)benzamide,
(376) N-[(1S)-1-(5-chloro-1H-benzimidazol-2-yl)-2-(4-fluorophenyl)ethyl]-3-methyl-4-(pyrrolidin-1-ylcarbonyl)benzamide,
(377) N-[(1R)-1-(5-chloro-1H-benzimidazol-2-yl)-2-mercaptoethyl]-3-methyl-4-(pyrrolidin-1-ylcarbonyl)benzamide,
(378) N-[(1S)-1-(5-chloro-1H-benzimidazol-2-yl)-2-(1-methyl-1H-imidazol-5-yl)ethyl]-3-methyl-4-(pyrrolidin-1-ylcarbonyl)benzamide,
(379) rac.-N-[1-(5-chloro-1H-benzimidazol-2-yl)-2-(1H-benzimidazol-5-yl)ethyl]-3-methyl-4-(pyrrolidin-1-ylcarbonyl)benzamide,
(380) rac.-N-[(5-chloro-1H-benzimidazol-2-yl)thiophen-3-ylmethyl]-3-methyl-4-(pyrrolidin-1-ylcarbonyl)benzamide,
(381) N-[(1S)-1-(5-chloro-1H-benzimidazol-2-yl)-2-(thiophen-3-yl)ethyl]-3-methyl-4-(pyrrolidin-1-ylcarbonyl)benzamide,
(382) N-[(1S)-1-(5-chloro-1H-benzimidazol-2-yl)but-3-enyl]-3-methyl-4-(pyrrolidin-1-ylcarbonyl)benzamide,
(383) N-[(1S)-1-(5-chloro-1H-benzimidazol-2-yl)-2-(4-chlorophenyl)ethyl]-3-methyl-4-(pyrrolidin-1-ylcarbonyl)benzamide,
(384) N-[(1S)-1-(5-chloro-1H-benzimidazol-2-yl)-2-cyclopropylethyl]-3-methyl-4-(pyrrolidin-1-ylcarbonyl)benzamide,
(385) 3-chloro-N-[(1S)-1-(5-chloro-1H-benzimidazol-2-yl)ethyl]4-[2-(pyrrolidin-1-yl)-methyl-5,6-dihydro-4H-cyclopentaimidazol-1-yl]benzamide,
(386) 3-chloro-N-[(1S)-1-(5-chloro-1H-benzimidazol-2-yl)ethyl]4-[2-(2-(pyrrolidin-1-yl)-ethyl)-5,6-dihydro-4H-cyclopentaimidazol-1-yl])benzamide,
(387) 3-chloro-N-[(1S)-1-(5-chloro-1H-benzimidazol-2-yl)ethyl]-4-[2-(pyrrolidin-1-yl)-methyl-4,5,6,7-tetrahydrobenzimidazol-1-yl]benzamide,
(388) 3-chloro-N-[(1S)-1-(5-chloro-1H-benzimidazol-2-yl)ethyl]-4-[2-(2-pyrrolidin-ylethyl)-4,5,6,7-tetrahydrobenzimidazol-1-yl]benzamide,
(389) 3-chloro-N-[(1S)-1-(5-chloro-1H-benzimidazol-2-yl)ethyl]4-[2-(morpholin-4-yl)-methyl-5,6-dihydro-4H-cyclopentaimidazol-1-yl]benzamide,
(390) 3-chloro-N-[(1S)-1-(5-chloro-1H-benzimidazol-2-yl)ethyl]4-[2-(2-(morpholin-4-yl)-ethyl)-5,6-dihydro-4H-cyclopentaimidazol-1-yl]benzamide,
(391) 3-chloro-N-[(1S)-1-(5-chloro-1H-benzimidazol-2-yl)ethyl]4-[2-(morpholin-4-yl)-methyl-4,5,6,7-tetrahydrobenzimidazol-1-yl]benzamide,
(392) 3-chloro-N-[(1S)-1-(5-chloro-1H-benzimidazol-2-yl)ethyl]4-[2-(2-(morpholin-4-yl)-ethyl)-4,5,6,7-tetrahydrobenzimidazol-1-yl]benzamide,
(393) 3-chloro-N-[(1S)-1-(5-chloro-1H-benzimidazol-2-yl)ethyl]4-(2-oxohexahydrocyclopentaimidazol-1-yl)benzamide,
(394) N-[(1S)-1-(5-chloro-1H-benzimidazol-2-yl)ethyl]-4-(4-oxo-4,5,6,7-tetrahydropyrrol[3,2-c]pyridin-1-yl)-3-trifluoromethylbenzamide,
(395) 3-chloro-N-[(1S)-1-(5-chloro-1H-benzimidazol-2-yl)ethyl]-4-(4-oxooctahydropyrrol[3,2-c]pyridin-1-yl)benzamide,
(396) 3-chloro-N-[(1S)-1-(5-chloro-1H-benzimidazol-2-yl)ethyl]-4-(octahydrocyclopentapyrazin-1-yl)benzamide,
(397) 3-chloro-N-[(1S)-1-(5-chloro-1H-benzimidazol-2-yl)ethyl]-4-(2,3-dioxooctahydrocyclopentapyrazin-1-yl)benzamide,
(398) N-[(1S)-1-(5-chloro-1H-benzimidazol-2-yl)ethyl]-3-methyl-4-(2-oxo-2,5,6,7-tetrahydrocyclopentapyrazin-1-yl)benzamide,
(399) 3-chloro-N-[(1S)-1-(5-chloro-1H-benzimidazol-2-yl)ethyl]-4-(5,6,7,7a-tetrahydro-1H-pyrrol-[1,2-c]-imidazol-3-yl)benzamide,
(400) N-[(1S)-1-(5-chloro-1H-benzimidazol-2-yl)ethyl]-4-(3,4,4a,5,6,7-hexahydropyrrol-[1,2-c]pyrimidin-1-yl)-3-methylbenzamide,
(401) N-[(1R)-1-(5-chloro-1H-benzimidazol-2-yl)-2-(2,2,2-trifluoroethoxy)ethyl]-3-methyl-4-(pyrrolidin-1-ylcarbonyl)benzamide,
(402) N-[(1R)-1-(5-chloro-1H-benzimidazol-2-yl)-2-trifluoromethoxyethyl]-3-methyl-4-(pyrrolidin-1-ylcarbonyl)benzamide,
(403) N-[(1R)-1-(5-chloro-1H-benzimidazol-2-yl)-2-difluoromethoxyethyl]-3-methyl-4-(pyrrolidin-1-ylcarbonyl)benzamide,
(404) N-[(1R)-1-(5-chloro-1H-benzimidazol-2-yl)-2-fluoromethoxyethyl]-3-methyl-4-(pyrrolidin-1-ylcarbonyl)benzamide,
(405) 3-chloro-N-[(1S)-1-(5-chloro-1H-benzimidazol-2-yl)ethyl]-4-((2R)-2-dimethylamino-methylpyrrolidin-1-ylcarbonyl)benzamide,
(406) 3-chloro-N-[(1R)-1-(5-bromo-1H-benzimidazol-2-yl)-2-hydroxyethyl]4-(2,5-dihydropyrrol-1-ylcarbonyl)benzamide,
(407) 3-bromo-N-[(1R)-1-(5-bromo-1H-benzimidazol-2-yl)-2-hydroxyethyl]4-(pyrrolidin-1-ylcarbonyl)benzamide,
(408) 3-methyl-N-[(1R)-1-(5-bromo-1H-benzimidazol-2-yl)-2-hydroxyethyl]4-(pyrrolidin-1-ylcarbonyl)benzamide, the tautomers, stereoisomers, and salts thereof.
According to the invention, the following compounds of general formula I are of exceptional importance:
(1) N-[1-(5-chloro-1H-benzimidazol-2-yl)ethyl]-3-methyl-4-(2,5-dihydropyrrol-1-ylcarbonyl)benzamide,
(2) N-[1-(5-chloro-1H-benzimidazol-2-yl)ethyl]-3-methyl-4-(pyrrolidin-1-ylcarbonyl)benzamide,
(3) N-[1-(5-chloro-1H-benzimidazol-2-yl)ethyl]-3-ethyl-4-(pyrrolidin-1-ylcarbonyl)benzamide,
(4) (S)—N-[1-(5-chloro-1H-benzimidazol-2-yl)-2-(pyridin-4-yl)ethyl]-3-methyl-4-(pyrrolidin-1-ylcarbonyl)benzamide,
(5) (S)—N-[1-(5-chloro-1H-benzimidazol-2-yl)-2-(1H-imidazol-4-yl)ethyl]-3-methyl-4-(pyrrolidin-1-ylcarbonyl)benzamide,
(6) N-[1-(5-chloro-1H-benzimidazol-2-yl)ethyl]-3-chloro-4-(2-aminomethylpyrrolidin-1-ylcarbonyl)benzamide,
(7) 3-chloro-N-(5-chloro-1H-benzimidazol-2-ylmethyl)-4-(2-methylpyrrolidin-1-ylcarbonyl)benzamide,
(8) N-[1-(5-bromo-1H-benzimidazol-2-yl)ethyl]-3-methyl-4-(pyrrolidin-1-ylcarbonyl)benzamide,
(9) N-[(5-chloro-1H-benzimidazol-2-yl)phenylmethyl]-3-methyl-4-(pyrrolidin-1-ylcarbonyl)benzamide,
(10) N-[1-(5-chloro-1H-benzimidazol-2-yl)-5-benzyloxycarbonylaminopentyl]-3-methyl-4-(pyrrolidin-1-ylcarbonyl)benzamide,
(11) N-[1-(5-chloro-1H-benzimidazol-2-yl)ethyl]-3-chloro-4-(3-oxopiperazin-1-ylcarbonyl)benzamide,
(12) (S)—N-[1-(5-chloro-1H-benzimidazol-2-yl)]ethyl-3-methyl-4-(pyrrolidin-1-ylcarbonyl)benzamide,

(13) N-[1-(5-chloro-1H-benzimidazol-2-yl)]ethyl-3-bromo-4-(pyrrolidin-1-ylcarbonyl)benzamide,
(14) N-[1-(5-chloro-1H-benzimidazol-2-yl)]ethyl-3-trifluoromethyl-4-(pyrrolidin-1-ylcarbonyl)benzamide,
(15) N-[(1S)-1-(5-chloro-1H-benzimidazol-2-yl)ethyl]-3-methyl-4-[(2R/S)-2-aminomethylpyrrolidin-1-ylcarbonyl]benzamide,
(16) N-[(1S)-1-(5-chloro-1H-benzimidazol-2-yl)ethyl]-3-chloro-4-[(2R/S)-2-aminomethylpyrrolidin-1-ylcarbonyl)benzamide,
(17) N-[(1S)-1-(5-chloro-1H-benzimidazol-2-yl)ethyl]-3-chloro-4-[(2S)-2-aminomethylpyrrolidin-1-ylcarbonyl]benzamide,
(18) N-[(1S)-1-(5-chloro-1H-benzimidazol-2-yl)ethyl]-3-chloro-4-[(2R)-2-aminomethylpyrrolidin-1-ylcarbonyl]benzamide,
(19) N-[(1S)-1-(5-chloro-1H-benzimidazol-2-yl)ethyl]-3-chloro-4-[(2S)-2-(2-aminoethyl)pyrrolidin-1-ylcarbonyl]benzamide,
(20) N-[(1S)-1-(5-chloro-1H-benzimidazol-2-yl)-3-methylsulfanylpropyl]-3-chloro-4-[(2S)-2-(N-tert-butoxycarbonylaminomethyl)pyrrolidin-1-ylcarbonyl]benzamide,
(21) N-[(1S)-1-(5-chloro-1H-benzimidazol-2-yl)butyl]-3-chloro-4-[(2S)-2aminomethylpyrrolidin-1-ylcarbonyl]benzamide,
(22) N-[(1S)-1-(5-chloro-1H-benzimidazol-2-yl)-3-methylsulfonylpropyl]-3-chloro-4-[(2S)-2-(N-tert-butoxycarbonylaminomethyl)pyrrolidin-1-ylcarbonyl]benzamide,
(23) N-[(1S)-1-(5-chloro-1H-benzimidazol-2-yl)-3-methylsulfanylpropyl]-3-chloro-4-[(2S)-2-aminomethylpyrrolidin-1-ylcarbonyl]benzamide,
(24) N-[(1S)-1-(5-chloro-1H-benzimidazol-2-yl)-3-methylsulfinylpropyl]-3-chloro-4-[(2S)-2-aminomethylpyrrolidin-1-ylcarbonyl]benzamide,
(25) N-[(1S)-1-(5-chloro-1H-benzimidazol-2-yl)-3-methylsulfonylpropyl]-3-chloro-4-[(2S)-2-aminomethylpyrrolidin-1-ylcarbonyl]benzamide,
(26) N-[(1S)-5-(benzyloxycarbonylamino)-1-(5-chloro-1H-benzimidazol-2-yl)pentyl]-3-methyl-4-(pyrrolidin-1-ylcarbonyl)benzamide,
(27) N-[(1S)-1-(5-chloro-1H-benzimidazol-2-yl)-3-phenylpropyl]-3-methyl-4-(pyrrolidin-1-ylcarbonyl)benzamide,
(28) N-[(1S)-5-acetylamino-1-(5-chloro-1H-benzimidazol-2-yl)pentyl]-3-methyl-4-(pyrrolidin-1-ylcarbonyl)benzamide,
(29) N-[(1S)-1-(5-chloro-1H-benzimidazol-2-yl)-3-methylsulfanylpropyl]-3-methyl-4-(pyrrolidin-1-ylcarbonyl)benzamide,
(30) rac.-N-[1-(5-chloro-1H-benzimidazol-2-yl)-2-hydroxyethyl]-3-methyl-4-(pyrrolidin-1-ylcarbonyl)benzamide,
(31) rac.-N-[2-acetylamino-1-(5-chloro-1H-benzimidazol-2-yl)ethyl]-3-methyl-4-(pyrrolidin-1-ylcarbonyl)benzamide,
(32) rac.-N-[2-benzoylamino-1-(5-chloro-1H-benzimidazol-2-yl)ethyl]-3-methyl-4-(pyrrolidin-1-ylcarbonyl)benzamide,
(33) rac.-N-[1-(5-chloro-1H-benzimidazol-2-yl)-3-hydroxycarbonylpropyl]-3-methyl-4-(pyrrolidin-1-ylcarbonyl)benzamide,
(34) N-[(1S)-1-(5-chloro-1H-benzimidazol-2-yl)-3-hydroxycarbonylpropyl]-3-methyl-4-(pyrrolidin-1-ylcarbonyl)benzamide,
(35) rac.-N-[3-benzyloxycarbonyl-1-(5-chloro-1H-benzimidazol-2-yl)propyl]-3-methyl-4-(pyrrolidin-1-ylcarbonyl)benzamide,
(36) N-[(1S)-3-benzyloxycarbonyl-1-(5-chloro-1H-benzimidazol-2-yl)propyl]-3-methyl-4-(pyrrolidin-1-ylcarbonyl)benzamide,
(37) rac.-N-[1-(5-chloro-1H-benzimidazol-2-yl)-3-ethylamino carbonylpropyl]-3-methyl-4-(pyrrolidin-1-ylcarbonyl)benzamide,
(38) rac.-N-[1-(5-chloro-1H-benzimidazol-2-yl)-3-(pyrrolidin-1-ylcarbonyl)propyl]-3-methyl-4-(pyrrolidin-1-ylcarbonyl)benzamide,
(39) N-[(1S)-1-(5-chloro-1H-benzimidazol-2-yl)-3-(pyrrolidin-1-ylcarbonyl)propyl]-3-methyl-4-(pyrrolidin-1-ylcarbonyl)benzamide,
(40) rac.-N-[1-(5-chloro-1H-benzimidazol-2-yl)-3-diethylaminocarbonylpropyl]-3-methyl-4-(pyrrolidin-1-ylcarbonyl)benzamide,
(41) N-[(1R)-1-(5-chloro-1H-benzimidazol-2-yl)-2-hydroxyethyl]-3-methyl-4-(pyrrolidin-1-ylcarbonyl)benzamide,
(42) N-[(1R,2R)-1-(5-chloro-1H-benzimidazol-2-yl)-2-hydroxypropyl]-3-methyl-4-(pyrrolidin-1-ylcarbonyl)benzamide,
(43) N-[(1S)-2-acetylamino-1-(5-chloro-1H-benzimidazol-2-yl)ethyl]-3-methyl-4-(pyrrolidin-1-ylcarbonyl)benzamide,
(44) N-[(1S)-1-(5-chloro-1H-benzimidazol-2-yl)-2-methylsulfonylaminoethyl]-3-methyl-4-(pyrrolidin-1-ylcarbonyl)benzamide,
(45) rac.-N-[-(5-chloro-1H-benzimidazol-2-yl)-2-methoxyethyl]-3-methyl-4-(pyrrolidin-1-ylcarbonyl)benzamide,
(46) 3-bromo-N-[(1S)-1-(5-chloro-1H-benzimidazol-2-yl)-2-ethyl]-4-(2,5-dihydropyrrol-1-ylcarbonyl)benzamide,
(47) N-[(1S)-1-(5-chloro-1H-benzimidazol-2-yl)-3-methoxypropyl]-3-methyl-4-(pyrrolidin-1-ylcarbonyl)benzamide,
(48) N-[(1S)-4-acetylamino-1-(5-chloro-1H-benzimidazol-2-yl)butyl]-3-methyl-4-(pyrrolidin-1-ylcarbonyl)benzamide,
(49) rac.-N-[(5-chloro-1H-benzimidazol-2-yl)-(3-chlorophenyl)methyl]-3-methyl-4-(pyrrolidin-1-ylcarbonyl)benzamide,
(50) N-[(1R)-2-(C-tert-butoxycarbonylmethyloxy)-1-(5-chloro-1H-benzimidazol-2-yl)ethyl]-3-methyl-4-(pyrrolidin-1-ylcarbonyl)benzamide,
(51) 3-chloro-N-[(1S)-1-(5-chloro-1H-benzimidazol-2-yl)ethyl]-4-(3-oxopiperazin-1-ylcarbonyl)benzamide,
(52) N-[(1S)-1-(5-chloro-1H-benzimidazol-2-yl)-3-methylsulfinylpropyl]-3-methyl-4-(pyrrolidin-1-ylcarbonyl)benzamide,
(53) N-[(1S)-1-(5-chloro-1H-benzimidazol-2-yl)-3-methylsulfonylpropyl]-3-methyl-4(pyrrolidin-1-ylcarbonyl)benzamide,
(54) rac.-N-[1-(5-chloro-1H-benzimidazol-2-yl)phenylmethyl]-4-(2,5-dihydropyrrol-1-ylcarbonyl)-3-methylbenzamide,
(55) N-[(1S)-1-(5-chloro-1H-benzimidazol-2-yl)propyl]-3-methyl-4-(pyrrolidin-1-ylcarbonyl)benzamide,
(56) N-[(1S)-3-(benzyloxycarbonylamino)-1-(5-chloro-1H-benzimidazol-2-yl)propyl]-3-methyl-4-(pyrrolidin-1-ylcarbonyl)benzamide,
(57) N-[(1S)-1-(5-chloro-1H-benzimidazol-2-yl)-3-methylsulfonylaminopropyl]-3-methyl-4-(pyrrolidin-1-ylcarbonyl)benzamide,
(58) N-[(1S)-1-(5-chloro-1H-benzimidazol-2-yl)-3-(2-oxoimidazolidin-1-yl)propyl]-3-methyl-4-(pyrrolidin-1-ylcarbonyl)benzamide,

(59) N-{(1S)-1-(5-chloro-1H-benzimidazol-2-yl)-3-[3-(2-chloroethyl)ureido]propyl}-3-methyl-4-(pyrrolidin-1-ylcarbonyl)benzamide,

(60) 3-chloro-N-[(1R)-1-(5-chloro-1H-benzimidazol-2-yl)-2-ethylsulfanylethyl]-4-(pyrrolidin-1-ylcarbonyl)benzamide,

(61) N-[(1S)-1-(5-chloro-1H-benzimidazol-2-yl)butyl]-3-methyl-4-(pyrrolidin-1-ylcarbonyl)benzamide,

(62) N-[(1S)-1-(5-chloro-1H-benzimidazol-2-yl)-3-hydroxypropyl]-3-methyl-4-(pyrrolidin-1-ylcarbonyl)benzamide,

(63) 3-bromo-N-[(1S)-1-(5-chloro-1H-benzimidazol-2-yl)-3-methylsulfanylpropyl]-4-(pyrrolidin-1-ylcarbonyl)benzamide,

(64) 3-chloro-N-[(1S)-1-(5-chloro-1H-benzimidazol-2-yl)-3-(methylsulfanyl)propyl]-4-(pyrrolidin-1-ylcarbonyl)benzamide,

(65) 3-bromo-N-[(1S)-1-(5-chloro-1H-benzimidazol-2-yl)-3-(methylsulfonyl)propyl]-4-(pyrrolidin-1-ylcarbonyl)benzamide,

(66) 3-bromo-N-[(1S)-1-(5-chloro-1H-benzimidazol-2-yl)-3-methylsulfinylpropyl]-4-(pyrrolidin-1-ylcarbonyl)benzamide,

(67) 3-chloro-N-[(1S)-1-(5-chloro-1H-benzimidazol-2-yl)ethyl]4-[(2R,S)-(2-methylpyrrolidin-1-ylcarbonyl)]benzamide,

(68) 3-chloro-N-[(1S)-1-(5-chloro-1H-benzimidazol-2-yl)ethyl]4-[(2R)-2-(methyl-sulfonylaminomethyl)pyrrolidin-1-ylcarbonyl]benzamide,

(69) (1R)-3-bromo-N-[1-(5-chloro-1H-benzimidazol-2-yl)-2-hydroxyethyl]-4-(2,5-dihydropyrrol-1-ylcarbonyl)benzamide,

(70) (1R)-3-methyl-N-[1-(5-chloro-1H-benzimidazol-2-yl)-2-methoxyethyl]-4-(2,5-dihydropyrrol-1-ylcarbonyl)benzamide,

(71) (1R)-3-chloro-N-[1-(5-chloro-1H-benzimidazol-2-yl)-2-hydroxyethyl]4-(2,5-dihydropyrrol-1-ylcarbonyl)benzamide,

(72) N-[(1S)-1-(5-chloro-1H-benzimidazol-2-yl)-3-(pyridin-4-yl)propyl]-3-methyl-4-(pyrrolidin-1-ylcarbonyl)benzamide,

(73) N-[(1S)-3-(benzyloxycarbonylamino)-1-(5-chloro-1H-benzimidazol-2-yl)propyl]-3-methyl-4-(2,5-dihydropyrrol-1-ylcarbonyl)benzamide,

(74) N-{(1S)-1-(5-chloro-1H-benzimidazol-2-yl)-3-[(3R,S)-3-dimethylaminopyrrolidin-1-yl]carbonylpropyl}-3-methyl-4-(pyrrolidin-1-ylcarbonyl)benzamide,

(75) N-{(1S)-1-(5-chloro-1H-benzimidazol-2-yl)-3-[(3R)-3-hydroxypyrrolidin-yl]carbonylpropyl}-3-methyl-4-(pyrrolidin-1-ylcarbonyl)benzamide,

(76) N-{(1S)-1-(5-chloro-1H-benzimidazol-2-yl)-3-[(3S)-3-hydroxypyrrolidin-1-ylcarbonyl]propyl}-3-methyl-4-(pyrrolidin-1-ylcarbonyl)benzamide,

(77) N-{(1S)-1-(5-chloro-1H-benzimidazol-2-yl)-3-[(2R)-2-hydroxymethylpyrrolidin-1-ylcarbonyl]propyl}-3-methyl-4-(pyrrolidin-1-ylcarbonyl)benzamide,

(78) N-{(1S)-1-(5-chloro-1H-benzimidazol-2-yl)-3-[(2'-2-hydroxymethylpyrrolidin-1-ylcarbonyl]propyl}-3-methyl-4-(pyrrolidin-1-ylcarbonyl)benzamide,

(79) N-[(1S)-1-(5-chloro-1H-benzimidazol-2-yl)-3-(2-methyl-2,6-diazaspiro[3.4]oct-6-ylcarbonyl)propyl]-3-methyl-4-(pyrrolidin-1-ylcarbonyl)benzamide,

(80) N-{(1S)-3-[(1S)-2-(aminocarbonyl)pyrrolidin-1-ylcarbonyl]-1-(5-chloro-1H-benzimidazol-2-yl)propyl}-3-methyl-4-(pyrrolidin-1-ylcarbonyl)benzamide,

(81) N-{(1S)-3-[(1R)-2-(aminocarbonyl)pyrrolidin-1-ylcarbonyl]-1-(5-chloro-1H-benzimidazol-2-yl)propyl}-3-methyl-4-(pyrrolidin-1-ylcarbonyl)benzamide,

(82) N-{(1S)-1-(5-chloro-1H-benzimidazol-2-yl)-3-[(2S)-2-tert-butoxycarbonylamino-methylpyrrolidin-1-ylcarbonyl]propyl}-3-methyl-4-(pyrrolidin-ylcarbonyl)benzamide,

(83) N-{(1S)-1-(5-chloro-1H-benzimidazol-2-yl)-3-[(2R)-2-tert-butoxycarbonylamino-methylpyrrolidin-1-ylcarbonyl]propyl}-3-methyl-4-(pyrrolidin-1-ylcarbonyl)benzamide,

(84) N-{(1S)-1-(5-chloro-1H-benzimidazol-2-yl)-3-[(3R,S)-hydroxymethylpyrrolidin-yl)carbonyl]propyl}-3-methyl-4-(pyrrolidin-1-ylcarbonyl)benzamide,

(85) N-[(1S)-1-(5-chloro-1H-benzimidazol-2-yl)-3-(1,1-dioxo-1-thiomorpholin-4-ylcarbonyl]propyl]-3-methyl-4-(pyrrolidin-1-ylcarbonyl)benzamide,

(86) N-[(1S)-1-(5-chloro-1H-benzimidazol-2-yl)-3-[(4-methyl-3-oxopiperazin-1-ylcarbonyl)propyl]-3-methyl-4-(pyrrolidin-1-ylcarbonyl)benzamide,

(87) N-[(1R)-1-(5-chloro-1H-benzimidazol-2-yl)-2-methoxyethyl]-3-methyl-4-(pyrrolidin-1-ylcarbonyl)benzamide,

(88) 3-chloro-N-[(1R)-1-(5-chloro-1H-benzimidazol-2-yl)-2-methoxyethyl]-4-(2,5-dihydropyrrol-1-ylcarbonyl)benzamide,

(89) 3-bromo-N-[(1R)-1-(5-chloro-1H-benzimidazol-2-yl)-2-methoxyethyl]4-(pyrrolidin-1-ylcarbonyl)benzamide,

(90) 4-[(2R)-2-(2-aminoethyl)pyrrolidin-1-ylcarbonyl]-3-chloro-N-[(1S)-1-(5-chloro-1H-benzimidazol-2-yl)ethyl]benzamide,

(91) 3-bromo-N-[(1R)-1-(5-chloro-1H-benzimidazol-2-yl)-2-methoxyethyl]-4-(2,5-dihydropyrrol-1-ylcarbonyl)benzamide,

(92) 4-(3-aminomethyl-5,6-dihydro-4H-cyclopentapyrazol-1-yl)-N-[(1S)-1-(5-chloro-1H-benzimidazol-2-yl)ethyl]-3-trifluoromethylbenzamide,

(93) 3-methyl-N-[(1R)-1-(5-chloro-1H-benzimidazol-2-yl)-2-hydroxyethyl]-4-(2,5-dihydropyrrol-1-ylcarbonyl)benzamide,

(94) N-{(1S)-1-(5-chloro-1H-benzimidazol-2-yl)-3-[(2S)-2-aminomethylpyrrolidin-1-ylcarbonyl]propyl}-3-methyl-4-(pyrrolidin-1-ylcarbonyl)benzamide,

(95) N-{(1S)-1-(5-chloro-1H-benzimidazol-2-yl)-3-[(2R)-2-aminomethylpyrrolidin-1ylcarbonyl]propyl}-3-methyl-4-(pyrrolidin-1-ylcarbonyl)benzamide,

(96) 3-bromo-N-[(1R)-1-(5-chloro-1H-benzimidazol-2-yl)-2-hydroxyethyl]-4-(pyrrolidin-1-ylcarbonyl)benzamide,

(97) N-[(1R)-1-(5-chloro-1H-benzimidazol-2-yl)-2-methoxyethyl]-4-(2,5-dihydropyrrol-1-ylcarbonyl)-3-trifluoromethylbenzamide,

(98) N-[(1R)-1-(5-chloro-1H-benzimidazol-2-yl)-2-methoxyethyl]-4-(pyrrolidin-1-ylcarbonyl)-3-trifluoromethylbenzamide,

(99) N-[(1S)-1-(5-chloro-1H-benzimidazol-2-yl)-3-(2-isopropylaminothiazol-4-yl)propyl]-3-methyl-4-(pyrrolidin-1-ylcarbonyl)benzamide, (100) N-[(1S)-1,3-bis-(5-chloro-1H-benzimidazol-2-yl)propyl]-3-methyl-4-(pyrrolidin-1-ylcarbonyl)benzamide, (101) 3-chloro-N-[(1S)-1-(5-chloro-1H-benzimidazol-2-yl)ethyl]-4-[(2R/S)-2-dimethyl-aminomethylpyrrolidin-1-ylcarbonyl]benzamide, (102) rac.-N-[(5-chloro-1H-benzimidazol-2-yl)thiophen-3-ylmethyl]-4-(2,5-dihydropyrrol-1-ylcarbonyl)-3-methylbenzamide, (103) N-[(1S)-1-(5-chloro-1H-benzimidazol-2-yl)-3-methanesulfonylaminopropyl]-4-(2,5-dihydropyrrol-1-ylcarbonyl)-3-methylbenzamide,
(104) 3-bromo-N-[(1S)-1-(5-chloro-1H-benzimidazol-2-yl)ethyl]-4-(thiazolidin-3-ylcarbonyl)benzamide,
(105) N-[(1S)-1-(5-chloro-1H-benzimidazol-2-yl)butyl]-4-(2,5-dihydropyrrol-1-ylcarbonyl)-3-methylbenzamide,
(106) 3-chloro-N-[(1S)-1-(5-chloro-1H-benzimidazol-2-yl)butyl]-4-(2,5-dihydropyrrol-1-ylcarbonyl)benzamide,
(107) 3-bromo-N-[(1S)-1-(5-chloro-1H-benzimidazol-2-yl)butyl]-4-(2,5-dihydropyrrol-1-ylcarbonyl)benzamide,
(108) N-[(1S)-1-(5-chloro-1H-benzimidazol-2-yl)ethyl]-4-(2,5-dihydropyrrol-1-ylcarbonyl)-3-methylbenzamide,
(109) 3-chloro-N-[(1S)-1-(5-chloro-1H-benzimidazol-2-yl)ethyl]-4-(2,5-dihydropyrrol-1-ylcarbonyl)benzamide,
(110) 3-bromo-N-[(1S)-1-(5-bromo-1H-benzimidazol-2-yl)ethyl]-4-(2,5-dihydropyrrol-1-ylcarbonyl)benzamide,
(111) 4-(N-acetyl-N-cyclopentylamino)-N-[(1S)-1-(5-chloro-1H-benzimidazol-2-yl)-2-methylsulfanylethyl]-3-methylbenzamide,
(112) N-[(1S)-1-(5-chloro-1H-benzimidazol-2-yl)ethyl]-4-(2,5-dihydropyrrol-1-ylcarbonyl)-3-trifluoromethylbenzamide,
(113) 3-chloro-N-[(1S)-1-(5-chloro-1H-benzimidazol-2-yl)ethyl]-4-[(2R)-2-(pyrrolidin-1-ylmethyl)pyrrolidin-1-ylcarbonyl]benzamide,
(114) 3-bromo-N-[(1R)-1-(5-bromo-1H-benzimidazol-2-yl)-2-methoxyethyl]-4-(2,5-di-hydropyrrol-1-ylcarbonyl)benzamide,
(115) N-[(1S)-1-(5-chloro-1H-benzimidazol-2-yl)-3-(1,1-dioxoisothiazolidin-2-yl)propyl]-3-methyl-4-(pyrrolidin-1-ylcarbonyl)benzamide,
(116) 3-bromo-N-[(1R)-1-(5-chloro-1H-benzimidazol-2-yl)-2-ethoxyethyl]-4-(2,5-dihydropyrrol-1-ylcarbonyl)benzamide,
(117) N-[(1R)-2-allyloxy-1-(5-chloro-1H-benzimidazol-2-yl)ethyl]-4-(2,5-dihydropyrrol-1-ylcarbonyl)-3-methylbenzamide,
(118) 3-bromo-N-[(1R)-1-(5-chloro-1H-benzimidazol-2-yl)-2-prop-2-ynyloxyethyl]-4-(2,5-dihydropyrrol-1-ylcarbonyl)benzamide,
(119) N-[(1S)-1-(5-chloro-1H-benzimidazol-2-yl)-3-(1H-tetrazol-5-yl)propyl]-3-methyl-4-(pyrrolidin-1-ylcarbonyl)benzamide,
(120) N-[(1R)-1-(5-chloro-1H-benzimidazol-2-yl)-2-hydroxyethyl]-4-(2,5-dihydropyrrol-1-ylcarbonyl)-3-trifluoromethylbenzamide, the tautomers, stereoisomers, and salts thereof.

The present invention also relates to the following embodiments:

In the above general formula I in a 12th embodiment $R^1$ denotes an amino, $C_{1-5}$-alkylamino, $C_{3-7}$-cycloalkylamino or (phenyl-$C_{1-3}$-alkyl)-amino group which may additionally be substituted in each case at the amino nitrogen atom by a phenylcarbonyl or phenylsulfonyl group or by a $C_{1-5}$-alkyl or $C_{1-5}$-alkylcarbonyl group optionally substituted in the alkyl moiety by a hydroxy, $C_{1-3}$-alkyloxy or carboxy group, a group which may be converted in vivo into a carboxy group, an amino, $C_{1-3}$-alkylamino, di-($C_{1-3}$-alkyl)-amino or a 4- to 7-membered cycloalkyleneimino group, while in the abovementioned substituted $C_{1-5}$-alkyl group two heteroatoms are separated from one another by at least two carbon atoms, a 4- to 7-membered cycloalkyleneiminocarbonyl or cycloalkyleneiminosulfonyl group, while the cycloalkyleneimino moiety in the carbon skeleton may be substituted by one or two $C_{1-3}$-alkyl, $C_{2-3}$-alkenyl, $C_{2-3}$-alkynyl, hydroxy-$C_{1-3}$-alkyl, $C_{1-3}$-alkyloxy-$C_{1-3}$-alkyl, phenyl-$C_{1-3}$-alkyl, diphenyl-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, phenylamino-$C_{1-3}$-alkyl, $C_{1-5}$-alkylamino-$C_{1-3}$-alkyl, di-($C_{1-5}$-alkyl)-amino-$C_{1-3}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-3}$-alkylsulfonylamino-$C_{1-3}$-alkyl, aminocarbonylamino-$C_{1-3}$-alkyl, $C_{1-3}$-alkylaminocarbonylamino-$C_{1-3}$-alkyl, di-($C_{1-3}$-alkyl)-aminocarbonylamino-$C_{1-3}$-alkyl, carboxy, $C_{1-3}$-alkyloxycarbonyl, benzyloxycarbonyl, $C_{1-3}$-alkylcarbonyl, aminocarbonyl, $C_{1-3}$-alkylaminocarbonyl, di-($C_{1-3}$-alkyl)-aminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, a 4- to 7-membered cycloalkyleneiminocarbonyl, aminocarbonyl-$C_{1-3}$-alkylaminocarbonyl, hydroxy, $C_{1-3}$-alkyloxy, allyloxy, propargyloxy, benzyloxy, amino, $C_{1-3}$-alkylamino, di-($C_{1-3}$-alkyl)-amino, a 4- to 7-membered cycloalkyleneimino, trifluoromethylcarbonylamino, a mono-, di- or trifluoromethylamino, an aryl or a 5- to 6-membered heteroaryl group, with the proviso that in the substitution of a methylene group adjacent to the imino group two heteroatoms are separated from one another by at least two carbon atoms, and/or a methylene group in the 3 position of a 5-membered cycloalkyleneimino group may be replaced by a sulfur atom, a sulfinyl or sulfonyl group or a methylene group in the 4 position of a 6- or 7-membered cycloalkyleneimino group may be replaced by an oxygen or sulfur atom, a carbonyl, sulfinyl or sulfonyl group or by an —NH— group optionally substituted by a $C_{1-3}$-alkyl, hydroxy, formyl or $C_{1-3}$-alkylcarbonyl group, while additionally a methylene group adjacent to the abovementioned —NH— group may be replaced by a carbonyl group, with the proviso that in the substitution of the abovementioned 5- to 7-membered cycloalkyleneimino groups wherein a methylene group is replaced by an oxygen or sulfur atom, a sulfinyl or sulfonyl group, two heteroatoms are separated from one another by at least two carbon atoms, a 5- to 7-membered cycloalkenyleneiminocarbonyl or cycloalkenyleneiminosulfonyl group optionally substituted by one or two $C_{1-3}$-allyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-6}$-cycloalkylamino-$C_{1-3}$-alkyl, aryl, aryl-$C_{1-3}$-alkyl, heteroaryl, heteroaryl-$C_{1-3}$-alkyl, aminocarbonyl, $C_{1-3}$-alkylaminocarbonyl, di-($C_{1-3}$-alkyl)-aminocarbonyl or 4- to 7-membered cycloalkyleneiminocarbonyl groups, while the double bond is not bound to a nitrogen atom and may be fused to a 5- or 6-membered heteroaryl group, an aminocarbonyl or aminosulfonyl group optionally substituted by one or two $C_{1-5}$-alkyl, $C_{3-6}$-cycloalkyl or 5- to 7-membered cycloalkyleneimino groups, while the substituents may be identical or different and
in each, case one of the $C_{1-5}$-alkyl groups may be substituted by one or two hydroxy-$C_{1-3}$-alkyl, $C_{1-3}$-alkoxy-$C_{1-3}$-alkyl, benzyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylaminocarbonyl, N—($C_{3-7}$-cycloalkyl)-$C_{1-3}$-alkylaminocarbonyl, N-(phenyl-$C_{1-3}$-alkyl)-$C_{1-5}$-alkylaminocarbonyl, di-($C_{1-3}$-alkyl)-aminocarbonyl or a 4- to 7-membered cycloalkyleneiminocarbonyl group, a $C_{1-7}$-alkylcarbonyl or $C_{3-7}$-cycloalkylcarbonyl group, while
the methylene group in the 2, 3 or 4 position in a $C_{3-7}$-cycloalkylcarbonyl group may be replaced by an oxygen or sulfur atom, a carbonyl, sulfinyl, sulfonyl or a —NH— group, wherein:
the hydrogen atom of the —NH— group may be replaced by a $C_{1-3}$-alkyl or $C_{1-3}$-alkylcarbonyl group, a phenylcarbonyl or heteroarylcarbonyl group which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while
the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group and/or
the hydrogen atom of the —NH— group may be replaced by a $C_{1-3}$-alkyl or $C_{1-3}$-alkyl-carbonyl group, and/or
a —CH$_2$—CH$_2$— group in a 5- to 7-membered cycloalkyleneimino group may be replaced by a —NH—CO—, —CO—NH—, —CO—N(CH$_3$)— or a —N(CH$_3$)—CO— group or
a methylene group, which is adjacent to the nitrogen atom, in a 5- to 7-membered cycloalkyleneimino group may be replaced by a carbonyl group, or a group of formula

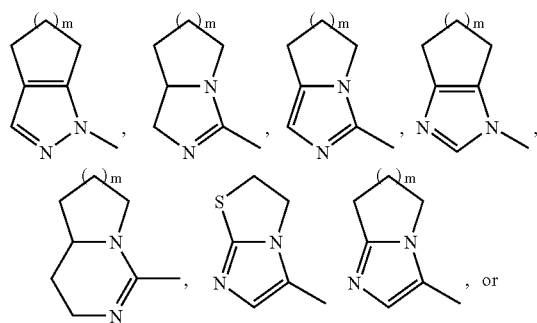

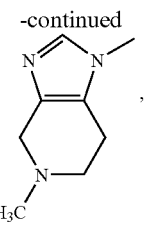

wherein in the heterocyclic moiety in each case a hydrogen atom may be replaced by a $C_{1-3}$-alkyloxycarbonyl, $C_{1-5}$-alkyloxycarbonylamino-$C_{1-3}$-alkyl, methylsulfonylmethyl, amino-$C_{1-3}$-alkyl, $C_{1-3}$-alkylamino-$C_{1-3}$-alkyl, di-($C_{1-3}$-alkyl)-amino-$C_{1-3}$-alkyl, aminocarbonyl, $C_{1-3}$-alkylaminocarbonyl or di-($C_{1-3}$-alkyl)-aminocarbonyl group and
m denotes the number 1 or 2, $R^2$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, $C_{1-3}$-alkoxy, a mono-, di- or trifluoromethoxy group, $R^3$ denotes a hydrogen atom or a $C_{1-3}$-alkyl group, $R^4$ denotes a hydrogen atom or a straight-chain or branched $C_{1-5}$-alkyl group which is optionally substituted by a fluorine atom, a mono-, di- or trifluoromethyl, a hydroxy, a $C_{1-3}$-alkyloxy group wherein the hydrogen atoms may be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-3}$-alkyloxy, $C_{1-5}$-alkyloxycarbonyl-$C_{1-3}$-alkyloxy, $C_{1-8}$-alkyloxycarbonylamino, chloro-$C_{1-3}$-alkylaminocarbonylamino, mercapto, $C_{1-3}$-alkylsulfanyl, $C_{1-3}$-alkylsulfinyl, $C_{1-3}$-alkylsulfonyl, carboxy, benzyloxycarbonyl, aminocarbonyl, $C_{1-3}$-alkylaminocarbonyl, di-($C_{1-3}$-alkyl)-aminocarbonyl, aminosulfonyl, amino, $C_{1-3}$-alkylamino, di-($C_{1-3}$-alkyl)-amino, a 4- to 7-membered cycloalkyleneimino, $C_{1-5}$-alkylcarbonylamino, $C_{1-3}$-alkylsulfonylamino, $C_{3-6}$-cycloalkylcarbonylamino, benzyloxycarbonylamino, phenylcarbonylamino or guanidino group, a 4- to 7-membered cycloalkyleneiminocarbonyl-$C_{1-3}$-alkyl group, while
a methylene group of the cycloalkyleneimino moiety may be substituted by a $C_{1-3}$-alkyl group optionally substituted by a hydroxy, amino, $C_{1-3}$-alkylamino, di-($C_{1-3}$-alkyl)-amino, a 4- to 7-membered cycloalkyleneimino or $C_{1-5}$-alkyloxycarbonylamino group and a methylene group of the cycloalkyleneimino moiety not adjacent to the imino group may be substituted by a hydroxy, amino, $C_{1-3}$-alkylamino, di-($C_{1-3}$-alkyl)-amino, aminocarbonyl, $C_{1-3}$-alkylaminocarbonyl or di-($C_{1-3}$-alkyl)-aminocarbonyl group, and/or
a methylene group in the 4 position of a 6- or 7-membered cycloalkyleneimino group may be replaced by an oxygen or sulfur atom, by a carbonyl, sulfinyl, sulfonyl, or by an —NH— group optionally substituted by a $C_{1-3}$-alkyl group and additionally a methylene group adjacent to an abovementioned —NH— or —N($C_{1-3}$-alkyl)-group may be replaced by a carbonyl group, a $C_{1-3}$-alkyl group which is terminally substituted by a group of formula

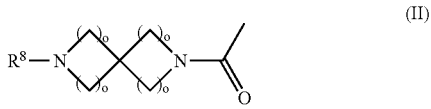

(II)

wherein:
o in each case denotes one of the numbers 1 or 2, and
$R^8$ denotes a hydrogen atom, a $C_{1-3}$-alkyl or $C_{1-3}$-alkyl-carbonyl group, a phenyl or heteroaryl, phenyl-$C_{1-3}$-alkyl or heteroaryl-$C_{1-3}$-alkyl group which is optionally substituted by a fluorine, chlorine or bromine atom, a hydroxy, $C_{1-4}$-alkyloxy, a mono-, di- or trifluoromethoxy, benzyloxy, carboxy-$C_{1-3}$-alkyloxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, a 4- to 7-membered cycloalkyleneiminocarbonyl-$C_{1-3}$-alkoxy, carboxy or $C_{1-3}$-alkyloxycarbonyl group, a $C_{3-6}$-cycloalkyl or a 4- to 7-membered cycolalkyleneimino group, optionally substituted by a $C_{1-3}$-alkylcarbonyl or $C_{1-4}$-alkyloxycarbonyl group, which is bound via a carbon atom, or a 4- to 7-membered cycloalkyl-$C_{1-3}$-alkyl or cycloalkyleneimino-$C_{1-3}$-alkyl group wherein in the cyclic moiety one or two methylene groups may be replaced by an —NH— group optionally substituted by a $C_{1-3}$-alkyl or $C_{1-3}$-alkylcarbonyl group and wherein one or two of the methylene groups adjacent to an —NH— or —N($C_{1-3}$-alkyl)-group may each be replaced by a carbonyl group, with the proviso that a cycloalkyl group as hereinbefore defined wherein two —NH— or —N($C_{1-3}$-alkyl)-groups are separated from one another by precisely one —CH$_2$— group are excluded, $R^5$ denotes a hydrogen atom or a $C_{1-3}$-alkyl group or $R^4$ and $R^5$ together with the carbon atom to which they are bound denote a $C_{3-7}$-cycloalkyl group, while
one of the methylene groups of the $C_{3-7}$-cycloalkyl group may be replaced by a imino, $C_{1-3}$-alkylimino, acylimino or sulfonylimino group, A denotes a carbonylamino or aminocarbonyl group, while the hydrogen atom of the amino function may optionally be substituted by a $C_{1-3}$-alkyl group, and B denotes a group of formula

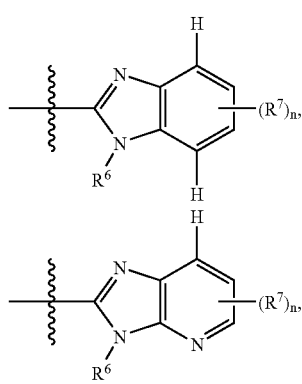

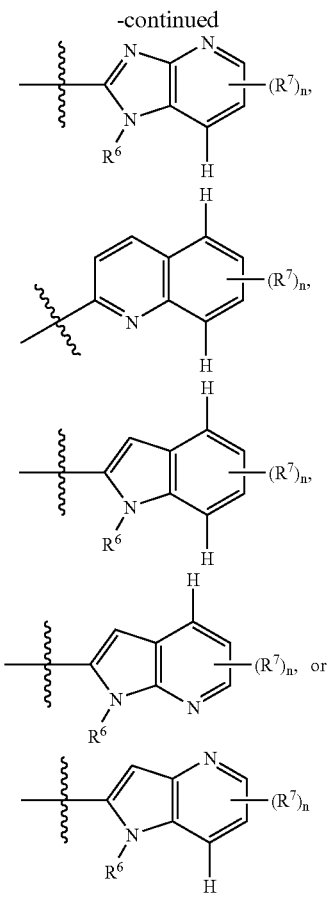

wherein:
n denotes the number 1 or 2,
$R^6$ denotes a hydrogen atom or a $C_{1-3}$-alkyl, hydroxy, carboxy-$C_{1-3}$-alkyl, $C_{1-3}$-alkyloxycarbonyl-$C_{1-3}$-alkyl, amino, or $C_{1-3}$-alkylamino group, and
$R^7$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy, amino, nitro or cyano group, while, unless otherwise stated, by the term "heteroaryl group" is meant a monocyclic 5- or 6-membered heteroaryl group optionally substituted in the carbon skeleton by a fluorine, chlorine, bromine or iodine atom, a $C_{1-3}$-alkyl, $C_{1-3}$-alkyloxy, carboxy, $C_{1-3}$-alkoxy-carbonyl or $C_{1-3}$-alkoxycarbonylamino group, while
the 6-membered heteroaryl group contains one, two or three nitrogen atoms, and
the 5-membered heteroaryl group contains an imino group optionally substituted by a $C_{1-3}$-alkyl or phenyl-$C_{1-3}$-alkyl group, or an oxygen or sulfur atom or
an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or phenyl-$C_{1-3}$-alkyl group or an oxygen or sulfur atom and additionally a nitrogen atom or
an imino group optionally substituted by a $C_{1-3}$-alkyl or phenyl-$C_{1-3}$-alkyl group and two or three nitrogen atoms, and moreover a phenyl ring may be fused to the above-mentioned monocyclic heteroaryl groups via two adjacent carbon atoms and the bond is effected via a nitrogen atom or via a carbon atom of the heterocyclic moiety or a fused-on phenyl ring, while the alkyl and alkoxy groups contained in the definitions which have more than two carbon atoms may, unless otherwise stated, be straight-chain or branched, and the hydrogen atoms of the methyl or ethyl groups contained in the definitions may be wholly or partly replaced by fluorine atoms.

A 13th embodiment of the present invention comprises those compounds of the above general formula I, wherein:

$R^1$, $R^2$, $R^4$, $R^5$, A and B are defined as described in the 12th embodiment and $R^3$ denotes the hydrogen atom, the tautomers, the diastereomers, the enantiomers, the mixtures thereof and the salts thereof.

A 14th embodiment of the present invention comprises the compounds of the above general formula (Ia), wherein:

$R^1$, $R^2$, $R^4$, $R^5$ and B are defined as described in the 12th embodiment, while $R^4$ does not denote the hydrogen atom, and $R^6$ denotes the hydrogen atom, the tautomers, the diastereomers, the enantiomers, the mixtures thereof and the salts thereof.

A 15th embodiment of the present invention comprises the compounds of the above general formula I, wherein:

$R^1$ to $R^5$ and A are defined as described in the 12th embodiment, while $R^2$ does not denote the hydrogen atom, and B denotes a group of formula

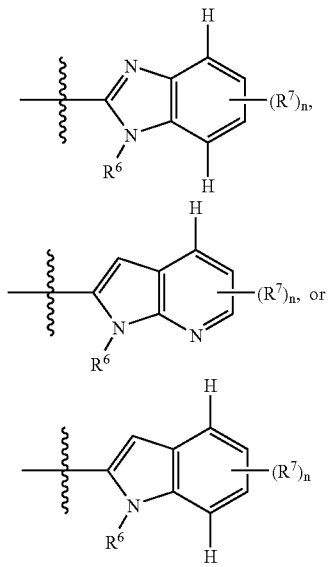

while n, $R^6$ and $R^7$ are defined as described in the first embodiment, the tautomers, the enantiomers, the diastereomers, the mixtures thereof and the salts thereof.

A 16th embodiment comprises those compounds of the above general formula I, wherein:

$R^1$, $R^2$, $R^4$, $R^5$, A and B are defined as described in the 15th embodiment and $R^3$ denotes the hydrogen atom, the tautomers, the diastereomers, the enantiomers, the mixtures thereof and the salts thereof.

A 17th embodiment of the present invention comprises the compounds of the above general formula (Ib), wherein:

$R^1$, $R^2$, $R^4$ and $R^5$ are defined as in the 15th embodiment, while $R^4$ does not denote the hydrogen atom, and $R^7$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkyloxy, trifluoromethoxy, amino, nitro or cyano group, the tautomers, the diastereomers, the enantiomers, the mixtures thereof and the salts thereof.

An 18th embodiment of the present invention comprises the compounds of the above general formula I, wherein:

$R^1$ denotes an amino, $C_{1-5}$-alkylamino, $C_{3-7}$-cycloalkylamino or (phenyl-$C_{1-3}$-alkyl)-amino group which may additionally be substituted in each case at the amino nitrogen atom by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or a 4- to 7-membered cycloalkyleneimino group, while in the above-mentioned substituted $C_{1-5}$-alkyl group two heteroatoms are separated from one another by at least two carbon atoms, a 4- to 7-membered cycloalkyleneiminocarbonyl or cycloalkyleneiminosulfonyl group, while the cycloalkyleneimino moiety in the carbon skeleton may be substituted by one or two $C_{1-3}$-alkyl, hydroxy-$C_{1-3}$-alkyl, $C_{1-3}$-alkyloxy-$C_{1-3}$-alkyl, phenyl-$C_{1-3}$-alkyl, heteroaryl-$C_{1-3}$-alkyl, amino-$C_{1-3}$-alkyl, $C_{3-6}$-cycloalkylamino-$C_{1-3}$-alkyl, $C_{1-5}$-alkylamino-$C_{1-3}$-alkyl, di-($C_{1-5}$-alkyl)-amino-$C_{1-3}$-alkyl, N—($C_{3-6}$-cycloalkyl)-$C_{1-3}$-alkylamino-$C_{1-3}$-alkyl, a 4- to 7-membered cycloalkyleneimino-$C_{1-3}$-alkyl, carboxy-$C_{1-3}$-alkyl, $C_{1-3}$-alkyloxycarbonyl-$C_{1-3}$-alkyl, aminocarbonyl-$C_{1-3}$-alkyl, $C_{1-3}$-alkylaminocarbonyl-$C_{1-3}$-alkyl, di-($C_{1-3}$-alkyl)-aminocarbonyl-$C_{1-3}$-alkyl, a 4- to 7-membered cycloalkyleneiminocarbonyl-$C_{1-3}$-alkyl, $C_{1-5}$-alkyloxycarbonylamino-$C_{1-3}$-alkyl, $C_{1-3}$-alkylcarbonylamino-$C_{1-3}$-alkyl, $C_{1-3}$-alkylsulfonylamino-$C_{1-3}$-alkyl, aminocarbonylamino-$C_{1-3}$-alkyl, $C_{1-3}$-alkylaminocarbonylamino-$C_{1-3}$-alkyl, di-($C_{1-3}$-alkyl)-aminocarbonylamino-$C_{1-3}$-alkyl, $C_{1-3}$-alkyloxycarbonyl, aminocarbonyl, $C_{1-3}$-alkylaminocarbonyl, di-($C_{1-3}$-alkyl)-aminocarbonyl, amino, $C_{1-3}$-alkylamino, di-($C_{1-3}$-alkyl)-amino, an aryl or a 5- to 6-membered heteroaryl group, with the proviso that in the substitution of a methylene group adjacent to the imino group two heteroatoms are separated from one another by at least two carbon atoms, and/or a methylene group in the 3 position of a 5-membered cycloalkyleneimino group may be replaced by a sulfur atom, a sulfinyl or sulfonyl group or a methylene group in the 4 position of a 6- or 7-membered cycloalkyleneimino group may be replaced by an oxygen or sulfur atom, a carbonyl or by an —NH— group optionally substituted by a methyl or hydroxy group, while additionally a methylene group adjacent to the abovementioned —NH— group may be replaced by a carbonyl group, a 5- to 7-membered cycloalkenyleneiminocarbonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl or $C_{3-6}$-cycloalkylamino-$C_{1-3}$-alkyl groups, while the double bond is not bound to a nitrogen atom and may be fused to a 5- or 6-membered heteroaryl group, an aminocarbonyl or aminosulfonyl group optionally substituted by one or two $C_{1-5}$-alkyl, $C_{3-6}$-cycloalkyl or 5- to 7-membered cycloalkyleneimino groups,
while the substituents may be identical or different and in each case one of the $C_{1-5}$-alkyl groups may be substituted by one or two hydroxy-$C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, a 4- to 7-membered cycloalkyleneimino-$C_{1-3}$-alkyl or $C_{3-6}$-cycloalkylamino-$C_{1-3}$-alkyl group, a $C_{1-3}$-alkyl group optionally monosubstituted by a di-($C_{1-3}$-alkyl)-amino, heteroaryl or a 4- to 7-membered cycloalkyleneimino group, while
  a —$CH_2$—$CH_2$— group in a 5- to 7-membered cycloalkyleneimino group may be replaced by an —NH—CO—, —CO—NH—, —CO—N($CH_3$)—, or an —N($CH_3$)—CO— group or
  a methylene group, which is adjacent to the nitrogen atom, in a 5- to 7-membered cycloalkyleneimino group may be replaced by a carbonyl group, or a group of formula

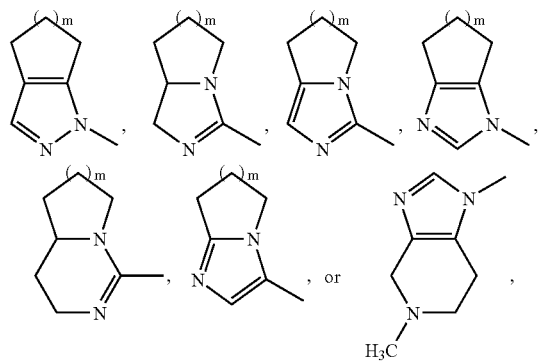

wherein in the heterocyclic moiety in each case a hydrogen atom may be replaced by a $C_{1-3}$-alkyloxycarbonyl, $C_{1-5}$-alkyloxycarbonylamino-$C_{1-3}$-alkyl, methylsulfonylmethyl, amino-$C_{1-3}$-alkyl or aminocarbonyl group and
m denotes the number 1 or 2, $R^2$ denotes a fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl or $C_{1-3}$-alkyloxy group wherein the hydrogen atoms may be wholly or partly replaced by fluorine atoms, $R^3$ denotes a hydrogen atom, $R^4$ denotes a hydrogen atom or a straight-chain or branched $C_{1-5}$-alkyl group which is optionally substituted by a hydroxy, a $C_{1-3}$-alkyloxy group wherein the hydrogen atoms may be wholly or partly replaced by fluorine atoms, a carboxy-$C_{1-3}$-alkyloxy, $C_{1-5}$-alkyloxycarbonyl-$C_{1-3}$-alkyloxy, $C_{1-5}$-alkyloxycarbonylamino, chloro-$C_{1-3}$-alkylaminocarbonylamino, mercapto, $C_{1-3}$-alkylsulfanyl, $C_{1-3}$-alkylsulfinyl, $C_{1-3}$-alkylsulfonyl, carboxy, aminocarbonyl, $C_{1-3}$-alkylaminocarbonyl, di-($C_{1-3}$-alkyl)-aminocarbonyl, amino, $C_{1-3}$-alkylamino, di-($C_{1-3}$-alkyl)-amino, a 4- to 7-membered cycloalkyleneimino, $C_{1-5}$-alkylcarbonylamino, $C_{3-6}$-cycloalkylcarbonylamino, benzyloxycarbonylamino or phenylcarbonylamino group, a 4- to 7-membered cycloalkyleneiminocarbonyl-$C_{1-3}$-alkyl group, while
  a methylene group of the cycloalkyleneimino moiety may be substituted by a $C_{1-3}$-alkyl group optionally substituted by a hydroxy, amino, $C_{1-3}$-alkylamino, di-($C_{1-3}$-alkyl)-amino, a 4- to 7-membered cycloalkyleneimino or $C_{1-5}$-alkyloxycarbonylamino group and a methylene group of the cycloalkyleneimino moiety not adjacent to the imino group may be substituted by a hydroxy, amino, $C_{1-3}$-alkylamino, di-($C_{1-3}$-alkyl)-amino, aminocarbonyl, $C_{1-3}$-alkylaminocarbonyl or di-($C_{1-3}$-alkyl)-aminocarbonyl group and/or
  a methylene group in the 4 position of a 6- or 7-membered cycloalkyleneimino group may be replaced by an oxygen or sulfur atom, by a carbonyl, sulfinyl, sulfonyl, or by an —NH— group optionally substituted by a $C_{1-3}$-alkyl group and additionally a methylene group adjacent to an abovementioned —NH— or —N($C_{1-3}$-alkyl)-group may be replaced by a carbonyl group, a $C_{1-3}$-alkyl group which is terminally substituted by a group of formula

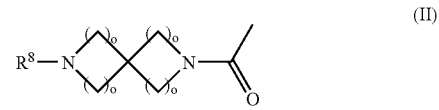

(II)

wherein:
  o denotes one of the numbers 1 or 2 and
  $R^8$ denotes a hydrogen atom, a $C_{1-3}$-alkyl or $C_{1-3}$-alkylcarbonyl group, a phenyl or heteroaryl, phenyl-$C_{1-3}$-alkyl or heteroaryl-$C_{1-3}$-alkyl group which is optionally substituted by a chlorine atom, a hydroxy, $C_{1-4}$-alkyloxy, trifluoromethoxy, carboxy or $C_{1-3}$-alkyloxycarbonyl group, a 4- to 7-membered cycolalkyleneimino-$C_{1-3}$-alkyl group optionally substituted by a $C_{1-3}$-alkylcarbonyl or $C_{1-4}$-alkyloxycarbonyl group, which is bound via a carbon atom, or a 4- to 7-membered cycloalkyl-$C_{1-3}$-alkyl or cycloalkyleneimino-$C_{1-3}$-alkyl group wherein in the cyclic moiety one or two methylene groups may be replaced by an —NH— or —N($C_{1-3}$-alkyl)-group and wherein one or two methylene groups adjacent to the —NH— or —N($C_{1-3}$-alkyl)-group may each be replaced by a carbonyl group, with the proviso that a cycloalkyl group as hereinbefore defined wherein two —NH— or —N($C_{1-3}$-alkyl)-groups are separated from one another by precisely one —$CH_2$— group is excluded, $R^5$ denotes a hydrogen atom, A denotes a carbonylamino or aminocarbonyl group and B denotes a group of formula

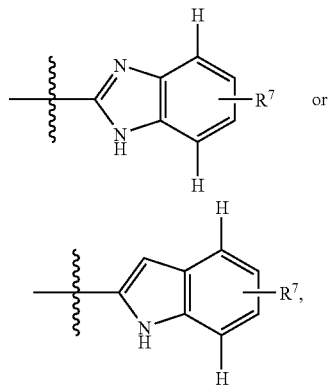

wherein:

$R^7$ denotes a fluorine, chlorine or bromine atom, while, unless otherwise stated, the term "heteroaryl group" denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulfur atom or an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, or phenyl-$C_{1-3}$-alkyl group or an oxygen or sulfur atom and additionally a nitrogen atom or an imino group optionally substituted by a $C_{1-3}$-alkyl or phenyl-$C_{1-3}$-alkyl group and two or three nitrogen atoms, and moreover a phenyl ring may be fused to the above-mentioned monocyclic heteroaryl groups via two adjacent carbon atoms and the bond is effected via a nitrogen atom or via a carbon atom of the heterocyclic moiety or a fused-on phenyl ring, while unless otherwise stated the alkyl and alkoxy groups contained in the definitions which have more than two carbon atoms may be straight-chain or branched, and the hydrogen atoms of the methyl or ethyl groups contained in the definitions may be wholly or partly replaced by fluorine atoms, the tautomers, the enantiomers, the diastereomers, the mixtures thereof and the salts thereof.

A 19th embodiment of the present invention comprises the compounds of the above general formula (Ib), wherein:

$R^1$, $R^2$, $R^4$ and $R^5$ are defined as described in the 18th embodiment, while $R^4$ does not denote the hydrogen atom, and $R^7$ denotes a chlorine or bromine atom, the tautomers, the diastereomers, the enantiomers, the mixtures thereof and the salts thereof.

A 20th embodiment of the present invention comprises the compounds of the above general formula (Ic), wherein:

$R^1$ denotes a group of formula

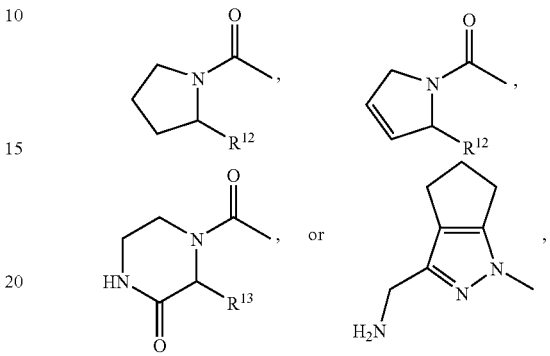

while $R^{12}$ denotes the hydrogen atom, a methyl, aminomethyl, $C_{1-3}$-alkylamino-$C_{1-2}$-alkyl, di-($C_{1-3}$-alkyl)-amino-$C_{1-2}$-alkyl, pyrrolidin-1-ylmethyl or 2-(pyrrolidin-1-yl) ethyl group and $R^{13}$ denotes a hydrogen atom, a methyl or aminomethyl group, $R^2$ denotes a fluorine, chlorine or bromine atom, a methyl, trifluoromethyl or methoxy group, $R^4$ denotes a $C_{1-4}$-alkyl group which may be substituted by a fluorine atom, a hydroxy, $C_{1-3}$-alkyloxy, trifluoromethoxy, 2,2,2-trifluoroethyloxy, mercapto, $C_{1-4}$-alkylsulfanyl, $C_{1-4}$-alkylsulfinyl, $C_{1-4}$-alkylsulfonyl, amino, $C_{1-3}$-alkylcarbonylamino, $C_{1-3}$-alkylsulfonylamino, carboxy, aminocarbonyl, $C_{1-3}$-alkylaminocarbonyl, di-($C_{1-3}$-alkyl)-aminocarbonyl or a 4- to 7-membered cycloalkyleneimino group and $R^7$ denotes a chlorine or bromine atom, the tautomers, the enantiomers, the diastereomers, the mixtures thereof and the salts thereof.

A 21st embodiment of the present invention comprises the compounds of the above general formula (Ic), wherein:

$R^1$ denotes a group of formula

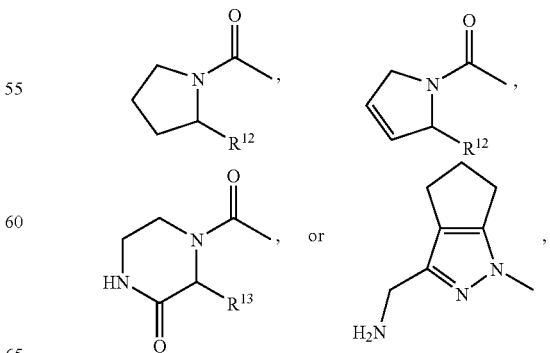

while
- $R^{12}$ denotes the hydrogen atom, a methyl, aminomethyl, $C_{1-3}$-alkylamino-$C_{1-2}$-alkyl, di-($C_{1-3}$-alkyl)-amino-$C_{1-2}$-alkyl, pyrrolidin-1-ylmethyl or 2-(pyrrolidin-1-yl)ethyl group and
- $R^{13}$ denotes a hydrogen atom, a methyl or aminomethyl group, $R^2$ denotes a fluorine, chlorine or bromine atom, a methyl, trifluoromethyl or methoxy group, $R^4$ denotes a $C_{1-4}$-alkyl group which is substituted by a fluorine atom, a hydroxy, $C_{1-3}$-alkyloxy, trifluoromethoxy, 2,2,2-trifluoroethyloxy, mercapto, $C_{1-4}$-alkylsulfanyl, $C_{1-4}$-alkylsulfinyl, $C_{1-4}$-alkylsulfonyl, amino, $C_{1-3}$-alkylcarbonylamino, $C_{1-3}$-alkylsulfonylamino, carboxy, aminocarbonyl, $C_{1-3}$-alkylaminocarbonyl, di-($C_{1-3}$-alkyl)-aminocarbonyl or a 4- to 7-membered cycloalkyleneimino group and $R^7$ denotes a chlorine or bromine atom, the tautomers, the diastereomers, the enantiomers, the mixtures thereof and the salts thereof.

A 22nd embodiment of the present invention comprises the compounds of the above general formula (Ic), wherein:

$R^1$ denotes a 2,5-dihydro-1H-pyrrol-1-ylcarbonyl, pyrrolidin-1-ylcarbonyl, N-acetyl-N-cyclobutylamino, 2-(N-tert-butoxycarbonylaminomethyl)pyrrolidin-1-ylcarbonyl, 2-(aminomethyl)pyrrolidin-1-ylcarbonyl, 3-oxopiperazin-1-ylcarbonyl, 4-methyl-3-oxopiperazin-1-ylcarbonyl, 2,3-dihydroimidazo[2,1-b]thiazol-5-yl, thiazolidin-3-ylcarbonyl, 1,2,3,6-tetrahydropyridin-1-ylcarbonyl, 2-methylthiomorpholin-4-ylcarbonyl, thiomorpholin-4-ylcarbonyl, N-isopropyl-N-methylaminocarbonyl, 2-methoxymethylpyrrolidin-1-ylcarbonyl, 3-(pyrrolidin-1-ylmethyl)piperidin-1-ylcarbonyl, azetidin-1-ylcarbonyl, 2-methylpyrrolidin-1-ylcarbonyl, N-isobutyl-N-methylaminocarbonyl, [1,4]oxazepan-1-ylcarbonyl, 2,5-dimethylpyrrolidin-1-ylcarbonyl, piperidin-1-ylcarbonyl, 4-hydroxypiperidin-1-ylcarbonyl, 4-acetylpiperazin-1-ylcarbonyl, N,N-diethylaminocarbonyl, 3-methylpiperidin-1-ylcarbonyl, 4-methylpiperidin-1-ylcarbonyl, 2-aminomethylpiperidin-1-ylcarbonyl, 3-aminomethylpiperidin-1-ylcarbonyl, 3-(2-aminoethyl)piperidin-1-ylcarbonyl, 3-aminopiperidin-1-ylcarbonyl or N-(2-dimethylamino)ethyl-N-ethylaminocarbonyl, 2-(N-tert-butoxycarbonylaminoethyl]pyrrolidin-1-ylcarbonyl, 2-(aminoethyl)pyrrolidin-1-ylcarbonyl, 2-(aminocarbonyl)pyrrolidin-1-ylcarbonyl, 1-oxothiazolidin-3-ylcarbonyl, 1,1-dioxothiazolidin-3-ylcarbonyl, 2-ethoxycarbonylmethyl-3-oxopiperazin-1-ylcarbonyl, 2-dimethylaminocarbonylmethyl-3-oxopiperazin-1-ylcarbonyl, 2-aminomethyl-3-oxopiperazin-1-ylcarbonyl, (2-acetylaminoethyl)pyrrolidin-1-ylcarbonyl, dimethylaminocarbonyl, 2-hydroxymethyl-(pyrrolidin-1-ylcarbonyl, 2-(methylsulfonylaminomethyl)pyrrolidin-1-ylcarbonyl, 2-(acetylaminomethyl)pyrrolidin-1-ylcarbonyl, pyrrolidin-1-ylsulfonyl, 2-(2-ethoxycarbonylethyl)pyrrolidin-1-ylcarbonyl, 2-[(3-ethylureido)methyl]pyrrolidin-1-ylcarbonyl, 4,5,6,7-tetrahydrobenzimidazol-1-yl, 3-(ethoxycarbonyl)-5,6-dihydro-4H-cyclopentapyrazol-1-yl, 3-(tert-butoxycarbonylamino)methyl-5,6-dihydro-4H-cyclopentapyrazol-1-yl, 3-(aminocarbonyl)-5,6-dihydro-4H-cyclopentapyrazol-1-yl, 3-aminomethyl-5,6-dihydro-4H-cyclopentapyrazol-1-yl, 4-formylpiperazin-1-ylcarbonyl, N-ethyl-N-(piperidin-4-yl)aminocarbonyl, 2-(2-dimethylaminoethyl)piperidin-1-ylcarbonyl, 2-(piperidin-1-ylmethyl)piperidin-1-ylcarbonyl, 2-(3-diethylaminopropyl)piperidin-1-ylcarbonyl, 2-(N-butyl-N-ethylaminomethyl)piperidin-1-ylcarbonyl, 2-(N-cyclohexyl-N-methylaminomethyl)piperidin-1-ylcarbonyl, 1,4,6,7-tetrahydroimidazo[4,5-c]pyridin-5-ylcarbonyl, 6,7-dihydro-4H-thieno[3,2-c]pyridin-5-ylcarbonyl, 2-(pyrrolidin-1ylmethyl)pyrrolidin-1-ylcarbonyl, 2-(ethoxycarbonyl)pyrrolidin-1-ylcarbonyl, 4-hydroxypiperazin-1-ylcarbonyl, 2-(methyloxycarbonyl)pyrrolidin-1-ylcarbonyl, 2-(benzyloxycarbonyl)pyrrolidin-1-ylcarbonyl, 3,4,5,6-tetrahydro-2H-[2,3]-bipyridinyl-1-ylcarbonyl, N-(2-aminoethyl)-N-ethylaminocarbonyl, N-(3-aminopropyl)-N-ethylaminocarbonyl, N-cyclopropyl-N-methylaminocarbonyl, 1,4,6,7-tetrahydropyrazol-[4,3-c]pyridin-5-ylcarbonyl, 2-(pyridin-2-yl)pyrrolidin-1-ylcarbonyl, 2-(pyridin-4-yl)pyrrolidin-1-ylcarbonyl, 2,5-dimethyl-2,5-dihydropyrrol-1-ylcarbonyl, 2,5-dimethyl-2,5-dihydropyrrol-1-ylcarbonyl, 2-phenylaminomethylpyrrolidin-1-ylcarbonyl, 2-benzylpyrrolidin-1-ylcarbonyl, 2-phenethylpyrrolidin-1-ylcarbonyl, 2-isopropylpyrrolidin-1-ylcarbonyl, 2-methylpiperidin-1-ylcarbonyl, 4-oxopiperidin-1-ylcarbonyl, [1,4]-diazepan-1-ylcarbonyl, 2-(dimethylaminocarbonyl)pyrrolidin-1-ylcarbonyl, 2-(methylaminocarbonyl)pyrrolidin-1-ylcarbonyl, 2-(aminocarbonylmethylaminocarbonyl)pyrrolidin-1-ylcarbonyl, 2-benzhydrylpyrrolidin-1-ylcarbonyl, 3-(2,2,2-trifluoroacetylamino)pyrrolidin-1-ylcarbonyl, 3-dimethylaminopyrrolidin-1-ylcarbonyl, imidazol-1-ylmethyl, 2-oxopyrrolidin-1-ylmethyl or 3-oxopiperazin-1-ylmethyl group, $R^2$ denotes a fluorine, chlorine or bromine atom, a $C_{1-3}$-alkyl group wherein the hydrogen atoms may be wholly or partly replaced by fluorine atoms, a $C_{1-3}$-alkyloxy or a $C_{2-3}$-alkynyl group, $R^3$ denotes a hydrogen atom, $R^4$ denotes the methyl, ethyl, propyl, isopropyl, isobutyl, tert-butyl, hydroxymethyl, 1-hydroxyethyl, methoxymethyl, 2-methoxyethyl, phenyl, 2-chlorophenyl, 3-chlorophenyl, 4-chlorophenyl, benzyl, 4-hydroxybenzyl, 4-methoxycarbonylmethoxyphenylmethyl, pyridin-4-ylmethyl, pyridin-2-ylmethyl, piperidin-1-ylmethyl, piperidin-3-ylmethyl, 1H-imidazol-4-ylmethyl, aminocarbonylmethyl, 4-benzyloxycarbonylaminobutyl, 2-methylsulfanylethyl, 2-methylsulfinylethyl, 2-methylsulfonylethyl, ethylsulfanylmethyl, ethylsulfinylmethyl, ethylsulfonylmethyl, aminomethyl, 2-aminoethyl, 3-aminopropyl, 4-aminobutyl, 2-phenylethyl, acetylaminomethyl, methylsulfonylaminomethyl, phenylcarbonylaminomethyl, 3-acetylaminopropyl, 4-acetylaminobutyl, 2,2,2-trifluoroethyl, hydroxymethyl, tert-butoxycarbonylaminomethyl, 3-(tert-butoxycarbonylamino)propyl, 4hydroxybenzyl, 2-carboxyethyl, 2-(benzyloxycarbonyl)ethyl, 2-(ethylaminocarbonyl)ethyl, 2-(pyrrolidin-1-ylcarbonyl)ethyl, 2-(diethylaminocarbonyl)ethyl, tetrazol-2-ylmethyl, carboxymethyloxymethyl, tert-butoxycarbonylmethyloxymethyl, 2-(benzyloxycarbonylamino)ethyl, 2-(aminosulfonyl)ethyl, 2-(2-oxoimidazolidin-1-yl)ethyl, 2-(2-chloroethyl)ureido]ethyl, 1-methoxy-1-methylethyl, 1-(3-tert-butoxycarbonyl)piperidin-3-yl, 1-acetylpiperidin-3-yl, 2-(pyridin-4-yl)ethyl, 2-[3-(dimethylamino)pyrrolidin-1-ylcarbonyl]ethyl, 2-(3-hydroxypyrrolidin-1-yl)carbonylethyl, 2-[2-(hydroxymethyl)pyrrolidin-1-ylcarbonyl]ethyl, 2-(2-methyl-2,6-diazaspiro[3.4]oct-6-ylcarbonyl)ethyl, 2-[2-(aminocarbonyl)pyrrolidin-1-ylcarbonyl)ethyl, 2-[2-(tert-butoxycarbonylaminomethyl)pyrrolidin-1-ylcarbonyl]ethyl, 2-[3-(hydroxymethylpyrrolidin-1-yl)carbonyl]ethyl, 2-(1,1-dioxo-1-thiomorpholin-4-ylcarbonyl)ethyl, 2-(4-methyl-3-oxopiperazin-1-ylcarbonyl)ethyl, 2-(2-aminomethylpyrrolidin-1-ylcarbonyl)ethyl group, $R^5$ denotes a hydrogen atom, A denotes an aminocarbonyl or carbonylamino group and B denotes a group of formula

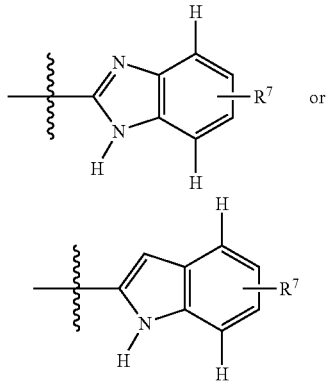

wherein:
$R^7$ denotes a fluorine, chlorine or bromine atom or a methyl group, the tautomers, the enantiomers, the diastereomers, the mixtures thereof and the salts thereof.

A 23rd embodiment of the present invention comprises the compounds of the above general formula I, wherein:

$R^1$ denotes an amino, $C_{1-5}$-alkylamino, $C_{3-7}$-cycloalkylamino or (phenyl-$C_{1-3}$-alkyl)-amino group which may be substituted in each case at the amino nitrogen atom by a phenylcarbonyl or phenylsulfonyl group or by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or $C_{3-6}$-cycloalkyleneimino group, while two nitrogen atoms are separated from one another by at least two carbon atoms, a di-($C_{1-5}$-alkyl)amino or N—($C_{3-7}$-cycloalkyl)-$C_{1-5}$-alkylamino group, while the $C_{1-5}$-alkyl moiety may, with the exception of the I position, be substituted in each case by a hydroxy, $C_{1-3}$-alkoxy, amino, $C_{1-3}$-alkylamino, di-($C_{1-3}$-alkyl)-amino or $C_{3-6}$-cycloalkyleneimino group, a 4- to 7-membered cycloalkyleneiminocarbonyl or cycloalkyleneiminosulfonyl group, while
the cycloalkyleneimino moiety may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylaminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl or di-($C_{1-3}$-alkyl)-aminocarbonyl group or
a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-4}$-cycloalkyleneimino group and/or
a methylene group in the 3 position of a 5-membered cycloalkyleneimino group may be replaced by a sulfur atom, a sulfinyl or sulfonyl group or
a methylene group in the 4 position of a 6- or 7-membered cycloalkyleneimino group may be replaced by an oxygen or sulfur atom or by an —NH—, —N—$C_{1-3}$-alkyl-, —N($C_{2-3}$-alkanoyl)-, sulfinyl, or sulfonyl group and/or
a —$CH_2$—$CH_2$— group in a 5- to 7-membered cycloalkyleneimino group may be replaced by a —NH—CO—, —CO—NH—, —CO—N($CH_3$)—, or a —N($CH_3$)—CO— group, a 5- to 7-membered cycloalkenyleneiminocarbonyl or cycloalkenyleneiminosulfonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-6}$-cycloalkylamino-$C_{1-3}$-alkyl, aminocarbonyl, $C_{1-3}$-alkylaminocarbonyl, di-($C_{1-3}$-alkyl)-aminocarbonyl or $C_{3-6}$-cycloalkyleneiminocarbonyl groups, while the double bond is not bound to a nitrogen atom, an aminocarbonyl or aminosulfonyl group optionally substituted by one or two $C_{1-5}$-alkyl groups,
while the substituents may be identical or different and
in each case one of the $C_{1-5}$-alkyl groups may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or
a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-4}$-cycloalkyleneimino group, a $C_{1-7}$-alkylcarbonyl or $C_{3-7}$-cycloalkylcarbonyl group, while
the methylene group in the 2, 3 or 4 position in a $C_{3-7}$-cycloalkylcarbonyl group may be replaced by an oxygen or sulfur atom, a carbonyl, sulfinyl, sulfonyl, or a —NH— group, wherein:
the hydrogen atom of the —NH— group may be replaced by a $C_{1-3}$-alkyl or $C_{1-3}$-alkylcarbonyl group, a phenylcarbonyl or heteroarylcarbonyl group which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group, a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while
the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group and/or
a —$CH_2$—$CH_2$— group in a 5- to 7-membered cycloalkyleneimino group may be replaced by an —NH—CO—, —CO—NH—, —CO—N($CH_3$)—, or a —N($CH_3$)—CO— group or
a methylene group, which is adjacent to the nitrogen atom, in a 5- to 7-membered cycloalkyleneimino group may be replaced by a carbonyl group, or a group of formula

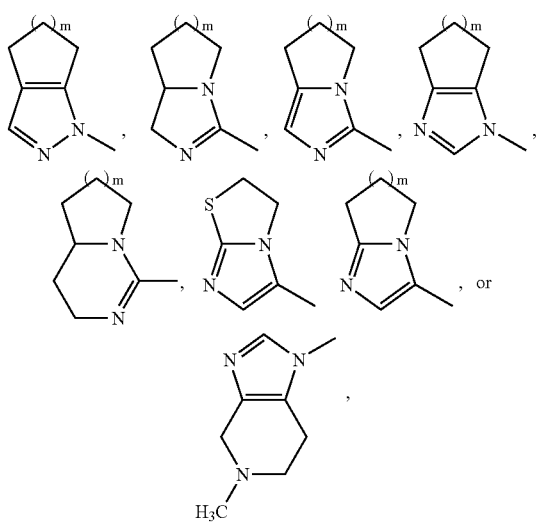

wherein in the heterocyclic moiety in each case a hydrogen atom may be replaced by a methylsulfonylmethyl, amino-$C_{1-3}$-alkyl or aminocarbonyl group and m denotes the number 1 or 2, $R^2$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl, $C_{1-3}$-alkoxy or trifluoromethoxy group, $R^3$ denotes a hydrogen atom or a $C_{1-3}$-alkyl group, $R^4$ denotes a hydrogen atom or a straight-chain or branched $C_{1-5}$-alkyl group which is optionally substituted by a hydroxy, $C_{1-3}$-alkyloxy, mercapto, $C_{1-3}$-alkylsulfanyl, $C_{1-3}$-alkylsulfinyl, $C_{1-3}$-alkylsulfonyl, carboxy, aminocarbonyl, $C_{1-3}$-alkylaminocarbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{3-6}$-cycloalkyleneimino, $C_{1-3}$-alkylcarbonylamino, $C_{3-6}$-cycloalkylcarbonylamino, benzyloxycarbonylamino or guanidino group, a phenyl or heteroaryl, phenyl-$C_{1-3}$-alkyl or heteroaryl-$C_{1-3}$-alkyl group which is optionally substituted by a hydroxy, $C_{1-4}$-alkyloxy, benzyloxy, hydroxycarbonyl-$C_{1-3}$-alkoxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, $C_{3-6}$-cycloalkyleneiminocarbonyl-$C_{1-3}$-alkoxy, carboxy, $C_{1-3}$-alkyloxycarbonyl group, a 4- to 7-membered cycolalkyleneimino-$C_{1-3}$-alkyl group or a 4- to 7-membered cycloalkyl-$C_{1-3}$-alkyl group wherein one or two methylene groups may be replaced by an —NH— or —N($C_{1-3}$-alkyl)-group and wherein one or two methylene groups adjacent to the —NH— or —N($C_{1-3}$-alkyl)-group may each be replaced by a carbonyl group, with the proviso that a cycloalkyl group as hereinbefore defined wherein two —NH— or —N($C_{1-3}$-alkyl)-groups are separated from one another by precisely one —CH$_2$— group, is excluded, $R^5$ denotes a hydrogen atom or a $C_{1-3}$-alkyl group or $R^4$ and $R^5$ together with the carbon atom to which they are bound, denote a $C_{3-7}$-cycloalkyl group, while one of the methylene groups of the $C_{3-7}$-cycloalkyl group may be replaced by an imino, $C_{1-3}$-alkylimino, acylimino or sulfonylimino group, A denotes a carbonylamino or aminocarbonyl group, while the hydrogen atom of the amino function may optionally be substituted by a $C_{1-3}$-alkyl group, and B denotes a group of formula

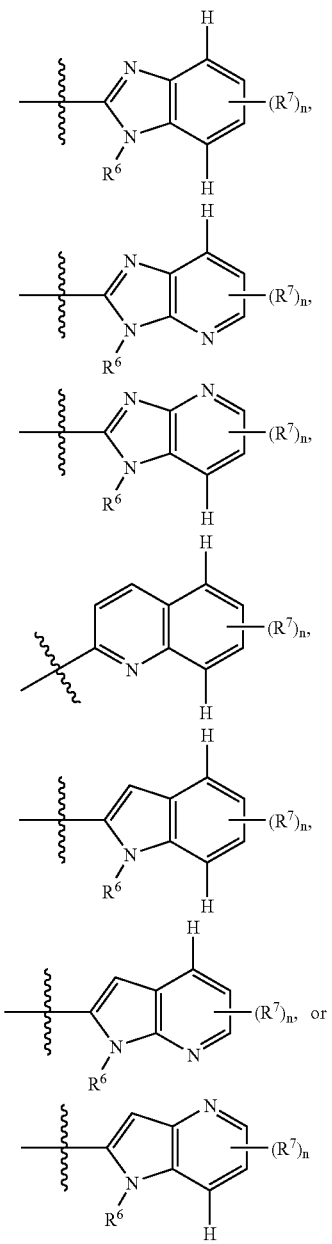

wherein:

n denotes the number 1 or 2, $R^6$ denotes a hydrogen atom or a $C_{1-3}$-alkyl, hydroxy, amino, $C_{1-3}$-alkylamino group and $R^7$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy or cyano group, while, unless otherwise stated, the term "heteroaryl group" denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulfur atom or an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or phenyl-$C_{1-3}$-alkyl group or an oxygen or sulfur atom and additionally a nitrogen atom or an imino group optionally substituted by a $C_{1-3}$-alkyl or phenyl-$C_{1-3}$-alkyl group and two or three nitrogen atoms, and moreover a phenyl ring may be fused to the above-mentioned monocyclic heteroaryl groups via two adjacent carbon atoms and the bond is effected via a nitrogen atom or via a carbon atom of the heterocyclic moiety or a fused-on phenyl ring, while unless otherwise stated the alkyl and alkoxy groups contained in the definitions which have more than two carbon atoms may be straight-chain or branched, and the hydrogen atoms of the methyl or ethyl groups contained in the definitions may be wholly or partly replaced by fluorine atoms.

A 24th embodiment of the present invention comprises the compounds of the above general formula I, wherein:

$R^1$ denotes an amino, $C_{1-5}$-alkylamino, $C_{3-7}$-cycloalkylamino or (phenyl-$C_{1-3}$-alkyl)-amino group which may be substituted in each case at the amino nitrogen atom by a phenylcarbonyl or phenylsulfonyl group or by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or $C_{3-6}$-cycloalkyleneimino group, while two nitrogen atoms are separated from one another by at least two carbon atoms, a di-($C_{1-5}$-alkyl) amino or N—($C_{3-7}$-cycloalkyl)-$C_{1-5}$-alkylamino group, while the $C_{1-5}$-alkyl moiety with the exception of the 1 position may be substituted in each case by a hydroxy, $C_{1-3}$-alkoxy, amino, $C_{1-3}$-alkylamino, di-($C_{1-3}$-alkyl)-amino or $C_{3-6}$-cycloalkyleneimino group, a 4- to 7-membered cycloalkyleneiminocarbonyl or cycloalkyleneiminosulfonyl group, while the cycloalkyleneimino moiety may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylaminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group and/or a methylene group in the 3 position of a 5-membered cycloalkyleneimino group may be replaced by a sulfur atom, a sulfinyl or sulfonyl group or a methylene group in the 4 position of a 6- or 7-membered cycloalkyleneimino group may be replaced by an oxygen or sulfur atom or by an —NH—, —N—$C_{1-3}$-alkyl-, —N($C_{2-3}$-alkanoyl)-, sulfinyl, or sulfonyl group and/or a —$CH_2$—$CH_2$— group in a 5- to 7-membered cycloalkyleneimino group may be replaced by an —NH—CO—, —CO—NH—, —CO—N($CH_3$)—, or a —N($CH_3$)—CO— group, a 5- to 7-membered cycloalkenyleneiminocarbonyl or cycloalkenyleneiminosulfonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-6}$-cycloalkylamino-$C_{1-3}$-alkyl, aminocarbonyl, $C_{1-3}$-alkylaminocarbonyl, di-($C_{1-3}$-alkyl)-aminocarbonyl or $C_{3-6}$-cycloalkyleneiminocarbonyl groups, while the double bond is not bound to a nitrogen atom, an aminocarbonyl or aminosulfonyl group optionally substituted by one or two $C_{1-5}$-alkyl groups, while the substituents may be identical or different and in each case one of the $C_{1-5}$-alkyl groups may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group, a $C_{1-7}$-alkylcarbonyl or $C_{3-7}$-cycloalkylcarbonyl group, while the methylene group in the 2, 3 or 4 position in a $C_{3-7}$-cycloalkylcarbonyl group may be replaced by an oxygen or sulfur atom, a carbonyl, sulfinyl, sulfonyl, or an —NH— group, wherein:

the hydrogen atom of the —NH— group may be replaced by a $C_{1-3}$-alkyl or $C_{1-3}$-alkylcarbonyl group, a phenylcarbonyl or heteroarylcarbonyl group which may be substituted in the phenyl or heteroaryl moiety by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group, a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group and/or a —$CH_2$—$CH_2$— group in a 5- to 7-membered cycloalkyleneimino group may be replaced by an —NH—CO—, —CO—NH—, —CO—N($CH_3$)—, or a —N($CH_3$)—CO— group or a methylene group, which is adjacent to the nitrogen atom, in a 5- to 7-membered cycloalkyleneimino group may be replaced by a carbonyl group, or a group of formula

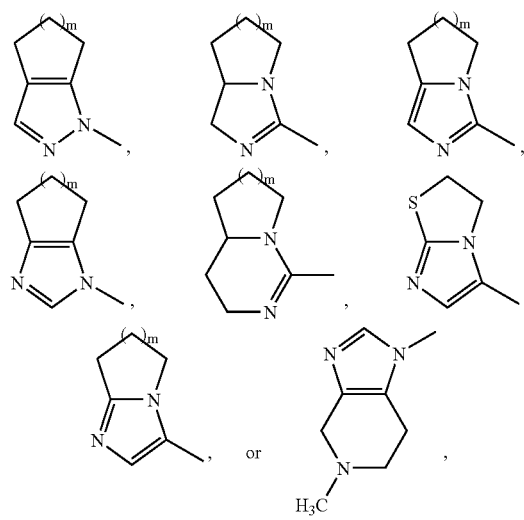

wherein in the heterocyclic moiety in each case a hydrogen atom may be replaced by a methylsulfonylmethyl, amino-$C_{1-3}$-alkyl or aminocarbonyl group and m denotes the number 1 or 2, $R^2$ denotes a chlorine or bromine atom, a $C_{1-3}$-alkyl group wherein the hydrogen atoms may be wholly or partly replaced by fluorine atoms, or a $C_{2-3}$-alkenyl group, $R^3$ denotes a hydrogen atom or a $C_{1-3}$-alkyl group, $R^4$ denotes a hydrogen atom or a straight-chain or branched $C_{1-5}$-alkyl group which is optionally substituted by a hydroxy, $C_{1-3}$-alkyloxy, mercapto, $C_{1-3}$-alkylsulfanyl, $C_{1-3}$-alkylsulfinyl, $C_{1-3}$-alkylsulfonyl, carboxy, aminocarbonyl, $C_{1-3}$-alkylaminocarbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{3-6}$-cycloalkyleneimino, $C_{1-3}$-alkylcarbonylamino, $C_{3-6}$-cycloalkylcarbonylamino, benzyloxycarbonylamino or guanidino group, a phenyl or heteroaryl, phenyl-$C_{1-3}$-alkyl or heteroaryl-$C_{1-3}$-alkyl group which is optionally substituted by a hydroxy, $C_{1-4}$-alkyloxy, benzyloxy, hydroxycarbonyl-$C_{1-3}$-alkoxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, $C_{3-6}$-cycloalkyleneiminocarbonyl-$C_{1-3}$-alkoxy, carboxy, $C_{1-3}$-alkyloxycarbonyl group, a 4- to 7-membered cycolalkyleneimino-$C_{1-3}$-alkyl group or a 4- to 7-membered cycloalkyl-$C_{1-3}$-alkyl group wherein one or two methylene groups may be replaced by an —NH— or —N($C_{1-3}$-alkyl)-group and wherein one or two methylene groups adjacent to the —NH— or —N($C_{1-3}$-alkyl)-group may each be replaced by a carbonyl group, with the proviso that a cycloalkyl group as hereinbefore defined wherein two —NH— or —N($C_{1-3}$-alkyl)-groups are separated from one another by precisely one —CH$_2$— group, is excluded, $R^5$ denotes a hydrogen atom or a $C_{1-3}$-alkyl group or $R^4$ and $R^5$ together with the carbon atom to which they are bound denote a $C_{3-7}$-cycloalkyl group, while one of the methylene groups of the $C_{3-7}$-cycloalkyl group may be replaced by an imino, $C_{1-3}$-alkylimino, acylimino or sulfonylimino group, A denotes a carbonylamino or aminocarbonyl group, while the hydrogen atom of the amino function may optionally be substituted by a $C_{1-3}$-alkyl group, and B denotes a group of formula

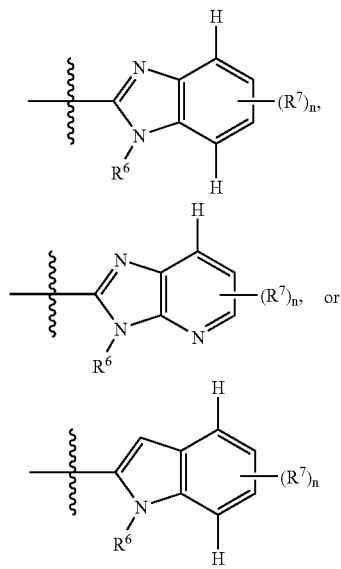

wherein:
n denotes the number 1,
$R^6$ denotes a hydrogen atom or a $C_{1-3}$-alkyl, hydroxy, amino, $C_{1-3}$-alkylamino group and
$R^7$ denotes a hydrogen, fluorine, chlorine or bromine atom, a $C_{1-3}$-alkyl group wherein the hydrogen atoms may be wholly or partly replaced by fluorine atoms, a $C_{2-3}$-alkenyl or $C_{2-3}$-alkynyl, a hydroxy, $C_{1-3}$-alkoxy, trifluoromethoxy or cyano group, while, unless otherwise stated, the term "heteroaryl group" denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while
  the 6-membered heteroaryl group contains one, two or three nitrogen atoms and
  the 5-membered heteroaryl group contains an imino group optionally substituted by a $C_{1-3}$-alkyl or phenyl-$C_{1-3}$-alkyl group, an oxygen or sulfur atom or
  an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or phenyl-$C_{1-3}$-alkyl group or an oxygen or sulfur atom and additionally a nitrogen atom or
  an imino group optionally substituted by a $C_{1-3}$-alkyl or phenyl-$C_{1-3}$-alkyl group and two or three nitrogen atoms,
  and moreover a phenyl ring may be fused to the above-mentioned monocyclic heteroaryl groups via two adjacent carbon atoms
  and the bond is effected via a nitrogen atom or via a carbon atom of the heterocyclic moiety or a fused-on phenyl ring, while unless otherwise stated the alkyl and alkoxy groups contained in the definitions which have more than two carbon atoms may be straight-chain or branched, and the hydrogen atoms of the methyl or ethyl groups contained in the definitions may be wholly or partly replaced by fluorine atoms, the tautomers, the enantiomers, the diastereomers, the mixtures thereof and the salts thereof.

Of the preferred compounds mentioned above under the 24th embodiment particular importance is attached to those compounds of the above general formula I wherein $R^3$ denotes the hydrogen atom.

A 25th embodiment of the present invention comprises the compounds of the above general formula I, wherein:

$R^1$ denotes an amino, $C_{1-5}$-alkylamino, $C_{3-7}$-cycloalkylamino or (phenyl-$C_{1-3}$-alkyl)-amino group which may be substituted in each case at the amino nitrogen atom by a phenylcarbonyl or phenylsulfonyl group or by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or $C_{3-6}$-cycloalkyleneimino group, while two nitrogen atoms are separated from one another by at least two carbon atoms, a di-($C_{1-5}$-alkyl)amino or N—($C_{3-7}$-cycloalkyl)-$C_{1-5}$-alkylamino group, while the $C_{1-5}$-alkyl moiety with the exception of the 1 position may be substituted in each case by a hydroxy, $C_{1-3}$-alkoxy, amino, $C_{1-3}$-alkylamino, di-($C_{1-3}$-alkyl)-amino or $C_{3-6}$-cycloalkyleneimino group, a 4- to 7-membered cycloalkyleneiminocarbonyl or cycloalkyleneiminosulfonyl group, while the cycloalkyleneimino moiety may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylaminocarbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-(C 1-3-alkyl)-aminocarbonyl or $C_{3-6}$-cycloalkyleneiminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group and/or a methylene group in the 3 position of a 5-membered cycloalkyleneimino group may be replaced by a sulfur atom, a sulfinyl or sulfonyl group or a methylene group in the 4 position of a 6- or 7-membered cycloalkyleneimino group may be replaced by an oxygen or sulfur atom or by a —NH—, —N—$C_{1-3}$-alkyl-, —N($C_{2-3}$-alkanoyl)-, sulfinyl or sulfonyl group and/or a —$CH_2$—$CH_2$— group in a 5- to 7-membered cycloalkyleneimino group may be replaced by a —NH—CO—, —CO—NH—, —CO—N($CH_3$)— or a —N($CH_3$)—CO— group, a 5- to 7-membered cycloalkenyleneiminocarbonyl or cycloalkenyleneiminosulfonyl group optionally substituted by one or two $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-6}$-cycloalkylamino-$C_{1-3}$-alkyl, aminocarbonyl, $C_{1-3}$-alkylaminocarbonyl, di-(C_{1-3}-alkyl)-aminocarbonyl or $C_{3-6}$-cycloalkyleneiminocarbonyl groups, while the double bond is not bound to a nitrogen atom, an aminocarbonyl or aminosulfonyl group optionally substituted by one or two $C_{1-5}$-alkyl groups, while the substituents may be identical or different and in each case one of the $C_{1-5}$-alkyl groups may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—($C_{3-7}$-cycloalkyl)-$C_{1-5}$-alkylaminocarbonyl, N-(phenyl-$C_{1-3}$-alkyl)-$C_{1-5}$-alkylaminocarbonyl, di-($C_{1-3}$-alkyl)-aminocarbonyl or $C_{3-6}$-cycloalkyleneiminocarbonyl group or a methylene group not adjacent to the imino group may be substituted by a hydroxy, benzyloxy, $C_{1-3}$-alkoxy, amino, $C_{1-3}$-alkylamino, di-($C_{1-3}$-alkyl)-amino or $C_{3-6}$-cycloalkyleneimino group, a $C_{1-3}$-alkyl group optionally monosubstituted by an amino, $C_{1-3}$-alkylamino, di-($C_{1-3}$-alkyl)-amino, hydroxy, phenyl, heteroaryl or a 4- to 7-membered cycloalkyleneimino group, while the phenyl moiety may be substituted by a fluorine, chlorine or bromine atom, by a trifluoromethyl, $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl or $C_{1-3}$-alkoxy group and/or a —$CH_2$—$CH_2$— group in a 5- to 7-membered cycloalkyleneimino group may be replaced by an —NH—CO—, —CO—NH—, —CO—N($CH_3$)— or a —N($CH_3$)—CO— group or a methylene group, which is adjacent to the nitrogen atom, in a 5- to 7-membered cycloalkyleneimino group may be replaced by a carbonyl group, or a group of formula

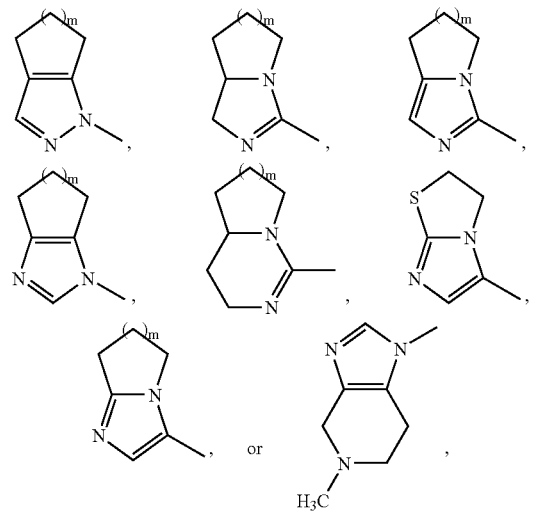

wherein in the heterocyclic moiety in each case a hydrogen atom may be replaced by a methylsulfonylmethyl, amino-$C_{1-3}$-alkyl or aminocarbonyl group and m denotes the number 1 or 2, R² denotes a chlorine or bromine atom, a $C_{1-3}$-alkyl group wherein the hydrogen atoms may be wholly or partly replaced by fluorine atoms, or a $C_{2-3}$-alkenyl group, R³ denotes a hydrogen atom, R⁴ denotes a hydrogen atom or a straight-chain or branched $C_{1-5}$-alkyl group which is optionally substituted by a hydroxy, $C_{1-3}$-alkyloxy, mercapto, $C_{1-3}$-alkylsulfanyl, $C_{1-3}$-alkylsulfinyl, $C_{1-3}$-alkylsulfonyl, carboxy, aminocarbonyl, $C_{1-3}$-alkylaminocarbonyl, di-($C_{1-3}$-alkyl)-aminocarbonyl, $C_{3-6}$-cycloalkyleneiminocarbonyl, amino, $C_{1-3}$-alkylamino, di-($C_{1-3}$-alkyl)-amino, $C_{3-6}$-cycloalkyleneimino, $C_{1-3}$-alkylcarbonylamino, $C_{3-6}$-cycloalkylcarbonylamino, benzyloxycarbonylamino or guanidino group, a phenyl or heteroaryl, phenyl-$C_{1-3}$-alkyl or heteroaryl-$C_{1-3}$-alkyl group which is optionally substituted by a hydroxy, $C_{1-4}$-alkyloxy, benzyloxy, hydroxycarbonyl-$C_{1-3}$-alkoxy, $C_{1-3}$-alkyloxycarbonyl-$C_{1-3}$-alkyloxy, aminocarbonyl-$C_{1-3}$-alkyloxy, $C_{1-3}$-alkylaminocarbonyl-$C_{1-3}$-alkyloxy, di-($C_{1-3}$-alkyl)-aminocarbonyl-$C_{1-3}$-alkyloxy, $C_{3-6}$-cycloalkyleneiminocarbonyl-$C_{1-3}$-alkyloxy, carboxy, $C_{1-3}$-alkyloxycarbonyl group, a 4- to 7-membered cycolalkyleneimino-$C_{1-3}$-alkyl group or a 4- to 7-membered cycloalkyl-$C_{1-3}$-alkyl group wherein one or two methylene groups may be replaced by a —NH— or —N($C_{1-3}$-alkyl)-group and wherein one or two methylene groups adjacent to the —NH— or —N($C_{1-3}$-alkyl)-group may each be replaced by a carbonyl group, with the proviso that a cycloalkyl group as hereinbefore defined wherein two —NH— or —N($C_{1-3}$-alkyl)-groups are separated from one another by precisely one —CH₂— group, is excluded, R⁵ denotes a hydrogen atom or R⁴ and R⁵ together with the carbon atom to which they are bound denote a $C_{3-7}$-cycloalkyl group, while
one of the methylene groups of the $C_{3-7}$-cycloalkyl group may be replaced by an imino, $C_{1-3}$-alkylimino, acylimino or sulfonylimino group, A denotes a carbonylamino or aminocarbonyl group, while the hydrogen atom of the amino function may optionally be substituted by a $C_{1-3}$-alkyl group, and B denotes a group of formula

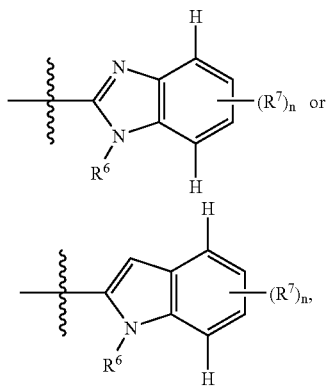

wherein:
n denotes the number 1,
R⁶ denotes a hydrogen atom or a $C_{1-3}$-alkyl, hydroxy, amino, $C_{1-3}$-alkylamino group and R⁷ denotes a fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl or a hydroxy group, while, unless otherwise stated, the term "heteroaryl group" denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while
the 6-membered heteroaryl group contains one, two or three nitrogen atoms and
the 5-membered heteroaryl group contains an imino group optionally substituted by a $C_{1-3}$-alkyl or phenyl-$C_{1-3}$-alkyl group, an oxygen or sulfur atom or
an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, or phenyl-$C_{1-3}$-alkyl group or an oxygen or sulfur atom and additionally a nitrogen atom or
an imino group optionally substituted by a $C_{1-3}$-alkyl or phenyl-$C_{1-3}$-alkyl group and two or three nitrogen atoms,
and moreover a phenyl ring may be fused to the above-mentioned monocyclic heteroaryl groups via two adjacent carbon atoms
and the bond is effected via a nitrogen atom or via a carbon atom of the heterocyclic moiety or a fused-on phenyl ring, while unless otherwise stated the alkyl and alkoxy groups contained in the definitions which have more than two carbon atoms may be straight-chain or branched, and the hydrogen atoms of the methyl or ethyl groups contained in the definitions may be wholly or partly replaced by fluorine atoms, the tautomers, the enantiomers, the diastereomers, the mixtures thereof and the salts thereof.

A 26th embodiment of the present invention comprises the compounds of the above general formula I, wherein:

R¹ denotes an amino, $C_{1-5}$-alkylamino, $C_{3-7}$-cycloalkylamino or (phenyl-$C_{1-3}$-alkyl)-amino group which may be substituted at the amino nitrogen atom in each case by a phenylcarbonyl or phenylsulfonyl group or by a $C_{1-5}$-alkyl or $C_{1-5}$-alkylcarbonyl group optionally substituted in the alkyl moiety by a carboxy group, a group which may be converted in vivo into a carboxy group, an amino, $C_{1-3}$-alkylamino, di-($C_{1-3}$-alkyl)-amino or $C_{3-6}$-cycloalkyleneimino group, while two nitrogen atoms are separated from one another by at least two carbon atoms, a di-($C_{1-5}$-alkyl)amino or N—($C_{3-7}$-cycloalkyl)-$C_{1-5}$-alkylamino group, while the $C_{1-5}$-alkyl moiety with the exception of the I position may be substituted in each case by a hydroxy, $C_{1-3}$-alkoxy, amino, $C_{1-3}$-alkylamino, di-($C_{1-3}$-alkyl)-amino or $C_{3-6}$-cycloalkyleneimino group, a 4- to 7-membered cycloalkyleneiminocarbonyl or cycloalkyleneiminosulfonyl group, while
the cycloalkyleneimino moiety may be substituted by one or two $C_{1-3}$-alkyl, $C_{1-3}$-alkoxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkyleneimino-$C_{1-3}$-alkyl, $C_{1-5}$-alkyloxycarbonylamino-$C_{1-3}$-alkyl, $C_{3-6}$-cycloalkylamino-$C_{1-3}$-alkyl, aminocarbonyl, $C_{1-3}$-alkylamino-carbonyl, N—(C$_{3-7}$-cycloalkyl)-C$_{1-5}$-alkylaminocarbonyl, N-(phenyl-C$_{1-3}$-alkyl)-C$_{1-5}$-alkylaminocarbonyl, di-(C$_{1-3}$-alkyl)-aminocarbonyl or C$_{3-6}$-cycloalkyleneiminocarbonyl group or a methylene group not adjacent to the imino group may be substituted by a hydroxy, benzyloxy, C$_{1-3}$-alkoxy, amino, C$_{1-3}$-alkylamino, di-(C$_{1-3}$-alkyl)-amino or C$_{3-6}$-cycloalkyleneimino group and/or a methylene group in the 3 position of a 5-membered cycloalkyleneimino group may be replaced by a sulfur atom, a sulfinyl or sulfonyl group or a methylene group in the 4 position of a 6- or 7-membered cycloalkyleneimino group may be replaced by an oxygen or sulfur atom or by a —NH—, —N—C$_{1-3}$-alkyl-, —N(C$_{2-3}$-alkanoyl)-, sulfinyl, or sulfonyl group, and/or a —CH$_2$—CH$_2$— group in a 5- to 7-membered cycloalkyleneimino group may be replaced by a —NH—CO—, —CO—NH—, —CO—N(CH$_3$)—, or a —N(CH$_3$)—CO— group, a 5- to 7-membered cycloalkenyleneiminocarbonyl or cycloalkenyleneiminosulfonyl group optionally substituted by one or two C$_{1-3}$-alkyl, amino-C$_{1-3}$-alkyl, C$_{1-3}$-alkylamino-C$_{1-3}$-alkyl, di-(C$_{1-3}$-alkyl)-amino-C$_{1-3}$-alkyl, C$_{3-6}$-cycloalkyleneimino-C$_{1-3}$-alkyl, C$_{1-6}$-cycloalkylamino-C$_{1-3}$-alkyl, aminocarbonyl, C$_{1-3}$-alkylaminocarbonyl, di-(C$_{1-3}$-alkyl)-aminocarbonyl or C$_{3-6}$-cycloalkyleneiminocarbonyl groups, while the double bond is not bound to a nitrogen atom, an aminocarbonyl or aminosulfonyl group optionally substituted by one or two C$_{1-5}$-alkyl groups, while the substituents may be identical or different and in each case one of the C$_{1-5}$-alkyl groups may be substituted by one or two C$_{1-3}$-alkyl, C$_{1-3}$-alkoxy-C$_{1-3}$-alkyl, amino-C$_{1-3}$-alkyl, C$_{1-3}$-alkylamino-C$_{1-3}$-alkyl, di-(C$_{1-3}$-alkyl)-amino-C$_{1-3}$-alkyl, C$_{3-6}$-cycloalkyleneimino-C$_{1-3}$-alkyl, C$_{1-5}$-alkyloxycarbonylamino-C$_{1-3}$-alkyl, C$_{3-6}$-cycloalkylamino-C$_{1-3}$-alkyl, aminocarbonyl, C$_{1-3}$-alkylamino-carbonyl, N—(C$_{3-7}$-cycloalkyl)-C$_{1-5}$-alkylaminocarbonyl, N-(phenyl-C$_{1-3}$-alkyl)-C$_{1-5}$-alkylaminocarbonyl, di-(C$_{1-3}$-alkyl)-aminocarbonyl or C$_{3-6}$-cycloalkyleneiminocarbonyl group or a methylene group not adjacent to the imino group may be substituted by a hydroxy, benzyloxy, C$_{1-3}$-alkoxy, amino, C$_{1-3}$-alkylamino, di-(C$_{1-3}$-alkyl)-amino or C$_{3-4}$-cycloalkyleneimino group, a C$_{1-3}$-alkyl group optionally monosubstituted by an amino, C$_{1-3}$-alkylamino, di-(C$_{1-3}$-alkyl)-amino, hydroxy, phenyl, heteroaryl or a 4- to 7-membered cycloalkyleneimino group, while the phenyl moiety may be substituted by a fluorine, chlorine or bromine atom, by a trifluoromethyl, C$_{1-3}$-alkyl, amino-C$_{1-3}$-alkyl, C$_{1-3}$-alkylamino-C$_{1-3}$-alkyl, di-(C$_{1-3}$-alkyl)-amino-C$_{1-3}$-alkyl, C$_{3-6}$-cycloalkyleneimino-C$_{1-3}$-alkyl or C$_{1-3}$-alkoxy group, and/or a —CH$_2$—CH$_2$— group in a 5- to 7-membered cycloalkyleneimino group may be replaced by a —NH—CO—, —CO—NH—, —CO—N(CH$_3$)—, or a —N(CH$_3$)—CO— group or a methylene group, which is adjacent to the nitrogen atom, in a 5- to 7-membered cycloalkyleneimino group may be replaced by a carbonyl group, or a group of formula

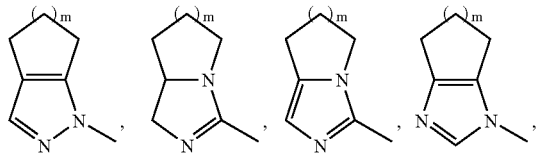

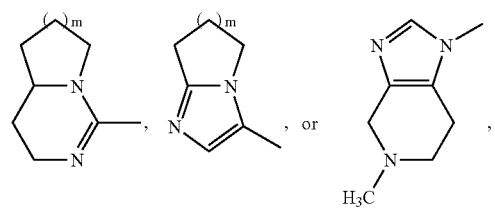

wherein in the heterocyclic moiety in each case a hydrogen atom may be replaced by a methylsulfonylmethyl, amino-C$_{1-3}$-alkyl or aminocarbonyl group, and m denotes the number 1 or 2, $R^2$ denotes a chlorine or bromine atom, a C$_{1-3}$-alkyl group wherein the hydrogen atoms may be wholly or partly replaced by fluorine atoms, or a C$_{2-3}$-alkenyl group, $R^3$ denotes a hydrogen atom, $R^4$ denotes a hydrogen atom or a straight-chain or branched C$_{1-5}$-alkyl group which is optionally substituted by a hydroxy, C$_{1-3}$-alkyloxy, mercapto, C$_{1-3}$-alkylsulfanyl, C$_{1-3}$-alkylsulfinyl, C$_{1-3}$-alkylsulfonyl, carboxy, aminocarbonyl, C$_{1-3}$-alkylaminocarbonyl, di-(C$_{1-3}$-alkyl)-aminocarbonyl, C$_{3-6}$-cycloalkyleneiminocarbonyl, amino, C$_{1-3}$-alkylamino, di-(C$_{1-3}$-alkyl)-amino, C$_{3-6}$-cycloalkyleneimino, C$_{1-3}$-alkylcarbonylamino, C$_{3-6}$-cycloalkylcarbonylamino, benzyloxycarbonylamino or guanidino group, a phenyl or heteroaryl, phenyl-C$_{1-3}$-alkyl or heteroaryl-C$_{1-3}$-alkyl group which is optionally substituted by a hydroxy, C$_{1-4}$-alkyloxy, benzyloxy, hydroxycarbonyl-C$_{1-3}$-alkoxy, C$_{1-3}$-alkyloxycarbonyl-C$_{1-3}$-alkyloxy, aminocarbonyl-C$_{1-3}$-alkyloxy, C$_{1-3}$-alkylaminocarbonyl-C$_{1-3}$-alkyloxy, di-(C$_{1-3}$-alkyl)-aminocarbonyl-C$_{1-3}$-alkyloxy, C$_{3-6}$-cycloalkyleneiminocarbonyl-C$_{1-3}$-alkyloxy, carboxy, C$_{1-3}$-alkyloxycarbonyl group, a 4- to 7-membered cycolalkyleneimino-C$_{1-3}$-alkyl group or a 4- to 7-membered cycloalkyl-C$_{1-3}$-alkyl group wherein one or two methylene groups may be replaced by a —NH— or —N(C$_{1-3}$-alkyl)-group and wherein one or two methylene groups adjacent to the —NH— or —N(C$_{1-3}$-alkyl)-group may each be replaced by a carbonyl group, with the proviso that a cycloalkyl group as hereinbefore defined wherein two —NH— or —N(C$_{1-3}$-alkyl)-groups are separated from one another by precisely one —CH$_2$— group, is excluded, R⁵ denotes a hydrogen atom, A denotes a carbonylamino or aminocarbonyl group, and B denotes a group of formula

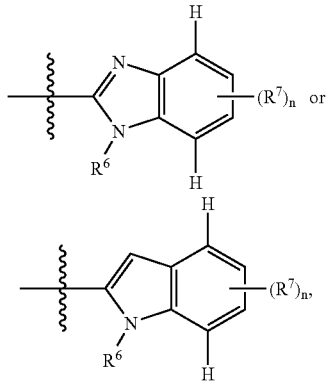

wherein:
n denotes the number 1,
R⁶ denotes a hydrogen atom or a $C_{1-3}$-alkyl, hydroxy, amino, $C_{1-3}$-alkylamino group, and
R⁷ denotes a fluorine, chlorine or bromine atom, a $C_{1-3}$-alkyl group wherein the hydrogen atoms may be wholly or partly replaced by fluorine atoms, a $C_{2-3}$-alkenyl, $C_{2-3}$-alkynyl or a hydroxy group, while, unless otherwise stated, the term "heteroaryl group" denotes a monocyclic 5- or 6-membered heteroaryl group optionally substituted in the carbon skeleton by a $C_{1-3}$-alkyl, carboxy, $C_{1-3}$-alkoxy-carbonyl or $C_{1-3}$-alkoxy-carbonylamino group, while
the 6-membered heteroaryl group contains one, two or three nitrogen atoms, and
the 5-membered heteroaryl group contains an imino group optionally substituted by a $C_{1-3}$-alkyl or phenyl-$C_{1-3}$-alkyl group, an oxygen or sulfur atom or
an imino group optionally substituted by a $C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, $C_{3-6}$-cycloalkylene-imino-$C_{1-3}$-alkyl or phenyl-$C_{1-3}$-alkyl group or an oxygen or sulfur atom and additionally a nitrogen atom or
an imino group optionally substituted by a $C_{1-3}$-alkyl or phenyl-$C_{1-3}$-alkyl group and two or three nitrogen atoms,
and moreover a phenyl ring may be fused to the above-mentioned monocyclic heteroaryl groups via two adjacent carbon atoms
and the bond is effected via a nitrogen atom or via a carbon atom of the heterocyclic moiety or a fused-on phenyl ring, while unless otherwise stated the alkyl and alkoxy groups contained in the definitions which have more than two carbon atoms may be straight-chain or branched, and the hydrogen atoms of the methyl or ethyl groups contained in the definitions may be wholly or partly replaced by fluorine atoms, the tautomers, the enantiomers, the diastereomers, the mixtures thereof and the salts thereof.

A 27th embodiment of the present invention comprises the compounds of the above general formula I, wherein:

R¹ denotes a 2,5-dihydro-1H-pyrrol-1-ylcarbonyl, pyrrolidin-1-ylcarbonyl, N-acetyl-N-cyclobutylamino, 2-(N-tert-butoxycarbonylaminomethyl)pyrrolidin-1-ylcarbonyl, 2-(aminomethyl)pyrrolidin-1-ylcarbonyl, 3-oxopiperazin-1-ylcarbonyl, 4-methyl-3-oxopiperazin-1-ylcarbonyl, thiazolidin-3-ylcarbonyl, 1,2,3,6-tetrahydropyridin-1-ylcarbonyl, 2-methylthiomorpholin-4-ylcarbonyl, thiomorpholin-4-ylcarbonyl, N-isopropyl-N-methylaminocarbonyl, 2-methoxymethylpyrrolidin-1-ylcarbonyl, 3-(pyrrolidin-1-ylmethyl)piperidin-1-ylcarbonyl, azetidin-1-ylcarbonyl, 2-methylpyrrolidin-1-ylcarbonyl, N-isobutyl-N-methylaminocarbonyl, [1,4]oxazepan-1-ylcarbonyl, 2,5-dimethylpyrrolidin-1-ylcarbonyl, piperidin-1-ylcarbonyl, 4-hydroxypiperidin-1-ylcarbonyl, 4-acetylpiperazin-1-ylcarbonyl, N,N-diethylaminocarbonyl, 3-methylpiperidin-1-ylcarbonyl, 4-methylpiperidin-1-ylcarbonyl, 2-aminomethylpiperidin-1-ylcarbonyl, 3-aminomethylpiperidin-1-ylcarbonyl, 3-(2-aminoethyl)piperidin-1-ylcarbonyl, 3-aminopiperidin-1-ylcarbonyl or N-(2-dimethylamino)ethyl-N-ethylaminocarbonyl group, R² denotes a chlorine or bromine atom, a $C_{1-3}$-alkyl group wherein the hydrogen atoms may be wholly or partly replaced by fluorine atoms, or a $C_{2-3}$-alkenyl group, R³ denotes a hydrogen atom, R⁴ denotes a hydrogen atom, the methyl, isobutyl, phenyl, benzyl, pyridin-4-ylmethyl, pyridin-2-ylmethyl, 1H-imidazol-4-ylmethyl, aminocarbonylmethyl or 4-benzyloxy-carbonylaminobutyl group, R⁵ denotes a hydrogen atom, A denotes an aminocarbonyl or carbonylamino group and B denotes a group of formula

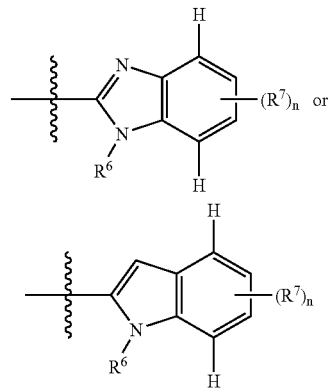

wherein:
R⁶ denotes a hydrogen atom,
R⁷ denotes a fluorine, chlorine or bromine atom or a methyl group, the tautomers, the enantiomers, the diastereomers, the mixtures thereof and the salts thereof.

According to the invention the compounds of general formula I are obtained by methods known per se, for example, by the following methods:

(a) In order to prepare a compound of general formula

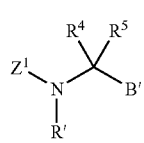
(IV)

wherein R⁴ and R⁵ are as hereinbefore defined, R' denotes the hydrogen atom or a $C_{1-3}$-alkyl group and $Z^1$ denotes the hydrogen atom or a protective group and B' denotes a group of formula

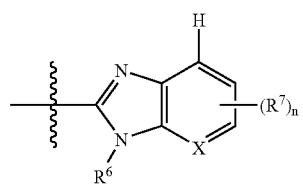
(V)

wherein R⁶ and R⁷ are as hereinbefore defined and X denotes the nitrogen atom or the CH group:

Cyclizing a compound of general formula

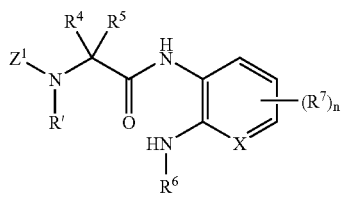
(VI)

optionally formed in the reaction mixture, wherein:

R⁴ to R⁷ are as hereinbefore defined, X denotes the nitrogen atom or the CH group, R' denotes the hydrogen atom or a $C_{1-3}$-alkyl group and $Z^1$ denotes the hydrogen atom or a protective group, then cleaving any protective group which may be present.

The cyclization is conveniently carried out in a solvent or mixture of solvents such as ethanol, isopropanol, glacial acetic acid, benzene, chlorobenzene, toluene, xylene, glycol, glycol monomethylether, diethylene glycol dimethylether, sulfolane, dimethylformamide or tetraline, dimethylsulfoxide, methylene chloride, chloroform, tetrachloromethane, for example, at temperatures between 0° C. and 250° C., but preferably between 20° C. and 100° C., optionally in the presence of a condensing agent such as phosphorus oxychloride, thionyl chloride, sulfuryl chloride, sulfuric acid, p-toluenesulfonic acid, methanesulfonic acid, hydrochloric acid, phosphoric acid, polyphosphoric acid, acetic acid, acetic anhydride, N,N-dicyclohexylcarbodiimide, or optionally also in the presence of a base such as potassium ethoxide or potassium-tert-butoxide. The cyclization may, however, also be carried out with a solvent and/or condensing agent.

(b) In order to prepare a compound of general formula

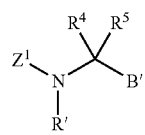
(IV)

wherein R⁴ and R⁵ are as hereinbefore defined, R' denotes the hydrogen atom or a $C_{1-3}$-alkyl group and $Z^1$ denotes the hydrogen atom or a protective group, for example, a $C_{1-5}$-alkyloxycarbonyl or benzyloxycarbonyl group, and B' denotes a group of formula

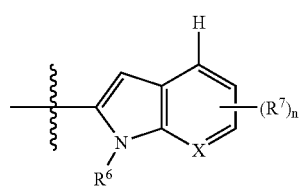
(VII)

wherein R⁶ and R⁷ are as hereinbefore defined and X denotes the nitrogen atom or the CH group:

i) transition metal-catalyzed coupling and cyclization of a compound of general formula

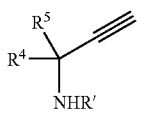
(VIII)

wherein R⁴ represents a phenyl or heteroaryl group and R⁵ denotes a hydrogen atom and R' denotes the hydrogen atom or a $C_{1-3}$-alkyl group, with a compound of general formula

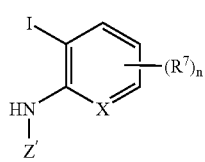
(IX)

wherein R⁷ is as hereinbefore defined, X denotes the nitrogen atom or the CH group and $Z^1$ denotes a protective group, for example, an acetyl or methylsulfonyl group, this protective group then being cleaved.

The reaction sequence is conveniently carried out in a solvent or mixture of solvents such as ethanol, isopropanol, glacial acetic acid, benzene, chlorobenzene, toluene, xylene, glycol, glycolmonomethylether, diethylene glycol dimethylether, sulfolane, dimethylformamide, N-methylpyrrolidinone, tetraline, dimethylsulfoxide, methylene chloride, chloroform, or tetrachloromethane, for example, at temperatures between 0° C. and 250° C., but preferably between 20° C. and 120° C., conveniently in the presence of transition metal catalysts such as bis(triphenylphosphine)palladium(II) chloride, bis(tricyclohexylphosphine)palladium(II) chloride, bis(triethylphosphine)palladium(II) chloride, or bis(tri-o-tolylphosphine)palladium(II) chloride and optionally in the presence of a transition metal catalyst such as copper(I) iodide, copper(I) bromide or copper(I) acetate and conveniently in the presence of a base such as tetramethylguanidine, tetramethylethylenediamine, or N,N'-dimethylethylenediamine as well as optionally using an inert gas atmosphere (for example, nitrogen or argon).

ii) alkylation of a compound of general formula

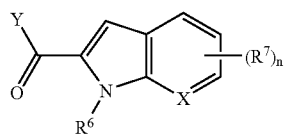

(X)

wherein $R^6$ and $R^7$ are as hereinbefore defined, X denotes the nitrogen atom or the CH group and Y denotes a hydroxy, $C_{1-4}$-alkyloxy, hydroxylamino, $C_{1-4}$-alkyloxyamino or a $C_{1-4}$-alkyloxy-$C_{1-4}$-alkylamino group, with a compound of general formula $R^4$—M (XI)

wherein $R^4$ is as hereinbefore defined, with the proviso that a phenyl or heteroaryl group is excluded, and M denotes a metal, such as, for example, lithium, sodium, or potassium, or a metal such as, for example, magnesium, cadmium, copper, or zinc, with a suitable counter-ion, such as, for example, chloride, bromide, or iodide, or also a combination of two metals, such as, for example, magnesium and copper, lithium and copper, or zinc and copper, with suitable counter-ions, such as, for example, cyanide, chloride, bromide, or iodide, and groups containing combinations thereof, followed by reductive amination of the compounds thus obtained.

The alkylation is conveniently carried out in a solvent or mixture of solvents such as benzene, chlorobenzene, toluene, xylene, glycol dimethylether, diethylene glycol dimethylether, sulfolane, dimethylformamide, N-methylpyrrolidinone, tetraline, dimethylsulfoxide, methylene chloride, chloroform, tetrachloromethane, diethyl ether, tert-butylmethylether or tetrahydrofuran, for example, at temperatures between −100° C. and +100° C., but preferably between −100° C. and 30° C., with alkylating reagents such as Grignard reagents, organolithium reagents, Gilman or Knochel cuprates, which may be produced by methods known from the literature, optionally under an inert gas atmosphere (e.g., nitrogen or argon). The subsequent reductive amination of the ketones formed after alkylation is carried out by reacting, for example, with ammonia, hydroxylamine, alkoxylamines, primary amines, hydroxylalkylamines, or alkoxy-alkylamines followed by or accompanied by reduction, for example, with hydride donors such as sodium borohydride, lithium aluminum hydride, sodium cyanoborohydride, sodium triacetoxyborohydride, or diisobutyl aluminum hydride in a solvent or mixture of solvents such as ethanol, isopropanol, benzene, toluene, pyridine, ethylene glycol dimethylether, diethylene glycol dimethylether, N-alkylmorpholine, diethyl ether, tert-butylmethylether, tetrahydrofuran, hexane, or cyclohexane or by hydrogenation optionally under pressure and conveniently in the presence of a catalyst such as Raney nickel, palladium, palladium charcoal, platinum, or platinum oxide, in a solvent or mixture of solvents such as ethyl acetate, ethanol, isopropanol, benzene, toluene, pyridine, ethylene glycol dimethylether, diethylene glycol dimethylether, N-alkylmorpholine, diethyl ether, tert-butylmethylether, tetrahydrofuran, hexane, or cyclohexane.

(c) In order to prepare a compound of general formula

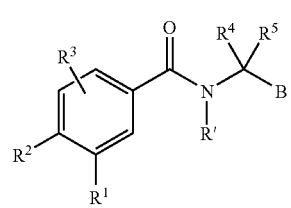

(Id)

wherein B and $R^1$ to $R^5$ are defined as in claim 1 and R' denotes the hydrogen atom or a $C_{1-3}$-alkyl group:

acylation of a compound of general formula

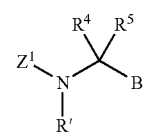

(IV)

wherein B, $R^4$ and $R^5$ are as hereinbefore defined, R' denotes the hydrogen atom or a $C_{1-3}$-alkyl group and $Z^1$ represents the hydrogen atom, with a carboxylic acid or a reactive carboxylic acid derivative of general formula

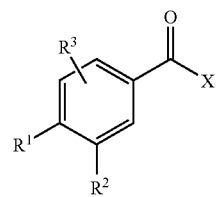

(XII)

wherein $R^1$ to $R^3$ are as hereinbefore defined and X denotes a hydroxy, $C_{1-4}$-alkoxy group, a halogen atom or an anhydride.

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, sodium hydroxide solution or sulfolane optionally in the presence of an inorganic or organic base at temperatures between −20 and 200° C., but preferably at temperatures between −10 and 160° C.

The acylation may however also be carried out with the free acid optionally in the presence of an acid-activating agent or a dehydrating agent, e.g., in the presence of isobutyl chloroformate, thionyl chloride, trimethylchlorosilane, hydrogen chloride, sulfuric acid, methanesulfonic acid, p-toluenesulfonic acid, phosphorus trichloride, phosphorus pentoxide, N,N'-dicyclohexylcarbodiimide, N,N'-dicyclohexylcarbodiimide/N-hydroxysuccinimide, or 1-hydroxybenzotriazole, N,N-carbonyldiimidazole, O-(benzotriazol- 1-yl)-N,N,N',N-tetramethyluronium tetrafluoroborate/N-methylmorpholine, O-(benzotriazol-1-yl)-N,N,N'N'-tetramethyluronium tetrafluoroborate/N-ethyldiisopropylamine, O-pentafluorophenyl-N,N,N',N'-tetramethyluroniumhexafluorophosphate/triethylamine, N,N'-thionyldiimidazole, or triphenylphosphine/carbon tetrachloride, at temperatures between −20° C. and 200° C., but preferably at temperatures between −10° C. and 160° C.

(d) In order to prepare a compound of general formula

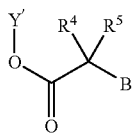

(XIII)

wherein $R^4$ and $R^5$ are as hereinbefore defined, Y' denotes a hydrogen atom or a protective group and B' denotes a group of formula

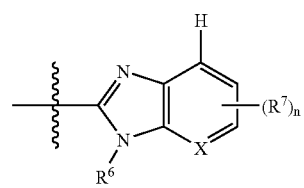

(V)

wherein $R^6$ and $R^7$ are as hereinbefore defined and X denotes the nitrogen atom or the CH group:

cyclizing a compound of general formula

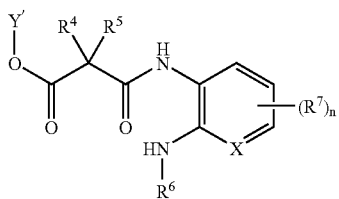

(XIV)

optionally formed in the reaction mixture, wherein $R^4$ to $R^7$ are as hereinbefore defined, X denotes the nitrogen atom or the CH group and Y' denotes the hydrogen atom or a protective group, then cleaving any protective group present.

The cyclization is conveniently carried out in a solvent or mixture of solvents such as ethanol, isopropanol, glacial acetic acid, benzene, chlorobenzene, toluene, xylene, glycol, glycolmonomethylether, diethylene glycol dimethylether, sulfolane, dimethylformamide, or tetraline, dimethylsulfoxide, methylene chloride, chloroform, tetrachloromethane, for example, at temperatures between 0° C. and 250° C., but preferably between 20° C. and 100° C., optionally in the presence of a condensing agent such as phosphorus oxychloride, thionyl chloride, sulfuryl chloride, sulfuric acid, p-toluenesulfonic acid, methanesulfonic acid, hydrochloric acid, phosphoric acid, polyphosphoric acid, acetic acid, acetic anhydride, N,N-dicyclohexylcarbodiimide, or optionally also in the presence of a base such as potassium ethoxide or potassium tert-butoxide. The cyclization may however also be carried out without a solvent and/or condensing agent.

(e) In order to prepare a compound of general formula

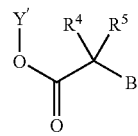

(XIII)

wherein $R^4$ and $R^5$ are as hereinbefore defined, Y' denotes the hydrogen atom or a protective group and B' denotes a group of formula

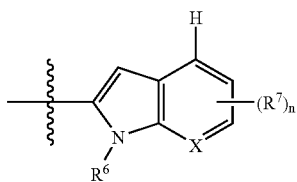

(VII)

wherein $R^6$ and $R^7$ are as hereinbefore defined and X denotes the nitrogen atom or the CH group:

i) cyclizing and subsequently alkylating a compound of general formula

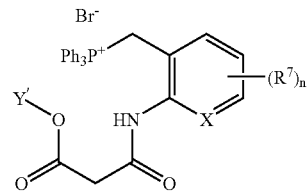

(XV)

wherein $R^7$ is as hereinbefore defined, X denotes the nitrogen atom or the CH group and Y' denotes the hydrogen atom or a protective group, such as, for example, a $C_{1-3}$-alkyl group.

The cyclization is conveniently carried out in a solvent or mixture of solvents such as ethanol, isopropanol, benzene, chlorobenzene, toluene, xylene, glycol, glycol dimethylether, diethylene glycol dimethylether, sulfolane, dimethylformamide, N-methylpyrrolidinone, tetraline, dimethylsulfoxide, methylene chloride, chloroform, or tetrachloromethane, for example, at temperatures between 0° C. and 250° C., but preferably between 20° C. and 150° C., conveniently in the presence of bases such as potassium-tert-butoxide, sodium ethoxide, potassium hexamethyldisilazane, sodium hydride or lithium diisopropylamide. After blocking of the indole-nitrogens, for example, by a tert-butoxycarbonyl group, other protective groups or a group $R^6$ according to the description by alkylation the groups $R^4$ and $R^5$ may be introduced sequentially by alkylation. For this, the reaction is conveniently carried out in a solvent or mixture of solvents such as tetrahydrofuran, tert-butylmethylether, diethyl ether, pyridine, benzene, chlorobenzene, toluene, xylene, glycol, glycol dimethylether, diethylene glycol dimethylether, sulfolane, dimethylformamide, N-methylpyrrolidinone, or tetraline, dimethylsulfoxide, methylene chloride, chloroform, tetrachloromethane, for example, at temperatures between –75° C. and 150° C., but preferably between –20° C. and 100° C., conveniently in the presence of bases such as potassium-tert-butoxide, sodium ethoxide, potassium hexamethyldisilazane, sodium hydride, or lithium diisopropylamide with an alkylating reagent such as $R^4$- or $R^5$-chloride, -bromide, -iodide, -tosylate, -triflate, or -mesylate, optionally in the presence of a suitable complexing adjuvant such as hexamethylphosphoric acid triamide. Subsequently the protective group Y' may be cleaved by methods known from the literature.

ii) cyclizing a compound of general formula

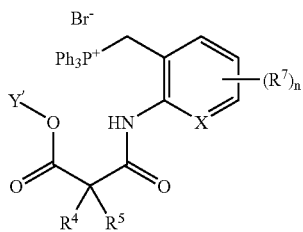

(XVI)

wherein $R^4$, $R^5$ and $R^7$ are as hereinbefore defined, X denotes the nitrogen atom or the CH group and Y' denotes a hydrogen atom or a protective group.

The cyclization is conveniently carried out in a solvent or mixture of solvents such as ethanol, isopropanol, benzene, chlorobenzene, toluene, xylene, glycol, glycol dimethylether, diethylene glycol dimethylether, sulfolane, dimethylformamide, N-methylpyrrolidinone, tetraline, dimethylsulfoxide, methylene chloride, chloroform, or tetrachloromethane, for example, at temperatures between 0° C. and 250° C., but preferably between 20° C. and 150° C., conveniently in the presence of bases such as potassium-tert-butoxide, sodium ethoxide, potassium hexamethyldisilazane, sodium hydride, or lithium diisopropylamide. Subsequently, the group $R^6$ may be introduced by alkylation. For this, a reaction is conveniently carried out in a solvent or mixture of solvents such as tetrahydrofuran, tert-butylmethylether, diethyl ether, pyridine, benzene, chlorobenzene, toluene, xylene, glycol, glycol dimethylether, diethylene glycol dimethylether, sulfolane, dimethylformamide, N-methylpyrrolidinone, or tetraline, dimethylsulfoxide, methylene chloride, chloroform, tetrachloromethane, for example, at temperatures between –75° C. and 150° C., but preferably between –20° C. and 100° C., conveniently in the presence of bases such as potassium-tert-butoxide, sodium ethoxide, sodium methoxide, potassium hexamethyldisilazane, sodium hydride, or lithium diisopropyl-amide with an alkylating reagent such as $R^6$-chloride, -bromide, -iodide, -tosylate, -triflate, or -mesylate. Subsequently the protective group Y' may be cleaved by methods known from the literature.

(f) In order to prepare a compound of general formula

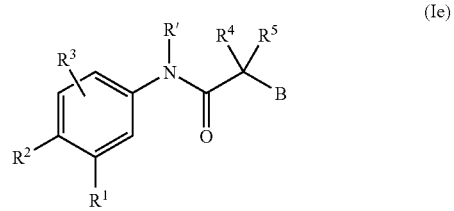

(Ie)

wherein B and $R^1$ to $R^5$ are as hereinbefore defined and R' denotes the hydrogen atom or a $C_{1-3}$-alkyl group:

acylating a compound of general formula

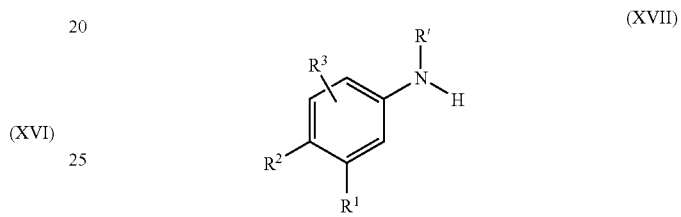

(XVII)

wherein $R^1$ to $R^3$ are as hereinbefore defined and R' denotes the hydrogen atom or a $C_{1-3}$-alkyl group, with a carboxylic acid or a reactive carboxylic acid derivative of general formula

(XVIII)

wherein B, $R^4$ and $R^5$ are as hereinbefore defined and X denotes a hydroxy, $C_{1-4}$-alkoxy group, or a halogen atom.

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, or sulfolane optionally in the presence of an inorganic or organic base at temperatures between –20° C. and 200° C., but preferably at temperatures between –10° C. and 160° C.

The acylation may however also be carried out with the free acid or an ester optionally in the presence of an acid-activating agent or a dehydrating agent, e.g., in the presence of isobutyl chloroformate, thionyl chloride, trimethylchlorosilane, hydrogen chloride, sulfuric acid, methanesulfonic acid, p-toluenesulfonic acid, phosphorus trichloride, phosphorus pentoxide, triethylamine, 1-hydroxybenzotriazole, N,N'-dicyclohexylcarbodiimide, N,N'-dicyclohexylcarbodiimide/N-hydroxysuccinimide, O-(benzotriazol-1-yl)-N,N,N'-tetramethyluronium tetrafluoroborate/N-methylmorpholine, propanephosphonic acid-cycloanhydride/N-methylmorpholine, N,N'-carbonyldiimidazole, N,N'-thionyldiimidazole, or triphenylphosphine/ carbon tetrachloride, at temperatures between −20° C. and 200° C., but preferably at temperatures between −10° C. and 160° C.

Other methods of amide coupling are described, for example, in P. D. Bailey, I.D. Collier, and K. M. Morgan in "Comprehensive Functional Group Interconversions", Vol. 5, page 257ff., Pergamon 1995.

In the reactions described above any reactive groups present such as hydroxy, carboxy, amino, alkylamino or imino groups may be protected during the reaction by conventional protective groups which are cleaved again after the reaction.

For example a suitable protective group for a hydroxy group is the methoxy, benzyloxy, trimethylsilyl, acetyl, benzoyl, tert-butyl, trityl, benzyl, or tetrahydropyranyl group, a suitable protective group for a carboxyl group is the trimethylsilyl, methyl, ethyl, tert-butyl, benzyl, or tetrahydropyranyl group, and a suitable protective group for an amino, alkylamino or imino group is the acetyl, trifluoro-acetyl, benzoyl, ethoxycarbonyl, tert-butoxycarbonyl, benzyloxycarbonyl, benzyl, methoxybenzyl, or 2,4-dimethoxybenzyl group and additionally a suitable protective group for the amino group is the phthalyl group.

Other protective groups and their cleaving are described in T. W. Greene and P. G. M. Wuts, "Protective Groups in Organic Synthesis", Wiley, 1991 and 1999, which is hereby incorporated by reference in its entirety.

Any protective group used is optionally subsequently cleaved, for example, by hydrolysis in an aqueous solvent, e.g., in water, isopropanol/water, tetrahydrofuran/water, or dioxane/water, in the presence of an acid such as trifluoroacetic acid, hydrochloric acid, or sulfuric acid or in the presence of an alkali metal base such as lithium hydroxide, sodium hydroxide, or potassium hydroxide or by means of ether splitting, e.g., in the presence of iodotrimethylsilane, at temperatures between 0° C. and 100° C., preferably at temperatures between 10° C. and 50° C.

A benzyl, methoxybenzyl or benzyloxycarbonyl group, however, is cleaved by hydrogenolysis, for example, e.g., with hydrogen in the presence of a catalyst such as palladium/charcoal in a solvent such as methanol, ethanol, ethyl acetate, dimethylformamide, dimethylformamide/acetone, or glacial acetic acid, optionally with the addition of an acid such as hydrochloric acid at temperatures between 0° C. and 50° C., but preferably at ambient temperature, and under a hydrogen pressure of 1 to 7 bar, but preferably 1 to 5 bar.

A methoxybenzyl group may also be cleaved in the presence of an oxidizing agent such as cerium(IV) ammonium nitrate in a solvent such as methylene chloride, acetonitrile or acetonitrile/water at temperatures between 0° C. and 50° C., but preferably at ambient temperature.

A methoxy group is conveniently cleaved in the presence of boron tribromide in a solvent such as methylene chloride at temperatures between −35° C. and −25° C.

A 2,4-dimethoxybenzyl group, however, is preferably cleaved in trifluoroacetic acid in the presence of anisole.

A tert-butyl or tert-butyloxycarbonyl group is preferably cleaved by treatment with an acid such as trifluoroacetic acid, or hydrochloric acid, optionally using a solvent such as methylene chloride, dioxane, or ether.

A phthalyl group is preferably cleaved in the presence of hydrazine or a primary amine such as methylamine, ethylamine, or n-butylamine in a solvent such as methanol, ethanol, isopropanol, toluene/water, or dioxane at temperatures between 20° C. and 50° C.

An allyloxycarbonyl group is cleaved by treatment with a catalytic amount of tetrakis(triphenylphosphine)palladium (0), preferably in a solvent such as tetrahydrofuran and preferably in the presence of an excess of a base such as morpholine or 1,3-dimedone at temperatures between 0° C. and 100° C., preferably at ambient temperature and under inert gas, or by treatment with a catalytic amount of tris (triphenylphosphine)rhodium(I) chloride in a solvent such as aqueous ethanol and optionally in the presence of a base such as 1,4-diazabicyclo[2.2.2]octane at temperatures between 20° C. and 70° C.

The compounds of general formulae IV to XVII used as starting materials, some of which are known from the literature, may be obtained by methods known from the literature. Their preparation is also described in the Examples.

The compounds of general formulae IV, VI, XII, and XIII (in each case with the structure V) may, for example, be prepared analogously to K. Maekawa and J. Ohtani, *Agr. Biol. Chem.* 1976, 40, 791-799.

Thus, for example, a compound of general formulae V and XIII is obtained by acylation of a corresponding o-diamino compound with a corresponding reactive acyl derivative.

Compounds of general formulae IV with the structure VII may, for example, be obtained analogously to F. Messina, M. Botta, F. Corelli, and C. Villani, *Tetrahedron Asymm.* 2000, 11, 1681-1685 or R. M. Wilson, R. A. Farr, and D. J. Burlett, *J. Org. Chem.* 1981, 46, 3293-3302.

Compounds of general formulae XII with the structure VII may, for example, be obtained analogously to L. Capuano, A. Ahlhelm, and H. Hartmann, *Chem. Ber.* 1986, 119, 2069-2074.

Thus, for example, a compound of general formula XIV and XV is obtained by acylation of a corresponding o-aminohydroxymethyl compound with a corresponding reactive acyl derivative, followed by bromination under Appel conditions or with phosphorus tribromide in pyridine followed by reaction with triphenylphosphine.

The preparation of carboxylic acid derivatives of general formulae XI and XVII is described in "Methoden der organischen Chemie" (Houben-Weyl), volume E5, Carboxylic acids and carboxylic acid derivatives, 4th edition, published by Thieme, Stuttgart 1985.

Compounds of general formulae IV and XII with structure VII in each case may, for example, also be prepared analogously to methods described in E. Müller and O. Bayer (Eds.): Methoden der Organischen Chemie (Houben-Weyl), Volume E6b, Hetarene I (ed. R. P. Kreher), supplementary and subsequent volumes to the 4th edition, published by Thieme, Stuttgart 1994, pp. 546-1336.

Moreover, the compounds of general formula I obtained may be resolved into their enantiomers and/or diastereomers.

Thus, for example, the compounds of general formula I obtained which occur as racemates may be separated by methods known per se (cf. N. L. Allinger and E. L. Eliel in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g., by chromatography and/or fractional crystallization, and, if these compounds are obtained in racemic form, they may subsequently be resolved into the enantiomers as mentioned above.

The enantiomers are preferably separated by column separation on chiral phases or by recrystallization from an optically active solvent or by reacting with an optically active substance which forms salts or derivatives such as, e.g., esters or amides with the racemic compound, particularly acids and the activated derivatives or alcohols thereof, and separating the diastereomeric mixture of salts or derivatives thus obtained, e.g., on the basis of their differences in solubility, whilst the free antipodes may be released from the pure diastereomeric salts or derivatives by the action of suitable agents. Optically active acids in common use are, e.g., the D- and L-forms of tartaric acid or dibenzoyltartaric acid, di-o-tolyltartaric acid, malic acid, mandelic acid, camphorsulfonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include, for example, hydrochloric acid, hydrobromic acid, sulfuric acid, methanesulfonic acid, phosphoric acid, fumaric acid, succinic acid, lactic acid, citric acid, tartaric acid, or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include, for example, sodium hydroxide, potassium hydroxide, cyclohexylamine, ethanolamine, diethanolamine, and triethanolamine.

As already mentioned, the compounds of general formula I and the tautomers, enantiomers, diastereomers and physiologically acceptable salts thereof have valuable pharmacological properties, particularly an antithrombotic activity which is preferably based on an effect on thrombin or factor Xa, for example, on a thrombin-inhibiting or factor Xa-inhibiting activity, on a prolonging effect on the aPTT time and on an inhibitory effect on related serine proteases such as, e.g., urokinase, factor VIIa, factor IX, factor XI, and factor XII.

The compounds listed in the Experimental Section were investigated for their effect on the inhibition of factor Xa as follows:

Method:

Enzyme-kinetic measurement with chromogenic substrate. The quantity of p-nitroaniline (pNA) released from the colorless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)aminomethane buffer (100 mM) and sodium chloride (150 mM), pH 8.0 plus 1 mg/mL Human Albumin Fraction V, protease-free Factor Xa (Calbiochem), spec. activity: 217 IU/mg, final concentration: 7 IU/mL for each reaction mixture Substrate S 2765 (Chromogenix), final concentration: 0.3 mM/L (1 KM) for each reaction mixture Test substance: final concentration 100, 30, 10, 3, 1, 0.3, 0.1, 0.03, 0.01, 0.003, and 0.001 µmol/L Procedure:

10 µL of a 23.5-times concentrated starting solution of the test substance or solvent (control), 175 µL of TRIS/HSA buffer and 25 µL of a 65.8 µL Factor Xa working solution are incubated for 10 minutes at 37° C. After the addition of 25 µL of S 2765 working solution (2.82 mmol/L), the sample is measured in a photometer (SpectraMax 250) at 405 nm for 600 seconds at 37° C.

Evaluation:

1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 µmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as, for example, the prevention and treatment of deep leg vein thrombosis, for preventing reocclusions after bypass operations or angioplasty (PT(C)A), and occlusion in peripheral arterial diseases, and for preventing and treating pulmonary embolism, disseminated intravascular coagulation, for preventing and treating coronary thrombosis, for preventing stroke and the occlusion of shunts. In addition, the compounds according to the invention are suitable for antithrombotic support in thrombolytic treatment, such as, for example, with alteplase, reteplase, tenecteplase, staphylokinase or streptokinase, for preventing long-term restenosis after PT(C)A, for the prevention and treatment of ischemic incidents in patients with all forms of coronary heart disease, for preventing metastasis and the growth of tumors and inflammatory processes, e.g., in the treatment of pulmonary fibrosis, for preventing and treating rheumatoid arthritis, for preventing and treating fibrin-dependent tissue adhesions and/or the formation of scar tissue and for promoting wound healing processes. The new compounds and the physiologically acceptable salts thereof may be used therapeutically in conjunction with acetylsalicylic acid, with inhibitors of platelet aggregation such as fibrinogen receptor antagonists (e.g., abciximab, eptifibatide, tirofiban, or roxifiban), with physiological activators and inhibitors of the clotting system and the recombinant analogues thereof (e.g., Protein C, TFPI, or antithrombin), with inhibitors of ADP-induced aggregation (e.g., clopidogrel or ticlopidine), with $P_2T$ receptor antagonists (e.g., cangrelor), or with combined thromboxane receptor antagonists/synthetase inhibitors (e.g., terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances such as hard fat or suitable mixtures thereof, to produce conventional galenic preparations such as plain or coated tablets, capsules, powders, suspensions or suppositories.

The Examples which follow are intended to illustrate the invention without restricting its scope.

EXPERIMENTAL SECTION

As a rule, melting points, IR, UV, $^1$H-NMR and/or mass spectra have been obtained for the compounds prepared. Unless otherwise stated, $R_f$ values were determined using ready-made silica gel 60 $F_{254}$ TLC plates (E. Merck, Darmstadt, Item No. 1.05714) without chamber saturation. The $R_f$ values given under the heading Alox were determined using ready-made aluminum oxide 60 $F_{254}$ TLC plates (E. Merck, Darmstadt, Item No. 1.05713) without chamber saturation. The $R_f$ values given under the heading Reversed-phase-8 were determined using ready-made RP-8 $F_{254}$, TLC plates (E. Merck, Darmstadt, Item No. 1.15684) without chamber saturation. The ratios given for the eluents refer to units by volume of the solvents in question. For chromatographic purification silica gel made by Messrs Millipore (MATREX™, 35-70 my) was used. Unless more detailed information is provided as to the configuration, it is not clear whether the products are pure stereoisomers or mixtures of enantiomers and diastereomers.

The following abbreviations are used in the descriptions of the experiments:

$R_f$ retention factor $R_t$ retention time

Boc tert-butoxycarbonyl

DMSO dimethylsulfoxide

DMF dimethylformamide o ortho rac. racemic

TBTU: O-(benzotriazol-1-yl)-N,N,N',N'-tetramethyluronium tetrafluoroborate

PFTU O-pentafluorophenyl-N,N,N',N'-tetramethyluronium hexafluorophosphate tert tertiary The HPLC/MS data for Examples 27 to 51 were obtained under the following conditions: (a) Waters ZMD, Alliance 2690 HPLC, Waters 2700 Autosampler, Waters 996 diode array detector.

The following was used as the mobile phase:

A: water with 0.1% trifluoroacetic acid

B: acetonitrile with 0.1% trifluoroacetic acid

| time in min | % A | % B | flow rate in mL/min |
|---|---|---|---|
| 0.0 | 95 | 5 | 1.00 |
| 0.1 | 95 | 5 | 1.00 |
| 5.1 | 2 | 98 | 1.00 |
| 6.5 | 2 | 98 | 1.00 |
| 7.0 | 95 | 5 | 1.00 |

The stationary phase used was a Waters column X-Terra™ MS $C_{18}$ 3.5 µm, 4.6 mm×50 mm (column temperature: constant at 25° C.).

The diode array detection took place in a wavelength range from 210-500 nm Range of mass-spectrometric detection: m/z 120 to m/z 950

(b) The HPLC/MS data for Examples 227-273 were obtained under the following conditions: HP 1100 with quaternary pump, Gilson G215 Autosampler, HP diode array detector.

The following was used as the mobile phase:

A: water with 0.1% trifluoroacetic acid

B: acetonitrile with 0.08% trifluoroacetic acid

| time in min | % A | % B | flow rate in mL/min |
|---|---|---|---|
| 0.0 | 95 | 5 | 0.4 |
| 0.15 | 95 | 5 | 0.4 |
| 4.65 | 2 | 98 | 0.4 |
| 6.0 | 2 | 98 | 0.4 |
| 6.5 | 95 | 5 | 0.4 |

The stationary phase used was a Waters column X-Terra™ MS $C_{18}$ 2.5 µm, 2.1 mm×50 mm (column temperature: constant at 25° C.).

The diode array detection took place in a wavelength range from 210-550 nm Range of mass-spectrometric detection: m/z 120 to m/z 1000

(c) The HPLC/MS data for Examples 353-357 were obtained under the following conditions: HP 1100 with quaternary pump, PAL CTC Autosampler, HP diode array detector.

The following was used as the mobile phase:

A: water with 0.1% trifluoroacetic acid

B: acetonitrile with 0.1% trifluoroacetic acid

| time in min | % A | % B | flow rate in mL/min |
|---|---|---|---|
| 0.0 | 95 | 5 | 0.8 |
| 3.00 | 2 | 98 | 0.8 |
| 3.75 | 2 | 98 | 0.8 |
| 4.0 | 95 | 5 | 0.8 |
| 5.0 | 95 | 5 | 0.8 |

The stationary phase used was a Waters column X-Terra™ MS $C_{18}$ 3.5 µm, 2.1 mm×50 mm (column temperature: constant at 40° C.).

The diode array detection took place in a wavelength range from 210-550 nm Range of mass-spectrometric detection: m/z 125 to m/z 1200.

Example 1 rac.-N-[1-(5-chloro-1H-benzimidazol-2-yl)ethyl]-3-methyl-4-(2,5-dihydropyrrol-1-ylcarbonyl)benzamide

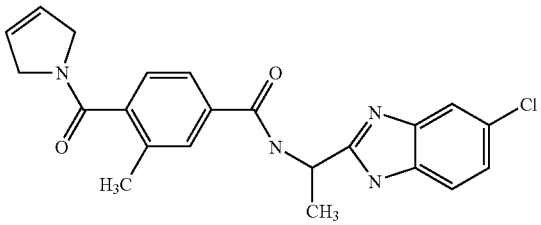

(a) rac.-N'-benzyloxycarbonyl-N-(2-amino-4-chloro)phenylalaninamide and rac.-N'-benzyloxycarbonyl-N-(2-amino-5-chloro)phenylalaninamide 4.50 g (20.2 mmol) of rac.-N-benzyloxycarbonylalanine and 3.60 g (22.2 mmol) of N,N'-carbonyldiimidazole are stirred in 25 mL of dimethylformamide for 10 minutes and then slowly combined with a solution of 4-chloro-o-phenylenediamine (6.00 g, 42.1 mmol) and 4.88 mL (44.4 mmol) of N-methylmorpholine in 25 mL of dimethylformamide and stirred for 16 hours at ambient temperature. Then water is added and the mixture is extracted three times with methylene chloride. The combined organic phases are dried with sodium sulfate and evaporated down. The residue is purified by chromatography with silica gel (gradient: methylene chloride/ethanol=100:0□95:5). The title compounds were obtained as a 4:1 mixture with diacylated phenylenediamine. Yield: 6.00 g (mixture); $R_f$ value: 0.35 (silica gel; dichloromethane/ethanol=19:1).

(b) rac.-N-benzyloxycarbonyl-1-(5-chloro-1H-benzimidazol-2-yl)ethylamine

The mixture prepared in Example 1a (6.00 g) is dissolved in 30 mL glacial acetic acid, heated to boiling for 8 hours, and stirred for a further 16 hours at ambient temperature. The acetic acid is distilled off and the crude product purified by chromatography with silica gel (gradient: methylene chloride/ethanol=100:0□98:2). Yield: 5.00 g (contaminated, approx. 80% title compound); $R_f$ value: 0.40 (silica gel; dichloromethane/ethanol=19:1).

(c) rac.-1-(5-chlorobenzimidazol-2-yl)ethylamine 5.00 g (contaminated) of rac.-N-benzyloxycarbonyl-1-(5-chloro-1H-benzimidazol-2-yl)ethylamine is dissolved in a mixture of 100 mL of methanol and 40 mL methylene chloride, combined with 1.0 g palladium on charcoal, and hydrogenated for 1 hour at 3.4 bar hydrogen pressure. The solvents are distilled off and the crude product is purified by chromatography with silica gel (eluent: methylene chloride/ethanol=95:5+0.2% ammonia). Yield: 1.08 g (25% over 3 steps); $R_f$ value: 0.37 (silica gel; dichloromethane/ethanol=4:1+2% ammonia); $C_9H_{10}ClN_3$ (195.65); mass spectrum: $(M+H)^+$=196/198 (chlorine isotope).

(d) 4-(2,5-dihydropyrrol-1-ylcarbonyl)-3-methylbromobenzene 25.0 g (0.12 mol) of 4-bromo-2-methylbenzoic acid is dissolved in 250 mL of dimethylformamide and after the addition of 41.7 g (0.13 mol) of O-(benzotriazol-1-yl)-N,N,N',N'-tetramethyluronium tetrafluoroborate (TBTU), 14.3 mL (0.13 mol) of N-methylmorpholine and 9.6 mL (0.12 mol) of 2,5-dihydropyrrole, the mixture is stirred for 16 hours at ambient temperature. Then it is poured onto ice water and extracted with ethyl acetate. The combined organic extracts are washed with sodium hydrogen carbonate solution, dried over sodium sulfate and concentrated by evaporation. Yield: 31.6 g (97% of theory); $R_f$ value: 0.45 (silica gel; dichloromethane/ethanol=19:1).

(e) 4-(2,5-dihydropyrrol-1-ylcarbonyl)-3-methylbenzonitrile 31.6 g (0.11 mol) of 4-(2,5-dihydropyrrol-1-ylcarbonyl)-3-methylbromobenzene is dissolved in 125 mL of dimethylformamide and combined with 20.2 g (0.23 mol) of copper cyanide and 3.2 g (2.7 mmol) of tetrakis-triphenylphosphinepalladium(0). The suspension is stirred for 20 hours at 140° C. Then it is cooled to 80° C., combined with 150 mL of water, 150 mL of ethyl acetate, and 25 g of CELITE® filter aid and filtered through CELITE® filter aid. The organic phase is separated off, washed with sodium chloride solution, dried over sodium sulfate, and concentrated by evaporation. The residue is chromatographed on silica gel, eluting with ethyl acetate/ethanol (50:1 and 19:1). The corresponding fractions are combined and concentrated by evaporation. Yield: 11.7 g (49% of theory); $R_f$ value: 0.55 (silica gel; ethyl acetate/ethanol=9:1).

(f) 4-(2,5-dihydropyrrol-1-ylcarbonyl)-3-methylbenzoic acid 10.6 g (0.05 mol) of 4-(2,5-dihydropyrrol-1-ylcarbonyl)-3-methylbenzonitrile are stirred in 106 mL of ethanol and 106 mL of 10 molar sodium hydroxide solution for 30 minutes at 80° C. Then the ethanol is distilled off, the residue is dissolved in water, filtered through activated charcoal and acidified with 6 molar hydrochloric acid. The acid precipitated is suction filtered and dried at 40° C. Yield: 7.5 g (64% of theory); $R_f$ value: 0.29 (silica gel; dichloromethane/ethanol=9:1).

(g) rac.-N-[1-(5-chloro-1H-benzimidazol-2-yl)ethyl]-3-methyl-4-(2,5-dihydropyrrol-1-ylcarbonyl)benzamide A solution of 0.201 g (0.869 mmol) of 3-methyl-4-(2,5-dihydropyrrol-1-ylcarbonyl)benzoic acid, 0.335 g (1.04 mmol) of TBTU and 0.33 mL (1.9 mmol) of diisopropylethylamine in 15 mL of tetrahydrofuran is stirred for 10 minutes at ambient temperature and then 0.170 g (0.869 mmol) rac.-1-(5-chloro-1H-benzimidazol-2-yl)ethylamine are added. The mixture is stirred for 16 hours at ambient temperature, combined with water, and extracted three times with ethyl acetate. The combined organic phases are washed once with 2M NaOH and three times with water, dried with sodium sulfate, and concentrated. Yield: 0.34 g (96% of theory); $R_f$ value: 0.50 (silica gel; dichloromethane/ethanol=9:1); $C_{22}H_{21}ClN_4O_2$ (408.89); mass spectrum: $(M-H)^-$=407/409 (chlorine isotope) and $(M+H)^+$=409/411 (chlorine isotope).

Example 2 rac.-N-[1-(5-chloro-1H-benzimidazol-2-yl)ethyl]-3-methyl-4-(pyrrolidin-1-ylcarbonyl)benzamide

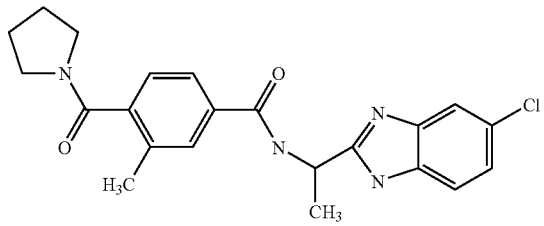

Prepared analogously to Example 1g from 3-methyl-4-(pyrrolidin-1-ylcarbonyl)benzoic acid, TBTU, diisopropylethylamine, and rac.-1-(5-chloro-1H-benzimidazol-2-yl)ethylamine in tetrahydrofuran. Yield: quantitative; $R_f$ value: 0.50 (silica gel; dichloromethane/ethanol=9:1); $C_{22}H_{23}ClN_4O_2$ (410.91); mass spectrum: $(M-H)^-=409/411$ (chlorine isotope).

Example 3

N-(5-chloro-1H-benzimidazol-2-yl)methyl-3-methyl-4-(pyrrolidin-1-ylcarbonyl)benzamide

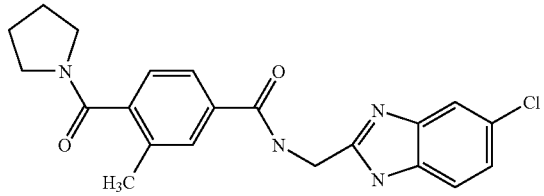

(a) N'-tert-butoxycarbonyl-N-(2-amino-4-chlorophenyl)glycinamide and regioisomer Prepared analogously to Example 1a from N-tert-butoxycarbonylglycine, N,N'-carbonyldiimidazole, 4-chloro-o-phenylenediamine, and N-methylmorpholine in dimethylformamide and subsequent purification by chromatography on silica gel (gradient: methylene chloride/ethanol=100:0□88:12). Yield: 40% (mixture); $R_f$ value: 0.24 (silica gel; dichloromethane/ethanol=95:5).

(b) N-tert-butoxycarbonyl-C-(5-chloro-1H-benzimidazol-2-yl)methylamine

Prepared analogously to Example 1b from N'-tert-butoxycarbonyl-N-(2-amino-4-chloro)phenylglycinamide in glacial acetic acid and subsequent purification by chromatography on silica gel (gradient: methylene chloride/ethanol=100:0□94:6). Yield: 23%; $R_f$ value: 0.45 (silica gel; petroleum ether/ethyl acetate=8:2); $C_{13}H_{16}ClN_3O_2$ (281.74); mass spectrum: $(M+H)^+=282/284$ (chlorine isotope).

(c) C-(5-chloro-1H-benzimidazol-2-yl)methylamine 4.62 g (16.398 mmol) N'-tert-butoxycarbonyl-C-(5-chloro-1H-benzimidazol-2-yl)methylamine are dissolved in 100 mL saturated ethanolic hydrogen chloride solution and stirred for 2 hours at ambient temperature. Then all the volatile constituents are removed under reduced pressure and the crude product is further reacted. Yield: quantitative; $R_f$ value: 0.35 (silica gel; petroleum ether/ethyl acetate=8:2).

(d) N-(5-chloro-1H-benzimidazol-2-yl)methyl-3-methyl-4-(pyrrolidin-1ylcarbonyl)benzamide Prepared analogously to Example 1g from 3-methyl-4-(pyrrolidin-1-ylcarbonyl)benzoic acid, TBTU, diisopropylethylamine and C-(5-chloro-1H-benzimidazol-2-yl)methylamine in tetrahydrofuran. Yield: 99% (over 2 steps); $R_f$ value: 0.77 (silica gel; dichloromethane/ethanol=4:1); $C_{21}H_{21}ClN_4O_2$ (396.88); mass spectrum: $(M+H)^+=397/399$ (chlorine isotope).

Example 4 rac.-N-[1-(5-chloro-1H-benzimidazol-2-yl)-2-phenylethyl]-3-methyl-4-(pyrrolidin 1-ylcarbonyl)benzamide

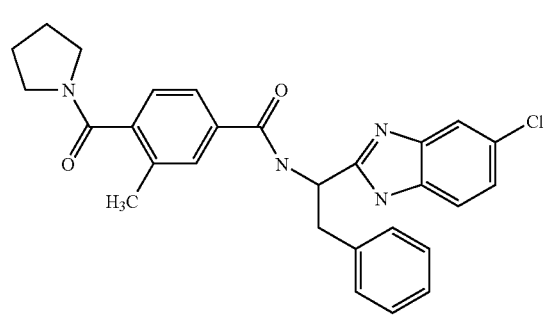

(a) rac.-N'-tert-butoxycarbonyl-N-(2-amino-4-chlorophenyl)phenylalaninamide and regioisomer Prepared analogously to Example 1a from rac.-N-tert-butoxycarbonylphenylalanine, N,N-carbonyldiimidazole, 4-chloro-o-phenylenediamine, and N-methylmorpholine in dimethylformamide and subsequent purification by chromatography on silica gel (gradient: methylene chloride/ethanol=100:0□98:2). Yield: 50%; $R_f$ value: 0.67 (silica gel; dichloromethane/ethanol=9:1); $C_{20}H_{24}ClN_3O_3$ (389.89); mass spectrum: $(M-H)^-=388/390$ (chlorine isotope).

(b) rac.-N-acetyl-1-(5-chlorobenzimidazol-2-yl)-2-phenylethylamine

Prepared analogously to Example 1b from rac.-N'-tert-butoxycarbonyl-N-(2-amino-4-chlorophenyl)phenylalanineamide and its regioisomer in glacial acetic acid and subsequent purification by chromatography on silica gel (gradient: methylene chloride/ethanol=99:1□97:3). Yield: 50%; $R_f$ value: 0.30 (silica gel; dichloromethane/ethanol=19:1); $C_{17}H_{16}ClN_3O$ (313.79); mass spectrum: $(M+H)^+=314/316$ (chlorine isotope).

(c) rac.-1-(5-chlorobenzimidazol-2-yl)-2-phenyl-ethylamine 1.35 g (4.302 mmol) of rac.-N-acetyl-1-(5-chlorobenzimidazol-2-yl)-2-phenylethylamine is placed in a mixture of 20 mL of 4 molar hydrochloric acid and 15 mL of methanol and the mixture is refluxed for 2 hours. Then all the volatile constituents are removed under reduced pressure. The crude product is further reacted directly. $R_f$ value: 0.50 (silica gel; dichloromethane/ethanol=8:2).

(d) rac.-N-[1-(5-chloro-1H-benzimidazol-2-yl)-2-phenylethyl]-3-methyl-4-(pyrrolidin-1-ylcarbonyl)benzamide Prepared analogously to Example 1g from 3-methyl-4-(pyrrolidin-1-ylcarbonyl)benzoic acid, TBTU, diisopropylethylamine, and rac.-1-(5-chlorobenzimidazol-2-yl)-2-phenylethylamine in tetrahydrofuran. Yield: 85% (over 2 steps); $R_f$ value: 0.52 (silica gel; dichloromethane/ethanol=9:1); $C_{28}H_{27}ClN_4O_2$ (487.01); mass spectrum: $(M-H)^-=485/487$ (chlorine isotope).

Example 5 rac.-N-[1-(5-chloro-1H-benzimidazol-2-yl)-2-phenylethyl]-3-methyl-4-(2,5-dihydropyrrol-1-ylcarbonyl)benzamide

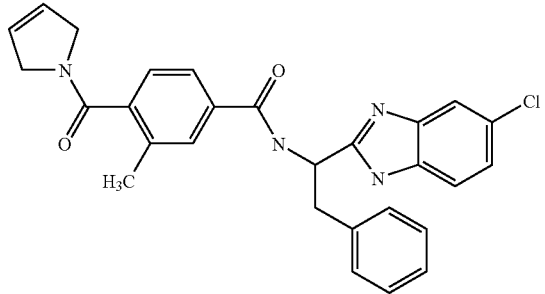

Prepared analogously to Example 1g from 3-methyl-4-(2,5-dihydropyrrol-1-ylcarbonyl)benzoic acid, TBTU, diisopropylethylamine, and rac.-1-(5-chlorobenzimidazol-2-yl)-2-phenylethylamine in tetrahydrofuran. Yield: 90%; $R_f$ value: 0.52 (silica gel; dichloromethane/ethanol=9:1); $C_{28}H_{25}ClN_4O_2$ (484.99); mass spectrum: $(M+H)^+=485/487$ (chlorine isotope).

Example 6 rac.-N-[1-(5-chloro-1H-benzimidazol-2-yl)ethyl]-3-ethynyl-4-(pyrrolidin-1-ylcarbonyl)benzamide

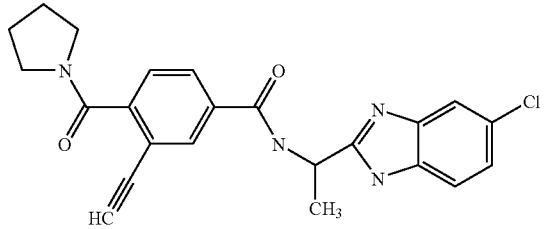

(a) 3-bromo-4-(pyrrolidin-1-ylcarbonyl)benzoic acid 100 g (0.388 mol) of 2-bromoterephthalic acid is dissolved in 700 mL of N,N-dimethylformamide and slowly combined with 69.2 g (0.427 mol) of N,N'-carbonyldiimidazole with stirring. After total dissolution, the mixture is stirred for 15 minutes at ambient temperature and then 48.5 mL (0.582 mol) of pyrrolidine and 93.9 mL (0.854 mol) of N-methylmorpholine are slowly added dropwise one after the other. The mixture is stirred for 2.5 days at ambient temperature and then concentrated in vacuo. The residue is combined with distilled water and acidified with 2 molar hydrochloric acid solution. The aqueous phase is extracted with ethyl acetate. The precipitate formed is suction filtered and dried at 40° C. Yield: 29.4 g (25%); $R_f$ value: 0.30 (silica gel; dichloromethane/ethanol=9:1); $C_{12}H_{12}BrNO_3$ (298.14); mass spectrum: $(M+H)^+=298/300$ (bromine isotope).

(b) methyl 3-bromo-4-(pyrrolidin-1-ylcarbonyl)benzoate 20 g (67.1 mmol) of 3-bromo-4-(pyrrolidin-1-ylcarbonyl)benzoic acid is dissolved in 400 mL of N,N-dimethylformamide and combined with 21.9 g (67.1 mmol) of cesium carbonate with stirring. Then 4.21 mL (67.1 mmol) of iodomethane is slowly added dropwise at ambient temperature and the mixture is stirred for 16 hours at ambient temperature. After the solid constituents have been removed by filtration with suction, volatile constituents are removed in vacuo. Yield: 20.94 g (75%); $R_f$ value: 0.42 (silica gel; dichloromethane/ethanol=98:2); $C_{13}H_{14}BrNO_3$ (312.17); mass spectrum: $(M+H)^+=312/314$ (bromine isotope).

(c) methyl 4-(pyrrolidin-1-ylcarbonyl)-3-(2-trimethylsilylethynyl)benzoate 18 g (57.7 mmol) of methyl 3-bromo-4-(pyrrolidin-1-ylcarbonyl)benzoate is placed under a nitrogen atmosphere together with 6.66 g (5.77 mmol) of tetrakis-triphenylphosphinepalladium(0) and 0.439 g (2.31 mmol) of copper(1) iodide in 150 mL of N,N-diisopropylamine, the mixture is heated to 80° C. and 16.6 mL (115 mmol) trimethylsilylethyne is added. The reaction mixture is stirred for 8 hours at 80° C. and then for 16 hours at ambient temperature. Then volatile constituents are eliminated in vacuo, the residue is taken up in ethyl acetate, insoluble matter is filtered off, and the solvent is eliminated in vacuo. The residue is purified by chromatography on silica gel (gradient: dichloromethane/ethanol 100:0□95:5). Yield: 7.7 g (41%); $R_f$ value: 0.44 (silica gel; dichloromethane/ethanol=95:5); $C_{18}H_{23}NO_3Si$ (329.48); mass spectrum: $(M+H)^+=330$.

(d) 3-ethynyl-4-(pyrrolidin-1-ylcarbonyl)benzoic acid 7.70 g (23.4 mmol) of methyl 4-(pyrrolidin-1-ylcarbonyl)-3-(2-trimethylsilylethynyl)benzoate is dissolved in 30 mL of methanol, combined with 46.7 mL (93.4 mmol) 2 molar potassium hydroxide solution, and refluxed for 2 hours. After the elimination of volatile constituents in vacuo, the residue is diluted with demineralized water and acidified with 2 molar hydrochloric acid solution. The aqueous phase is extracted three times with ethyl acetate, the combined organic phases are dried over sodium sulfate, and then the solvent is eliminated in vacuo. Yield: 3.14 g (55%); $R_f$ value: 0.59 (silica gel; dichloromethane/ethanol=4:1); $C_{14}H_{13}NO_3$ (243.27); mass spectrum: $(M+H)^+=244$.

(e) rac.-N-[1-(5-chloro-1H-benzimidazol-2-yl)ethyl]-3-ethynyl-4-(pyrrolidin-1-ylcarbonyl)benzamide Prepared analogously to Example 1g from 3-ethynyl-4-(pyrrolidin-1-ylcarbonyl)benzoic acid, TBTU, diisopropylethylamine, and rac.-1-(5-chlorobenzimidazol-2-yl)ethylamine in tetrahydrofuran. Yield: 46%; $R_f$ value: 0.48 (silica gel; dichloromethane/ethanol=9:1); $C_{23}H_{21}ClN_4O_2$ (420.90); mass spectrum: $(M+H)^+=421/423$ (chlorine isotope).

Example 7

N-[1-(5-chloro-1H-benzimidazol-2-yl)ethyl]-3-ethyl-4-(pyrrolidin-1-ylcarbonyl)benzamide

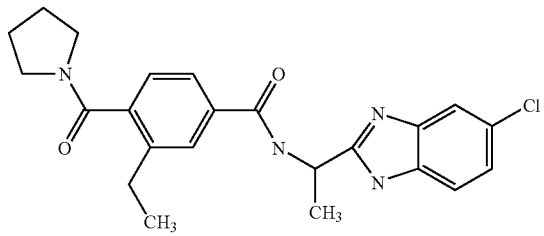

60 mg (0.143 mmol) of N-[1-(5-chloro-1H-benzimidazol-2-yl)ethyl]-3-ethynyl-4-(pyrrolidin-1-ylcarbonyl)benzamide is dissolved in 6.0 mL dioxane/water (1:1), combined with 8.0 mg platinum/activated charcoal and hydrogenated for 7 hours with hydrogen (3 bar). Then the catalyst is filtered off and the solvent is distilled off. Yield: 99%; $R_f$ value: 0.15 (Reversed-phase-8; methanol/5%-NaCl solution=3:2); $C_{23}H_{25}ClN_4O_2$ (424.93); mass spectrum: $(M-H)^-=423/425$ (chlorine isotope) and $(M+H)^+=425/427$ (chlorine isotope).

Example 8

N-[1-(5-chloro-1H-benzimidazol-2-yl)ethyl]-3-methyl-4-(N-cyclobutyl-N-acetylamino)benzamide

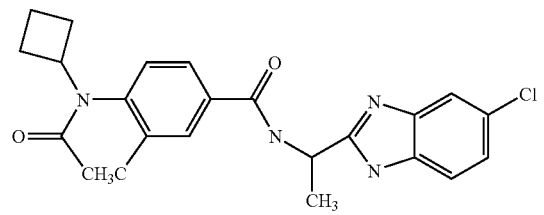

Prepared analogously to Example 1g from 3-methyl-4-(N-cyclobutyl-N-acetylamino)benzoic acid, TBTU, diisopropylethylamine, and 1-(5-chlorobenzimidazol-2-yl)ethylamine in tetrahydrofuran. Yield: quantitative; $R_f$ value: 0.50 (silica gel; methylene chloride/ethanol=9:1); $C_{23}H_{25}ClN_4O_2$ (424.93); mass spectrum: $(M+H)^+=425/427$ (chlorine isotope).

Example 9

N-[1-(5-chloro-1H-benzimidazol-2-yl)ethyl]-3-chloro-4-[2-(N-tert-butoxycarbonylamino-methyl)pyrrolidin-1-ylcarbonyl]benzamide

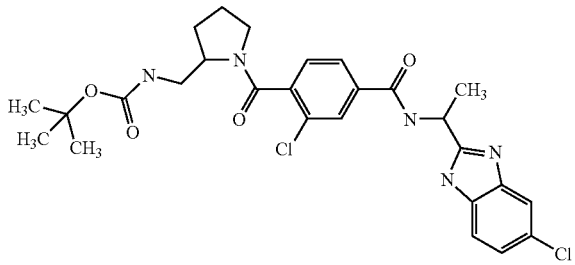

(a) rac.-4-[2-(N-tert-butoxycarbonylaminomethyl)pyrrolidin-1-ylcarbonyl]-3-chlorobenzonitrile Prepared analogously to Example I d from 2-chloro-4-cyanobenzoic acid, TBTU, N,N-diisopropylethylamine, and rac.-2-(N-tert-butoxycarbonylaminomethyl)pyrrolidine in tetrahydrofuran. Yield: quantitative; $R_f$ value: 0.52 (silica gel; dichloromethane/ethanol=95:5); $C_{18}H_{22}ClN_3O_3$ (363.85); mass spectrum: $(M+H)^+=364/366$ (chlorine isotope).

(b) rac.-4-[2-(N-tert-butoxycarbonylaminomethyl)pyrrolidin-1-ylcarbonyl]-3-chlorobenzoic acid 4.08 g (11.2 mmol) of rac.-4-[2-(N-tert-butoxycarbonylaminomethyl)pyrrolidin-1-ylcarbonyl]-3-chlorobenzonitrile is stirred for 2 hours at 80° C. in 40 mL of ethanol and 10 molar sodium hydroxide solution. The ethanol is then eliminated in vacuo and the residue diluted with ice water. After the aqueous phase has been washed with diethyl ether, the aqueous phase is combined with potassium hydrogen sulfate solution while cooling with ice and extracted three times with ethyl acetate. The combined organic phases are dried over sodium sulfate and then the solvent is eliminated in vacuo. Yield: 3.34 g (78%); $R_f$ value: 0.25 (silica gel; dichloromethane/ethanol=95:5); $C_{18}H_{23}ClN_2O_5$ (382.85); mass spectrum: $(M+H)^+=383/385$ (chlorine isotope).

(c) N-[1-(5-chloro-1H-benzimidazol-2-yl)ethyl]-3-chloro-4-[2-(N-tert-butoxycarbonylaminomethyl)pyrrolidin-1-ylcarbonyl]benzamide Prepared analogously to Example 1g from rac.-3-chloro-4-[2-(N-tert-butoxycarbonylmethyl-amino)pyrrolidin-1-ylcarbonyl]benzoic acid, TBTU, diisopropylethylamine, and rac.-1-(5-chlorobenzimidazol-2-yl)ethylamine in tetrahydrofuran. Yield: quantitative (mixture of all four stereoisomers); $R_f$ value: 0.50 (silica gel; dichloromethane/ethanol=9:1); $C_{22}H_{23}ClN_4O_2$ (410.91); mass spectrum: $(M-H)^-=409/411$ (chlorine isotope).

Example 10

(S)—N-[1-(5-chloro-1H-benzimidazol-2-yl)-2-(pyridin-4-yl)ethyl]-3-methyl-4-(pyrrolidin-1-ylcarbonyl)benzamide

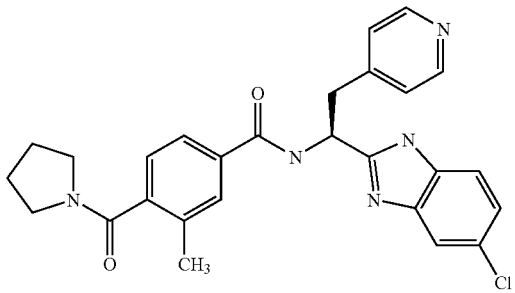

(a) (S)—N'-tert-butoxycarbonyl-N-(2-amino-5-chloro)phenyl-3-(pyridin-4-yl)alaninamide and (S)—N'-tert-butoxycarbonyl-N-(2-amino-4-chloro)phenyl-3-(pyridin-4-yl)alaninamide 2.70 g (13.1 mmol) of N,N'-dicyclohexylcarbodiimide at ambient temperature is added to a solution of 3.48 g (13.1 mmol) of (S)—N-tert-butoxycarbonyl-3-(pyridin-4-yl)alanine and 1.87 g (13.1 mmol) of 4-chloro-o-phenylenediamine in 75 mL of tetrahydrofuran (analogously to K. Maekawa and J. Ohtani, Agr. Biol. Chem. 1976, 40, 791-799). The mixture is stirred for 16 hours at ambient temperature and then the solvent is distilled off. The residue is combined with water, made alkaline, and extracted three times with ethyl acetate. The combined organic phases are dried with sodium sulfate and concentrated. The residue is chromatographed on silica gel, eluting with dichloromethane/methanol (100:5). The corresponding fractions are combined and concentrated by evaporation. Yield: 2.03 g (mixture of the regioisomers; 40% of theory); $R_f$ value: 0.23 (silica gel; dichloromethane/methanol=95:5); $C_{19}H_{23}ClN_4O_3$ (390.87); mass spectrum: $(M+H)^+=391/393$ (chlorine isotope).

(b) (S)—N-tert-butoxycarbonyl-1-(5-chloro-1H-benzimidazol-2-yl)-2-(pyridin-4-yl)ethylamine 2.03 g (5.19 mmol) of the regioisomers (S)—N'-tert-butoxycarbonyl-N-(2-amino-5-chloro)phenyl-3-(pyridin-4-yl)alaninamide and (S)—N'-tert-butoxycarbonyl-N-(2-amino-4-chloro)phenyl-3-(pyridin-4-yl)alaninamide obtained above are dissolved in 20 mL of glacial acetic acid. The mixture is stirred for 1 hour at 55° C. and then the solvent is distilled off. The residue is combined with 2 molar sodium hydroxide solution and extracted three times with ethyl acetate. The combined organic phases are dried with sodium sulfate and concentrated. The residue is triturated with diisopropylether. Yield: 1.88 g (97% of theory); $R_f$ value: 0.75 (silica gel; dichloromethane/methanol=95:5); $C_{19}H_{21}ClN_4O_2$ (372.86); mass spectrum: $(M+H)^+=373/375$ (chlorine isotope).

(c) (S)-1-(5-chloro-1H-benzimidazol-2-yl)-2-(pyridin-4-yl)ethylamine 1.88 g (5.04 mmol) of (S)—N-tert-butoxycarbonyl-1-(5-chloro-1H-benzimidazol-2-yl)-2-(pyridin-4-yl)ethylamine is dissolved in 35 mL of dichloromethane and combined with 5 mL of trifluoroacetic acid. The mixture is stirred for 16 hours at ambient temperature and then the volatile constituents are distilled off. The residue is made alkaline with 2 molar sodium hydroxide solution, evaporated down and then digested with a little water and ethyl acetate. The crystals thus obtained are dried. Yield: 1.38 g (quantitative); $R_f$ value: 0.09 (silica gel; dichloromethane/methanol=9:1); $C_{14}H_{13}ClN_4$ (272.74); mass spectrum: $(M+H)^+=273/275$ (chlorine isotope).

(d) (S)—N-[1-(5-chloro-1H-benzimidazol-2-yl)-2-(pyridin-4-yl)ethyl]-3-methyl-4-(pyrrolidin-1-ylcarbonyl)benzamide A solution of 0.150 g (0.579 mmol) of 3-methyl-4-(pyrrolidin-1-ylcarbonyl)benzoic acid, 0.186 g (0.579 mmol) of TBTU, and 0.20 mL (1.78 mmol) of N-methylmorpholine in 2 mL of N,N-dimethylformamide is stirred for 10 minutes at ambient temperature and then combined with a solution of 0.158 g (0.579 mmol) of (S)-1-(5-chloro-1H-benzimidazol-2-yl)-2-pyridin-4-ylethylamine. The reaction mixture is stirred for one day at ambient temperature, then poured onto ice water and extracted three times with ethyl acetate. The combined organic phases are dried with sodium sulfate and concentrated. The residue is chromatographed on silica gel, eluting with dichloromethane/methanol (95:10). Yield: 61.5 mg (22% of theory); $R_f$ value: 0.44 (silica gel; dichloromethane/methanol=9:1); $C_{27}H_{26}ClN_5O_2$ (487.99); mass spectrum: $(M-H)^-=486/488$ (chlorine isotope).

Example 11

(S)—N-[1-(5-chloro-1H-benzimidazol-2-yl)-2-(pyridin-2-yl)ethyl]-3-methyl-4-(pyrrolidin 1-ylcarbonyl)benzamide

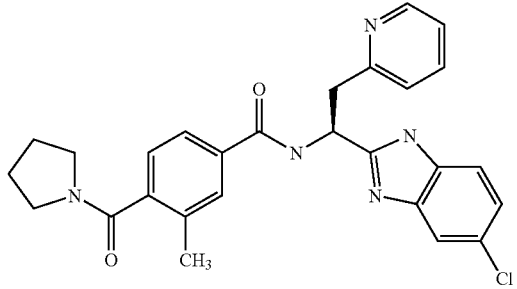

(a) (S)—N-tert-butoxycarbonyl-N-(2-amino-5-chloro)phenyl-3-(pyridin-2-yl)alaninamide and (S)—N'-tert-butoxycarbonyl-N-(2-amino-4-chloro)phenyl-3-(pyridin-2-yl)alaninamide 6.03 g (15.8 mmol) of TBTU and 6.3 mL (44.8 mmol) of triethylamine are added at 0° C. to a solution of 4.00 g (15.0 mmol) of (S)—N-tert-butoxycarbonyl-3-(pyridin-2-yl)alanine and 2.15 g (15.1 mmol) of 4-chloro-o-phenylenediamine in 90 mL dichloromethane. The mixture is heated to ambient temperature and stirred for 72 hours; then the reaction mixture is poured onto ice water and extracted three times with dichloromethane. The combined organic phases are dried with sodium sulfate and concentrated. The residue is chromatographed on silica gel, eluting with ethyl acetate/petroleum ether (60:40). The corresponding fractions are combined and concentrated by evaporation. Yield: 1.36 g (mixture of regioisomers; 23% of theory); $R_f$ value: 0.19 and 0.28 (silica gel; ethyl acetate/petroleum ether=60:40); $C_{19}H_{23}ClN_4O_3$ (390.87); mass spectrum: $(M-H)^-=389/391$ (chlorine isotope).

(b) (S)—N-tert-butoxycarbonyl-1-(5-chloro-1H-benzimidazol-2-yl)-2-(pyridin-2-yl)ethylamine Prepared analogously to Example 10b from 1.36 g (3.48 mmol) of the mixture of (S)—N'-tert-butoxycarbonyl-N-(2-amino-4-chloro)phenyl-3-(pyridin-2-yl)alaninamide and (S)—N'-tert-butoxycarbonyl-N-(2-amino-4-chloro)phenyl-3-(pyridin-2-yl)alaninamide obtained above. Yield: 1.03 g (79% of theory); $R_f$ value: 0.7 (silica gel; dichloromethane/methanol=9:1); $C_{19}H_{21}ClN_4O_2$ (372.86); mass spectrum: $(M-H)^-=371/373$ (chlorine isotope).

(c) (S)-1-(5-chloro-1H-benzimidazol-2-yl)-2-(pyridin-2-yl)ethylamine

Prepared analogously to Example 10c from 1.02 g (2.74 mmol) of (S)—N-tert-butoxycarbonyl-1-(5-chloro-1H-benzimidazol-2-yl)-2-(pyridin-2-yl)ethylamine. The crude product is chromatographed on silica gel, eluting with dichloromethane/methanol (90:10). Yield: 0.2 g (27% of theory); $R_f$ value: 0.44 (silica gel; dichloromethane/methanol=9:1); $C_{14}H_{13}ClN_4$ (272.74); mass spectrum: $(M+H)^+=273/275$ (chlorine isotope).

(d) (S)—N-[1-(5-chloro-1H-benzimidazol-2-yl)-2-(pyridin-2-yl)ethyl]-3-methyl-4-(pyrrolidin-1-ylcarbonyl)benzamide Prepared analogously to Example 10d from 0.20 g (0.733 mmol) of (S)-1-(5-chloro-1H-benzimidazol-2-yl)-2-(pyridin-2-yl)ethylamine. Yield: 149 mg (42% of theory); $R_f$ value: 0.27 (silica gel; dichloromethane/methanol=95:5); $C_{27}H_{26}ClN_5O_2$ (487.99); mass spectrum: (M–H)-=486/488 (chlorine isotope).

Example 12 rac.-N-[1-(5-fluoro-1H-benzimidazol-2-yl)ethyl]-3-methyl-4-(pyrrolidin-1-ylcarbonyl)benzamide

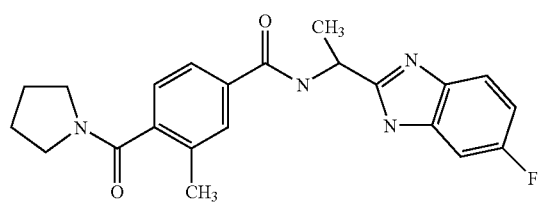

A solution of 0.10 g (0.43 mmol) of 3-methyl-4-(pyrrolidin-1-ylcarbonyl)benzoic acid, 0.184 g (0.450 mmol) of 1-(5-fluoro-1H-benzimidazol-2-yl)ethylamine×2 (CF$_3$COOH) (prepared analogously to Methods 1a, 10b, 10c) and 0.35 mL (2.50 mmol) of triethylamine in 3 mL of dimethylsulfoxide is stirred at ambient temperature and combined with 0.193 g (0.600 mmol) of TBTU. The reaction mixture is stirred for 1 hour at ambient temperature, then diluted with ethyl acetate and washed successively with 10% aqueous citric acid, twice with 2 molar sodium hydroxide solution and with water. The organic phase is dried with sodium sulfate and concentrated. The crude product is taken up in ethyl acetate, precipitated with tert-butylmethylether, and dried. Yield: 83 mg (49% of theory); $R_f$ value: 0.34 (silica gel; ethyl acetate/ethanol=9:1); $C_{22}H_{23}FN_4O_2$ (394.45); mass spectrum: $(M+H)^+=395$ Example 13 rac.-N-[1-(5-cyano-1H-benzimidazol-2-yl)ethyl]-3-methyl-4-(pyrrolidin-1-ylcarbonyl)benzamide

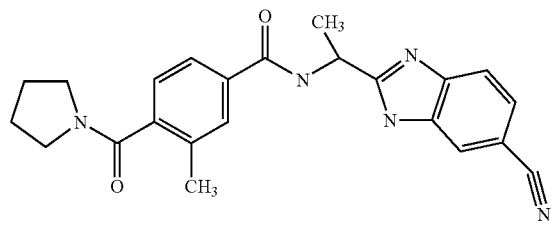

Prepared analogously to Example 12a from 0.135 g (0.450 mmol) of 1-(5-cyano-1H-benzimidazol-2-yl)ethylammonium trifluoroacetate. Yield: 23 mg (13% of theory); $R_f$ value: 0.30 (silica gel; ethyl acetate/ethanol=9:1); $C_{23}H_{23}N_5O_2$ (401.47); mass spectrum: $(M+H)^+=402$ Example 14 rac.-N-[1-(5-methoxy-1H-benzimidazol-2-yl)ethyl]-3-methyl-4-(pyrrolidin-1-ylcarbonyl)benzamide Prepared analogously to Example 12a from 86 mg (0.45 mmol) of 1-(5-methoxy-1H-benzimidazol-2-yl)ethylamine. Yield: 41 mg (24% of theory); $R_f$ value: 0.25 (silica gel; ethyl acetate/ethanol=9:1); $C_{23}H_{26}N_4O_3$ (406.49); mass spectrum: $(M+H)^+=407$

Example 15

(S)—N-[1-(5-chloro-1H-benzimidazol-2-yl)-2-(1H-imidazol-4-yl)ethyl]-3-methyl-4-(pyrrolidin-1-ylcarbonyl)benzamide

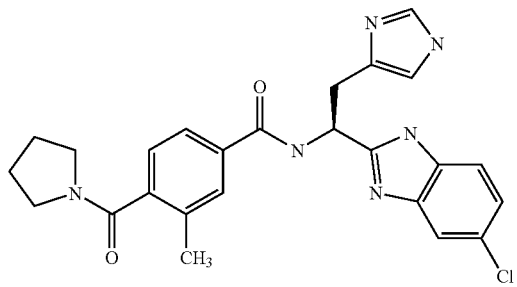

Prepared analogously to Example 10d from (S)-1-(5-chloro-1H-benzimidazol-2-yl)-2-(1H-imidazol-4-yl)ethylamine and 3-methyl-4-(pyrrolidin-1-ylcarbonyl)benzoic acid. Yield: 55% of theory. $R_f$ value: 0.72 (silica gel; dichloromethane/methanol=4:1); $C_{25}H_{25}ClN_6O_2$ (476.97); mass spectrum: $(M+H)^+$=477/479 (chlorine isotope).

Example 16

4-[(2R/S)-aminomethylpyrrolidin-1-ylcarbonyl]-3-chloro-N-[(1S)-1-(5-chloro-1H-benzimidazol-2-yl)-2-(pyridin-4-yl)ethyl]benzamide

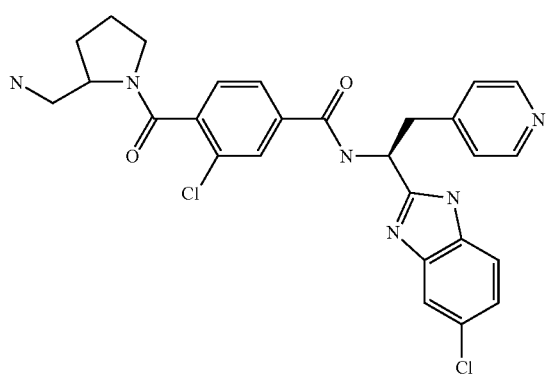

Prepared analogously to Example 10d from rac.-4-[2-(tert-butoxycarbonylaminomethyl)pyrrolidin-1-ylcarbonyl]-3-chlorobenzoic acid and (S)-(5-chloro-1H-benzimidazol-2-yl)-2-pyridin-4-ylethylamine with subsequent cleaving of the protective group with trifluoroacetic acid analogously to Example 10c. Yield: 52 mg (11% over 2 steps); $R_f$ value: 0.15 (silica gel; dichloromethane/methanol=9:1); $C_{27}H_{28}Cl_2N_6O_2 \times 2\ C_2F_3O_2$ (765.50); mass spectrum: $(M-H)^-$=537/539/541 (chlorine isotope).

Example 17

N-[1-(5-chloro-1H-benzimidazol-2-yl)ethyl]-3-chloro-4-(2-aminomethylpyrrolidin-1-ylcarbonyl)benzamide

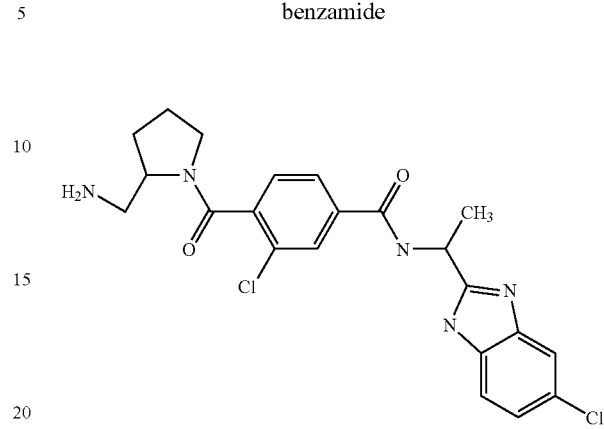

0.25 g (0.446 mmol) of N-[1-(5-chloro-1H-benzimidazol-2-yl)ethyl]-3-chloro-4-[2-(N-tert-butoxycarbonylaminomethyl)pyrrolidin-1-ylcarbonyl]benzamide (Example 9) is dissolved in 10 mL of dichloromethane and after the addition of 0.68 mL (8.9 mmol) of trifluoroacetic acid stirred for 1 hour at ambient temperature. After elimination of the volatile constituents in vacuo, the residue is taken up in ethyl acetate, the solution washed twice with 2 molar sodium hydroxide solution and three times with demineralized water, and dried over sodium sulfate. Finally, the solvent is eliminated in vacuo. Yield: 120 mg (58%; mixture of all four stereoisomers); $R_f$ value: 0.10 (silica gel; dichloromethane/ethanol=9:1); $C_{22}H_{23}Cl_2N_5O_2$ (460.36); mass spectrum: $(M+H)^+$=460/462/464 (chlorine isotope).

Example 18

1-[N-(5-methyl-1H-benzimidazol-2-yl)]ethyl-3-methyl-4-(pyrrolidin-1-ylcarbonyl)benzamide

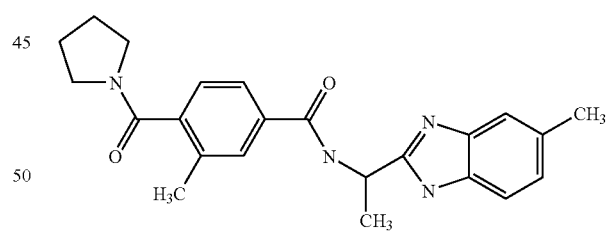

(a) Isomer mixture of rac.-N'-benzyloxycarbonyl-N-(2-amino-4-methyl)phenylalaninamide and rac.-N'-benzyloxycarbonyl-N-(2-amino-5-methyl)phenylalaninamide 1.57 g (7.03 mmol) of rac.-N-benzyloxycarbonylalanine is placed together with 0.86 g (7.03 mmol) of 3,4-diaminotoluene in 100 mL of tetrahydrofuran at 0° C. and 1.45 g (7.03 mmol) of N,N'-dicyclohexylcarbodiimide are added slowly with stirring. The mixture is allowed to come up to ambient temperature and then stirred for another 16 hours. Then the precipitate formed is filtered off and the solvent is distilled off in vacuo. The residue is recrystallized from a little ethyl acetate. Yield: 1.1 g (48%); $R_f$ value: 0.50 (silica gel; dichloromethane/ethanol=9:1); $C_{18}H_{21}N_3O_3$ (327.39); mass spectrum: $(M+H)^+=328$ (b) 1-[N-(5-methyl-1H-benzimidazol-2-yl)]ethyl-3-methyl-4-(pyrrolidin-1-ylcarbonyl)benzamide Prepared analogously to Example 1g from 3-methyl-4-(pyrrolidin-1-ylcarbonyl)benzoic acid, TBTU, diisopropylethylamine, and (5-methylbenzimidazol-2-yl)ethylamine (prepared from the isomer mixture of Example 18a and the synthesis sequence 1b, 1c) in tetrahydrofuran. Yield: 47%; $R_f$ value: 0.35 (silica gel; dichloromethane/ethanol=9:1); $C_{23}H_{26}N_4O_2$ (390.49); mass spectrum: $(M+H)^+=391$ Example 19

3-chloro-N-(5-chloro-1H-benzimidazol-2-ylmethyl)-4-(3-oxopiperazin-1-ylcarbonyl)benzamide

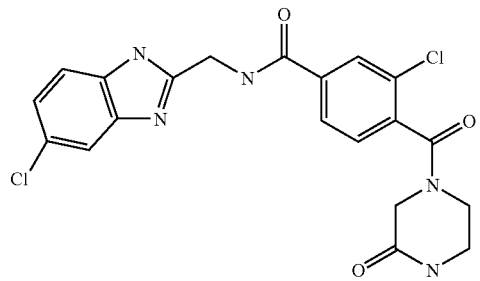

(a) 3-chloro-N-(5-chloro-1H-benzimidazol-2-ylmethyl)-4-methoxycarbonylbenzamide 1.61 g (7.50 mmol) of 3-chloro-4-methoxycarbonylbenzoic acid is dissolved in 40 mL of N,N-dimethylformamide and combined with 1.30 g (8.00 mmol) of N,N'-carbonyldiimidazole and stirred for 15 minutes at ambient temperature under a nitrogen atmosphere. Then 1.0 mL (7.5 mmol) of triethylamine, 1.5 mL (15 mmol) of N-methylmorpholine, and 1.69 g (7.75 mmol) of C-(5-chloro-1H-benzimidazol-2-yl)methylamine are added successively and stirred for a further 16 hours at ambient temperature under a nitrogen atmosphere. Then the reaction mixture is poured into 1 L of ice water, the precipitate is separated off by filtering, washed with a little demineralized water, and dried at 40° C. Finally the product is recrystallized from petroleum ether/ethyl acetate (2:1). Yield: 2.40 g (85%); $R_f$ value: 0.58 (silica gel; dichloromethane/ethanol=9:1); $C_{17}H_{13}Cl_2N_3O_3$ (378.22); mass spectrum: $(M-H)^-=376/78/80$ (chlorine isotope).

(b) 3-chloro-N-(5-chloro-1H-benzimidazol-2-ylmethyl)-4-hydroxycarbonylbenzamide 2.15 g of 3-chloro-N-(5-chloro-1H-benzimidazol-2-ylmethyl)-4-methoxycarbonylbenzamide is dissolved in 50 mL of isopropanol, and 50 mL of 1 molar sodium hydroxide solution is added and the mixture is stirred for 3 hours at ambient temperature. Then it is poured into 250 mL ice water and extracted twice with ethyl acetate. The aqueous phase is adjusted to pH 4 with 1 molar hydrochloric acid and the precipitate formed is separated off by filtration. The solid is washed with a little demineralized water and dried at 40° C. Then the solid obtained is treated with 150 mL of solvent mixture comprising petroleum ether/diethyl ether/ethyl acetate and dried again. Yield: quantitative; $C_{16}H_{11}Cl_2N_3O_3$ (364.19); mass spectrum: $(M+H)^+=364/66/68$ (chlorine isotope).

(c) 3-chloro-N-(5-chloro-1H-benzimidazol-2-ylmethyl)-4-(3-oxopiperazin-1-ylcarbonyl)benzamide 0.182 g (0.50 mmol) of 3-chloro-N-(5-chloro-1H-benzimidazol-2-ylmethyl)-4-hydroxy-carbonylbenzamide is dissolved in 5 mL of N,N-dimethylformamide and 160.5 mg (0.50 mmol) of TBTU and 85.6 µL (0.50 mmol) of diisopropylethylamine are added successively with stirring at ambient temperature. Then a solution of 50 mg (0.50 mmol) of 2-oxopiperazine in 5 mL of N,N-dimethylformamide is added dropwise and the reaction mixture is stirred for 3 hours at ambient temperature. Then the solvent is eliminated in vacuo and the residue purified by chromatography on silica gel (gradient: dichloromethane/methanol=100:0 □93:7). Yield: 99 mg (44%); $C_{20}H_{17}Cl_2N_5O_3$ (446.30); mass spectrum: $(M+H)^+=446/448/450$ (chlorine isotope).

Example 20

3-chloro-N-(5-chloro-1H-benzimidazol-2-ylmethyl)-4-(4-methyl-3-oxopiperazin-1-ylcarbonyl)benzamide

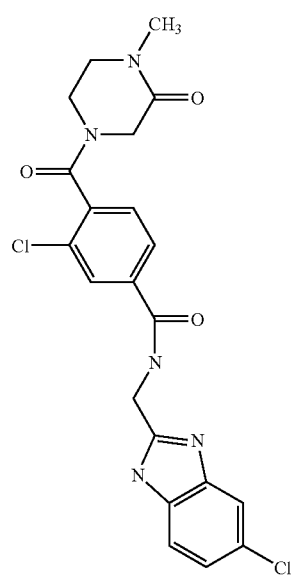

Prepared analogously to Example 19c from 2-chloro-4-[N-(5-chlorobenzimidazol-2-ylmethyl)carbamoyl]benzoic acid, TBTU, diisopropylethylamine, and N-methylpiperazinone in N,N-dimethylformamide. Yield: 8.7%; $C_{21}H_{19}Cl_2N_5O_3$ (460.32); mass spectrum: $(M+H)^+=460/462/464$ (chlorine isotope).

Example 21

3-chloro-N-(5-chloro-1H-benzimidazol-2-ylmethyl)-4-(2-aminomethylpyrrolidin-1'-ylcarbonyl)benzamide

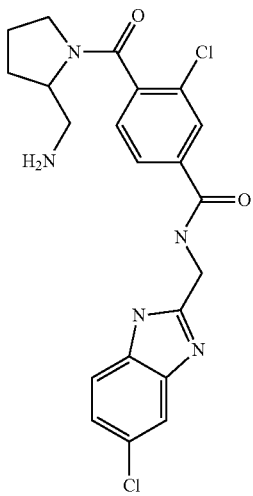

Prepared analogously to Example 19c from 2-chloro-4-[N-(5-chlorobenzimidazol-2-ylmethyl)carbamoyl]benzoic acid, TBTU, diisopropylethylamine, and 2-(N-tert-butoxycarbonylaminomethyl)pyrrolidine in N,N-dimethylformamide and subsequent reaction with trifluoroacetic acid and NaOH analogously to Example 17. Yield: 104 mg (47% over 2 steps); $C_{21}H_{21}Cl_2N_5O_2$ (446.34); mass spectrum: $(M+H)^+$=446/448/450 (chlorine isotope).

Example 22

N-(5-chloro-1H-benzimidazol-2-ylmethyl)-4-(2,3-dihydroimidazo[2,1-b]thiazol-5-yl)benzamide

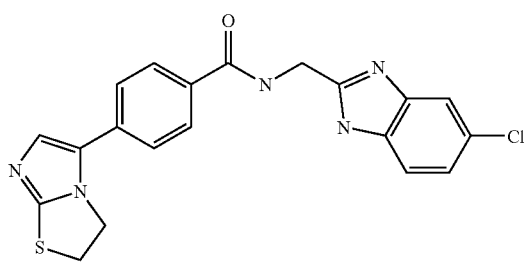

(a) 4-(2,3-dihydroimidazo[2,1-b]thiazol-5-yl)benzonitrile 3.00 g (12.72 mmol) of 4-bromoacetylbenzonitrile is dissolved in 40 mL acetonitrile, and combined with 2.65 g (25.42 mmol) of 2-amino-4,5-dihydrothiazole and 2.00 g of molecular sieve 4 Å. Then the mixture is stirred for 2.5 days at ambient temperature. Then the solvent is eliminated in vacuo, and the residue is taken up with 100 mL of 1 molar hydrochloric acid solution and the insoluble matter is taken up with a little methanol and concentrated ammonia solution. After filtration, the filtrate is concentrated in vacuo and purified by chromatography on silica gel (gradient: initially ethyl acetate/ethanol=100:0 □40:60+0.5% ammonia, then dichloromethane/methanol=6:4+2% triethylamine). Yield: 2.4 g; $R_f$ value: 0.65 (silica gel; ethyl acetate/ethanol=8:2+1% ammonia); $C_{12}H_9N_3S$ (227.29); mass spectrum: $(M+H)^+$=228

(b) 4-(2,3-dihydroimidazo[2,1-b]thiazol-5-yl)benzoic acid 2.00 g (8.80 mmol) of contaminated 4-(2,3-dihydroimidazo[2,1-b]thiazol-5-yl)benzonitrile is placed in 60 mL of 50% acetic acid solution at 0° C. and slowly combined with 30 mL of concentrated sulfuric acid with stirring and cooling in the ice bath. The reaction mixture is heated to 100° C. for 17 hours and then poured into 500 mL of ice water. The precipitated product formed is filtered off. The mother liquor is combined with sodium chloride and extracted with 300 mL of ethyl acetate, washed with saturated sodium chloride solution, dried with magnesium sulfate, and the solvent is distilled off. The residue remaining is combined with the above precipitate. Yield: 1.25 g (40% over 2 steps); $R_f$ value: 0.55 (silica gel; ethyl acetate/ethanol=9:1); $C_{12}H_{10}N_2O_2S$ (246.29); mass spectrum: $(M+H)^+$=247

(c) N-(5-chloro-1H-benzimidazol-2-ylmethyl)-4-(2,3-dihydroimidazo[2,1-b]thiazol-5-yl)benzamide Prepared analogously to Example 1g from 4-(2,3-dihydroimidazo[2,1-b]thiazol-5-yl)benzoic acid, TBTU, triethylamine and (5-chloro-1H-benzimidazol-2-yl)methylamine in N,N-dimethylformamide. Yield: 73%; $R_f$ value: 0.50 (silica gel; ethyl acetate/ethanol=9:1); $C_{20}H_{16}ClN_5OS$ (409.90); mass spectrum: $(M+H)^+$=410/412 (chlorine isotope).

Example 23

2-(5-chloro-1H-benzimidazol-2-yl)-N-[3-methyl-4-(pyrrolidin-1-ylcarbonyl)phenyl]acetamide

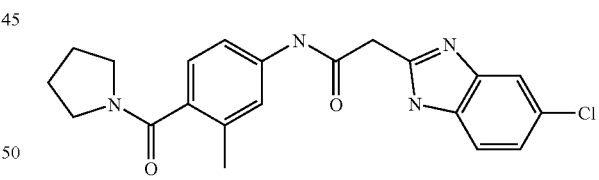

(a) methyl N-(2-amino-4-chlorophenyl)carbamoylacetate and N-(2-methylamino-5chlorophenyl)carbamoylacetate 5.70 g (40.0 mmol) of 4-chloro-o-phenylenediamine is placed in 75 mL of dichloromethane, combined with 5.8 mL (42.0 mmol) of triethylamine and while being cooled in the ice bath slowly combined with 3 mL (41.0 mL) of methyl malonate chloride. Then the mixture is heated to ambient temperature and stirred for 24 hours. The reaction mixture is poured into ice water and extracted three times with dichloromethane. The combined organic phases are washed with saturated sodium chloride solution, dried over sodium sulfate, and concentrated. The residue is purified by chromatography on silica gel (gradient: petroleum ether/ethyl acetate=9:1□7:3□1:1). Yield: 1.15 g (12%); $R_f$ value: 0.20 (silica gel; petroleum ether/ethyl acetate=1:1); $C_{10}H_{11}ClN_2O_3$ (242.66); mass spectrum: $(M+H)^+=243/245$ (chlorine isotope).

(b) methyl (5-chloro-1H-benzimidazol-2-yl)acetate 1.10 g (4.53 mmol) of methyl N-(2-amino-4-chlorophenyl)carbamoylacetate and methyl N-(2-amino-5-chlorophenyl)carbamoylacetate are refluxed for 25 minutes in 25 mL of glacial acetic acid. Then the mixture is neutralized cold with concentrated ammonia solution and the precipitate formed is filtered off and dried. Yield: 0.78 g (58%) (purity: 75%); $R_f$ value: 0.30 (silica gel; dichloromethane/ethanol=19:1); $C_{10}H_9ClN_2O_2$ (224.65); mass spectrum: $(M+H)^+=225/227$ (chlorine isotope).

(c) (5-chloro-1H-benzimidazol-2-yl)acetic acid hydrochloride 0.68 g (2.27 mmol) of 75% methyl (5-chloro-1H-benzimidazol-2-yl)acetate is suspended in 20 mL of concentrated hydrochloric acid solution and stirred for 16 hours at ambient temperature. The precipitate formed is suction filtered and the filtrate concentrated in vacuo at 50° C. The residue is taken up twice in toluene and twice in diethyl ether, the volatile constituents are eliminated in vacuo. The residue is washed with diethyl ether. Yield: 0.23 g (41%) (hydrochloride); $R_f$ value: 0.15 (silica gel; dichloromethane/ethanol=8:2+1% glacial acetic acid); $C_9H_7ClN_2O_2$ x HCl (210.62/247.08); mass spectrum: $(M+H)^+=211/213$ (chlorine isotope).

(d) 2-(5-chloro-1H-benzimidazol-2-yl)-N-[3-methyl-4-(pyrrolidin-1-ylcarbonyl)phenyl]acetamide Prepared analogously to Example 1g from (5-chloro-1H-benzimidazol-2-yl)acetic acid, TBTU, N-methylmorpholine, and 4-amino-2-methylbenzoic acid pyrrolidine amide in N,N-dimethylformamide and subsequent chromatography on silica gel (gradient: dichloromethane/ethanol=100:0□25:1□19:1□19:1); Yield: 14 mg (7.1%); $R_f$ value: 0.45 (silica gel; dichloromethane/ethanol=9:1); $C_{21}H_{21}ClN_4O_2$ (396.88); mass spectrum: $(M-H)^-=395/397$ (chlorine isotope).

Example 24

3-methyl-4-(pyrrolidine-1-carbonyl)-N-[1-(5-trifluoromethyl-1H-benzimidazol-2-yl)ethyl]benzamide

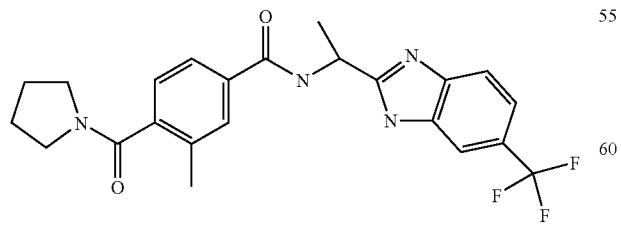

Prepared analogously to Example 10d from 3-methyl-4-(pyrrolidin-1-ylcarbonyl)benzoic acid, TBTU, diisopropylethylamine, and rac.-1-(5-trifluoromethyl-1H-benzimidazol-2-yl)ethylamine in dimethylformamide. Yield: 90 mg (47% of theory); $R_f$ value: 0.38 (silica gel; ethyl acetate/ethanol=9:1); $C_{23}H_{23}F_4N_3O_2$ (444.46); mass spectrum: $(M+H)^+=445$ Example 25

(S)—N-[2-aminocarbonyl-1-(5-chloro-1H-benzimidazol-2-yl)ethyl]-3-methyl-4-(pyrrolidin-1-ylcarbonyl)benzamide

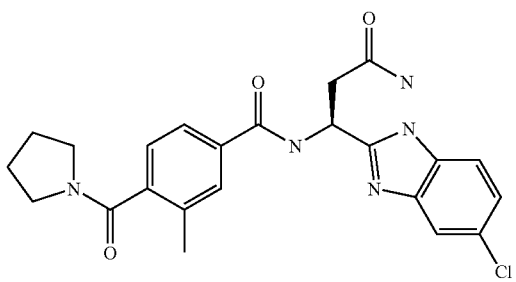

Prepared analogously to Example 10d from 3-methyl-4-(pyrrolidin-1-ylcarbonyl)benzoic acid, TBTU, diisopropylethylamine, and (S)-3-amino-3-(5-chloro-1H-benzimidazol-2-yl)propionic acid amide in dimethylformamide. Yield: 97 mg (43% of theory); $R_f$ value: 0.37 (silica gel; dichloromethane/methanol=9:1); $C_{23}H_{24}ClN_5O_3$ (453.93); mass spectrum: $(M+H)^+=454/456$ (chlorine isotope).

Example 26

3-chloro-N-(5-chloro-1H-benzimidazol-2-ylmethyl)-4-(2,5-dihydropyrrol-1-ylcarbonyl)benzamide

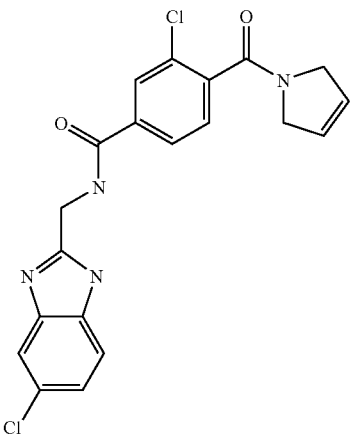

Prepared analogously to Example 1d from 3-chloro-N-(5-chloro-1H-benzimidazol-2-ylmethyl)-4-carboxybenzamide and 2,5-dihydropyrrole, TBTU, and triethylamine in DMSO.

Example 27

3-chloro-N-(5-chloro-1H-benzimidazol-2-ylmethyl)-4-(thiazolidin-3-ylcarbonyl)benzamide

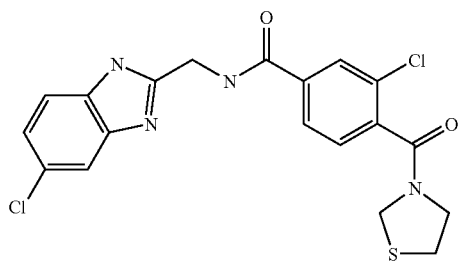

Prepared analogously to Example 1d from 3-chloro-N-(5-chloro-1H-benzimidazol-2-ylmethyl)-4-carboxybenzamide, thiazolidine, TBTU, and triethylamine in DMSO at ambient temperature. HPLC-MS results: retention time: 3.51 minutes; $C_{19}H_{16}Cl_2N_4O_2S$ (435.33); mass spectrum: $(M+H)^+=435.1$.

Example 28

3-chloro-N-(5-chloro-1H-benzimidazol-2-ylmethyl)-4-(1,2,3,6-tetrahydropiperidin-1-ylcarbonyl)benzamide

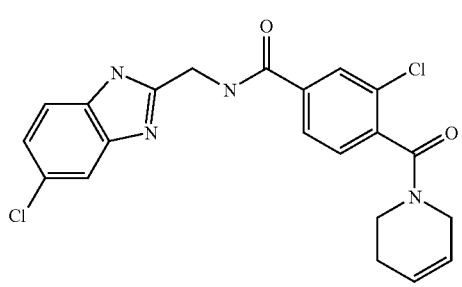

Prepared analogously to Example 1d from 3-chloro-N-(5-chloro-1H-benzimidazol-2ylmethyl)-4-carboxybenzamide, 1,2,3,6-tetrahydropyridine, TBTU, and triethylamine in DMSO at ambient temperature. HPLC-MS results: retention time: 3.61 minutes; $C_{21}H_{18}Cl_2N_4O_2$ (429.31); mass spectrum: $(M+H)^+=429.1$.

Example 29

3-chloro-N-(5-chloro-1H-benzimidazol-2-ylmethyl)-4-(2-methylthiomorpholin-4-ylcarbonyl)benzamide

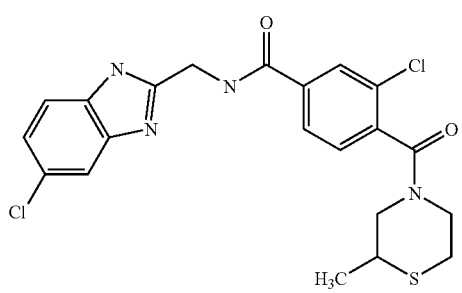

Prepared analogously to Example 1d from 3-chloro-N-(5-chloro-1H-benzimidazol-2-ylmethyl)-4-carboxybenzamide, 2-methylthiomorpholine, TBTU, and triethylamine in DMSO at ambient temperature. HPLC-MS results: retention time: 3.78 minutes; $C_{21}H_{20}Cl_2N_4O_2S$ (463.39); mass spectrum: $(M+H)^+=463.1$.

Example 30

3-chloro-N-(5-chloro-1H-benzimidazol-2-ylmethyl)-4-(thiomorpholin-4-ylcarbonyl)benzamide

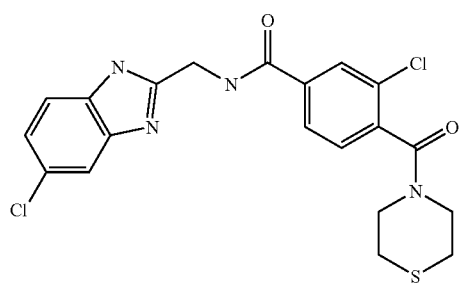

Prepared analogously to Example 1d from 3-chloro-N-(5-chloro-1H-benzimidazol-2-ylmethyl)-4-carboxybenzamide, thiomorpholine, TBTU, and triethylamine in DMSO at ambient temperature. HPLC-MS results: retention time: 3.60 minutes; $C_{20}H_{18}Cl_2N_4O_2S$ (449.36); mass spectrum: $(M+H)^+=449.1$.

Example 31

3-chloro-N-(5-chloro-1H-benzimidazol-2-ylmethyl)-4-(N-isopropyl-N-methylamino-carbonyl)benzamide

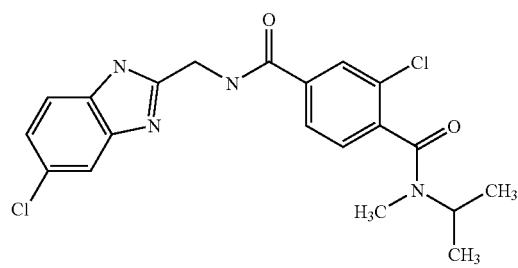

Prepared analogously to Example 1d from 3-chloro-N-(5-chloro-1H-benzimidazol-2-ylmethyl)-4-carboxybenzamide, N-isopropylmethylamine, TBTU, and triethylamine in DMSO at ambient temperature. HPLC-MS results: retention time: 3.49 minutes; $C_{20}H_{20}Cl_2N_4O_2$ (419.31); mass spectrum: $(M+H)^+=419.2$.

Example 32

(R)-3-chloro-N-(5-chloro-1H-benzimidazol-2-ylmethyl)-4-(2-methoxymethylpyrrolidin-1-ylcarbonyl)benzamide

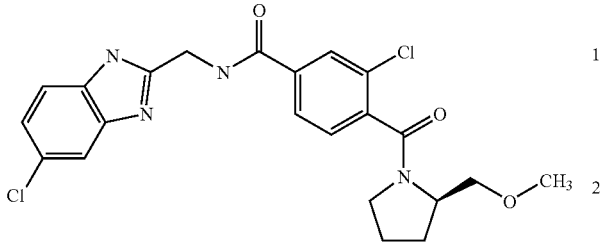

Prepared analogously to Example 1d from 3-chloro-N-(5-chloro-1H-benzimidazol-2-ylmethyl)-4-carboxybenzamide, (R)-2-methoxymethylpyrrolidine, TBTU, and triethylamine in DMSO at ambient temperature. HPLC-MS results: retention time: 3.56 minutes; $C_{22}H_{22}Cl_2N_4O_3$ (461.35); mass spectrum: $(M+H)^+=461.2$.

Example 33

3-chloro-N-(5-chloro-1H-benzimidazol-2-ylmethyl)-4-[3-(pyrrolidin-1-ylmethyl)piperidin-1-ylcarbonyl]benzamide

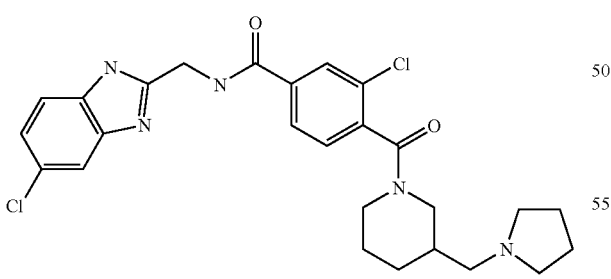

Prepared analogously to Example 1d from 3-chloro-N-(5-chloro-1H-benzimidazol-2-ylmethyl)-4-carboxybenzamide, 3-(pyrrolidin-1-ylmethyl)piperidine, TBTU, and triethylamine in DMSO at ambient temperature. HPLC-MS results: retention time: 3.05 minutes; $C_{26}H_{29}Cl_2N_5O_2$ (514.45); mass spectrum: $(M+H)^+=514.2$.

Example 34

(S)-3-chloro-N-(5-chloro-1H-benzimidazol-2-ylmethyl)-4-(2-methoxymethylpyrrolidin-1-ylcarbonyl)benzamide

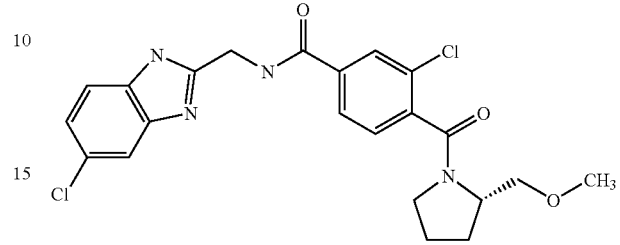

Prepared analogously to Example 1d from 3-chloro-N-(5-chloro-1H-benzimidazol-2-ylmethyl)-4-carboxybenzamide, (S)-2-methoxymethylpyrrolidine, TBTU, and triethylamine in DMSO at ambient temperature. HPLC-MS results: retention time: 3.56 minutes; $C_{22}H_{22}Cl_2N_4O_3$ (461.35); mass spectrum: $(M+H)^+=461.1$.

Example 35

3-chloro-N-(5-chloro-1H-benzimidazol-2-ylmethyl)-4-(azetidin-1-ylcarbonyl)benzamide

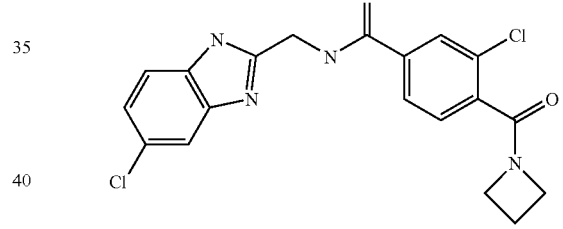

Prepared analogously to Example 1d from 3-chloro-N-(5-chloro-1H-benzimidazol-2-ylmethyl)-4-carboxybenzamide, azetidine, TBTU, and triethylamine in DMSO at ambient temperature. HPLC-MS results: retention time: 3.25 minutes; $C_{19}H_{16}Cl_2N_4O_3$ (403.27); mass spectrum: $(M+H)^+=403.1$.

Example 36

3-chloro-N-(5-chloro-1H-benzimidazol-2-ylmethyl)-4-(2-methylpyrrolidin-1-ylcarbonyl)benzamide

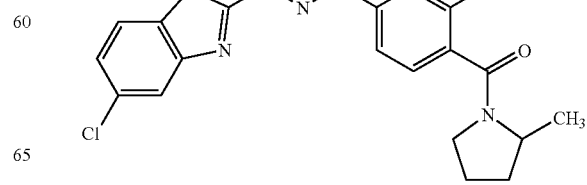

Prepared analogously to Example 1d from 3-chloro-N-(5-chloro-1H-benzimidazol-2-ylmethyl)-4-carboxybenzamide, 2-methylpyrrolidine, TBTU, and triethylamine in DMSO at ambient temperature. HPLC-MS results: retention time: 3.62 minutes; $C_{21}H_{20}Cl_2N_4O_2$ (431.32); mass spectrum: $(M+H)^+=431.2$.

Example 37

3-chloro-N-(5-chloro-1H-benzimidazol-2-ylmethyl)-4-(N-isobutyl-N-methylamino-carbonyl)benzamide

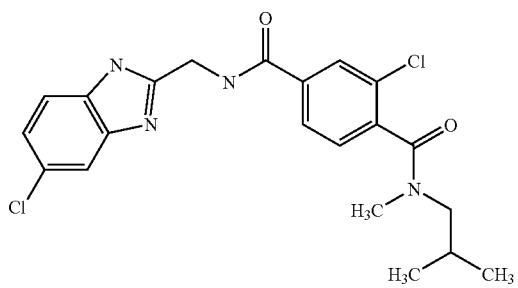

Prepared analogously to Example 1d from 3-chloro-N-(5-chloro-1H-benzimidazol-2-ylmethyl)-4-carboxybenzamide, N-isobutylmethylamine, TBTU, and triethylamine in DMSO at ambient temperature.

Example 38

3-chloro-N-(5-chloro-1H-benzimidazol-2-ylmethyl)-4-([1,4]oxazepan-1-ylcarbonyl)benzamide

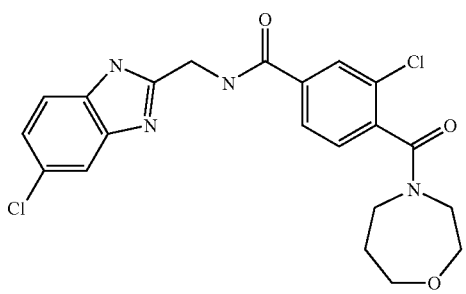

Prepared analogously to Example 1d from 3-chloro-N-(5-chloro-1H-benzimidazol-2-ylmethyl)-4-carboxybenzamide, [1,4]oxazepan, TBTU, and triethylamine in DMSO at ambient temperature. HPLC-MS results: retention time: 3.28 minutes; $C_{21}H_{20}Cl_2N_4O_3$ (447.32); mass spectrum: $(M+H)^+=447.2$.

Example 39

3-chloro-N-(5-chloro-1H-benzimidazol-2-ylmethyl)-4-(2,5-dimethylpyrrolidin-1-ylcarbonyl)benzamide

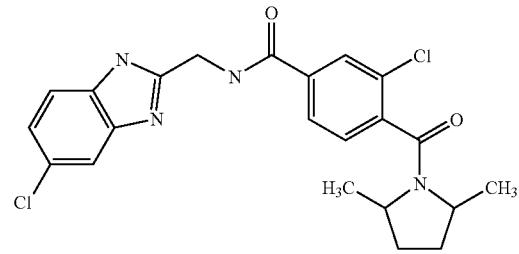

Prepared analogously to Example 1d from 3-chloro-N-(5-chloro-1H-benzimidazol-2-ylmethyl)-4-carboxybenzamide, 2,5-dimethylpyrrolidine, TBTU, and triethylamine in DMSO at ambient temperature. HPLC-MS results: retention time: 3.77 minutes; $C_{22}H_{22}Cl_2N_4O_2$ (445.35); mass spectrum: $(M+H)^+=445.2$.

Example 40

3-chloro-N-(5-chloro-1H-benzimidazol-2-ylmethyl)-4-(piperidin-1-ylcarbonyl)benzamide

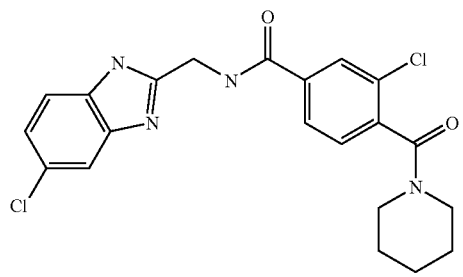

Prepared analogously to Example 1d from 3-chloro-N-(5-chloro-1H-benzimidazol-2-ylmethyl)-4-carboxybenzamide, piperidine, TBTU, and triethylamine in DMSO at ambient temperature. HPLC-MS results: retention time: 3.65 minutes; $C_{21}H_{20}Cl_2N_4O_2$ (431.32); mass spectrum: $(M+H)^+=431.2$.

Example 41

3-chloro-N-(5-chloro-1H-benzimidazol-2-ylmethyl)-4-(4-hydroxypiperidin-1-ylcarbonyl)benzamide

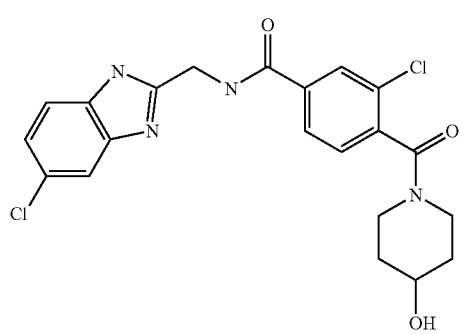

Prepared analogously to Example 1d from 3-chloro-N-(5-chloro-1H-benzimidazol-2-ylmethyl)-4-carboxybenzamide, 4-hydroxypiperidine, TBTU, and triethylamine in DMSO at ambient temperature. HPLC-MS results: retention time: 3.09 minutes; $C_{21}H_{20}Cl_2N_4O_3$ (447.32); mass spectrum: $(M+H)^+=447.2$.

Example 42

4-(4-acetylpiperazin-1-ylcarbonyl)-3-chloro-N-(5-chloro-1H-benzimidazol-2-ylmethyl)benzamide

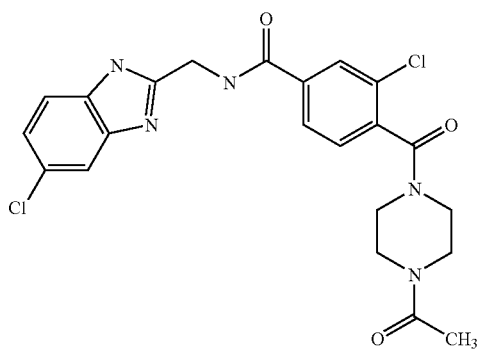

Prepared analogously to Example 1d from 3-chloro-N-(5-chloro-1H-benzimidazol-2-ylmethyl)-4-carboxybenzamide, N-acetylpiperazine, TBTU, and triethylamine in DMSO at ambient temperature. HPLC-MS results: retention time: 3.13 minutes; $C_{22}H_{21}Cl_2N_5O_3$ (474.35); mass spectrum: $(M+H)^+=474.2$.

Example 43

3-chloro-N-(5-chloro-1H-benzimidazol-2-ylmethyl)-4-(pyrrolidin-1-ylcarbonyl)benzamide

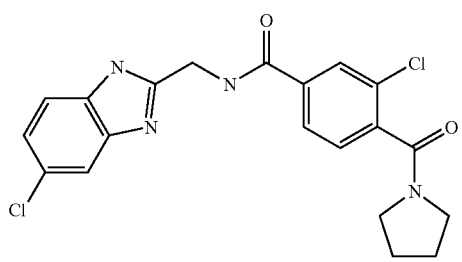

Prepared analogously to Example 1d from 3-chloro-N-(5-chloro-1H-benzimidazol-2ylmethyl)-4-carboxybenzamide, pyrrolidine, TBTU, and triethylamine in DMSO at ambient temperature. HPLC-MS results: retention time: 3.43 minutes; $C_{20}H_{18}Cl_2N_4O_2$ (417.29); mass spectrum: $(M+H)^+=417.2$.

Example 44

3-chloro-N-(5-chloro-1H-benzimidazol-2-ylmethyl)-4-(N,N-diethylaminocarbonyl)benzamide

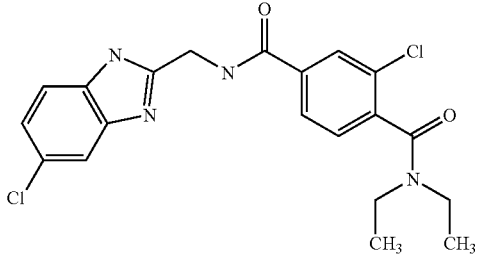

Prepared analogously to Example 1d from 3-chloro-N-(5-chloro-1H-benzimidazol-2-ylmethyl)-4-carboxybenzamide, diethylamine, TBTU, and triethylamine in DMSO at ambient temperature. HPLC-MS results: retention time: 3.59 minutes; $C_{20}H_{20}Cl_2N_4O_2$ (419.31); mass spectrum: $(M+H)^+=419.2$.

Example 45

3-chloro-N-(5-chloro-1H-benzimidazol-2-ylmethyl)-4-(3-methylpiperidin-1-ylcarbonyl)benzamide

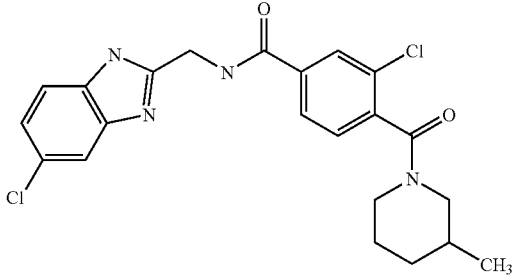

Prepared analogously to Example 1d from 3-chloro-N-(5-chloro-1H-benzimidazol-2-ylmethyl)-4-carboxybenzamide, 3-methylpiperidine, TBTU, and triethylamine in DMSO at ambient temperature. HPLC-MS results: retention time: 3.87 minutes; $C_{22}H_{22}Cl_2N_4O_2$ (445.35); mass spectrum: $(M+H)^+=445.2$.

Example 46

3-chloro-N-(5-chloro-1H-benzimidazol-2-ylmethyl)-4-(4-methylpiperidin-1-ylcarbonyl)benzamide

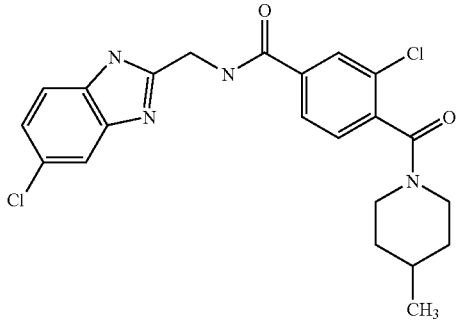

Prepared analogously to Example 1d from 3-chloro-N-(5-chloro-1H-benzimidazol-2-ylmethyl)-4-carboxybenzamide, 4-methylpiperidine, TBTU, and triethylamine in DMSO at ambient temperature. HPLC-MS results: retention time: 3.90 minutes; $C_{22}H_{22}Cl_2N_4O_2$ (445.35); mass spectrum: $(M+H)^+=445.2$.

Example 47

4-(2-aminomethylpiperidin-1-ylcarbonyl)-3-chloro-N-(5-chloro-1H-benzimidazol-2-ylmethyl)benzamide

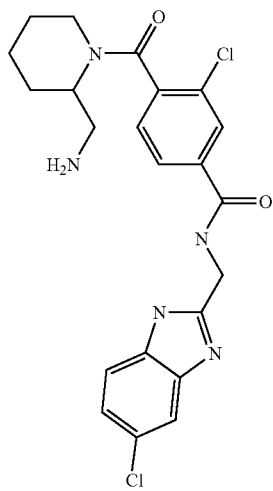

Prepared analogously to Example 1d from 3-chloro-N-(5-chloro-1H-benzimidazol-2-ylmethyl)-4-carboxybenzamide, tert-butyl piperidin-2-ylmethylcarbamate, TBTU, and triethylamine in DMSO at ambient temperature followed by Boc cleaving with trifluoroacetic acid analogously to Example 17.

Example 48

4-(3-aminomethylpiperidin-1-ylcarbonyl)-3-chloro-N-(5-chloro-1H-benzimidazol-2-ylmethyl)benzamide

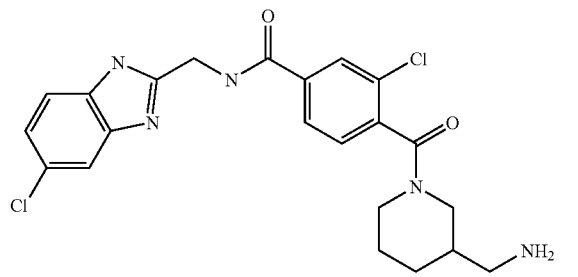

Prepared analogously to Example 1d from 3-chloro-N-(5-chloro-1H-benzimidazol-2-ylmethyl)-4-carboxybenzamide, tert-butyl piperidin-3-ylmethylcarbamate, TBTU, and triethylamine in DMSO at ambient temperature followed by Boc cleaving with trifluoroacetic acid analogously to Example 17. HPLC-MS results: retention time: 2.96 minutes; $C_{22}H_{23}Cl_2N_5O_2$ (460.36); mass spectrum: $(M+H)^+=460.2$.

Example 49

4-[3-(2-aminoethyl)piperidin-1-ylcarbonyl]-3-chloro-N-(5-chloro-1H-benzimidazol-2-ylmethyl)benzamide

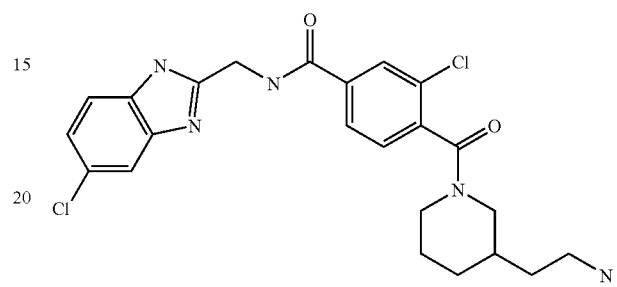

Prepared analogously to Example 1d from 3-chloro-N-(5-chloro-1H-benzimidazol-2-ylmethyl)-4-carboxybenzamide, tert-butyl (2-piperidin-3-ylethyl)carbamate, TBTU, and triethylamine in DMSO at ambient temperature followed by Boc cleaving with trifluoroacetic acid analogously to Example 17. HPLC-MS results: retention time: 3.01 minutes; $C_{23}H_{25}Cl_2N_5O_2$ (474.39); mass spectrum: $(M+H)^+=474.2$.

Example 50

4-(2-aminomethylpyrrolidin-1-ylcarbonyl)-3-chloro-N-(5-chloro-1H-benzimidazol-2-ylmethyl)benzamide

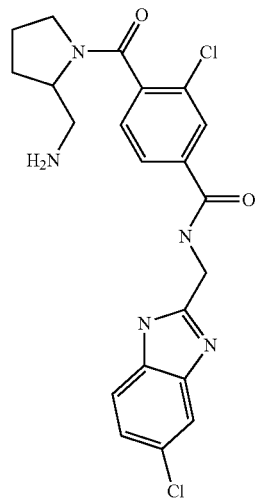

Prepared analogously to Example 1d from 3-chloro-N-(5-chloro-1H-benzimidazol-2-ylmethyl)-4-carboxybenzamide, tert-butyl pyrrolidin-2-ylmethylcarbamate, TBTU, and triethylamine in DMSO at ambient temperature followed by Boc cleaving with trifluoroacetic acid analogously to Example 17. HPLC-MS results: retention time: 2.98 minutes; $C_{21}H_{21}Cl_2N_5O_2$ (446.34); mass spectrum: $(M+H)^+=446.2$.

Example 51

4-(3-aminopiperidin-1-ylcarbonyl)-3-chloro-N-(5-chloro-1H-benzimidazol-2-ylmethyl)benzamide

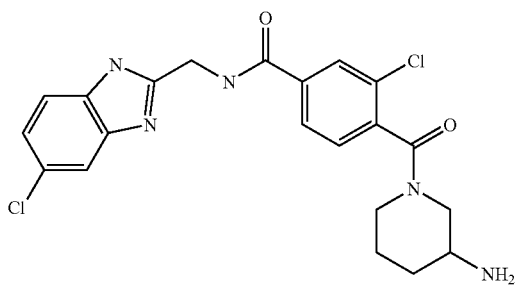

Prepared analogously to Example 1d from 3-chloro-N-(5-chloro-1H-benzimidazol-2-ylmethyl)-4-carboxybenzamide, tert-butyl piperidin-3-ylcarbamate, TBTU, and triethylamine in DMSO at ambient temperature followed by Boc cleaving with trifluoroacetic acid analogously to Example 17. HPLC-MS results: retention time: 2.91 minutes; $C_{21}H_{21}Cl_2N_5O_2$ (446,34); mass spectrum: $(M+H)^+=446.2$.

Example 52

N-(6-chloroquinolin-2-ylmethyl)-3-methyl-4-(pyrrolidin-1-ylcarbonyl)benzamide

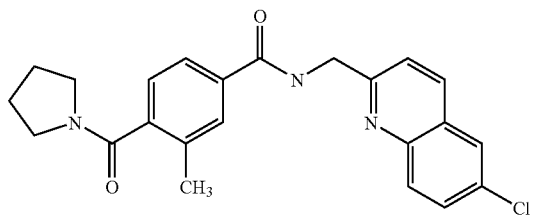

(a) 6-chloroquinoline-2-carbaldehydeoxime 0.33 g (4.8 mmol) of hydroxylamine hydrochloride and then 0.9 mL (4.6 mmol) of triethylamine are added to a solution of 0.83 g (4.34 mmol) of 6-chloroquinoline-2-carbaldehyde in 20 mL of DMF/ethanol (v/v 1:1). The reaction mixture is stirred for 16 hours at ambient temperature; then it is poured into water. The precipitated solid is filtered off and dried. Yield: 0.79 g (88% of theory); $R_f$ value: 0.73 (silica gel; dichloromethane/methanol=9:1); $C_{10}H_7ClN_2O$ (206.63); mass spectrum: $(M+H)^+=407/209$ (chlorine isotope).

(b) C-(6-chloroquinolin-2-yl)methylamine

A solution of 0.78 g (3.79 mmol) of 6-chloroquinoline-2-carbaldehydeoxime in 30 mL of saturated ammoniacal methanol and 10 mL of tetrahydrofuran is hydrogenated with Raney nickel for 48 hours at 3 bar hydrogen pressure. The catalyst is filtered off and the solution is concentrated. The residue is chromatographed on silica gel, eluting with a gradient of dichloromethane/methanol (90:10) to dichloromethane/methanol/25% aqueous ammonia (90:10:1). The corresponding fractions are combined and concentrated by evaporation. Yield: 0.33 g (45% of theory); $R_f$ value: 0.43 (silica gel; dichloromethane/methanol=9:1); $C_{10}H_9ClN_2$ (192.65); mass spectrum: $(M+H)^+=193/195$ (chlorine isotope).

(c) N-(6-chloroquinolin-2-ylmethyl)-3-methyl-4-(pyrrolidin-1-ylcarbonyl)benzamide Prepared analogously to Example 10d from 0.16 g (0.83 mmol) of C-(6-chloroquinolin-2-yl)methylamine. Yield: 135 mg (40% of theory); $R_f$ value: 0.40 (silica gel; dichloromethane/ethanol=100:5); $C_{23}H_{22}ClN_3O_2$ (407.90); mass spectrum: $(M+H)^+=408/410$ (chlorine isotope).

Example 53

N-[1-(5-chloro-1H-benzimidazol-2-yl)ethyl]-N-ethyl-3-methyl-4-(pyrrolidin-1-ylcarbonyl)benzamide

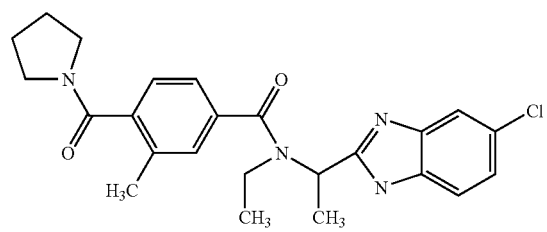

Prepared analogously to Example 1g from 3-methyl-4-(pyrrolidin-1-ylcarbonyl)benzoic acid, TBTU, diisopropylethylamine, and N-[1-(5-chlorobenzimidazol-2-yl)ethyl]ethylamine in tetrahydrofuran. Yield: 36%; $R_f$ value: 0.45 (silica gel; dichloromethane/ethanol=9:1); $C_{24}H_{27}ClN_4O_2$ (438.96); mass spectrum: $(M-H)^-=437/439$ (chlorine isotope).

Example 54

N-(6-bromo-3H-imidazo[4,5-b]pyridin-2-yl)methyl-3-methyl-4-(pyrrolidin-1-ylcarbonyl)benzamide

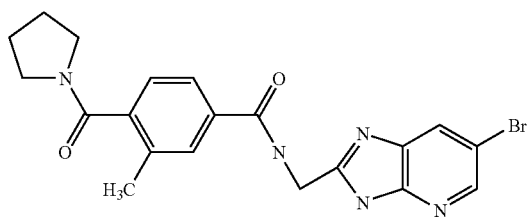

(a) N'-(tert-butoxycarbonyl)-N-(5-bromo-3-nitropyridin-2-yl)glycinamide 7.80 g (44.49 mmol) of N-tert-butoxycarbonylglycine is placed together with 7.94 g (48.9 mmol) of N,N-carbonyldiimidazole in 40 mL of N,N-dimethylformamide under a nitrogen atmosphere and combined successively with 10 g (44.5 mmol) of 2-amino-5-bromo-3-nitropyridine and 10.8 mL (97.9 mmol) of N-methylmorpholine. Then the reaction mixture is stirred for 2.5 days at ambient temperature. It is then heated to 100° C. for 1 hour and refluxed for 4 hours, then left to cool to ambient temperature and stirred for a further 16 hours. The reaction mixture is concentrated in vacuo, combined with dichloromethane and demineralized water, and stirred for 20 minutes. The precipitate formed is removed by filtration, the organic phase is dried over sodium sulfate, and the solvent eliminated in vacuo. Yield: 4.71 g (49%).

(b) N'-(tert-butoxycarbonyl)-N-(5-bromo-3-aminopyridin-2-yl)glycinamide 2.74 g of the product obtained above is dissolved in 70 mL of ethyl acetate, combined with 13.88 g (61.5 mmol) of tin(II) chloride, and refluxed for 1 hour. The reaction mixture is cooled to ambient temperature and then poured into a solution of 12.7 g (150 mmol) of sodium hydrogen carbonate in 400 mL of ice water. After filtration the organic phase is dried over sodium sulfate and the solvent is eliminated in vacuo. Yield: 1.62 g (69%); $R_f$ value: 0.63 (RP8; methanol/5% sodium chloride solution=6:4); $C_{12}H_{17}BrN_4O_3$ (345.20); mass spectrum: $(M-H)^-=188/190$ (bromine isotope).

(c) N-(6-bromo-3H-imidazo[4,5-b]pyridin-2-yl)methylacetamide 3.19 g (9.24 mmol) of N'-(tert-butoxycarbonyl)-N-(5-bromo-3-aminopyridin-2-yl)glycinamide is refluxed for 4 hours in 15 mL of glacial acetic acid under an argon atmosphere. The reaction mixture is concentrated in vacuo and the residue is treated with diethyl ether. The crystals are filtered off and dried. Yield: 2.03 g (82%), purity 55%; $R_f$ value: 0.13 (silica gel; dichloromethane/ethanol=9:1); $C_9H_9BrN_4O$ (269.10); mass spectrum: $(M+H)^+=269/271$ (bromine isotope).

(d) C-(6-bromo-3H-imidazo[4,5-b]pyridin-2-yl)methylamine 2.03 g (7.54 mmol) of N-(6-bromo-3H-imidazo[4,5-b]pyridin-2-yl)methylacetamide is combined with 30 mL of 6 molar hydrochloric acid solution in 15 mL of ethanol and heated to 40° C. for 2 hours. After cooling to ambient temperature, the mixture is extracted with dichloromethane, and the organic phase is extracted with 5% sodium hydrogen carbonate solution. The aqueous phase is concentrated in vacuo and the residue treated with diethyl ether. After the solvent has been eliminated in vacuo the residue is combined with 30 mL of 6 molar hydrochloric acid solution and heated to 50° C. for 16 hours. After elimination of the solvent, the residue is twice taken up in methanol and in each case concentrated in vacuo. The crystals formed are washed with methanol and dried at 50° C. Yield: 560 mg (28%; hydrochloride); $R_f$ value: 0.15 (silica gel; dichloromethane/ethanol=9:1+2% ammonia solution); $C_7H_7BrN_4$ × HCl (227.06/263.53); mass spectrum: $(M-H)^-=225/227$ (bromine isotope).

(e) N-(6-bromo-3H-imidazo[4,5-b]pyridin-2-yl)methyl-3-methyl-4-(pyrrolidin-1-ylcarbonyl)benzamide Prepared analogously to Example 1g from C-(6-bromo-3H-imidazo[4,5-b]pyridin-2-yl)methylamine, TBTU, diisopropylethylamine, and 3-methyl-4-(pyrrolidin-1-ylcarbonyl)benzoic acid in tetrahydrofuran. Yield: 190 mg (76%); $R_f$ value: 0.67 (silica gel; dichloromethane/ethanol=8:2+2% ammonia solution); $C_{20}H_{20}BrN_5O_2$ (442,32); mass spectrum: $(M+H)^+=442/444$ (bromine isotope).

Example 55

N-(6-bromo-3H-imidazo[4,5-b]pyridin-2-yl)methyl-3-methyl-4-(2,5-dihydropyrrol-1-ylcarbonyl)benzamide

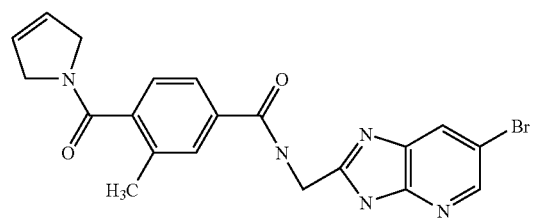

Prepared analogously to Example 1g from C-(6-bromo-3H-imidazo[4,5-b]pyridin-2-yl)methylamine, TBTU, diisopropylethylamine, and 3-methyl-4-(2,5-dihydropyrrol-1-ylcarbonyl)benzoic acid in tetrahydrofuran. Purification is effected by chromatography on silica gel (gradient: dichloromethane/ethanol=100:0□80:20). Yield: 240 mg (96%); $R_f$ value: 0.68 (silica gel; dichloromethane/ethanol=8:2+2% ammonia solution); $C_{20}H_{18}BrN_5O_2$ (440.30); mass spectrum: $(M+H)^+=440/442$ (bromine isotope).

Example 56

N-[1-(5-bromo-1H-benzimidazol-2-yl)ethyl]-3-methyl-4-(pyrrolidin-1-ylcarbonyl)benzamide

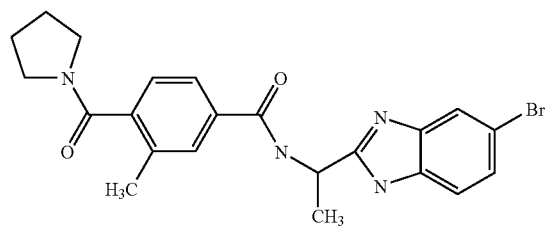

Prepared analogously to Example 1g from 3-methyl-4-(pyrrolidin-1-ylcarbonyl)benzoic acid, TBTU, diisopropylethylamine, and 1-(5-bromo-1H-benzimidazol-2-yl)ethylamine in tetrahydrofuran. Yield: 49%; $R_f$ value: 0.52 (silica gel; methylene chloride/ethanol=9:1); $C_{22}H_{23}BrN_4O_2$ (455.35); mass spectrum: $(M+H)^+=455/457$ (bromine isotope).

Example 57

N-[(5-chloro-1H-benzimidazol-2-yl)phenylmethyl]-3-methyl-4-(pyrrolidin-1-ylcarbonyl)benzamide

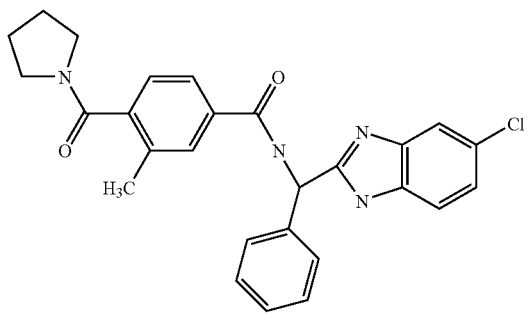

Prepared analogously to Example 1g from 3-methyl-4-(pyrrolidin-1-ylcarbonyl)benzoic acid, TBTU, diisopropylethylamine, and C-(5-chlorobenzimidazol-2-yl)-C-phenylmethylamine in tetrahydrofuran. Yield: quantitative; $R_f$ value: 0.59 (silica gel; methylene chloride/ethanol=9:1); $C_{27}H_{25}ClN_4O_2$ (472.97); mass spectrum: $(M+H)^+=473$ and $(M-H)^-=471$.

Example 58

N-[1-(1H-benzimidazol-2-yl)ethyl]-3-methyl-4-(pyrrolidin-1-ylcarbonyl)benzamide

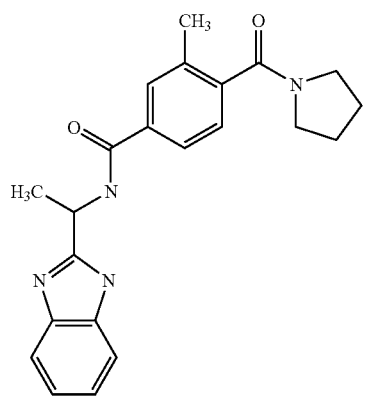

Prepared analogously to Example 1g from 3-methyl-4-(pyrrolidin-1-ylcarbonyl)benzoic acid, TBTU, diisopropylethylamine, and 1-(1H-benzimidazol-2-yl)ethylamine in tetrahydrofuran. Yield: 83%; $R_f$ value: 0.67 (silica gel; methylene chloride/ethanol=9:1); $C_{22}H_{24}N_4O_2$ (376.46); mass spectrum: $(M+H)^+=377$.

Example 59

N-[1-(5-chloro-1H-benzimidazol-2-yl)-5-benzyloxycarbonylaminopentyl]-3-methyl-4-(pyrrolidin-1-ylcarbonyl)benzamide

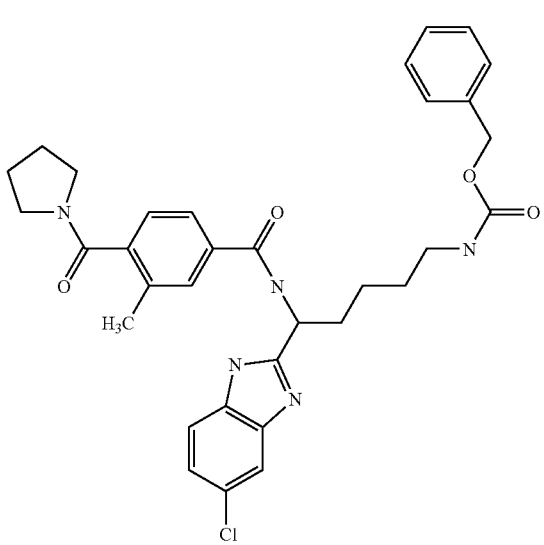

Prepared analogously to Example 1g from 3-methyl-4-(pyrrolidin-1-ylcarbonyl)benzoic acid, TBTU, diisopropylethylamine, and 1-(5-chloro-1H-benzimidazol-2-yl)-5-benzyloxycarbonyl-aminopentylamine in tetrahydrofuran. Yield: quantitative; $R_f$ value: 0.52 (silica gel; methylene chloride/ethanol=9:1); $C_{33}H_{36}ClN_5O_4$ (602.13); mass spectrum: $(M-H)^-=600/602$ (chlorine isotope).

Example 60

N-[1-(5-chloro-1H-benzimidazol-2-yl)ethyl]-3-chloro-4-(3-oxopiperazin-1-ylcarbonyl)benzamide

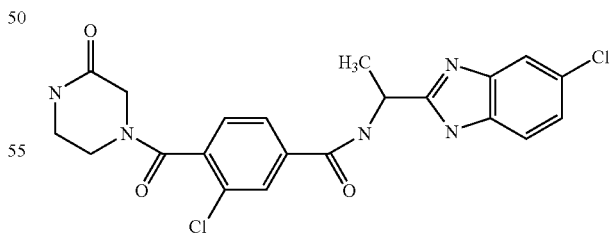

Prepared analogously to Example 1d from 3-chloro-N-(5-chloro-1H-benzimidazol-2-ylmethyl)-4-hydroxycarbonylbenzamide, TBTU, diisopropylethylamine, and 2-oxopiperazine in tetrahydrofuran. Yield: 36%; $R_f$ value: 0.75 (silica gel; methylene chloride/ethanol=4:1); $C_{21}H_{19}Cl_2N_5O_3$ (460.32); mass spectrum: $(M+H)^+=460/462/464$ (chlorine isotope).

Example 61

N-[1-(5-chloro-1H-benzimidazol-2-yl)-3-methylbutyl]-3-methyl-4-(pyrrolidin-1-ylcarbonyl)benzamide

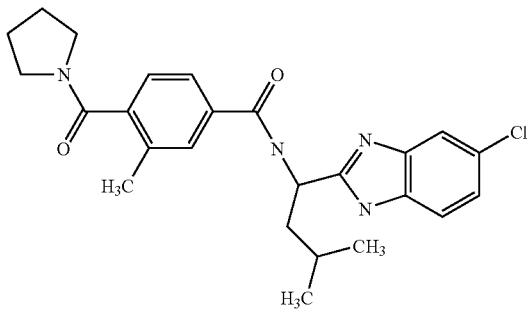

Prepared analogously to Example 1g from 3-methyl-4-(pyrrolidin-1-ylcarbonyl)benzoic acid, TBTU, diisopropylethylamine, and 1-(5-chloro-1H-benzimidazol-2-yl)-3-methylbutylamine in tetrahydrofuran. Yield: 82%; $R_f$ value: 0.54 (silica gel; methylene chloride/ethanol=9:1); $C_{25}H_{29}ClN_4O_2$ (452.98); mass spectrum: $(M+H)^+=453/455$ (chlorine isotope) and (M–H)-=451/453 (chlorine isotope).

Example 62

N-[1-(5-chloro-1H-benzimidazol-2-yl)]ethyl-4-(pyrrolidin-1-ylcarbonyl)benzamide

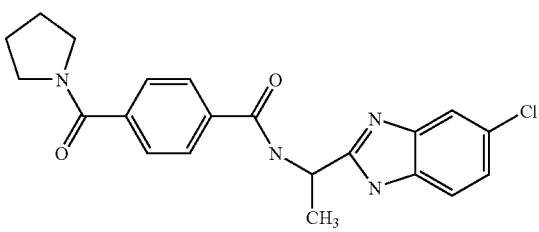

Prepared analogously to Example 1g from 4-(pyrrolidin-1-ylcarbonyl)benzoic acid, TBTU, diisopropylethylamine, and 1-(5-chloro-1H-benzimidazol-2-yl)ethylamine in tetrahydrofuran. Yield: 98%; $R_f$ value: 0.50 (silica gel; methylene chloride/ethanol=9:1); $C_{21}H_{21}ClN_4O_2$ (396.88); mass spectrum: $(M+H)^+=397/399$ (chlorine isotope).

Example 63

(S)—N-[1-(5-chloro-1H-benzimidazol-2-yl)]ethyl-3-methyl-4-(pyrrolidin-1-ylcarbonyl)benzamide

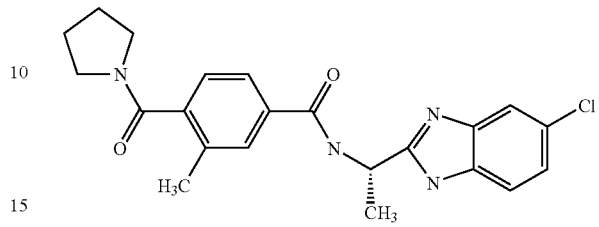

Prepared analogously to Example 1g from 3-methyl-4-(pyrrolidin-1-ylcarbonyl)benzoic acid, TBTU, diisopropylethylamine, and (S)-1-(5-chlorobenzimidazol-2-yl)ethylamine in tetrahydrofuran. Yield: 76%; $R_f$ value: 0.50 (silica gel; methylene chloride/ethanol=9:1); $C_{22}H_{23}ClN_4O_2$ (410.91); mass spectrum: $(M-H)^-=409/411$ (chlorine isotope).

Example 64 rac.-N-[1-(5-chloro-1H-benzimidazol-2-yl)]ethyl-3-chloro-4-[N-(2-dimethylamino)ethyl-N-ethylaminocarbonyl]benzamide

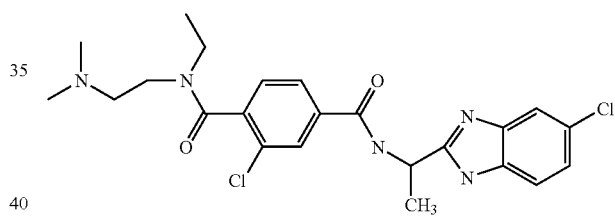

Prepared analogously to Example 1d from 3-chloro-N-(5-chloro-1H-benzimidazol-2-ylmethyl)-4-carboxybenzamide, TBTU, diisopropylethylamine, and N-(2-dimethylamino)ethylethylamine in tetrahydrofuran. Yield: 99%; $R_f$ value: 0.10 (silica gel; methylene chloride/ethanol=9:1); $C_{23}H_{27}Cl_2N_5O_2$ (476.40); mass spectrum: $(M+H)^+=476/478/479$ (chlorine isotope) and $(M-H)^-=474/476/477$ (chlorine isotope).

Example 65 rac.-N-[1-(5-chloro-1H-benzimidazol-2-yl)]ethyl-3-bromo-4-(pyrrolidin 1-ylcarbonyl)benzamide

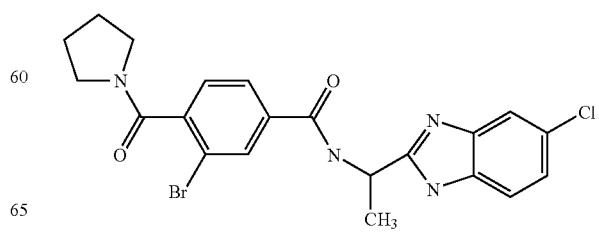

123

Prepared analogously to Example 1g from 3-bromo-4-(pyrrolidin-1-ylcarbonyl)benzoic acid, TBTU, diisopropylethylamine, and rac.-1-(5-chloro-1H-benzimidazol-2-yl)ethylamine in tetrahydrofuran. Yield: 73%; $R_f$ value: 0.50 (silica gel; methylene chloride/ethanol=9:1); $C_{21}H_{20}BrClN_4O_2$ (475.78); mass spectrum: (M–H)⁻=473/475/477 (bromine/chlorine isotope).

Example 66 rac.-N-[1-(5-chloro-1H-benzimidazol-2-yl)]ethyl-3-trifluoromethyl-4-(pyrrolidin-1-ylcarbonyl)benzamide

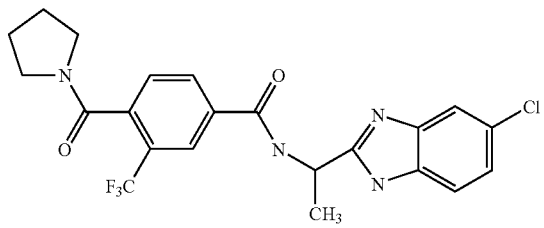

Prepared analogously to Example 1g from 3-trifluoromethyl-4-(pyrrolidin-1-ylcarbonyl)benzoic acid, TBTU, diisopropylethylamine and rac.-1-(5-chloro-1H-benzimidazol-2-yl)ethylamine in tetrahydrofuran. Yield: quantitative; $R_f$ value: 0.50 (silica gel; methylene chloride/ethanol=9:1); $C_{22}H_{20}ClF_3N_4O_2$ (464.88); mass spectrum: (M–H)⁻=463/465 (chlorine isotope).

Example 67

4-(2-aminomethylpyrrolidin-1-ylcarbonyl)-N-[2-aminocarbonyl-1-(5-chloro-1H-benzimidazol-2-yl)ethyl]-3-chlorobenzamide

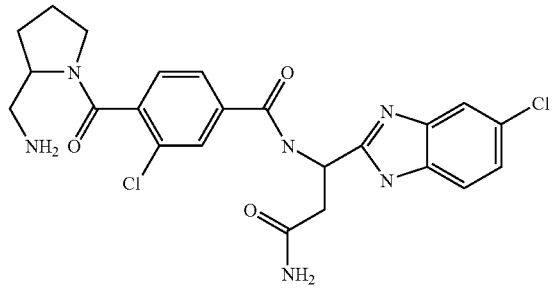

Prepared analogously to Example 17 from 4-[2-(N-tert-butoxycarbonylaminomethyl)pyrrolidine-1-carbonyl]-N-[2-aminocarbonyl-1-(5-chloro-1H-benzimidazol-2-yl)ethyl]-3-chlorobenzamide and trifluoroacetic acid. Yield: 59% (mixture of all four stereoisomers); $R_f$ value: 0.23 (silica gel; dichloromethane/methanol=7:3); $C_{23}H_{24}Cl_2N_6O_3$ (503.39); mass spectrum: (M+H)⁺=503/505/507 (chlorine isotope).

124

Example 68

4-(2-aminomethylpyrrolidin-1-ylcarbonyl)-3-chloro-N-[1-(5-chloro-1H-benzimidazol-2-yl)-2-(1H-imidazol-4-yl)ethyl]benzamide

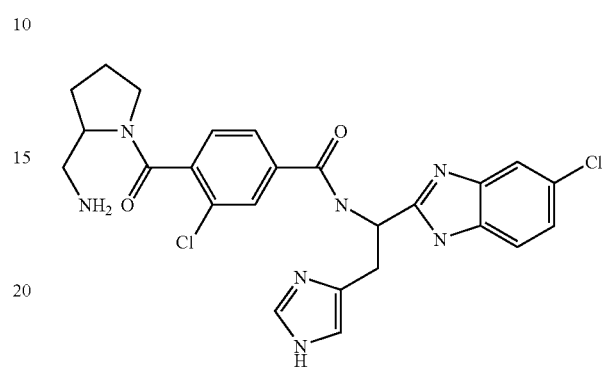

Prepared analogously to Example 17 from 4-[2-(N-tert-butoxycarbonylaminomethyl)pyrrolidin-1-ylcarbonyl]-3-chloro-N-[1-(5-chloro-1H-benzimidazol-2-yl)-2-(1H-imidazol-4-yl)ethyl]benzamide and trifluoroacetic acid. Yield: 98% of theory; $R_f$ value: 0.47 (silica gel; dichloromethane/methanol=7:3); $C_{25}H_{25}C_{12}N_7O_2$ (526.43); mass spectrum: (M+H)⁺=526/528/530 (chlorine isotope).

Example 69

4-(2-aminomethylpyrrolidin-1-ylcarbonyl)-3-chloro-N-[1-(5-chloro-1H-benzimidazol-2-yl)-2-(pyridin-2-yl)ethyl]benzamide

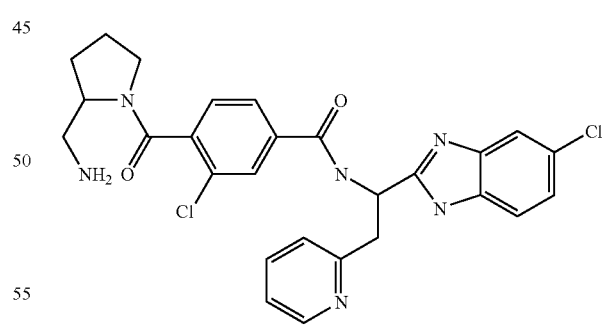

Prepared analogously to Example 17 from 4-[2-(N-tert-butoxycarbonylaminomethyl)pyrrolidin-1-ylcarbonyl]-3-chloro-N-[1-(5-chloro-1H-benzimidazol-2-yl)-2-(pyridin-2-yl)ethyl]benzamide and trifluoroacetic acid. Yield: 216 mg (85%, mixture of four stereoisomers); $R_f$ value: 0.27 (silica gel; dichloromethane/methanol/ammonia=9:1:0.1); $C_{27}H_{26}Cl_2N_6O_2$ (537.45); mass spectrum: (M–H)⁻=535/537/539 (chlorine isotope).

Example 70

N-[(1S)-1-(5-chloro-1H-benzimidazol-2-yl)ethyl]-3-methyl-4-[(2R/S)-2-(N-tert-butoxy-carbonylaminomethyl)pyrrolidin-1-ylcarbonyl]benzamide

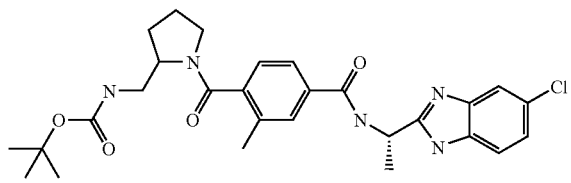

Prepared analogously to Example 1g from rac.-3-methyl-4-[2-(N-tert-butoxycarbonylmethyl-amino)pyrrolidin-1-ylcarbonyl]benzoic acid, TBTU, diisopropylethylamine, and (1S)-1-(5-chloro-1H-benzimidazol-2-yl)ethylamine in tetrahydrofuran. Yield: quantitative; $R_f$ value: 0.40 (silica gel; dichloromethane/ethanol=9:1); $C_{28}H_{34}ClN_5O_4$ (540.06); mass spectrum: $(M-H)^-=538/540$ (chlorine isotope) and $(M+H)^+=540/542$ (chlorine isotope).

Example 71

N-[(1S)-1-(5-chloro-1H-benzimidazol-2-yl)ethyl]-3-methyl-4-[(2R/S)-2-aminomethylpyrrolidin-1-ylcarbonyl]benzamide

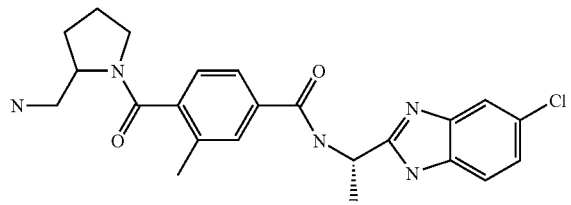

Prepared analogously to Example 17 from N-[(1S)-1-(5-chloro-1H-benzimidazol-2-yl)ethyl]-3-methyl-4-[(2R/S)-2-(N-tert-butoxycarbonylaminomethyl)pyrrolidin-1-ylcarbonyl]benzamide and trifluoroacetic acid. Yield: quantitative; $R_f$ value: 0.10 (silica gel; dichloromethane/methanol/ammonia=9:1:0.1); $C_{23}H_{26}ClN_5O_2$ (439.94); mass spectrum: $(M+H)^+=440/442$ (chlorine isotope).

Example 72

N-[(1S)-1-(5-chloro-1H-benzimidazol-2-yl)ethyl]-3-chloro-4-[(2R/S)-2-(N-tert-butoxy-carbonylaminomethyl)pyrrolidin-1-ylcarbonyl]benzamide

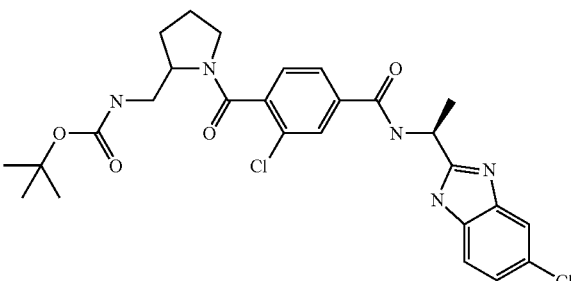

Prepared analogously to Example 1g from (S)-3-chloro-4-[2-(N-tert-butoxycarbonylaminomethylamino)pyrrolidin-1-ylcarbonyl]benzoic acid, TBTU, diisopropylethylamine, and rac.-1-(5-chloro-1H-benzimidazol-2-yl)ethylamine in tetrahydrofuran. Yield: 87%; $R_f$ value: 0.50 (silica gel; dichloromethane/ethanol=9:1); $C_{27}H_{31}Cl_2N_5O_4$ (560.48); mass spectrum: $(M+H)^+=560/562/564$ (chlorine isotope).

Example 73

N-[(1S)-1-(5-chloro-1H-benzimidazol-2-yl)ethyl]-3-chloro-4-[(2R/S)-2-aminomethylpyrrolidin-1-ylcarbonyl)benzamide

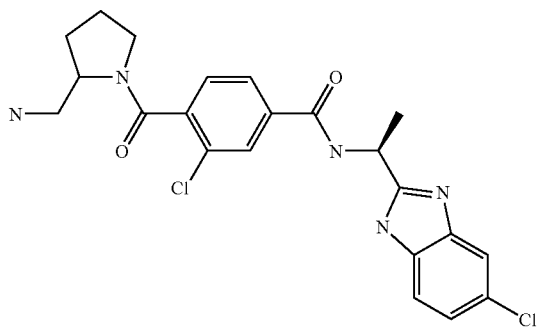

Prepared analogously to Example 17 from N-[(1S)-1-(5-chloro-1H-benzimidazol-2-yl)ethyl]-3chloro-4-[(2R/S)-2-(N-tert-butoxycarbonylaminomethyl)pyrrolidin-1-ylcarbonyl]benzamide and trifluoroacetic acid. Yield: quantitative; $R_f$ value: 0.15 (silica gel; dichloromethane/methanol/ammonia=9:1:0.1); $C_{22}H_{23}Cl_2N_5O_2$ (460.36); mass spectrum: $(M+H)^+=460/462/464$ (chlorine isotope).

Example 74

N-[(1S)-1-(5-chloro-1H-benzimidazol-2-yl)ethyl]-3-chloro-4-[(2S)-2-(N-tert-butoxy-carbonylaminomethyl)pyrrolidin-1-ylcarbonyl]benzamide

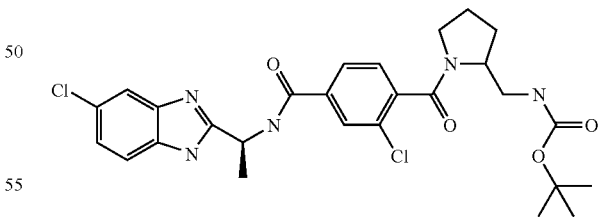

Prepared analogously to Example 1g from (1S)-2-chloro-4-{N-[1-(5-chloro-1H-benzimidazol-2-yl)ethyl]aminocarbonyl}benzoic acid, TBTU, diisopropylethylamine, and (2S)-2-(N-tert-butoxycarbonylaminomethyl)pyrrolidine in tetrahydrofuran. Yield: 29%; $R_f$ value: 0.53 (silica gel; dichloromethane/ethanol=9:1); $C_{27}H_{31}Cl_2N_5O_4$ (560.48); mass spectrum: $(M+H)^+=560/562$ (chlorine isotope) and $(M-H)^-=558/560$ (chlorine isotope).

Example 75

N-[(1S)-1-(5-chloro-1H-benzimidazol-2-yl)ethyl]-3-chloro-4-[(2R)-2-(N-tert-butoxy-carbonylaminomethyl)pyrrolidin-1-ylcarbonyl]benzamide

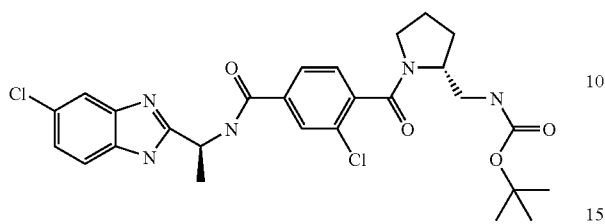

Prepared analogously to Example 1g from (1S)-2-chloro-4-{N-[1-(5-chloro-1H-benzimidazol-2-yl)ethyl]aminocarbonyl}benzoic acid, TBTU, diisopropylethylamine, and (2R)-2-(N-tert-butoxycarbonylaminomethyl)pyrrolidine in tetrahydrofuran. Yield: 67%; $R_f$ value: 0.52 (silica gel; dichloromethane/ethanol=9:1); $C_{27}H_{31}Cl_2N_5O_4$ (560.48); mass spectrum: $(M+H)^+=560/562$ (chlorine isotope).

Example 76

N-[(1S)-1-(5-chloro-1H-benzimidazol-2-yl)ethyl]-3-chloro-4-{(2S)-2-[2-(N-tert-butoxy-carbonylamino)ethyl]pyrrolidin-1-ylcarbonyl}benzamide

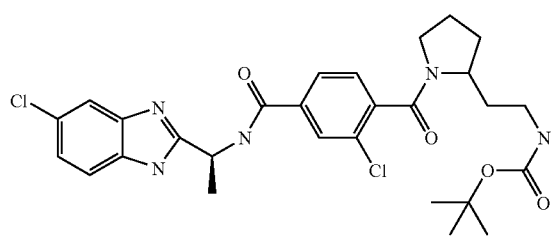

Prepared analogously to Example 1g from (1S)-2-chloro-4-{N-[1-(5-chloro-1H-benzimidazol-2-yl)ethyl]aminocarbonyl}benzoic acid, TBTU, diisopropylethylamine, and (2S)-2-[2-(N-tert-butoxycarbonylamino)ethyl]pyrrolidine in tetrahydrofuran. Yield: 61%; $R_f$ value: 0.62 (silica gel; dichloromethane/ethanol=9:1); $C_{28}H_{33}Cl_2N_5O_4$ (574.51); mass spectrum: $(M+H)^+=574/576/578$ (chlorine isotope).

Example 77

N-[(1S)-1-(5-chloro-1H-benzimidazol-2-yl)ethyl]-3-chloro-4-[(2S)-2-aminomethylpyrrolidin-1-ylcarbonyl]benzamide

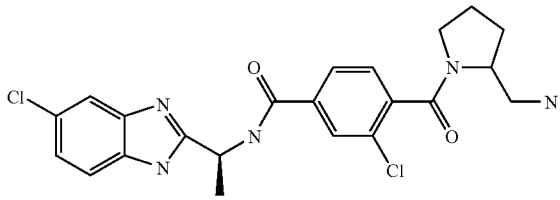

Prepared analogously to Example 17 from N-[(1S)-1-(5-chloro-1H-benzimidazol-2-yl)ethyl]-3-chloro-4-[(2S)-2-(N-tert-butoxycarbonylaminomethyl)pyrrolidin-1-ylcarbonyl]benzamide and trifluoroacetic acid. Yield: 91%; $R_f$ value: 0.10 (silica gel; dichloromethane/methanol/ammonia=9:1:0.1); $C_{22}H_{23}Cl_2N_5O_2$ (460.36); mass spectrum: $(M+H)^+=460/462$ (chlorine isotope) and $(M-H)^-=458/460$ (chlorine isotope).

Example 78

N-[(1S)-1-(5-chloro-1H-benzimidazol-2-yl)ethyl]-3-chloro-4-[(2R)-2-aminomethylpyrrolidin-1-ylcarbonyl]benzamide

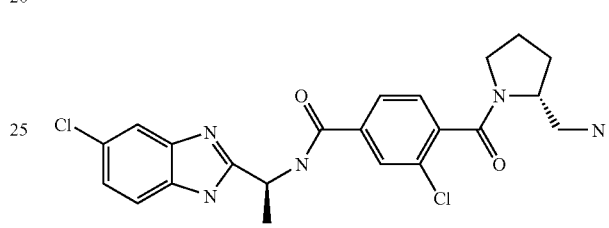

Prepared analogously to Example 17 from N-[(1S)-1-(5-chloro-1H-benzimidazol-2-yl)ethyl]-3-chloro-4-[(2R)-2-(N-tert-butoxycarbonylaminomethyl)pyrrolidin-1-ylcarbonyl]benzamide and trifluoroacetic acid. Yield: 86%; $R_f$ value: 0.10 (silica gel; dichloromethane/methanol/ammonia=9:1:0.1); $C_{22}H_{23}Cl_2N_5O_2$ (460.36); mass spectrum: $(M+H)^+=460/462$ (chlorine isotope) and $(M-H)^-=458/460$ (chlorine isotope).

Example 79

N-[(1S)-1-(5-chloro-1H-benzimidazol-2-yl)ethyl]-3-chloro-4-[(2S)-2-(2-aminoethyl)pyrrolidin-1-ylcarbonyl]benzamide

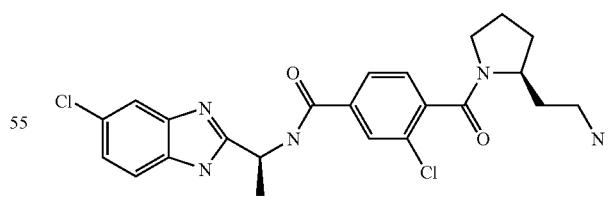

Prepared analogously to Example 17 from N-[(1S)-1-(5-chloro-1H-benzimidazol-2-yl)ethyl]-3-chloro-4-{(2S)-2-[2-(N-tert-butoxycarbonylamino)ethyl]pyrrolidin-1-ylcarbonyl}benzamide and trifluoroacetic acid. Yield: quantitative; $R_f$ value: 0.10 (silica gel; dichloromethane/methanol/ammonia=9:1:0.1); $C_{23}H_{25}Cl_2N_5O_2$ (474.39); mass spectrum: $(M+H)^+=474/476/478$ (chlorine isotope).

Example 80

N-[(1R/S)-1-(5-chloro-1H-benzimidazol-2-yl)ethyl]-3-chloro-4-[(2S)-2-aminocarbonylpyrrolidin-1-ylcarbonyl]benzamide

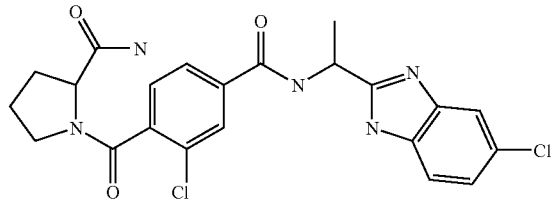

Prepared analogously to Example 1g from rac.-2-chloro-4-{N-[1-(5-chloro-1H-benzimidazol-2-yl)ethyl]aminocarbonyl}benzoic acid, TBTU, diisopropylethylamine, and S-prolinamide in tetrahydrofuran. Yield: 31%; $R_f$ value: 0.15 (silica gel; dichloromethane/ethanol=9:1); $C_{22}H_{21}Cl_2N_5O_3$ (474.35); mass spectrum: $(M+H)^+=474/476/478$ (chlorine isotope).

Example 81

N-[(1R/S)-1-(5-chloro-1H-benzimidazol-2-yl)ethyl]-3-chloro-4-[(2R)-2-aminocarbonylpyrrolidin-1-ylcarbonyl]benzamide

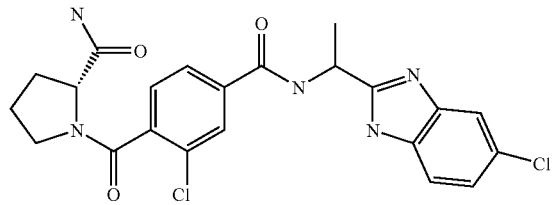

Prepared analogously to Example 1g from rac.-2-chloro-4-{N-[1-(5-chloro-1H-benzimidazol-2-yl)ethyl]aminocarbonyl}benzoic acid, TBTU, diisopropylethylamine, and R-prolinamide in tetrahydrofuran. Yield: 47%; $R_f$ value: 0.15 (silica gel; dichloromethane/ethanol=9:1); $C_{22}H_{21}Cl_2N_5O_3$ (474.35); mass spectrum: $(M+H)^+=474/476/478$ (chlorine isotope).

Example 82

N-[(1S)-1-(5-chloro-1H-benzimidazol-2-yl)butyl]-3-chloro-4-[(2S)-2-(N-tert-butoxy-carbonylaminomethyl)pyrrolidin-1-ylcarbonyl]benzamide

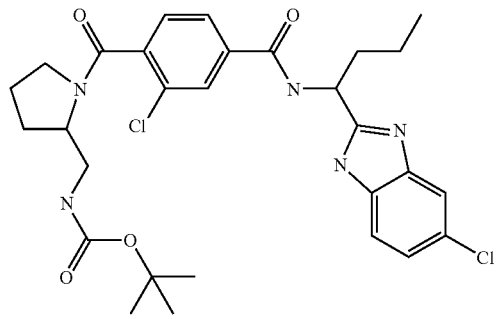

Prepared analogously to Example 1g from (S)-3-chloro-4-[2-(N-tert-butoxycarbonylmethyl-amino)pyrrolidin-1-ylcarbonyl]benzoic acid, TBTU, diisopropylethylamine, and (S)-1-(5-chloro-1H-benzimidazol-2-yl)butylamine in tetrahydrofuran. Yield: 69%; $R_f$ value: 0.37 (silica gel; dichloromethane/ethanol=9:1); $C_{29}H_{35}Cl_2N_5O_4$ (588.53); mass spectrum: $(M+H)^+=588/90/92$ (chlorine isotope).

Example 83

N-[(1S)-1-(5-chloro-1H-benzimidazol-2-yl)-3-methylsulfanylpropyl]-3-chloro-4-[(2S)-2-(N-tert-butoxycarbonylaminomethyl)pyrrolidin-1-ylcarbonyl]benzamide

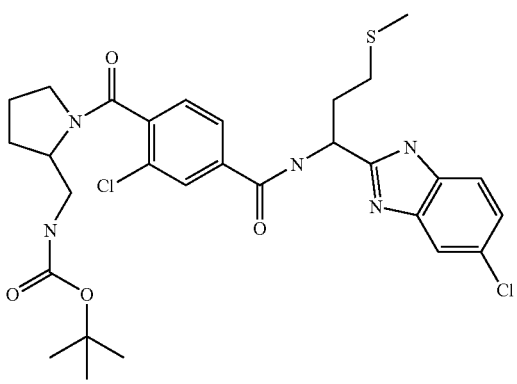

Prepared analogously to Example 1g from (S)-3-chloro-4-[2-(N-tert-butoxycarbonylmethyl-amino)pyrrolidin-1-ylcarbonyl]benzoic acid, TBTU, diisopropylethylamine, and (S)-1-(5-chloro-1H-benzimidazol-2-yl)-3-methylsulfanylpropylamine in tetrahydrofuran. Yield: 87%; $R_f$ value: 0.59 (silica gel; dichloromethane/ethanol=9:1); $C_{29}H_{35}Cl_2N_5O_4S$ (620.6); mass spectrum: $(M+H)^+=620/622/624$ (chlorine isotope).

Example 84

N-[(1S)-1-(5-chloro-1H-benzimidazol-2-yl)butyl]-3-chloro-4-[(2S)-2-aminomethylpyrrolidin-1-ylcarbonyl]benzamide

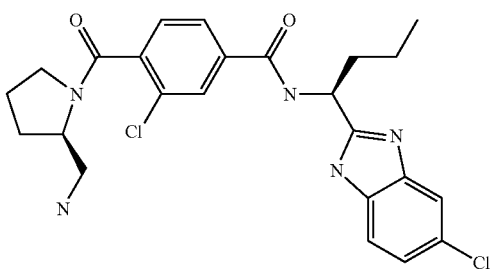

Prepared analogously to Example 17 from N-[(1S)-1-(5-chloro-1H-benzimidazol-2-yl)butyl]-3-chloro-4-[(2S)-2-(N-tert-butoxycarbonylaminomethyl)pyrrolidin-1-ylcarbonyl]benzamide and trifluoroacetic acid. Yield: quantitative; $R_f$ value: 0.06 (silica gel; dichloromethane/methanol/ammonia=9:1:0.1); $C_{24}H_{27}Cl_2N_5O_2$ (488.42); mass spectrum: $(M+H)^+=488/490/492$ (chlorine isotope).

Example 85

N-[(1S)-1-(5-chloro-1H-benzimidazol-2-yl)-3-methylsulfinylpropyl]-3-chloro-4-[(2S)-2-(N-tert-butoxycarbonylaminomethyl)pyrrolidin-1-ylcarbonyl]benzamide

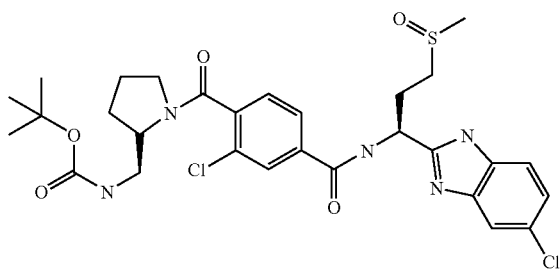

0.1 g (0.4 mmol) of 3-chloroperoxybenzoic acid is added at −10° C. to a solution of 0.3 g (0.4 mmol) of N-[(1S)-1-(5-chloro-1H-benzimidazol-2-yl)-3-methylsulfanylpropyl]-3-chloro-4-[(2S)-2-(N-tert-butoxycarbonylaminomethyl)pyrrolidin-1-ylcarbonyl]benzamide in 10 mL of dichloromethane and 1 mL of glacial acetic acid and stirred for 30 minutes. Then the mixture is stirred for 4 hours at ambient temperature and washed with 5% sodium carbonate solution. The combined organic phases are dried with sodium sulfate and concentrated. The residue is chromatographed on silica gel, eluting with dichloromethane/methanol (0%-10%). Yield: 0.1 g (59%); $R_f$ value: 0.42 (silica gel; dichloromethane/methanol=9:1); $C_{29}H_{35}Cl_2N_5O_5S$ (636.60); mass spectrum: $(M+H)^+$=636/638/640 (chlorine isotope) and $(M-H)^-$=634/636/638 (chlorine isotope).

Example 86

N-[(1S)-1-(5-chloro-1H-benzimidazol-2-yl)-3-methylsulfonylpropyl]-3-chloro-4-[(2S)-2-(N-tert-butoxycarbonylaminomethyl)pyrrolidin-1-ylcarbonyl]benzamide

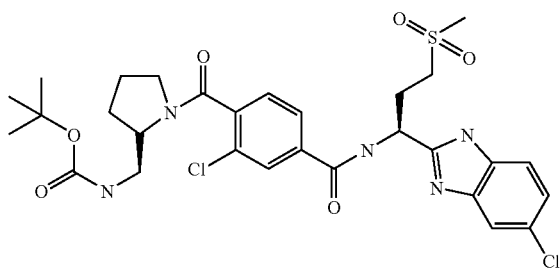

Prepared analogously to Example 85 from N-[(1S)-1-(5-chloro-1H-benzimidazol-2-yl)-3-methylsulfinylpropyl]-3-chloro-4-[(2S)-2-(N-tert-butoxycarbonylaminomethyl)pyrrolidin-1-ylcarbonyl]benzamide and 2 equivalents of 3-chloroperoxybenzoic acid in dichloromethane/glacial acetic acid. Yield: 46%; $R_f$ value: 0.38 (silica gel; dichloromethane/methanol=9:1); $C_{29}H_{35}Cl_2N_5O_6S$ (652.60); mass spectrum: $(M+H)^+$=652/654/656 (chlorine isotope).

Example 87

N-[(1S)-1-(5-chloro-1H-benzimidazol-2-yl)-3-methylsulfanylpropyl]-3-chloro-4-[(2S)-2-aminomethylpyrrolidin-1-ylcarbonyl]benzamide

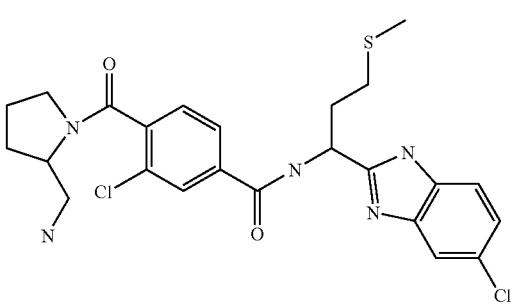

Prepared analogously to Example 17 from N-[(1S)-1-(5-chloro-1H-benzimidazol-2-yl)-3-methylsulfanylpropyl]-3-chloro-4-[(2S)-2-(N-tert-butoxycarbonylaminomethyl)pyrrolidin-1-ylcarbonyl]benzamide and trifluoroacetic acid. Yield: 81%; $R_f$ value: 0.18 (silica gel; dichloromethane/methanol/ammonia=9:1:0.1); $C_{24}H_{27}Cl_2N_5O_2S$ (520.48); mass spectrum: (M+H)-=520/522/524 (chlorine isotope).

Example 88

N-[(1S)-1-(5-chloro-1H-benzimidazol-2-yl)-3-methylsulfinylpropyl]-3-chloro-4-[(2S)-2-aminomethylpyrrolidin-1-ylcarbonyl]benzamide

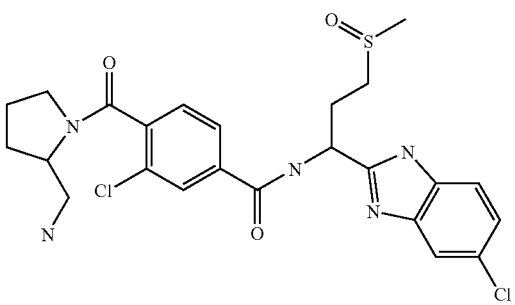

Prepared analogously to Example 17 from N-[(1S)-1-(5-chloro-1H-benzimidazol-2-yl)-3-methylsulfinylpropyl]-3-chloro-4-[(2S)-2-(N-tert-butoxycarbonylaminomethyl)pyrrolidin-1-ylcarbonyl]benzamide and trifluoroacetic acid. Yield: quantitative; $R_f$ value: 0.10 (silica gel; dichloromethane/methanol/ammonia=9:1:0.1); $C_{24}H_{27}Cl_2N_5O_3S$ (536.48); mass spectrum: $(M+H)^+$=536/538/540 (chlorine isotope).

Example 89

N-[(1S)-1-(5-chloro-1H-benzimidazol-2-yl)-3-methylsulfonylpropyl]-3-chloro-4-[(2S)-2-aminomethylpyrrolidin-1-ylcarbonyl]benzamide

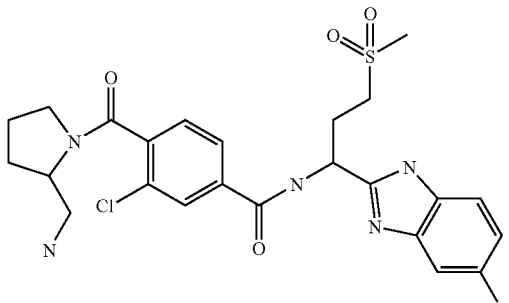

Prepared analogously to Example 17 from N-[(1S)-1-(5-chloro-1H-benzimidazol-2-yl)-3-methylsulfonylpropyl]-3-chloro-4-[(2S)-2-(N-tert-butoxycarbonylaminomethyl)pyrrolidin 1-ylcarbonyl]benzamide and trifluoroacetic acid. Yield: quantitative; $R_f$ value: 0.10 (silica gel; dichloromethane/methanol/ammonia=9:1:0.1); $C_{24}H_{27}Cl_2N_5O_4S$ (552.48); mass spectrum: $(M+H)^+=552/554/556$ (chlorine isotope).

Example 90 rac.-3-chloro-N-[1-(5-chloro-1H-benzimidazol-2-yl)ethyl]-4-(thiazolidin-3-ylcarbonyl)benzamide

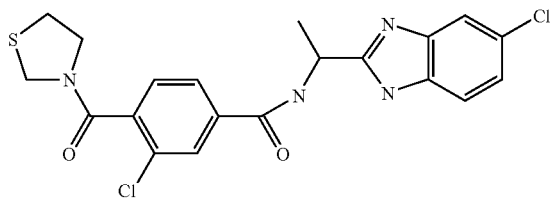

Prepared analogously to Example 1g from 2-chloro-4-{N-[1-(5-chloro-1H-benzimidazol-2yl)ethyl]aminocarbonyl}benzoic acid, TBTU, diisopropylethylamine, and thiazolidine in tetrahydrofuran. Yield: 67%; $R_f$ value: 0.50 (silica gel; dichloromethane/ethanol=9:1); $C_{20}H_{18}Cl_2N_4O_2S$ (449.36); mass spectrum: $(M+H)^+=449/451/453$ (chlorine isotope).

Example 91 rac.-3-chloro-N-[1-(5-chloro-1H-benzimidazol-2-yl)ethyl]-4-(1-oxothiazolidin-3-ylcarbonyl)benzamide

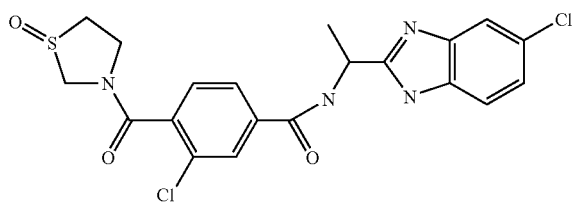

Prepared analogously to Example 85 from rac.-3-chloro-N-[1-(5-chloro-1H-benzimidazol-2-yl)ethyl]4-(thiazolidin-3-ylcarbonyl)benzamide and 3-chloroperoxybenzoic acid in dichloromethane/glacial acetic acid. Yield: 46%; $R_f$ value: 0.20 (silica gel; dichloromethane/methanol=9:1); $C_{20}H_{18}Cl_2N_4O_3S$ (465.36); mass spectrum: $(M+H)^+=465/467$ (chlorine isotope) and $(M-H)^-=463/465$ (chlorine isotope).

Example 92 rac.-3-chloro-N-[1-(5-chloro-1H-benzimidazol-2-yl)ethyl]-4-(1,1-dioxothiazolidin-3-ylcarbonyl)benzamide

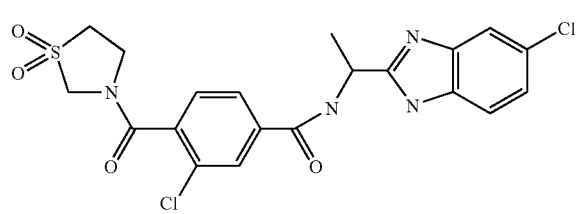

Prepared analogously to Example 85 from rac.-3-chloro-N-[1-(5-chloro-1H-benzimidazol-2-yl)ethyl]-4-(thiazolidin-3-ylcarbonyl)benzamide and 2 equivalents of 3-chloroperoxybenzoic acid in dichloromethane/glacial acetic acid. Yield: 40%; $R_f$ value: 0.50 (silica gel; dichloromethane/methanol=9:1); $C_{20}H_{18}Cl_2N_4O_4S$ (481.36); mass spectrum: $(M+H)^+=481/483/485$ (chlorine isotope).

Example 93

N-[(1S)-5-(benzyloxycarbonylamino)-1-(5-chloro-1H-benzimidazol-2-yl)pentyl]-3-methyl-4-(pyrrolidin-1-ylcarbonyl)benzamide

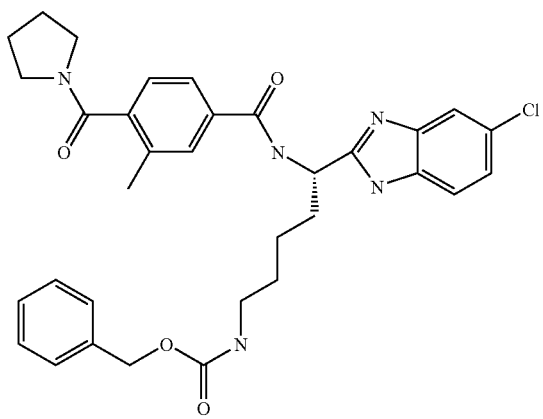

Prepared analogously to Example 1g from 3-methyl-4-(pyrrolidin-1-ylcarbonyl)benzoic acid, TBTU, diisopropylethylamine, and N-[(1S)-5-(benzyloxycarbonylamino)-1-(5-chloro-1H-benzimidazol-2-yl)pentylamine in tetrahydrofuran. Yield: 71%; $R_f$ value: 0.53 (silica gel; dichloromethane/methanol=9:1); $C_{33}H_{36}ClN_5O_4$ (602.13); mass spectrum: $(M+H)^+=602/604$ (chlorine isotope) and $(M-H)^-=600/602$ (chlorine isotope).

Example 94

N-[(1S)-5-amino-1-(5-chloro-1H-benzimidazol-2-yl)pentyl]-3-methyl-4-(pyrrolidin-1-ylcarbonyl)benzamide

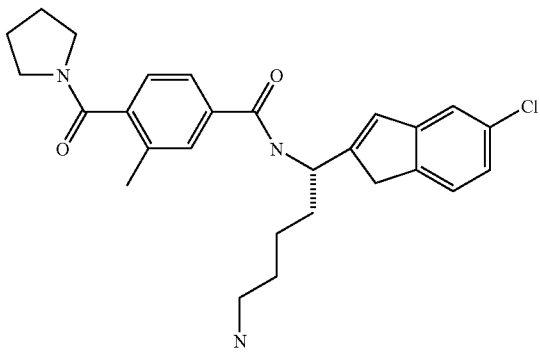

0.3 g (0.49 mmol) of N-[(1S)-5-(benzyloxycarbonylamino)-1-(5-chloro-1H-benzimidazol-2-yl)pentyl]-3-methyl-4-(pyrrolidin-1-ylcarbonyl)benzamide is dissolved in 15 mL of dichloromethane and, after the addition of 0.25 mL (0.76 mmol) of iodotrimethylsilane, stirred for 3 hours at ambient temperature. Then 10 mL of methanol is added and the mixture is stirred for a further 30 minutes. The solvent is distilled off and the residue is chromatographed on silica gel, eluting with dichloromethane/methanol (80:20). Yield: 0.22 g (96%); $R_f$ value: 0.15 (silica gel; dichloromethane/methanol=9:1); $C_{25}H_{30}ClN_5O_2$ (468.00); mass spectrum: $(M+H)^+$=468/470 (chlorine isotope).

Example 95

N-[(1S)-1-(5-chloro-1H-benzimidazol-2-yl)-3-phenylpropyl]-3-methyl-4-(pyrrolidin 1-ylcarbonyl)benzamide

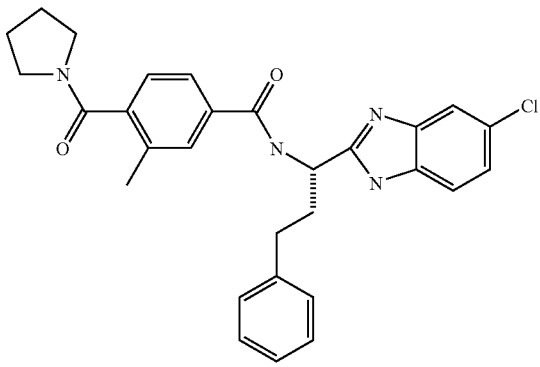

Prepared analogously to Example 1g from 3-methyl-4-(pyrrolidin-1-ylcarbonyl)benzoic acid, TBTU, diisopropylethylamine, and N-[(1S)-(5-chloro-1H-benzimidazol-2-yl)-3-phenylpropylamine in tetrahydrofuran. Yield: 92%; $R_f$ value: 0.5 (silica gel; dichloromethane/methanol=9:1); $C_{29}H_{29}ClN_4O_2$ (501.03); mass spectrum: $(M-H)^-$=499/501 (chlorine isotope).

Example 96

N-[(1S)-5-acetylamino-1-(5-chloro-1H-benzimidazol-2-yl)pentyl]-3-methyl-4-(pyrrolidin 1-ylcarbonyl)benzamide

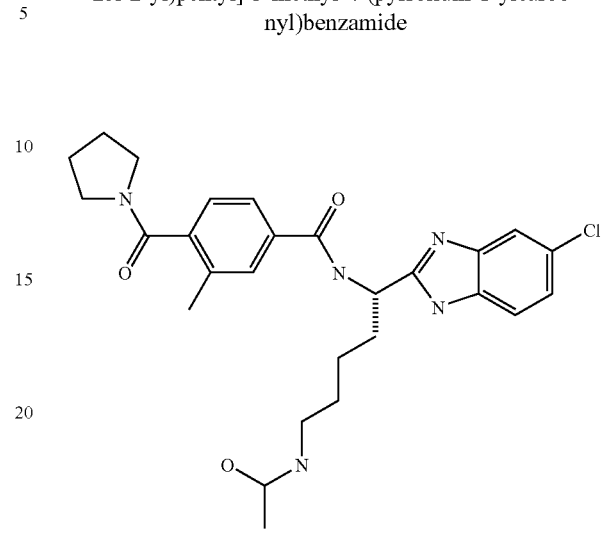

Prepared analogously to Example 23a from N-[(1S)-5-amino-1-(5-chloro-1H-benzimidazol-2-yl)pentyl]-3-methyl-4-(pyrrolidin-1-ylcarbonyl)benzamide, acetyl chloride, and triethylamine in tetrahydrofuran. Yield: 55%; $R_f$ value: 0.2 (silica gel; dichloromethane/methanol=9:1); $C_{27}H_{32}ClN_5O_3$ (510.04); mass spectrum: $(M-H)^-$=510/512 (chlorine isotope).

Example 97

N-[(1S)-1-(5-chloro-1H-benzimidazol-2-yl)-3-methylsulfanylpropyl]-3-methyl-4-(pyrrolidin-1-ylcarbonyl)benzamide

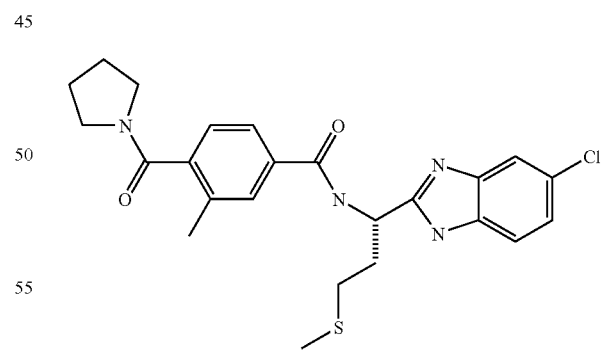

Prepared analogously to Example 1g from 3-methyl-4-(pyrrolidin-1-ylcarbonyl)benzoic acid, TBTU, diisopropylethylamine, and N-[(1S)-1-(5-chloro-1H-benzimidazol-2-yl)-3-methylsulfanylpropylamine in tetrahydrofuran. Yield: 64%; $R_f$ value: 0.5 (silica gel; dichloromethane/methanol=9:1); $C_{24}H_{27}ClN_4O_2S$ (471.02); mass spectrum: $(M+H)^+$=471/473 (chlorine isotope).

Example 98 rac.-N-[1-(5-chloro-1H-benzimidazol-2-yl)ethyl]-3-chloro-4-(pyrrolidin-1-ylcarbonyl)benzamide

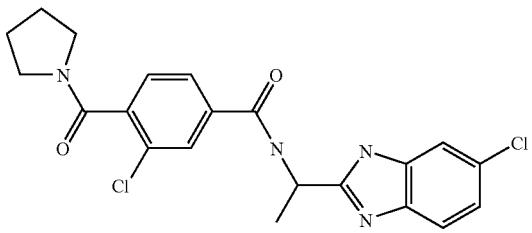

Prepared analogously to Example 1g from 2-chloro-4-{N-[1-(5-chloro-1H-benzimidazol-2-yl)ethyl]aminocarbonyl}benzoic acid, TBTU, diisopropylethylamine, and pyrrolidine in tetrahydrofuran. Yield: 56%; $R_f$ value: 0.49 (silica gel; dichloromethane/ethanol=9:1); $C_{21}H_{20}Cl_2N_4O_2$ (431.32); mass spectrum: $(M+H)^+$=433/433/435 (chlorine isotope).

Example 99 rac.-N-[1-(5-chloro-1H-benzimidazol-2-yl)-3,3,3-trifluoropropyl]-3-methyl-4-(pyrrolidin-1-ylcarbonyl)benzamide

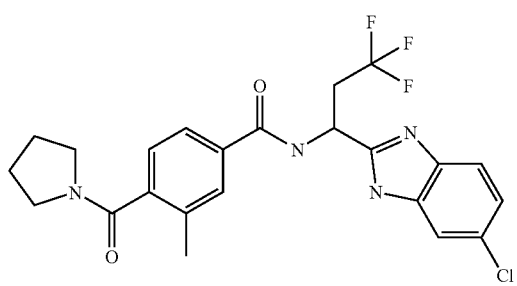

Prepared analogously to Example 1g from 3-methyl-4-(pyrrolidin-1-ylcarbonyl)benzoic acid, TBTU, diisopropylethylamine, and 1-(5-chloro-1H-benzimidazol-2-yl)-3,3,3-trifluoropropylamine in tetrahydrofuran. Yield: 52%; $R_f$ value: 0.50 (silica gel; dichloromethane/ethanol=9:1); $C_{23}H_{22}ClF_3N_4O_2$ (478.90); mass spectrum: $(M+H)^+$=479/481 (chlorine isotope).

Example 100 rac.-N-[1-(5-chloro-1H-benzimidazol-2-yl)-2-hydroxyethyl]-3-methyl-4-(pyrrolidin-1ylcarbonyl)benzamide

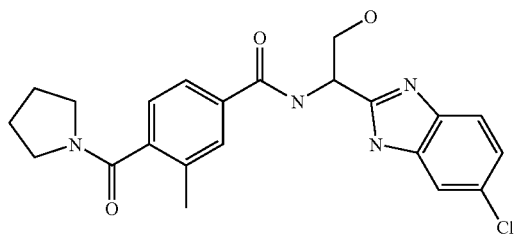

Prepared analogously to Example 1g from 3-methyl-4-(pyrrolidin-1-ylcarbonyl)benzoic acid, TBTU, diisopropylethylamine, and 2-hydroxy-1-(5-chloro-1H-benzimidazol-2-yl)ethylamine in tetrahydrofuran. Yield: 68%; $R_f$ value: 0.40 (silica gel; dichloromethane/ethanol=95:5); $C_{22}H_{23}ClN_4O_3$ (426.90); mass spectrum: $(M+H)^+$=427/429 (chlorine isotope) and $(M-H)^-$=425/427 (chlorine isotope).

Example 101 rac.-N-[2-tert-butoxycarbonylamino-1-(5-chloro-1H-benzimidazol-2-yl)ethyl]-3-methyl-4-(pyrrolidin-1-ylcarbonyl)benzamide

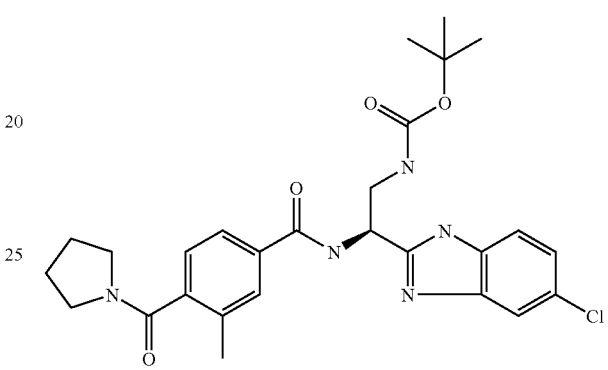

Prepared analogously to Example 1g from 3-methyl-4-(pyrrolidin-1-ylcarbonyl)benzoic acid, TBTU, diisopropylethylamine, and 2-tert-butoxycarbonylamino-1-(5-chloro-1H-benzimidazol-2-yl)ethylamine in tetrahydrofuran. Yield: 64%; $R_f$ value: 0.67 (silica gel; cyclohexane/ethanol=7:3); $C_{27}H_{32}ClN_5O_4$ (526.03); mass spectrum: $(M+H)^+$=526/528 (chlorine isotope) and $(M-H)^-$=524/526 (chlorine isotope).

Example 102 rac.-N-[2-amino-1-(5-chloro-1H-benzimidazol-2-yl)ethyl]-3-methyl-4-(pyrrolidin-1-ylcarbonyl)benzamide

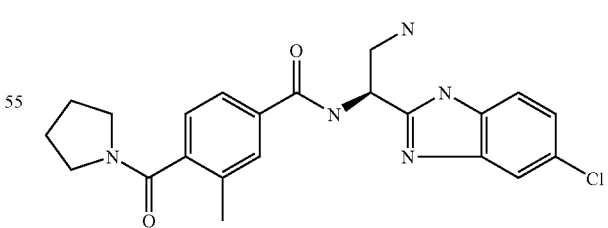

Prepared analogously to Example 17 from rac.-N-[2-tert-butoxycarbonylamino-1-(5-chloro-1H-benzimidazol-2-yl)ethyl]-3-methyl-4-(pyrrolidin-1-ylcarbonyl)benzamide and trifluoroacetic acid. Yield: 60%; $C_{22}H_{24}ClN_5O_2$ (425.92); mass spectrum: $(M+H)^+$=426/428 (chlorine isotope).

Example 103 rac.-N-[1-(5-chloro-1H-benzimidazol-2-yl)-2-(4-hydroxyphenyl)ethyl]-3-methyl-4-(pyrrolidin-1-yl-carbonyl)benzamide

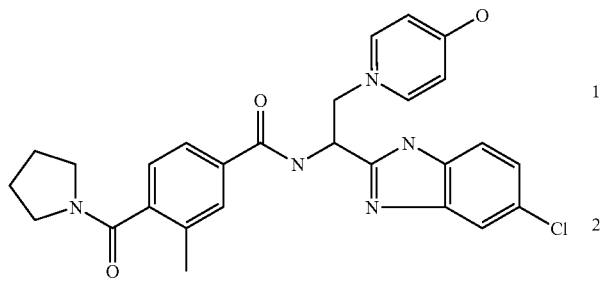

Prepared analogously to Example 1g from 3-methyl-4-(pyrrolidin-1-ylcarbonyl)benzoic acid, TBTU, diisopropyl-ethylamine, and 1-(5-chloro-1H-benzimidazol-2-yl)-2-(4-hydroxyphenyl)ethylamine in tetrahydrofuran. Yield: 64%; $R_f$ value: 0.14 (silica gel; dichloromethane/methanol=19:1); $C_{28}H_{27}ClN_4O_3$ (503.00); mass spectrum: $(M+H)^+$=503/505 (chlorine isotope).

Example 104 rac.-N-[2-acetylamino-1-(5-chloro-1H-benzimidazol-2-yl)ethyl]-3-methyl-4-(pyrrolidin-1-ylcarbonyl)benzamide

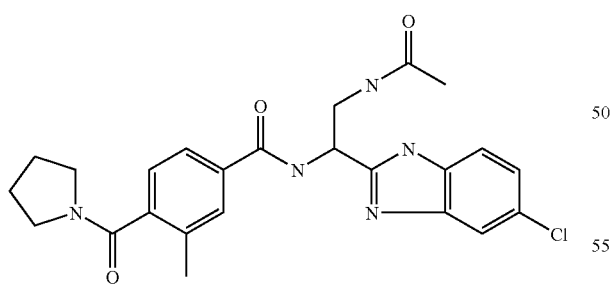

Prepared analogously to Example 124 from N-[2-amino-1-(5-chloro-1H-benzimidazol-2-yl)ethyl]-3-methyl-4-(pyrrolidin-1-ylcarbonyl)benzamide, acetic anhydride, and triethylamine in tetrahydrofuran. Yield: 62%; $R_f$ value: 0.16 (silica gel; dichloromethane/methanol=19:1); $C_{24}H_{26}ClN_5O_3$ (467.95); mass spectrum: $(M+H)^+$=468/470 (chlorine isotope) and $(M-H)^-$=466/468 (chlorine isotope).

Example 105 rac.-N-[2-benzoylamino-1-(5-chloro-1H-benzimidazol-2-yl)ethyl]-3-methyl-4-(pyrrolidin 1ylcarbonyl)benzamide

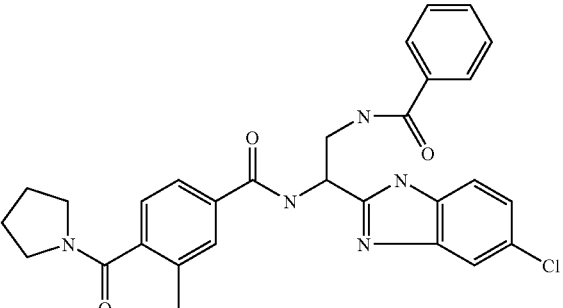

Prepared analogously to Example 125 from N-[2-amino-1-(5-chloro-1H-benzimidazol-2-yl)ethyl]-3-methyl-4-(pyrrolidin-1-ylcarbonyl)benzamide, benzoyl chloride, and triethylamine in tetrahydrofuran. Yield: 65%; $R_f$ value: 0.32 (silica gel; dichloromethane/methanol=19:1); $C_{29}H_{28}ClN_5O_3$ (530.03); mass spectrum: $(M+H)^+$=530/532 (chlorine isotope) and $(M-H)^-$=528/530 (chlorine isotope).

Example 106

N-[1-(5-chloro-1H-benzimidazol-2-yl)-1-methylethyl]-3-methyl-4-(pyrrolidin-1-ylcarbonyl)benzamide

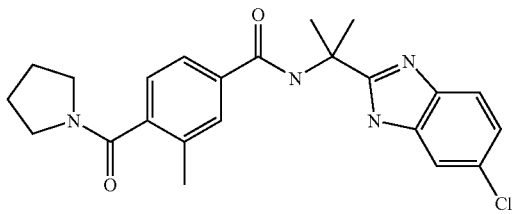

Prepared analogously to Example 1g from 3-methyl-4-(pyrrolidin-1-ylcarbonyl)benzoic acid, TBTU, diisopropyl-ethylamine, and 1-(5-chloro-1H-benzimidazol-2-yl)-1-methylethylamine in tetrahydrofuran. Yield: 71%; $R_f$ value: 0.37 (silica gel; ethyl acetate/ethanol=9:1); $C_{23}H_{25}ClN_4O_2$ (424.93); mass spectrum: $(M+H)^+$=425/427 (chlorine isotope).

Example 107

N-[1-(5-chloro-1H-benzimidazol-2-yl)cyclopropyl]-3-methyl-4-(pyrrolidin-1-ylcarbonyl)benzamide

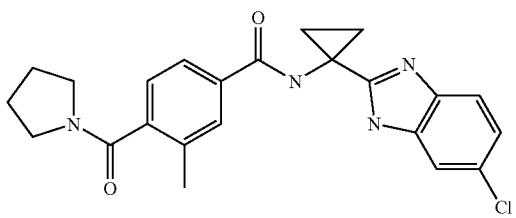

Prepared analogously to Example 1g from 3-methyl-4-(pyrrolidin-1-ylcarbonyl)benzoic acid, TBTU, diisopropylethylamine, and 1-(5-chloro-1H-benzimidazol-2-yl)cyclopropylamine in tetrahydrofuran. Yield: 44%; $R_f$ value: 0.37 (silica gel; ethyl acetate/ethanol=9:1); $C_{23}H_{23}ClN_4O_2$ (422.91); mass spectrum: $(M+H)^+=423/425$ (chlorine isotope).

Example 108

N-[1-(5-chloro-1H-benzimidazol-2-yl)cyclohexyl]-3-methyl-4-(pyrrolidin-1-ylcarbonyl)benzamide

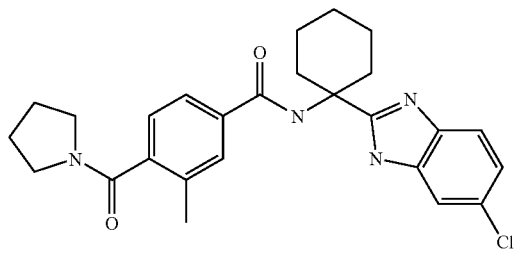

Prepared analogously to Example 1g from 3-methyl-4-(pyrrolidin-1-ylcarbonyl)benzoic acid, TBTU, diisopropylethylamine, and 1-(5-chloro-1H-benzimidazol-2-yl)cyclohexylamine in tetrahydrofuran. Yield: 78%; $R_f$ value: 0.28 (silica gel; ethyl acetate); $C_{26}H_{29}ClN_4O_2$ (464.99); mass spectrum: $(M+H)^+=465/467$ (chlorine isotope).

Example 109 rac.-N-[1-(5-chloro-1H-benzimidazol-2-yl)-3-hydroxycarbonylpropyl]-3-methyl-4-(pyrrolidin-1-ylcarbonyl)benzamide

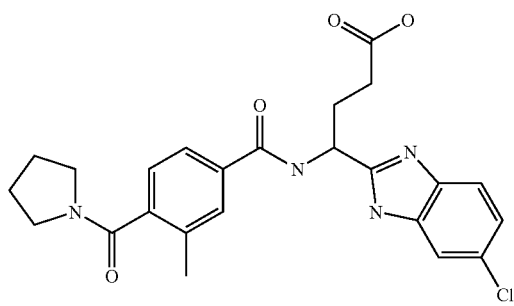

Prepared analogously to Example 1g from 3-methyl-4-(pyrrolidin-1-ylcarbonyl)benzoic acid, TBTU, diisopropylethylamine, 3-benzyloxycarbonyl-1-(5-chloro-1H-benzimidazol-2-yl)propylamine in dimethylsulfoxide and sodium hydroxide solution. Yield: 53%; $R_f$ value: 0.16 (silica gel; ethyl acetate/acetic acid=95:5); $C_{24}H_{25}ClN_4O_4$ (468.94); mass spectrum: $(M+H)^+=469/471$ (chlorine isotope).

Example 110

N-[(1S)-1-(5-chloro-1H-benzimidazol-2-yl)-3-hydroxycarbonylpropyl]-3-methyl-4-(pyrrolidin-1-ylcarbonyl)benzamide

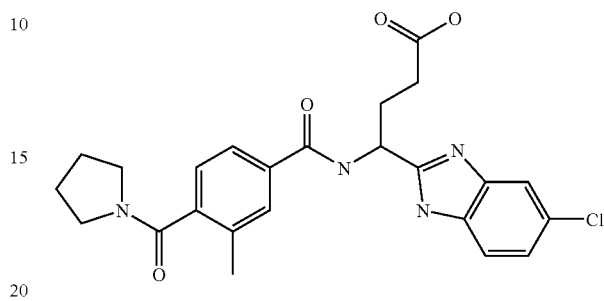

Prepared analogously to Example 17 from N-[(1S)-1-(1-tert-butoxycarbonyl-5-chlorobenzimidazol-2-yl)-3-hydroxycarbonylpropyl]-3-methyl-4-(pyrrolidin-1-ylcarbonyl)benzamide and trifluoroacetic acid. Yield: 68%; $R_f$ value: 0.50 (silica gel; ethyl acetate/ethanol/acetic acid=85:15:5); $C_{24}H_{25}ClN_4O_4$ (468.94); mass spectrum: $(M+H)^+=469/471$ (chlorine isotope).

Example 111 rac.-N-[3-benzyloxycarbonyl-1-(5-chloro-1H-benzimidazol-2-yl)propyl]-3-methyl-4-(pyrrolidin-1-ylcarbonyl)benzamide

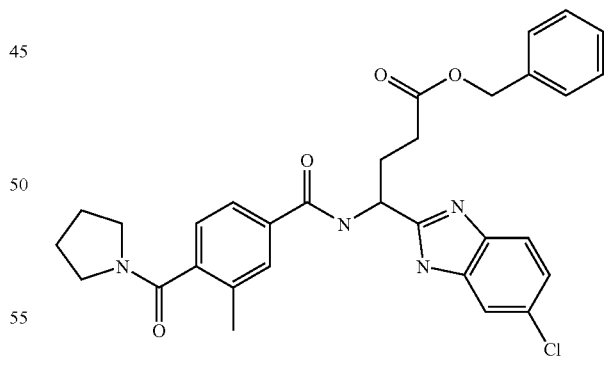

Prepared analogously to Example 1g from 3-methyl-4-(pyrrolidin-1-ylcarbonyl)benzoic acid, TBTU, diisopropylethylamine, and 3-benzyloxycarbonyl-1-(5-chloro-1H-benzimidazol-2-yl)propylamine in tetrahydrofuran. Yield: 70%; $R_f$ value: 0.24 (silica gel; ethyl acetate/ethanol=95:5); $C_{31}H_{31}ClN_4O_4$ (559.06); mass spectrum: $(M+H)^+=559/561$ (chlorine isotope).

Example 112

N-[(1S)-3-benzyloxycarbonyl-1-(5-chloro-1H-benz-imidazol-2-yl)propyl]-3-methyl-4-(pyrrolidin-1-yl-carbonyl)benzamide

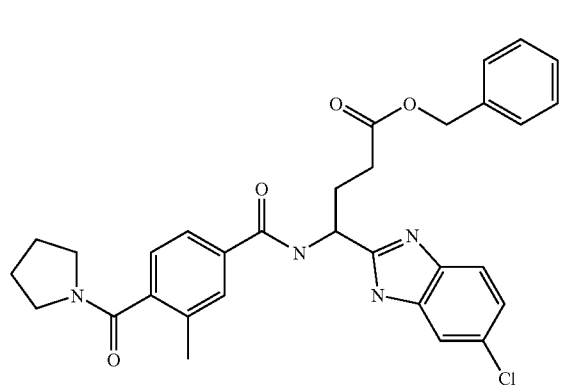

Prepared analogously to Example 1g from 3-methyl-4-(pyrrolidin-1-ylcarbonyl)benzoic acid, TBTU, diisopropylethylamine, and (S)-3-benzyloxycarbonyl-1-(5-chloro-1H-benzimidazol-2-yl)propylamine in tetrahydrofuran. Yield: 71%; $R_f$ value: 0.24 (silica gel; ethyl acetate/ethanol=95:5); $C_{31}H_{31}ClN_4O_4$ (559.06); mass spectrum: $(M+H)^+$=559/561 (chlorine isotope).

Example 113 rac.-N-[1-(5-chloro-1H-benzimidazol-2-yl)-3-ethy-laminocarbonylpropyl]-3-methyl-4-(pyrrolidin-1-ylcarbonyl)benzamide

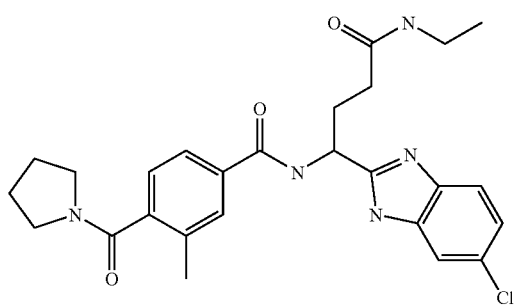

Prepared analogously to Example 1g from rac.-N-[1-(5-chloro-1H-benzimidazol-2-yl)-3-hydroxycarbonylpropyl]-3-methyl-4-(pyrrolidin-1-ylcarbonyl)benzamide, TBTU, diisopropylethylamine, and ethylamine in tetrahydrofuran. Yield: 67%; $R_f$ value: 0.24 (silica gel; ethyl acetate/ethanol=95:5); $C_{26}H_{30}ClN_5O_3$ (496.01); mass spectrum: $(M+H)^+$=496/498 (chlorine isotope).

Example 114 rac.-N-[1-(5-chloro-1H-benzimidazol-2-yl)-3-(pyrro-lidin-1-ylcarbonyl)propyl]-3-methyl-4-(pyrrolidin-1-ylcarbonyl)benzamide Prepared analogously to Example 1g from rac.-N-[1-(5-chloro-1H-benzimidazol-2-yl)-3-hydroxycarbonylpropyl]-3-methyl-4-(pyrrolidin-1-ylcarbonyl)benzamide, TBTU, diisopropylethylamine, and pyrrolidine in tetrahydrofuran. Yield: 54%; $R_f$ value: 0.22 (silica gel; ethyl acetate/ethanol=9:1); $C_{28}H_{32}ClN_5O_3$ (522.05); mass spectrum: $(M+H)^+$=522/524 (chlorine isotope).

Example 115

N-[(1S)-1-(5-chloro-1H-benzimidazol-2-yl)-3-(pyr-rolidin-1-ylcarbonyl)propyl]-3-methyl-4-(pyrrolidin-1-ylcarbonyl)benzamide Prepared analogously to Example 1g from (1S)—N-[1-(1-tert-butoxycarbonyl-5-chloro-1H-benzimidazol-2-yl)-3-hydroxycarbonylpropyl]-3-methyl-4-(pyrrolidin-1-ylcarbo-nyl)benzamide, TBTU, diisopropylethylamine, and pyrrolidine in tetrahydrofuran followed by treatment with trifluoroacetic acid analogously to Example 17. Yield: 56%; $R_f$ value: 0.22 (silica gel; ethyl acetate/ethanol=9:1); $C_{28}H_{32}ClN_5O_3$ (522.05); mass spectrum: $(M+H)^+$=522/524 (chlorine isotope).

Example 116 rac.-N-[1-(5-chloro-1H-benzimidazol-2-yl)-3-diethyl-aminocarbonylpropyl]-3-methyl-4-(pyrrolidin-1-ylcarbonyl)benzamide

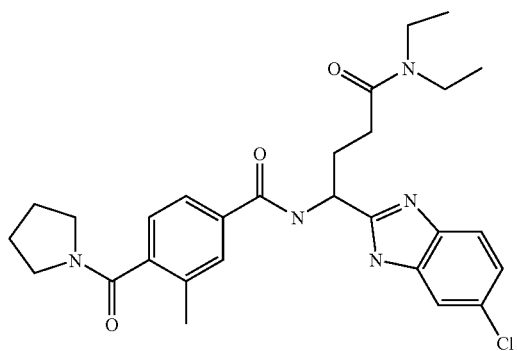

Prepared analogously to Example 1g from N-[1-(1-tert-butoxycarbonyl-5-chlorobenzimidazol-2-yl)-3-hydroxycarbonylpropyl]-3-methyl-4-(pyrrolidin-1-ylcarbonyl)benzamide, TBTU, diisopropylethylamine, and diethylamine in tetrahydrofuran followed by treatment analogously to Example 17 with trifluoroacetic acid. Yield: 76%; $R_f$ value: 0.16 (silica gel; ethyl acetate/ethanol=9:1); $C_{28}H_{34}ClN_5O_3$ (524.06); mass spectrum: $(M+H)^+=524/526$ (chlorine isotope).

Example 117

N-[(1S)-1-(5-chloro-1H-benzimidazol-2-yl)-2-tetrazol-2-ylethyl]-3-methyl-4-(pyrrolidin-1-ylcarbonyl)benzamide

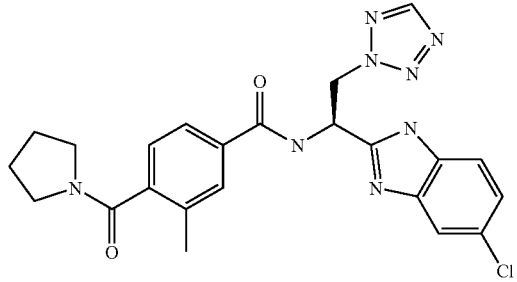

Prepared analogously to Example 1g from 3-methyl-4-(pyrrolidin-1-ylcarbonyl)benzoic acid, TBTU, diisopropylethylamine, and (S)-1-(5-chloro-1H-benzimidazol-2-yl)-2-tetrazol-2-yl-ethylamine in tetrahydrofuran. Yield: 22%; $R_f$ value: 0.64 (silica gel; dichloromethane/ethanol=9:1); $C_{23}H_{23}ClN_8O_2$ (478.94); mass spectrum: $(M+H)^+=479/481$ (chlorine isotope).

Example 118

N-[(1R)-1-(5-chloro-1H-benzimidazol-2-yl)-2-hydroxyethyl]-3-methyl-4-(pyrrolidin-1-ylcarbonyl)benzamide

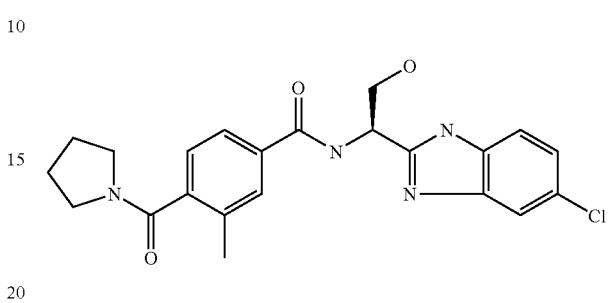

Prepared analogously to Example 1g from 3-methyl-4-(pyrrolidin-1-ylcarbonyl)benzoic acid, TBTU, diisopropylethylamine, and (R)-(5-chloro-1H-benzimidazol-2-yl)-2-hydroxyethylamine in tetrahydrofuran. Yield: 43%; $R_f$ value: 0.28 (silica gel; dichloromethane/methanol/ammonia=9:1:0.1); $C_{22}H_{23}ClN_4O_3$ (426.90); mass spectrum: $(M+H)^+=427/429$ (chlorine isotope) and $(M-H)^-=425/427$ (chlorine isotope).

Example 119

N-[(1S)-4-(tert-butoxycarbonylamino)-1-(5-chloro-1H-benzimidazol-2-yl)butyl]-3-methyl-4-(pyrrolidine-1-carbonyl)benzamide

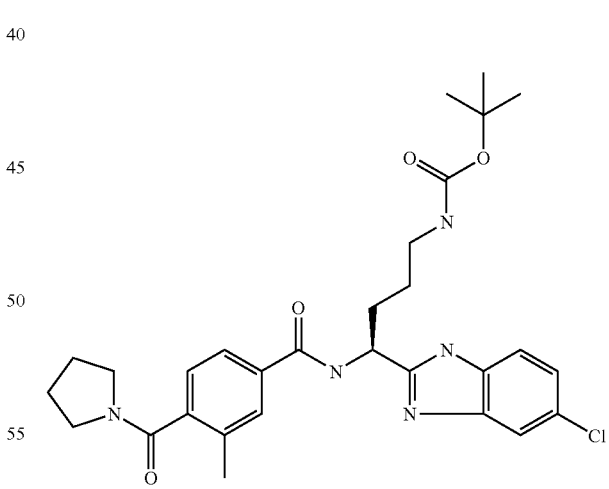

Prepared analogously to Example 1g from 3-methyl-4-(pyrrolidin-1-ylcarbonyl)benzoic acid, TBTU, diisopropylethylamine, and (S)-4-(tert-butoxycarbonylamino)-1-(5-chloro-1H-benzimidazol-2-yl)butylamine in tetrahydrofuran. Yield: 82%; $R_f$ value: 0.60 (silica gel; dichloromethane/methanol/ammonia=95:5:0.1); $C_{29}H_{36}ClN_5O_4$ (554.09); mass spectrum: $(M+H)^+=554/556$ (chlorine isotope).

Example 120 rac.-N-[1-(5-chloro-1H-benzimidazol-2-yl)-2-(piperdin-1-yl)ethyl]-3-methyl-4-(pyrrolidin-1-ylcarbonyl)benzamide

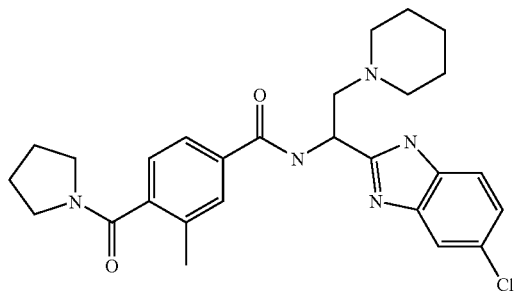

Prepared analogously to Example 1g from 3-methyl-4-(pyrrolidin-1-ylcarbonyl)benzoic acid, TBTU, diisopropylethylamine, and rac.-1-(5-chloro-1H-benzimidazol-2-yl)-2-(piperidin-1-yl)-ethylamine in tetrahydrofuran. Yield: 41%; $R_f$ value: 0.56 (silica gel; dichloromethane/ethanol=9:1); $C_{27}H_{32}ClN_5O_2$ (494.04); mass spectrum: $(M+H)^+=494/496$ (chlorine isotope).

Example 121

N-[(1R,2R)-1-(5-chloro-1H-benzimidazol-2-yl)-2-hydroxypropyl]-3-methyl-4-(pyrrolidin-1-ylcarbonyl)benzamide

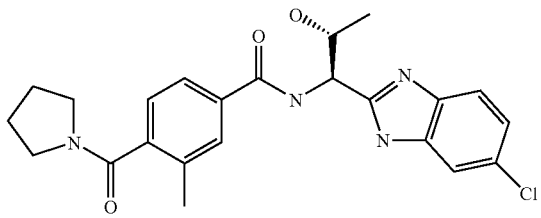

Prepared analogously to Example 1g from 3-methyl-4-(pyrrolidin-1-ylcarbonyl)benzoic acid, TBTU, diisopropylethylamine, and (1R,2R)-1-(5-chloro-1H-benzimidazol-2-yl)-2-hydroxypropylamine in tetrahydrofuran. Yield: 45%; $R_f$ value: 0.36 (silica gel; ethyl acetate/ethanol=9:1); $C_{23}H_{25}ClN_4O_3$ (440.93); mass spectrum: $(M+H)^+=441/443$ (chlorine isotope).

Example 122

N-[(5-chloro-1H-benzimidazol-2-yl)cyclobutyl]-3-methyl-4-(pyrrolidin-1-ylcarbonyl)benzamide

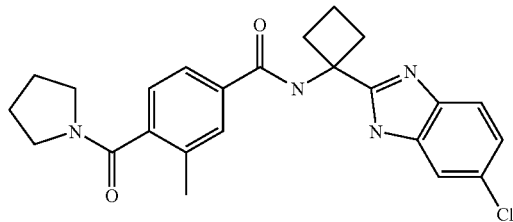

Prepared analogously to Example 1g from 3-methyl-4-(pyrrolidin-1-ylcarbonyl)benzoic acid, TBTU, diisopropylethylamine, and 1-(5-chloro-1H-benzimidazol-2-yl)cyclobutylamine in tetrahydrofuran. Yield: 88%; $R_f$ value: 0.42 (silica gel; ethyl acetate/ethanol=9:1); $C_{24}H_{25}ClN_4O_2$ (436.94); mass spectrum: $(M+H)^+=437/439$ (chlorine isotope).

Example 123

N-[(1S)-4-amino-1-(5-chloro-1H-benzimidazol-2-yl)butyl]-3-methyl-4-(pyrrolidin-1-ylcarbonyl)benzamide

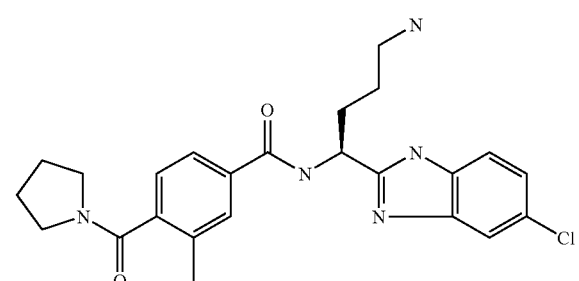

Prepared analogously to Example 17 from (S)—N-[4-(tert-butoxycarbonylamino)-1-(5-chloro-1H-benzimidazol-2-yl)butyl]-3-methyl-4-(pyrrolidin-1-ylcarbonyl)benzamide and trifluoroacetic acid. Yield: 54%; $R_f$ value: 0.21 (silica gel; dichloromethane/methanol=9:1); $C_{24}H_{28}ClN_5O_2$ (453.97); mass spectrum: $(M+H)^+=454/456$ (chlorine isotope) and $(M-H)^-=452/454$ (chlorine isotope).

Example 124

N-[(1S)-2-acetylamino-1-(5-chloro-1H-benzimidazol-2-yl)ethyl]-3-methyl-4-(pyrrolidin-1-ylcarbonyl)benzamide

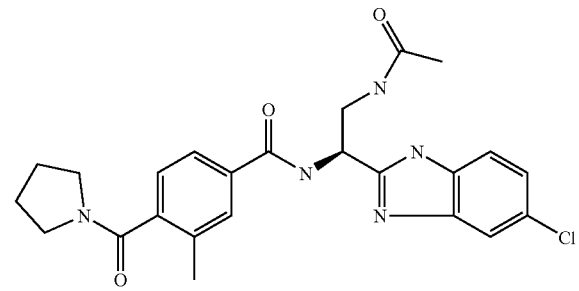

170 mg (0.4 mmol) of (1S)—N-[2-amino-1-(5-chloro-1H-benzimidazol-2-yl)ethyl]-3-methyl-4-(pyrrolidin-1-ylcarbonyl)benzamide is placed in 3.4 mL of tetrahydrofuran, while being cooled in the ice bath with 0.1 mL (0.6 mmol) of triethylamine and then combined with 0.05 g (0.45 mmol) of acetic anhydride. Then the mixture is heated to ambient temperature and stirred for 24 hours. Then the solvent is eliminated in vacuo and the residue purified by chromatography (gradient: dichloromethane/methanol=100:2). Yield: 23.5 mg (13%); $R_f$ value: 0.28 (silica gel; dichloromethane/methanol=95:5); $C_{24}H_{26}ClN_5O_3$ (467.95); mass spectrum: $(M+H)^+=468/470$ (chlorine isotope).

Example 125

N-[(1S)-1-(5-chloro-1H-benzimidazol-2-yl)-2-methylsulfonylaminoethyl]-3-methyl-4-(pyrrolidin-1-ylcarbonyl)benzamide

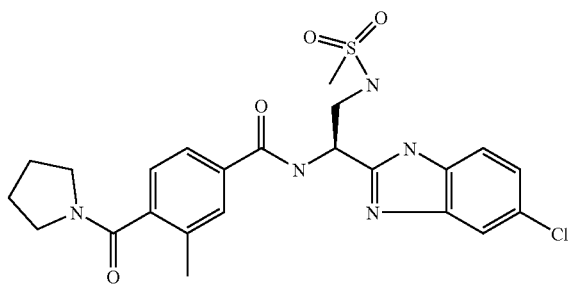

90 mg (0.2 mmol) of N-[(1S)-2-amino-1-(5-chloro-1H-benzimidazol-2-yl)ethyl]-3-methyl-4-(pyrrolidin-1-ylcarbonyl)benzamide is placed in 2 mL of dichloromethane, combined with 0.03 g (0.25 mmol) of triethylamine and while being cooled in the ice bath combined with 0.03 g (0.23 mmol) of methanesulfonic acid chloride. Then the mixture is heated to ambient temperature and stirred for 24 hours. Then the solvent is eliminated in vacuo and the residue purified by chromatography on silica gel (gradient: dichloromethane/methanol=100:5). Yield: 27 mg (25%); $R_f$ value: 0.20 (silica gel; dichloromethane/methanol=95:5); $C_{23}H_{26}ClN_5O_4S$ (504.01); mass spectrum: (M+H)$^+$=504/506 (chlorine isotope).

Example 126 rac.-N-[1-(5-chloro-1H-benzimidazol-2-yl)-2-methoxyethyl]-3-methyl-4-(pyrrolidin-1-ylcarbonyl)benzamide

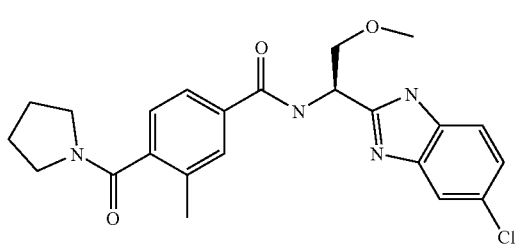

Prepared analogously to Example 1g from 3-methyl-4-(pyrrolidin-1-ylcarbonyl)benzoic acid, TBTU, diisopropylethylamine, and 1-(5-chloro-1H-benzimidazol-2-yl)-2-methoxyethylamine in tetrahydrofuran. Yield: 47%; $R_f$ value: 0.66 (silica gel; dichloromethane/methanol=9:1); $C_{23}H_{25}ClN_4O_3$ (440.93); mass spectrum: (M−H)$^-$=439/441 (chlorine isotope).

Example 127

3-bromo-N-[(1S)-1-(5-chloro-1H-benzimidazol-2-yl)-2-ethyl]-4-(2,5-dihydropyrrol-1-ylcarbonyl)benzamide

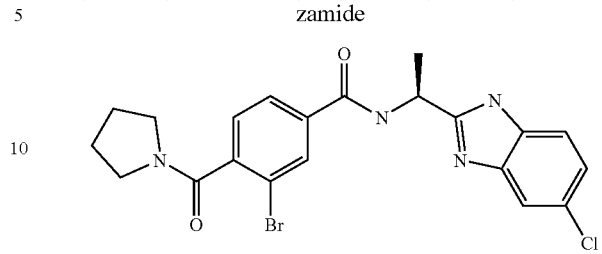

Prepared analogously to Example 1g from (S)-2-bromo-4-{N-[1-(5-chloro-1H-benzimidazol-2-yl)ethyl]aminocarbonyl}benzoic acid, TBTU, triethylamine, and 3-pyrroline in N,N-dimethylformamide. Yield: 57%; $R_f$ value: 0.35 (silica gel; dichloromethane/methanol=9:1); $C_{21}H_{18}BrClN_4O_2$ (473.76); mass spectrum: (M+H)$^+$=473/475/477 (bromine/chlorine isotope).

Example 128

N-[(1S)-1-(5-chloro-1H-benzimidazol-2-yl)-3-methoxypropyl]-3-methyl-4-(pyrrolidin-1-ylcarbonyl)benzamide

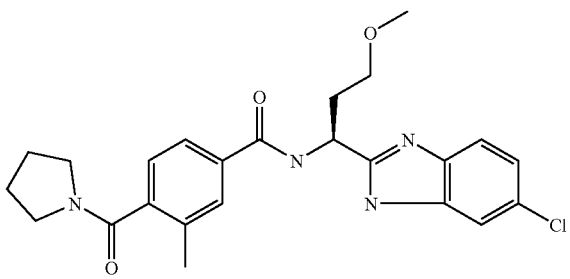

Prepared analogously to Example 1g from 3-methyl-4-(pyrrolidin-1-ylcarbonyl)benzoic acid, TBTU, diisopropylethylamine, and (S)-1-(5-chloro-1H-benzimidazol-2-yl)-3-methoxypropylamine in tetrahydrofuran. Yield: 77%; $R_f$ value: 0.34 (silica gel; dichloromethane/methanol=9:1); $C_{24}H_{27}ClN_4O_3$ (454.96); mass spectrum: (M+H)$^+$=455/457 (chlorine isotope).

Example 129

N-[(1S)-4-acetylamino-1-(5-chloro-1H-benzimidazol-2-yl)butyl]-3-methyl-4-(pyrrolidin-1-ylcarbonyl)benzamide

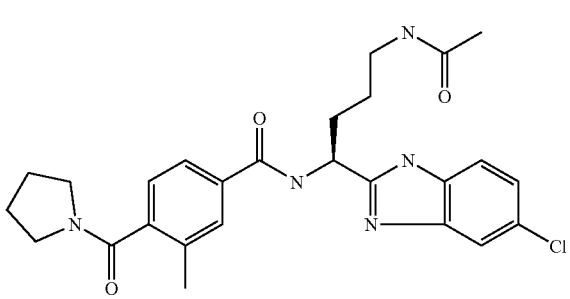

Prepared analogously to Example 124 from (1S)—N-[4-amino-1-(5-chloro-1H-benzimidazol-2-yl)butyl]-3-methyl-4-(pyrrolidin-1-ylcarbonyl)benzamide, acetic anhydride, and triethylamine in tetrahydrofuran. Yield: 73%; $R_f$ value: 0.73 (silica gel; dichloromethane/methanol=95:5); $C_{26}H_{30}ClN_5O_3$ (496.01); mass spectrum: $(M+H)^+$=496/498 (chlorine isotope) and (M–H)-=494/496 (chlorine isotope).

Example 130 rac.-N-[(5-chloro-1H-benzimidazol-2-yl)-(3-chlorophenyl)methyl]-3-methyl-4-(pyrrolidin-1-ylcarbonyl)benzamide

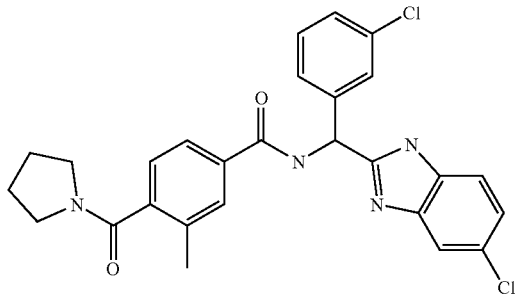

Prepared analogously to Example 1g from 3-methyl-4-(pyrrolidin-1-ylcarbonyl)benzoic acid, TBTU, diisopropylethylamine, and C-(5-chloro-1H-benzimidazol-2-yl)-C-(3chlorophenyl)methylamine in tetrahydrofuran. Yield: 48%; $R_f$ value: 0.33 (silica gel; dichloromethane/methanol=20:1); $C_{27}H_{24}C_{12}N_4O_2$ (507.42); mass spectrum: $(M+H)^+$=507/509/511 (chlorine isotope).

Example 131

N-[(1R)-2-(C-tert-butoxycarbonylmethyloxy)-1-(5-chloro-1H-benzimidazol-2-yl)ethyl]-3-methyl-4-(pyrrolidin-1-ylcarbonyl)benzamide

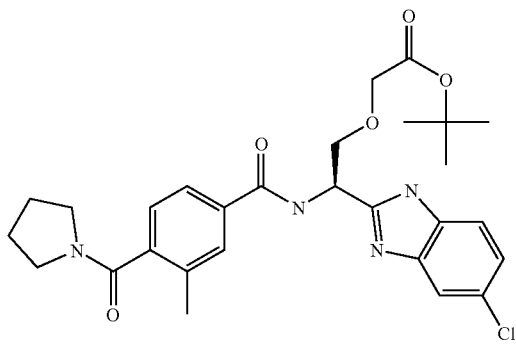

Prepared analogously to Example 1g from 3-methyl-4-(pyrrolidin-1-ylcarbonyl)benzoic acid, TBTU, diisopropylethylamine, and (R)-2-(C-tert-butoxycarbonylmethyloxy)-1-(5-chloro-1H-benzimidazol-2-yl)ethylamine in tetrahydrofuran. Yield: 82%; $R_f$ value: 0.70 (silica gel; dichloromethane/methanol=95:5); $C_{28}H_{33}ClN_4O_5$ (541.05); mass spectrum: $(M+H)^+$=541/543 (chlorine isotope) and (M–H)-=539/541 (chlorine isotope).

Example 132

N-[(1R)-2-(hydroxycarbonylmethyloxy)-1-(5-chloro-1H-benzimidazol-2-yl)ethyl]-3-methyl-4-(pyrrolidin-1-ylcarbonyl)benzamide

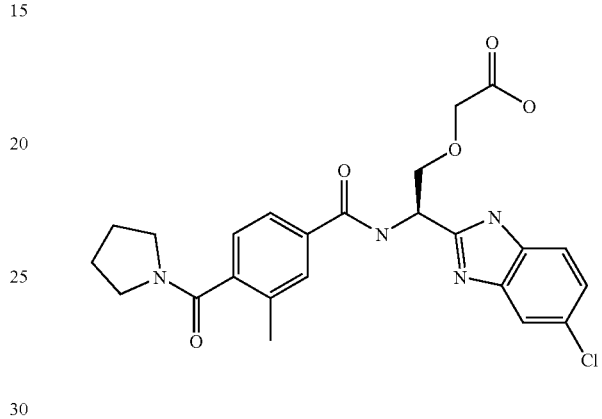

Prepared analogously to Example 17 from N-[(1R)-2-(tert-butoxycarbonylmethyloxy)-1-(5-chloro-1H-benzimidazol-2-yl)ethyl]-3-methyl-4-(pyrrolidin-1-ylcarbonyl)benzamide and trifluoroacetic acid. Yield: 90%; $R_f$ value: 0.50 (silica gel; dichloromethane/methanol=4:1); $C_{24}H_{25}ClN_4O_5$ (484.94); mass spectrum: $(M+H)^+$=485/487 (chlorine isotope) and (M–H)-=483/485 (chlorine isotope).

Example 133

3-chloro-N-(5-chloro-1H-benzimidazol-2-ylmethyl)-4-(3-oxopiperazin-1-ylcarbonyl)benzamide

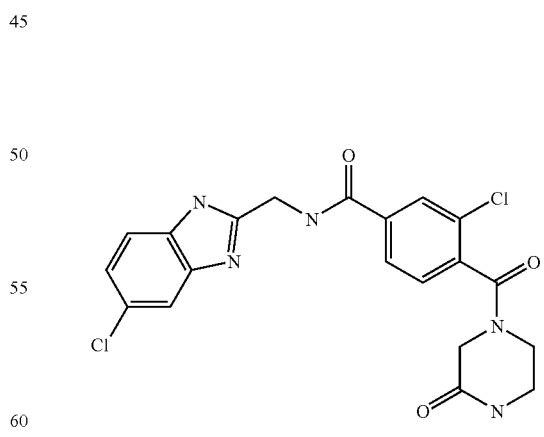

Prepared analogously to Example 1g from 3-chloro-N-(5-chloro-1H-benzimidazol-2-ylmethyl)-4-carboxybenzamide, TBTU, diisopropylethylamine, and piperazinone in DMF. Yield: 44%; $C_{20}H_{17}Cl_2N_5O_3$ (446.29); mass spectrum: $(M+H)^+$=446/448/450 (chlorine isotope).

Example 134 rac.-4-(2-aminomethylpyrrolidin-1-ylcarbonyl)-3-chloro-N-(5-chloro-1H-benzimidazol-2-ylmethyl)benzamide

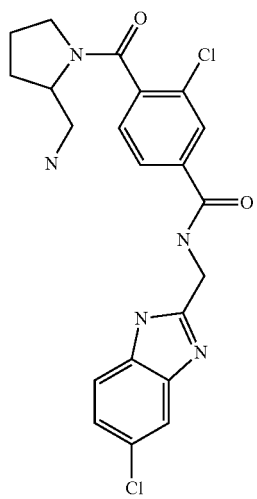

Prepared analogously to Example 1g from 3-chloro-N-(5-chloro-1H-benzimidazol-2-ylmethyl)-4-carboxybenzamide, TBTU, diisopropylethylamine, and rac.-2-tert-butoxycarbonylaminomethylpyrrolidine in DMF followed by treatment with trifluoroacetic acid analogously to Example 17. Yield: 47%; $C_{21}H_{21}Cl_2N_5O_2$ (446.34); mass spectrum: $(M+H)^+=446/448/450$ (chlorine isotope).

Example 135

3-chloro-N-(5-chloro-1H-benzimidazol-2-ylmethyl)-4-(4-methyl-3-oxopiperazin 1-ylcarbonyl)benzamide

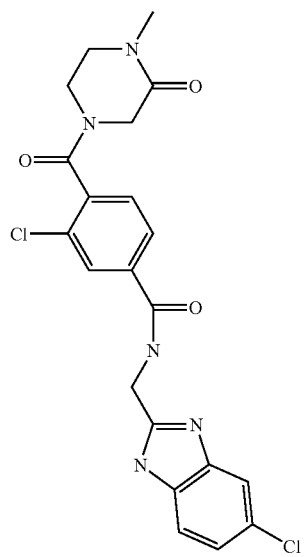

Prepared analogously to Example 1g from 3-chloro-N-(5-chloro-1H-benzimidazol-2-ylmethyl)-4-carboxybenzamide, TBTU, diisopropylethylamine, and 1-methylpiperazin-2-one in DMF. Yield: 9%; $C_{21}H_{19}Cl_2N_5O_3$ (460.32); mass spectrum: $(M+H)^+=460/462/464$ (chlorine isotope).

Example 136

3-chloro-N-[1-(5-chloro-1H-benzimidazol-2-yl)ethyl]-4-(2-ethoxycarbonylmethyl-3-oxopiperazin-1-ylcarbonyl)benzamide

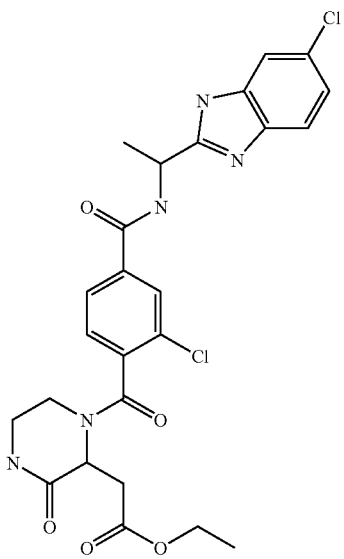

Prepared analogously to Example 1g from rac.-2-chloro-4-{N-[1-(5-chloro-1H-benzimidazol-2-yl)ethyl]aminocarbonyl}benzoic acid, TBTU, diisopropylethylamine, and 3-(ethoxycarbo-nylmethyl)piperazin-2-one in DMF. Yield: 37%; $R_f$ value: 0.49 (silica gel; dichloromethane/ethanol=10:1); $C_{25}H_{25}Cl_2N_5O_5$ (546.41); mass spectrum: $(M+H)^+=546/548/550$ (chlorine isotope).

Example 137

3-chloro-N-[1-(5-chloro-1H-benzimidazol-2-yl)ethyl]-4-(2-dimethylaminocarbonylmethyl-3-oxopiperazin-1-ylcarbonyl)benzamide

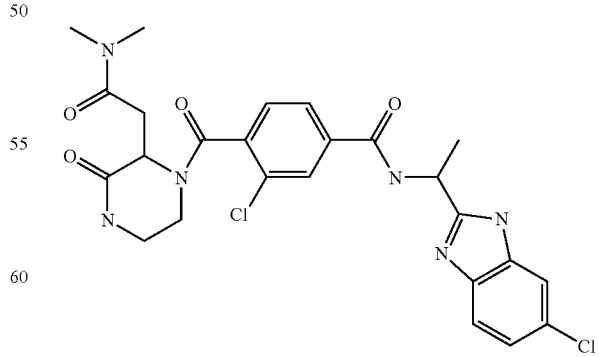

Prepared analogously to Example 1g from rac.-2-chloro-4-{N-[1-(5-chloro-1H-benzimidazol-2-yl)ethyl]aminocarbonyl}benzoic acid, TBTU, diisopropylethylamine, and rac.-3-(dimethyl-aminocarbonylmethyl)piperazin-2-one in DMSO. Yield: 42%; $C_{25}H_{26}Cl_2N_6O_4$ (545.42); mass spectrum: $(M+H)^+=545/547/549$ (chlorine isotope).

Example 138

4-(2-aminomethyl-3-oxopiperazin-1-ylcarbonyl)-3-chloro-N-[1-(5-chloro-1H-benzimidazol-2-yl)ethyl]benzamide

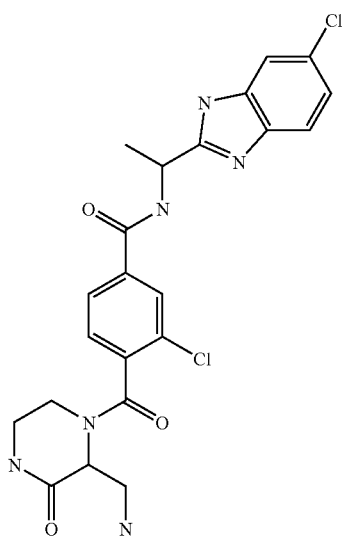

Prepared analogously to Example 17 from 4-(2-tert-butoxycarbonylaminomethyl-3-oxopiperazin-1-ylcarbonyl)-3-chloro-N-[1-(5-chloro-1H-benzimidazol-2-yl)ethyl]benzamide and trifluoroacetic acid. Yield: 91%; $C_{22}H_{22}Cl_2N_6O_3$ (489.36); mass spectrum: $(M+H)^+=489/491/493$ (chlorine isotope).

Example 139

3-chloro-N-[(1S)-1-(5-chloro-1H-benzimidazol-2-yl)ethyl]-4-(3-oxopiperazin-1-ylcarbonyl)benzamide

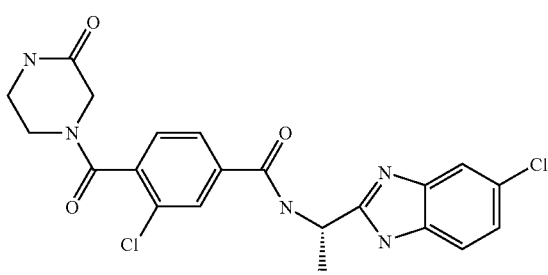

Prepared analogously to Example 1g from 2-chloro-4-{N-[(1S)-1-(5-chloro-1H-benzimidazol-2-yl)ethyl]aminocarbonyl}benzoic acid, TBTU, diisopropylethylamine, and piperazin-2-one in tetrahydrofuran. Yield: 58%; $R_f$ value: 0.22 (silica gel; dichloromethane/ethanol=9:1);

$C_{21}H_{19}Cl_2N_5O_3$ (460.32); mass spectrum: $(M+H)^+=460/462/464$ (chlorine isotope) and $(M-H)^-=458/460/462$ (chlorine isotope).

Example 140

N-[(1S)-1-(5-chloro-1H-benzimidazol-2-yl)-3-methylsulfinylpropyl]-3-methyl-4-(pyrrolidin-1-ylcarbonyl)benzamide

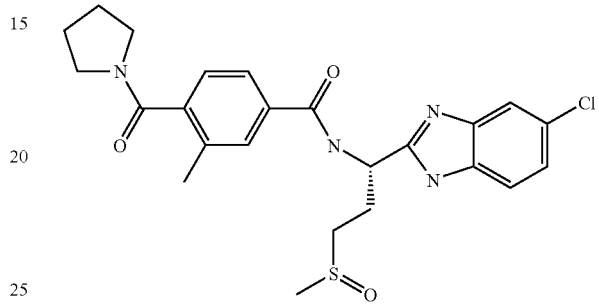

Prepared analogously to Example 85 from N-[(1S)-1-(5-chloro-1H-benzimidazol-2-yl)-3-methylsulfanylpropyl]-3-methyl-4-(pyrrolidin-1-ylcarbonyl)benzamide and 3-chloroperoxybenzoic acid in dichloromethane/glacial acetic acid. Yield: 57%; $R_f$ value: 0.15 (silica gel; dichloromethane/ethanol=9:1); $C_{24}H_{27}ClN_4O_3S$ (487.02); mass spectrum: $(M+H)^+=487/489$ (chlorine isotope).

Example 141

N-[(1S)-1-(5-chloro-1H-benzimidazol-2-yl)-3-methylsulfonylpropyl]-3-methyl-4-(pyrrolidin-1-ylcarbonyl)benzamide

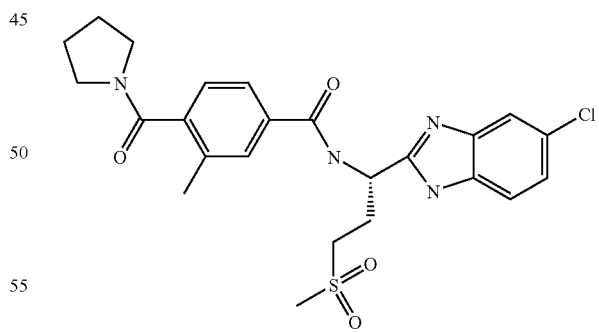

Prepared analogously to Example 85 from N-[(1S)-1-(5-chloro-1H-benzimidazol-2-yl)-3-methylsulfanylpropyl]-3-methyl-4-(pyrrolidin-1-ylcarbonyl)benzamide and 2 equivalents of 3-chloroperoxybenzoic acid in dichloromethane/glacial acetic acid. Yield: quantitative; $R_f$ value: 0.35 (silica gel; dichloromethane/ethanol=9:1); $C_{24}H_{27}ClN_4O_4S$ (503.02); mass spectrum: $(M+H)^+=503/505$ (chlorine isotope).

Example 142 rac.-N-[(5-chloro-1H-benzimidazol-2-yl)phenylmethyl]-3-methyl-4-(pyrrolidin-1-ylcarbonyl)benzamide

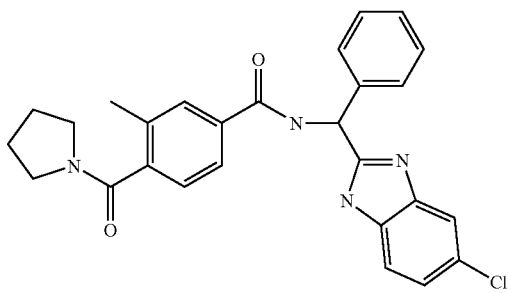

Prepared analogously to Example 1g from 3-methyl-4-(pyrrolidin-1-ylcarbonyl)benzoic acid, TBTU, diisopropylethylamine, and rac.—C-(5-chloro-1H-benzimidazol-2-yl)-C-phenylmethylamine in tetrahydrofuran. Yield: quantitative; $R_f$ value: 0.39 (silica gel; dichloromethane/methanol=9:1); $C_{27}H_{25}ClN_4O_2$ (472.97); mass spectrum: $(M+H)^+=473/475$ (chlorine isotope).

Example 143 rac.-N-[1-(5-chloro-1H-benzimidazol-2-yl)phenylmethyl]4-(2,5-dihydropyrrol-1-ylcarbonyl)-3-methylbenzamide

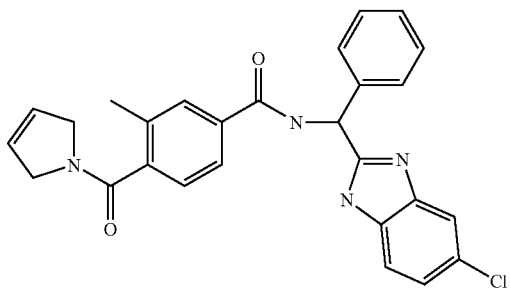

Prepared analogously to Example 1g from 3-methyl-4-(2,5-dihydropyrrol-1-ylcarbonyl)benzoic acid, TBTU, diisopropylethylamine, and rac.—C-(5-chloro-1H-benzimidazol-2-yl)-C-phenylmethylamine in tetrahydrofuran. Yield: quantitative; $R_f$ value: 0.39 (silica gel; dichloromethane/methanol=9:1); $C_{27}H_{23}ClN_4O_2$ (470.96); mass spectrum: $(M+H)^+=471/473$ (chlorine isotope).

Example 144

N-[(1S)-1-(5-chloro-1H-benzimidazol-2-yl)propyl]-3-methyl-4-(pyrrolidin 1-ylcarbonyl)benzamide

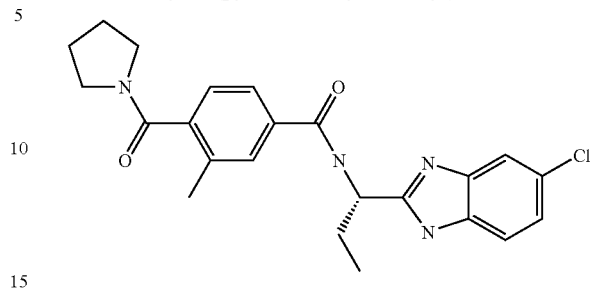

Prepared analogously to Example 1g from 3-methyl-4-(pyrrolidin-1-ylcarbonyl)benzoic acid, TBTU, diisopropylethylamine, and (S)-1-(5-chloro-1H-benzimidazol-2-yl)propylamine in tetrahydrofuran. Yield: 67%; $R_f$ value: 0.50 (silica gel; dichloromethane/methanol=9:1); $C_{23}H_{25}ClN_4O_2$ (424.93); mass spectrum: $(M+H)^+=425/427$ (chlorine isotope).

Example 145

N-[(1S)-1-(5-chloro-1H-benzimidazol-2-yl)-2-methylpropyl]-4-(2,5-dihydropyrrol-1-ylcarbonyl)-3-methylbenzamide

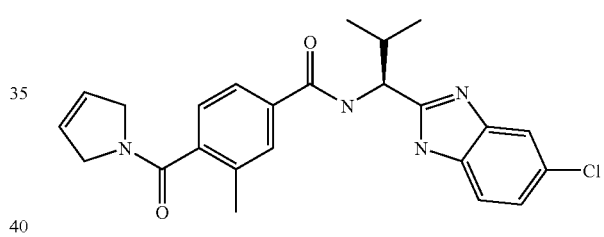

Prepared analogously to Example 1g from 3-methyl-4-(2,5-dihydropyrrol-1-ylcarbonyl)benzoic acid, TBTU, diisopropylethylamine, and (1S)-1-(5-chloro-1H-benzimidazol-2-yl)-2-methylpropylamine in tetrahydrofuran. Yield: 60%; $R_f$ value: 0.50 (silica gel; dichloromethane/methanol=9:1); $C_{24}H_{25}ClN_4O_2$ (436.94); mass spectrum: $(M+H)^+=437/439$ (chlorine isotope).

Example 146

N-[(1S)-1-(5-chloro-1H-benzimidazol-2-yl)-2-methylpropyl]-3-methyl-4-(pyrrolidin-1-ylcarbonyl)benzamide

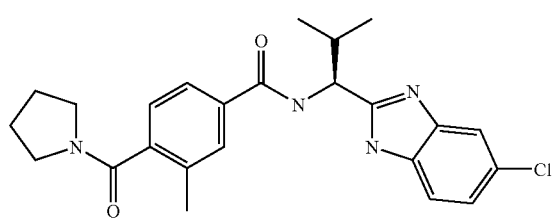

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-2-methylpropylamine in tetrahydrofuran. Yield: 72%; $R_f$ value: 0.43 (silica gel; dichloromethane/methanol=9:1); $C_{24}H_{27}ClN_4O_2$ (438.96); Mass spectrum: $(M+H)^+$=439 (chlorine isotope) and $(M-H)^-$=437 (chlorine isotope).

Example 147

4-[(2S)-2-(2-acetylaminoethyl)pyrrolidin-1-ylcarbonyl]-3-chloro-N-[(1S)-1-(5-chloro-1H-benzimidazol-2-yl)ethyl]benzamide

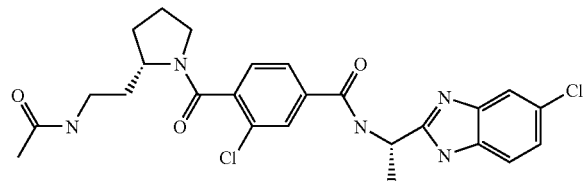

Prepared analogously to Example 124 from 4-[(2S)-2-(2-aminoethyl)pyrrolidin-1-ylcarbonyl]-3-chloro-N-[(1S)-1-(5-chloro-1H-benzimidazol-2-yl)ethyl]benzamide and acetic anhydride in glacial acetic acid. Yield: 67%; $R_f$ value: 0.32 (Reversed phase RP 8; methanol:5% sodium chloride solution=6:4); $C_{25}H_{27}Cl_2N_5O_3$ (516.43); mass spectrum: $(M+H)^+$=516/518/520 (chlorine isotope).

Example 148

N-[(1S)-3-(benzyloxycarbonylamino)-1-(5-chloro-1H-benzimidazol-2-yl)propyl]-3-methyl-4-(pyrrolidin-1-ylcarbonyl)benzamide

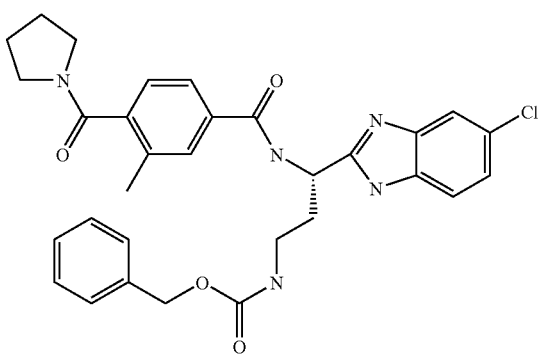

Prepared analogously to Example 1g from 3-methyl-4-(pyrrolidin-1-ylcarbonyl)benzoic acid, TBTU, diisopropylethylamine, and (1S)-[3-(benzyloxycarbonylamino)-1-(5-chloro-1H-benzimidazol-2-yl)propylamine in tetrahydrofuran. Yield: 87%; $R_f$ value: 0.50 (silica gel; dichloromethane/methanol=9:1); $C_{31}H_{32}ClN_5O_4$ (574.08); mass spectrum: $(M+H)^+$=574/576 (chlorine isotope) and $(M-H)^-$=572/574 (chlorine isotope).

Example 149

N-[(1S)-1-(5-chloro-1H-benzimidazol-2-yl)-2,2-dimethylpropyl]-3-methyl-4-(pyrrolidin-1-ylcarbonyl)benzamide

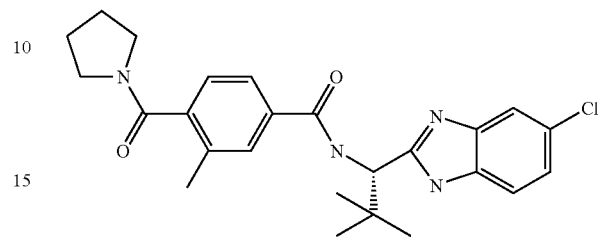

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-2,2-dimethylpropylamine in tetrahydrofuran. Yield: 21%; $R_f$ value: 0.18 (silica gel; ethyl acetate); $C_{25}H_{29}ClN_4O_2$ (452.98); mass spectrum: $(M+H)^+$=453/455 (chlorine isotope).

Example 150

3-chloro-N-[(1S)-1-(5-chloro-1H-benzimidazol-2-yl)ethyl]-4-(dimethylaminocarbonyl)benzamide

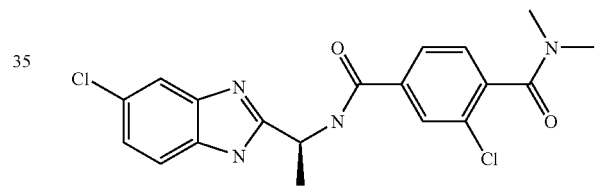

Prepared analogously to Example 1g from (1S)-2-chloro-4-{N-[1-(5-chloro-1H-benzimidazol-2-ylethyl]aminocarbonyl}benzoic acid, TBTU, diisopropylethylamine, and dimethylamine in tetrahydrofuran. Yield: 24%; $R_f$ value: 0.38 (silica gel; dichloromethane/ethanol=9:1); $C_{19}H_8Cl_2N_4O_2$ (405.28); mass spectrum: $(M+H)^+$=405/407/409 (chlorine isotope) and $(M-H)^-$=403/405/407 (chlorine isotope).

Example 151

N-[(1S)-3-amino-1-(5-chloro-1H-benzimidazol-2-yl)propyl]-3-methyl-4-(pyrrolidin-1-ylcarbonyl)benzamide

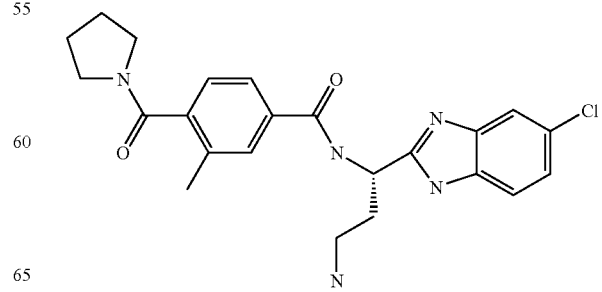

Prepared analogously to Example 94 from N-[(1S)-3-(benzyloxycarbonylamino)-1-(5-chloro-1H-benzimidazol-2-yl)propyl]-3-methyl-4-(pyrrolidin-1-ylcarbonyl)benzamide and iodotrimethylsilane in dichloromethane. Yield: quantitative; $R_f$ value: 0.25 (silica gel; dichloromethane/ethanol=4:1); $C_{23}H_{26}ClN_5O_2$ (439.94); mass spectrum: $(M+H)^+=440/442$ (chlorine isotope).

Example 152

N-[(1S)-1-(5-chloro-1H-benzimidazol-2-yl)ethyl]-3-fluoro-4-(pyrrolidin-1-ylcarbonyl)benzamide

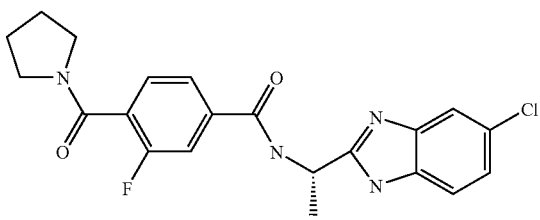

Prepared analogously to Example 1g from (1S)-2-fluoro-4-{N-[1-(5-chloro-1H-benzimidazol-2-ylethyl]aminocarbonyl}benzoic acid, TBTU, diisopropylethylamine, and pyrrolidine in tetrahydrofuran. Yield: 87%; $R_f$ value: 0.40 (silica gel; dichloromethane/ethanol=9:1); $C_{21}H_{20}ClFN_4O_2$ (414.87); mass spectrum: $(M+H)^+=415/417$ (chlorine isotope).

Example 153

N-[(1S)-1-(5-chloro-1H-benzimidazol-2-yl)-3-methylsulfonylaminopropyl]-3-methyl-4-(pyrrolidin-1-ylcarbonyl)benzamide

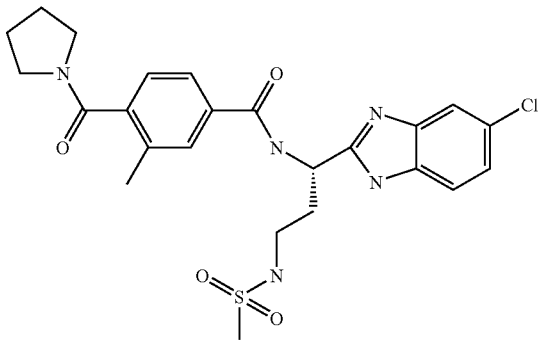

Prepared analogously to Example 125 from N-[(1S)-3-amino-1-(5-chloro-1H-benzimidazol-2-yl)propyl]-3-methyl-4-(pyrrolidin-1-ylcarbonyl)benzamide, methanesulfonic acid chloride, and triethylamine in dichloromethane. Yield: 37%; $R_f$ value: 0.30 (silica gel; dichloromethane/ethanol=9:1); $C_{24}H_{28}ClN_5O_4S$ (518.04); mass spectrum: $(M+H)^+=518/520$ (chlorine isotope) and $(M-H)^-=516/518$ (chlorine isotope).

Example 154

N-[(1S)-1-(5-chloro-1H-benzimidazol-2-yl)-3-(2-oxoimidazolidin-1-yl)propyl]-3-methyl-4-(pyrrolidin-1-ylcarbonyl)benzamide

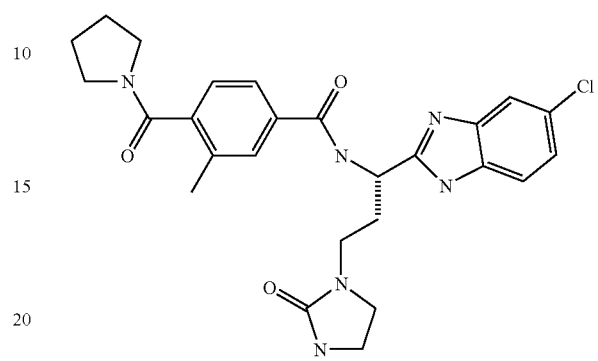

0.1 g (0.257 mmol) of N-{(1S)-1-(5-chloro-1H-benzimidazol-2-yl)-3-[3-(2-chloroethyl)ureido]propyl}-3-methyl-4-(pyrrolidin-1-ylcarbonyl)benzamide is dissolved in 5 mL of dimethylformamide and, after the addition of 50 mg (0.45 mmol) of potassium tert-butoxide, stirred for 5 hours at 40° C. Then the mixture is poured onto ice water and extracted with dichloromethane. The combined organic extracts are dried over sodium sulfate and concentrated by evaporation. The crude product is triturated with diethyl ether and suction filtered. Yield: 61%; $R_f$ value: 0.70 (silica gel; dichloromethane/ethanol=4:1); $C_{26}H_{29}ClN_6O_3$ (509.01); mass spectrum: $(M+H)^+=509/511$ (chlorine isotope) and $(M-H)^-=507/509$ (chlorine isotope).

Example 155

N-{(1S)-1-(5-chloro-1H-benzimidazol-2-yl)-3-[3-(2-chloroethyl)ureido]propyl}-3-methyl-4-(pyrrolidin-1-ylcarbonyl)benzamide

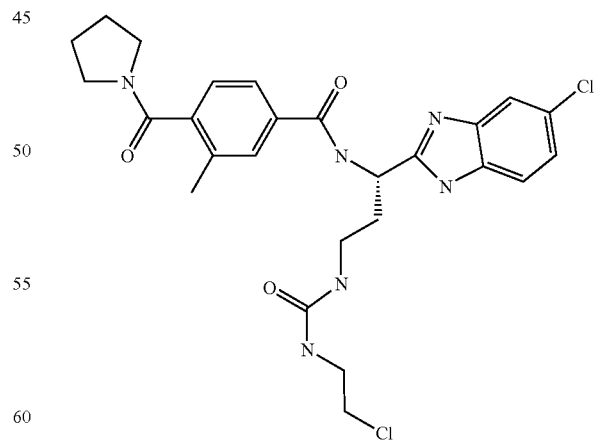

0.3 g (0.528 mmol) of (1S)—N-[3-amino-1-(5-chloro-1H-benzimidazol-2-yl)propyl]-3-methyl-4-(pyrrolidin-1-ylcarbonyl)benzamide is suspended in 10 mL of tetrahydrofuran and 0.1 mL (1.056 mmol) of triethylamine and, after the addition of 56 mg (0.528 mmol) of 2-chloroethyl isocyanate, stirred for 16 hours at ambient temperature. Then the solution is concentrated, the residue is taken up in dichloromethane, washed several times with water, and the combined organic extracts are dried and concentrated by evaporation. Yield: 49%; $R_f$ value: 0.30 (silica gel; dichloromethane/ethanol=9:1); $C_{26}H_{30}Cl_2N_6O_3$ (545.47); mass spectrum: $(M+H)^+=545/547$ (chlorine isotope).

Example 156 rac.-N-[1-(5-chloro-1H-benzimidazol-2-yl)-2-methoxy-2-methylpropyl]-3-methyl-4-(pyrrolidin-1-ylcarbonyl)benzamide

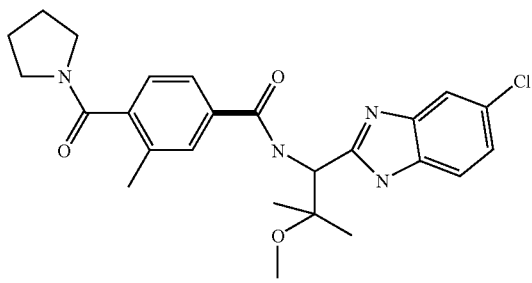

Prepared analogously to Example 1g from 3-methyl-4-(pyrrolidin-1-ylcarbonyl)benzoic acid, TBTU, diisopropylethylamine, and 1-(5-chloro-1H-benzimidazol-2-yl)-2-methoxy-2-methylpropylamine in tetrahydrofuran. Yield: 76%; $R_f$ value: 0.50 (silica gel; dichloromethane/ethanol=9:1); $C_{25}H_{29}ClN_4O_3$ (468.98); mass spectrum: $(M+H)^+=469/471$ (chlorine isotope) and $(M-H)^-=467/469$ (chlorine isotope).

Example 157

3-chloro-N-[(1R)-1-(5-chloro-1H-benzimidazol-2-yl)-2-ethylsulfanylethyl]4-(pyrrolidin-1-ylcarbonyl)benzamide

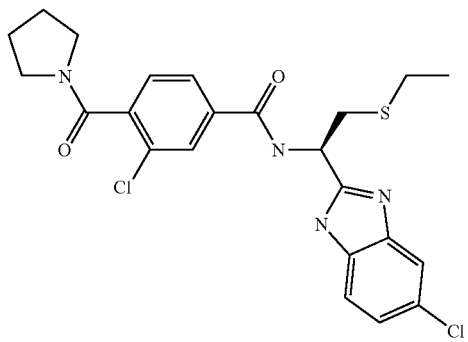

Prepared analogously to Example 1g from 3-chloro-4-(pyrrolidin-1-ylcarbonyl)benzoic acid, TBTU, diisopropylethylamine, and (R)-1-(5-chloro-1H-benzimidazol-2-yl)-2-ethylsulfanylethylamine in tetrahydrofuran. Yield: 75%; $R_f$ value: 0.41 (silica gel; dichloromethane/ethanol=9:1); $C_{23}H_{24}Cl_2N_4O_2S$ (491.44); mass spectrum: $(M+H)^+=491/493/495$ (chlorine isotope).

Example 158

N-[(1S)-1-(5-chloro-1H-benzimidazol-2-yl)butyl]-3-methyl-4-(pyrrolidin 1-ylcarbonyl)benzamide

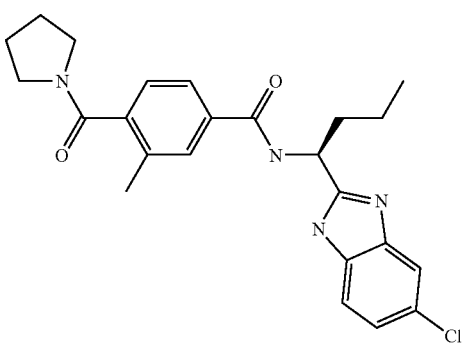

Prepared analogously to Example 1g from 3-methyl-4-(pyrrolidin-1-ylcarbonyl)benzoic acid, TBTU, diisopropylethylamine, and (S)-1-(5-chloro-1H-benzimidazol-2-yl)butylamine in tetrahydrofuran. Yield: 60%; $R_f$ value: 0.36 (silica gel; dichloromethane/ethanol=9:1); $C_{24}H_{27}ClN_4O_2$ (438.96); mass spectrum: $(M+H)^+=439/441$ (chlorine isotope).

Example 159

N-[(1S)-1-(5-chloro-1H-benzimidazol-2-yl)ethyl]-3-methoxy-4-(pyrrolidin 1-ylcarbonyl)benzamide

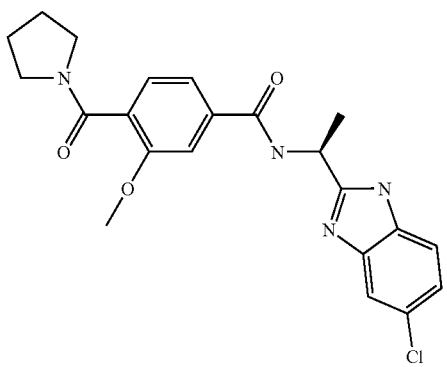

Prepared analogously to Example 1g from 3-methoxy-4-(pyrrolidin-1-ylcarbonyl)benzoic acid, TBTU, diisopropylethylamine, and (S)-1-(5-chloro-1H-benzimidazol-2-yl)ethylamine in tetrahydrofuran. Yield: 29%; $R_f$ value: 0.31 (silica gel; dichloromethane/ethanol=9:1); $C_{22}H_{23}ClN_4O_3$ (426.90); mass spectrum: $(M+H)^+=427/429$ (chlorine isotope).

Example 160

N-[(1S)-1-(5-chloro-1H-benzimidazol-2-yl)-3-hydroxypropyl]-3-methyl-4-(pyrrolidin-1-ylcarbonyl)benzamide

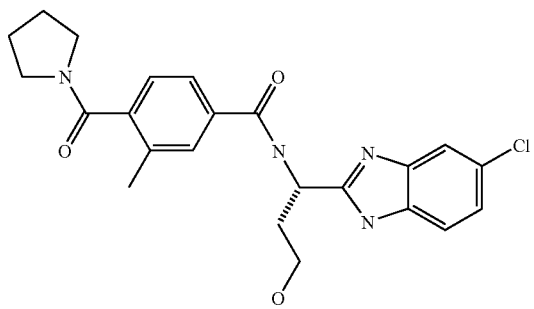

Prepared analogously to Example 1g from 3-methyl-4-(pyrrolidin-1-ylcarbonyl)benzoic acid, TBTU, diisopropylethylamine, and (S)-1-(5-chloro-1H-benzimidazol-2-yl)-3hydroxypropylamine in tetrahydrofuran. Yield: 65%; $R_f$ value: 0.43 (silica gel; dichloromethane/ethanol=9:1); $C_{23}H_{25}ClN_4O_3$ (440.93); mass spectrum: $(M+H)^+=441/443$ (chlorine isotope).

Example 161

3-bromo-N-[(1S)-1-(5-chloro-1H-benzimidazol-2-yl)-3-methylsulfanylpropyl]4-(pyrrolidin-1-ylcarbonyl)benzamide

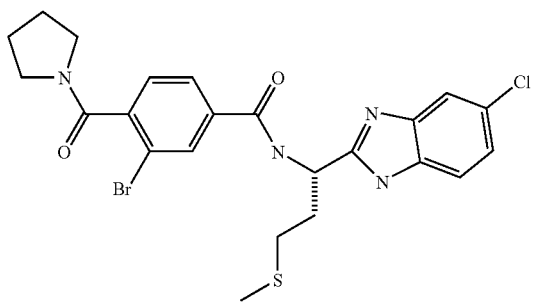

Prepared analogously to Example 1g from 3-bromo-4-(pyrrolidin-1-ylcarbonyl)benzoic acid, TBTU, diisopropylethylamine, and (S)-1-(5-chloro-1H-benzimidazol-2-yl)-3-methylsulfanylpropylamine in tetrahydrofuran. Yield: 60%; $R_f$ value: 0.40 (silica gel; dichloromethane/ethanol=9:1); $C_{23}H_{24}BrClN_4O_2S$ (535.89); mass spectrum: $(M+H)^+=535/537/539$ (bromo-chlorine isotope).

Example 162

3-chloro-N-[(1R)-1-(5-chloro-1H-benzimidazol-2-yl)-2-(ethylsulfinyl)ethyl]4-(pyrrolidin-1-ylcarbonyl)benzamide

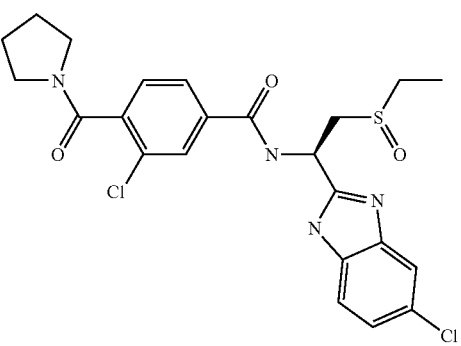

Prepared analogously to Example 85 from 3-chloro-N-[(1R)-1-(5-chloro-1H-benzimidazol-2-yl)-2-(ethylsulfanyl)ethyl]-4-(pyrrolidin-1-ylcarbonyl)benzamide, 3-chloroperoxybenzoic acid, and glacial acetic acid in dichloromethane. Yield: 97%; $R_f$ value: 0.31 (silica gel; dichloromethane/ethanol=9:1); $C_{23}H_{24}C_{12}N_4O_3S$ (507.44); mass spectrum: $(M+H)^+=507/509/511$ (chlorine isotope).

Example 163

3-chloro-N-[(1S)-1-(5-chloro-1H-benzimidazol-2-yl)-3-(methylsulfanyl)propyl]-4-(pyrrolidin-1-ylcarbonyl)benzamide

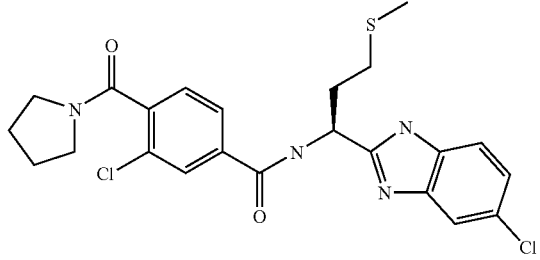

Prepared analogously to Example 1g from 3-chloro-4-(pyrrolidin-1-ylcarbonyl)benzoic acid, TBTU, diisopropylethylamine, and (S)-1-(5-chloro-1H-benzimidazol-2-yl)-3-(methyl-sulfanyl)propylamine in tetrahydrofuran. Yield: 62%; $R_f$ value: 0.50 (silica gel; dichloromethane/ethanol=9:1); $C_{23}H_{24}Cl_2N_4O_2S$ (491.44); mass spectrum: $(M+H)^+=391/393/395$ (chlorine isotope).

Example 164

3-chloro-N-[(1R)-1-(5-chloro-1H-benzimidazol-2-yl)-2-(ethylsulfonyl)ethyl]-4-(pyrrolidin-1-ylcarbonyl)benzamide

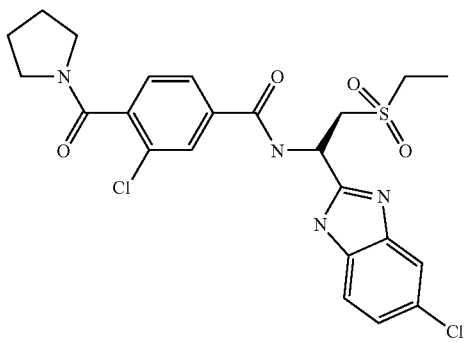

Prepared analogously to Example 85 from 3-chloro-N-[(1R)-1-(5-chloro-1H-benzimidazol-2-yl)-2-(ethylsulfanyl)ethyl]-4-(pyrrolidin-1-ylcarbonyl)benzamide, 2.8 equivalents of 3-chloroperoxybenzoic acid, and glacial acetic acid in dichloromethane. Yield: 54%; $R_f$ value: 0.40 (silica gel; dichloromethane/ethanol=9:1); $C_{23}H_{24}Cl_2N_4O_4S$ (523.44); mass spectrum: $(M+H)^+=523/525/527$ (chlorine isotope) and $(M-H)^-=521/523/525$ (chlorine isotope)

Example 165

3-bromo-N-[(1S)-1-(5-chloro-1H-benzimidazol-2-yl)-3-(methylsulfonyl)propyl]-4-(pyrrolidin-1-ylcarbonyl)benzamide

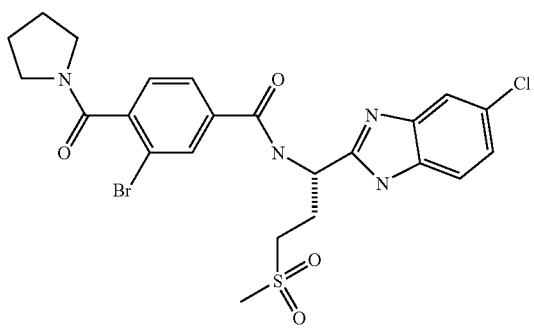

Prepared analogously to Example 85 from 3-bromo-N-[(1S)-1-(5-chloro-1H-benzimidazol-2-yl)-3-(methylsulfanyl)propyl]4-(pyrrolidin-1-ylcarbonyl)benzamide, 2.8 equivalents of 3-chloroperoxybenzoic acid, and glacial acetic acid in dichloromethane. Yield: 89%; $R_f$ value: 0.35 (silica gel; dichloromethane/ethanol=9:1); $C_{23}H_{24}BrClN_4O_4S$ (567.89); mass spectrum: $(M+H)^+=567/569/571$ (bromo-chlorine isotope).

Example 166

3-chloro-N-[(1S)-1-(5-chloro-1H-benzimidazol-2-yl)ethyl]-4-[(2R)-2-hydroxymethylpyrrolidin-1-ylcarbonyl]benzamide

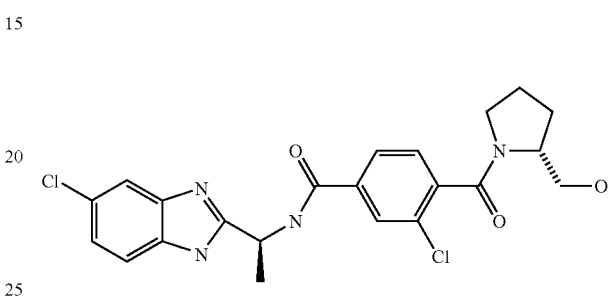

Prepared analogously to Example 1g from (1S)-2-chloro-4-{N-[1-(5-chloro-1H-benzimidazol-2-ylethyl]aminocarbonyl}benzoic acid, TBTU, diisopropylethylamine, and D-prolinol in tetrahydrofuran. Yield: 68%; $R_f$ value: 0.32 (silica gel; dichloromethane/ethanol=9:1); $C_{22}H_{22}Cl_2N_4O_3$ (461.35); mass spectrum: $(M+H)^+=461/463/465$ (chlorine isotope).

Example 167

3-chloro-N-[(1S)-1-(5-chloro-1H-benzimidazol-2-yl)ethyl]4-[(2S)-2-hydroxymethylpyrrolidin-1-ylcarbonyl]benzamide

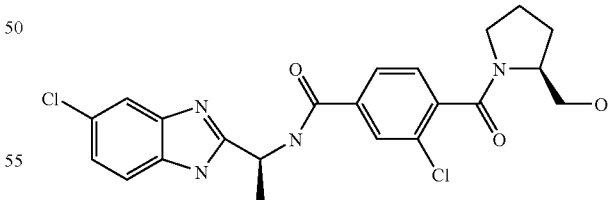

Prepared analogously to Example 1g from (1S)-2-chloro-4-{N-[1-(5-chloro-1H-benzimidazol-2-ylethyl]aminocarbonyl}benzoic acid, TBTU, diisopropylethylamine, and L-prolinol in tetrahydrofuran. Yield: quantitative; $R_f$ value: 0.32 (silica gel; dichloromethane/ethanol=9:1); $C_{22}H_{22}Cl_2N_4O_3$ (461.35); mass spectrum: $(M+H)^+=461/463/465$ (chlorine isotope).

Example 168

N-{(1H-benzimidazol-2-yl)-[1-(3-tert-butoxycarbonyl)piperidin-3-yl]methyl}-3-methyl-4-(pyrrolidin-1-ylcarbonyl)benzamide

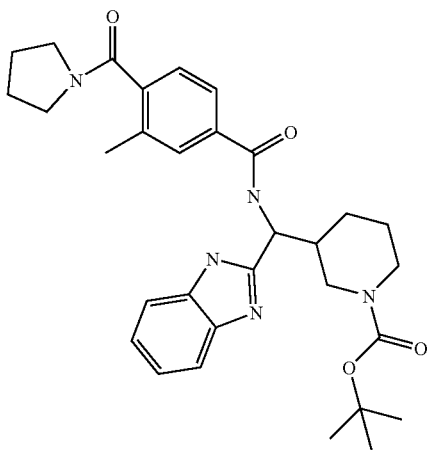

Prepared analogously to Example 1g from 3-methyl-4-(pyrrolidin-1-ylcarbonyl)benzoic acid, TBTU, diisopropylethylamine, and C-(1H-benzimidazol-2-yl)-C-[1-(3-tert-butoxycarbonyl)piperidin-3-yl]methylamine in tetrahydrofuran. Yield: 27%; $R_f$ value: 0.09 (Reversed phase RP8; methanol/5% sodium chloride solution=6:4); $C_{31}H_{39}N_5O_4$ (545.68); mass spectrum: $(M+H)^+$=546.

Example 169

N-{[1-(3-tert-butoxycarbonyl)piperidin-3-yl]-(5-chloro-1H-benzimidazol-2-yl)methyl}-3-methyl-4-(pyrrolidin-1-ylcarbonyl)benzamide (4 stereoisomers)

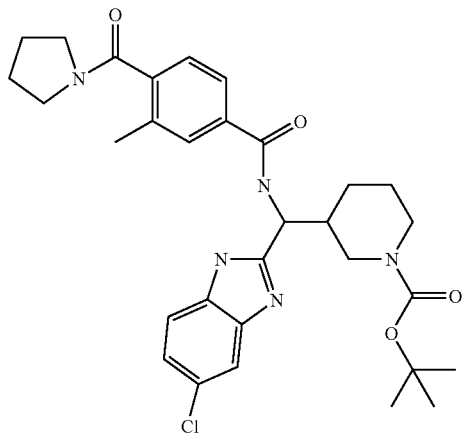

Prepared analogously to Example 1g from 3-methyl-4-(pyrrolidin-1-ylcarbonyl)benzoic acid, TBTU, diisopropylethylamine, and C-(5-chloro-1H-benzimidazol-2-yl)-C-[1-(3-tert-butoxycarbonyl)piperidin-3-yl]methylamine in tetrahydrofuran. Yield: 25%; $R_f$ value: 0.03 (Reversed phase RP8; methanol/5% sodium chloride solution=6:4); $C_{31}H_{38}ClN_5O_4$ (580.13); mass spectrum: $(M+H)^+$=580/582 (chlorine isotope).

Example 170

3-bromo-N-[(1S)-1-(5-chloro-1H-benzimidazol-2-yl)-3-methylsulfinylpropyl]-4-(pyrrolidin 1-ylcarbonyl)benzamide

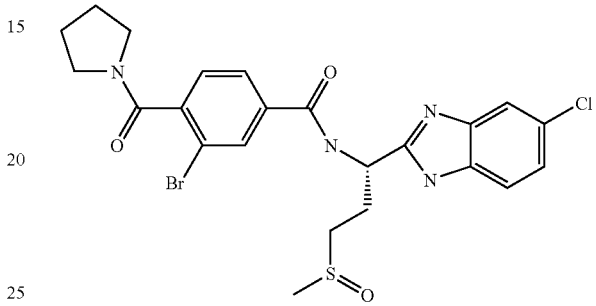

Prepared analogously to Example 85 from 3-bromo-N-[(1S)-1-(5-chloro-1H-benzimidazol-2-yl)-3-methylsulfanylpropyl]-4-(pyrrolidin-1-ylcarbonyl)benzamide, 1 equivalent of 3-chloroperoxybenzoic acid, and glacial acetic acid in dichloromethane. Yield: 81%; $R_f$ value: 0.20 (silica gel; dichloromethane/ethanol=9:1); $C_{23}H_{24}BrClN_4O_3S$ (551.89); mass spectrum: $(M+H)^+$=551/553/555 (chlorine isotope).

Example 171

N-[(5-chloro-1H-benzimidazol-2-yl)-(piperidin-3-yl)methyl]-3-methyl-4-(pyrrolidin-1-ylcarbonyl)benzamide

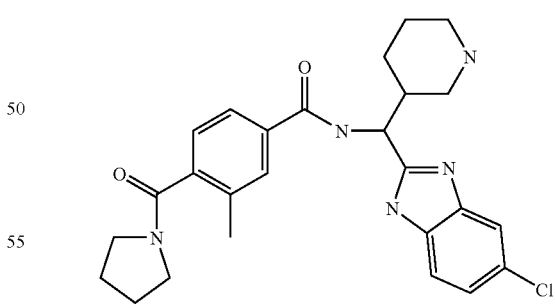

Prepared analogously to Example 17 from N-{[1-(3-tert-butoxycarbonyl)piperidin-3-yl]-(5-chloro-1H-benzimidazol-2-yl)methyl}-3-methyl-4-(pyrrolidin-1-ylcarbonyl)benzamide and trifluoroacetic acid. Yield: 87%; $R_f$ value: 0.10 (silica gel; dichloromethane/ethanol=9:1); $C_{26}H_{30}ClN_5O_2$ (480.01); mass spectrum: $(M+H)^+$=480/482 (chlorine isotope).

Example 172

3-chloro-N-[(1S)-1-(5-chloro-1H-benzimidazol-2-yl)ethyl]-4-[(2R,S)-(2-methylpyrrolidin-1-ylcarbonyl)]benzamide

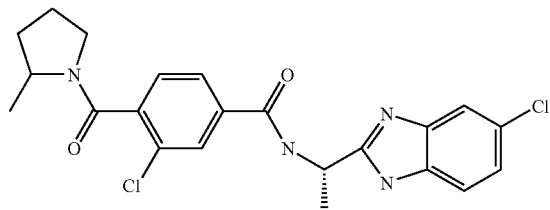

Prepared analogously to Example 1g from (1S)-2-chloro-4-{N-[1-(5-chloro-1H-benzimidazol-2-ylethyl]aminocarbonyl}benzoic acid, TBTU, diisopropylethylamine, and rac.-2-methyl-pyrrolidine in tetrahydrofuran. Yield: 71%; $R_f$ value: 0.48 (silica gel; dichloromethane/ethanol=9:1); $C_{22}H_{22}Cl_2N_4O_2$ (445.35); mass spectrum: $(M+H)^+=445/447/449$ (chlorine isotope) and $(M-H)^-=443/445/447$ (chlorine isotope).

Example 173

3-chloro-N-[(1S)-1-(5-chloro-1H-benzimidazol-2-yl)ethyl]-4-[(2R)-2-(methylsulfonylaminomethyl)pyrrolidin-1-ylcarbonyl]benzamide

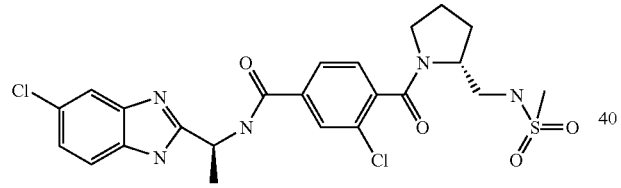

Prepared analogously to Example 125 from 4-((2R)-2-aminomethylpyrrolidin-1-ylcarbonyl)-3-chloro-N-[(1S)-1-(5-chloro-1H-benzimidazol-2-yl)ethyl]benzamide, methanesulfonic acid chloride, and triethylamine in tetrahydrofuran. Yield: 62%; $R_f$ value: 0.31 (silica gel; dichloromethane/ethanol=9:1); $C_{23}H_{25}Cl_2N_5O_4S$ (538.45); mass spectrum: $(M+H)^+=538/549/542$ (chlorine isotope) and $(M-H)^-=536/538/540$ (chlorine isotope).

Example 174

4-[(2R)-2-(acetylaminomethyl)pyrrolidin-1-ylcarbonyl]-3-chloro-N-[(1S)-1-(5-chloro-1H-benzimidazol-2-yl)ethyl]benzamide

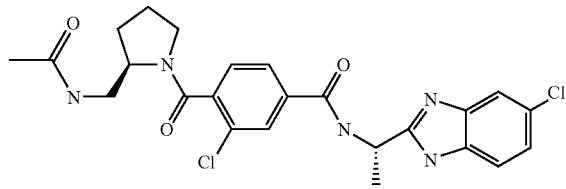

Prepared analogously to Example 124 from 4-((2R)-2-aminomethylpyrrolidin-1-ylcarbonyl)-3-chloro-N-[(1S)-1-(5-chloro-1H-benzimidazol-2-yl)ethyl]benzamide and acetic anhydride in glacial acetic acid. Yield: 78%; $R_f$ value: 0.30 (silica gel; dichloromethane/ethanol=9:1); $C_{24}H_{25}Cl_2N_5O_3$ (502.40); mass spectrum: $(M+H)^+=502/504/506$ (chlorine isotope) and $(M-H)^-=500/502/504$ (chlorine isotope).

Example 175

N-[(1R)-1-(5-chloro-1H-benzimidazol-2-yl)ethyl]-3-methyl-4-(pyrrolidin-1ylcarbonyl)benzamide

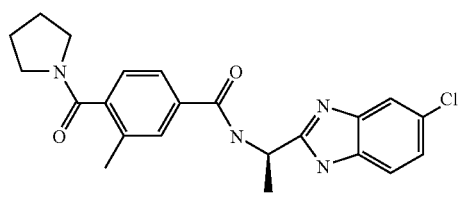

Prepared analogously to Example 1g from 3-methyl-4-(pyrrolidin-1-ylcarbonyl)benzoic acid, TBTU, diisopropylethylamine, and (R)-1-(5-chloro-1H-benzimidazol-2-yl)ethylamine in tetrahydrofuran. Yield: quantitative; $R_f$ value: 0.50 (silica gel; dichloromethane/ethanol=9:1); $C_{22}H_{23}ClN_4O_2$ (410.90); mass spectrum: $(M+H)^+=411/413$ (chlorine isotope) and $(M-H)-=409/411$ (chlorine isotope).

Example 176

(1R)-3-bromo-N-[1-(5-chloro-1H-benzimidazol-2-yl)-2-hydroxyethyl]-4-(2,5-dihydropyrrol-1-ylcarbonyl)benzamide

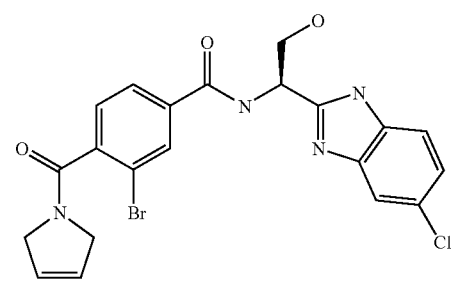

Prepared analogously to Example 1g from 3-bromo-4-(2,5-dihydropyrrol-1-ylcarbonyl)benzoic acid, TBTU, diisopropylethylamine, and (1R)-1-(5-chloro-1H-benzimidazol-2-yl)-2-hydroxyethylamine in tetrahydrofuran. Yield: 84%; $R_f$ value: 0.40 (silica gel; dichloromethane/methanol=95:5); $C_{21}H_{18}BrClN_4O_3$ (489.76); mass spectrum: $(M+H)^+=489/491/493$ (chlorobromine isotope).

Example 177

(1R)-3-methyl-N-[1-(5-chloro-1H-benzimidazol-2-yl)-2-methoxyethyl]-4-(2,5-dihydropyrrol-1-ylcarbonyl)benzamide

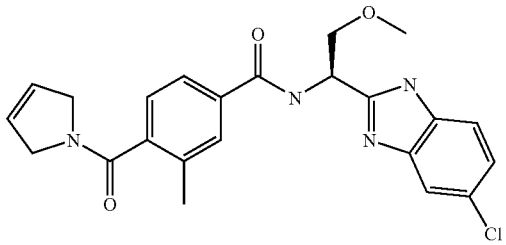

Prepared analogously to Example 1g from 3-methyl-4-(2,5-dihydropyrrol-1-ylcarbonyl)benzoic acid, TBTU, N-methylmorpholine, and (1R)-1-(5-chloro-1H-benzimidazol-2-yl)-2-methoxyethylamine in N,N-dimethylformamide. Yield: 74%; $R_f$ value: 0.38 (silica gel; dichloromethane/methanol=95:5); $C_{23}H_{23}ClN_4O_3$ (438.92); mass spectrum: (M+H)$^+$=439/441 (chlorine isotope).

Example 178

(1R)-3-chloro-N-[1-(5-chloro-1H-benzimidazol-2-yl)-2-hydroxyethyl]4-(2,5-dihydropyrrol 1-ylcarbonyl)benzamide

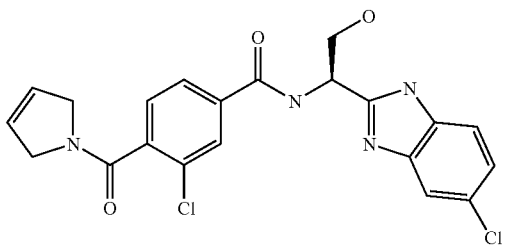

Prepared analogously to Example 1g from 3-chloro-4-(2,5-dihydropyrrol-1-ylcarbonyl)benzoic acid, TBTU, N-methylmorpholine, and (1R)-1-(5-chloro-1H-benzimidazol-2-yl)-2-hydroxyethylamine in N,N-dimethylformamide. Yield: 20%; $R_f$ value: 0.6 (silica gel; dichloromethane/methanol=95:5); $C_{21}H_{18}Cl_2N_4O_3$ (445.31); mass spectrum: (M+H)$^+$=445/447/449 (chlorine isotope) and (M−H)$^-$=443/445/447 (chlorine isotope).

Example 179 rac.-N-[1-(5-chloro-1H-imidazo[4,5-b]pyridin-2-yl)ethyl]-3-methyl-4-(pyrrolidin-1-ylcarbonyl)benzamide

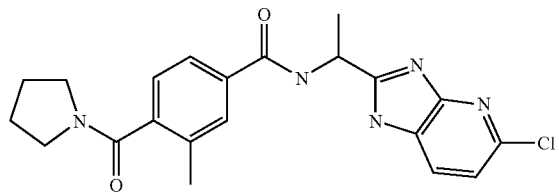

Prepared analogously to Example 1g from 3-methyl-4-(pyrrolidin-1-ylcarbonyl)benzoic acid, TBTU, diisopropylethylamine, and 1-(5-chloro-1H-imidazo[4,5-b]pyridin-2-yl)ethylamine in dimethylformamide. Yield: 42%; $R_f$ value: 0.45 (silica gel; dichloromethane/ethanol=9:1); $C_{21}H_{22}ClN_5O_2$ (411.89); mass spectrum: (M+H)$^+$=410/412 (chlorine isotope).

Example 180 rac.-N-[1-(5-chloro-1-methyl-1H-benzimidazol-2-yl)ethyl]-3-methyl-4-(pyrrolidin-1-ylcarbonyl)benzamide

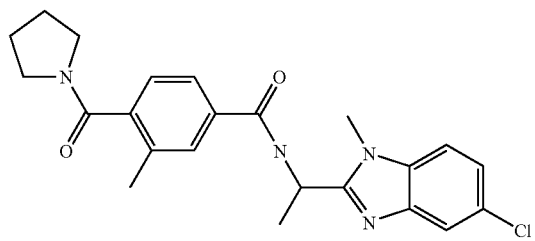

Prepared analogously to Example 1g from 3-methyl-4-(pyrrolidin-1-ylcarbonyl)benzoic acid, TBTU, diisopropylethylamine, and rac.-1-(5-chloro-1-methyl-1H-benzimidazol-2-yl)ethylamine in dimethylformamide. Yield: 71%; $R_f$ value: 0.47 (silica gel; dichloromethane/ethanol=9:1); $C_{23}H_{25}ClN_4O_2$ (424.93); mass spectrum: (M+H)$^+$=425/427 (chlorine isotope) and (M−H)$^-$=423/425 (chlorine isotope).

Example 181 rac.-N-[1-(6-chloro-1-methyl-1H-benzimidazol-2-yl)ethyl]-3-methyl-4-(pyrrolidin-1

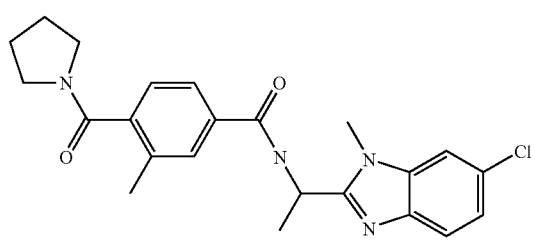

Prepared analogously to Example 1g from 3-methyl-4-(pyrrolidin-1-ylcarbonyl)benzoic acid, TBTU, diisopropylethylamine, and rac.-1-(6-chloro-1-methyl-1H-benzimidazol-2-yl)ethylamine in dimethylformamide. Yield: 69%; $R_f$ value: 0.47 (silica gel; dichloromethane/ethanol=9:1); $C_{23}H_{25}ClN_4O_2$ (424.93); mass spectrum: (M+H)$^+$=425/427 (chlorine isotope) and (M−H)$^-$=423/425 (chlorine isotope).

Example 182 rac.-N-{1-[6-chloro-1-(methoxycarbonylmethyl)-1H-benzimidazol-2-yl]-2-(4-hydroxyphenyl)ethyl}-3-methyl-4-(pyrrolidin-1-ylcarbonyl)benzamide

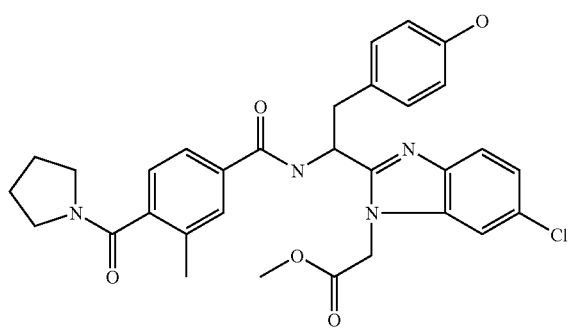

Prepared analogously to Example 6b from N-[1-(6-chloro-1H-benzimidazol-2-yl)-2-(4-hydroxyphenyl)ethyl]-3-methyl-4-(pyrrolidin-1-ylcarbonyl)benzamide, methyl bromoacetate, and potassium carbonate in dimethylformamide. Yield: 30%; $R_f$ value: 0.33 (silica gel; dichloromethane/ethanol=19:1); $C_{31}H_{31}ClN_4O_5$ (575.06); mass spectrum: $(M+H)^+$=575/577 (chlorine isotope) and $(M-H)^-$=573/575 (chlorine isotope).

Example 183 rac.-N-{1-[6-chloro-1-(methoxycarbonylmethyl)-1H-benzimidazol-2-yl]-2-(4-methoxy-carbonyl-methoxyphenyl)ethyl}-3-methyl-4-(pyrrolidin-1-ylcarbonyl)benzamide

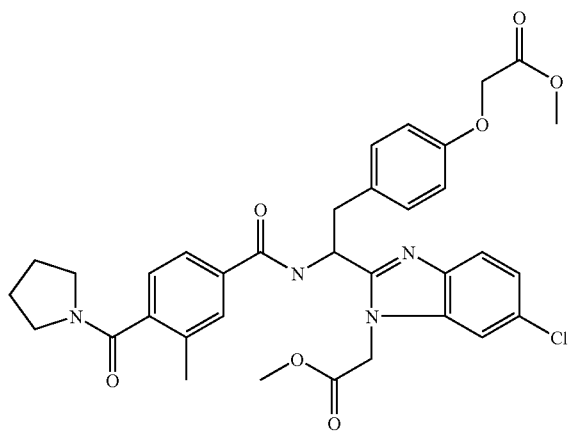

Prepared analogously to Example 6b from N-[1-(6-chloro-1H-benzimidazol-2-yl)-2-(4-hydroxyphenyl)ethyl]-3-methyl-4-(pyrrolidin-1-ylcarbonyl)benzamide, methyl bromoacetate, and potassium carbonate in dimethylformamide. Yield: 17%; $R_f$ value: 0.65 (silica gel; dichloromethane/ethanol=19:1); $C_{34}H_{35}ClN_4O_7$ (647.13); mass spectrum: $(M+H)^+$=647/649 (chlorine isotope).

Example 184 rac.-N-{1-[6-chloro-1-(hydroxycarbonylmethyl)-1H-benzimidazol-2-yl]-2-(4-hydroxyphenyl)ethyl}-3-methyl-4-(pyrrolidin-1-ylcarbonyl)benzamide

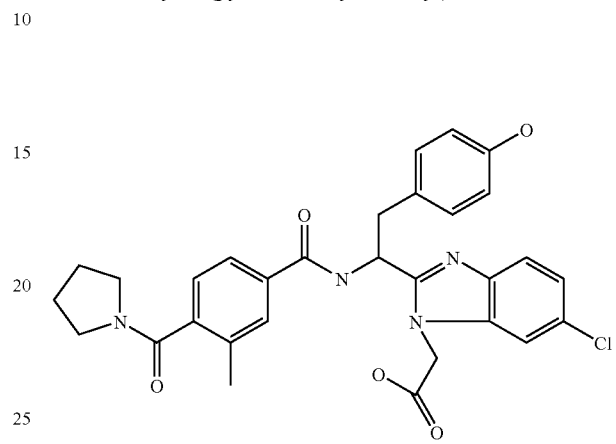

Prepared analogously to Example 19b from rac.-N-{1-[6-chloro-1-(methoxycarbonylmethyl)-1H-benzimidazol-2-yl]-2-(4-hydroxyphenyl)ethyl}-3-methyl-4-(pyrrolidin-1-ylcarbonyl)benzamide and sodium hydroxide solution in methanol. Yield: 79%; $R_f$ value: 0.18 (silica gel; dichloromethane/ethanol/ammonia=9:1:0.1); $C_{30}H_{29}ClN_4O_5$ (561.04); mass spectrum: $(M+H)^+$=561/563 (chlorine isotope).

Example 185

N-[(1S)-1-(7-amino-5-chloro-1H-benzimidazol-2-yl)ethyl]-3-methyl-4-(pyrrolidin-1-ylcarbonyl)benzamide

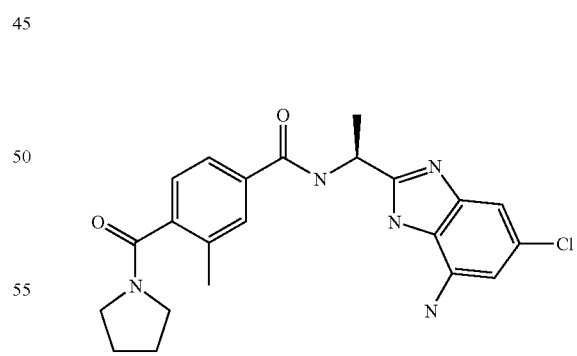

Prepared analogously to Example 1g from 3-methyl-4-(pyrrolidin-1-ylcarbonyl)benzoic acid, TBTU, diisopropylethylamine, and (1S)-1-(7-amino-5-chloro-1H-benzimidazol-2-yl)ethylamine in dimethylformamide. Yield: 22%; $R_f$ value: 0.45 (silica gel; dichloromethane/ethanol/ammonia=9:1:0.1); $C_{22}H_{24}ClN_5O_2$ (425.92); mass spectrum: $(M+H)^+$=426/428 (chlorine isotope).

Example 186

3-methyl-N-[(1S)-1-(5-nitro-1H-benzimidazol-2-yl)ethyl]-4-(pyrrolidin 1-ylcarbonyl)benzamide

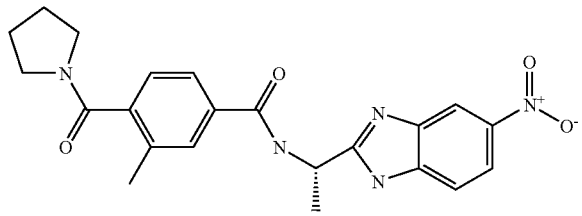

Prepared analogously to Example 1g from 3-methyl-4-(pyrrolidin-1-ylcarbonyl)benzoic acid, TBTU, diisopropylethylamine, and (1S)-1-(5-nitro-1H-benzimidazol-2-yl)ethylamine in dimethylformamide. Yield: 87%; $R_f$ value: 0.40 (silica gel; dichloromethane/ethanol=9:1); $C_{22}H_{23}N_5O_4$ (421.46); mass spectrum: $(M+H)^+=422$ and $(M-H)^-=420$

Example 187

3-methyl-N-[(1S)-1-(5-amino-1H-benzimidazol-2-yl)ethyl]-4-(pyrrolidin-1-ylcarbonyl)benzamide

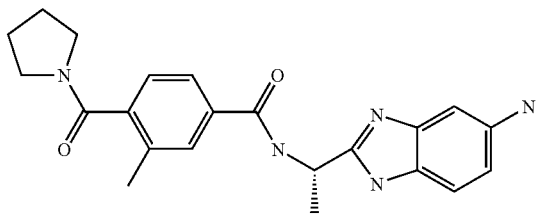

40 mg of 3-methyl-N-[(1S)-1-(5-nitro-1H-benzimidazol-2-yl)ethyl]-4-(pyrrolidin-1-ylcarbonyl)benzamide if dissolved in 40 mL of methanol, combined with 10 mg of palladium on activated charcoal (10%), and hydrogenated for 3 hours with hydrogen (3 bar). Then the catalyst is filtered off and the solvent is distilled off. Yield: 83%; $R_f$ value: 0.50 (silica gel; dichloromethane/ethanol=4:1); $C_{22}H_{25}N_5O_2$ (391.47); mass spectrum: $(M+H)^+=392$ and $(M-H)^-=390$

Example 188

3-chloro-N-[(1S)-1-(6-chloro-1H-benzimidazol-2-yl)ethyl]4-(pyrrolidin 1-ylsulfonyl)benzamide

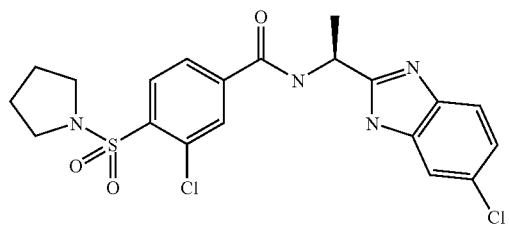

(a) 3-chloro-4-(pyrrolidin-1-ylsulfonyl)benzonitrile 900 mg (4 mmol) of 2-chloro-4-cyanobenzenesulfonic acid chloride is dissolved in 3 mL of pyridine and, after the addition of 0.5 mL (5.8 mmol) of pyrrolidine, stirred for one hour at 80° C. Then the mixture is cooled, mixed with ice, and adjusted to pH 5-6 with 1 molar hydrochloric acid. The precipitate formed is suction filtered, washed with water and dried. Yield: 1.1 g (100% of theory); $R_f$ value: 0.20 (silica gel; petroleum ether/ethyl acetate=4:1).

(b) 3-chloro-4-(pyrrolidin-1-ylsulfonyl)benzoic acid

Prepared analogously to Example 1f from 3-chloro-4-(pyrrolidin-1-ylsulfonyl)benzonitrile and sodium hydroxide solution in ethanol. Yield: 89% of theory; $C_{11}H_{21}ClNO_4S$ (289.74); mass spectrum: $(M+H)^+=290/292$ (chlorine isotope).

(c) 3-chloro-N-[(1S)-1-(6-chloro-1H-benzimidazol-2-yl)ethyl]-4-(pyrrolidin-1-ylsulfonyl)benzamide Prepared analogously to Example 1g from 3-chloro-4-(pyrrolidin-1-ylsulfonyl)benzoic acid, TBTU, diisopropylethylamine, and (1S)-1-(6-chloro-1H-benzimidazol-2-yl)ethylamine in dimethylformamide. Yield: 50%; $R_f$ value: 0.57 (silica gel; ethyl acetate); $C_{20}H_{20}Cl_2N_4O_3S$ (467.38); mass spectrum: $(M+H)^+=467/469/471$ (chlorine isotope).

Example 189

N-[(1-acetylpiperidin-3-yl)-(5-chloro-1H-benzimidazol-2-yl)methyl]-3-methyl-4-(pyrrolidin-1-ylcarbonyl)benzamide

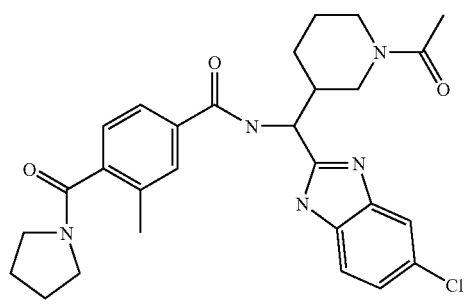

90 mg (0.16 mmol) of rac.-N-[(5-chloro-1H-benzimidazol-2-yl)-(piperidin-3-yl)methyl]-3-methyl-4-(pyrrolidin-1-ylcarbonyl)benzamide is dissolved in 3 mL of tetrahydrofuran and, after the addition of 8.4 mg (0.17 mmol) of sodium hydride (50% solution in oil), stirred for one hour at 40° C. Then the mixture is cooled to ambient temperature and stirred for a further 16 hours with 11.4 μL (0.16 mmol) of acetyl chloride. Then water is added and the mixture is extracted with dichloromethane. The combined organic extracts are dried over sodium sulfate and concentrated by evaporation. The residue is chromatographed on silica gel, eluting with dichloromethane/ethanol (100:0 and 90:10).

The 4 possible stereoisomers were separated into one pair of enantiomers with a high $R_f$ value (Example 189) and one pair of enantiomers with a low $R_f$ value (Example 190). Yield: 30 mg (36% of theory); $R_f$ value: 0.37 (silica gel; dichloromethane/ethanol=9:1); $C_{28}H_{32}ClN_5O_3$ (522.05); mass spectrum: $(M+H)^+=522/524$ (chlorine isotope).

Example 190

N-[(1-acetylpiperidin-3-yl)-(5-chloro-1H-benzimidazol-2-yl)methyl]-3-methyl-4-(pyrrolidin-1-ylcarbonyl)benzamide

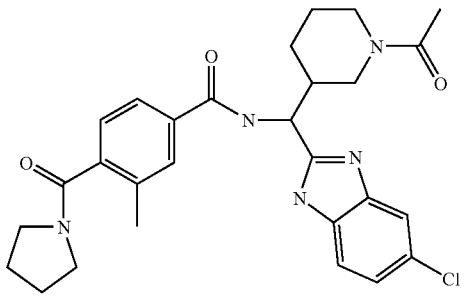

Yield: 12%; $R_f$ value: 0.29 (silica gel; dichloromethane/ethanol=9:1); $C_{28}H_{32}ClN_5O_3$ (522.05); mass spectrum: $(M+H)^+=522/524$ (chlorine isotope).

Example 191

N-[(1S)-1-(5-chloro-1H-benzimidazol-2-yl)-3-(pyridin-4-yl)propyl]-3-methyl-4-(pyrrolidin 1-ylcarbonyl)benzamide

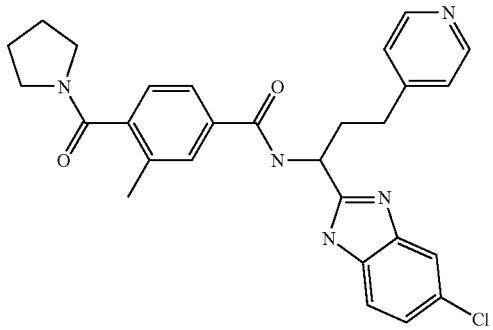

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-3-(pyridin-4-yl)propylamine in dimethylformamide. Yield: 34%; $R_f$ value: 0.25 (silica gel; dichloromethane/ethanol=9:1); $C_{28}H_{28}ClN_5O_2$ (502.02); mass spectrum: $(M+H)^+=502/504$ (chlorine isotope).

Example 192

N-[(1S)-3-(benzyloxycarbonylamino)-1-(5-chloro-1H-benzimidazol-2-yl)propyl]-3-methyl-4-(2,5-dihydropyrrol-1-ylcarbonyl)benzamide

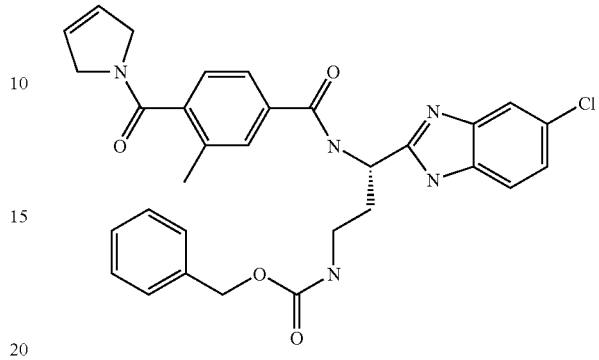

Prepared analogously to Example 1g from 3-methyl-4-(2,5-dihydropyrrol-1-ylcarbonyl)benzoic acid, TBTU, diisopropylethylamine and (1S)-3-(benzyloxycarbonylamino)-1-(5-chloro-1H-benzimidazol-2-yl)propylamine in dimethylformamide. Yield: 100%; $R_f$ value: 0.50 (silica gel; dichloromethane/ethanol=9:1); $C_{31}H_{30}ClN_5O_4$ (572.06); mass spectrum: $(M+H)^+=572/574$ (chlorine isotope).

Example 193

N-{(1S)-1-(5-chloro-1H-benzimidazol-2-yl)-3-[(3R,S)-3-dimethylaminopyrrolidin-1-yl]-carbonylpropyl}-3-methyl-4-(pyrrolidin-1-ylcarbonyl)benzamide

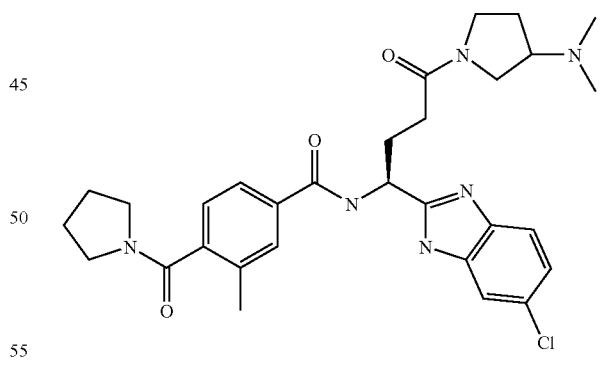

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin 1-ylcarbonyl)benzamide, TBTU, diisopropylethylamine, rac.-3-dimethylaminopyrrolidine in acetonitrile, and subsequent reaction with trifluoroacetic acid analogously to Example 17. Yield: 72%; $R_f$ value: 0.05 (silica gel; ethyl acetate/ethanol/triethylamine=70:27:3); $C_{30}H_{37}ClN_6O_3$ (565.11); mass spectrum: $(M+H)^+=565/567$ (chlorine isotope).

Example 194

N-{(1S)-1-(5-chloro-1H-benzimidazol-2-yl)-3-[(3R)-3-hydroxypyrrolidin-1-yl]-carbonylpropyl}-3-methyl-4-(pyrrolidin-1-ylcarbonyl)benzamide

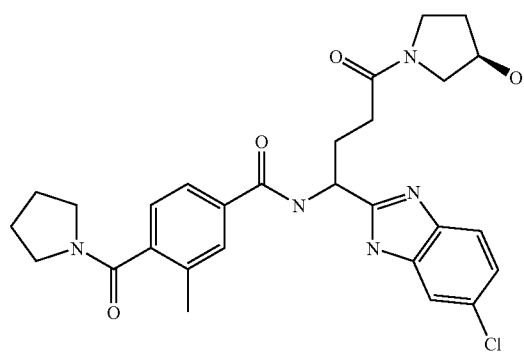

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin-1-ylcarbonyl)benzamide, TBTU, diisopropylethylamine, (R)pyrrolidine-3-ol in acetonitrile, and subsequent reaction with trifluoroacetic acid analogously to Example 17. Yield: 90%; $R_f$ value: 0.18 (silica gel; ethyl acetate/ethanol=85:15); $C_{28}H_{32}ClN_5O_4$ (538.05); mass spectrum: $(M+H)^+=538/540$ (chlorine isotope).

Example 195

N-{(1S)-1-(5-chloro-1H-benzimidazol-2-yl)-3-[(3S)-3-hydroxypyrrolidin-1-ylcarbonyl]propyl}-3-methyl-4-(pyrrolidin-1-ylcarbonyl)benzamide

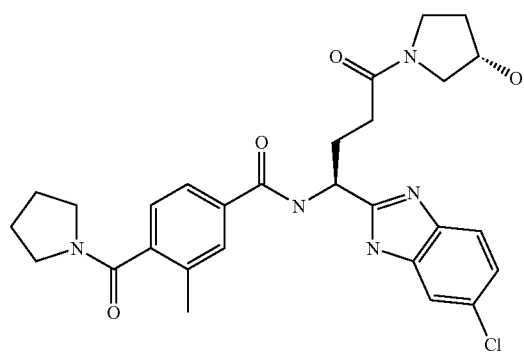

Prepared analogously to Example 1g from (S)—N-[1-(1-tert-butoxycarbonyl-5-chloro-1H-benzimidazol-2-yl)-3-hydroxycarbonylpropyl]-3-methyl-4-(pyrrolidin-1-ylcarbonyl)benzamide, TBTU, diisopropylethylamine, (S)pyrrolidine-3-ol in acetonitrile, and subsequent reaction with trifluoroacetic acid analogously to Example 17. Yield: 87%; $R_f$ value: 0.18 (silica gel; ethyl acetate/ethanol=85:15); $C_{28}H_{32}ClN_5O_4$ (538.05); mass spectrum: $(M+H)^+=538/540$ (chlorine isotope).

Example 196

N-{(1S)-1-(5-chloro-1H-benzimidazol-2-yl)-3-[(2R)-2-hydroxymethylpyrrolidin-1-ylcarbonyl]propyl}-3-methyl-4-(pyrrolidin-1-ylcarbonyl)benzamide

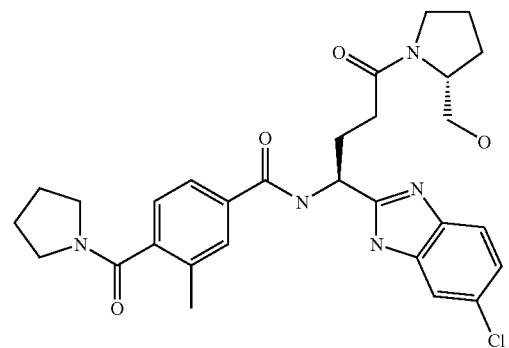

Prepared analogously to Example 1g from (1S)—N-[1-(1-tert-butoxycarbonyl-5-chloro-1H-benzimidazol-2-yl)-3-hydroxycarbonylpropyl]-3-methyl-4-(pyrrolidin 1-ylcarbonyl)benzamide, TB TU, diisopropylethyl amine, (R)-prolinol in acetonitrile, and subsequent reaction with trifluoroacetic acid analogously to Example 17. Yield: 67%; $R_f$ value: 0.30 (silica gel; ethyl acetate/ethanol=85:15); $C_{29}H_{34}ClN_5O_4$ (552.07); mass spectrum: $(M+H)^+=552/554$ (chlorine isotope).

Example 197

N-{(1S)-1-(5-chloro-1H-benzimidazol-2-yl)-3-[(2S)-2-hydroxymethylpyrrolidin-1-ylcarbonyl]propyl}-3-methyl-4-(pyrrolidin-1-ylcarbonyl)benzamide

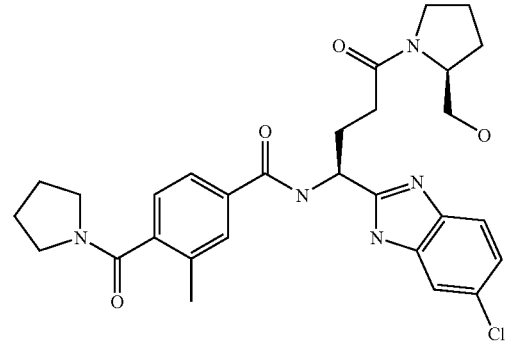

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin-1-ylcarbonyl)benzamide, TBTU, diisopropylethylamine, (S)-prolinol in acetonitrile, and subsequent reaction with trifluoroacetic acid analogously to Example 17. Yield: 60%; $R_f$ value: 0.25 (silica gel; ethyl acetate/ethanol=85:15); $C_{29}H_{34}ClN_5O_4$ (552.07); mass spectrum: $(M+H)^+=552/554$ (chlorine isotope).

Example 198

N-[(1S)-1-(5-chloro-1H-benzimidazol-2-yl)-3-(2-methyl-2,6-diazaspiro[3.4]oct-6-ylcarbonyl)propyl]-3-methyl-4-(pyrrolidin-1-ylcarbonyl)benzamide

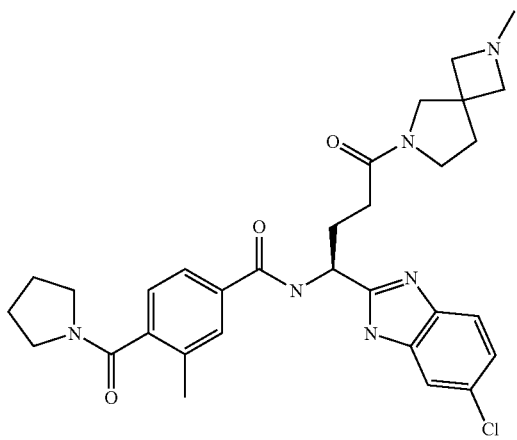

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin-1-ylcarbonyl)benzamide, TBTU, diisopropylethylamine, 2-methyl-2,6-diazaspiro[3.4]octane in acetonitrile, and subsequent reaction with trifluoroacetic acid analogously to Example 17. Yield: 67%; $R_f$ value: 0.05 (silica gel; ethyl acetate/ethanol/triethylamine=70:27:3); $C_{31}H_{37}ClN_6O_3$ (577.13); mass spectrum: $(M+H)^+$=577/579 (chlorine isotope).

Example 199

N-{(1S)-3-[(1S)-2-(aminocarbonyl)pyrrolidin-1-ylcarbonyl]-1-(5-chloro-1H-benzimidazol-2-yl)propyl}-3-methyl-4-(pyrrolidin-1-ylcarbonyl)benzamide

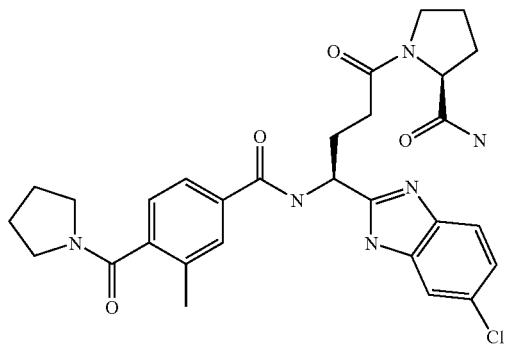

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin-1-ylcarbonyl)benzamide, TBTU, diisopropylethylamine, (S)-prolinamide in acetonitrile, and subsequent reaction with trifluoroacetic acid analogously to Example 17. Yield: 74%; $R_f$ value: 0.13 (silica gel; ethyl acetate/ethanol=7:3); $C_{29}H_{33}ClN_6O_4$ (565.07); mass spectrum: $(M+H)^+$=565/567 (chlorine isotope).

Example 200

N-{(1S)-3-[(1R)-2-(aminocarbonyl)pyrrolidin-1-ylcarbonyl]-1-(5-chloro-1H-benzimidazol-2-yl)propyl}-3-methyl-4-(pyrrolidin-1-ylcarbonyl)benzamide

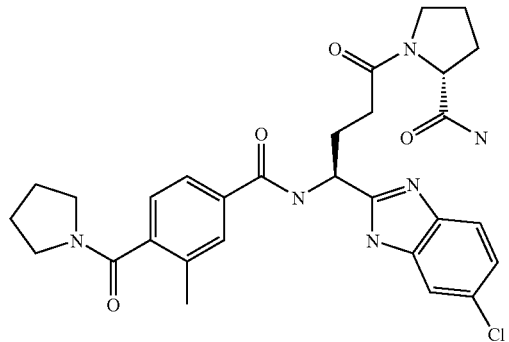

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin-1-ylcarbonyl)benzamide, TBTU, diisopropylethylamine, (R)-prolinamide in acetonitrile, and subsequent reaction with trifluoroacetic acid analogously to Example 17. Yield: 34%; $R_f$ value: 0.17 (silica gel; ethyl acetate/ethanol=7:3); $C_{29}H_{33}ClN_6O_4$ (565.07); mass spectrum: $(M+H)^+$=565/567 (chlorine isotope).

Example 201

N-{(1S)-1-(5-chloro-1H-benzimidazol-2-yl)-3-[(2S)-2-tert-butoxycarbonylaminomethylpyrrolidin-1-ylcarbonyl]propyl}-3-methyl-4-(pyrrolidin-1-ylcarbonyl)benzamide

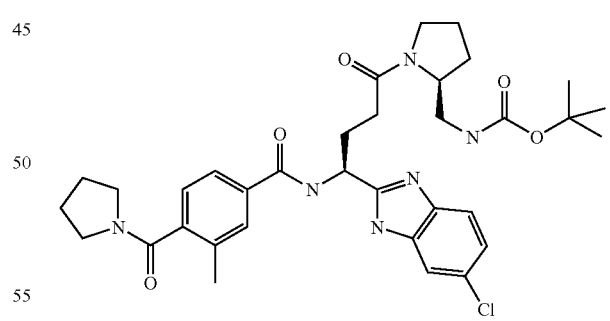

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin 1-ylcarbonyl)benzamide, TBTU, diisopropylethylamine, (S)-2-tert-butoxycarbonylaminomethylpyrrolidine in acetonitrile, and subsequent reaction with trifluoroacetic acid analogously to Example 17. Yield: 44%; $R_f$ value: 0.59 (silica gel; ethyl acetate/ethanol=7:3); $C_{34}H_{43}ClN_6O_5$ (651.20); mass spectrum: $(M+H)^+$=651/653 (chlorine isotope).

Example 202

N-{(1S)-1-(5-chloro-1H-benzimidazol-2-yl)-3-[(2R)-2-tert-butoxycarbonylaminomethylpyrrolidin-1-ylcarbonyl]propyl}-3-methyl-4-(pyrrolidin-1-ylcarbonyl)benzamide

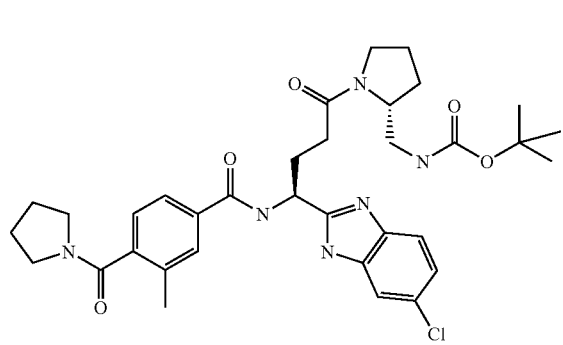

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin 1-ylcarbonyl)benzamide, TBTU, diisopropylethylamine, (R)-2-tert-butoxycarbonylaminomethylpyrrolidine in acetonitrile, and subsequent reaction with trifluoroacetic acid analogously to Example 17. Yield: 51%; $R_f$ value: 0.59 (silica gel; ethyl acetate/ethanol=7:3); $C_{34}H_{43}ClN_6O_5$ (651.20); mass spectrum: $(M+H)^+=651/653$ (chlorine isotope).

Example 203

N-{(1S)-1-(5-chloro-1H-benzimidazol-2-yl)-3-[(3R,S)-hydroxymethylpyrrolidin-1-yl)carbonyl]propyl}-3-methyl-4-(pyrrolidin-1-ylcarbonyl)benzamide

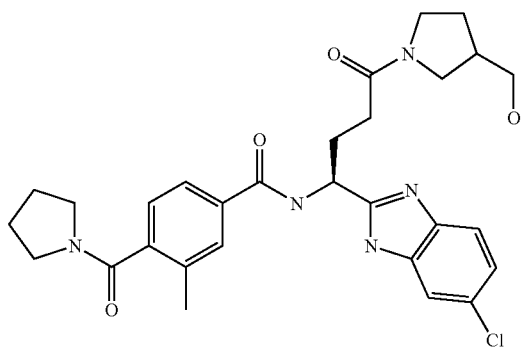

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin-1-ylcarbonyl)benzamide, TBTU, diisopropylethylamine, 3-hydroxymethylpyrrolidine in acetonitrile, and subsequent reaction with trifluoroacetic acid analogously to Example 17. Yield: 72%; $R_f$ value: 0.18 (silica gel; ethyl acetate/ethanol=7:3); $C_{29}H_{34}ClN_5O_4$ (552.07); mass spectrum: $(M+H)^+=552/554$ (chlorine isotope).

Example 204

N-[(1S)-1-(5-chloro-1H-benzimidazol-2-yl)-3-(1,1-dioxo-1-thiomorpholine-4-ylcarbonyl]propyl]-3-methyl-4-(pyrrolidin-1-ylcarbonyl)benzamide

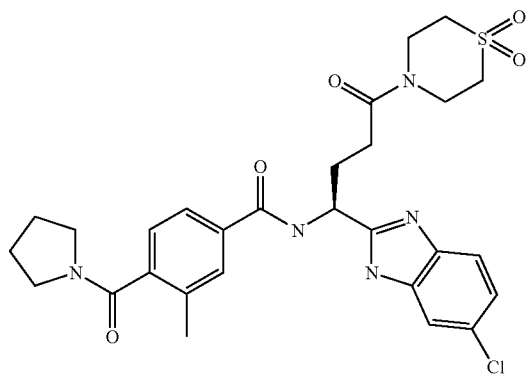

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin-1-ylcarbonyl)benzamide, TBTU, diisopropylethylamine, thiomorpholine-1,1-dioxide in acetonitrile, and subsequent reaction with trifluoroacetic acid analogously to Example 17. Yield: 69%; $R_f$ value: 0.50 (silica gel; ethyl acetate/ethanol=7:3); $C_{28}H_{32}ClN_5O_5S$ (586.11); mass spectrum: $(M+H)^+=586/588$ (chlorine isotope).

Example 205

N-[(1S)-1-(5-chloro-1H-benzimidazol-2-yl)-3-[(4-methyl-3-oxopiperazin-1ylcarbonyl)propyl]-3-methyl-4-(pyrrolidin-1-ylcarbonyl)benzamide

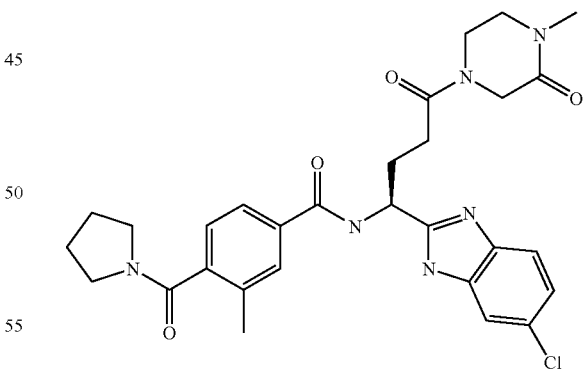

Prepared analogously to Example 1g from N-[1-(1-tert-butoxycarbonyl-5-chloro-1H-benzimidazol-2-yl)-3-hydroxycarbonylpropyl]-3-methyl-4-(pyrrolidin-1-ylcarbonyl)benzamide, TBTU, diisopropylethylamine, 1-methylpiperazin-2-one in acetonitrile, and subsequent reaction with trifluoroacetic acid analogously to Example 17. Yield: 75%; $R_f$ value: 0.18 (silica gel; ethyl acetate/ethanol=7:3); $C_{29}H_{33}ClN_6O_4$ (565.07); mass spectrum: $(M+H)^+=565/567$ (chlorine isotope).

Example 206 rac.-N-[(5-chloro-1H-benzimidazol-2-yl)-(4-chlorophenyl)methyl]-3-methyl-4-(pyrrolidin-1-ylcarbonyl)benzamide

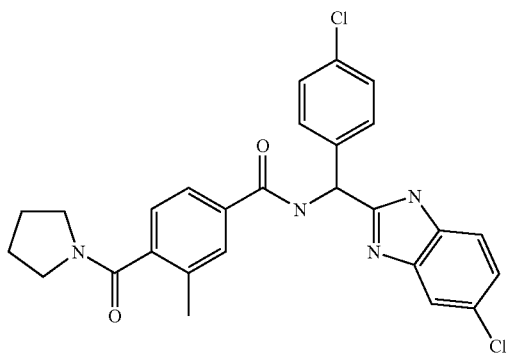

Prepared analogously to Example 1g from 3-methyl-4-(pyrrolidin-1-ylcarbonyl)benzoic acid, TBTU, diisopropylethylamine, and C-(5-chloro-1H-benzimidazol-2-yl)-C-(4-chlorophenyl)methylamine in dimethylformamide. Yield: 50%; $R_f$ value: 0.20 (silica gel; dichloromethane/methanol=95:5); $C_{27}H_{24}Cl_2N_4O_2$ (507.42); mass spectrum: $(M+H)^+$=507/509/511 (chlorine isotope) and $(M-H)^-$=505/507/509 (chlorine isotope).

Example 207 rac.-N-[(5-chloro-1H-benzimidazol-2-yl)-(2-chlorophenyl)methyl]-3-methyl-4-(pyrrolidin-1-ylcarbonyl)benzamide

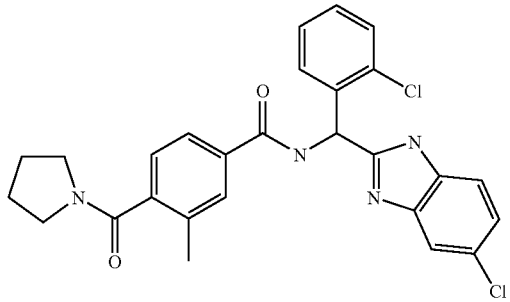

Prepared analogously to Example 1g from 3-methyl-4-(pyrrolidin-1-ylcarbonyl)benzoic acid, TBTU, diisopropylethylamine, and C-(5-chloro-1H-benzimidazol-2-yl)-C-(2-chlorophenyl)methylamine in dimethylformamide. Yield: 63%; $R_f$ value: 0.?? (silica gel; dichloromethane/methanol=95:5); $C_{27}H_{24}Cl_2N_4O_2$ (507.42); mass spectrum: $(M-H)^-$=505/507/509 (chlorine isotope).

Example 208

N-[(1R)-1-(5-chloro-1H-benzimidazol-2-yl)-2-methoxyethyl]-3-methyl-4-(pyrrolidin-1-ylcarbonyl)benzamide

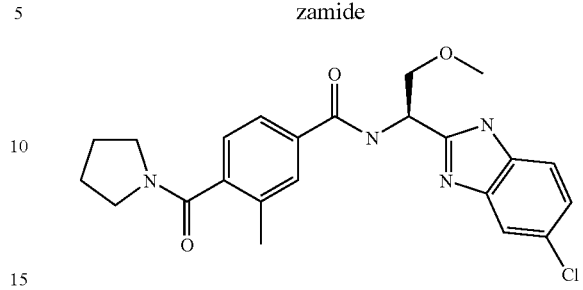

Prepared analogously to Example 1g from 3-methyl-4-(pyrrolidin-1-ylcarbonyl)benzoic acid, TBTU, diisopropylethylamine, and (1R)-1-(5-chloro-1H-benzimidazol-2-yl)-2-methoxyethylamine in dimethylformamide. Yield: 95%; $R_f$ value: 0.49 (silica gel; dichloromethane/methanol=95:5); $C_{23}H_{25}ClN_4O_3$ (440.93); mass spectrum: $(M+H)^+$=441/443 (chlorine isotope).

Example 209

3-chloro-N-[(1R)-1-(5-chloro-1H-benzimidazol-2-yl)-2-methoxyethyl]-4-(2,5-dihydropyrrol-1-ylcarbonyl)benzamide

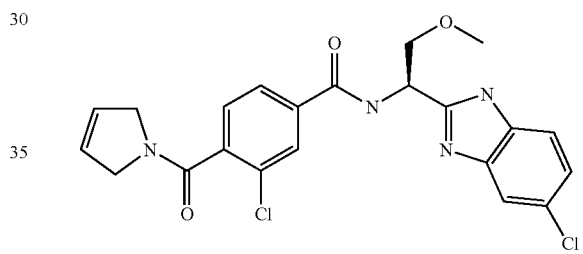

Prepared analogously to Example 1g from 3-chloro-4-(2,5-dihydropyrrol-1-ylcarbonyl)benzoic acid, TBTU, diisopropylethylamine, and (1R)-1-(5-chloro-1H-benzimidazol-2-yl)-2-methoxyethyl amine in dimethylformamide. Yield: 87%; $R_f$ value: 0.59 (silica gel; dichloromethane/methanol=95:5); $C_{22}H_{20}Cl_2N_4O_3$ (459.33); mass spectrum: $(M+H)^+$=459/461/463 (chlorine isotope) and $(M-H)^-$=457/459/461 (chlorine isotope).

Example 210

3-bromo-N-[(1R)-1-(5-chloro-1H-benzimidazol-2-yl)-2-methoxyethyl]-4-(pyrrolidin-1-ylcarbonyl)benzamide

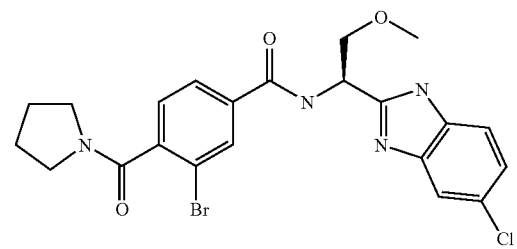

Prepared analogously to Example 1g from 3-bromo-4-(pyrrolidin-1-ylcarbonyl)benzoic acid, TBTU, diisopropylethylamine, and (1R)-1-(5-chloro-1H-benzimidazol-2-yl)-2-methoxyethylamine in dimethylformamide. Yield: 85%; $R_f$ value: 0.60 (silica gel; dichloromethane/methanol=95:5); $C_{22}H_{22}BrClN_4O_3$ (505.80); mass spectrum: $(M+H)^+=503/505/507$ (bromo-chlorine isotope).

Example 211

4-{(2R)-2-[2-(tert-butoxycarbonylamino)ethyl]pyrrolidin-1-ylcarbonyl}-3-chloro-N-[(1S)-1-(5-chloro-1H-benzimidazol-2-yl)ethyl]benzamide

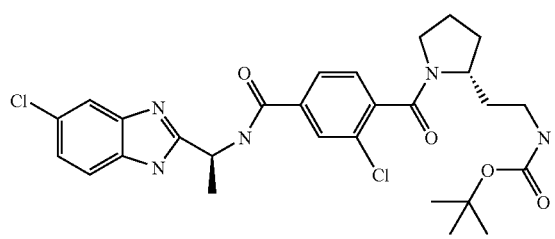

Prepared analogously to Example 1g from (1S)-2-chloro-4-{N-[1-(5-chloro-1H-benzimidazol-2-ylethyl]aminocarbonyl}benzoic acid, TBTU, diisopropylethylamine, and (R)-2-[2-(tert-butoxycarbonylamino)ethyl]pyrrolidine in tetrahydrofuran. Yield: 63%; $R_f$ value: 0.36 (silica gel; dichloromethane/ethanol=9:1); $C_{28}H_{33}Cl_2N_5O_4$ (574.51); mass spectrum: $(M+H)^+=574/576/578$ (chlorine isotope).

Example 212

3-chloro-N-[(1S)-1-(5-chloro-1H-benzimidazol-2-yl)ethyl]-4-[2-(2-ethoxycarbonylethyl)pyrrolidin-1-ylcarbonyl]benzamide

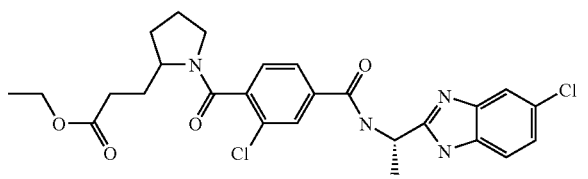

Prepared analogously to Example 1g from (1S)-2-chloro-4-{N-[1-(5-chloro-1H-benzimidazol-2-ylethyl]aminocarbonyl}benzoic acid, TBTU, diisopropylethylamine, and 2-(2-ethoxycarbonylethyl)pyrrolidine in tetrahydrofuran. Yield: 66%; $R_f$ value: 0.43 (silica gel; dichloromethane/ethanol=9:1); $C_{26}H_{28}Cl_2N_4O_4$ (531.44); mass spectrum: $(M+H)^+=531/533/535$ (chlorine isotope).

Example 213

3-chloro-N-[(1S)-1-(5-chloro-1H-benzimidazol-2-yl)ethyl]-4-{(2R)-2-[(3-ethyl-ureido)methyl]pyrrolidin-1-ylcarbonyl}benzamide

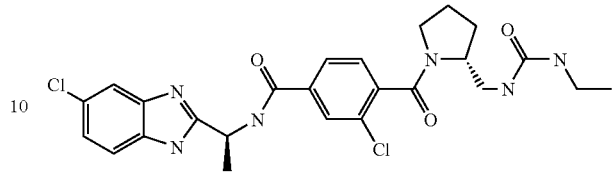

200 mg (0.3 mmol) of 4-[(2R)-2-aminomethylpyrrolidin-1-ylcarbonyl]-3-chloro-N-[(1S)-1-(5-chloro-1H-benzimidazol-2-yl)ethyl]benzamide, 26 mg (0.36 mmol) of ethyl isocyanate, and 0.2 mL (1.2 mmol) of triethylamine are stirred for 16 hours at ambient temperature in 20 mL of tetrahydrofuran. Then the solvent is distilled off and the residue is chromatographed on silica gel, eluting with dichloromethane/ethanol (9:1). Yield: 140 mg (86%); $R_f$ value: 0.38 (silica gel; dichloromethane/ethanol=9:1); $C_{25}H_{28}Cl_2N_6O_3$ (531.44); mass spectrum: $(M+H)^+=531/533$ (chlorine isotope) and $(M-H)^-=529/531$ (chlorine isotope).

Example 214

4-[(2R)-2-(2-aminoethyl)pyrrolidin-1-ylcarbonyl]-3-chloro-N-[(1S)-1-(5-chloro-1H-benzimidazol-2-yl)ethyl]benzamide

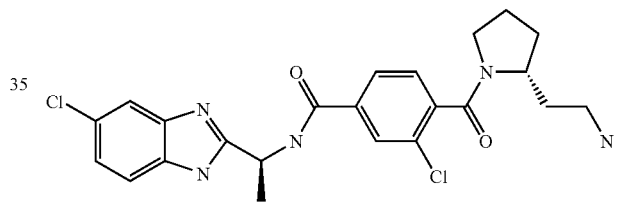

Prepared analogously to Example 17 from 4-[(2R)-2-(tert-butoxycarbonylamino)ethylpyrrolidin-1-ylcarbonyl]-3-chloro-N-[(1S)-1-(5-chloro-1H-benzimidazol-2-yl)ethyl]benzamide and trifluoroacetic acid. Yield: quantitative; $R_f$ value: 0.18 (silica gel; dichloromethane/methanol/ammonia=9:1:0.1); $C_{23}H_{25}Cl_2N_5O_2$ (474.39); mass spectrum: $(M+H)^+=474/476$ (chlorine isotope) and $(M-H)^-=472/474$ (chlorine isotope).

Example 215

3-bromo-N-[(1R)-1-(5-chloro-1H-benzimidazol-2-yl)-2-methoxyethyl]-4-(2,5-dihydropyrrol-1-ylcarbonyl)benzamide

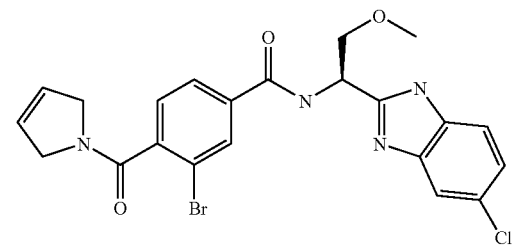

Prepared analogously to Example 1g from 3-bromo-4-(2,5-dihydropyrrol-1-ylcarbonyl)benzoic acid, TBTU, N-methylmorpholine, and (1R)-1-(5-chloro-1H-benzimidazol-2-yl)-2-methoxyethylamine in N,N-dimethylformamide. Yield: 83%; $R_f$ value: 0.41 (silica gel; dichloromethane/methanol=95:5); $C_{22}H_{20}BrClN_4O_3$ (503.79); mass spectrum: $(M+H)^+=503/505/507$ (bromine/chlorine isotope).

Example 216 rac.-N-[1-(5-chloro-1H-benzimidazol-2-yl)ethyl]-4-(4,5,6,7-tetrahydrobenzimidazol-1-yl)-3-trifluoromethylbenzamide

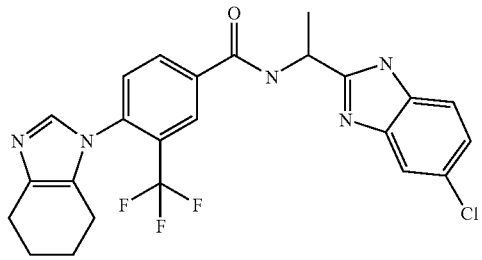

(a) 4-(4,5,6,7-tetrahydrobenzimidazol-1-yl)-3-trifluoromethylbenzonitrile 5.0 g (26.5 mmol) of 4-fluoro-(3-trifluoromethyl)benzonitrile and 3.2 g (26.5 mmol) of 4,5,6,7-tetrahydro-1H-benzimidazole are dissolved in 50 mL of dimethylformamide and combined batchwise with 1.1 g (26.5 mmol) of sodium hydride (50% in oil). After the addition has ended, the mixture is stirred for another 30 minutes. Then it is stirred with 250 mL of ice water and the product precipitated is suction filtered. The residue is chromatographed on silica gel, eluting with dichloromethane/methanol 19:1. Yield: 6.8 g (88%); $C_{15}H_{12}F_3N_3$ (291.28); mass spectrum: $(M+H)^+=292$ (b) 4-(4,5,6,7-tetrahydrobenzimidazol-1-yl)-3-trifluoromethylbenzoic acid Prepared analogously to Example 1f from 4-(4,5,6,7-tetrahydrobenzimidazol-1-yl)-3-trifluoromethylbenzonitrile and sodium hydroxide solution in ethanol. Yield: 94%; $C_{15}H_{13}F_3N_2O_2$ (310.28); mass spectrum: $(M+H)^+=311$ and $(M-H)^-=309$ (c) rac.-N-[1-(5-chloro-1H-benzimidazol-2-yl)ethyl]-4-(4,5,6,7-tetrahydrobenzimidazol-1-yl)-3-trifluoromethylbenzamide Prepared analogously to Example 1g from 4-(4,5,6,7-tetrahydrobenzimidazol-1-yl)-3-trifluoromethylbenzoic acid, TBTU, triethylamine, and (5-chloro-1H-benzimidazol-2-yl)ethylamine in tetrahydrofuran. Yield: 65%; $R_f$ value: 0.30 (silica gel; ethyl acetate/ethanol=4:1); $C_{24}H_{21}ClF_3N_5O$ (487.91); mass spectrum: $(M-H)^-=486/488$ (chlorine isotope).

Example 217 rac.-N-[1-(5-chloro-1H-benzimidazol-2-yl)ethyl]-4-[3-(ethoxycarbonyl)-5,6-dihydro-4H-cyclopentapyrazol-1-yl]-3-trifluoromethylbenzamide

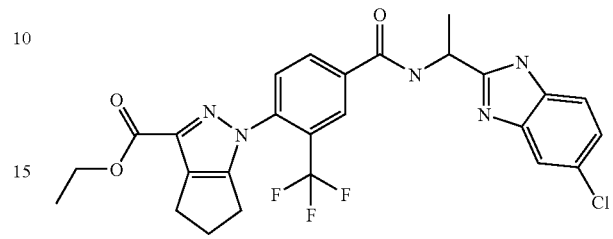

(a) ethyl oxo-(2-oxocyclopentyl)acetate

A solution of 15.5 mL (0.175 mol) of cyclopentanone and 23.8 mL (0.175 mol) of diethyl oxalate in 90 mL of tetrahydrofuran are added dropwise at 0° C. to a suspension of 7.0 g (0.175 mol) of sodium hydride (50% in oil) in 60 mL of tetrahydrofuran. The mixture is stirred for another 10 minutes at 0° C. and then heated to ambient temperature. After 5 hours, an exothermic reaction sets in and the mixture heats up to 50° C. After 16 hours, it is combined with ice water and extracted with ether. The aqueous phase is adjusted to pH 4 with glacial acetic acid and extracted with ethyl acetate, dried and concentrated by evaporation. The residue is distilled in vacuo. BP(23 mbar)=135° C.-141° C. Yield: 19.6 g (61%).

(b) 4-Hydrazino-3-trifluoromethylbenzoic acid 7.5 g (36 mmol) of 4-fluoro-3-trifluoromethylbenzoic acid is dissolved in 12 mL dimethylsulfoxide and, after the addition of 15 mL (0.24 mol) of hydrazine hydrate (80%), stirred for 5 hours at 100° C. After cooling, it is combined with ice and acidified with glacial acetic acid. The precipitated product is suction filtered and dried. Yield: 5.3 g (66%).

(c) 4-[3-(ethoxycarbonyl)-5,6-dihydro-4H-cyclopentapyrazol-1-yl]-3-trifluoromethylbenzoic acid 4.0 g (18.2 mmol) of 4-hydrazino-3-trifluoromethylbenzoic acid is dissolved in 20 mL of glacial acetic acid, combined with 3.3 g (18.2 mmol) of ethyl oxo-(2-oxocyclopentyl)acetate, and refluxed for 2 hours under a nitrogen atmosphere. After cooling, it is stirred with diethyl ether and the precipitate is suction filtered. Yield: 2.9 g (43%).

(d) rac.-N-[1-(5-chloro-1H-benzimidazol-2-yl)ethyl]-4-[3-(ethoxycarbonyl)-5,6-dihydro-4H-cyclopentapyrazol-1-yl]-3-trifluoromethylbenzamide Prepared analogously to Example 1g from 4-[3-(ethoxycarbonyl)-5,6-dihydro-4H-cyclopentapyrazol-1-yl]-3-trifluoromethylbenzoic acid, TBTU, triethylamine, and (5-chloro-1H-benzimidazol-2-yl)ethylamine in tetrahydrofuran. Yield: 52%; $R_f$ value: 0.40 (silica gel; ethyl acetate); $C_{26}H_{23}ClF_3N_5O_3$ (545.95); mass spectrum: $(M+H)^+=546$.

Example 218

4-[3-(tert-butoxycarbonylamino)methyl-5,6-dihydro-4H-cyclopentapyrazol-1-yl]-N-(5-chloro-1H-benzimidazol-2-ylmethyl)-3-trifluoromethylbenzamide

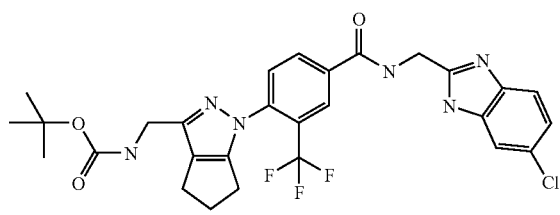

(a) 3-dimethoxymethyl-1,4,5,6-tetrahydrocyclopentapyrazole 5.7 g (30.6 mmol) of 2-(2,2-dimethoxyacetyl)cyclopentanone is dissolved in 50 mL of ethanol and after the addition of 6 g (96 mmol) of hydrazine hydrate (80%) refluxed for 2.5 hours. The ethanol is distilled off, the residue is combined with water and extracted with ethyl acetate. The organic extracts are dried and concentrated by evaporation. The crude product is chromatographed on silica gel, eluting with petroleum ether/ethyl acetate 1:2. Yield: 3.1 g (56%).

(b) 4-(3-dimethoxymethyl-5,6-dihydro-4H-cyclopentapyrazol-1-yl)-3trifluoromethylbenzonitrile Prepared analogously to Example 216a from 4-fluoro-3-trifluoromethylbenzonitrile, 3-dimethoxymethyl-1,4,5,6-tetrahydrocyclopentapyrazole, and sodium hydride in dimethylformamide. Yield: 54%.

(c) 4-(3-formyl-5,6-dihydro-4H-cyclopentapyrazol-1-yl)-3-trifluoromethylbenzonitrile 4.7 mL (12.2 mmol) of sulfuric acid is added dropwise with stirring to a suspension of 32 g of silica gel in 175 mL of dichloromethane. Then 4.3 g (12.2 mmol) of 4-(3-dimethoxymethyl-5,6-dihydro-4H-cyclopentapyrazol-1-yl)-3-trifluoromethylbenzonitrile in 75 mL of dichloromethane is added and the mixture is stirred for 20 hours at ambient temperature. The silica gel is filtered off and the solution is concentrated. Yield: 3.7 g (99%).

(d) 4-[3-(tert-butoxycarbonylamino)methyl-5,6-dihydro-4H-cyclopentapyrazol-1-yl]-3-trifluoromethylbenzonitrile 3.7 g (12.1 mmol) of 4-(3-formyl-5,6-dihydro-4H-cyclopentapyrazol-1-yl)-3-trifluoromethylbenzonitrile is dissolved in 60 mL acetonitrile and, after the addition of 4.3 g (36.4 mmol) of tert-butylcarbamate, 5.8 mL (36.4 mmol) of triethylsilane, and 1.9 mL (24.2 mmol) of trifluoroacetic acid, stirred for 20 hours at ambient temperature. The reaction solution is taken up in diethyl ether, washed with sodium hydrogen carbonate solution, and the organic phase is dried and concentrated by evaporation. Yield: quantitative.

(e) 4-[3-(tert-butoxycarbonylamino)methyl-5,6-dihydro-4H-cyclopentapyrazol-1-yl]-3-trifluoromethylbenzoic acid Prepared analogously to Example 1f from 4-[3-(tert-butoxycarbonylamino)methyl-5,6-dihydro-4H-cyclopentapyrazol-1-yl]-3-trifluoromethylbenzonitrile and sodium hydroxide solution in ethanol. Yield: 89%; $C_{20}H_{22}F_3N_3O_4$ (425.41); mass spectrum: $(M+H)^+=426$ and $(M-H)^-=424$ (f) 4-[3-(tert-butoxycarbonylamino)methyl]-5,6-dihydro-4H-cyclopentapyrazol-1-yl]-N-(5-chloro-1H-benzimidazol-2-ylmethyl)-3-trifluoromethylbenzamide Prepared analogously to Example 1g from 4-[3-(tert-butoxycarbonylamino)methyl]-5,6-dihydro-4H-cyclopentapyrazol-1-yl]-3-trifluoromethylbenzoic acid, TBTU, N-methylmorpholine, and C-(5-chloro-1H-benzimidazol-2-yl)methylamine in N-methylpyrrolidine. Yield: 51%; $R_f$ value: 0.70 (silica gel; ethyl acetate/ethanol/ammonia=9:1:0.1); $C_{28}H_{28}ClF_3N_6O_3$ (589.02); mass spectrum: $(M+H)^+=589/591$ (chlorine isotope) and $(M-H)^-=587/589$ (chlorine isotope).

Example 219 rac.-4-[3-(aminocarbonyl)-5,6-dihydro-4H-cyclopentapyrazol-1-yl]-N-[1-(5-chloro-1H-benzimidazol-2-yl)ethyl]-3-trifluoromethylbenzamide

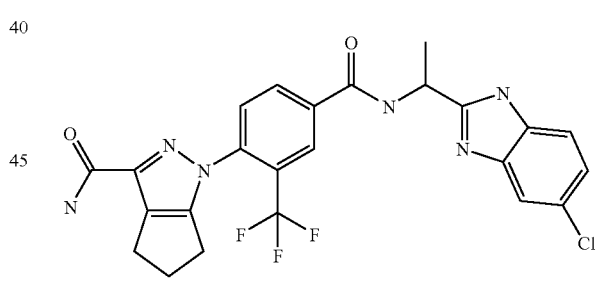

130 mg (0.19 mmol) of rac.-N-[1-(5-chloro-1H-benzimidazol-2-yl)ethyl]-4-[3-(ethoxycarbonyl)-5,6-dihydro-4H-cyclopentapyrazol-1-yl]-3-trifluoromethylbenzamide is dissolved in 5 mL of methanol, combined with 6 mL of concentrated ammonia solution, and stirred for 17 hours at 65° C. in a Schlenk flask. The cooled reaction solution is poured onto ice water, adjusted to pH 7.5 with concentrated hydrochloric acid and extracted with ethyl acetate. The organic phases are dried and concentrated by evaporation. The residue is chromatographed on silica gel, eluting with ethyl acetate/ethanol (0%-5%). Yield: 50 mg (51%); $R_f$ value: 0.38 (silica gel; ethyl acetate/ethanol=9:1); $C_{24}H_{20}ClF_3N_6O_2$ (516.91); mass spectrum: $(M-H)^-=515/517$ (chlorine isotope).

Example 220

4-(3-aminomethyl-5,6-dihydro-4H-cyclopentapyrazol-1-yl)-N-[(1S)-1-(5-chloro-1H-benzimidazol-2-yl)ethyl]-3-trifluoromethylbenzamide

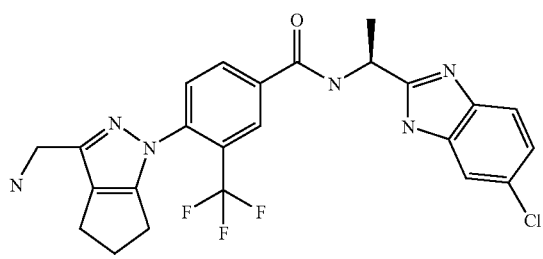

Prepared analogously to Example 17 from 4-[3-(tert-butoxycarbonylamino)methyl-5,6-dihydro-4H-cyclopentapyrazol-1-yl]-N-[(1S)-1-(5-chloro-1H-benzimidazol-2-yl)ethyl]-3-trifluoromethylbenzamide and trifluoroacetic acid. Yield: 55%; $R_f$ value: 0.25 (silica gel; dichloromethane/methanol=9:1); $C_{24}H_{22}ClF_3N_6O$ (502.93); mass spectrum: $(M–H)^-=503/505$ (chlorine isotope).

Example 221

4-[3-(tert-butoxycarbonylamino)methyl-5,6-dihydro-4H-cyclopentapyrazol-1-yl]-N-[(1S)-1-(5-chloro-1H-benzimidazol-2-yl)ethyl]-3-trifluoromethylbenzamide

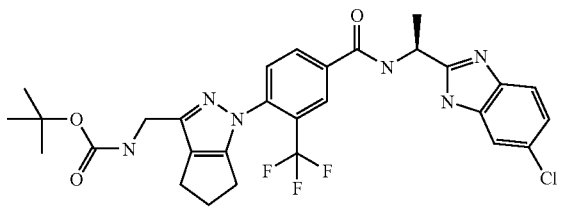

Prepared analogously to Example 1g from 4-[3-(tert-butoxycarbonylamino)methyl-5,6-dihydro-4H-cyclopentapyrazol-1-yl]-3-trifluoromethylbenzoic acid, TBTU, N-methylmorpholine, and 5-chloro-1H-benzimidazol-2-ylethylamine in N-methylpyrrolidine. Yield: 30%; $R_f$ value: 0.65 (silica gel; dichloromethane/methanol/ammonia=9:1:0.1); $C_{29}H_{30}ClF_3N_6O_3$ (603.04); mass spectrum: $(M+H)^+=603/605$ (chlorine isotope) and $(M–H)^-=601/603$ (chlorine isotope).

Example 222

4-(3-aminomethyl-5,6-dihydro-4H-cyclopentapyrazol-1-yl)-N-(5-chloro-1H-benzimidazol-2-ylmethyl)-3-trifluoromethylbenzamide

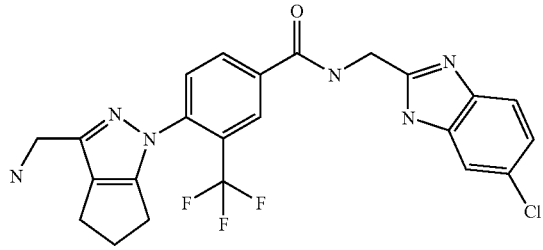

Prepared analogously to Example 17 from 4-[3-(tert-butoxycarbonylamino)methyl-5,6-dihydro-4H-cyclopentapyrazol-1-yl]-N-(5-chloro-1H-benzimidazol-2-ylmethyl)-3-trifluoromethylbenzamide and trifluoroacetic acid. Yield: 70%; $R_f$ value: 0.20 (silica gel; dichloromethane/methanol/ammonia=9:1:0.1); $C_{23}H_{20}ClF_3N_6O$ (488.90); mass spectrum: $(M+H)^+=489/491$ (chlorine isotope) and $(M–H)^-=487/489$ (chlorine isotope).

Example 223

3-methyl-N-[(1R)-1-(5-chloro-1H-benzimidazol-2-yl)-2-hydroxyethyl]-4-(2,5-dihydropyrrol-1-ylcarbonyl)benzamide

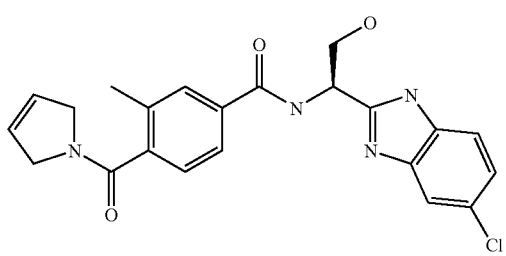

Prepared analogously to Example 1g from 3-methyl-4-(2,5-dihydropyrrol-1-ylcarbonyl)benzoic acid, TBTU, diisopropylethylamine, and (1R)-1-(5-chloro-1H-benzimidazol-2-yl)-2-hydroxyethylamine in tetrahydrofuran. Yield: 100%; $R_f$ value: 0.40 (silica gel; dichloromethane/methanol=9:1); $C_{22}H_{21}ClN_4O_3$ (424.89); mass spectrum: $(M+H)^+=425/427$ (chlorine isotope) and $(M+H)^+=423/425$ (chlorine isotope).

Example 224

N-{(1S)-1-(5-chloro-1H-benzimidazol-2-yl)-3-[(2S)-2-aminomethylpyrrolidin-1-ylcarbonyl]propyl}-3-methyl-4-(pyrrolidin-1-ylcarbonyl)benzamide

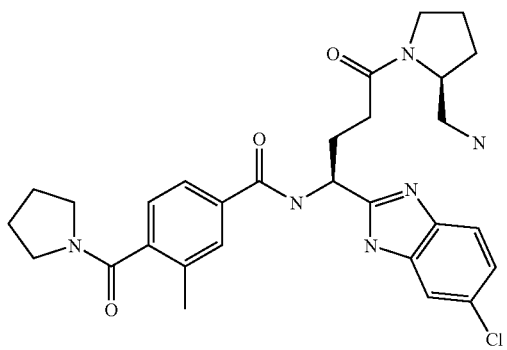

Prepared from N-{(1S)-1-(5-chloro-1H-benzimidazol-2-yl)-3-[(2S)-2-tert-butoxycarbonylaminomethylpyrrolidin-1-ylcarbonyl]propyl}-3-methyl-4-(pyrrolidin-1-ylcarbonyl)benzamide followed by treatment with trifluoroacetic acid analogously to Example 17. Yield: 100%; $R_f$ value: <0.1 (silica gel; ethyl acetate); $C_{29}H_{35}ClN_6O_5$ (551.09); mass spectrum: $(M+H)^+=551/553$ (chlorine isotope).

Example 225

N-{(1S)-1-(5-chloro-1H-benzimidazol-2-yl)-3-[(2R)-2-aminomethylpyrrolidin-1-ylcarbonyl]propyl}-3-methyl-4-(pyrrolidin-1-ylcarbonyl)benzamide

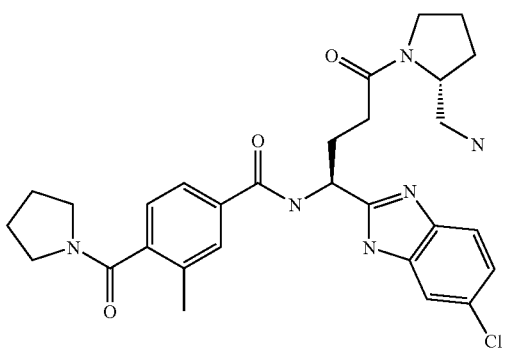

Prepared from N-{(1S)-1-(5-chloro-1H-benzimidazol-2-yl)-3-[(2R)-2-tert-butoxycarbonylaminomethylpyrrolidin-1-ylcarbonyl]propyl}-3-methyl-4-(pyrrolidin 1-ylcarbonyl)benzamide followed by treatment with trifluoroacetic acid analogously to Example 17. Yield: 100%; $R_f$ value: <0.1 (silica gel; ethyl acetate); $C_{29}H_{35}ClN_6O_5$ (551.09); mass spectrum: $(M+H)^+=551/553$ (chlorine isotope).

Example 226

N-(5-chloro-1H-indol-2-ylmethyl)-3-methyl-4-(pyrrolidin-1-ylcarbonyl)benzamide

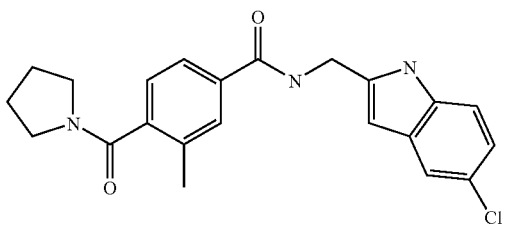

Prepared analogously to Example 1g from 3-methyl-4-(pyrrolidin-1-ylcarbonyl)benzoic acid, TBTU, diisopropylethylamine, and C-(5-chloro-1H-indol-2-yl)methylamine in dimethylformamide. Yield: 31%; $R_f$ value: 0.61 (silica gel; ethyl acetate/ethanol/ammonia=9:1:0.1); $C_{22}H_{22}ClN_3O_2$ (395.89); mass spectrum: $(M+H)^+=396/398$ (chlorine isotope) and $(M-H)^-=394/396$ (chlorine isotope).

Example 227 rac.-3-chloro-N-[1-(5-chloro-1H-benzimidazol-2-yl)ethyl]-4-(4-formylpiperazin-1-ylcarbonyl)benzamide

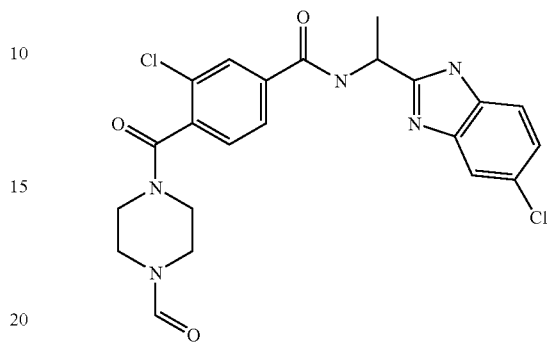

Prepared analogously to Example 1d from 2-chloro-4-{N-[1-(5-chloro-1H-benzimidazol-2yl)ethyl]aminocarbonyl}benzoic acid, 4-formylpiperazine, pentafluorophenyl-N,N',N'-tetramethyluroniumhexafluorophosphate (PFTU), and diisopropylethylamine in DMSO at ambient temperature. HPLC-MS results: retention time: 4.01 minutes; $C_{22}H_{21}Cl_2N_5O_3$ (474.35); mass spectrum: $(M-H)^-=473/475/477$ (chlorine isotope).

Example 228 rac.-3-chloro-N-[1-(5-chloro-1H-benzimidazol-2-yl)ethyl]-4-[N-ethyl-N-(piperidin-4-yl)aminocarbonyl]benzamide

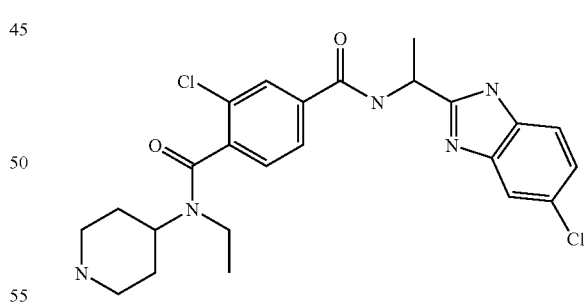

Prepared analogously to Example 1d from 2-chloro-4-{N-[1-(5-chloro-1H-benzimidazol-2-yl)ethyl]aminocarbonyl}benzoic acid, tert-butyl 4-ethylaminopiperidin-1-ylcarboxylate, PFTU, and diisopropylethylamine in DMSO at ambient temperature and subsequent reaction with trifluoroacetic acid analogously to Example 17. HPLC-MS results: retention time: 3.87 minutes; $C_{24}H_{27}Cl_2N_5O_2$ (488.42); mass spectrum: $(M-H)^-=487/489/491$ (chlorine isotope).

Example 229

3-chloro-N-[1-(5-chloro-1H-benzimidazol-2-yl)ethyl]-4-[2-(2-dimethylaminoethyl)piperidin-1-ylcarbonyl]benzamide

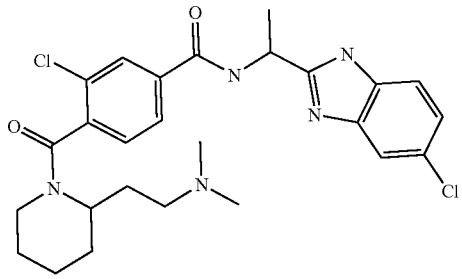

Prepared analogously to Example 1d from rac.-2-chloro-4-{N-[1-(5-chloro-1H-benzimidazol-2-yl)ethyl]aminocarbonyl}benzoic acid, rac.-2-(2-dimethylaminoethyl)piperidine, PFTU, and diisopropylethylamine in DMSO at ambient temperature. HPLC-MS results: retention time: 4.01 minutes; $C_{26}H_{31}Cl_2N_5O_2$ (516.47); mass spectrum: (M–H)⁻=515/517 (chlorine isotope).

Example 230

3-chloro-N-[1-(5-chloro-1H-benzimidazol-2-yl)ethyl]-4-[2-(piperidin-1-ylmethyl)piperidin-1-ylcarbonyl]benzamide

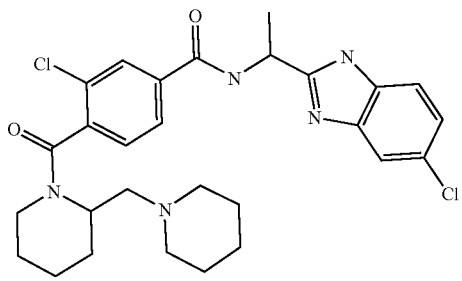

Prepared analogously to Example 1d from rac.-2-chloro-4-{N-[1-(5-chloro-1H-benzimidazol-2-yl)ethyl]aminocarbonyl}benzoic acid, rac.-2-(piperidin-1-ylmethyl)piperidine, PFTU, and diisopropylethylamine in DMSO at ambient temperature. HPLC-MS results: retention time: 4.09 minutes; $C_{28}H_{33}Cl_2N_5O_2$ (542.51); mass spectrum: (M–H)⁻=542/544/546 (chlorine isotope).

Example 231

3-chloro-N-[1-(5-chloro-1H-benzimidazol-2-yl)ethyl]-4-[2-(3-diethylaminopropyl)piperidin-1-ylcarbonyl]benzamide

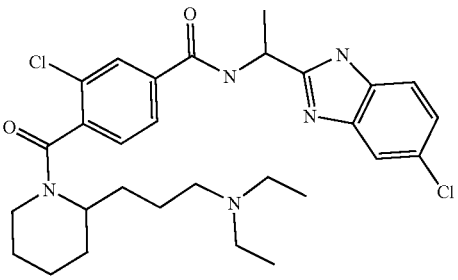

Prepared analogously to Example 1d from rac.-2-chloro-4-{N-[1-(5-chloro-1H-benzimidazol-2-yl)ethyl]aminocarbonyl}benzoic acid, 2-(3-diethylaminopropyl)piperidine, PFTU, and diisopropylethylamine in DMSO at ambient temperature. HPLC-MS results: retention time: 4.09 minutes; $C_{29}H_{37}Cl_2N_5O_2$ (558.55); mass spectrum: (M–H)⁻=558/560 (chlorine isotope).

Example 232

4-[2-(N-butyl-N-ethylaminomethyl)piperidin-1-ylcarbonyl]-3-chloro-N-[1-(5-chloro-1H-benzimidazol-2-yl)ethyl]benzamide

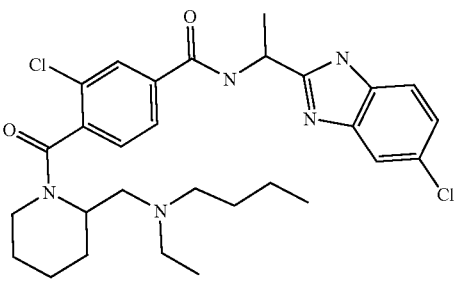

Prepared analogously to Example 1d from rac.-2-chloro-4-{N-[1-(5-chloro-1H-benzimidazol-2-yl)ethyl]aminocarbonyl}benzoic acid, rac.-2-(N-butyl-N-ethylaminomethyl)piperidine, PFTU, and diisopropylethylamine in DMSO at ambient temperature. HPLC-MS results: retention time: 4.23 minutes; $C_{29}H_{37}Cl_2N_5O_2$ (558.55); mass spectrum: (M–H)⁻=558/560 (chlorine isotope).

Example 233

3-chloro-N-[1-(5-chloro-1H-benzimidazol-2-yl)ethyl]-4-[2-(N-cyclohexyl-N-methylaminomethyl)piperidin-1-ylcarbonyl]benzamide

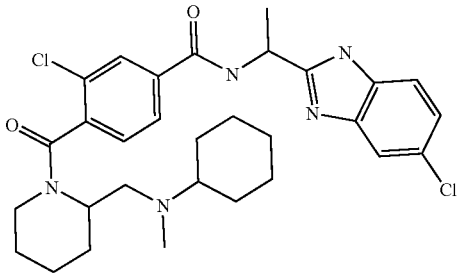

Prepared analogously to Example 1d from rac.-2-chloro-4-{N-[1-(5-chloro-1H-benzimidazol-2-yl)ethyl]aminocarbonyl}benzoic acid, 2-(N-cyclohexyl-N-methylaminomethyl)piperidine, PFTU, and diisopropylethylamine in DMSO at ambient temperature. HPLC-MS results: retention time: 4.25 minutes; $C_{30}H_{37}Cl_2N_5O_2$ (570.56); mass spectrum: (M–H)$^-$=570/572/574 (chlorine isotope).

Example 234

3-chloro-N-[1-(5-chloro-1H-benzimidazol-2-yl)ethyl]-4-(thiomorpholine-4-ylcarbonyl)benzamide

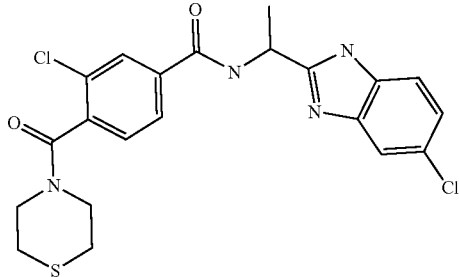

Prepared analogously to Example 1d from rac.-2-chloro-4-{N-[1-(5-chloro-1H-benzimidazol-2-yl)ethyl]aminocarbonyl}benzoic acid, thiomorpholine, PFTU, and diisopropylethylamine in DMSO at ambient temperature. HPLC-MS results: retention time: 4.45 minutes; $C_{21}H_{20}Cl_2N_4O_2S$ (463.39); mass spectrum: (M–H)$^-$=462/464/466 (chlorine isotope).

Example 235

3-chloro-N-[(1R,S)-1-(5-chloro-1H-benzimidazol-2-yl)ethyl]-4-[(2R)-2-methoxymethylpyrrolidin-1-ylcarbonyl]benzamide

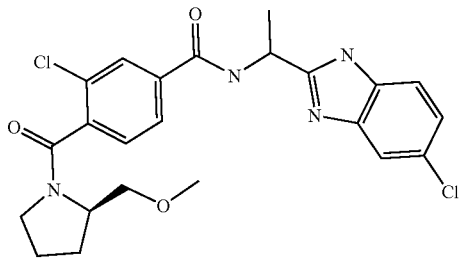

Prepared analogously to Example 1d from rac.-2-chloro-4-{N-[1-(5-chloro-1H-benzimidazol-2-yl)ethyl]aminocarbonyl}benzoic acid, (2R)-2-methoxymethylpyrrolidine, PFTU, and diisopropylethylamine in DMSO at ambient temperature. HPLC-MS results: retention time: 4.44 minutes; $C_{23}H_{24}Cl_2N_4O_3$ (475.37); mass spectrum: (M–H)$^-$=474/476/478 (chlorine isotope).

Example 236 rac.-3-chloro-N-[1-(5-chloro-1H-benzimidazol-2-yl)ethyl]-4-(1,4,6,7-tetrahydroimidazo[4,5-c]pyridin-5-ylcarbonyl)benzamide

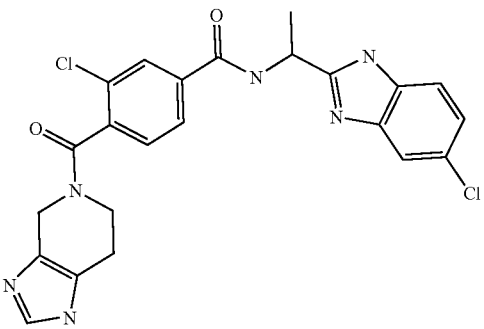

Prepared analogously to Example 1d from rac.-2-chloro-4-{N-[1-(5-chloro-1H-benzimidazol-2-yl)ethyl]aminocarbonyl}benzoic acid, 4,5,6,7-tetrahydro-1H-imidazo[4,5-c]pyridine, PFTU, and diisopropylethylamine in DMSO at ambient temperature. HPLC-MS results: retention time: 3.80 minutes; $C_{23}H_{20}Cl_2N_6O_2$ (483.36); mass spectrum: (M–H)$^-$=482/484/486 (chlorine isotope).

Example 237

3-chloro-N-[(1R,S)-1-(5-chloro-1H-benzimidazol-2-yl)ethyl]-4-[(2S)-2-methoxymethylpyrrolidin-1-ylcarbonyl]benzamide

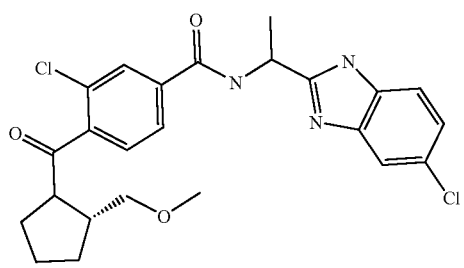

Prepared analogously to Example 1d from rac.-2-chloro-4-{N-[1-(5-chloro-1H-benzimidazol-2-yl)ethyl]aminocarbonyl}benzoic acid, (2S)-2-methoxymethylpyrrolidine, PFTU, and diisopropylethylamine in DMSO at ambient temperature. HPLC-MS results: retention time: 4.38 minutes; $C_{23}H_{24}Cl_2N_4O_3$ (475.37); mass spectrum: (M–H)$^-$=474/476/478 (chlorine isotope).

Example 238

4-(2-aminomethylpiperidin-1-ylcarbonyl)-3-chloro-N-[1-(5-chloro-1H-benzimidazol-2-yl)ethyl]benzamide

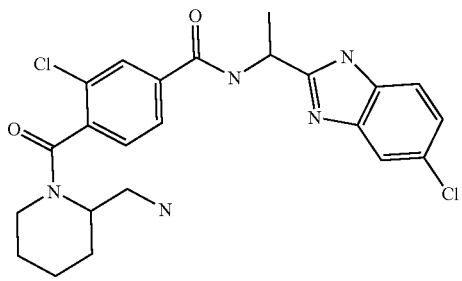

Prepared analogously to Example 1d from rac.-2-chloro-4-{N-[1-(5-chloro-1H-benzimidazol-2-yl)ethyl]aminocarbonyl}benzoic acid, rac.-2-aminomethylpiperidine, PFTU, and diisopropylethylamine in DMSO at ambient temperature. HPLC-MS results: retention time: 3.93 minutes; $C_{23}H_{25}Cl_2N_5O_2$ (474.39); mass spectrum: (M–H)$^-$=473/475/477 (chlorine isotope).

Example 239

4-(3-aminomethylpiperidin-1-ylcarbonyl)-3-chloro-N-[1-(5-chloro-1H-benzimidazol-2-yl)ethyl]benzamide

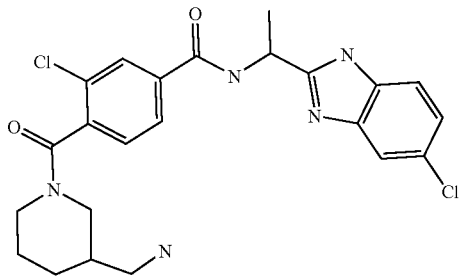

Prepared analogously to Example 1d from rac.-2-chloro-4-{N-[1-(5-chloro-1H-benzimidazol-2-yl)ethyl]aminocarbonyl}benzoic acid, rac.-3-aminomethylpiperidine, PFTU, and diisopropylethylamine in DMSO at ambient temperature. HPLC-MS results: retention time: 3.81 minutes; $C_{23}H_{25}C_{12}N_5O_2$ (474.39); mass spectrum: (M–H)$^-$=473/475/477 (chlorine isotope).

Example 240 rac.-3-chloro-N-[1-(5-chloro-1H-benzimidazol-2-yl)ethyl]-4-(6,7-dihydro-4H-thieno[3,2-c]pyridin-5-ylcarbonyl)benzamide

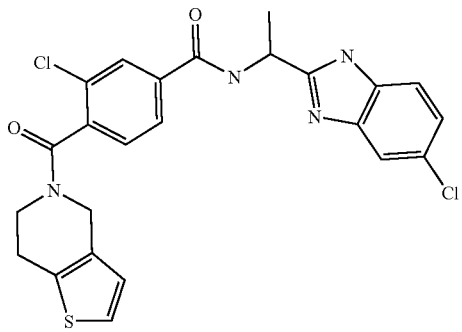

Prepared analogously to Example 1d from rac.-2-chloro-4-{N-[1-(5-chloro-1H-benzimidazol-2-yl)ethyl]aminocarbonyl}benzoic acid, 4,5,6,7-tetrahydrothieno[3,2-c]pyridine, PFTU, and diisopropylethylamine in DMSO at ambient temperature. HPLC-MS results: retention time: 3.81 minutes; $C_{24}H_{20}Cl_2N_4O_2S$ (499.42); mass spectrum: (M–H)$^-$=498/500/502 (chlorine isotope).

Example 241

3-chloro-N-[(1R,S)-1-(5-chloro-1H-benzimidazol-2-yl)ethyl]-4-[(2S)-2-(pyrrolidin-1-ylmethyl)pyrrolidin-1-ylcarbonyl]benzamide

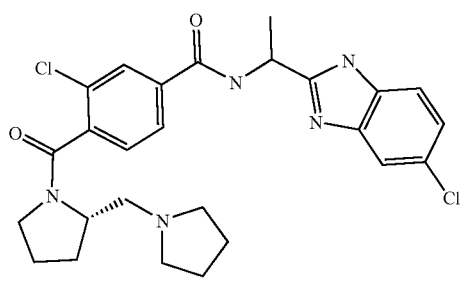

Prepared analogously to Example 1d from rac.-2-chloro-4-{N-[1-(5-chloro-1H-benzimidazol-2-yl)ethyl]aminocarbonyl}benzoic acid, (2S)-2-(pyrrolidin-1-ylmethyl)pyrrolidine, PFTU, and diisopropylethylamine in DMSO at ambient temperature. HPLC-MS results: retention time: 3.93 minutes; $C_{26}H_{29}Cl_2N_5O_2$ (514.45); mass spectrum: (M–H)$^-$=513/515/517 (chlorine isotope).

Example 242

3-chloro-N-[(1R,S)-1-(5-chloro-1H-benzimidazol-2-yl)ethyl]-4-[(2S)-2-(ethoxycarbonyl)pyrrolidin-1-ylcarbonyl]benzamide

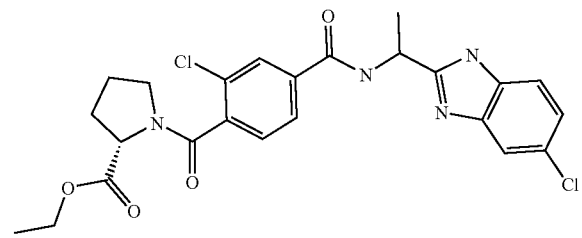

Prepared analogously to Example 1d from rac.-2-chloro-4-{N-[1-(5-chloro-1H-benzimidazol-2-yl)ethyl]aminocarbonyl}benzoic acid, (2S)-2-(ethoxycarbonyl)pyrrolidine, PFTU, and diisopropylethylamine in DMSO at ambient temperature. HPLC-MS results: retention time: 4.48 minutes; $C_{24}H_{24}Cl_2N_4O_4$ (503.38); mass spectrum: (M–H)$^-$=502/504/506 (chlorine isotope).

Example 243

4-[3-(2-aminoethyl)piperidin-1-ylcarbonyl]-3-chloro-N-[1-(5-chloro-1H-benzimidazol-2-yl)ethyl]benzamide

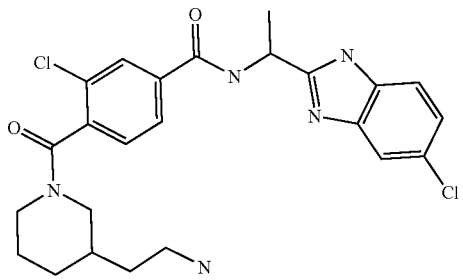

Prepared analogously to Example 1d from rac.-2-chloro-4-{N-[1-(5-chloro-1H-benzimidazol-2-yl)ethyl]aminocarbonyl}benzoic acid, rac.-3-(2-aminoethyl)piperidine, PFTU, and diisopropylethylamine in DMSO at ambient temperature. HPLC-MS results: retention time: 3.88 minutes; $C_{24}H_{27}Cl_2N_5O_2$ (488.42); mass spectrum: $(M-H)^-=487/489/491$ (chlorine isotope).

Example 244 rac.-3-chloro-N-[1-(5-chloro-1H-benzimidazol-2-yl)ethyl]-4-(4-hydroxypiperazin-1-ylcarbonyl)benzamide

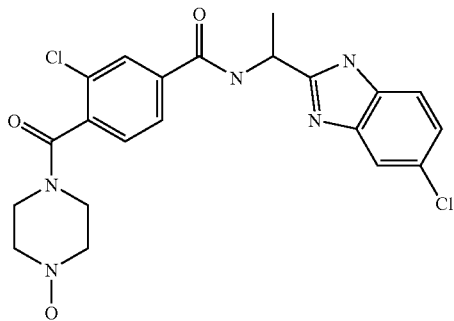

Prepared analogously to Example 1d from rac.-2-chloro-4-{N-[1-(5-chloro-1H-benzimidazol-2-yl)ethyl]aminocarbonyl}benzoic acid, 4-hydroxypiperazine, PFTU, and diisopropylethylamine in DMSO at ambient temperature. HPLC-MS results: retention time: 3.80 minutes; $C_{21}H_{21}Cl_2N_5O_3$ (462.34); mass spectrum: $(M-H)^-=461/463/465$ (chlorine isotope).

Example 245

3-chloro-N-[1-(5-chloro-1H-benzimidazol-2-yl)ethyl]-4-[2-(methyloxycarbonyl)pyrrolidin-1-ylcarbonyl]benzamide

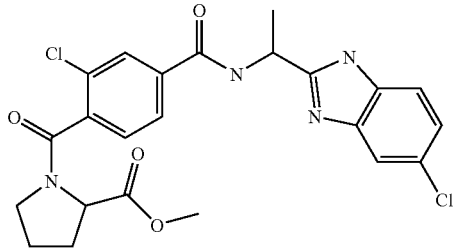

Prepared analogously to Example 1d from rac.-2-chloro-4-{N-[1-(5-chloro-1H-benzimidazol-2-yl)ethyl]aminocarbonyl}benzoic acid, rac.-2-(methyloxycarbonyl)pyrrolidine, PFTU, and diisopropylethylamine in DMSO at ambient temperature. HPLC-MS results: retention time: 4.30 minutes; $C_{23}H_{22}Cl_2N_4O_4$ (489.36); mass spectrum: $(M-H)^-=488/490/492$ (chlorine isotope).

Example 246

4-[2-(benzyloxycarbonyl)pyrrolidin-1-ylcarbonyl]-3-chloro-N-[1-(5-chloro-1H-benzimidazol-2-yl)ethyl]benzamide

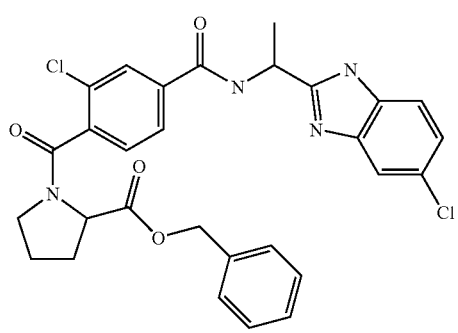

Prepared analogously to Example 1d from rac.-2-chloro-4-{N-[1-(5-chloro-1H-benzimidazol-2-yl)ethyl]aminocarbonyl}benzoic acid, rac.-2-(benzyloxycarbonyl)pyrrolidine, PFTU, and diisopropylethylamine in DMSO at ambient temperature. HPLC-MS results: retention time: 4.82 minutes; $C_{29}H_{26}Cl_2N_4O_4$ (565.45); mass spectrum: $(M-H)=564/566/568$ (chlorine isotope).

Example 247

3-chloro-N-[1-(5-chloro-1H-benzimidazol-2-yl)ethyl]-4-(3,4,5,6-tetrahydro-2H-[2,3]-bipyridinyl-1-ylcarbonyl)benzamide

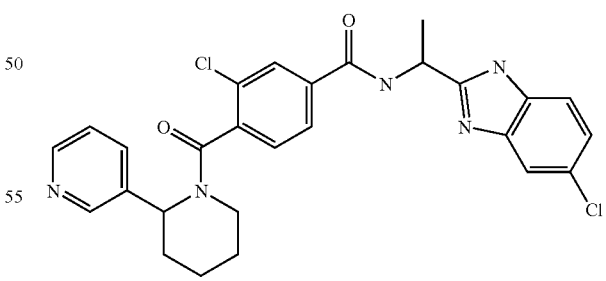

Prepared analogously to Example 1d from rac.-2-chloro-4-{N-[1-(5-chloro-1H-benzimidazol-2-yl)ethyl]aminocarbonyl}benzoic acid, rac.-2-(pyridin-3-yl)piperidine, PFTU, and diisopropylethylamine in DMSO at ambient temperature. HPLC-MS results: retention time: 3.99 minutes; $C_{27}H_{25}Cl_2N_5O_2$ (522.43); mass spectrum: $(M-H)^-=521/523/525$ (chlorine isotope).

Example 248 rac.-4-[N-(2-aminoethyl)-N-ethylaminocarbonyl]-3-chloro-N-[1-(5-chloro-1H-benzimidazol-2-yl)ethyl]benzamide

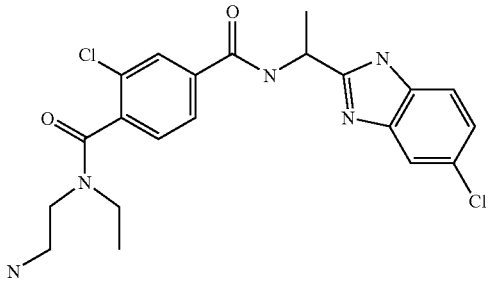

Prepared analogously to Example 1d from rac.-2-chloro-4-{N-[1-(5-chloro-1H-benzimidazol-2-yl)ethyl]aminocarbonyl}benzoic acid, N-(2-aminoethyl)ethylamine, PFTU, and diisopropylethylamine in DMSO at ambient temperature. HPLC-MS results: retention time: 3.82 minutes; $C_{21}H_{23}Cl_2N_5O_2$ (448.35); mass spectrum: $(M-H)^-=447/449/451$ (chlorine isotope).

Example 249 rac.-4-[N-(3-aminopropyl)-N-ethylaminocarbonyl]-3-chloro-N-[1-(5-chloro-1H-benzimidazol-2-yl)ethyl]benzamide

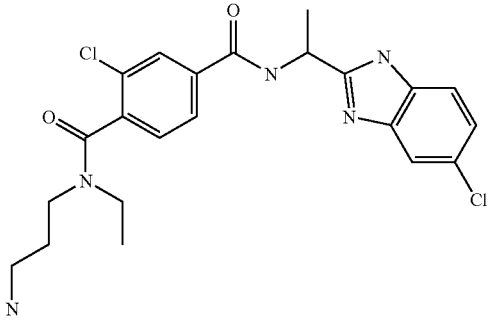

Prepared analogously to Example 1d from rac.-2-chloro-4-{N-[1-(5-chloro-1H-benzimidazol-2-yl)ethyl]aminocarbonyl}benzoic acid, N-(3-aminopropyl)ethylamine, PFTU, and diisopropylethylamine in DMSO at ambient temperature. HPLC-MS results: retention time: 3.82 minutes; $C_{22}H_{25}Cl_2N_5O_2$ (462.38); mass spectrum: $(M-H)^-=461/463/465$ (chlorine isotope).

Example 250 rac.-3-chloro-N-[1-(5-chloro-1H-benzimidazol-2-yl)ethyl]-4-(N-cyclopropyl-N-methylaminocarbonyl]benzamide

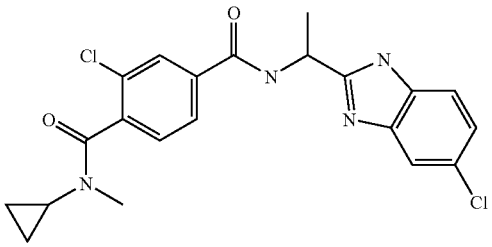

Prepared analogously to Example 1d from rac.-2-chloro-4-{N-[1-(5-chloro-1H-benzimidazol-2-yl)ethyl]aminocarbonyl}benzoic acid, N-cyclopropylmethylamine, PFTU, and diisopropylethylamine in DMSO at ambient temperature. HPLC-MS results: retention time: 4.33 minutes; $C_{21}H_{20}Cl_2N_4O_2$ (431.32); mass spectrum: $(M-H)^-=430/432/434$ (chlorine isotope).

Example 251 rac.-3-chloro-N-[1-(5-chloro-1H-benzimidazol-2-yl)ethyl]-4-(2,5-dimethylpyrrolidin 1-ylcarbonyl)benzamide

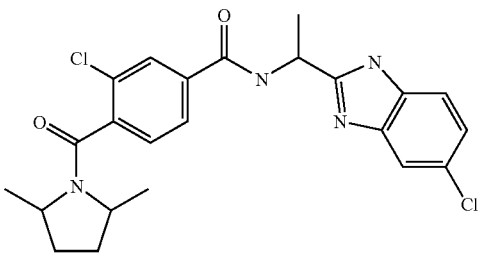

Prepared analogously to Example 1d from rac.-2-chloro-4-{N-[1-(5-chloro-1H-benzimidazol-2-yl)ethyl]aminocarbonyl}benzoic acid, 2,5-dimethylpyrrolidine, PFTU, and diisopropylethylamine in DMSO at ambient temperature. HPLC-MS results: retention time: 4.53 minutes; $C_{23}H_{24}Cl_2N_4O_2$ (459.38); mass spectrum: $(N-H)^-=458/460/462$ (chlorine isotope).

Example 252 rac.-3-chloro-N-[1-(5-chloro-1H-benzimidazol-2-yl)ethyl]-4-(1,4,6,7-tetrahydropyrazol-[4,3-c]pyridin-5-ylcarbonyl)benzamide

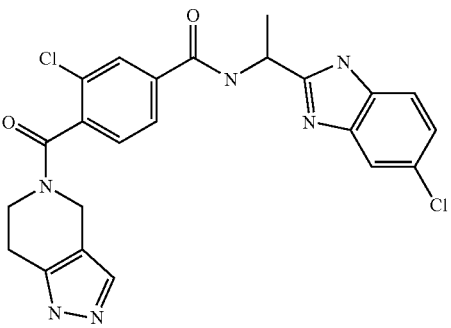

Prepared analogously to Example 1d from rac.-2-chloro-4-{N-[1-(5-chloro-1H-benzimidazol-2-yl)ethyl]aminocarbonyl}benzoic acid, 4,5,6,7-tetrahydro-1H-pyrazol-[4,3-c]pyridine, PFTU, and diisopropylethylamine in DMSO at ambient temperature. HPLC-MS results: retention time: 4.03 minutes; $C_{23}H_{20}Cl_2N_6O_2$ (483.36); mass spectrum: $(M-H)^-=482/484/486$ (chlorine isotope).

Example 253

3-chloro-N-[1-(5-chloro-1H-benzimidazol-2-yl)ethyl]-4-[2-(pyridin-2-yl)pyrrolidin-1-ylcarbonyl]benzamide

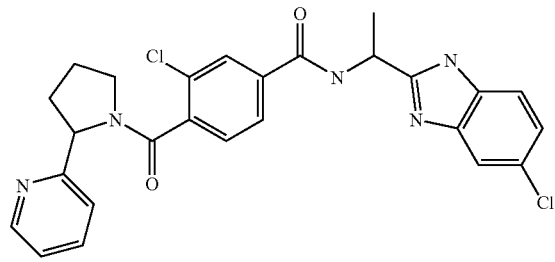

Prepared analogously to Example 1d from rac.-2-chloro-4-{N-[1-(5-chloro-1H-benzimidazol-2-yl)ethyl]aminocarbonyl}benzoic acid, rac.-2-(pyridin-2-yl)pyrrolidine, PFTU, and diisopropylethylamine in DMSO at ambient temperature. HPLC-MS results: retention time: 3.98 minutes; $C_{26}H_{23}Cl_2N_5O_2$ (508.41); mass spectrum: $(M-H)^-=507/509/511$ (chlorine isotope).

Example 254 rac.-3-chloro-N-[1-(5-chloro-1H-benzimidazol-2-yl)ethyl]-4-[2-(pyridin-4-yl)pyrrolidin 1-ylcarbonyl]benzamide

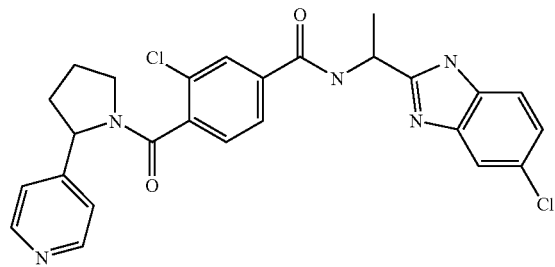

Prepared analogously to Example 1d from rac.-2-chloro-4-{N-[1-(5-chloro-1H-benzimidazol-2-yl)ethyl]aminocarbonyl}benzoic acid, rac.-2-(pyridin-4-yl)pyrrolidine, PFTU, and diisopropylethylamine in DMSO at ambient temperature. HPLC-MS results: retention time: 3.87 minutes; $C_{26}H_{23}Cl_2N_5O_2$ (508.41); mass spectrum: $(M-H)^-=507/509/511$ (chlorine isotope).

Example 255 rac.-3-chloro-N-[1-(5-chloro-1H-benzimidazol-2-yl)ethyl]-4-(2,5-dimethyl-2,5-dihydropyrrol-1-ylcarbonyl)benzamide

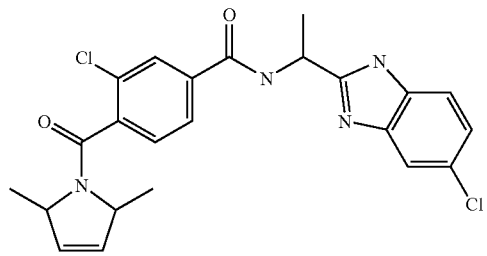

Prepared analogously to Example 1d from rac.-2-chloro-4-{N-[1-(5-chloro-1H-benzimidazol-2-yl)ethyl]aminocarbonyl}benzoic acid, 2,5-dimethyl-2,5-dihydropyrrole, PFTU, and diisopropylethylamine in DMSO at ambient temperature. HPLC-MS results: retention time: 4.52 minutes; $C_{23}H_{22}Cl_2N_4O_2$ (457.36); mass spectrum: $(M-H)^-=456/458/460$ (chlorine isotope).

Example 256

3-chloro-N-[(1R,S)-1-(5-chloro-1H-benzimidazol-2-yl)ethyl]-4-[(2S)-2-phenylaminomethylpyrrolidin-1-ylcarbonyl]benzamide

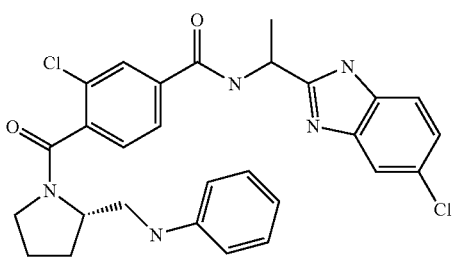

Prepared analogously to Example 1d from 2-chloro-4-{N-[1-(5-chloro-1H-benzimidazol-2-yl)ethyl]aminocarbonyl}benzoic acid, (2S)-2-phenylaminomethylpyrrolidine, PFTU, and diisopropylethylamine in DMSO at ambient temperature. HPLC-MS results: retention time: 4.56 minutes; $C_{28}H_{27}Cl_2N_5O_2$ (536.46); mass spectrum: $(M-H)^-=535/537/539$ (chlorine isotope).

Example 257

4-(2-benzylpyrrolidin-1-ylcarbonyl)-3-chloro-N-[1-(5-chloro-1H-benzimidazol-2-yl)ethyl]benzamide

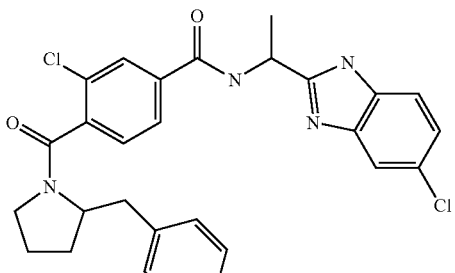

Prepared analogously to Example 1d from rac.-2-chloro-4-{N-[1-(5-chloro-1H-benzimidazol-2-yl)ethyl]aminocarbonyl}benzoic acid, rac.-2-benzylpyrrolidine, PFTU, and diisopropylethylamine in DMSO at ambient temperature. HPLC-MS results: retention time: 4.79 minutes; $C_{28}H_{26}C_{12}N_4O_2$ (521.45); mass spectrum: $(M-H)^-=520/522/524$ (chlorine isotope).

Example 258

3-chloro-N-[1-(5-chloro-1H-benzimidazol-2-yl)ethyl]-4-(2-phenethylpyrrolidin 1-ylcarbonyl)benzamide

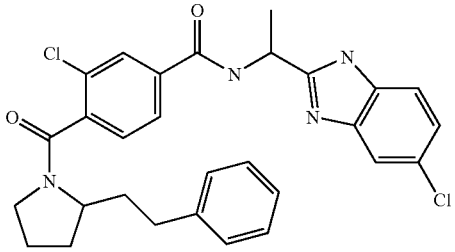

Prepared analogously to Example 1d from rac.-2-chloro-4-{N-[1-(5-chloro-1H-benzimidazol-2-yl)ethyl]aminocarbonyl}benzoic acid, rac.-2-phenethylpyrrolidine, PFTU, and diisopropylethylamine in DMSO at ambient temperature. HPLC-MS results: retention time: 4.99 minutes; $C_{29}H_{28}Cl_2N_4O_2$ (535.47); mass spectrum: $(M-H)^-=535/537$ (chlorine isotope).

Example 259

3-chloro-N-[1-(5-chloro-1H-benzimidazol-2-yl)ethyl]-4-(2-isopropylpyrrolidin-1-ylcarbonyl)benzamide

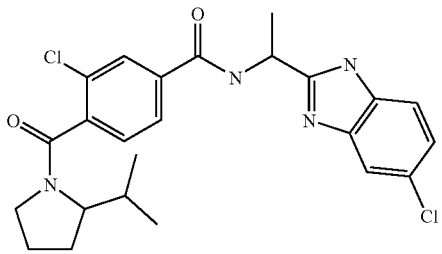

Prepared analogously to Example 1d from rac.-2-chloro-4-{N-[1-(5-chloro-1H-benzimidazol-2-yl)ethyl]aminocarbonyl}benzoic acid, rac.-2-isopropylpyrrolidine, PFTU, and diisopropylethylamine in DMSO at ambient temperature. HPLC-MS results: retention time: 4.71 minutes; $C_{24}H_{26}Cl_2N_4O_2$ (473.40); mass spectrum: $(M-H)^-=472/474/476$ (chlorine isotope).

Example 260

3-chloro-N-[(1R,S)-1-(5-chloro-1H-benzimidazol-2-yl)ethyl]-4-[(2R)-2-phenylaminomethylpyrrolidin-1-ylcarbonyl]benzamide

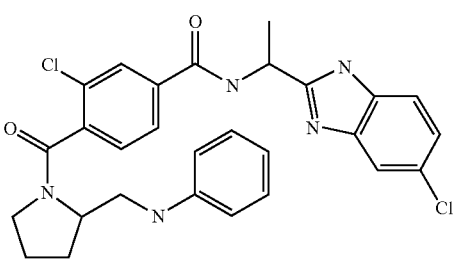

Prepared analogously to Example 1d from 2-rac.-chloro-4-{N-[1-(5-chloro-1H-benzimidazol-2-yl)ethyl]aminocarbonyl}benzoic acid, (2R)-2-phenylaminomethylpyrrolidine, PFTU, and diisopropylethylamine in DMSO at ambient temperature. HPLC-MS results: retention time: 4.55 minutes; $C_{28}H_{27}Cl_2N_5O_2$ (536.46); mass spectrum: $(M-H)^-=535/537$ (chlorine isotope).

Example 261 rac.-3-chloro-N-[1-(5-chloro-1H-benzimidazol-2-yl)ethyl]4-(piperidin-1-ylcarbonyl)benzamide

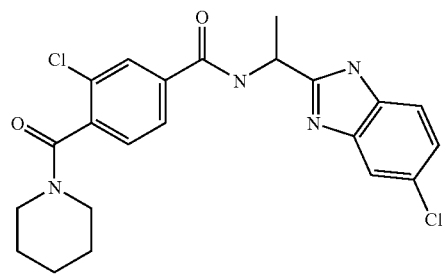

Prepared analogously to Example 1d from rac.-2-chloro-4-{N-[1-(5-chloro-1H-benzimidazol-2-yl)ethyl]aminocarbonyl}benzoic acid, piperidine, PFTU, and diisopropylethylamine in DMSO at ambient temperature. HPLC-MS results: retention time: 4.45 minutes; $C_{22}H_{22}Cl_2N_4O_2$ (445.35); mass spectrum: $(M-H)^-=444/446/448$ (chlorine isotope).

Example 262

3-chloro-N-[1-(5-chloro-1H-benzimidazol-2-yl)ethyl]-4-(2-methylpiperidin-1-ylcarbonyl)benzamide

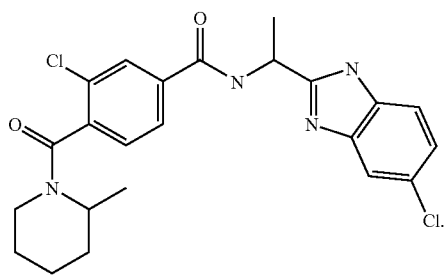

Prepared analogously to Example 1d from rac.-2-chloro-4-{N-[1-(5-chloro-1H-benzimidazol-2-yl)ethyl]aminocarbonyl}benzoic acid, rac.-2-methylpiperidine, PFTU, and diisopropylethylamine in DMSO at ambient temperature. HPLC-MS results: retention time: 4.58 minutes; $C_{23}H_{24}Cl_2N_4O_2$ (459.38); mass spectrum: $(M-H)^-=458/460/462$ (chlorine isotope).

Example 263 rac.-3-chloro-N-[1-(5-chloro-1H-benzimidazol-2-yl)ethyl]4-(4-hydroxypiperidin-1-ylcarbonyl)benzamide

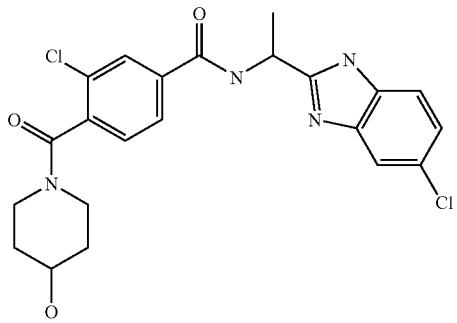

Prepared analogously to Example 1d from rac.-2-chloro-4-{N-[1-(5-chloro-1H-benzimidazol-2-yl)ethyl]aminocarbonyl}benzoic acid, 4-hydroxypiperidine, PFTU, and diisopropylethylamine in DMSO at ambient temperature. HPLC-MS results: retention time: 3.97 minutes; $C_{22}H_{22}Cl_2N_4O_3$ (461.35); mass spectrum: $(M-H)^-=460/462/464$ (chlorine isotope).

Example 264 rac.-4-(4-acetylpiperazin-1-ylcarbonyl)-3-chloro-N-[1-(5-chloro-1H-benzimidazol-2-yl)ethyl]benzamide

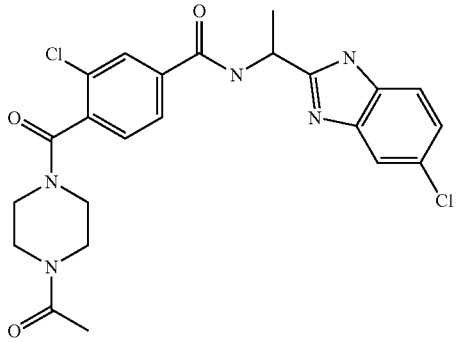

Prepared analogously to Example 1d from rac.-2-chloro-4-{N-[1-(5-chloro-1H-benzimidazol-2-yl)ethyl]aminocarbonyl}benzoic acid, 4-acetylpiperazine, PFTU, and diisopropylethylamine in DMSO at ambient temperature. HPLC-MS results: retention time: 3.99 minutes; $C_{23}H_{23}Cl_2N_5O_3$ (488.37); mass spectrum: $(M-H)^-=487/489/491$ (chlorine isotope).

Example 265

3-chloro-N-[(1R,S)-1-(5-chloro-1H-benzimidazol-2-yl)ethyl]-4-[(2R)-2-(ethoxycarbonyl)pyrrolidin-1-ylcarbonyl]benzamide

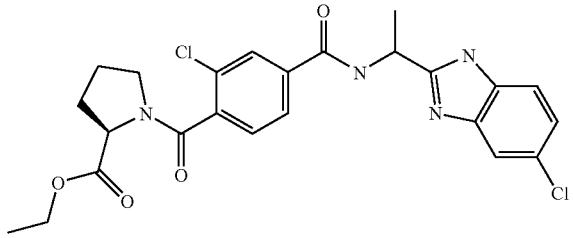

Prepared analogously to Example 1d from 2-chloro-4-{N-[1-(5-chloro-1H-benzimidazol-2-yl)ethyl]aminocarbonyl}benzoic acid, (2R)-2-(ethoxycarbonyl)pyrrolidine, PFTU, and diisopropylethylamine in DMSO at ambient temperature. HPLC-MS results: retention time: 4.45 minutes; $C_{24}H_{24}C_{12}N_4O_4$ (503.38); mass spectrum: $(M-H)^-=502/504/506$ (chlorine isotope).

Example 266 rac.-3-chloro-N-[1-(5-chloro-1H-benzimidazol-2-yl)ethyl]-4-(4-oxopiperidin-1-ylcarbonyl)benzamide

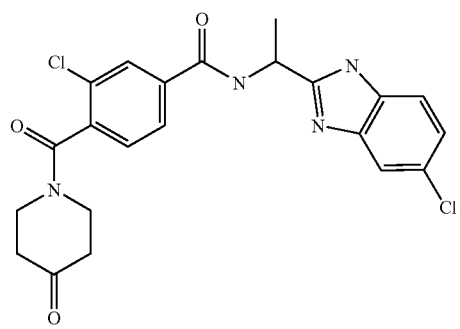

Prepared analogously to Example 1d from 2-chloro-4-{N-[1-(5-chloro-1H-benzimidazol-2-yl)ethyl]aminocarbonyl}benzoic acid, 4-oxopiperidine, PFTU, and diisopropylethylamine in DMSO at ambient temperature. HPLC-MS results: retention time: 4.04 minutes; $C_{22}H_{20}Cl_2N_4O_3$ (459.33); mass spectrum: $(M-H)^-=458/460/462$ (chlorine isotope).

Example 267 rac.-3-chloro-N-[1-(5-chloro-1H-benzimidazol-2-yl)ethyl]-4-([1,4]-diazepan-1-ylcarbonyl)benzamide

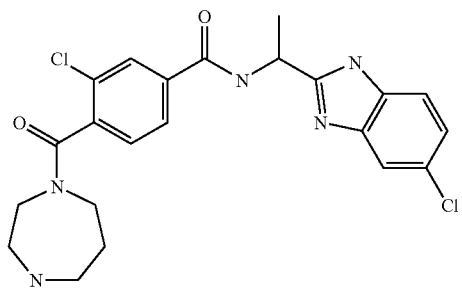

215

Prepared analogously to Example 1d from 2-chloro-4-{N-[1-(5-chloro-1H-benzimidazol-2-yl)ethyl]aminocarbonyl}benzoic acid, 1,4-diazepan, PFTU, and diisopropylethylamine in DMSO at ambient temperature. HPLC-MS results: retention time: 3.69 minutes; $C_{22}H_{23}Cl_2N_5O_2$ (460.36); mass spectrum: $(M-H)^- = 459/461/463$ (chlorine isotope).

Example 268

3-chloro-N-[(1R,S)-1-(5-chloro-1H-benzimidazol-2-yl)ethyl]-4-[(2S)-2-(dimethylaminocarbonyl)pyrrolidin-1-ylcarbonyl]benzamide

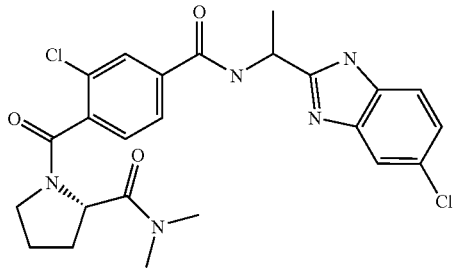

Prepared analogously to Example 1d from rac.-2-chloro-4-{N-[1-(5-chloro-1H-benzimidazol-2-yl)ethyl]aminocarbonyl}benzoic acid, (2S)-2-(dimethylaminocarbonyl)pyrrolidine, PFTU, and diisopropylethylamine in DMSO at ambient temperature. HPLC-MS results: retention time: 4.15 minutes; $C_{24}H_{25}Cl_2N_5O_3$ (502.40); mass spectrum: $(M-H)^- = 501/503/505$ (chlorine isotope).

Example 269

3-chloro-N-[(1R,S)-1-(5-chloro-1H-benzimidazol-2-yl)ethyl]-4-[(2S)-2-(methylaminocarbonyl)pyrrolidin-1-ylcarbonyl]benzamide

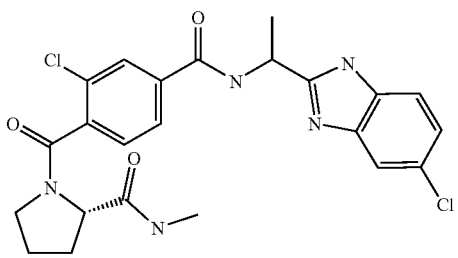

Prepared analogously to Example 1d from rac.-2-chloro-4-{N-[1-(5-chloro-1H-benzimidazol-2-yl)ethyl]aminocarbonyl}benzoic acid, (2S)-2-(methylaminocarbonyl)pyrrolidine, PFTU, and diisopropylethylamine in DMSO at ambient temperature. HPLC-MS results: retention time: 4.03 minutes; $C_{23}H_{23}Cl_2N_5O_3$ (488.37); mass spectrum: $(M-H)^- = 487/489/491$ (chlorine isotope).

216

Example 270

4-[(2S)-2-(aminocarbonylmethylaminocarbonyl)pyrrolidin-1-ylcarbonyl]-3-chloro-N-[(1R,S)-1-(5-chloro-1H-benzimidazol-2-yl)ethyl]benzamide

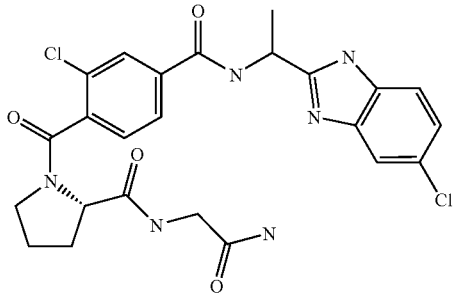

Prepared analogously to Example 1d from rac.-2-chloro-4-{N-[1-(5-chloro-1H-benzimidazol-2-yl)ethyl]aminocarbonyl}benzoic acid, (2S)-2-(aminocarbonylmethylaminocarbonyl)pyrrolidine, PFTU, and diisopropylethylamine in DMSO at ambient temperature. HPLC-MS results: retention time: 3.98 minutes; $C_{24}H_{24}Cl_2N_6O_4$ (531.40); mass spectrum: $(M-H)^- = 530/532/534$ (chlorine isotope).

Example 271

4-((2S)-2-benzhydrylpyrrolidin-1-ylcarbonyl)-3-chloro-N-[1-(5-chloro-1H-benzimidazol-2-yl)ethyl]benzamide

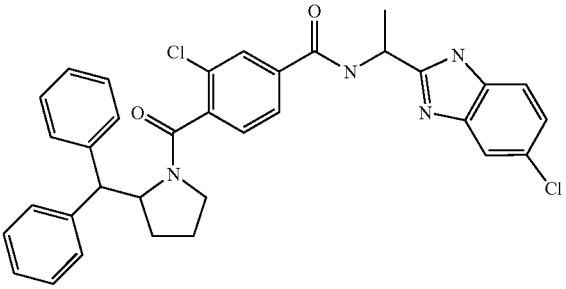

Prepared analogously to Example 1d from rac.-2-chloro-4-{N-[1-(5-chloro-1H-benzimidazol-2-yl)ethyl]aminocarbonyl}benzoic acid, (2S)-2-benzhydrylpyrrolidine, PFTU, and diisopropylethylamine in DMSO at ambient temperature. HPLC-MS results: retention time: 5.18 minutes; $C_{34}H_{30}Cl_2N_4O_2$ (597.54); mass spectrum: $(M-H)^- = 597/599/601$ (chlorine isotope).

Example 272 rac.-3-chloro-N-[1-(5-chloro-1H-benzimidazol-2-yl)ethyl]-4-[3-(2,2,2-trifluoroacetylamino)pyrrolidin-1-ylcarbonyl]benzamide

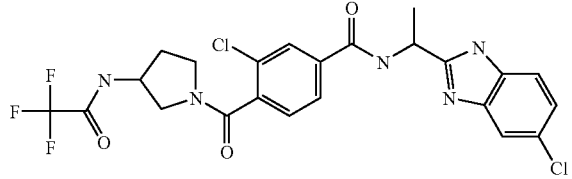

Prepared analogously to Example 1d from rac.-2-chloro-4-{N-[1-(5-chloro-1H-benzimidazol-2-yl)ethyl]aminocarbonyl}benzoic acid, 3-(2,2,2-trifluoroacetylamino)pyrrolidine, PFTU, and diisopropylethylamine in DMSO at ambient temperature. HPLC-MS results: retention time: 4.34 minutes; $C_{23}H_{20}Cl_2F_3N_5O_3$ (542.34); mass spectrum: $(M-H)^-=541/543/545$ (chlorine isotope).

Example 273

3-chloro-N-[1-(5-chloro-1H-benzimidazol-2-yl)ethyl]4-(3-dimethylaminopyrrolidin-1-ylcarbonyl)benzamide

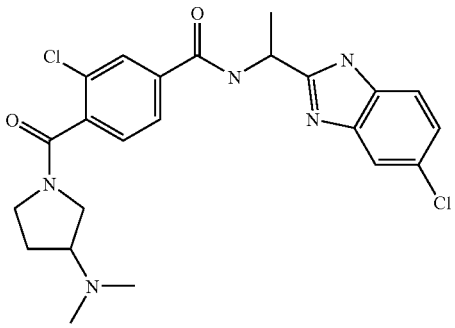

Prepared analogously to Example 1d from rac.-2-chloro-4-{N-[1-(5-chloro-1H-benzimidazol-2-yl)ethyl]aminocarbonyl}benzoic acid, rac.-3-dimethylaminopyrrolidine, PFTU, and diisopropylethylamine in DMSO at ambient temperature. HPLC-MS results: retention time: 3.69 minutes; $C_{23}H_{25}Cl_2N_5O_2$ (474.39); mass spectrum: $(M-H)^-=473/475/477$ (chlorine isotope).

Example 274

N-[(1S)-1-(5-chloro-1H-benzimidazol-2-yl)ethyl]4-(imidazol-1-ylmethyl)-3-methoxybenzamide

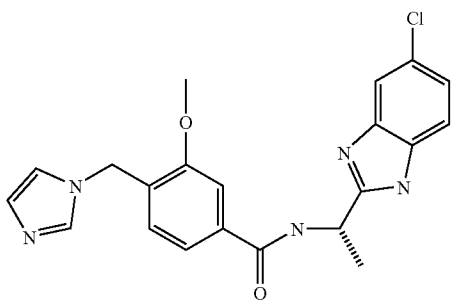

(a) methyl 4-(imidazol-1-ylmethyl)-3-methoxybenzoate 0.39 g (5.8 mmol) of imidazole are dissolved in 50 mL of tetrahydrofuran and, after the addition of 305.6 mg (6.4 mmol) of sodium hydride (50% in oil), stirred for 10 minutes at ambient temperature. Then 1.5 g (5.8 mmol) of methyl 4-(bromomethyl)-3-methoxybenzoate are added and the mixture is stirred for a further 16 hours. The solvent is distilled off, decomposed with water and extracted with ethyl acetate. The combined organic extracts are dried and concentrated by evaporation. Yield: 1.4 g (99%); $C_{13}H_{14}N_2O_3$ (246.268); mass spectrum: $(M+H)^+=247$ (b) 4-(imidazol-1-ylmethyl)-3-methoxybenzoic acid Prepared analogously to Example 19b from methyl 4-(imidazol-1-ylmethyl)-3-methoxybenzoate and sodium hydroxide solution in methanol. Yield: 85%; $C_{12}H_{12}N_2O_3$ (232.24); mass spectrum: $(M+H)^+=233$.

(c) N-[(1S)-1-(5-chloro-1H-benzimidazol-2-yl)ethyl]-4-(imidazol-1-ylmethyl)-3-methoxybenzamide Prepared analogously to Example 1g from 4-(imidazol-1-ylmethyl)-3-methoxybenzoic acid, TBTU, diisopropylethylamine and (1S)-1-(5-chloro-1H-benzimidazol-2-yl)ethylamine in tetrahydrofuran. Yield: 98%; $R_f$ value: 0.48 (silica gel; dichloromethane/ethanol=4:1); $C_{21}H_{20}ClN_5O_2$ (409.879); mass spectrum: $(M+H)^+=410/412$ (chlorine isotope) and $(M-H)^-=408/410$ (chlorine isotope).

Example 275

N-[(1S)-1-(5-chloro-1H-benzimidazol-2-yl)ethyl]-3-methoxy-4-(2-oxopyrrolidin-1-ylmethyl)benzamide

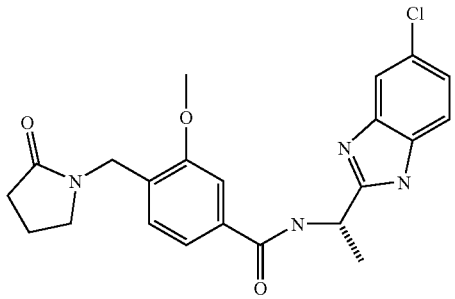

Prepared analogously to Example 1g from 3-methoxy-4-(2-oxopyrrolidin-1-ylmethyl)benzoic acid, TBTU, diisopropylethylamine and (1S)-1-(5-chloro-1H-benzimidazol-2-yl)ethylamine in tetrahydrofuran. Yield: 59%; $R_f$ value: 0.41 (silica gel; dichloromethane/ethanol=9:1); $C_{22}H_{23}ClN_4O_3$ (426.9); mass spectrum: $(M+H)^+=427/429$ (chlorine isotope) and $(M-H)-=425/427$ (chlorine isotope).

Example 276

N-[(1S)-1-(5-chloro-1H-benzimidazol-2-yl)ethyl]-3-methoxy-4-(3-oxopiperazin 1-ylmethyl)benzamide

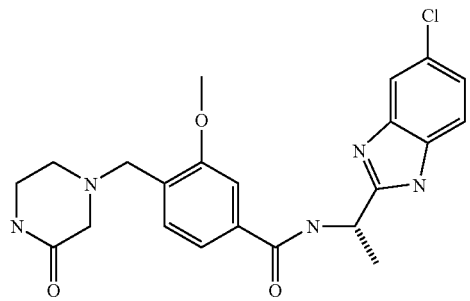

Prepared analogously to Example 1g from 3-methoxy-4-(3-oxopiperazin-1-ylmethyl)benzoic acid, TBTU, diisopropylethylamine and (1S)-1-(5-chloro-1H-benzimidazol-2-yl)ethylamine in tetrahydrofuran. Yield: 35%; $R_f$ value: 0.39 (silica gel; dichloromethane/ethanol=4:1); $C_{22}H_{24}ClN_5O_3$ (441.92); mass spectrum: $(M+H)^+$=442/444 (chlorine isotope) and $(M-H)^-$=440/442 (chlorine isotope).

Example 277

3-bromo-N-[(1R)-1-(5-chloro-1H-benzimidazol-2-yl)-2-hydroxyethyl]-4-(pyrrolidin-1-ylcarbonyl)benzamide

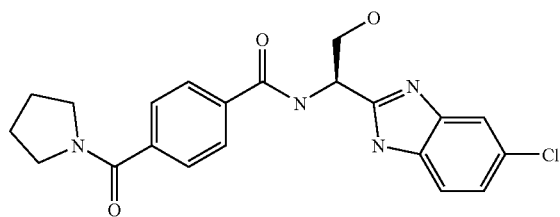

Prepared analogously to Example 1g from 3-bromo-4-(pyrrolidin-1-ylcarbonyl)benzoic acid, TBTU, diisopropylethylamine and (1R)-1-(5-chloro-1H-benzimidazol-2-yl)-2-hydroxyethylamine in tetrahydrofuran. Yield: 90%; $R_f$ value: 0.40 (silica gel: dichloromethane/methanol=9:1); $C_{21}H_{20}BrClN_4O_3$ (491.77); mass spectrum: $(M+H)^+$=491/493/495 (bromine/chlorine isotope).

Example 278

N-[(1R)-1-(5-chloro-1H-benzimidazol-2-yl)-2-methoxyethyl]-4-(2,5-dihydropyrrol-1-ylcarbonyl)-3-trifluoromethylbenzamide

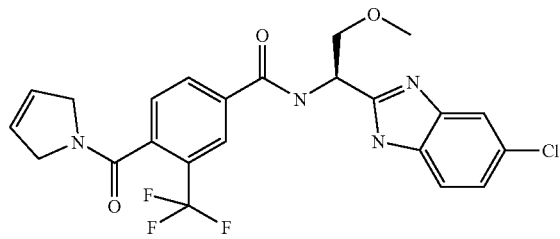

Prepared analogously to Example 1g from 4-{N-[(1R)-1-(5-chloro-1H-benzimidazol-2-yl)-2-methoxyethyl]aminocarbonyl}-2-trifluoromethylbenzoic acid, TBTU, diisopropylethylamine, and 3-pyrroline in tetrahydrofuran. Yield: 23%; $C_{23}H_{20}ClF_3N_4O_3$ (492.88); mass spectrum: $(M+H)^+$=493/495 (chlorine isotope) and $(M-H)^-$=491/493 (chlorine isotope).

Example 279

N-[(1R)-1-(5-chloro-1H-benzimidazol-2-yl)-2-methoxyethyl]-4-(pyrrolidin-1-ylcarbonyl)-3-trifluoromethylbenzamide

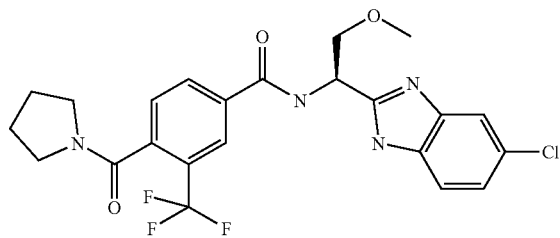

Prepared analogously to Example 1g from 4-{N-[(1R)-1-(5-chloro-1H-benzimidazol-2-yl)-2-methoxyethyl]aminocarbonyl}-2-trifluoromethylbenzoic acid, TBTU, diisopropylethylamine and pyrrolidine in tetrahydrofuran. Yield: 11%; $R_f$ value: 0.72 (silica gel: dichloromethane/methanol=9:1); $C_{23}H_{22}ClF_3N_4O_3$ (494.899); mass spectrum: $(M+H)^+$=495/497 (chlorine isotope).

Example 280

3-chloro-N-[(1R)-1-(5-chloro-1H-benzimidazol-2-yl)-2-isopropoxycarbonyloxyethyl]-4-(2,5-dihydropyrrol-1-ylcarbonyl)benzamide

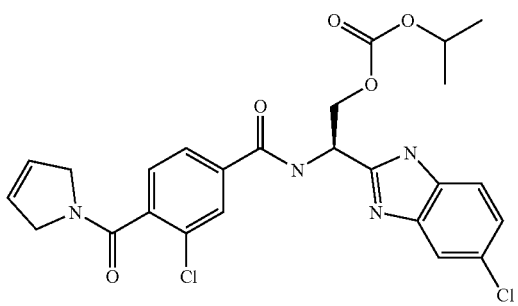

Prepared analogously to Example 1g from 3-chloro-4-(2,5-dihydropyrrol-1-ylcarbonyl)benzoic acid, TBTU, diisopropylethylamine and (R)-1-(5-chloro-1H-benzimidazol-2-yl)-2-isopropoxycarbonyloxyethylamine in tetrahydrofuran. Yield: 40%; $C_{25}H_{24}Cl_2N_4O_5$ (531.394); mass spectrum: $(M+H)^+$=531/533/535 (chlorine isotope).

Example 281

N-[(1S)-1-(5-chloro-1H-benzimidazol-2-yl)-3-(2-isopropylaminothiazol-4-yl)propyl]-3-methyl-4-(pyrrolidin-1-ylcarbonyl)benzamide

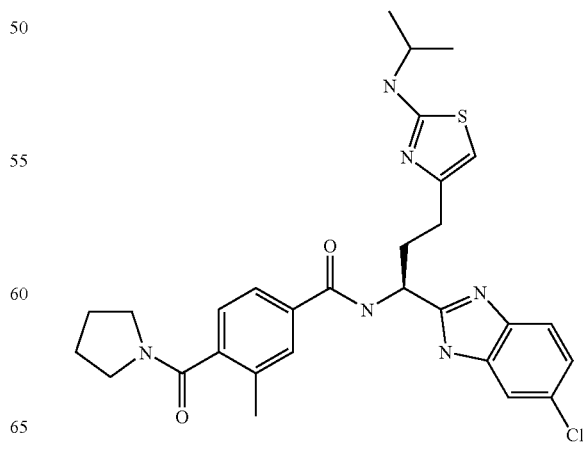

(a) benzyl(S)-2-tert-butoxycarbonylamino-6-diazo-5-oxohexanoate 5.0 g (14.9 mmol) of 1-benzyl tert-butoxycarbonyl-(S)-glutamate is placed in 75 mL of tetrahydrofuran while cooling with ice, combined with 2.1 mL (16.5 mmol) of isobutylchloroformate and 2.5 mL (18 mmol) of triethylamine, and stirred for 60 minutes. Then 30 mL, (20 mmol) of diazomethane (0.7 molar in diethyl ether) and 200 mL of tert-butylmethylether are added and the mixture is stirred overnight at ambient temperature. After the addition of 1 mL glacial acetic acid, the phases are separated, and the organic phase is dried and concentrated by evaporation. The residue is chromatographed on silica gel, eluting with dichloromethane/ethyl acetate (0%-20%). Yield: 2.2 g (41%); $R_f$ value: 0.42 (silica gel: petroleum ether/ethyl acetate=6:4); $C_{18}H_{23}N_3O_5$ (361.40); mass spectrum: $(M+H)^+=362$

(b) benzyl (1S)-2-tert-butoxycarbonylamino-4-(2-isopropylaminothiazol-4-yl)butyrate 2.1 g (5.8 mmol) of benzyl (S)-2-tert-butoxycarbonylamino-6-diazo-5-oxohexanoate is placed in 50 mL of tert-butylmethylester at 0° C., combined with 0.8 mL (4.6 mmol) of hydrogen bromide in glacial acetic acid. Then 685 mg (5.8 mmol) of isopropylthiourea are added and the solution is concentrated by evaporation. The residue is taken up in 50 mL of acetonitrile and stirred for 16 hours at ambient temperature. The solvent is distilled off, the residue is taken up in 150 mL of ethyl acetate and washed with sodium hydrogen carbonate solution. The organic phase is dried and concentrated by evaporation. The crude product is chromatographed on silica gel, eluting with dichloromethane/ethyl acetate (0%-20%). Yield: 335 mg (13%); $R_f$-value: 0.64 (silica gel: dichloromethane/ethyl acetate=73); $C_{22}H_{31}N_3O_4S$ (433.57); mass spectrum: $(M+H)^+=434$.

(c) (1S)-2-tert-butoxycarbonylamino-4-(2-isopropylaminothiazol-4-yl)butyric acid Prepared analogously to Example 19b from benzyl (1S)-2-tert-butoxycarbonylamino-4-(2-isopropylaminothiazol-4-yl)butyrate and sodium hydroxide solution. Yield: 91%; $C_{15}H_{25}N_3O_4S$ (343.448); mass spectrum: $(M+H)^+=344$.

(d) N-(tert-butoxycarbonyl)-[(1S)-1-(5-chloro-1H-benzimidazol-2-yl)-3-(2-isopropyl-aminothiazol-4-yl)propylamine]

Prepared analogously to Example 1g from (1S)-2-tert-butoxycarbonylamino-4-(2-isopropyl-aminothiazol-4-yl)butyric acid, TBTU, triethylamine, and 4-chlorobenzene-1,2-diamine in tetrahydrofuran and subsequent reaction with glacial acetic acid analogously to Example 1b. Yield: 37%; $C_{21}H_{28}ClN_5O_2S$ (450.01); mass spectrum: $(M+H)^+=450$

(e) N-[(1S)-1-(5-chloro-1H-benzimidazol-2-yl)-3-(2-isopropylaminothiazol-4-yl)propyl]-3-methyl-4-(pyrrolidin-1-ylcarbonyl)benzamide Prepared analogously to Example 17 from N-(tert-butoxycarbonyl)-[(1S)-1-(5-chloro-1H-benzimidazol-2-yl)-3-(2-isopropylaminothiazol-4-yl)propylamine] and trifluoroacetic acid and subsequent reaction with 3-methyl-4-(pyrrolidin-1-ylcarbonyl)benzoic acid, TBTU, and diisopropylamine in dimethylformamide. Yield: 45%; $C_{29}H_{33}ClN_6O_2$ (565.139); mass spectrum: $(M+H)^+=565/567$ (chlorine isotope).

Example 282

N-[(1S)-1,3-bis-(5-chloro-1H-benzimidazol-2-yl)propyl]-3-methyl-4-(pyrrolidin-1-ylcarbonyl)benzamide

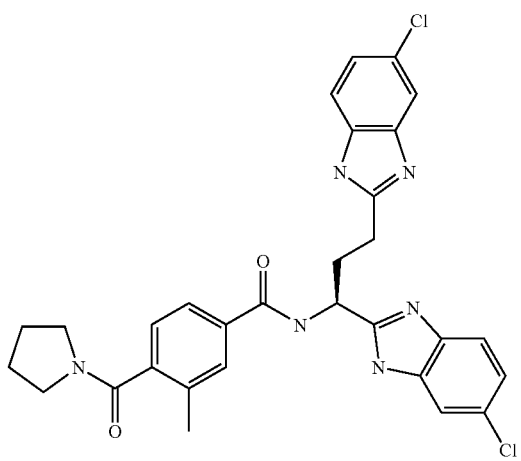

Prepared analogously to Example 1g from 3-methyl-(4-pyrrolidin-1-ylcarbonyl)benzoic acid, TBTU, diisopropylethylamine, and (1S)-1,3-bis-(5-chloro-1H-benzimidazol-2-yl)propylamine in dimethylformamide. Yield: 42%; $C_{30}H_{28}Cl_2N_6O_2$ (575.497); mass spectrum: $(M+H)^+=575/577/579$ (chlorine isotope).

Example 283

3-chloro-N-[(1S)-1-(5-chloro-1H-benzimidazol-2-yl)ethyl]4-[(2S)-2-(ethoxycarbonyl-methyl)pyrrolidin-1-ylcarbonyl]benzamide

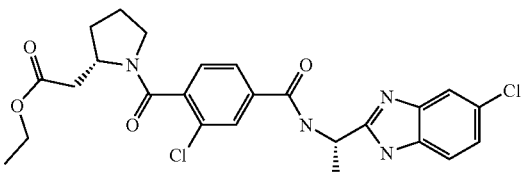

Prepared analogously to Example 1g from (1S)-2-chloro-4-{N-[1-(5-chloro-1H-benzimidazol-2-yl)ethyl]aminocarbonyl}benzoic acid, TBTU, diisopropylethylamine, and (S)-2-(ethoxycarbonylmethyl)pyrrolidine in tetrahydrofuran. Yield: 64%; $R_f$ value: 0.42 (silica gel: dichloromethane/ethanol=9:1); $C_{25}H_{26}C_{12}N_4O_4$ (517.728); mass spectrum: $(M-H)^-=515/517/519$ (chlorine isotope).

Example 284

3-chloro-N-[(1S)-1-(5-chloro-1H-benzimidazol-2-yl)ethyl]4-[(2R/S)-2-dimethylamino-methylpyrrolidin-1-ylcarbonyl]benzamide

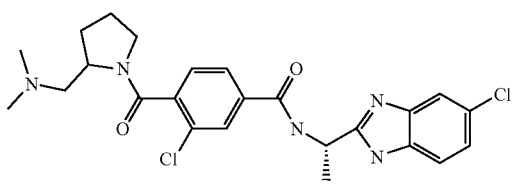

Prepared analogously to Example 1g from (1S)-2-chloro-4-{N-[1-(5-chloro-1H-benzimidazol-2-yl)ethyl]aminocarbonyl}benzoic acid, TBTU, diisopropylethylamine, and rac-2-(dimethylaminomethyl)pyrrolidine in tetrahydrofuran. Yield: 50%; $R_f$ value: 0.32 (Reversed phase RP 8: methanol/5% sodium chloride solution=6:4); $C_{24}H_{27}Cl_2N_5O_2$ (488.416); mass spectrum: $(M+H)^+$=488/490/492 (chlorine isotope) and $(M-H)^-$=486/488/490 (chlorine isotope).

Example 285

3-chloro-N-[(1S)-1-(5-chloro-1H-benzimidazol-2-yl)ethyl]-4-[(2S)-2-(hydroxycarbonyl-methyl)pyrrolidin-1-ylcarbonyl]benzamide

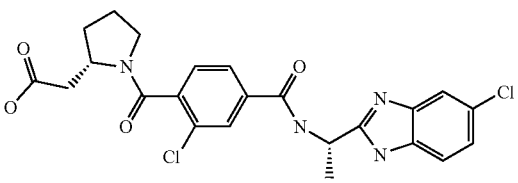

Prepared analogously to Example 19b from 3-chloro-N-[(1S)-1-(5-chloro-1H-benzimidazol-2-yl)ethyl]-4-[(2S)-2-(ethoxycarbonylmethyl)pyrrolidin-1-ylcarbonyl]benzamide and lithium hydroxide in tetrahydrofuran. Yield: 63%; $R_f$ value: 0.32 (Reversed phase RP 8: methanol/5% sodium chloride solution=6:4); $C_{23}H_{22}Cl_2N_4O_4$ (489.357); mass spectrum: (M−H)−=487/489/451 (chlorine isotope).

Example 286

3-chloro-N-[(1S)-1-(5-chloro-1H-benzimidazol-2-yl)ethyl]4-[(2R/S)-2-(hydroxycarbonyl-ethyl)pyrrolidin-1-ylcarbonyl]benzamide

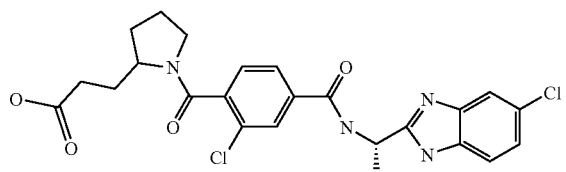

Prepared analogously to Example 19b from 3-chloro-N-[(1S)-1-(5-chloro-1H-benzimidazol-2-yl)ethyl]-4-[(2R/S)-2-(ethoxycarbonylethyl)pyrrolidin-1-ylcarbonyl]benzamide and lithium hydroxide in tetrahydrofuran. Yield: 23%; $R_f$ value: 0.34 (Reversed phase RP 8: methanol/5% sodium chloride solution=6:4); $C_{24}H_{24}C_{12}N_4O_4$ (503.384); mass spectrum: $(M+H)^+$=503/505/507 (chlorine isotope).

Example 287

N-[(1S)-3-[1-(benzyloxycarbonyl)piperidin-4-yl]-1-(5-chloro-1H-benzimidazol-2-yl)propyl]-3-methyl-4-(pyrrolidin-1-ylcarbonyl)benzamide

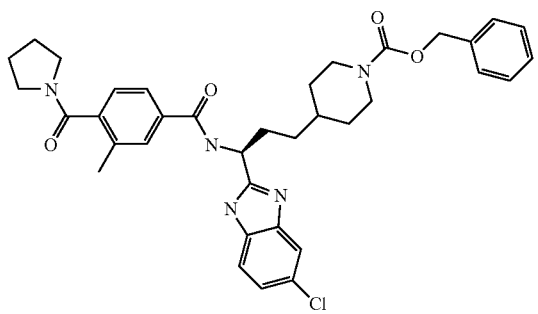

Prepared analogously to Example 1g from 3-methyl-(4-pyrrolidin-1-ylcarbonyl)benzoic acid, TBTU, diisopropylethylamine, and N-[(1S)-3-[1-(benzyloxycarbonyl)piperidin-4-yl]-1-(5-chloro-1H-benzimidazol-2-yl)propylamine in tetrahydrofuran. Yield: 9%; $R_f$ value: 0.40 (silica gel: dichloromethane/ethanol=9:1); $C_{36}H_{40}ClN_5O_4$ (642.196); mass spectrum: (M−H)−=640/642 (chlorine isotope).

Example 288 rac.-N-[(5-chloro-1H-benzimidazol-2-yl)thiophen-3-ylmethyl]4-(2,5-dihydropyrrol-1-ylcarbonyl)-3-methylbenzamide

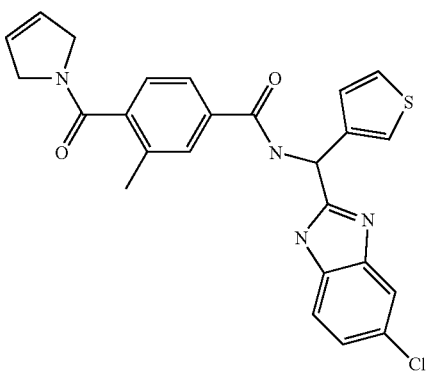

Prepared analogously to Example 1g from 3-methyl-4-(2,5-dihydropyrrol-1-ylcarbonyl)benzoic acid, TBTU, diisopropylethylamine, and (5-chloro-1H-benzimidazol-2-yl)thiophen-3-ylmethylamine in tetrahydrofuran. Yield: 81%; $R_f$ value: 0.49 (silica gel: dichloromethane/ethanol=9:1); $C_{25}H_{21}ClN_4O_2$ (476.986); mass spectrum: $(M+H)^+$=477/479 (chlorine isotope).

Example 289

N-[(1S)-1-(5-chloro-1H-benzimidazol-2-yl)-3-methanesulfonylaminopropyl]-4-(2,5-dihydropyrrol-1-ylcarbonyl)-3-methylbenzamide

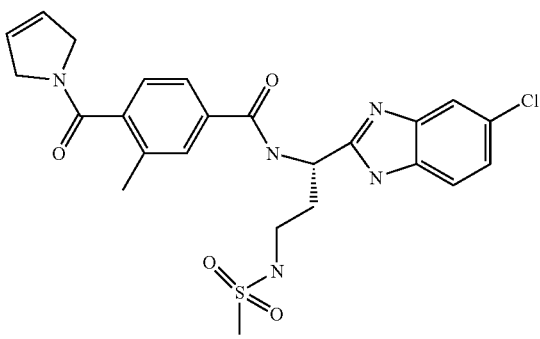

Prepared analogously to Example 125 from N-[(1S)-3-amino-1-(5-chloro-1H-benzimidazol-2-yl)propyl]-4-(2,5-dihydropyrrol-1-ylcarbonyl)-3-methylbenzamide, methanesulfonic acid chloride and triethylamine in tetrahydrofuran. Yield: 58%; $R_f$ value: 0.40 (silica gel: dichloromethane/ethanol=9:1); $C_{24}H_{26}ClN_5O_4$ (516.019); mass spectrum: $(M+H)^+=516/518$ (chlorine isotope).

Example 290

N-[1S)-1-(5-chloro-1H-benzimidazol-2-yl)-3-piperidin-4-ylpropyl]-3-methyl-4-(pyrrolidin-1-ylcarbonyl)benzamide

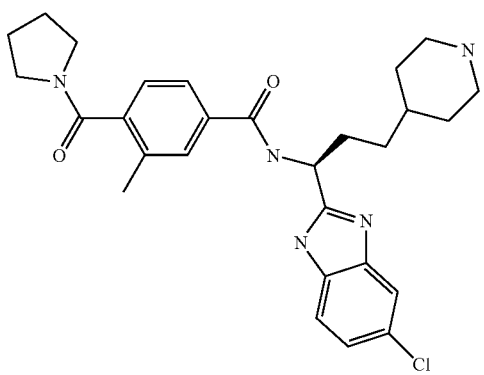

Prepared analogously to Example 94 from N-[(1S)-3-[1-(benzyloxycarbonyl)piperidin-4-yl]-1-(5-chloro-1H-benzimidazol-2-yl)propyl]-3-methyl-4-(pyrrolidin-1-ylcarbonyl)benzamide and iodotrimethylsilane in dichloromethane. Yield: quantitative; $R_f$ value: 0.11 (silica gel: dichloromethane/ethanol=9:1); $C_{28}H_{34}ClN_5O_2$ (508.063); mass spectrum: $(M+H)^+=508/510$ (chlorine isotope).

Example 291 rac.-N-[1-(5-chloro-1H-benzimidazol-2-yl)ethyl]-3-methyl-4-(pyrrol-1-ylcarbonyl)benzamide

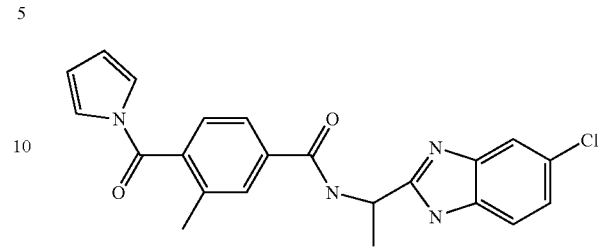

200 mg (0.49 mmol) of rac.-N-[1-(5-chloro-1H-benzimidazol-2-yl)ethyl]-3-methyl-4-(2,5-dihydropyrrol-1-ylcarbonyl)benzamide and 167 mg (0.73 mmol) of 2,3-dichloro-5,6-dicyano-p-benzoquinone are stirred in 5 mL dioxane for 10 hours at 100° C. Then the solvent is distilled off and the residue is chromatographed on silica gel, eluting with dichloromethane/methanol (0%-6%). Yield: 30 mg (15%); $R_f$ value: 0.62 (silica gel: dichloromethane/ethanol=9:1); $C_{22}H_{19}ClN_4O_2$ (406.875); mass spectrum: $(M+H)^+=407/409$ (chlorine isotope).

Example 292

3-bromo-N-[(1S)-1-(5-chloro-1H-benzimidazol-2-yl)ethyl]-4-(thiazolidin-3-ylcarbonyl)benzamide

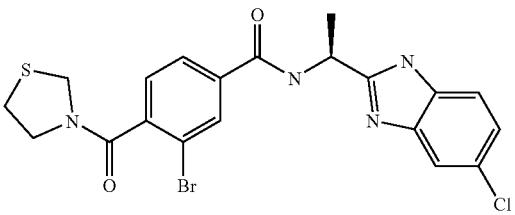

Prepared analogously to Example 1g from (1S)-2-bromo-4-{N-[1-(5-chloro-1H-benzimidazol-2-yl)ethyl]aminocarbonyl}benzoic acid, TBTU, diisopropylethylamine and thiazolidine in dimethylformamide. Yield: 43%; $R_f$ value: 0.40 (silica gel: dichloromethane/ethanol=9:1); $C_{20}H_{18}BrClN_4O_2S$ (493.813); mass spectrum: $(M-H)^-=493/495/497$ (bromo-chlorine isotope).

Example 293

3-bromo-N-[(1S)-1-(5-chloro-1H-benzimidazol-2-yl)ethyl]4-[(2R/S)-2-methylpyrrolidin-1-ylcarbonyl]benzamide

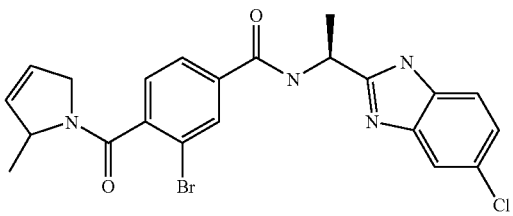

227

Prepared analogously to Example 1g from (1S)-2-bromo-4-{N-[1-(5-chloro-1H-benzimidazol-2-yl)ethyl]aminocarbonyl}benzoic acid, TBTU, diisopropylethylamine and rac.-2-methylpyrrolidine in dimethylformamide. Yield: 22%; $R_f$ value: 0.45 (silica gel: dichloromethane/ethanol=9:1); $C_{22}H_{22}BrClN_4O_2$ (489.799); mass spectrum: $(M+H)^+$=489/491/493 (bromo-chlorine isotope).

Example 294

3-bromo-4-[(2R/S)-2-(tert-butoxycarbonylaminomethyl)thiazolidin-3-ylcarbonyl]-N-[(1S)-1-(5-chloro-1H-benzimidazol-2-yl)ethyl]benzamide

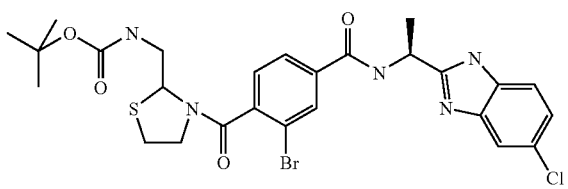

Prepared analogously to Example 1g from (1S)-2-bromo-4-{N-[1-(5-chloro-1H-benzimidazol-2-yl)ethyl]aminocarbonyl}benzoic acid, TBTU, diisopropylethylamine and rac.-2-(tert-butoxycarbonylaminomethyl)thiazolidine in dimethylformamide. Yield: 23%; $R_f$ value: 0.52 (silica gel: dichloromethane/methanol/glacial acetic acid=9:1:0.1); $C_{26}H_{29}BrClN_5O_4S$ (622.969); mass spectrum: $(M-H)^-$=620/622/624 (bromo-chlorine isotope).

Example 295

N-[1S)-1-(6-amino-5-chloro-1H-benzimidazol-2-yl)ethyl]-3-methyl-4-(pyrrolidin-1-ylcarbonyl)benzamide

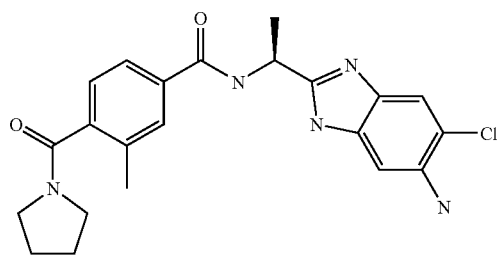

Prepared analogously to Example 187 from N-[(1S)-1-(5-chloro-6-nitro-1H-benzimidazol-2-yl)ethyl]-3-methyl-4-(pyrrolidin-1-ylcarbonyl)benzamide, Raney nickel and hydrogen in ethyl acetate. Yield: 50%; $R_f$ value: 0.55 (silica gel: dichloromethane/methanol/ammonia=9:1:0.1); $C_{22}H_{24}ClN_5O_2$ (425.918); mass spectrum: $(M+H)^+$=426/428 (chlorine isotope).

228

Example 296

4-[(2R/S)-2-aminomethylthiazolidin-3-ylcarbonyl]-3-bromo-N-[(1S)-1-(5-chloro-1H-benzimidazol-2-yl)ethyl]benzamide

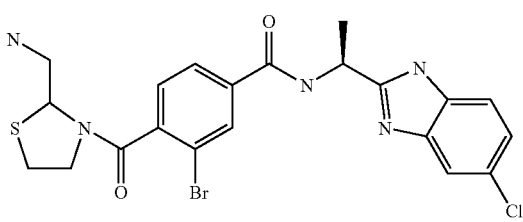

Prepared analogously to Example 17 from 3-bromo-4-[(2R/S)-2-(tert-butoxycarbonyl-aminomethyl)thiazolidin-3-ylcarbonyl]-N-[(1S)-1-(5-chloro-1H-benzimidazol-2-yl)ethyl]benzamide and trifluoroacetic acid. Yield: 58%; $R_f$ value: 0.30 (silica gel: dichloromethane/methanol/ammonia=9:1:0.1); $C_{21}H_{21}BrClN_5O_2S$ (522.853); mass spectrum: $(M+H)^+$=522/524/526 (bromo-chlorine. isotope).

Example 297

N-[(1S)-1-(5-chloro-H-benzimidazol-2-yl)ethyl]-4-[N-ethyl-N-(6-methoxyhexanoyl)amino]-3-methyl-benzamide

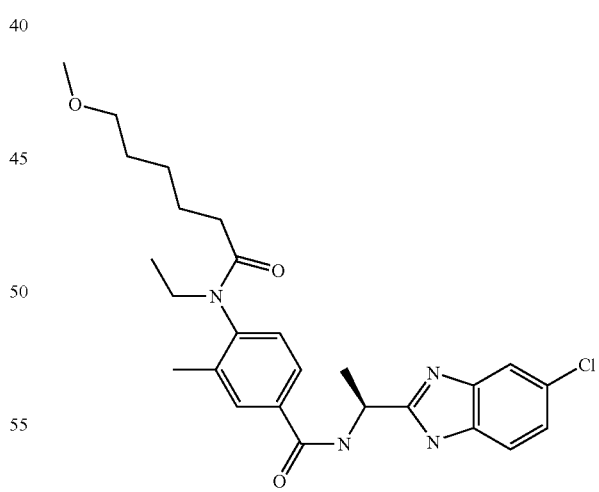

Prepared analogously to Example 1g from 4-[N-ethyl-N-(6-methoxyhexanoyl)amino]-3-methylbenzoic acid, TBTU, diisopropylethylamine and (1S)-1-(5-chloro-1H-benzimidazol-2-yl)ethylamine in tetrahydrofuran. Yield: 72%; $R_f$ value: 0.50 (silica gel: dichloromethane/ethanol=19:1); $C_{26}H_{33}ClN_4O_3$ (485.025); mass spectrum: $(M+H)^+$=485/487 (chlorine isotope).

Example 298

N-[(1S)-1-(5-chloro-1H-benzimidazol-2-yl)ethyl]-4-[(3R/S)-3-fluoropyrrolidin-1-ylcarbonyl]-3-methyl-benzamide

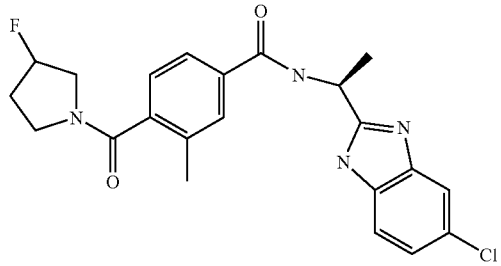

Prepared analogously to Example 1g from rac.-4-(3-fluoropyrrolidin-1-ylcarbonyl)-3-methylbenzoic acid, TBTU, diisopropylethylamine and (1S)-1-(5-chloro-1H-benzimidazol-2-yl)ethylamine in tetrahydrofuran. Yield: 49%; $R_f$ value: 0.30 (silica gel: dichloromethane/ethanol=9:1); $C_{22}H_{22}ClFN_4O_2$ (428.893); mass spectrum: $(M+H)^+=429/431$ (chlorine isotope).

Example 299

N-[(1R)-2-benzyloxy-1-(5-chloro-1H-benzimidazol-2-yl)ethyl]-3-bromo-4-(2,5-dihydropyrrol-1-ylcarbonyl)benzamide

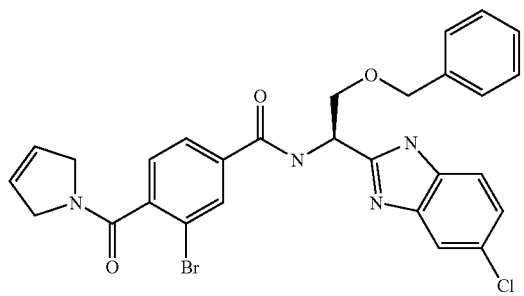

Prepared analogously to Example 1g from 3-bromo-4-(2,5-dihydropyrrol-1-ylcarbonyl)benzoic acid, TBTU, diisopropylethylamine, and (1R)-2-benzyloxy-1-(5-chloro-1H-benzimidazol-2-yl)ethylamine in tetrahydrofuran. Yield: 86%; $R_f$ value: 0.53 (silica gel: dichloromethane/ethanol=9:1); $C_{28}H_{24}BrClN_4O_3$ (579.88); mass spectrum: $(M+H)^+=579/581/583$ (bromo-chlorine isotope).

Example 300

N-[(1S)-1-(5-chloro-1H-benzimidazol-2-yl)butyl]-4-(2,5-dihydropyrrol-1-ylcarbonyl)-3-methylbenzamide

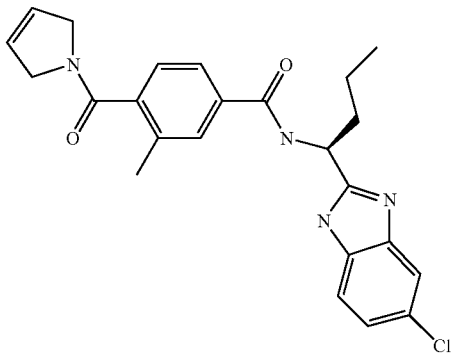

Prepared analogously to Example 1g from 4-(2,5-dihydropyrrol-1-ylcarbonyl)-3-methylbenzoic acid, TBTU, diisopropylethylamine and (1S)-1-(5-chloro-1H-benzimidazol-2-yl)butylamine in tetrahydrofuran. Yield: quantitative; $R_f$ value: 0.55 (silica gel: dichloromethane/ethanol=9:1); $C_{24}H_{25}ClN_4O_2$ (436.94); mass spectrum: $(M+H)^+=437/439$ (chlorine isotope).

Example 301

3-chloro-N-[(1S)-1-(5-chloro-1H-benzimidazol-2-yl)butyl]4-(2,5-dihydropyrrol-1-ylcarbonyl)benzamide

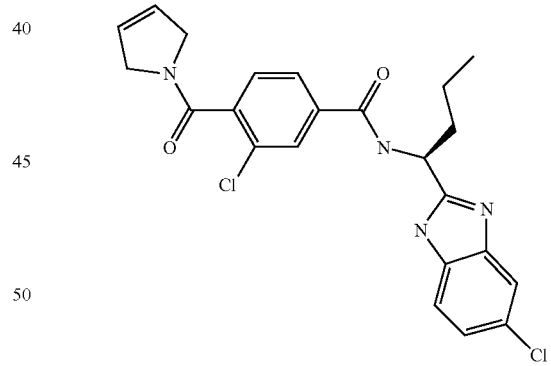

Prepared analogously to Example 1g from 3-chloro-4-(2,5-dihydropyrrol-1-ylcarbonyl)benzoic acid, TBTU, diisopropylethylamine, and (1S)-1-(5-chloro-1H-benzimidazol-2-yl)butylamine in tetrahydrofuran. Yield: quantitative; $R_f$ value: 0.49 (silica gel: dichloromethane/ethanol=9:1); $C_{23}H_{22}Cl_2N_4O_2$ (457.359); mass spectrum: $(M+H)^+=457/459/461$ (chlorine isotope).

Example 302

3-bromo-N-[(1S)-1-(5-chloro-1H-benzimidazol-2-yl)butyl]-4-(2,5-dihydropyrrol-1-ylcarbonyl)benzamide

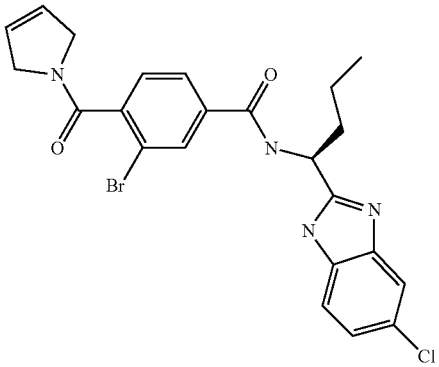

Prepared analogously to Example 1g from 3-bromo-4-(2,5-dihydropyrrol-1-ylcarbonyl)benzoic acid, TBTU, diisopropylethylamine, and (1S)-1-(5-chloro-1H-benzimidazol-2-yl)butylamine in tetrahydrofuran. Yield: quantitative; $R_f$ value: 0.57 (silica gel: dichloromethane/ethanol=9:1); $C_{23}H_{22}BrClN_4O_2$ (501.814); mass spectrum: $(M+H)^+=501/503/505$ (bromo-chlorine isotope).

Example 303

3-chloro-N-[(1S)-1-(5-chloro-1H-benzimidazol-2-yl)ethyl]4-[(2S)-2-(pyrrolidin-1-ylmethyl)pyrrolidin-1-ylcarbonyl]benzamide

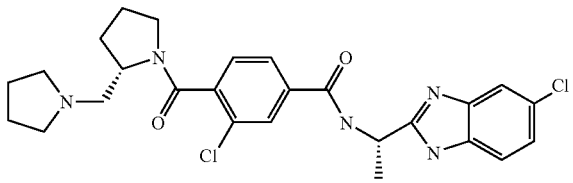

Prepared analogously to Example 1g from (1S)-2-chloro-4-{N-[1-(5-chloro-1H-benzimidazol-2-yl)ethyl]aminocarbonyl}benzoic acid, TBTU, diisopropylethylamine, and (2S)-2-(pyrrolidin-1-ylmethyl)pyrrolidine in tetrahydrofuran. Yield: 74%; $R_f$ value: 0.10 (silica gel: dichloromethane/ethanol=4:1); $C_{26}H_{29}Cl_2N_5O_2$ (514.454); mass spectrum: $(M+H)^+=514/516/518$ (chlorine isotope).

Example 304

3-chloro-N-[(1S)-1-(5-chloro-1H-benzimidazol-2-yl)ethyl]-4-[(2R/S)-2-(2-pyrrolidin 1-ylcarbonylethyl)pyrrolidin-1-ylcarbonyl]benzamide

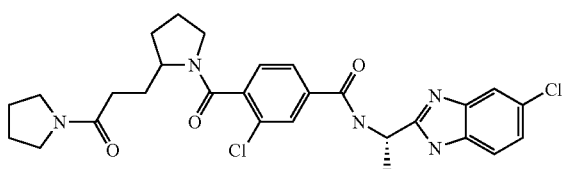

Prepared analogously to Example 1g from 3-chloro-N-[(1S)-1-(5-chloro-1H-benzimidazol-2-yl)ethyl]-4-[(2R/S)-2-(hydroxycarbonylethyl)pyrrolidin-1-ylcarbonyl]benzamide, TBTU, diisopropylethylamine, and pyrrolidine in tetrahydrofuran. Yield: 22%; $R_f$ value: 0.53 (silica gel: dichloromethane/ethanol=9:1); $C_{28}H_{31}Cl_2N_5O_3$ (556.497); mass spectrum: $(M+H)^+=556/558/560$ (chlorine isotope).

Example 305

3-chloro-N-[(1S)-1-(5-chloro-1H-benzimidazol-2-yl)ethyl]4-[(2R)-2-(ethoxycarbonyl-methyl)pyrrolidin-1-ylcarbonyl]benzamide

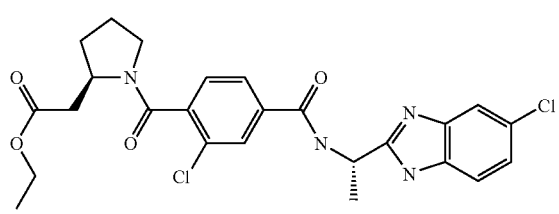

Prepared analogously to Example 1g from (1S)-2-chloro-4-{N-[1-(5-chloro-1H-benzimidazol-2-yl)ethyl]aminocarbonyl}benzoic acid, TBTU, diisopropylethylamine, and (2R)-2-(ethoxy-carbonylmethyl)pyrrolidine in tetrahydrofuran. Yield: 59%; $R_f$ value: 0.42 (silica gel: dichloromethane/ethanol=9:1); $C_{25}H_{26}Cl_2N_4O_4$ (517.271); mass spectrum: $(M+H)^+=517/519/521$ (chlorine isotope).

Example 306

N-[(1S)-1-(5-chloro-1H-benzimidazol-2-yl)ethyl]4-(2,5-dihydropyrrol-1-ylcarbonyl)-3-methylbenzamide

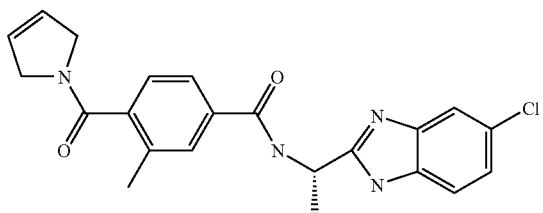

Prepared analogously to Example 1g from 4-(2,5-dihydropyrrol-1-ylcarbonyl)-3-methylbenzoic acid, TBTU, diisopropylethylamine, and (1S)-1-(5-chloro-1H-benzimidazol-2-yl)ethylamine in tetrahydrofuran. Yield: 96%; $R_f$ value: 0.50 (silica gel: dichloromethane/ethanol=9:1); $C_{22}H_{21}ClN_4O_2$ (408.887); mass spectrum: $(M+H)^+=409/411$ (chlorine isotope).

Example 307

3-chloro-N-[(1S)-1-(5-chloro-1H-benzimidazol-2-yl)ethyl]-4-(2,5-dihydropyrrol-1-ylcarbonyl)benzamide

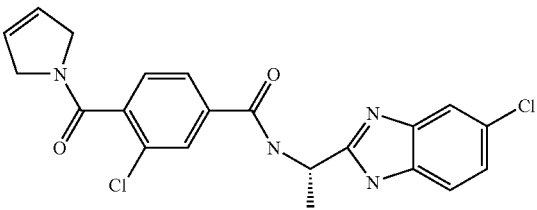

Prepared analogously to Example 1 g from 3-chloro-4-(2,5-dihydropyrrol-1-ylcarbonyl)benzoic acid, TBTU, diisopropylethylamine, and (1S)-1-(5-chloro-1H-benzimidazol-2-yl)ethylamine in tetrahydrofuran. Yield: quantitative; $R_f$ value: 0.50 (silica gel: dichloromethane/ethanol=9:1); $C_{21}H_{18}Cl_2N_4O_2$ (429.305); mass spectrum: $(M+H)^+=429/431/433$ (chlorine isotope).

Example 308

3-chloro-N-[(1S)-1-(5-chloro-1H-benzimidazol-2-yl)ethyl]-4-[(2R/S)-2-(2-methylamino-carbonylethyl)pyrrolidin-1-ylcarbonyl]benzamide

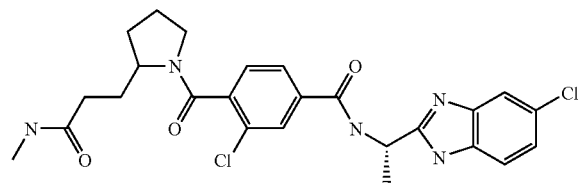

Prepared analogously to Example 1g from 3-chloro-N-[(1S)-1-(5-chloro-1H-benzimidazol-2-yl)ethyl]-4-[(2R/S)-2-(hydroxycarbonylethyl)pyrrolidin-1-ylcarbonyl]benzamide, TBTU, diisopropylethylamine, and methylamine in tetrahydrofuran. Yield: 35%; $R_f$ value: 0.38 (silica gel: dichloromethane/ethanol=9:1); $C_{25}H_{27}Cl_2N_5O_3$ (516.426); mass spectrum: $(M+H)^+=516/518/520$ (chlorine isotope).

Example 309

3-chloro-N-[(1S)-1-(5-chloro-1H-benzimidazol-2-yl)ethyl]-4-[(2R)-2-(hydroxycarbonyl-methyl)pyrrolidin-1-ylcarbonyl]benzamide

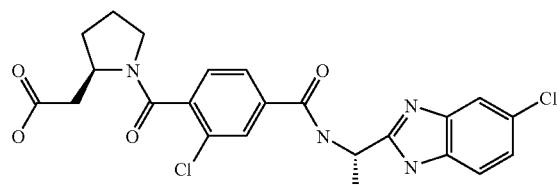

Prepared analogously to Example 19b from 3-chloro-N-[(1S)-1-(5-chloro-1H-benzimidazol-2-yl)ethyl]-4-[(2R)-2-(ethoxycarbonylmethyl)pyrrolidin-1-ylcarbonyl]benzamide and lithium hydroxide in tetrahydrofuran. Yield: 74%; $R_f$ value: 0.32 (Reversed phase RP 8: methanol/5% sodium chloride solution=6:4); $C_{23}H_{22}Cl_2N_4O_4$ (489.357); mass spectrum: $(M+H)^+=489/491/493$ (chlorine isotope).

Example 310

3-bromo-N-[(1S)-1-(5-bromo-1H-benzimidazol-2-yl)ethyl]-4-(2,5-dihydropyrrol-1-ylcarbonyl)benzamide

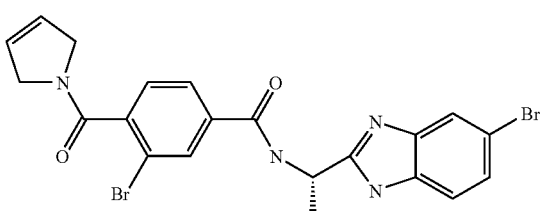

Prepared analogously to Example 1g from 3-bromo-4-(2,5-dihydropyrrol-1-ylcarbonyl)benzoic acid, TBTU, diisopropylethylamine, and (1S)-1-(5-bromo-1H-benzimidazol-2-yl)ethylamine in tetrahydrofuran. Yield: 72%; $R_f$ value: 0.50 (silica gel: dichloromethane/ethanol=9:1); $C_{21}H_{18}Br_2N_4O_2$ (518.207); mass spectrum: $(M+H)^+=517/519/521$ (bromo-chlorine isotope).

Example 311

N-[(1R)-1-(5-chloro-1H-benzimidazol-2-yl)-2-methylsulfanylethyl]-4-(2,5-dihydropyrrol-1-ylcarbonyl)-3-methylbenzamide

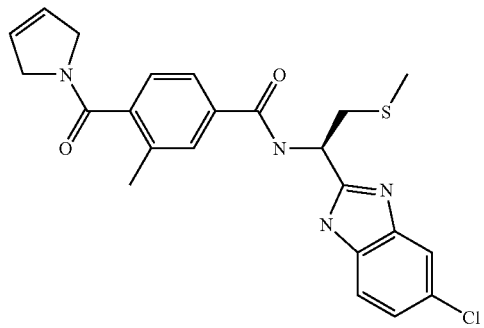

Prepared analogously to Example 1g from 4-(2,5-dihydropyrrol-1-ylcarbonyl)-3-methylbenzoic acid, TBTU, diisopropylethylamine, and (1R)-1-(5-chloro-1H-benzimidazol-2-yl)-2-methylsulfanylethylamine in tetrahydrofuran. Yield: 43%; $R_f$ value: 0.47 (silica gel: dichloromethane/ethanol=9:1); $C_{23}H_{23}ClN_4O_2S$ (454.98); mass spectrum: $(M+H)^+=455/457$ (chlorine isotope).

Example 312

4-(N-acetyl-N-cyclopentylamino)-N-[(1S)-1-(5-chloro-1H-benzimidazol-2-yl)-2-methyl-sulfanylethyl]-3-methylbenzamide

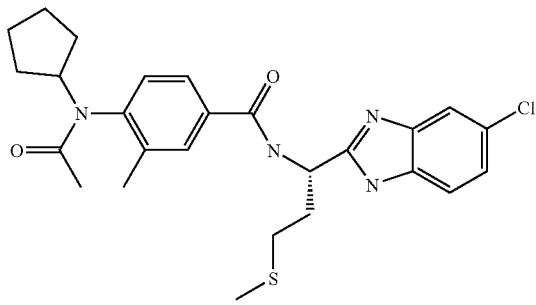

Prepared analogously to Example 1g from 4-(N-acetyl-N-cyclopentylamino)-3-methylbenzoic acid, TBTU, diisopropylethylamine, and (1S)-1-(5-chloro-1H-benzimidazol-2-yl)-3-methylsulfanylpropylamine in tetrahydrofuran. Yield: 9%; $R_f$ value: 0.68 (silica gel: dichloromethane/ethanol=9:1); $C_{26}H_{31}ClN_4O_2S$ (499.076); mass spectrum: $(M+H)^+=499/501$ (chlorine isotope) and $(M-H)^-=497/499$ (chlorine isotope).

Example 313

4-(N-acetyl-N-cyclopentylamino)-N-[(1S)-1-(5-chloro-1H-benzimidazol-2-yl)ethyl]-3-methylbenzamide

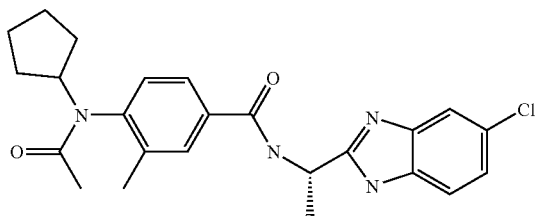

Prepared analogously to Example 1g from 4-(N-acetyl-N-cyclopentylamino)-3-methylbenzoic acid, TBTU, diisopropylethylamine, and (1S)-1-(5-chloro-1H-benzimidazol-2-yl)ethylamine in tetrahydrofuran. Yield: quantitative; $R_f$ value: 0.64 (silica gel: dichloromethane/ethanol=9:1); $C_{24}H_{27}ClN_4O_2$ (438.956); mass spectrum: $(M+H)^+=439/441$ (chlorine isotope). Example 314

3-chloro-N-[(1S)-1-(5-chloro-1H-benzimidazol-2-yl)ethyl]-4-[(2R)-2-methylaminocarbonylmethylpyrrolidin-1-yl]benzamide

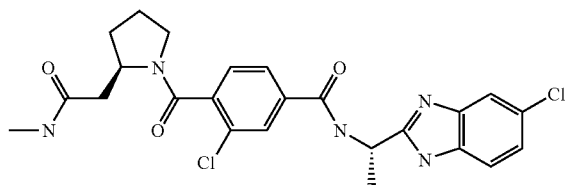

Prepared analogously to Example 1g from 3-chloro-N-[(1S)-1-(5-chloro-1H-benzimidazol-2-yl)ethyl]-4-[(2R)-2-(hydroxycarbonylmethyl)pyrrolidin-1-ylcarbonyl]benzamide, TBTU, diisopropylethylamine, and methylamine in tetrahydrofuran. Yield: 60%; $R_f$ value: 0.44 (silica gel: dichloromethane/ethanol=9:1); $C_{24}H_{25}Cl_2N_5O_3$ (502.405); mass spectrum: $(M+H)^+=502/504/506$ (chlorine isotope) and $(M-H)^-=500/502/504$ (chlorine isotope).

Example 315

N-[(1S)-1-(5-chloro-1H-benzimidazol-2-yl)ethyl]-4-(2,5-dihydropyrrol-1-ylcarbonyl)-3-trifluoromethyl-benzamide

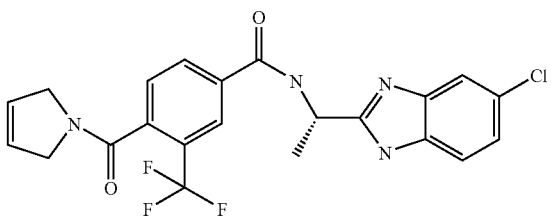

Prepared analogously to Example 1g from (1S)-2-trifluoromethyl-4-{N-[1-(5-chloro-1H-benzimidazol-2-yl)ethyl]aminocarbonyl}benzoic acid, TBTU, diisopropylethylamine, and 3-pyrroline in tetrahydrofuran. Yield: 55%; $R_f$ value: 0.50 (silica gel: dichloromethane/ethanol=9:1); $C_{22}H_{18}ClF_3N_4O_2$ (462.863); mass spectrum: $(M+H)^+=463/465$ (chlorine isotope) and $(M-H)^-=461/463$ (chlorine isotope).

Example 316

3-chloro-N-[(1S)-1-(5-chloro-1H-benzimidazol-2-yl)ethyl]-4-[(2R)-2-(imidazol-1-ylmethyl)pyrrolidin-1-ylcarbonyl]benzamide

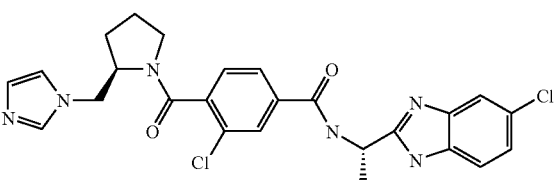

Prepared analogously to Example 1g from 2-chloro-4-{N-[(1S)-1-(5-chloro-1H-benzimidazol-2-yl)ethyl]aminocarbonyl}benzoic acid, TBTU, diisopropylethylamine, and (R)-1-(pyrrolidin-2-ylmethyl)-1H-imidazole in tetrahydrofuran. Yield: 50%; $R_f$ value: 0.20 (silica gel: dichloromethane/methanol=9:1); $C_{25}H_{24}C_{12}N_6O_2$ (511.415); mass spectrum: $(M+H)^+=511/513/515$ (chlorine isotope).

Example 317

3-chloro-N-[(1S)-1-(5-chloro-1H-benzimidazol-2-yl)ethyl]-4-[(2R)-2-(pyrrolidin-1-ylmethyl)pyrrolidin-1-ylcarbonyl]benzamide

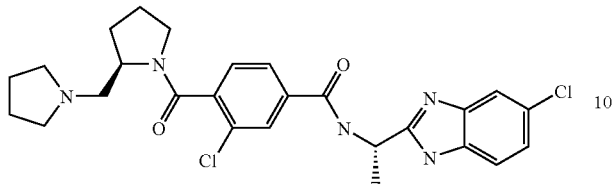

Prepared analogously to Example 1g from (1S)-2-chloro-4-{N-[1-(5-chloro-1H-benzimidazol-2-yl)ethyl]aminocarbonyl}benzoic acid, TBTU, diisopropylethylamine, and (2R)-2-(pyrrolidin-1-ylmethyl)pyrrolidine in tetrahydrofuran. Yield: 11%; $C_{26}H_{29}Cl_2N_5O_2$ (514.454); mass spectrum: $(M+H)^+=514/516/518$ (chlorine isotope).

Example 318

3-bromo-N-[(1R)-1-(5-bromo-1H-benzimidazol-2-yl)-2-methoxyethyl]-4-(2,5-dihydropyrrol 1-ylcarbonyl)benzamide

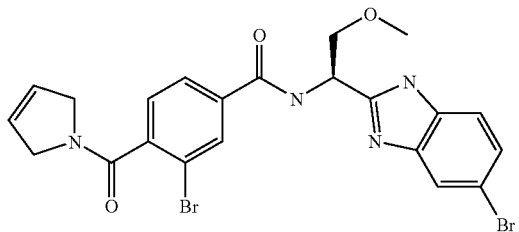

Prepared analogously to Example 1g from 3-bromo-4-(2,5-dihydropyrrol-1-ylcarbonyl)benzoic acid, TBTU, diisopropylethylamine, and (1R)-1-(5-bromo-1H-benzimidazol-2-yl)-2-methoxyethylamine in tetrahydrofuran. Yield: 62%; $R_f$ value: 0.45 (silica gel: dichloromethane/ethanol=95:5); $C_{22}H_{20}Br_2N_4O_3$ (548.233); mass spectrum: $(M+H)^+=547/549/551$ (chlorine isotope).

Example 319

N-[(1S)-1-(5-chloro-1H-benzimidazol-2-yl)butyl]-4-(2,5-dihydropyrrol-1-ylcarbonyl)-2-trifluoromethyl-benzamide

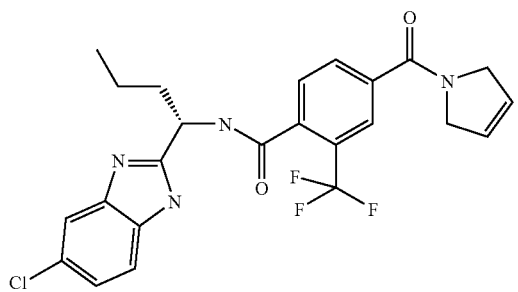

Prepared analogously to Example 1g from (1S)-3-trifluoromethyl-4-{N-[1-(5-chloro-1H-benzimidazol-2-yl)butyl]aminocarbonyl}benzoic acid, TBTU, diisopropylethylamine, and 3-pyrroline in tetrahydrofuran. Yield: 64%; $R_f$ value: 0.47 (silica gel: dichloromethane/ethanol=9:1); $C_{24}H_{22}ClF_3N_4O_2$ (490.911); mass spectrum: $(M+H)^+=491/493$ (chlorine isotope).

Example 320

N-[(1S)-1-(5-chloro-1H-benzimidazol-2-yl)-3-(1,1-dioxoisothiazolidin-2-yl)propyl]-3-methyl-4-(pyrrolidin-1-ylcarbonyl)benzamide

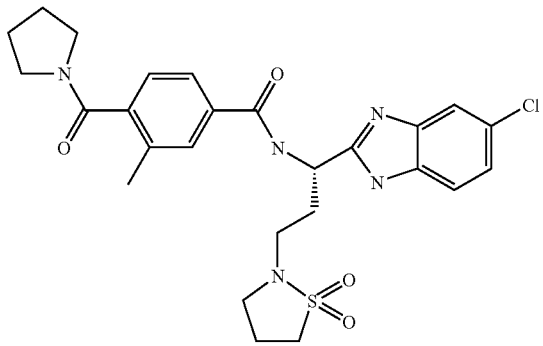

130 mg (0.22 mmol) of N-[(1S)-1-(5-chloro-1H-benzimidazol-2-yl)-3-(3-chloropropylsulfonylamino)propyl]-3-methyl-4-(pyrrolidin-1-ylcarbonyl)benzamide is dissolved in 5 mL of dimethylformamide and, after the addition of 21 mg (0.45 mmol) of sodium hydride (50% in oil), stirred for 2 hours at ambient temperature. Then it is combined with water and extracted with ethyl acetate. The combined organic extracts are dried over sodium sulfate and concentrated by evaporation. Yield: 90 mg (70%); $R_f$ value: 0.40 (silica gel: dichloromethane/ethanol=9:1); $C_{26}H_{30}ClN_5O_4S$ (544.077); mass spectrum: $(M+H)^+=545/547$ (chlorine isotope).

Example 321

3-bromo-N-[(1R)-1-(5-chloro-1H-benzimidazol-2-yl)-2-ethoxyethyl]-4-(2,5-dihydropyrrol-1-ylcarbonyl)benzamide

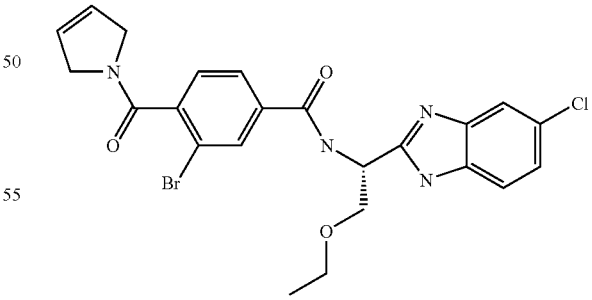

Prepared analogously to Example 1g from 3-bromo-4-(2,5-dihydropyrrol-1-ylcarbonyl)benzoic acid, TBTU, diisopropylethylamine and (1R)-1-(5-chloro-1H-benzimidazol-2-yl)-2-ethoxyethylamine in tetrahydrofuran. Yield: 32%; $R_f$ value: 0.5 (silica gel: dichloromethane/ethanol=9:1); $C_{23}H_{22}BrClN_4O_3$ (517.809); mass spectrum: $(M+H)^+=517/519/521$ (bromo-chlorine isotope).

Example 322

3-chloro-N-[(1R,2R)-1-(5-chloro-1H-benzimidazol-2-yl)-2-methoxypropyl]-4-(2,5-dihydropyrrol-1-ylcarbonyl)benzamide

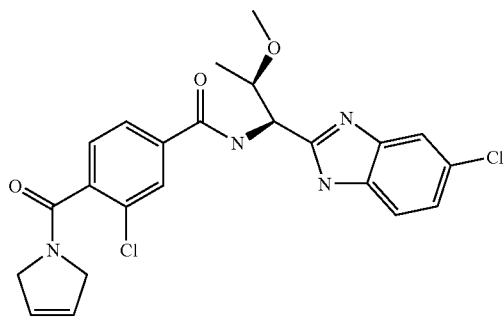

Prepared analogously to Example 1g from 3-chloro-4-(2,5-dihydropyrrol-1-ylcarbonyl)benzoic acid, TBTU, diisopropylethylamine and (1R,2R)-1-(5-chloro-1H-benzimidazol-2-yl)-2-methoxypropylamine in tetrahydrofuran. Yield: 72%; $R_f$ value: 0.56 (silica gel: dichloromethane/ethanol=9:1); $C_{23}H_{22}Cl_2N_4O_3$ (473.358); mass spectrum: $(M+H)^+$=473/475/479 (chlorine isotope) and $(M-H)^-$=471/473/475 (chlorine isotope).

Example 323

N-[(1R)-2-allyloxy-1-(5-chloro-1H-benzimidazol-2-yl)ethyl]-4-(2,5-dihydropyrrol 1-ylcarbonyl)-3-methylbenzamide

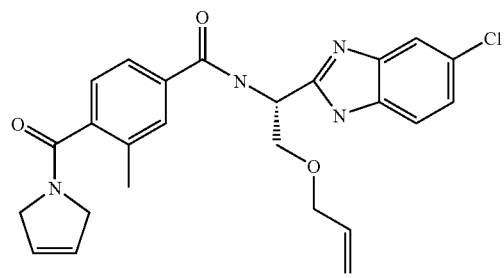

Prepared analogously to Example 1g from 3-methyl-4-(2,5-dihydropyrrol-1-ylcarbonyl)benzoic acid, TBTU, diisopropylethylamine, and (1R)-2-allyloxy-1-(5-chloro-1H-benzimidazol-2-yl)ethylamine in tetrahydrofuran. Yield: 63%; $R_f$ value: 0.60 (silica gel: dichloromethane/ethanol=9:1); $C_{25}H_{25}ClN_4O_3$ (464.951); mass spectrum: $(M+H)^+$=465/467 (chlorine isotope) and $(M-H)^-$=463/465 (chlorine isotope).

Example 324

N-[(1R,2S)-2-tert-butoxy-1-(5-chloro-1H-benzimidazol-2-yl)propyl]-4-(2,5-dihydropyrrol-1-ylcarbonyl)-3-methylbenzamide

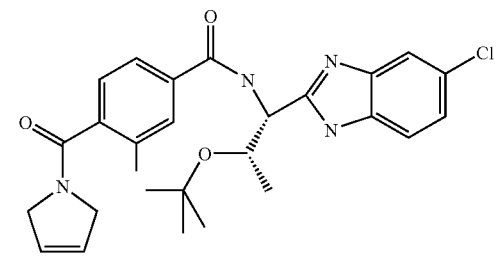

Prepared analogously to Example 1g from 3-methyl-4-(2,5-dihydropyrrol-1-ylcarbonyl)benzoic acid, TBTU, diisopropylethylamine, and (1R,2S)-2-tert-butoxy-1-(5-chloro-1H-benzimidazol-2-yl)propylamine in tetrahydrofuran. Yield: 86%; $R_f$ value: 0.61 (silica gel: dichloromethane/ethanol=9:1); $C_{27}H_{31}ClN_4O_3$ (495.02); mass spectrum: $(M+H)^+$=495/497 (chlorine isotope).

Example 325

N-[(1R,2S)-1-(5-chloro-1H-benzimidazol-2-yl)-2-hydroxypropyl]-4-(2,5-dihydropyrrol-1-ylcarbonyl)-3-methylbenzamide

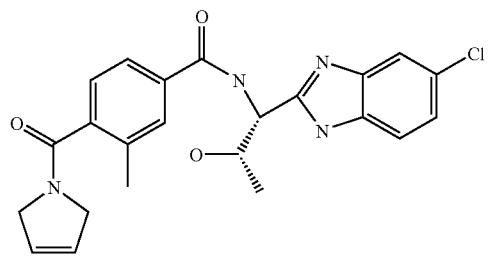

Prepared analogously to Example 17 from N-[(1R,2S)-2-tert-butoxy-1-(5-chloro-1H-benzimidazol-2-yl)propyl]-4-(2,5-dihydropyrrol-1-ylcarbonyl)-3-methylbenzamide, and trifluoroacetic acid. Yield: 99%; $R_f$ value: 0.48 (silica gel: dichloromethane/ethanol=9:1); $C_{23}H_{23}ClN_4O_3$ (438.913); mass spectrum: $(M+H)^+$=439/441 (chlorine isotope) and $(M-H)^-$=437/439 (chlorine isotope).

Example 326

4-{(2R)-2-[(N-acetyl-N-methylamino)methyl]pyrrolidin-1-ylcarbonyl}-N-[(1S)-1-(5-chloro-1H-benzimidazol-2-yl)ethyl]-3-chlorobenzamide

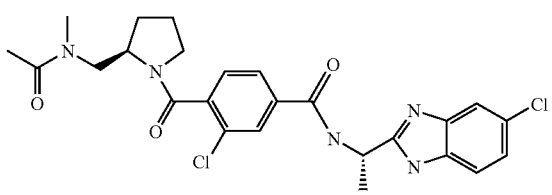

Prepared analogously to Example 1g from (1S)-2-chloro-4-{N-[1-(5-chloro-1H-benzimidazol-2-yl)ethyl]aminocarbonyl}benzoic acid, TBTU, diisopropylethylamine, and (R)-2-[(N-acetyl-N-methylamino)methyl]pyrrolidine in tetrahydrofuran. Yield: 17%; $R_f$ value: 0.40 (silica gel: dichloromethane/ethanol=9:1); $C_{25}H_{27}Cl_2N_5O_3$ (516.426); mass spectrum: $(M+H)^+$=516/518/520 (chlorine isotope).

Example 327

4-benzoyl-N-[(1S)-1-(5-chloro-1H-benzimidazol-2-yl)ethyl]-3-methylbenzamide

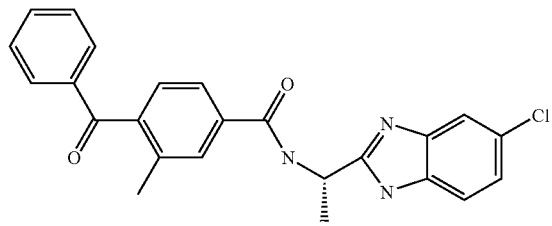

Prepared analogously to Example 1g from 4-benzoyl-3-methylbenzoic acid, TBTU, diisopropylethylamine, and (1S)-1-(5-chloro-1H-benzimidazol-2-yl)ethylamine in tetrahydrofuran. Yield: 91%; $R_f$ value: 0.54 (silica gel: dichloromethane/ethanol=9:1); $C_{24}H_{20}ClN_3O_2$ (417.894); mass spectrum: $(M+H)^+=418/420$ (chlorine isotope) and $(M-H)^-=416/418$ (chlorine isotope).

Example 328

3-bromo-N-[(1R)-1-(5-chloro-1H-benzimidazol-2-yl)-2-prop-2-ynyloxyethyl]-4-(2,5-dihydropyrrol-1-ylcarbonyl)benzamide

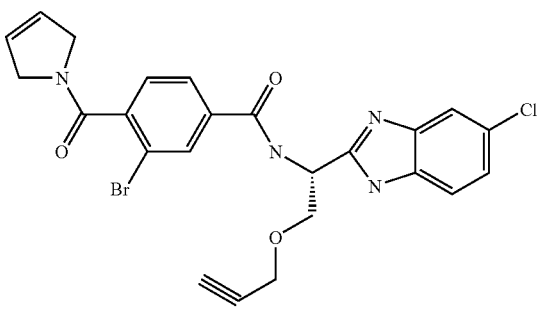

Prepared analogously to Example 1g from 3-bromo-4-(2,5-dihydropyrrol-1-ylcarbonyl)benzoic acid, TBTU, diisopropylethylamine, and (1R)-1-(5-chloro-1H-benzimidazol-2-yl)-2-prop-2-ynyloxyethylamine in tetrahydrofuran. Yield: 92%; $R_f$ value: 0.54 (silica gel: dichloromethane/ethanol=9:1); $C_{24}H_{20}BrClN_4O_3$ (527.804); mass spectrum: $(M+H)^+=527/529/531$ (chlorine isotope).

Example 329

N-[(1S)-1-(5-chloro-1H-benzimidazol-2-yl)-3-(1H-tetrazol-5-yl)propyl]-3-methyl-4-(pyrrolidin-1-ylcarbonyl)benzamide

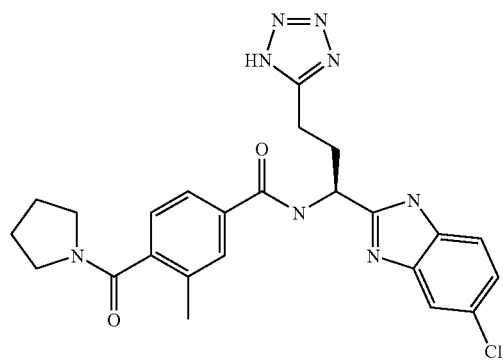

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-3-(1H-tetrazol-5-yl)propylamine in tetrahydrofuran. Yield: 37%; $R_f$ value: 0.25 (silica gel: dichloromethane/ethanol/ammonia=9:1:0.1); $C_{24}H_{25}ClN_8O_2$ (492.97); mass spectrum: $(M+H)^+=493/495$ (chlorine isotope).

Example 330

N-[(1S)-1-(5-chloro-1H-benzimidazol-2-yl)ethyl]-4-(3-methyl-5,6-dihydro-4H-cyclopentapyrazol-1-yl)-3-trifluoromethylbenzamide

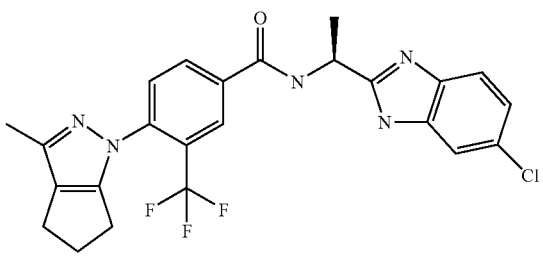

Prepared analogously to Example 1g from 4-(3-methyl-5,6-dihydro-4H-cyclopentapyrazol-1-yl)-3-trifluoromethylbenzoic acid, TBTU, diisopropylethylamine, and (1S)-1-(5-chloro-1H-benzimidazol-2-yl)ethylamine in tetrahydrofuran. Yield: 47%; $R_f$ value: 0.30 (silica gel: dichloromethane/ethanol=9:1); $C_{24}H_{21}ClF_3N_5O$ (487.911); mass spectrum: $(M+H)^+=488/490$ (chlorine isotope) and $(M-H)^-=487/489$ (chlorine isotope).

Example 331

3-chloro-N-[(1S)-1-(5-chloro-1H-benzimidazol-2-yl)ethyl]-4-(4-oxo-4,5,6,7-tetrahydroindol 1-yl)benzamide

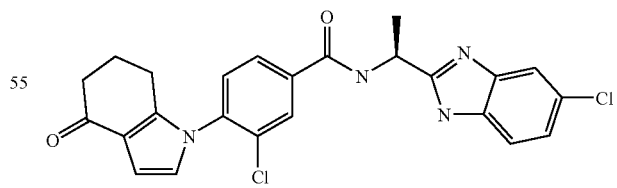

Prepared analogously to Example 1g from 4-(4-oxo-4,5,6,7-tetrahydroindol-1-yl)benzoic acid, TBTU, diisopropylethylamine, and (1S)-1-(5-chloro-1H-benzimidazol-2-yl)ethylamine in tetrahydrofuran. Yield: 54%; $R_f$ value: 0.41 (silica gel: ethyl acetate); $C_{24}H_{20}Cl_2N_4O_2$ (467.354); mass spectrum: $(M+H)^+=467/469/471$ (chlorine isotope).

Example 332

N-[(1R)-1-(5-chloro-1H-benzimidazol-2-yl)-2-hydroxyethyl]-4-(2,5-dihydropyrrol-1-ylcarbonyl)-3-trifluoromethylbenzamide

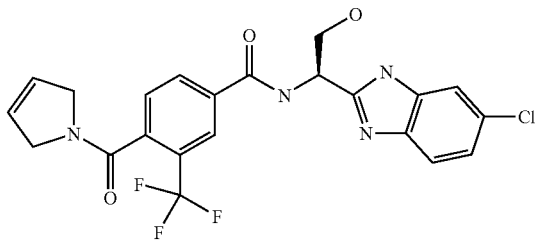

Prepared analogously to Example 1g from 4-(2,5-dihydropyrrol-1-ylcarbonyl)-3-trifluoromethylbenzoic acid, TBTU, diisopropylethylamine, and (1R)-1-(5-chloro-1H-benzimidazol-2-yl)-2-hydroxyethylamine in tetrahydrofuran. Yield: 20%; $R_f$ value: 0.43 (silica gel: dichloromethane/ethanol=9:1); $C_{22}H_{18}ClF_3N_4O_3$ (478.856); mass spectrum: $(M+H)^+=479/481$ (chlorine isotope).

Example 333

N-[(1S)-1-(5-chloro-1H-benzimidazol-2-yl)but-3-ynyl]-3-methyl-4-(pyrrolidin 1-ylcarbonyl)benzamide

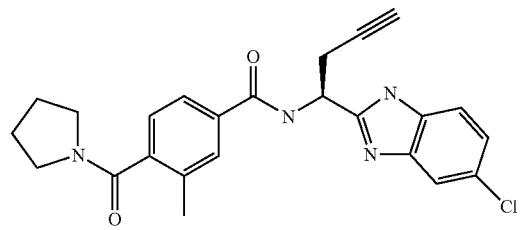

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)but-3-ynylamine in tetrahydrofuran. Yield: 46%; $R_f$ value: 0.42 (silica gel: dichloromethane/ethanol=9:1); $C_{24}H_{23}ClN_4O_2$ (434.925); mass spectrum: $(M+H)^+=435/437$ (chlorine isotope).

Example 334

N-[(1S)-1-(5-hydroxy-1H-benzimidazol-2-yl)ethyl]-3-methyl-4-(pyrrolidin-1-ylcarbonyl)benzamide

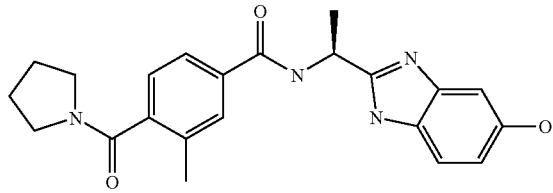

Prepared analogously to Example 1g from 3-methyl 4-(pyrrolidin-1-ylcarbonyl)benzoic acid, TB TU, diisopropylethyl amine, and (1S)-1-(5-hydroxy-1H-benzimidazol-2-yl)ethylamine in tetrahydrofuran. Yield: 12%; $R_f$ value: 0.40 (silica gel: dichloromethane/ethanol/ammonia=9:1:0.1); $C_{22}H_{24}N_4O_3$ (392.457); mass spectrum: $(M+H)^+=393$

Example 335

3-chloro-N-[(1S)-1-(5-chloro-1H-benzimidazol-2-yl)ethyl]-4-(4,5,6,7-tetrahydroindol-1-yl)benzamide

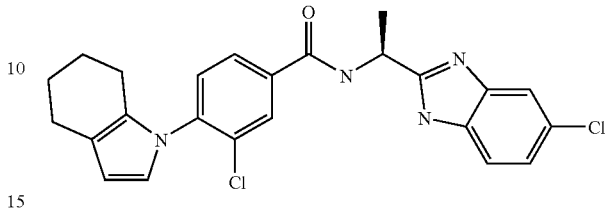

Prepared analogously to Example 1g from 3-chloro-4-(4,5,6,7-tetrahydroindol-1-yl)benzoic acid, TBTU, diisopropylethylamine, and (1S)-1-(5-chloro-1H-benzimidazol-2-yl)ethylamine in tetrahydrofuran. Yield: 25%; $R_f$ value: 0.90 (silica gel: dichloromethane/ethanol/ammonia=4:1:0.1); $C_{24}H_{22}Cl_2N_4O$ (453.371); mass spectrum: $(M+H)^+=453/455/457$ (chlorine isotope).

Example 336

3-chloro-N-[(1S)-1-(5-chloro-1H-benzimidazol-2-yl)ethyl]-4-(4,5,6,7-tetrahydroindazol-1-yl)benzamide

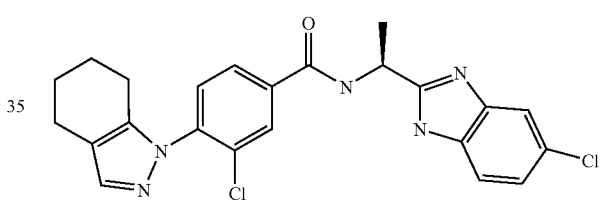

Prepared analogously to Example 1g from 3-chloro-4-(4,5,6,7-tetrahydroindazol-1-yl)benzoic acid, TBTU, diisopropylethylamine, and (1S)-1-(5-chloro-1H-benzimidazol-2-yl)ethylamine in tetrahydrofuran. Yield: 10%; $R_f$ value: 0.70 (silica gel: ethyl acetate); $C_{23}H_{21}Cl_2N_5O$ (454.359); mass spectrum: $(M+H)^+=454/456/458$ (chlorine isotope).

Example 337 rac.-N-[1-(5-chloro-1H-indol-2-yl)ethyl]-3-methyl-4-(pyrrolidin-1-ylcarbonyl)benzamide

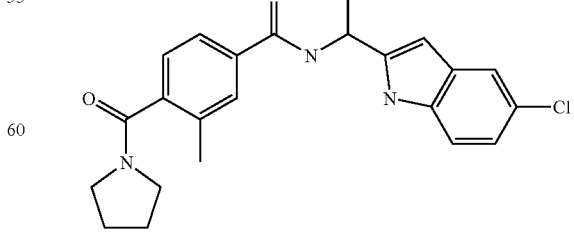

Prepared analogously to Example 1g from 3-methyl-4-(pyrrolidin-1-ylcarbonyl)benzoic acid, TBTU, diisopropylethylamine, and rac.-1-(5-chloro-1H-indol-2-yl)ethylamine in tetrahydrofuran. Yield: 95%; $R_f$ value: 0.65 (silica gel: dichloromethane/ethanol/ammonia=9:1:0.1); $C_{23}H_{24}ClN_3O_2$ (409.915); mass spectrum: $(M+H)^+=410/412$ (chlorine isotope).

Example 338 rac.-N-[(5-chloro-1H-indol-2-yl)phenylmethyl]-3-methyl-4-(pyrrolidin-1-ylcarbonyl)benzamide

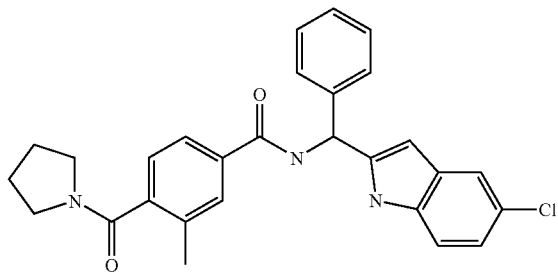

160 mg (0.29 mmol) of N-[(5-chloro-1-methanesulfonyl-1H-indol-2-yl)phenylmethyl]-3-methyl-4-(pyrrolidin-1-ylcarbonyl)benzamide [prepared by amide coupling analogously to Example 1g from rac.-(5-chloro-1H-1-methylsulfonyl-indol-2-yl)phenylmethylamine (synthesized analogously to Tetrahedron Asymmetry, 2000, 11, 1681-1685) and 3-methyl-4-(pyrrolidin-1-ylcarbonyl)benzoic acid] are refluxed for 4 hours in 5 mL of potassium hydroxide solution (5% in methanol). Then the solvent is distilled off, the residue is distributed in ethyl acetate/water, the combined organic extracts are dried and concentrated by evaporation. The crude product is triturated with petroleum ether and suction filtered. Yield: 64 mg (47%); $R_f$ value: 0.39 (silica gel: dichloromethane/ethanol=95:5); $C_{28}H_{26}ClN_3O_2$ (471.985); mass spectrum: $(M+H)^+=472/474$ (chlorine isotope). Example 339 rac.-3-chloro-N-[(5-chloro-1H-indol-2-yl)phenylmethyl]-4-(2,5-dihydropyrrol-1-ylcarbonyl)benzamide

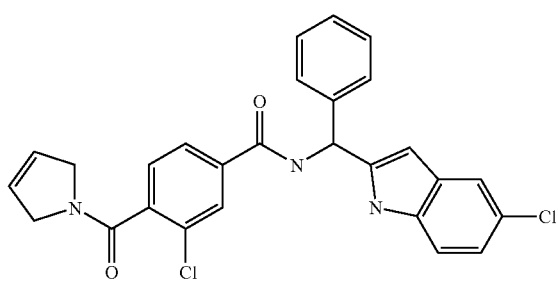

Prepared analogously to Example 1g from 3-chloro-4-(2,5-dihydropyrrol-1-ylcarbonyl)benzoic acid, TBTU, diisopropylethylamine, and rac.-(5-chloro-1H-indol-2-yl)phenylmethylamine in tetrahydrofuran. Yield: 42%; $R_f$ value: 0.58 (silica gel: dichloromethane/ethanol=95:5); $C_{27}H_{21}Cl_2N_3O_2$ (490.388); mass spectrum: $(M+H)^+=490/492/494$ (chlorine isotope).

Example 340 rac.-N-[3-chloro-4-(2,5-dihydropyrrol-1-ylcarbonyl)phenyl]-2-(5-chloro-1H-indol-2-yl)acetamide

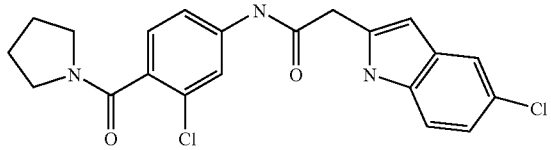

Prepared analogously to Example 1g from 2-(5-chloro-1H-indol-2-yl)acetic acid, TBTU, diisopropylethylamine, and 3-chloro-4-(2,5-dihydropyrrol-1-ylcarbonyl)phenylamine in tetrahydrofuran. Yield: 37%; $R_f$ value: 0.34 (silica gel: dichloromethane/ethanol=95:5); $C_{21}H_{19}Cl_2N_3O_2$ (416.306); mass spectrum: $(M+H)^+=416/418$ (chlorine isotope).

Example 341

N-[(1S)—1-(5-chloro-1H-benzimidazol-2-yl)-3-methylsulfanylpropyl]-4-(4-oxo-2-propyl-4,5-dihydroimidazo[4,5-c]pyridin-1-yl)-3-trifluoromethyl-benzamide

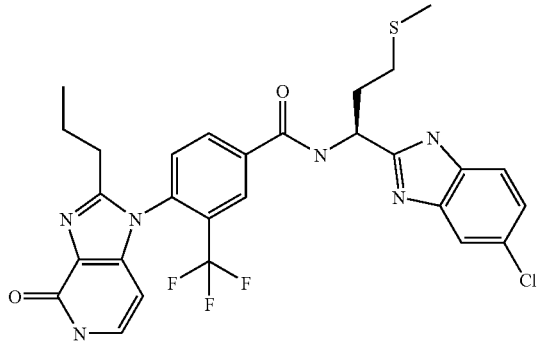

(a) 4-(4-oxo-2-propyl-4,5-dihydroimidazo[4,5-c]pyridin-1-yl)-3-trifluoromethylbenzonitrile 2 g (10.58 mmol) of 4-fluoro-(3-trifluoromethyl)benzonitrile and 2.1 g (11.62 mmol) of 2-propyl-1,5-dihydroimidazo[4,5-c]pyridin-4-one are dissolved in 20 mL of dimethylformamide and after the addition of 520 mg (13 mmol) of sodium hydride (50% in oil) stirred for 60 minutes at ambient temperature. Then the mixture is poured into 450 mL of water and the precipitate is suction filtered. The crude product is triturated in dichloromethane/methanol, suction filtered, and dried. Yield: 810 mg (22%); $R_f$ value: 0.38 (silica gel: dichloromethane/ethanol=9:1); $C_{17}H_{13}F_3N_4O$ (346.32); mass spectrum: $(M+H)^+=347$ (b) 4-(4-oxo-2-propyl-4,5-dihydroimidazo[4,5-c]pyridin-1-yl)-3-trifluoromethylbenzoic acid Prepared analogously to Example 1f from 4-(4-oxo-2-propyl-4,5-dihydroimidazo[4,5-c]-pyridin-1-yl)-3-trifluoromethylbenzonitrile and sodium hydroxide solution in ethanol. Yield: 98%; $R_f$ value: 0.42 (silica gel: dichloromethane/methanol/glacial acetic acid=4:1:0.1).

(c) N-[(1S)-1-(5-chloro-1H-benzimidazol-2-yl)-3-methylsulfanylpropyl]-4-(4-oxo-2-propyl-4,5-dihydroimidazo[4,5-c]pyridin-1-yl)-3-trifluoromethylbenzamide Prepared analogously to Example 1 g from 4-(4-oxo-2-propyl-4,5-dihydroimidazo[4,5-c]-pyridin-1-yl)-3-trifluoromethylbenzoic acid, TBTU, diisopropylethylamine, and (1S)-1-(5-chloro-1H-benzimidazol-2-yl)-3-methylsulfanylpropylamine in tetrahydrofuran. Yield: 40%; $R_f$ value: 0.35 (silica gel: dichloromethane/ethanol=9:1); $C_{28}H_{26}ClF_3N_6O_2S$ (603.066).

Example 342

N-[(1S)-1-(5-chloro-1H-benzimidazol-2-yl)ethyl]-4-(2-methyl-5,6-dihydro-4H-cyclo-pentaimidazol-1-yl)-3-trifluoromethylbenzamide

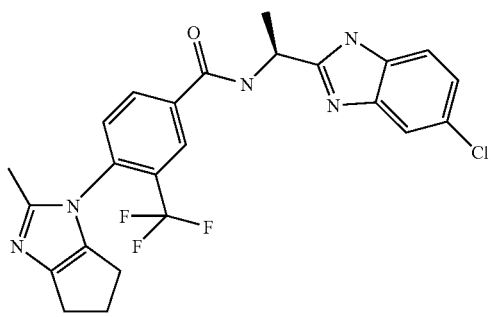

Prepared analogously to Example 1d from 4-(2-methyl-5,6-dihydro-4H-cyclopentaimidazol-1-yl)-3-trifluoromethylbenzoic acid, PFTU, diisopropylethylamine, and (1S)-1-(5-chloro-1H-benzimidazol-2-yl)ethylamine in dimethylformamide. Yield: 64%; $C_{24}H_{21}ClF_3N_5O$ (487.911); mass spectrum: (M–H)⁻=486/488 (chlorine isotope).

Example 343

N-[(1S)-1-(5-chloro-1H-benzimidazol-2-yl)ethyl]-4-(2-methyl-4,5,6,7-tetrahydrobenzimidazol-1-yl)-3-trifluoromethylbenzamide

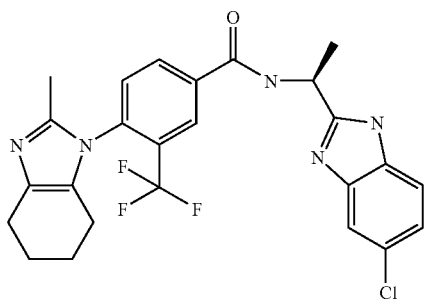

Prepared analogously to Example 1d from 4-(2-methyl-4,5,6,7-tetrahydrobenzimidazol-1-yl)-3-trifluoromethylbenzoic acid, PFTU, diisopropylethylamine, and (1S)-1-(5-chloro-1H-benzimidazol-2-yl)ethylamine in dimethylformamide. Yield: 45%; $C_{25}H_{23}ClF_3N_5O$ (501.938); mass spectrum: (M–H)⁻=500/502 (chlorine isotope).

Example 344 rac.-3-chloro-N-[1-(5-chloro-1H-benzimidazol-2-yl)ethyl]-4-[2-hydroxycarbonylmethyl-3-oxopiperazin-1-ylcarbonyl]benzamide

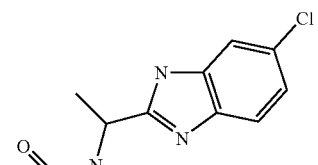

Prepared analogously to Example 1d from rac.-2-chloro-4-{N-[1-(5-chloro-1H-benzimidazol-2-yl)ethyl]aminocarbonyl}benzoic acid, PFTU, diisopropylethylamine, and 3-(hydroxycarbonylmethyl)piperazin-2-one in dimethylformamide. Yield: 32%; $C_{23}H_{21}Cl_2N_5O_5$ (518.355); mass spectrum: (M+H)⁺=518/520/522 (chlorine isotope).

Example 345

N-[(1S)-1-(5-chloro-1H-benzimidazol-2-yl)ethyl]-4-(4-methoxyimidazo[4,5-c]pyridin-1-yl)-3-trifluoromethylbenzamide

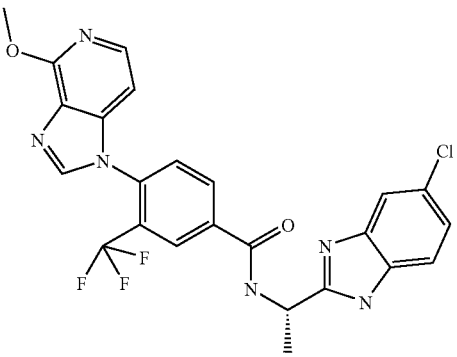

Prepared analogously to Example 1g from 4-(4-methoxy-imidazo[4,5-c]pyridin-1-yl)-3-trifluoromethylbenzoic acid, TBTU, diisopropylethylamine, and (1S)-1-(5-chloro-1H-benzimidazol-2-yl)ethylamine in dimethylsulfoxide. Yield: 46%; $R_f$ value: 0.39 (silica gel: dichloromethane/methanol=10:1); $C_{24}H_{18}ClF_3N_6O_2$ (514.893); mass spectrum: (M+H)$^+$=515/517 (chlorine isotope).

Example 346 rac.-3-chloro-N-[1-(5-chloro-1H-benzimidazol-2-yl)ethyl]-4-(2-hydroxycarbonylpyrrolidin-1-ylcarbonyl)benzamide

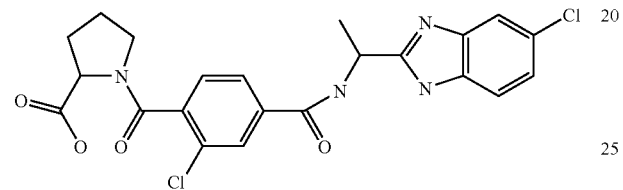

Prepared analogously to Example 19b from rac.-3-chloro-N-[1-(5-chloro-1H-benzimidazol-2-yl)ethyl]-4-(2-methoxycarbonylpyrrolidin-1-ylcarbonyl)benzamide, and sodium hydroxide solution in isopropanol. Yield: 85%; $C_{22}H_{20}Cl_2N_4O_4$ (475.33); mass spectrum: (M+H)$^+$=475/477/479 (chlorine isotope).

Example 347

N-[(1S)-1-(5-chloro-1H-benzimidazol-2-yl)ethyl]-4-(2-dimethylaminomethylbenzimidazol-1-yl)-3-trifluoromethylbenzamide

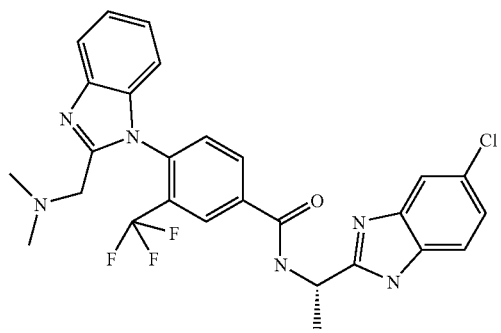

Prepared analogously to Example 1g from 4-(2-dimethylaminomethylbenzimidazol-1-yl)-3-trifluoromethylbenzoic acid, TBTU, diisopropylethylamine, and (1S)-1-(5-chloro-1H-benzimidazol-2-yl)ethylamine in dimethylsulfoxide. Yield: 26%; $R_f$ value: 0.25 (silica gel: dichloromethane/methanol=10:1); $C_{27}H_{24}ClF_3N_6O$ (540.975); mass spectrum: (M+H)$^+$=541/543 (chlorine isotope).

Example 348

N-[(1S)-1-(5-chloro-1H-benzimidazol-2-yl)ethyl]-4-(4-oxo-4,5-dihydroimidazo[4,5-c]pyridin-1-yl)-3-trifluoromethylbenzamide

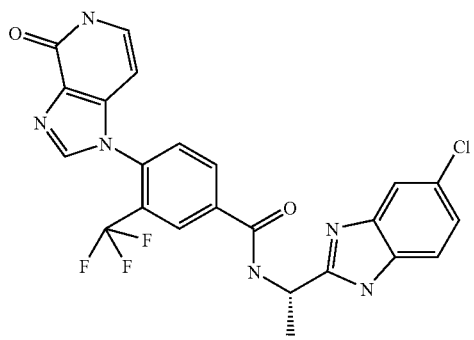

Prepared analogously to Example 1g from 4-(4-oxo-4,5-dihydroimidazo[4,5-c]pyridin-1-yl)-3-trifluoromethylbenzoic acid, TBTU, diisopropylethylamine, and (1S)-1-(5-chloro-1H-benzimidazol-2-yl)ethylamine in dimethylsulfoxide. Yield: 51%; $R_f$ value: 0.16 (silica gel: dichloromethane/methanol=10:1); $C_{23}H_{16}ClF_3N_6O_2$ (500.866); mass spectrum: (M+H)$^+$=501/503 (chlorine isotope).

Example 349

N-[(1S)-1-(5-chloro-1H-benzimidazol-2-yl)ethyl]-4-(2-dimethylaminomethyl-indol-1-yl)-3-trifluoromethylbenzamide

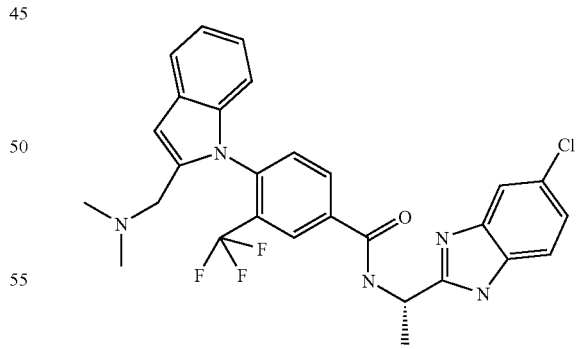

Prepared analogously to Example 1g from 4-(2-dimethylaminomethyl-indol-1-yl)-3-trifluoromethylbenzoic acid, TBTU, diisopropylethylamine, and (1S)-1-(5-chloro-1H-benzimidazol-2-yl)ethylamine in dimethylsulfoxide. Yield: 37%; $R_f$ value: 0.36 (silica gel: dichloromethane/methanol=10:1); $C_{28}H_{25}ClF_3N_5O$ (539.987); mass spectrum: (M+H)$^+$=540/542 (chlorine isotope).

Example 350

N-[(1S)-1-(5-chloro-1H-benzimidazol-2-yl)ethyl]-4-(4-oxo-4,5-dihydropyrrol-[3,2-c]pyridin 1-yl)-3-trifluoromethylbenzamide

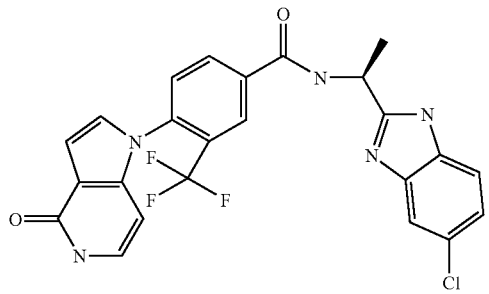

Prepared analogously to Example 1d from 4-(4-oxo-4,5-dihydropyrrol-[3,2-c]pyridin-1-yl)-3-trifluoromethylbenzoic acid, PFTU, diisopropylethylamine, and (1S)-1-(5-chloro-1H-benzimidazol-2-yl)ethylamine in dimethylformamide. Yield: 83%; $C_{24}H_{17}ClF_3N_5O_2$ (499.878); mass spectrum: (M+H)$^+$=500/502 (chlorine isotope).

Example 351

3-chloro-N-[(1S)-1-(5-chloro-1H-benzimidazol-2-yl)ethyl]-4-(2-methyl-4,5,6,7-tetra-hydrobenzimidazol-1-yl)benzamide

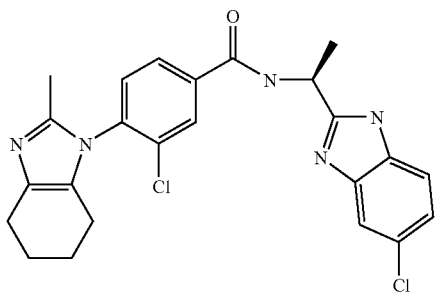

Prepared analogously to Example 1d from 3-chloro-4-(2-methyl-4,5,6,7-tetrahydrobenzimidazol-1-yl)benzoic acid, PFTU, diisopropylethylamine, and (1S)-1-(5-chloro-1H-benzimidazol-2-yl)ethylamine in dimethylformamide. Yield: 35%; $C_{24}H_{23}Cl_2N_5O$ (468.386); mass spectrum: (M+H)$^+$=466/468/470 (chlorine isotope).

Example 352

3-chloro-N-[(1S)-1-(5-chloro-1H-benzimidazol-2-yl)ethyl]-4-(3-oxo-[1,4]diazepan-1-ylcarbonyl)benzamide

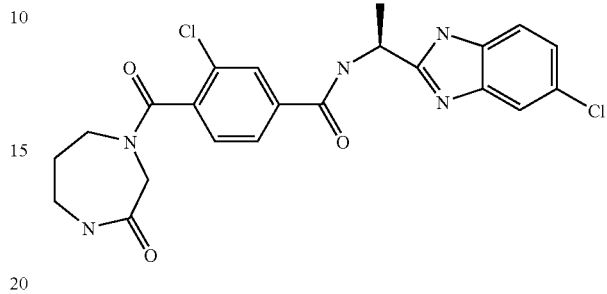

Prepared analogously to Example 1d from (1S)-2-chloro-4-{N-[1-(5-chloro-1H-benzimidazol-2-yl)ethyl]aminocarbonyl}benzoic acid, PFTU, diisopropylethylamine, and [1,4]diazepan-2-one in dimethylformamide. Yield: 63%; $C_{22}H_{21}Cl_2N_5O_3$ (474.346); mass spectrum: (M+H)$^+$=474/476 (chlorine isotope).

Example 353

N-{(1S)-1-(5-chloro-1H-benzimidazol-2-yl)-5-[(5-oxopyrrolidin-3-yl)carbonylamino]pentyl}-3-methyl-4-(pyrrolidin-1-ylcarbonyl)benzamide Prepared analogously to Example 1d from N-[(1S)-5-amino-1-(5-chloro-1H-benzimidazol-2-yl)pentyl]-3-methyl-4-(pyrrolidin-1-ylcarbonyl)benzamide, PFTU, diisopropylethylamine, and 5-oxopyrrolidine-3-carboxylic acid in dimethylsulfoxide. HPLC-MS results: retention time: 2.04 minutes; $C_{30}H_{35}ClN_6O_4$ (579.10); mass spectrum: (M−H)$^-$=578.

Example 354

N-{(1S)-1-(5-chloro-1H-benzimidazol-2-yl)-5-[(pyridin-3-yl-)carbonylamino]pentyl}-3-methyl-4-(pyrrolidin-1-ylcarbonyl)benzamide

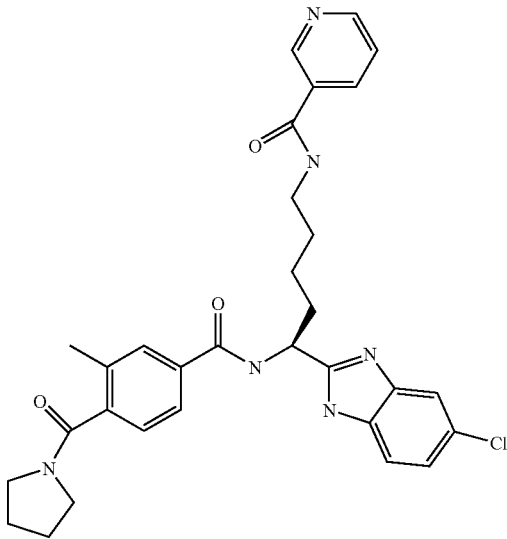

Prepared analogously to Example 1d from N-[(1S)-5-amino-1-(5-chloro-1H-benzimidazol-2-yl)pentyl]-3-methyl-4-(pyrrolidin-1-ylcarbonyl)benzamide, PFTU, diisopropylethylamine, and nicotinic acid in dimethylsulfoxide. HPLC-MS results: retention time: 2.01 minutes; $C_{31}H_{33}ClN_6O_3$ (573.10); mass spectrum: $(M-H)^-=572$.

Example 355

N-{(1S)-1-(5-chloro-1H-benzimidazol-2-yl)-5-[(5-oxopyrrolidin-2-yl)carbonylamino]pentyl}-3-methyl-4-(pyrrolidin-1-ylcarbonyl)benzamide

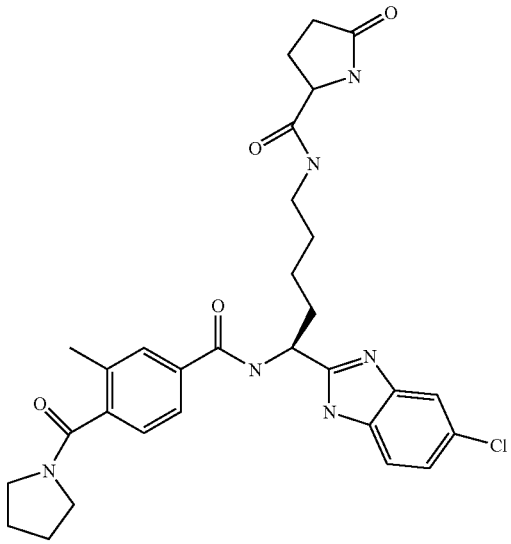

Prepared analogously to Example 1d from N-[(1S)-5-amino-1-(5-chloro-1H-benzimidazol-2-yl)pentyl]-3-methyl-4-(pyrrolidin-1-ylcarbonyl)benzamide, PFTU, diisopropylethylamine, and 5-oxopyrrolidine-2-carboxylic acid in dimethylsulfoxide. HPLC-MS results: retention time: 2.02 minutes; $C_{30}H_{35}ClN_6O_4$ (579.10); mass spectrum: $(M-H)^-=578$.

Example 356

N-{(1S)-1-(5-chloro-1H-benzimidazol-2-yl)-5-[(pyridin-4-yl)carbonylamino]pentyl}-3-methyl-4-(pyrrolidin-1-ylcarbonyl)benzamide

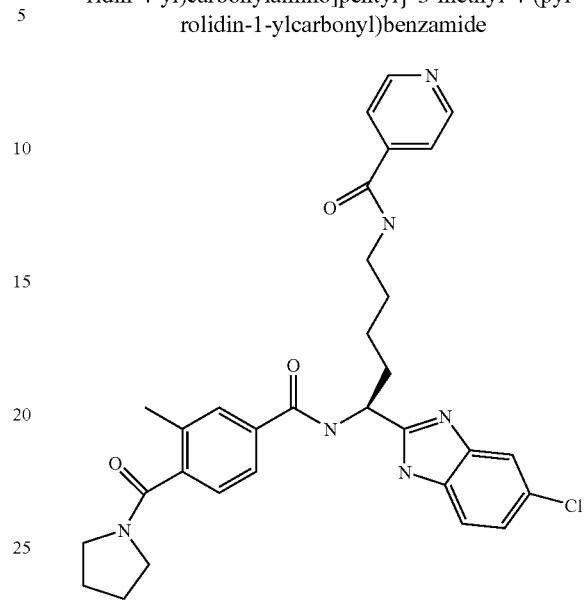

Prepared analogously to Example 1d from N-[(1S)-5-amino-1-(5-chloro-1H-benzimidazol-2-yl)pentyl]-3-methyl-4-(pyrrolidin-1-ylcarbonyl)benzamide, PFTU, diisopropylethylamine, and pyridine-4-carboxylic acid in dimethylsulfoxide. HPLC-MS results: retention time: 2.02 minutes; $C_{31}H_{33}ClN_6O_3$ (573.10); mass spectrum: $(M-H)^-=572$.

Example 357

N-{(1S)-1-(5-chloro-1H-benzimidazol-2-yl)-5-[(2S)-(1-methylpyrrolidin-2-yl)carbonylamino]pentyl}-3-methyl-4-(pyrrolidin-1-ylcarbonyl)benzamide

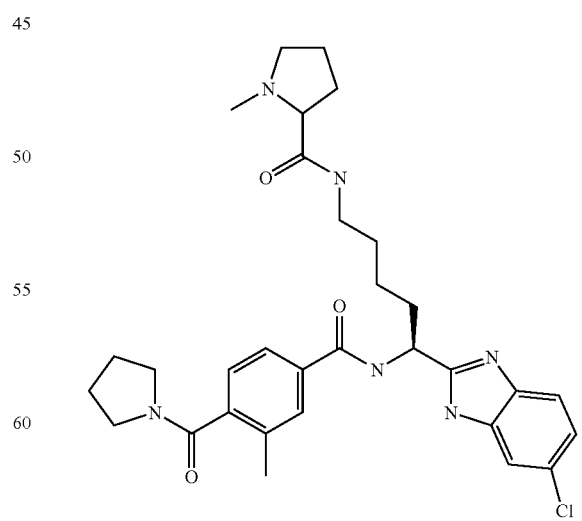

Prepared analogously to Example 1d from N-[(1S)-5-amino-1-(5-chloro-1H-benzimidazol-2-yl)pentyl]-3-methyl-4-(pyrrolidin-1-ylcarbonyl)benzamide, PFTU, diisopropylethylamine, and (S)-1-methylpyrrolidine-2-carboxylic acid in dimethylsulfoxide. HPLC-MS results: retention time: 2.03 minutes; $C_{31}H_{39}ClN_6O_3$ (579.15); mass spectrum: $(M-H)^-=578$.

Example 358

2-(5-chloro-1H-indol-2-yl)-N-[3-methyl-4-(pyrrolidin-1-ylcarbonyl)phenyl]pent-4-enoic acid amide

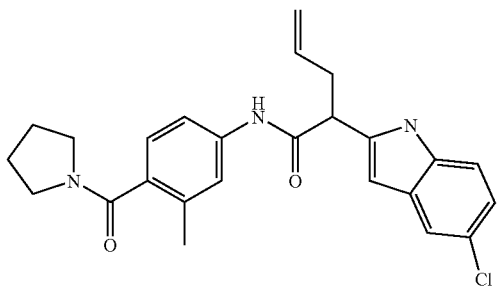

a) ethyl rac.-2-(1-tert-butoxycarbonyl-1H-5-chloroindol-2yl)pent-4-enoate

A solution of 0.75 g (2.2 mmol) of ethyl 2-(1-tert-butoxycarbonyl-1H-5-chloroindol-2-yl)acetate (prepared analogously to Chem. Ber. 1986, 119, 2069-2074 and subsequent reaction with $Boc_2O$ and catalytic amounts of dimethylaminopyridine in acetonitrile) in 15 mL of tetrahydrofuran is combined batchwise with 170 mg (4.4 mmol) of 60% sodium hydride suspension in mineral oil and stirred for 30 minutes at ambient temperature. The suspension is combined successively with 0.28 mL (3.3 mmol) of allyl bromide and 23 mg (0.15 mmol) of sodium iodide, the reaction flask is darkened with aluminum foil, and the mixture is stirred for several hours. Then it is carefully combined with water and extracted 3× with ethyl acetate. The combined organic phases are dried with sodium sulfate, concentrated, and the crude product is purified by chromatography on silica gel (petroleum ether:ethyl acetate 95:5). $C_{20}H_{24}ClNO_4$ (377.87); mass spectrum: $(M-H)^+=378/380$ (chlorine isotope).

b) 2-(5-chloro-1H-indol-2-yl)-N-[3-methyl-4-(pyrrolidin-1-ylcarbonyl)phenyl]pent-4-enoic acid amide Prepared by saponification of ethyl rac.-2-(1-tert-butoxycarbonyl-1H-5-chloroindol-2-yl)pent-4-enoate to rac.-2-(5-chloro-1H-indol-2-yl)pent-4-enoic acid analogously to Example 1f and subsequent amide coupling analogously to Example 1g with 3-methyl-4-(pyrrolidin-1-ylcarbonyl) aniline, TBTU, diisopropylethylamine in tetrahydrofuran. $C_{25}H_{26}ClN_3O_2$ (435.96); mass spectrum: $(M+H)^+=435$.

Example 359

N-[(1R)-2-benzyloxy-1-(5-chloro-1H-benzimidazol-2-yl)ethyl]-3-methyl-4-(pyrrolidin-1-ylcarbonyl)benzamide

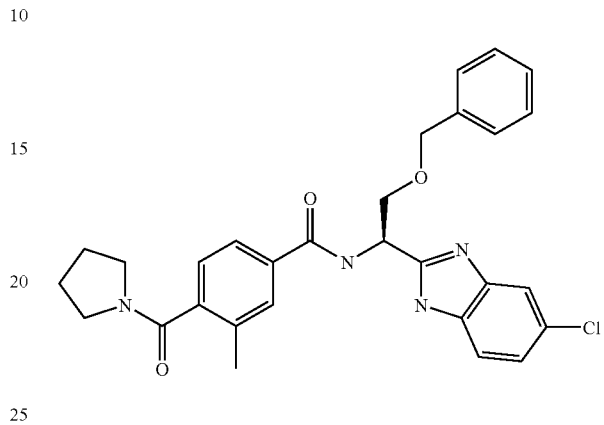

Prepared analogously to Example 1g from 3-methyl-4-(pyrrolidin-1-ylcarbonyl)benzoic acid, TBTU, diisopropylethylamine, and (1R)-2-benzyloxy-1-(5-chloro-1H-benzimidazol-2-yl)ethylamine in tetrahydrofuran. Yield: 71%; $R_f$ value: 0.63 (silica gel: dichloromethane/ethanol=9:1); $C_{29}H_{29}ClN_4O_3$ (517.03); mass spectrum: $(M+H)^+=517/519$ (chlorine isotope).

Example 360

N-[(1R)-2-(acetylaminomethylsulfanyl)-1-(5-chloro-1H-benzimidazol-2-yl)ethyl]-3-methyl-4-(pyrrolidin-1-ylcarbonyl)benzamide

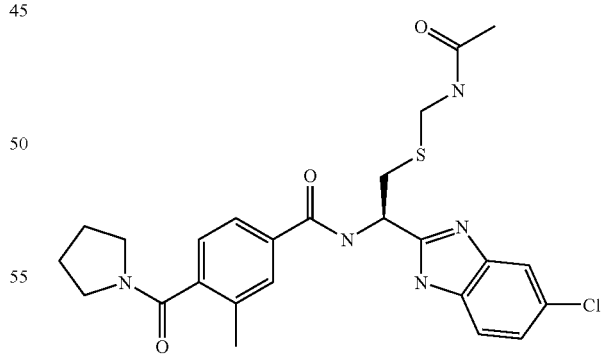

Prepared analogously to Example 1g from 3-methyl-4-(pyrrolidin-1-ylcarbonyl)benzoic acid, TBTU, diisopropylethylamine, and (1R)-2-(acetylaminomethylsulfanyl)-1-(5-chloro-1H-benzimidazol-2-yl)ethylamine in tetrahydrofuran. Yield: 89%; $R_f$ value: 0.40 (silica gel: dichloromethane/ethanol=9:1; $C_{25}H_{28}ClN_5O_3S$ (514.05); mass spectrum: $(M+H)^+=514/516$ (chlorine isotope).

Example 361

N-[(1S)-3-aminocarbonyl-1-(5-chloro-1H-benzimidazol-2-yl)propyl]-3-methyl-4-(pyrrolidin-1-ylcarbonyl)benzamide

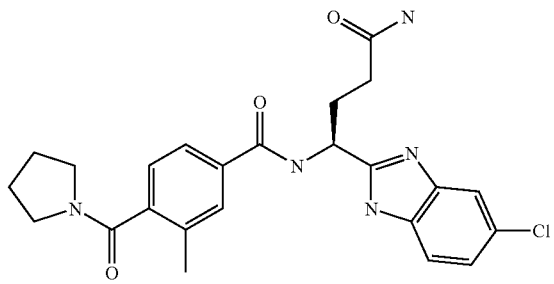

Example 362

N-[(1S)-1-(5-chloro-1H-benzimidazol-2-yl)-2-(1H-indol-3-yl)ethyl]-3-methyl-4-(pyrrolidin 1-ylcarbonyl)benzamide

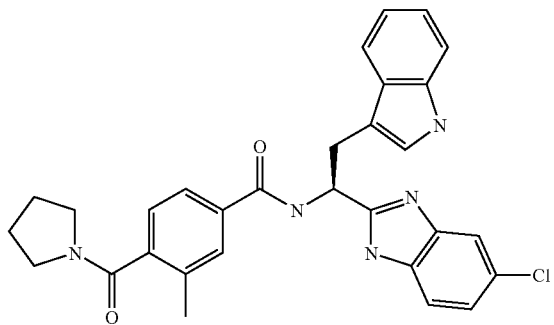

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-2-(1H-indol-3-yl)ethylamine in tetrahydrofuran. Yield: %; $R_f$ value: 0.48 (silica gel: dichloromethane/ethanol=9:1); $C_{30}H_{28}ClN_5O_2$ (526.04); mass spectrum: $(M+H)^+$=526/528 (chlorine isotope).

Example 363 rac.-N-[1-(5-chloro-1H-benzimidazol-2-yl)-2-(4-hydroxy-3,5-dimethylphenyl)ethyl]-3-methyl-4-(pyrrolidin-1-ylcarbonyl)benzamide

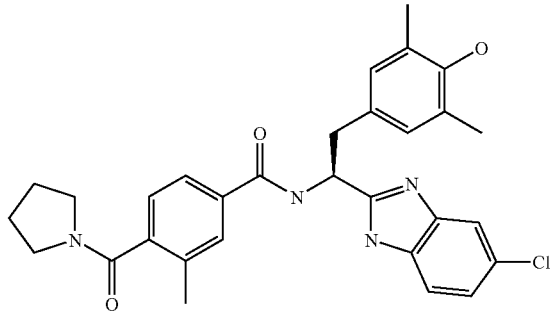

Prepared analogously to Example 1g from 3-methyl-4-(pyrrolidin-1-ylcarbonyl)benzoic acid, TBTU, diisopropylethylamine, and rac.-1-(5-chloro-1H-benzimidazol-2-yl)-2-(4-hydroxy-3,5-dimethylphenyl)ethylamine in tetrahydrofuran. Yield: %; $R_f$ value: 0.45 (silica gel: dichloromethane/ethanol=9:1); $C_{30}H_{31}ClN_4O_3$ (531.06); mass spectrum: $(M+H)^+$=531/533 (chlorine isotope).

Example 364

N-[(1S)-1-(5-chloro-1H-benzimidazol-2-yl)-2-methoxycarbonylethyl]-3-methyl-4-(pyrrolidin-1-ylcarbonyl)benzamide

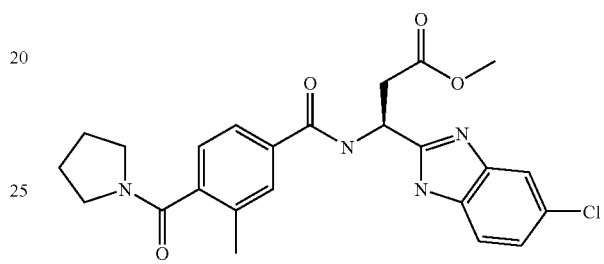

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-2-methoxy-carbonylethylamine in tetrahydrofuran. Yield: %; $R_f$ value: 0.45 (silica gel: dichloromethane/ethanol=9:1); $C_{24}H_{25}ClN_4O_4$ (468.94); mass spectrum: $(M+H)^+$=469/471 (chlorine isotope).

Example 365 rac.-N-[1-(5-chloro-1H-benzimidazol-2-yl)-2-(4-hydroxy-2,6-dimethylphenyl)ethyl]-3-methyl-4-(pyrrolidin-1-ylcarbonyl)benzamide

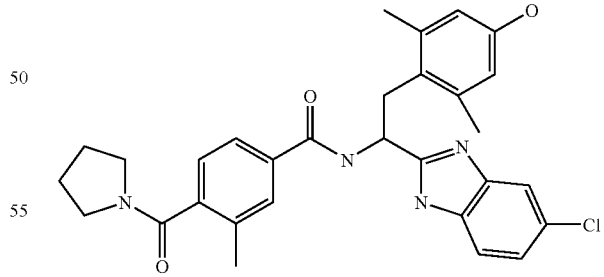

Prepared analogously to Example 1g from 3-methyl-4-(pyrrolidin-1-ylcarbonyl)benzoic acid, TBTU, diisopropylethylamine, and rac.-1-(5-chloro-1H-benzimidazol-2-yl)-2-(4-hydroxy-2,6-dimethylphenyl)ethylamine in tetrahydrofuran. Yield: %; $R_f$ value: 0.39 (silica gel: dichloromethane/ethanol=9:1); $C_{30}H_{31}ClN_4O_3$ (531.06); mass spectrum: $(M+H)^+$=531/533 (chlorine isotope).

Example 366 rac.-N-[1-(5-chloro-1H-benzimidazol-2-yl)-2-(4-difluoromethoxyphenyl)ethyl]-3-methyl-4-(pyrrolidin-1-ylcarbonyl)benzamide

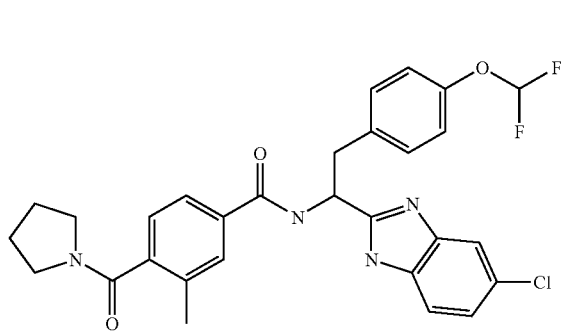

Prepared analogously to Example 1g from 3-methyl-4-(pyrrolidin-1-ylcarbonyl)benzoic acid, TBTU, diisopropylethylamine, and rac.-1-(5-chloro-1H-benzimidazol-2-yl)-2-(4-difluoromethoxyphenyl)ethylamine in tetrahydrofuran. Yield: %; $R_f$ value: 0.36 (silica gel: dichloromethane/ethanol=9:1); $C_{29}H_{27}ClF_2N_4O_3$ (553.01); mass spectrum: $(M+H)^+$=553/555 (chlorine isotope).

Example 367 rac.-N-[2-(3-bromophenyl)-1-(5-chloro-1H-benzimidazol-2-yl)ethyl]-3-methyl-4-(pyrrolidin-1-ylcarbonyl)benzamide

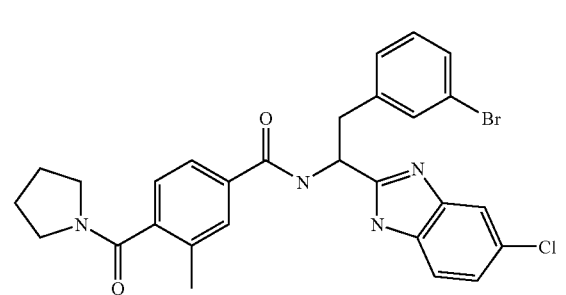

Prepared analogously to Example 1g from 3-methyl-4-(pyrrolidin-1-ylcarbonyl)benzoic acid, TBTU, diisopropylethylamine, and rac.-2-(3-bromophenyl)-1-(5-chloro-1H-benzimidazol-2-yl)ethylamine in tetrahydrofuran. Yield: %; $R_f$ value: 0.52 (silica gel: dichloromethane/ethanol=9:1); $C_{28}H_{26}BrClN_4O_2$ (565.90); mass spectrum: $(M+H)^+$=565/567/569 (bromo-chlorine isotope).

Example 368

N-[(1S)-1-(5-chloro-1H-benzimidazol-2-yl)-2-(4-trifluoromethylphenyl)ethyl]-3-methyl-4-(pyrrolidin-1-ylcarbonyl)benzamide

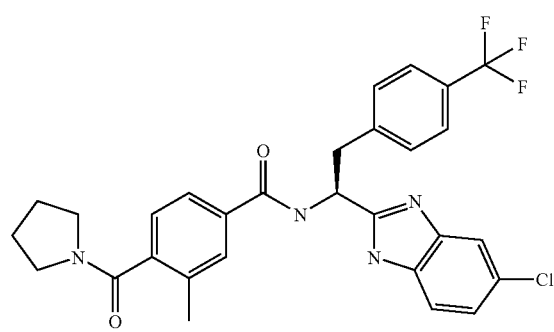

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-2-(4-trifluoromethylphenyl)ethylamine in tetrahydrofuran. Yield: %; $R_f$ value: 0.53 (silica gel: dichloromethane/ethanol=9:1); $C_{29}H_{26}ClF_3N_4O_2$ (555.00); mass spectrum: $(M+H)^+$=555/557 (chlorine isotope).

Example 369

N-[(1S)-1-(5-chloro-1H-benzimidazol-2-yl)-5-ureidopentyl]-3-methyl-4-(pyrrolidin 1-ylcarbonyl)benzamide

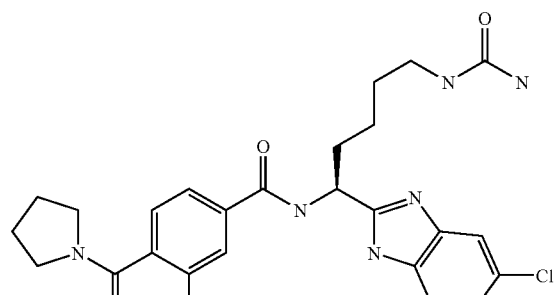

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-5-ureidopentylamine in tetrahydrofuran. Yield: %; $R_f$ value: 0.07 (silica gel: dichloromethane/ethanol=9:1); $C_{26}H_{31}ClN_6O_3$ (511.03); mass spectrum: $(M+H)^+$=511/513 (chlorine isotope).

Example 370

N-[(1S)-1-(5-chloro-1H-benzimidazol-2-yl)-5-ureidobutyl]-3-methyl-4-(pyrrolidin-1-ylcarbonyl)benzamide

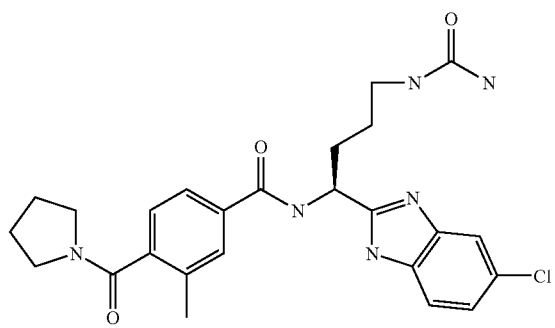

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-5-ureidobutylamine in tetrahydrofuran. Yield: %; $R_f$ value: 0.05 (silica gel: dichloromethane/ethanol=9:1); $C_{25}H_{29}ClN_6O_3$ (497.01); mass spectrum: $(M+H)^+$=497/499 (chlorine isotope).

Example 371 rac..-N-[2-(4-amino-3,5-dibromophenylcarbonyl)-1-(5-chloro-1H-benzimidazol-2-yl)-ethyl]-3-methyl-4-(pyrrolidin-1-ylcarbonyl)benzamide

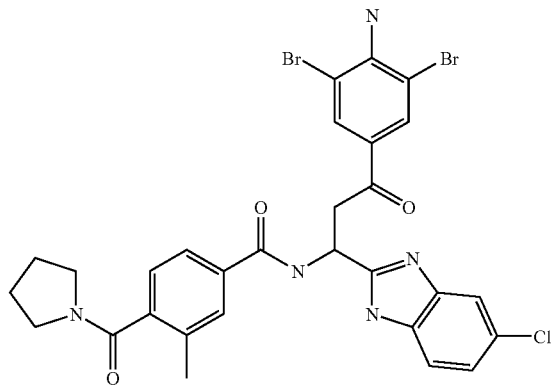

Example 372

N-[(1S)-2-allyloxycarbonyl-1-(5-chloro-1H-benzimidazol-2-yl)ethyl]-3-methyl-4-(pyrrolidin-1-ylcarbonyl)benzamide

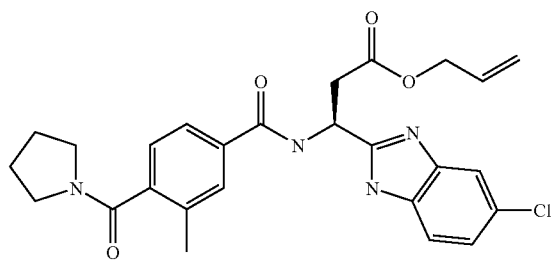

Prepared analogously to Example 1g from 3-methyl-4-(pyrrolidin-1-ylcarbonyl)benzoic acid, TBTU, diisopropylethylamine and (1S)-2-allyloxycarbonyl-1-(5-chloro-1H-benzimidazol-2-yl)ethylamine in tetrahydrofuran. Yield: %; $R_f$ value: 0.43 (silica gel: dichloromethane/ethanol=9:1); $C_{26}H_{27}ClN_4O_4$ (494.98); mass spectrum: $(M+H)^+$=495/497 (chlorine isotope).

Example 373

N-[(1S)-1-(5-chloro-1H-benzimidazol-2-yl)-2-(3,4-dimethoxyphenyl)ethyl]-3-methyl-4-(pyrrolidin-1-ylcarbonyl)benzamide

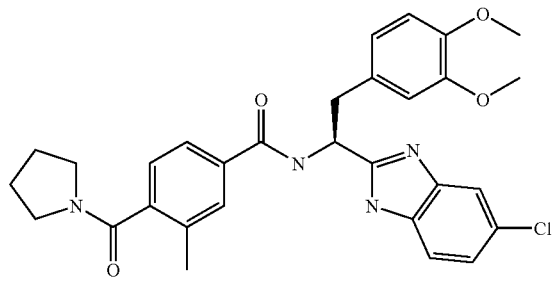

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-2-(3,4-di-methoxyphenyl)ethylamine in tetrahydrofuran. Yield: %; $R_f$ value: 0.38 (silica gel: dichloromethane/ethanol=9:1); $C_{30}H_{31}ClN_4O_4$ (547.06); mass spectrum: $(M+H)^+$=547/549 (chlorine isotope).

Example 374

N-[(1S)-1-(5-chloro-1H-benzimidazol-2-yl)-2-(thiazol-4-yl)ethyl]-3-methyl-4-(pyrrolidin-1-ylcarbonyl)benzamide

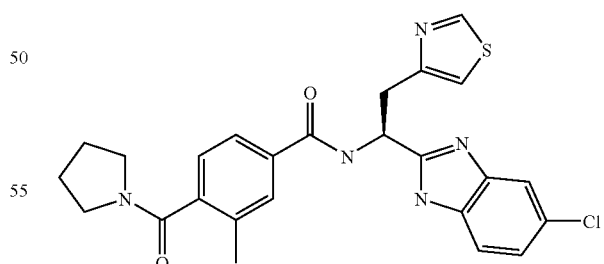

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-2-(thiazol-4-yl)ethylamine in tetrahydrofuran. Yield: %; $R_f$ value: 0.29 (silica gel: dichloromethane/ethanol=9:1); $C_{25}H_{24}ClN_5O_2S$ (494.02); mass spectrum: $(M+H)^+$=494/496 (chlorine isotope).

Example 375

N-[(1S)-1-(5-chloro-1H-benzimidazol-2-yl)-2-(3,5-difluorophenyl)ethyl]-3-methyl-4-(pyrrolidin-1-ylcarbonyl)benzamide

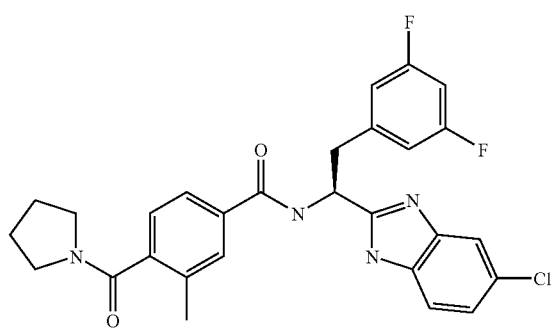

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-2-(3,5-difluorophenyl)ethylamine in tetrahydrofuran. Yield: %; $R_f$ value: 0.43 (silica gel: dichloromethane/ethanol=9:1); $C_{28}H_{25}ClF_2N_4O_2$ (522.99); mass spectrum: $(M+H)^+=523/525$ (chlorine isotope).

Example 376

N-[(1S)-1-(5-chloro-H-benzimidazol-2-yl)-2-(4-fluorophenyl)ethyl]-3-methyl-4-(pyrrolidin-1-ylcarbonyl)benzamide

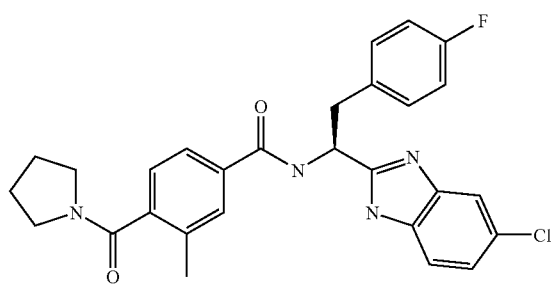

Prepared analogously to Example 1g from 3-methyl 4-(pyrrolidin-1-ylcarbonyl)benzoic acid, TBTU, diisopropylethylamine, and (1S)-1-(5-chloro-1H-benzimidazol-2-yl)-2-(4-fluorophenyl)ethylamine in tetrahydrofuran. Yield: %; $R_f$ value: 0.44 (silica gel: dichloromethane/ethanol=9:1); $C_{28}H_{26}ClFN_4O_2$ (505.01); mass spectrum: $(M+H)^+=505/507$ (chlorine isotope).

Example 377

N-[(1R)-1-(5-chloro-1H-benzimidazol-2-yl)-2-mercaptoethyl]-3-methyl-4-(pyrrolidin-1-ylcarbonyl)benzamide

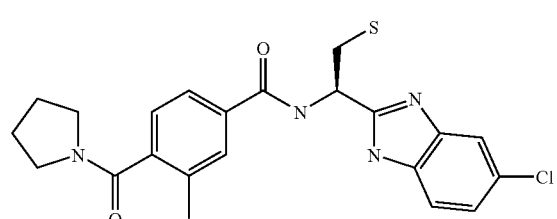

Example 378

N-[(1S)-1-(5-chloro-1H-benzimidazol-2-yl)-2-(1-methyl-1H-imidazol-5-yl)ethyl]-3-methyl-4-(pyrrolidin-1-ylcarbonyl)benzamide

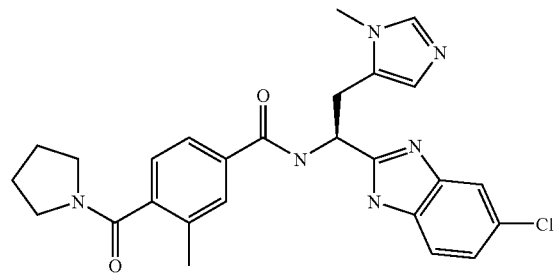

Prepared analogously to Example 1g from 3-methyl-4-(pyrrolidin-1-ylcarbonyl)benzoic acid, TBTU, diisopropylethylamine, and (1S)-1-(5-chloro-1H-benzimidazol-2-yl)-2-(1-methyl-1H-imidazol-5-yl)ethylamine in tetrahydrofuran. Yield: %; $R_f$ value: 0.12 (silica gel: dichloromethane/ethanol=9:1); $C_{26}H_{27}ClN_6O_2$ (491.01); mass spectrum: $(M+H)^+=491/493$ (chlorine isotope).

Example 379 rac.-N-[1-(5-chloro-1H-benzimidazol-2-yl)-2-(1H-benzimidazol-5-yl)ethyl]-3-methyl-4-(pyrrolidin-1-ylcarbonyl)benzamide

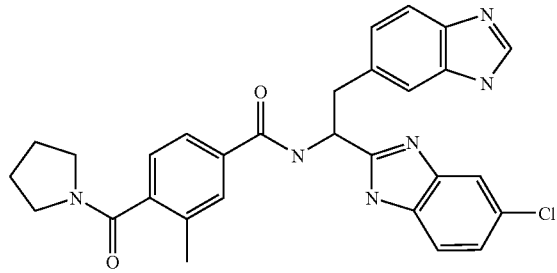

Example 380 rac.-N-[(5-chloro-1H-benzimidazol-2-yl)thiophen-3-yl-methyl]-3-methyl-4-(pyrrolidin-1-ylcarbonyl)benzamide

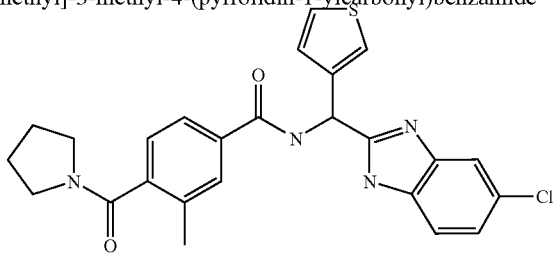

Prepared analogously to Example 1g from 3-methyl-4-(pyrrolidin-1-ylcarbonyl)benzoic acid, TBTU, diisopropyl-ethylamine, and rac.-(5-chloro-1H-benzimidazol-2-yl)thiophen-3-ylmethylamine in tetrahydrofuran. Yield: %; $R_f$ value: 0.39 (silica gel: dichloromethane/ethanol=9:1); $C_{25}H_{23}ClN_4O_2S$ (479.01); mass spectrum: (M+H)$^+$=479/481 (chlorine isotope).

Example 381

N-[(1S)-1-(5-chloro-1H-benzimidazol-2-yl)-2-(thiophen-3-yl)ethyl]-3-methyl-4-(pyrrolidin-1-yl-carbonyl)benzamide

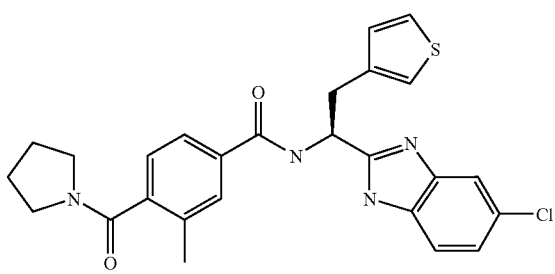

Prepared analogously to Example 1g from 3-methyl-4-(pyrrolidin-1-ylcarbonyl)benzoic acid, TBTU, diisopropyl-ethylamine, and N-[(1S)-1-(5-chloro-1H-benzimidazol-2-yl)-2-(thiophen-3-yl)ethylamine in tetrahydrofuran. Yield: %; $R_f$ value: 0.38 (silica gel: dichloromethane/ethanol=9:1); $C_{26}H_{25}ClN_4O_2S$ (493.03); mass spectrum: (M+H)$^+$=493/495 (chlorine isotope).

Example 382

N-[(1S)-1-(5-chloro-1H-benzimidazol-2-yl)but-3-enyl]-3-methyl-4-(pyrrolidin-1-ylcarbonyl)benzamide

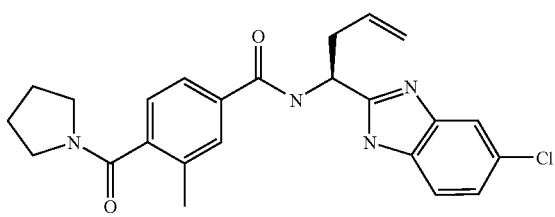

Prepared analogously to Example 1g from 3-methyl-4-(pyrrolidin-1-ylcarbonyl)benzoic acid, TBTU, diisopropyl-ethylamine, and (1S)-1-(5-chloro-1H-benzimidazol-2-yl)but-3-enylamine in tetrahydrofuran. Yield: %; $R_f$ value: 0.34 (silica gel: dichloromethane/ethanol=9:1); $C_{24}H_{25}ClN_4O_2$ (436.95); mass spectrum: (M+H)$^+$=437/439 (chlorine isotope).

Example 383

N-[(1S)-1-(5-chloro-1H-benzimidazol-2-yl)-2-(4-chlorophenyl)ethyl]-3-methyl-4-(pyrrolidin-1-ylcarbonyl)benzamide

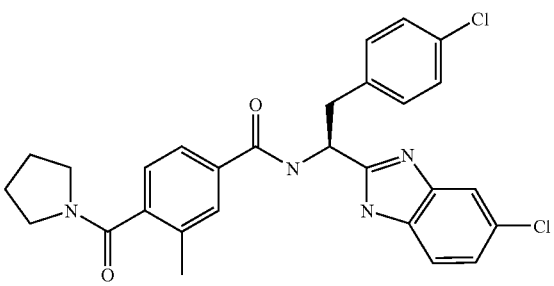

Prepared analogously to Example 1g from 3-methyl-4-(pyrrolidin-1-ylcarbonyl)benzoic acid, TBTU, diisopropyl-ethylamine, and (1S)-1-(5-chloro-1H-benzimidazol-2-yl)-2-(4-chlorophenyl)ethylamine in tetrahydrofuran. Yield: %; $R_f$ value: 0.40 (silica gel: dichloromethane/ethanol=9:1); $C_{28}H_{26}Cl_2N_4O_2$ (521.45); mass spectrum: (M+H)$^+$=521/523 (chlorine isotope).

Example 384

N-[(1S)-1-(5-chloro-1H-benzimidazol-2-yl)-2-cyclo-propylethyl]-3-methyl-4-(pyrrolidin-1-ylcarbonyl)benzamide

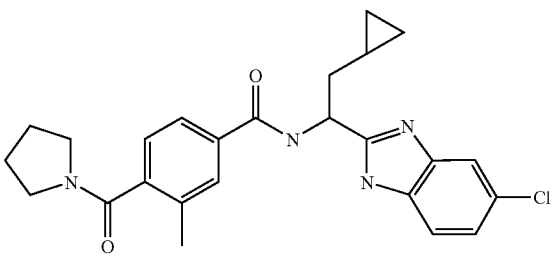

Example 385

3-chloro-N-[(1S)-1-(5-chloro-1H-benzimidazol-2-yl)ethyl]-4-[2-(pyrrolidin-1-yl)methyl-5,6-dihydro-4H-cyclopentaimidazol-1-yl]benzamide

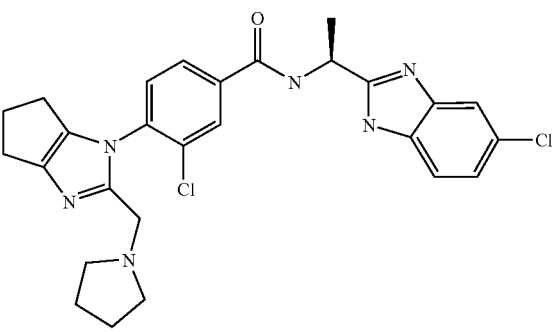

Example 386

3-chloro-N-[(1S)-1-(5-chloro-1H-benzimidazol-2-yl)
ethyl]-4-[2-(2-(pyrrolidin-1-yl)ethyl)-5,6-dihydro-
4H-cyclopentaimidazol-1-yl])benzamide

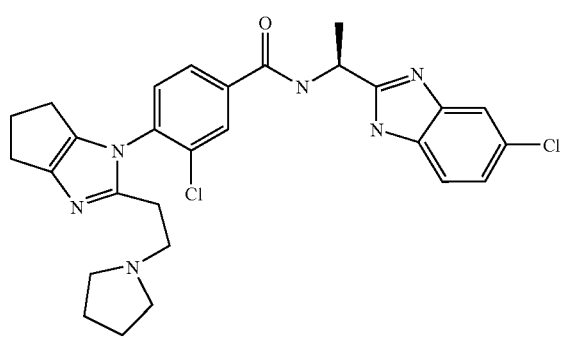

Example 387

3-chloro-N-[(1S)-1-(5-chloro-1H-benzimidazol-2-yl)
ethyl]-4-[2-(pyrrolidin-1-yl)methyl-4,5,6,7-tetrahy-
drobenzimidazol-1-yl]benzamide

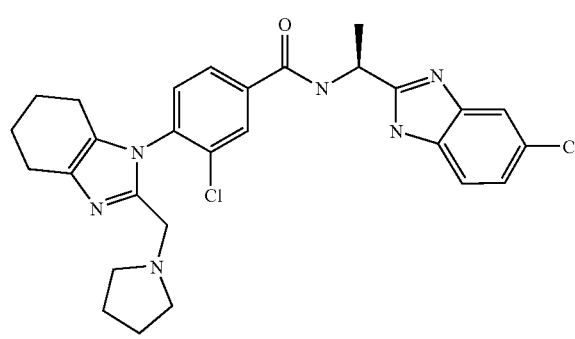

Example 388

3-chloro-N-[(1S)-1-(5-chloro-1H-benzimidazol-2-yl)
ethyl]-4-[2-(2-pyrrolidin-1-ylethyl)-4,5,6,7-tetrahy-
drobenzimidazol-1-yl]benzamide

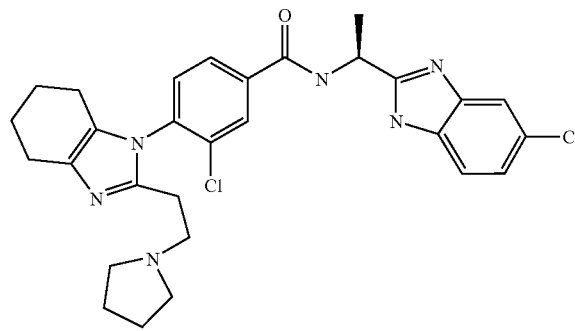

Example 389

3-chloro-N-[(1S)-1-(5-chloro-1H-benzimidazol-2-yl)
ethyl]-4-[2-(morpholin-4-yl)methyl-5,6-dihydro-4H-
cyclopentaimidazol-1-yl]benzamide

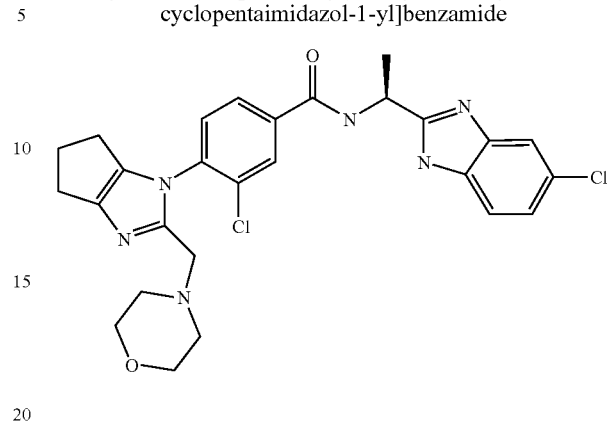

Example 390

3-chloro-N-[(1S)-1-(5-chloro-1H-benzimidazol-2-yl)
ethyl]-4-[2-(2-(morpholin-4-yl)ethyl)-5,6-dihydro-
4H-cyclopentaimidazol-1-yl]benzamide

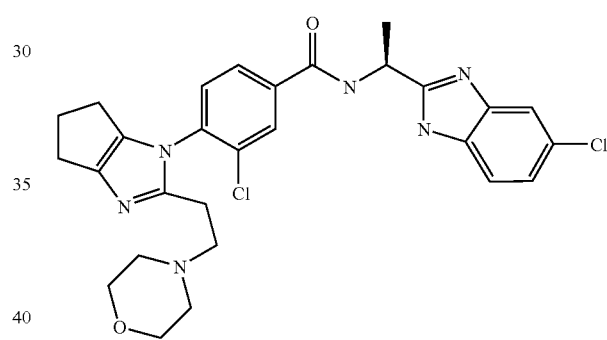

Example 391

3-chloro-N-[(1S)-1-(5-chloro-1H-benzimidazol-2-yl)
ethyl]-4-[2-(morpholin-4-yl)methyl-4,5,6,7-tetrahy-
drobenzimidazol-1-yl]benzamide

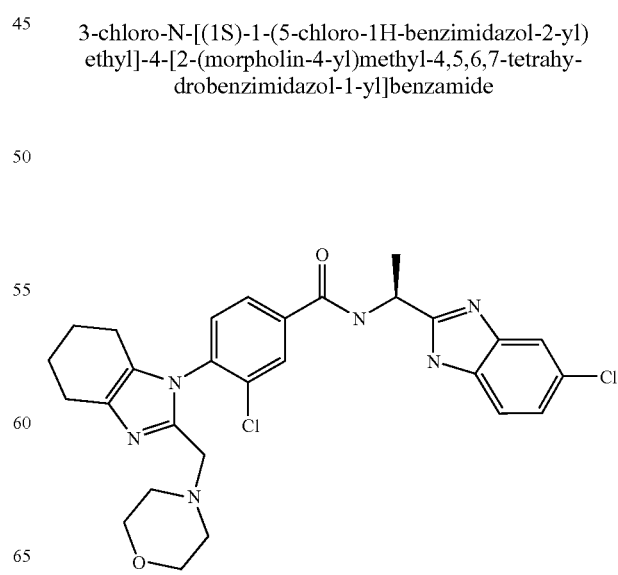

Example 392

3-chloro-N-[(1S)-1-(5-chloro-1H-benzimidazol-2-yl)ethyl]-4-[2-(2-(morpholin-4-yl)ethyl)-4,5,6,7-tetrahydrobenzimidazol-1-yl]benzamide

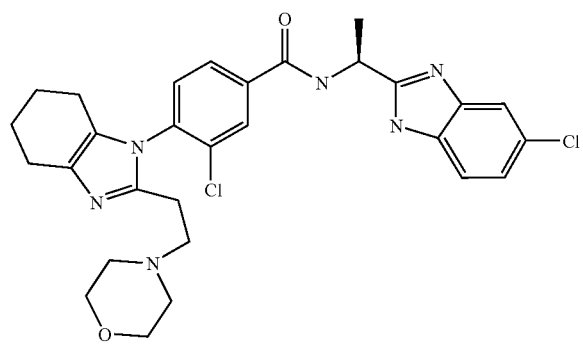

Example 393

3-chloro-N-[(1S)-1-(5-chloro-1H-benzimidazol-2-yl)ethyl]-4-(2-oxohexahydrocyclopentaimidazol-1-yl)benzamide

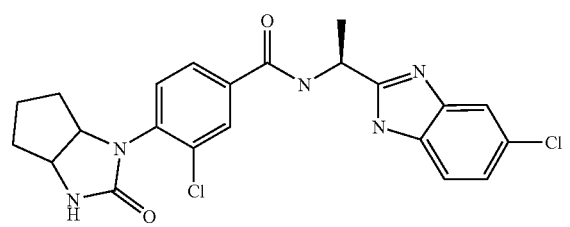

Example 394

N-[(1S)-1-(5-chloro-1H-benzimidazol-2-yl)ethyl]-4-(4-oxo-4,5,6,7-tetrahydropyrrol[3,2-c]pyridin-1-yl)-3-trifluoromethylbenzamide

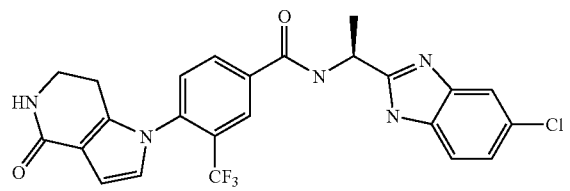

Example 395

3-chloro-N-[(1S)-1-(5-chloro-1H-benzimidazol-2-yl)ethyl]-4-(4-oxooctahydropyrrol[3,2-c]pyridin-1-yl)benzamide

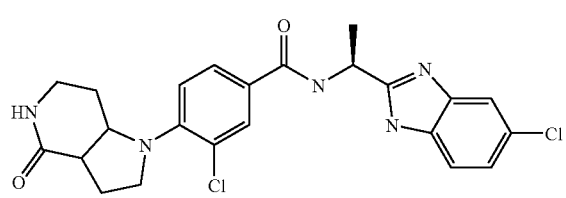

Example 396

3-chloro-N-[(1S)-1-(5-chloro-1H-benzimidazol-2-yl)ethyl]-4-(octahydrocyclopentapyrazin-1-yl)benzamide

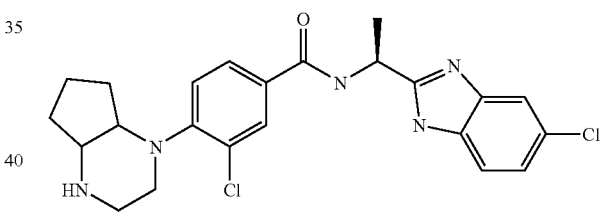

Example 397

3-chloro-N-[(1S)-1-(5-chloro-1H-benzimidazol-2-yl)ethyl]-4-(2,3-dioxooctahydrocyclopentapyrazin-1-yl)benzamide

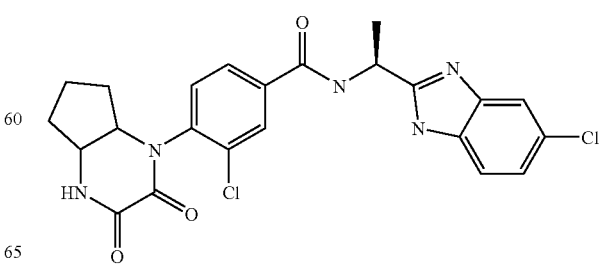

Example 398

N-[(1S)-1-(5-chloro-1H-benzimidazol-2-yl)ethyl]-3-methyl-4-(2-oxo-2,5,6,7-tetrahydrocyclopentapyrazin-1-yl)benzamide

Example 401

N-[(1R)-1-(5-chloro-1H-benzimidazol-2-yl)-2-(2,2,2-trifluoroethoxy)ethyl]-3-methyl-4-(pyrrolidin-1-ylcarbonyl)benzamide

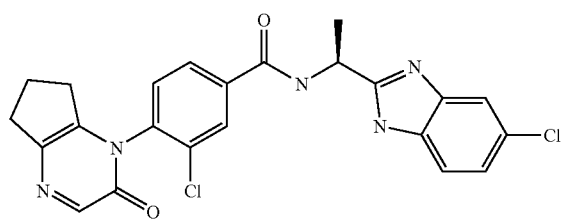

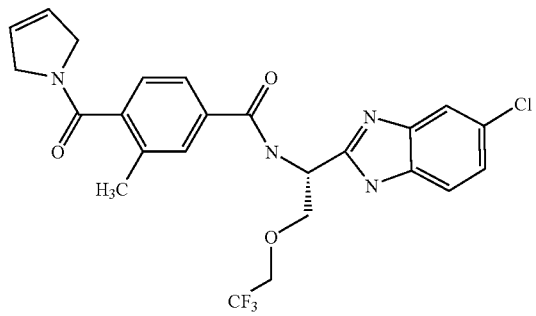

Example 399

3-chloro-N-[(1S)-1-(5-chloro-1H-benzimidazol-2-yl)ethyl]-4-(5,6,7,7a-tetrahydro-1H-pyrrol-[1,2-c]-imidazol-3-yl)benzamide

Example 402

N-[(1R)-1-(5-chloro-1H-benzimidazol-2-yl)-2-trifluoromethoxyethyl]-3-methyl-4-(pyrrolidin-1-ylcarbonyl)benzamide

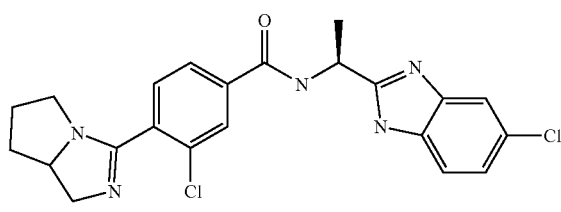

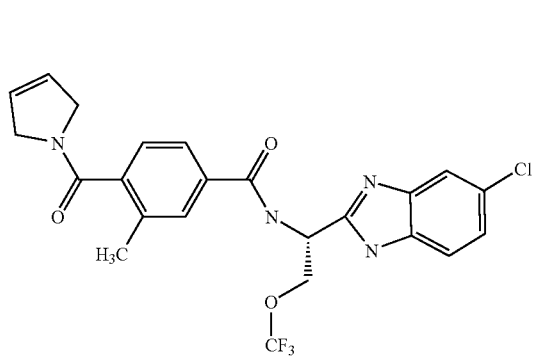

Example 400

N-[(1S)-1-(5-chloro-1H-benzimidazol-2-yl)ethyl]-4-(3,4,4a,5,6,7-hexahydropyrrol-[1,2-c]pyrimidin-1-yl)-3-methylbenzamide

Example 403

N-[(1R)—-(5-chloro-1H-benzimidazol-2-yl)-2-difluoromethoxyethyl]-3-methyl-4-(pyrrolidin-1-ylcarbonyl)benzamide

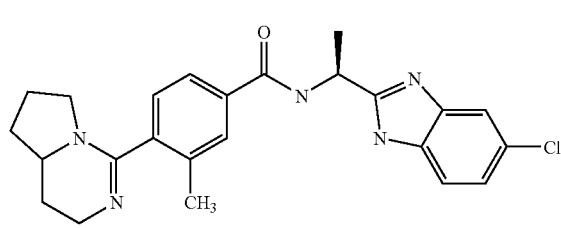

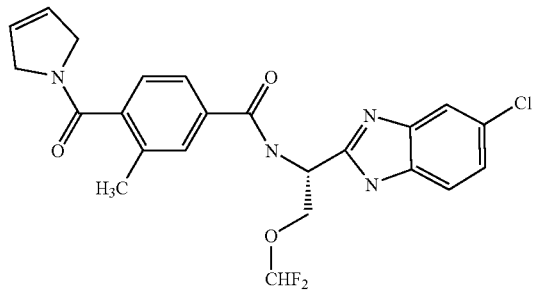

Example 404

N-[(1R)-1-(5-chloro-1H-benzimidazol-2-yl)-2-fluoromethoxyethyl]-3-methyl-4-(pyrrolidin-1-ylcarbonyl)benzamide

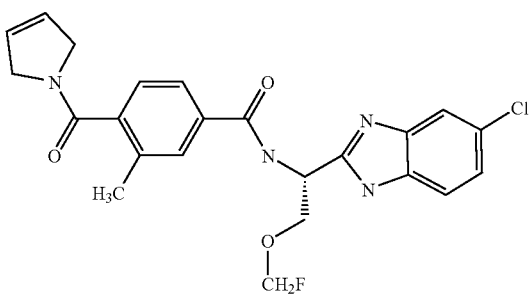

Example 405

3-chloro-N-[(1S)-1-(5-chloro-1H-benzimidazol-2-yl)ethyl]-4-((2R)-2-dimethylamino-methylpyrrolidin-1-ylcarbonyl)benzamide

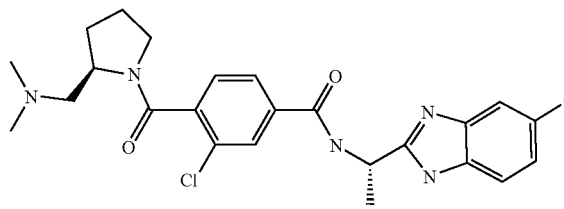

Example 406

3-chloro-N-[(1R)-1-(5-bromo-1H-benzimidazol-2-yl)-2-hydroxyethyl]-4-(2,5-dihydropyrrol-1-ylcarbonyl)benzamide

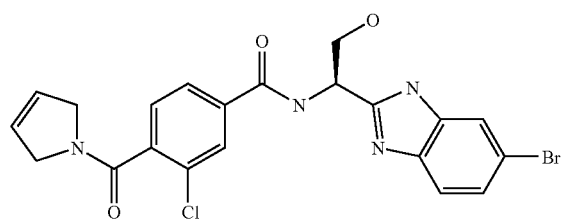

Prepared analogously to Example 1g from 3-bromo-4-(2,5-dihydropyrrol-1-ylcarbonyl)benzoic acid, TBTU, diisopropylethylamine, and (1R)-1-(5-bromo-1H-benzimidazol-2-yl)-2-hydroxyethylamine in tetrahydrofuran. Yield: 57%; melting point: 124° C.-126° C.; $C_{21}H_{18}BrClN_4O_3$ (489.76); mass spectrum: $(M+H)^+=489/491/493$ (bromine/chlorine isotope).

Example 407

3-bromo-N-[(1R)-1-(5-bromo-1H-benzimidazol-2-yl)-2-hydroxyethyl]-4-(pyrrolidin-1-ylcarbonyl)benzamide

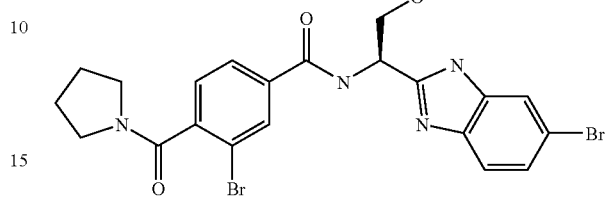

Prepared analogously to Example 1g from 3-bromo-4-(pyrrolidin-1-ylcarbonyl)benzoic acid, TBTU, diisopropylethylamine, and (1R)-1-(5-bromo-1H-benzimidazol-2-yl)-2-hydroxyethylamine in tetrahydrofuran. Yield: 50%; melting point: 114° C.-116° C.; $R_f$ value: 0.25 (silica gel: dichloromethane/ethanol=95:5); $C_{21}H_{20}Br_2N_4O_3$ (536.22); mass spectrum: $(M+H)^+=535/537/539$ (bromine isotope).

Example 408

3-methyl-N-[(1R)-1-(5-bromo-1H-benzimidazol-2-yl)-2-hydroxyethyl]-4-(pyrrolidin 1-ylcarbonyl)benzamide

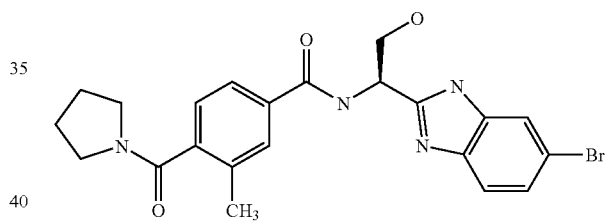

Prepared analogously to Example 1g from 3-methyl-4-(pyrrolidin-1-ylcarbonyl)benzoic acid, TBTU, diisopropylethylamine, and (1R)-1-(5-bromo-1H-benzimidazol-2-yl)-2-hydroxyethylamine in tetrahydrofuran. Yield: 43%; $R_f$ value: 0.23 (silica gel: dichloromethane/ethanol=95:5); $C_{22}H_{23}BrN_4O_3$ (471.36); mass spectrum: $(M+H)^+=471/473$ (bromine isotope). The Examples that follow describe the preparation of pharmaceutical formulations which contain as active substance any desired compound of general formula (1).

EXAMPLE I

| Dry Ampoule Containing 75 mg of Active Substance per 10 mL |  |
|---|---|
| Composition: |  |
| Active substance | 75.0 mg |
| Mannitol | 50.0 mg |
| water for injections | to 10.0 mL |

Preparation:

Active substance and mannitol are dissolved in water. After packaging the solution is freeze-dried. To produce the solution ready for use for injections, the product is dissolved in water.

EXAMPLE II

Dry Ampoule Containing 35 mg of Active Substance per 2 mL

Composition:

| | |
|---|---|
| Active substance | 35.0 mg |
| Mannitol | 100.0 mg |
| water for injections | to 2.0 mL |

Preparation:

Active substance and mannitol are dissolved in water. After packaging, the solution is freeze-dried. To produce the solution ready for use for injections, the product is dissolved in water.

EXAMPLE III

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2), and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE IV

Tablet Containing 350 mg of Active Substance

Composition:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE V

Capsules Containing 50 mg of Active Substance

Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing. This powder mixture is packed into size 3 hard gelatine capsules in a capsule filling machine.

EXAMPLE VI

Capsules Containing 350 mg of Active Substance

Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing. This powder mixture is packed into size 0 hard gelatine capsules in a capsule filling machine.

EXAMPLE VII

Suppositories Containing 100 mg of Active Substance 1 suppository contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds. Each of the references cited herein are incorporated by reference herein in its entirety.

We claim:

1. A compound of formula Ic

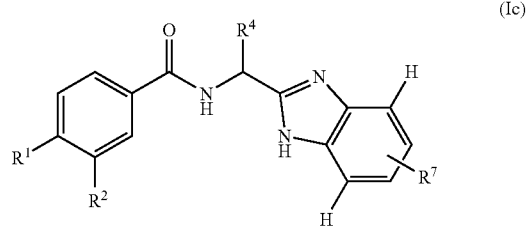

wherein:
R¹ is a group of formula

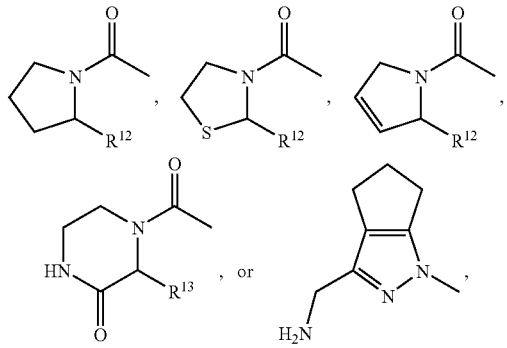

wherein:
R¹² is a hydrogen atom, or a methyl, aminomethyl, $C_{1-3}$-alkylamino-$C_{1-2}$-alkyl, di-($C_{1-3}$-alkyl)-amino-$C_{1-2}$-alkyl, pyrrolidin-1-ylmethyl, or 2-(pyrrolidin-1-yl)ethyl group, and
R¹³ is a hydrogen atom, a methyl or aminomethyl group;
R² is a fluorine, chlorine, or bromine atom, or a methyl, ethyl, trifluoromethyl, or methoxy group;
R⁴ is a $C_{1-4}$-alkyl group which may be substituted by a fluorine atom, a hydroxy, $C_{1-3}$-alkyloxy, trifluoromethoxy, 2,2,2-trifluoroethyloxy, allyloxy, propargyloxy, mercapto, $C_{1-4}$-alkylsulfanyl, $C_{1-4}$-alkylsulfinyl, $C_{1-14}$-alkylsulfonyl, amino, $C_{1-3}$-alkylcarbonylamino, $C_{1-3}$-alkylsulfonylamino, carboxy, aminocarbonyl, $C_{1-3}$-alkylaminocarbonyl, di-($C_{1-3}$-alkyl)-aminocarbonyl, or a 4- to 7-membered cycloalkyleneiminocarbonyl group,
a phenyl, thiophenyl, phenyl-$C_{1-3}$-alkyl, tetrazolyl-$C_{1-3}$-alkyl, imidazolyl-$C_{1-3}$-alkyl, thiazolyl-$C_{1-3}$-alkyl or thiophenyl-$C_{1-3}$-alkyl group, and
R⁷ is a chlorine or bromine atom, and
the tautomers and the salts thereof.

2. A compound according to claim 1 selected from:
(1) N-[1-(5-chloro-1H-benzimidazol-2-yl)ethyl]-3-methyl-4-(2,5-dihydropyrrol-1-ylcarbonyl)benzamide,
(2) N-[1-(5-chloro-1H-benzimidazol-2-yl)ethyl]-3-methyl-4-(pyrrolidin-1-ylcarbonyl)benzamide,
(3) N-[1-(5-chloro-1H-benzimidazol-2-yl)ethyl]-3-ethyl-4-(pyrrolidin-1-ylcarbonyl)benzamide,
(5) (S)—N-[1-(5-chloro-1H-benzimidazol-2-yl)-2-(1H-imidazol-4-yl)ethyl]-3-methyl-4-(pyrrolidin-1-ylcarbonyl)benzamide,
(6) N-[1-(5-chloro-1H-benzimidazol-2-yl)ethyl]-3-chloro-4-(2-aminomethylpyrrolidin-1-ylcarbonyl)benzamide,
(7) 3-chloro-N-(5-chloro-1H-benzimidazol-2-ylmethyl)-4-(2-methylpyrrolidin-1-ylcarbonyl)benzamide,
(8) N-[1-(5-bromo-1H-benzimidazol-2-yl)ethyl]-3-methyl-4-(pyrrolidin-1-ylcarbonyl)benzamide,
(9) N-[(5-chloro-1H-benzimidazol-2-yl)phenylmethyl]-3-methyl-4-(pyrrolidin-1-ylcarbonyl)benzamide,
(11) N-[1-(5-chloro-1H-benzimidazol-2-yl)ethyl]-3-chloro-4-(3-oxopiperazin-1-ylcarbonyl)benzamide,
(12) (S)—N-[1-(5-chloro-1H-benzimidazol-2-yl)]ethyl-3-methyl-4-(pyrrolidin-1-ylcarbonyl)benzamide,
(13) N-[1-(5-chloro-1H-benzimidazol-2-yl)]ethyl-3-bromo-4-(pyrrolidin-1-ylcarbonyl)benzamide,
(14) N-[1-(5-chloro-1H-benzimidazol-2-yl)]ethyl-3-trifluoromethyl-4-(pyrrolidin-1-ylcarbonyl)benzamide,
(15) N-[(1S)-1-(5-chloro-1H-benzimidazol-2-yl)ethyl]-3-methyl-4-[(2R/S)-2-amino-methylpyrrolidin-1-ylcarbonyl]benzamide,
(16) N-[(1S)-1-(5-chloro-1H-benzimidazol-2-yl)ethyl]-3-chloro-4-[(2R/S)-2-aminomethylpyrrolidin-1-ylcarbonyl)benzamide,
(17) N-[(1S)-1-(5-chloro-1H-benzimidazol-2-yl)ethyl]-3-chloro-4-[(2S)-2-aminomethylpyrrolidin-1-ylcarbonyl]benzamide,
(18) N-[(1S)-1-(5-chloro-1H-benzimidazol-2-yl)ethyl]-3-chloro-4-[(2R)-2-aminomethylpyrrolidin-1-ylcarbonyl]benzamide,
(19) N-[(1S)-1-(5-chloro-1H-benzimidazol-2-yl)ethyl]-3-chloro-4-[(2S)-2-(2-aminoethyl)pyrrolidin-1-ylcarbonyl]benzamide,
(21) N-[(1S)-1-(5-chloro-1H-benzimidazol-2-yl)butyl]-3-chloro-4-[(2S)-2-aminomethylpyrrolidin-1-ylcarbonyl]benzamide,
(23) N-[(1S)-1-(5-chloro-1H-benzimidazol-2-yl)-3-methylsulfanylpropyl]-3-chloro-4-[(2S)-2-aminomethylpyrrolidin-1-ylcarbonyl]benzamide,
(24) N-[(1S)-1-(5-chloro-1H-benzimidazol-2-yl)-3-methylsulfinylpropyl]-3-chloro-4-[(2S)-2-aminomethylpyrrolidin-1-ylcarbonyl]benzamide,
(25) N-[(1S)-1-(5-chloro-1H-benzimidazol-2-yl)-3-methylsulfonylpropyl]-3-chloro-4-[(2S)-2-aminomethylpyrrolidin-1-ylcarbonyl]benzamide,
(27) N-[(1S)-1-(5-chloro-1H-benzimidazol-2-yl)-3-phenylpropyl]-3-methyl-4-(pyrrolidin-1-ylcarbonyl)benzamide,
(28) N-[(1S)-5-acetylamino-1-(5-chloro-1H-benzimidazol-2-yl)pentyl]-3-methyl-4-(pyrrolidin-1-ylcarbonyl)benzamide,
(29) N-[(1S)-1-(5-chloro-1H-benzimidazol-2-yl)-3-methylsulfanylpropyl]-3-methyl-4-(pyrrolidin-1-ylcarbonyl)benzamide,
(30) rac.-N-[1-(5-chloro-1H-benzimidazol-2-yl)-2-hydroxyethyl]-3-methyl-4-(pyrrolidin-1-ylcarbonyl)benzamide,
(31) rac.-N-[2-acetylamino-1-(5-chloro-1H-benzimidazol-2-yl)ethyl]-3-methyl-4-(pyrrolidin-1-ylcarbonyl)benzamide,
(33) rac.-N-[1-(5-chloro-1H-benzimidazol-2-yl)-3-hydroxycarbonylpropyl]-3-methyl-4-(pyrrolidin-1-ylcarbonyl)benzamide,
(34) N-[(1S)-1-(5-chloro-1H-benzimidazol-2-yl)-3-hydroxycarbonylpropyl]-3-methyl-4-(pyrrolidin-1-ylcarbonyl)benzamide,
(37) rac.-N-[1-(5-chloro-1H-benzimidazol-2-yl)-3-ethylaminocarbonylpropyl]-3-methyl-4-(pyrrolidin-1-ylcarbonyl)benzamide,
(40) rac.-N-[1-(5-chloro-1H-benzimidazol-2-yl)-3-diethylaminocarbonylpropyl]-3-methyl-4-(pyrrolidin-1-ylcarbonyl)benzamide,
(41) N-[(1R)-1-(5-chloro-1H-benzimidazol-2-yl)-2-hydroxyethyl]-3-methyl-4-(pyrrolidin-1-ylcarbonyl)benzamide,
(42) N-[(1R,2R)-1-(5-chloro-1H-benzimidazol-2-yl)-2-hydroxypropyl]-3-methyl-4-(pyrrolidin-1-ylcarbonyl)benzamide,
(43) N-[(1S)-2-acetylamino-1-(5-chloro-1H-benzimidazol-2-yl)ethyl]-3-methyl-4-(pyrrolidin-1-ylcarbonyl)benzamide,
(44) N-[(1S)-1-(5-chloro-1H-benzimidazol-2-yl)-2-methylsulfonylaminoethyl]-3-methyl-4-(pyrrolidin-1-ylcarbonyl)benzamide,

(45) rac.-N-[1-(5-chloro-1H-benzimidazol-2-yl)-2-methoxyethyl]-3-methyl-4-(pyrrolidin-1-ylcarbonyl)benzamide,
(46) 3-bromo-N-[(1S)-1-(5-chloro-1H-benzimidazol-2-yl)-2-ethyl]-4-(2,5-dihydropyrrol-1-ylcarbonyl)benzamide,
(47) N-[(1S)-1-(5-chloro-1H-benzimidazol-2-yl)-3-methoxypropyl]-3-methyl-4-(pyrrolidin-1-ylcarbonyl)benzamide,
(48) N-[(1S)-4-acetylamino-1-(5-chloro-1H-benzimidazol-2-yl)butyl]-3-methyl-4-(pyrrolidin-1-ylcarbonyl)benzamide,
(51) 3-chloro-N-[(1S)-1-(5-chloro-1H-benzimidazol-2-yl)ethyl]-4-(3-oxopiperazin-1-ylcarbonyl)benzamide,
(52) N-[(1S)-1-(5-chloro-1H-benzimidazol-2-yl)-3-methylsulfinylpropyl]-3-methyl-4-(pyrrolidin-1-ylcarbonyl)benzamide,
(53) N-[(1S)-1-(5-chloro-1H-benzimidazol-2-yl)-3-methylsulfonylpropyl]-3-methyl-4-(pyrrolidin-1-ylcarbonyl)benzamide,
(54) rac.-N-[1-(5-chloro-1H-benzimidazol-2-yl)phenylmethyl]-4-(2,5-dihydropyrrol-1-ylcarbonyl)-3-methylbenzamide,
(55) N-[(1S)-1-(5-chloro-1H-benzimidazol-2-yl)propyl]-3-methyl-4-1-(pyrrolidin-1-ylcarbonyl)benzamide,
(57) N-[(1S)-1-(5-chloro-1H-benzimidazol-2-yl)-3-methylsulfonylaminopropyl]-3-methyl-4-(pyrrolidin-1-ylcarbonyl)benzamide,
(60) 3-chloro-N-[(1R)-1-(5-chloro-1H-benzimidazol-2-yl)-2-ethylsulfanylethyl]-4-(pyrrolidin-1-ylcarbonyl)benzamide,
(61) N-[(1S)-1-(5-chloro-1H-benzimidazol-2-yl)butyl]-3-methyl-4-(pyrrolidin-1-ylcarbonyl)benzamide,
(62) N-[(1S)-1-(5-chloro-1H-benzimidazol-2-yl)-3-hydroxypropyl]-3-methyl-4-(pyrrolidin-1-ylcarbonyl)benzamide,
(63) 3-bromo-N-[(1S)-1-(5-chloro-1H-benzimidazol-2-yl)-3-methylsulfanylpropyl]-4-(pyrrolidin-1-ylcarbonyl)benzamide,
(64) 3-chloro-N-[(1S)-1-(5-chloro-1H-benzimidazol-2-yl)-3-(methylsulfanyl)propyl]-4-(pyrrolidin-1-ylcarbonyl)benzamide,
(65) 3-bromo-N-[(1S)-1-(5-chloro-1H-benzimidazol-2-yl)-3-(methylsulfonyl)propyl]-4-(pyrrolidin-1-ylcarbonyl)benzamide,
(66) 3-bromo-N-[(1S)-1-(5-chloro-1H-benzimidazol-2-yl)-3-methylsulfinylpropyl]-4-(pyrrolidin-1-ylcarbonyl)benzamide,
(67) 3-chloro-N-[(1S)-1-(5-chloro-1H-benzimidazol-2-yl)ethyl]-4-[(2R,S)-(2-methylpyrrolidin-1-ylcarbonyl)]benzamide,
(69) (1R)-3-bromo-N-[1-(5-chloro-1H-benzimidazol-2-yl)-2-hydroxyethyl]-4-(2,5-dihydropyrrol-1-ylcarbonyl)benzamide,
(70) (1R)-3-methyl-N-[1-(5-chloro-1H-benzimidazol-2-yl)-2-methoxyethyl]-4-(2,5-dihydropyrrol-1-ylcarbonyl)benzamide,
(71) (1R)-3-chloro-N-[1-(5-chloro-1H-benzimidazol-2-yl)-2-hydroxyethyl]-4-(2,5-dihydropyrrol-1-ylcarbonyl)benzamide,
(87) N-[(1R)-1-(5-chloro-1H-benzimidazol-2-yl)-2-methoxyethyl]-3-methyl-4-(pyrrolidin-1-ylcarbonyl)benzamide,
(88) 3-chloro-N-[(1R)-1-(5-chloro-1H-benzimidazol-2-yl)-2-methoxyethyl]-4-(2,5-dihydropyrrol-1-ylcarbonyl)benzamide,
(89) 3-bromo-N-[(1R)-1-(5-chloro-1H-benzimidazol-2-yl)-2-methoxyethyl]-4-(pyrrolidin-1-ylcarbonyl)benzamide,
(91) 3-bromo-N-[(1R)-1-(5-chloro-1H-benzimidazol-2-yl)-2-methoxyethyl]-4-(2,5-dihydropyrrol-1-ylcarbonyl)benzamide,
(93) 3-methyl-N-[(1R)-1-(5-chloro-1H-benzimidazol-2-yl)-2-hydroxyethyl]-4-(2,5-dihydropyrrol-1-ylcarbonyl)benzamide,
(96) 3-bromo-N-[(1R)-1-(5-chloro-1H-benzimidazol-2-yl)-2-hydroxyethyl]-4-(pyrrolidin-1-ylcarbonyl)benzamide,
(97) N-[(1R)-1-(5-chloro-1H-benzimidazol-2-yl)-2-methoxyethyl]-4-(2,5-dihydropyrrol-1-ylcarbonyl)-3-trifluoromethylbenzamide, and
(98) N-[(1R)-1-(5-chloro-1H-benzimidazol-2-yl)-2-methoxyethyl]-4-(pyrrolidin-1-ylcarbonyl)-3-trifluoromethylbenzamide, the tautomers and salts thereof.

3. The physiologically acceptable salts of a compound according to claim 1 or 2.

4. A pharmaceutical composition comprising a compound according to claim 1 or 2 or a physiologically acceptable salt thereof and one or more inert carriers and/or diluents.

* * * * *